(12) United States Patent
Stehouwer et al.

(10) Patent No.: US 8,551,996 B2
(45) Date of Patent: Oct. 8, 2013

(54) COMPOUNDS, COMPOSITIONS, METHODS OF SYNTHESIS, AND METHODS OF TREATMENT

(75) Inventors: Jeff Stehouwer, Atlanta, GA (US);
Mark Goodman, Atlanta, GA (US);
Clint Kilts, Little Rock, AR (US);
Charles Nemeroff, Coconut Grove, FL (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/201,485

(22) PCT Filed: Mar. 12, 2010

(86) PCT No.: PCT/US2010/024393
§ 371 (c)(1),
(2), (4) Date: Aug. 31, 2011

(87) PCT Pub. No.: WO2010/096426
PCT Pub. Date: Aug. 26, 2010

(65) Prior Publication Data
US 2011/0305636 A1    Dec. 15, 2011

Related U.S. Application Data

(60) Provisional application No. 61/154,146, filed on Feb. 20, 2009.

(51) Int. Cl.
*A61K 31/4985* (2006.01)
*C07D 471/04* (2006.01)

(52) U.S. Cl.
USPC ............ 514/249; 544/336; 544/350; 514/247

(58) Field of Classification Search
USPC .................. 544/336, 338, 350; 514/247, 249
See application file for complete search history.

(56) References Cited

U.S. PATENT DOCUMENTS 6,083,948 A * 7/2000 Wilde ........................... 514/249
6,869,955 B2 * 3/2005 Wilde ........................... 514/249

* cited by examiner

*Primary Examiner* — Golam M M Shameem
(74) *Attorney, Agent, or Firm* — Emory Patent Group; James C. Mason; Susanne Hollinger

(57) ABSTRACT

Briefly described, embodiments of this disclosure include compounds as described herein, labeled compounds as described herein, pharmaceutical composition including compounds described herein, methods of imaging, method of forming a compound as described herein, and the like. In particular, embodiments of the disclosure include a series of triamino-pyridine derivatives and labeled triamino-pyridine derivatives, methods of synthesizing these compounds, intermediate compounds, methods of treatment using these compounds, methods of imaging, diagnosing, localizing, monitoring, and/or assessing a condition (e.g., corticotropin releasing factor type-1 (CRF1)) and/or related biological events, using triamino-pyridine derivatives, and the like. In addition, the present disclosure includes compositions (e.g., labeled triamino-pyridine derivatives that are ligands for the CRF1 receptor) used in and methods relating to non-invasive imaging (e.g., positron emission tomography (PET) imaging or SPECT imaging).

12 Claims, 2 Drawing Sheets

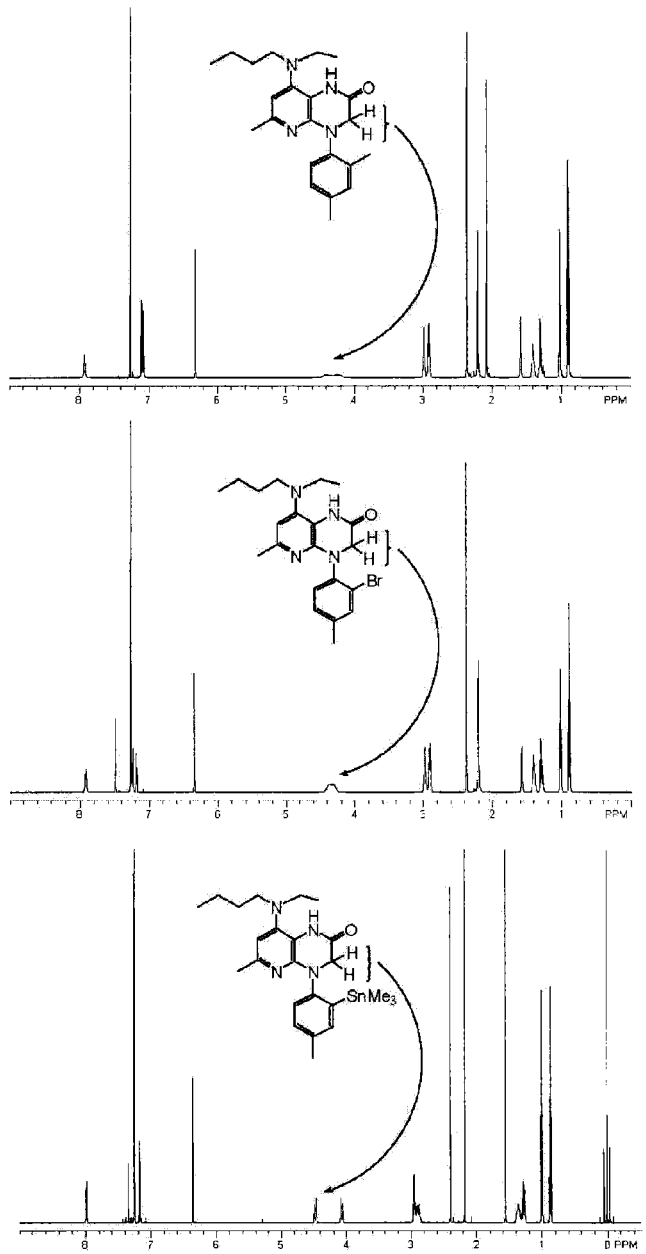
Figure 1. $^1$H NMR spectra (600 MHz, CDCl$_3$) of compounds 191, 185, and 190 demonstrating the existence of atropisomerism due to restricted rotation of the aniline ring.

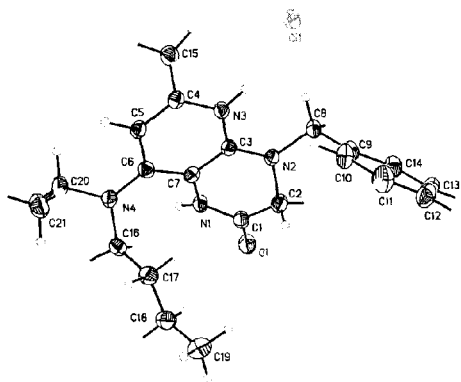
Figure 2.    Thermal ellipsoid representation of the X-ray crystal structure of 8374·HCl.
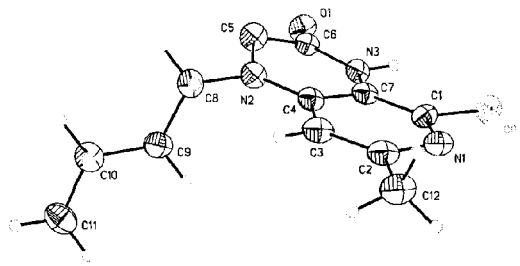
Figure 3.    Thermal ellipsoid representation of the X-ray crystal structure of XXXII.
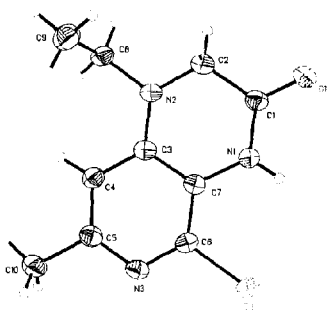
Figure 4.    Thermal ellipsoid representation of the X-ray crystal structure of XXXIII.

COMPOUNDS, COMPOSITIONS, METHODS OF SYNTHESIS, AND METHODS OF TREATMENT

CROSS-REFERENCE TO RELATED APPLICATION

The present application claims priority to International Patent Application entitled COMPOUNDS, COMPOSITIONS, METHODS OF SYNTHESIS, AND METHODS OF TREATMENT having serial number PCT/US2010/024393 filed on Feb. 17, 2010, and claims priority to US Provisional Patent Application No. 61/154,146 filed on Feb. 20, 2009 which application is incorporated herein fully by this reference.

ACKNOWLEDGEMENTS

This invention was made with government support under Grant No. U-19 MH-069056 awarded by the National Institutes of Health. The government has certain rights in the invention.

TECHNICAL FIELD

The present disclosure relates to organic chemistry and in particular to a series of corticotropin releasing factor type-1 ($CRF_1$) receptor ligand compounds and compositions, as well as methods of preparation and treatment.

BACKGROUND

Corticotropin releasing factor (CRF) is a peptide comprised of 41 amino acids. Vale et al. *Science* (1981) 213:1394. It is secreted by the hypothalamus, serving to coordinate the neuroendocrine response to stress by the hypothalamic-pituitary-adrenal (HPA) axis. Dunn et al. *Brain Res. Rev.* (1990) 15:71. As well as its role at the pituitary gland, CRF has demonstrated broad extrahypothalamic distribution in the central nervous system, producing a wide variety of autonomic, electrophysiological, and behavioral effects consistent with a neurotransmitter or neuromodulator role in the brain. Vale et al. *Rec. Prog. Horm. Res.* (1981) 39:245; Koob et al. *Persp. Behav. Med.* (1985) 2:39. De Souza (1985) 5:3189. CRF has been implicated in the pathophysiology of depression and other affective disorders which, in turn, has led to research of $CRF_1$ antagonists. Arborelius et al. *J. Endocrinol.* (1999) 160:1; Kasckow et al. *Peptides* (2001) 22:845; Nemeroff et al. *Science* (1984) 226:1342; Gilligan et al. *J. Med. Chem.* (2000) 43:1641; Grigoriadis et al. *Curr. Med. Chem.—CNS Agents* (2001) 1:63; Owens et al. *CNS Drugs* (1999) 12:85; Keck et al. *Peptides* (2001) 22:835; Arzt et al. *Trends Pharmacol. Sci.* (2006) 27:531.

Administration of CRF directly to the brain elicits behavioral, physiological, and endocrine responses identical to those observed for an animal exposed to a stressful environment. Accordingly, clinical data suggests that CRF receptor antagonists may be useful in the treatment of the neuropsychiatric disorders manifesting hypersecretion of CRF, and, in particular, may represent novel antidepressant and/or anxiolytic drugs. The first CRF receptor antagonists were peptides. U.S. Pat. No. 4,605,642; Rivier et al., *Science* (1984) 224:889. While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. Because of the physiological significance of CRF, biologically-active, small molecules having significant CRF receptor binding activity are thought to be useful in the treatment of endocrine, psychiatric and neurologic conditions or illnesses, including stress-related disorders in general.

In fact, CRF has been implicated in a variety of diseases to date, as indicated by the following publications. It was reported that elevated concentrations of CRF in the cerebrospinal fluid of patients with major depression compared with healthy individuals; CRF-mRNA levels in the hypothalamus of depressive patients are higher than that of healthy individuals; and CRF receptors in cerebral cortex are reduced in suicide victims; plasma ACTH increase is diminished with administration of CRF to depressive patients. *Journal of Endocrinology* (1999) 160:1. CRF levels in the cerebrospinal fluid of some anxiety patients with obsessive-compulsive disorder, posttraumatic stress disorder or Tourette's syndrome are higher than in that of healthy individuals. *Journal of Endocrinology* (1999) 160:1. Plasma ACTH increase is diminished with administration of CRF to panic disorder patients. *Exp. Clin. Endcrinol. Diabetes* (1997) 105:65. Anxiety behavior has been observed in experimental animals by intracerebral administration of CRF. In addition, anxiety behavior is observed more frequently in CRF overexpressing mice than in normal mice. *Journal of Endocrinology* (1999) 160:1. CRF levels in the locus coeruleus are reduced by administration of anxiolytics. *Exp. Clin. Endocrinol. Diabetes* (1997) 105:65. Also, α-helical CRF(9-41), a peptide CRF antagonist, exhibits an antianxiety action in animal models. *Brain Res.* (1990) 509:80; *Regulatory Peptides* (1987) 18:37; *J. Neurosci.* (1994) 14:2579. Abnormal behavior withdrawal from alcohol or addictive drugs such as cocaine are inhibited by α-helical CRF(9-41), a peptide CRF antagonist *Psychopharmacology* (1991) 103:227.

CRF inhibits sexual behavior in rats. *Nature* (1983) 305: 232. CRF reduces sleep in rats and is thus implicated the involvement in sleep disorder. *Pharmacol. Biochem. Behav.* (1987) 26:699. α-helical CRF(9-41), a peptide CRF antagonist, suppresses brain damage or electroencephalogram disturbances due to brain ischemia or NMDA receptor activation. *TIPS* (1996) 17:166. CRF elicits electroencephalogram and induces convulsions. *Brain Res.* (1983) 278:332. Cerebrospinal CRF levels are elevated in schizophrenic patients compared with healthy individuals. *Am. J. Psychiatry* (1987) 144:873. CRF content in the cerebral cortex is reduced in Alzheimer's disease patients, Parkinson's disease patients and progressive supranuclear palsy patients. *Neurology* (1987) 37, 905. CRF is reduced in the ganglia in Huntington's disease *Neurology* (1987) 37:905; *Brain Res.* (1987) 437:355. In addition, CRF administration has been found to enhance learning and memory in rats. *Exp. Clin. Endcrinol. Diabetes* (1997) 105:65.

CRF content in cerebrospinal fluid are reduced in amyotrophic lateral sclerosis patients. Oversecretion of ACTH and adrenocorticosteroids are exhibited in mice overexpressing CRF, these mice display abnormalities similar to Cushing's syndrome, including muscular atrophy, alopecia, and infertility. *Endocrinology* (1992) 130:3378. Cerebrospinal CRF is elevated in anorexia nervosa patients compared with healthy individuals, and plasma ACTH increase is low with administration of CRF to anorexia nervosa patients; and CRF suppress feeding in experimental animals. *TIPS* (1996) 17:166. Moreover, α-helical CRF(9-41), a peptide CRF antagonist, improves stress-induced hypophagia in animal models. *Brain Res. Bull.* (1986) 17:285. CRF has suppressed body weight gain in hereditary obese animals; a link has been suggested between low CRF levels and obesity syndrome; and the anorexic action and the body weight loss action of serotonin reuptake inhibitors has been possibly mediated by CRF release *TIPS* (1996) 17:166.

CRF acts centrally or peripherally to weaken gastric contraction and reduce gastric emptying *Annals of the New York Academy of Sciences* (1993) 697:233. Furthermore, reduced gastric function induced by abdominal surgery is recovered by α-helical CRF(9-41), a peptide CRF antagonist *Am. J. Physiol.* (1992) 262:G616. CRF promotes secretion of bicarbonate ion in the stomach, thereby lowering gastric acid secretion and suppressing cold restraint stress ulcers. *Am. J. Physiol.* (1990) 258:G152. Also, administration of CRF increases ulcers in non-restraint stress animals. *Life Sci.* (1989) 45:907. CRF suppresses small intestinal transit and promotes large intestinal transit, and defecation is induced. In addition, α-helical CRF(9-41), a peptide CRF antagonist, has a inhibiting action against restraint stress-induced gastric acid secretion, reduced gastric emptying, reduced small intestinal transit and promoted large intestinal transit. *Gastroenterology* (1988) 95:1510. Psychological stress in healthy individuals increases anxiety or sensations of gas and abdominal pain during colonic distension and CRF lowers the discomfort threshold. *Gastroenterol.* (1995) 109:1772; *Neurogastroenterol. Mot.* (1996) 8:9. Irritable bowel syndrome patients experience excessive acceleration of colonic motility with CRF administration compared to healthy individuals *Gut* (1998) 42:845.

Administration of CRF increases blood pressure, heart rate and body temperature, while α-helical CRF(9-41), a peptide CRF antagonist, suppresses stress-induced increases in blood pressure, heart rate and body temperature. *J. Physiol.* (1993) 460:221. CRF production is increased locally in inflammation sites in experimental animals and in the synovial fluid of rheumatic arthritis patients *TIPS* (1996) 17:166. CRF provokes degranulation of mast cells and promotes vascular permeability *Endocrinology* (1998) 139:403. CRF is detected in autoimmune thyroiditis patients *Am. J. Pathol.* (1994) 145:1159. Administration of CRF to experimental autoimmune encephalomyelitis rats has notably suppressed progression of symptoms such as paralysis. *J. Immunol.* (1997) 158:5751. Urocortin (a CRF analogue) has increased growth hormone secretion in a pituitary adenoma culture system from an acromegalia patient. *Endocri. J.* (1997) 44:627. Furthermore, CRF simulates secretion of cytokines such as interleukin-1 and interleukin-2 by leukocytes. *J. Neuroimmunol.* (1989) 23:256; *Neurosci. Lett.* (1990) 120:151. CRF administration and stress both suppress T lymphocyte proliferation and natural killer cell activity. α-helical CRF(9-41), a peptide CRF antagonist, improves the reduced function of these immune cells caused by CRF administration or stress. *Endocrinology* (1991) 128:1329. Breathing is notably increased by administration of CRF. *Eur. J. Pharmacol.* (1990) 182:405. Finally, aggravated breathing and insomnia have been observed as a result of CRF administration to elderly patients under chronic artificial respiration *Acta Endocrinol. Copenh* (1992) 127:200.

Thus, there is a need in the art for CRF antagonists.

SUMMARY

Briefly described, embodiments of this disclosure include compounds as described herein, labeled compounds as described herein, pharmaceutical composition including compounds described herein, methods of imaging, method of forming a compound as described herein, and the like. In particular, embodiments of the disclosure include a series of triamino-pyridine derivatives and labeled triamino-pyridine derivatives, methods of synthesizing these compounds, intermediate compounds, methods of treatment using these compounds, methods of imaging, diagnosing, localizing, monitoring, and/or assessing a condition (e.g., corticotropin releasing factor type-1 ($CRF_1$)) and/or related biological events, using triamino-pyridine derivatives, and the like. In addition, the present disclosure includes compositions (e.g., labeled triamino-pyridine derivatives that are ligands for the $CRF_1$ receptor) used in and methods relating to non-invasive imaging (e.g., positron emission tomography (PET) imaging or SPECT imaging).

One exemplary compound among others, includes: a compound selected from the group consisting of:

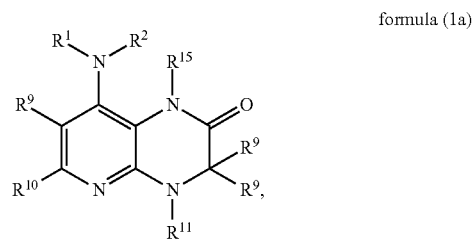

formula (1a)

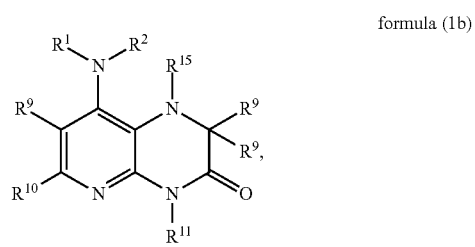

formula (1b)

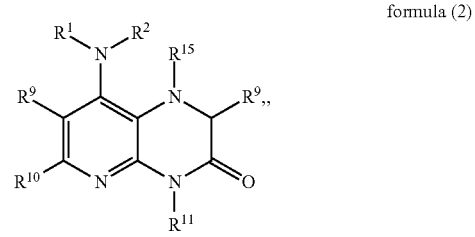

formula (2)

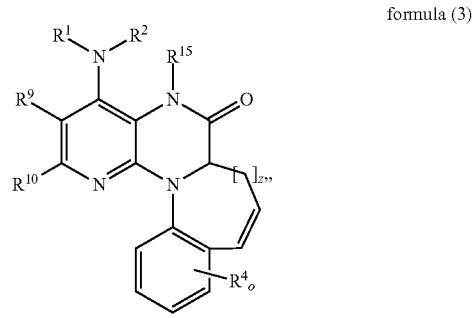

formula (3)

formula (4)

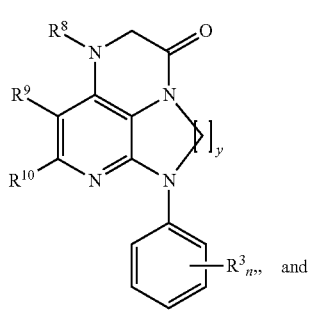

and formula (5)

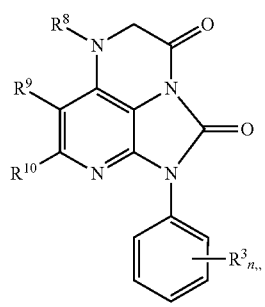

as well as an atropisomer of each of these, a racemic mixture of each of these, and a stereoisomer of each of these, and a pharmaceutically acceptable salt of any of the foregoing, wherein:

$R^1$ is selected from the group consisting of: —H, alkyl, alkenyl, haloalkyl, haloalkenyl,

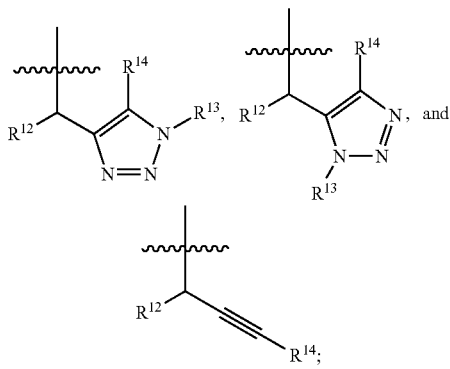

$R^2$ is selected from the group consisting of: —H, alkyl, and haloalkyl;

each $R^3$ is independently selected from the group consisting of: —H, —X, alkyl, haloalkyl, —OH, —O-alkyl, —O-haloalkyl, —NO$_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl, wherein n is 1, 2, or 3 and wherein if n is 2 or 3, each $R^3$ is chosen independently of any other $R^3$;

each of $R^4$, $R^5$, and $R^6$ ($R^5$ and $R^6$ are shown below) are each independently selected from the group consisting of: —H, —X, alkyl, haloalkyl, —OH, —O-alkyl, —O-haloalkyl, and —Sn(alkyl)$_3$, wherein o, p, and q are each independently 1, 2, or 3 and wherein if any of o, p, or q are 2 or 3, each of $R^4$, $R^5$, and $R^6$ are chosen independently of each other and any other $R^4$, $R^5$, and $R^6$;

$R^7$ is selected from the group consisting of: —H and alkyl;

$R^9$ is selected from the group consisting of: —H, alkyl, alkenyl, benzyl, haloalkyl, haloalkenyl, and

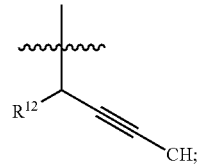

each $R^9$ are independently selected from the group consisting of: —H, halogen, alkyl, haloalkyl, and heteroalkyl, each $R^9$ is chosen independently of any other $R^9$;

$R^{10}$ is selected from the group consisting of: —H, halogen, alkyl, haloalkyl, and heteroalkyl;

$R^{11}$ is selected from the group consisting of:

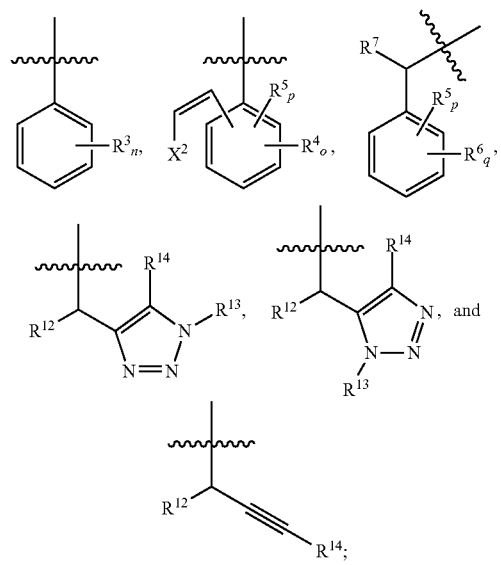

$R^{12}$ is selected from the group consisting of: —H, —OH, —O-alkyl, alkyl, X, haloalkyl, and heteroalkyl;

$R^{13}$ is selected from the group consisting of: —H, alkyl, haloalkyl, and heteroalkyl;

$R^{14}$ is selected from the group consisting of: —H, halogen, alkyl, haloalkyl, and heteroalkyl;

$R^{15}$ is selected from the group consisting of: —H, halogen, alkyl, haloalkyl, and heteroalkyl;

X is a halogen $X^2$ is selected from the group consisting of: —H, alkyl, —X, and —Sn(alkyl)$_3$;

y is selected from the group consisting of: 1 or 2; and z is selected from the group consisting of: 1, 2, or 3;

with the proviso that for formula (I), when $R^{11}$ is

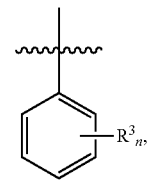

R[1] is butyl and R[2] is ethyl, R[3] is not: 2-Br-4-i-Pr; 2,4-Cl; 2,4,6-CH$_3$; 2-Cl-4-OCH$_3$; or 2-CH$_3$-4-OCH$_3$.

One exemplary compound, among others, includes: a labeled compound of any one of the compounds of described above and herein, where the label is selected from the group consisting of: $^2$H, $^3$H, $^{11}$C, $^{13}$C, $^{14}$C, $^{32}$Cl, $^{13}$N, $^{18}$F, $^{75}$Br, $^{76}$Br, $^{123}$I, $^{124}$I, $^{125}$I, and $^{131}$I.

One exemplary pharmaceutical composition, among others, includes: a composition including any of the compositions described above or herein a pharmaceutically acceptable salt thereof, and a pharmaceutically acceptable carrier. In an embodiment, the compound can be a labeled compound.

One exemplary method of imaging, among others, includes: contacting or administering to a tissue, cells, or a host a labeled compound described above or herein, and imaging the tissue, cells, or host, with an imaging system.

One exemplary method of diagnosing the presence of CRF$_1$ related disease or condition or related biological events in a tissue, cells, or a host, among others, includes: contacting or administering to a tissue, cells, or a host, a labeled compound described above or herein; and imaging the tissue, cells, or a host with an imaging system, wherein the location of the labeled compound corresponds to the location of the CRF$_1$ related disease or condition or related biological events.

One exemplary composition, among others, includes: a compound selected from the group consisting of:

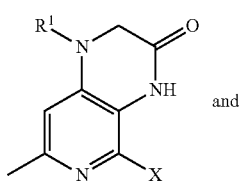

XXVI and

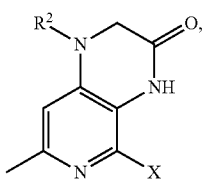

XXVII wherein X is a halogen; R[1] is selected from the group consisting of: —H, alkyl, alkenyl, haloalkyl, haloalkenyl,

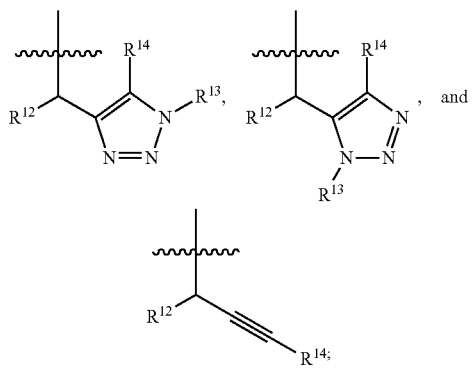

R[2] is selected from the group consisting of: —H, alkyl, and haloalkyl; wherein R[12] is selected from the group consisting of: —H, —OH, —O-alkyl, alkyl, X, haloalkyl, and het-eroalkyl; wherein R[13] is selected from the group consisting of: —H, alkyl, haloalkyl, and heteroalkyl; wherein R[14] is selected from the group consisting of: —H, halogen, alkyl, haloalkyl, and heteroalkyl.

One exemplary composition, among others, includes: reacting

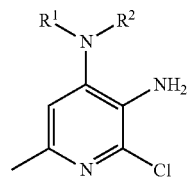

(XXIV)

with

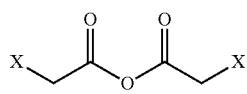

in the presence of a haloacetyl halide or a haloacetic anhydride to form

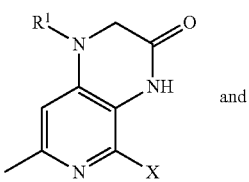

XXVI and

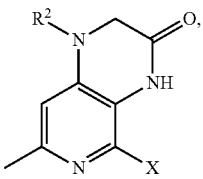

XXVII wherein X is a halogen; R[1] is selected from the group consisting of: —H, alkyl, alkenyl, haloalkyl, haloalkenyl,

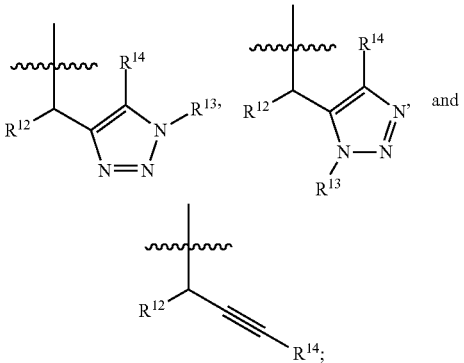

R[2] is selected from the group consisting of: —H, alkyl, and haloalkyl; wherein R[12] is selected from the group consisting of: —H, —OH, —O-alkyl, alkyl, X, haloalkyl, and heteroalkyl; wherein $R^{13}$ is selected from the group consisting of: —H, alkyl, haloalkyl, and heteroalkyl; wherein $R^{14}$ is selected from the group consisting of: —H, halogen, alkyl, haloalkyl, and heteroalkyl.

DRAWINGS

Many aspects of this disclosure can be better understood with reference to the following drawings. The components in the drawings are not necessarily to scale, emphasis instead being placed upon clearly illustrating the principles of the present disclosure.

FIG. 1 depicts an H NMR spectra demonstrating diastereotopic splitting due to atropisomerism.

FIG. 2 depicts a thermal ellipsoid representation of the X-ray crystal structure of compound number 8374.HCl (Table 8, $R^1$=Bu, $R^2$=Et, $R^6$=H, $R^7$=H).

FIG. 3 depicts a thermal ellipsoid representation of the X-ray crystal structure of XXXII.

FIG. 4 depicts a thermal ellipsoid representation of the X-ray crystal structure of XXXIII.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Ratios, concentrations, amounts, and other numerical data may be expressed herein in a range format. Such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. For illustration purposes only, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions:

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, "alkyl" or "alkyl group" refers to a saturated aliphatic hydrocarbon radical which may be straight or branched, having 1 to 20 carbon atoms, wherein the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like.

As used herein, "alkenyl" or "alkenyl group" refers to an aliphatic hydrocarbon radical which may be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

As used herein, "halo", "halogen", or "halogen radical" refers to a fluorine, chlorine, bromine, and iodine radicals. Further, when used in compound words, such as "haloalkyl" or "haloalkenyl", "halo" refers to an alkyl or alkenyl radical in which one or more hydrogens are substituted by halogen radicals.

As used herein, "heteroalkyl" refers to an alkyl group as defined above, in which one or more carbon atoms are substituted by nitrogen, oxygen, phosphorus, or sulfur atoms.

Examples of heteroalkyl groups include, but are not limited to, ethoxymethyl, cyano, 2,3-dioxyethyl, and the like.

The term "unit dosage form," as used herein, refers to physically discrete units suitable as unitary dosages for human and/or animal subjects, each unit containing a predetermined quantity of a compound (e.g., an anti-viral compound, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the agent (which may be referred to as a compound, an inhibitory agent, and/or a drug) being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the agents of the disclosure are also contemplated herein.

To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the terms "treatment", "treating", and "treat" are defined as acting upon a disease, disorder, or condition with an agent (e.g., compound described herein) to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of an agent (e.g., compound described herein) to provide a pharmacologic effect, even in the absence of a disease or condition. For example, "treatment" encompasses delivery of an agent that provides for enhanced or desirable effects in the subject (e.g., reduction of disease symptoms, etc.).

As used herein, the terms "prophylactically treat" or "prophylactically treating" refers completely or partially (e.g., about 70% or greater, about 80% or greater, about 90% or greater, about 95% or greater) preventing a disease or symptom thereof and/or may be therapeutic in terms of a partial or complete cure for a disease and/or adverse effect attributable to the disease. The terms "treatment", "treating", and "treat" are distinguishable from the terms "prophylactically treat" or "prophylactically treating" as their definitions disclose and thereby have distinct meanings.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion:

The present disclosure provides compounds including a series of triamino-pyridine derivatives and labeled triamino-pyridine derivatives, methods of synthesizing these compounds, intermediate compounds, methods of treatment using these compounds, methods of imaging, diagnosing, localizing, monitoring, and/or assessing a condition (e.g., corticotropin releasing factor type-1 ($CRF_1$)) and/or related biological events, using triamino-pyridine derivatives, and the like. In addition, the present disclosure includes compositions (e.g., labeled triamino-pyridine derivatives that are ligands for the $CRF_1$ receptor) used in and methods relating to non-invasive imaging (e.g., positron emission tomography (PET) imaging or SPECT imaging).

Embodiments of the present disclosure include methods for imaging tissue, cells, or a host (e.g., a human or a mammal) that includes contacting with or administering to a tissue, cells, or host (e.g., human), labeled triamino-pyridine derivatives, and imaging the tissue with and imaging systems such as a PET imaging system or a SPECT system. The imaging can be performed in vivo and/or in vitro. In particular, embodiments of the present disclosure can be used to image $CRF_1$ related diseases or conditions, or related biological events. In this regard, the tissue, cells, or host can be tested to determine if the tissue, cells, or host include a $CRF_1$ related disease or condition or related biological events, monitor the progression (or regression) of the disease or condition, assess the response of the disease or condition to treatment, and the like. The tissue or cells can be within a host or have been removed from a host.

The $CRF_1$ related diseases or conditions can include the following as well as or related biological events for any of these: depression and depressive symptoms such as major depression, single-episode depression, recurrent depression, depression-induced child abuse and postpartum depression, mania, anxiety, generalized anxiety disorder, panic disorder, phobia, obsessive-compulsive disorder, posttraumatic stress disorder, Tourette's syndrome, autism, affective disorder, dysthymia, bipolar disorder, cyclothymic personality, schizophrenia, Alzheimer's disease, senile dementia of Alzheimer's type, neurodegenerative disease such as Parkinson's disease and Huntington's disease, multi-infarct dementia, senile dementia, anorexia nervosa, hyperphagia and other eating disorders, obesity, diabetes, alcohol dependence, pharmacophilia for drugs such as cocaine, heroin or benzodiazepines, drug or alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neuroses such as cardiac neurosis, gastric neurosis and bladder neurosis, peptic ulcer, irritable bowel syndrome, ulcerative colitis, Crohn's disease, diarrhea, constipation, postoperative ileus, stress-associated gastrointestinal disorders and nervous vomiting, hypertension, cardiovascular disorders such as angina pectoris nervosa, tachycardia, congestive heart failure, hyperventilation syndrome, bronchial asthma, apneusis, sudden infant death syndrome, inflammatory disorders (e.g., rheumatic arthritis, osteoarthritis, lumbago, etc.), pain, allergosis (e.g., atopic dermatitis, eczema, hives, psoriasis, etc.), impotence (erectile dysfunction), menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence, osteoporosis, and the like. It should be noted that embodiments of the present disclosure contemplates that the $CRF_1$ related diseases or conditions can include any one of the above or any combination of two or more of the above.

As noted above, embodiments of the present disclosure include triamino-pyridine derivatives such as optionally substituted 6-methyl-2,3,4-triamino-pyridine derivatives or labeled compounds thereof, designed as ligands for the corticotropin releasing factor type-1 ($CRF_1$) receptor.

An embodiment of the present disclosure includes a compound according to either formula (1a)

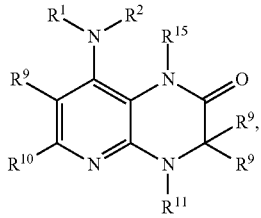

or (1b)

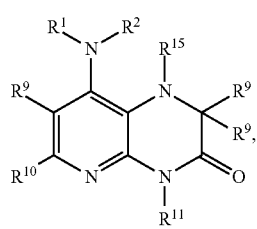

as well as atropisomers, racemic mixtures (racemate), and stereoisomers of any of the foregoing, and pharmaceutically acceptable salts of any of the foregoing, and labeled compounds of any of the foregoing, in which $R^1$ is selected from the group consisting of: —H, alkyl, alkenyl, haloalkyl, haloalkenyl,

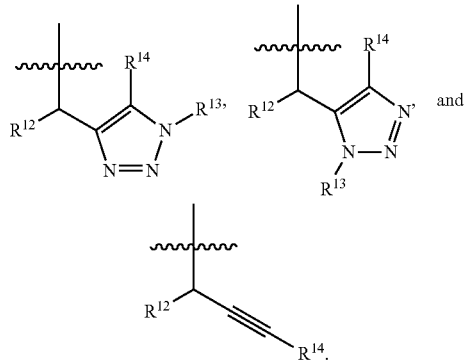

$R^2$ is selected from the group consisting of: —H, alkyl, and haloalkyl. Each of $R^9$ and $R^{10}$ are each independently selected from the group consisting of: —H, halogen, alkyl, haloalkyl, and heteroalkyl. In each instance of $R^9$, each $R^9$ can be independently selected from the other $R^9$ moieties of the formula.

$R^{11}$ is selected from the group consisting of:

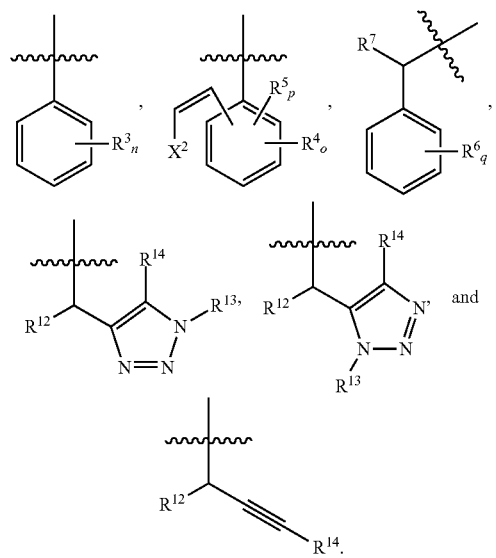

Each $R^3$ is independently selected from the group consisting of: —H, —X, alkyl, haloalkyl, —OH, —O-alkyl, —O-haloalkyl, —NO$_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl. If n is 2 or 3, $R^3$ is chosen independently of any other $R^3$. Each of $R^4$, $R^5$, and $R^6$ are each independently selected from the group consisting of: —H, —X, alkyl, haloalkyl, —OH, —O-alkyl, —O-haloalkyl, and —Sn(alkyl)$_3$, in which n, o, p, and q are each independently 1, 2, or 3. If any of o, p, or q are 2 or 3, each of $R^4$, $R^5$, and $R^6$ are chosen independently of each other and any other $R^4$, $R^5$, and $R^6$. $R^7$ is selected from the group consisting of: —H and alkyl. Each $R^4$ can be independently selected from the other $R^4$ groups. Each $R^5$ can be independently selected from the other $R^5$ groups. Each $R^6$ can be independently selected from the other $R^6$ groups.

$R^{12}$ is selected from the group consisting of: —H, —OH, —O-alkyl, alkyl, X, haloalkyl, and heteroalkyl. $R^{13}$ is selected from the group consisting of: H, alkyl, haloalkyl, and heteroalkyl. X represents a halogen moiety. $X^2$ is selected from the group consisting of: —H, alkyl, —X, and —Sn(alkyl)$_3$. $R^{15}$ is selected from the group consisting of: —H, halogen, alkyl, haloalkyl, and heteroalkyl. $R^{14}$ is selected from the group consisting of: —H, halogen, alkyl, haloalkyl, and heteroalkyl.

An embodiment of the present disclosure includes a compound according to formula (1), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and FCH$_2$—CH=CH—CH$_2$. $R^2$ is selected from the group consisting of: methyl, ethyl, propyl, fluoroethyl, and fluoropropyl. Each $R^3$ is independently selected from the group consisting of: H, methyl, ethyl, propyl, butyl, iodo, chloro, fluoro, bromo, —CH$_2$F, —CHF$_2$, —CF$_3$, —Sn(CH$_3$)$_3$, —OH, —OCH$_3$, —OCF$_3$, —OCH$_2$F, —OCHF$_2$, —OCH$_2$CH$_2$F, —OCH$_2$CH$_2$CH$_2$F, —SH, —SCH$_3$, —SCH$_2$F, —SCH$_2$CH$_2$F, —SCH$_2$CH$_2$CH$_2$F, —SCHF$_2$, —SCF$_3$, —NO$_2$, —NH$_2$, —NHCH$_3$, —N(CH$_3$)$_2$, —N(CH$_3$)$_3$OTf (Tf is triflate), and —N(CH$_3$)$_3$I. $R^9$ is H. $R^{10}$ is methyl. $R^{11}$ is

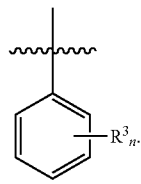

The variable n is 1, 2, or 3. Each $R^3$ can be independently selected from the other $R^3$ groups.

An embodiment of the present disclosure includes a compound according to formula (VI),

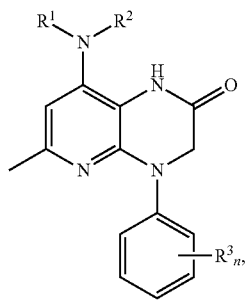

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^3$, and n are as previously defined. Each $R^3$ can be independently selected from the other $R^3$ groups.

An embodiment of the present disclosure includes a compound according to formula (1), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and FCH$_2$—CH=CH—CH$_2$. $R^2$ is selected from the group consisting of: methyl, ethyl, propyl, fluoroethyl, and fluoropropyl. $R^4$ is independently selected from the group consisting of: H, methyl, ethyl, propyl, butyl, iodo, chloro, fluoro, bromo, —CF$_3$, —Sn(CH$_3$)$_3$, —OH, —OCH$_3$, —OCF$_3$, —OCH$_2$F, —OCHF$_2$, —OCH$_2$CH$_2$F, and —OCH$_2$CH$_2$CH$_2$F. In an embodiment $R^5$ is H. $R^9$ is H. $R^{10}$ is methyl. $R^{11}$ is

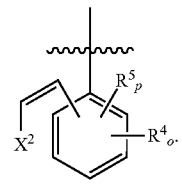

The variable o is 1 or 2. The variable p is 1. $X^2$ is selected from the group consisting of: H, methyl, iodo, chloro, bromo, fluoro, and Sn(CH$_3$)$_3$.

An embodiment of the present disclosure includes a compound according to formula (VII),

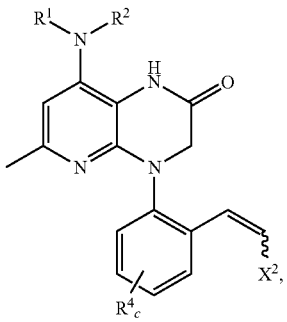

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^4$, o, and $X^2$ are as previously defined. Each $R^4$ can be independently selected from the other $R^4$ groups.

An embodiment of the present disclosure includes a compound according to formula (1), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and FCH$_2$—CH=CH—CH$_2$. $R^2$ is selected from the group consisting of: methyl, ethyl, propyl, fluoroethyl, and fluoropropyl. $R^{11}$ is

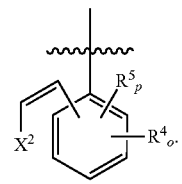

$R^9$ is H. $R^{10}$ is methyl. $R^4$ is H. $R^5$ is independently selected from the group consisting of: H, methyl, ethyl, propyl, butyl, iodo, chloro, fluoro, bromo, —$CF_3$, —$Sn(CH_3)_3$, —OH, —$OCH_3$, —$OCF_3$, —$OCH_2F$, —$OCHF_2$, —$OCH_2CH_2F$, and —$OCH_2CH_2CH_2F$. Each $R^5$ can be independently selected from the other $R^5$ groups. $X^2$ is selected from the group consisting of: H, methyl, iodo, chloro, bromo, fluoro, and $Sn(CH_3)_3$. The variable o is 1. The variable p is 1 or 2.

An embodiment of the present disclosure includes a compound according to formula (VIII),

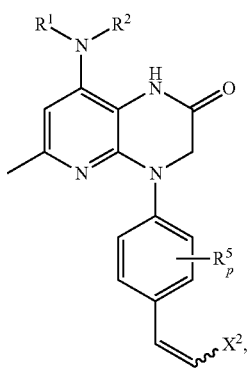

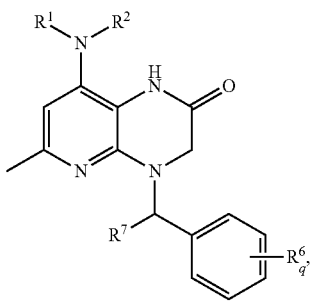

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^6$, $R^7$, and q are as previously defined. Each $R^6$ can be independently selected from the other $R^6$ groups.

An embodiment of the present disclosure includes a compound according to formula (1), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of:

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^5$, o, and $X^2$ are as previously defined. Each $R^5$ can be independently selected from the other $R^5$ groups.

An embodiment of the present disclosure includes a compound according to formula (1), in which $R^1$ is selected from the group consisting of: butyl, propyl, fluoropropyl, fluorobutyl, and $FCH_2$—CH=CH—$CH_2$. $R^2$ is selected from the group consisting of: methyl, ethyl, propyl, fluoroethyl, and fluoropropyl. $R^6$ is independently selected from the group consisting of: H, methyl, ethyl, propyl, butyl, iodo, chloro, fluoro, bromo, —$Sn(CH_3)_3$, —OH, —$OCH_3$, —$OCF_3$, —$OCH_2F$, —$OCHF_2$, —$OCH_2CH_2F$, and —$OCH_2CH_2CH_2F$. $R^7$ is H or methyl. $R^9$ is H. $R^{10}$ is methyl. $R^{11}$ is

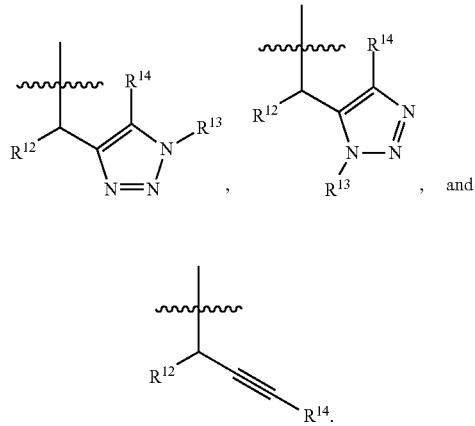

$R^2$ is selected from the group consisting of: methyl, ethyl, propyl, fluoroethyl, and fluoropropyl. $R^9$ is H. $R^{10}$ is methyl. $R^{11}$ is

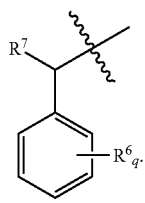

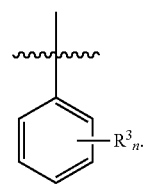

The variable q is 1 or 2. Each $R^6$ can be independently selected from the other $R^3$ groups.

An embodiment of the present disclosure includes a compound according to formula (XIII), $R^{12}$, $R^{13}$, and $R^{14}$ are previously described above. Each $R^3$ can be independently selected from the other $R^3$ groups.

For any of the aforementioned embodiments pertaining to formula (1), when $R^{11}$ is

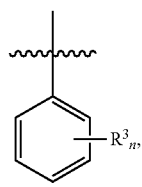

$R^1$ is butyl and $R^2$ is ethyl, $R^3$ is not: 2-Br-4-Pr; 2,4-Cl; 2,4,6-CH$_3$; 2-Cl-4-OCH$_3$; or 2-CH$_3$-4-OCH$_3$. Put alternatively, when $R^{11}$ is

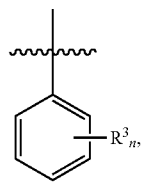

$R^1$ is butyl, and $R^2$ is ethyl, then $R^3$ is not:
(1) bromine at the 2-position and iso-propyl at the 4-position;
(2) chlorine at the 2- and 4-positions;
(3) methyl at the 2-, 4-, and 6-positions;
(4) chlorine at the 2-position and methoxy at the 4-position; or
(5) methyl at the 2-position and methoxy at the 4-position.

An embodiment of the present disclosure includes a compound according to formula (XXXXI),

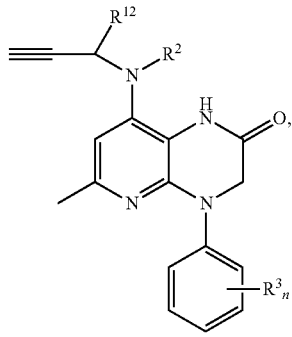

as well as atropisomers, racemic mixtures, and stereoisomers of any of the foregoing, and pharmaceutically acceptable salts of any of the foregoing, and labeled compounds of any of the foregoing, in which $R^2$, $R^3$, $R^{12}$, and n are as previously defined. Each $R^3$ can be independently selected from the other $R^3$ groups.

An embodiment of the present disclosure includes a compound according to formula (XXXXII),

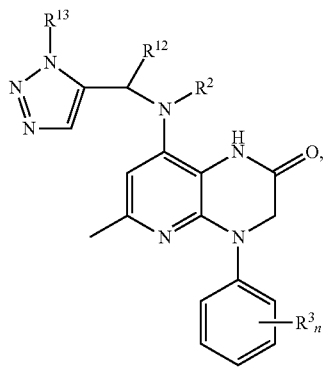

as well as atropisomers, racemic mixtures, and stereoisomers of any of the foregoing, and pharmaceutically acceptable salts of any of the foregoing, and labeled compounds of any of the foregoing, in which $R^2$, $R^3$, $R^{12}$, $R^{13}$, and n are as previously defined. Each $R^3$ can be independently selected from the other $R^3$ groups.

An embodiment of the present disclosure includes a compound according to formula (XXXXIII),

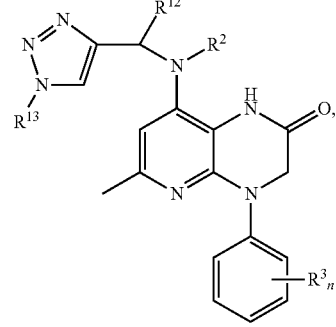

as well as atropisomers, racemic mixtures, and stereoisomers of any of the foregoing, and pharmaceutically acceptable salts of any of the foregoing, and labeled compounds of any of the foregoing, in which $R^2$, $R^3$, $R^{12}$, $R^{13}$, and n are as previously defined. Each $R^3$ can be independently selected from the other $R^3$ groups.

An embodiment of the present disclosure includes a compound according to formula (1), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and FCH$_2$—CH=CH—CH$_2$. $R^2$ is selected from the group consisting of: methyl, ethyl, propyl, fluoroethyl, and fluoropropyl. $R^{11}$ is selected from the group consisting of:

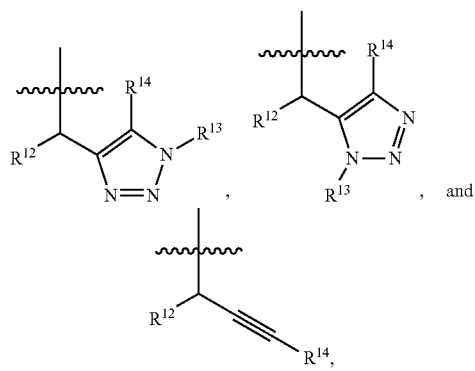

where $R^{12}$, $R^{13}$, and $R^{14}$ are as previously defined.

An embodiment of the present disclosure includes a compound according to formula (XXXVIII),

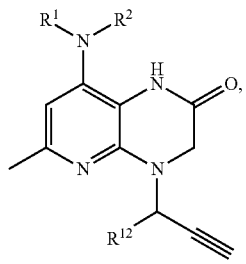

as well as atropisomers, racemic mixtures, and stereoisomers of any of the foregoing, and pharmaceutically acceptable salts of any of the foregoing, and labeled compounds of any of the foregoing, wherein $R^1$, $R^2$, and $R^{12}$ are as previously defined.

An embodiment of the present disclosure includes a compound according to formula (XXXIX),

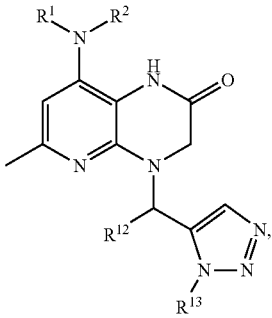

as well as atropisomers, racemic mixtures, and stereoisomers of any of the foregoing, and pharmaceutically acceptable salts of any of the foregoing, and labeled compounds of any of the foregoing, wherein $R^1$, $R^2$, $R^{12}$, and $R^{13}$ are as previously defined.

An embodiment of the present disclosure includes a compound according to formula (XXXIX),

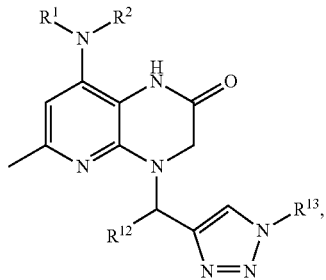

as well as atropisomers, racemic mixtures, and stereoisomers of any of the foregoing, and pharmaceutically acceptable salts of any of the foregoing, and labeled compounds of any of the foregoing, wherein $R^1$, $R^2$, $R^{12}$, and $R^{13}$ are as previously defined.

An embodiment of the present disclosure includes a compound according to formula (2),

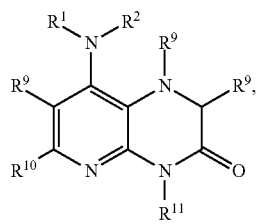

as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: —H, alkyl, alkenyl, haloalkyl, and haloalkenyl. $R^2$ is selected from the group consisting of: —H, alkyl, and haloalkyl. $R^9$ and $R^{10}$ are independently selected from the group consisting of: —H and alkyl. Each $R^9$ can be independently selected from the other $R^9$ moieties. $R^{11}$ is selected from the group consisting of:

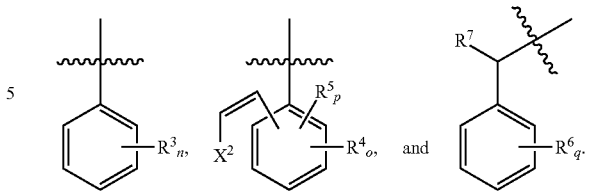

X represents a halogen moiety. $X^2$ is selected from the group consisting of: —H, alkyl, —X, and —Sn(alkyl)$_3$.

Each $R^3$ is independently selected from the group consisting of: —H, —X, alkyl, haloalkyl, —OH, —O-alkyl, —O-haloalkyl, —NO$_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl, in which n is selected from the group consisting of: 1, 2, and 3. Each $R^3$ can be independently selected from the other $R^3$ groups. $R^4$, $R^5$, and $R^6$ are each independently selected from the group consisting of: —H, —X, alkyl, haloalkyl, —OH, —O-alkyl, —O-haloalkyl, and —Sn(alkyl)$_3$, in which o, p, and q are each independently 1, 2, or 3. $R^7$ is selected from the group consisting of: —H and alkyl. Each $R^3$ can be independently selected from the other $R^3$ groups. Each $R^4$ can be independently selected from the other $R^4$ groups. Each $R^5$ can be independently selected from the other $R^5$ groups. Each $R^6$ can be independently selected from the other $R^6$ groups.

An embodiment of the present disclosure includes a compound according to formula (2), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and FCH$_2$—CH=CH—CH$_2$. $R^2$ is selected from the group consisting of: methyl, ethyl, propyl, fluoroethyl, and fluoropropyl. Each $R^3$ is independently selected from the group consisting of: H, methyl, ethyl, propyl, butyl, iodo, chloro, fluoro, bromo, —CF$_3$, —Sn(CH$_3$)$_3$, —OH, —OCH$_3$, —OCF$_3$, —OCH$_2$F, —OCH$_2$CH$_2$F, —OCH$_2$CH$_2$CH$_2$F, —SH, —SCH$_3$, —SCH$_2$F, —SCH$_2$CH$_2$F, —SCH$_2$CH$_2$CH$_2$F, —SCF$_3$, —NO$_2$, —NH$_2$, —NHCH$_3$, —N(CH$_3$)$_2$, —N(CH$_3$)$_3$OTf, and —N(CH$_3$)$_3$I. Each $R^3$ can be independently selected from the other $R^3$ groups. $R^9$ is H. $R^{10}$ is methyl. $R^{11}$ is

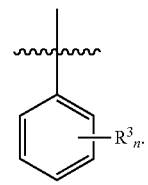

The variable n is 1, 2, or 3. Each $R^3$ can be independently selected from the other $R^3$ groups.

An embodiment of the present disclosure includes a compound according to formula (X),

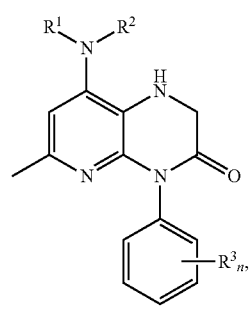

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^3$, and n are as previously defined. Each $R^3$ can be independently selected from the other $R^3$ groups.

An embodiment of the present disclosure includes a compound according to formula (2), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and $FCH_2—CH=CH—CH_2$. $R^2$ is selected from the group consisting of: methyl, ethyl, propyl, fluoroethyl, and fluoropropyl. $R^4$ is independently selected from the group consisting of: H, methyl, ethyl, propyl, butyl, iodo, chloro, fluoro, bromo, $—CF_3$, $—Sn(CH_3)_3$, $—OH$, $—OCH_3$, $—OCF_3$, $—OCH_2F$, $—OCHF_2$, $—OCH_2CH_2F$, and $—OCH_2CH_2CH_2F$. Each $R^4$ can be independently selected from the other $R^4$ groups. $R^5$ is H. $R^9$ is H. $R^{10}$ is methyl. $R^{11}$ is

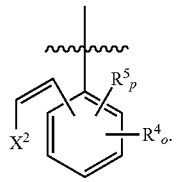

The variable o is 1 or 2. The variable p is 1. $X^2$ is selected from the group consisting of: H, methyl, iodo, chloro, bromo, fluoro, and $Sn(CH_3)_3$.

An embodiment of the present disclosure includes a compound according to formula (XI),

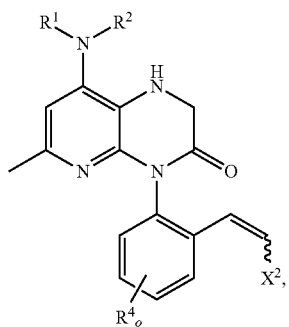

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^4$, o, and $X^2$ are as previously defined. Each $R^4$ can be independently selected from the other $R^4$ groups.

An embodiment of the present disclosure includes a compound according to formula (2), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and $FCH_2—CH=CH—CH_2$. $R^2$ is selected from the group consisting of: methyl, ethyl, propyl, fluoroethyl, and fluoropropyl. $R^{11}$ is

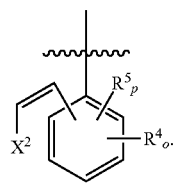

$R^9$ is H. $R^{10}$ is methyl. $R^4$ is H. Each $R^5$ is independently selected from the group consisting of: H, methyl, ethyl, propyl, butyl, iodo, chloro, fluoro, bromo, $—CF_3$, $—Sn(CH_3)_3$, $—OH$, $—OCH_3$, $—OCF_3$, $—OCH_2F$, $—OCHF_2—OCH_2CH_2F$, and $—OCH_2CH_2CH_2F$. Each $R^5$ can be independently selected from the other $R^5$ groups. $X^2$ is selected from the group consisting of: H, methyl, iodo, chloro, bromo, fluoro, and $Sn(CH_3)_3$. The variable o is 1. The variable p is 1 or 2.

An embodiment of the present disclosure includes a compound according to formula (XII),

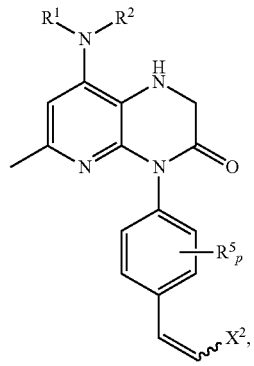

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^5$, o, and $X^2$ are as previously defined. Each $R^5$ can be independently selected from the other $R^5$ groups.

An embodiment of the present disclosure includes a compound according to formula (3),

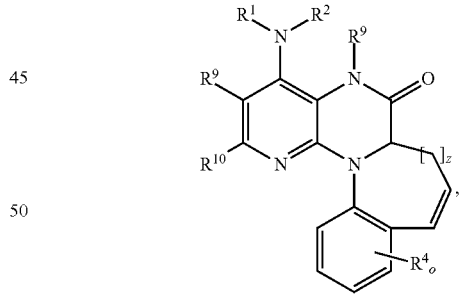

as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: $—H$, alkyl, alkenyl, haloalkyl, and haloalkenyl. $R^2$ is selected from the group consisting of: $—H$, alkyl, and haloalkyl. Each $R^4$ is selected from the group consisting of: $—H$, $—X$, alkyl, haloalkyl, $—OH$, $—O$-alkyl, $—O$-haloalkyl, and $—Sn(alkyl)_3$. Each $R^4$ can be independently selected from the other $R^4$ groups. $R^9$ and $R^{10}$ are independently selected from the group consisting of: $—H$ and alkyl. Each $R^9$ can be independently selected from the other $R^9$ groups. The variables o and z are independently 1, 2, or 3. X represents a halogen moiety.

An embodiment of the present disclosure includes a compound according to formula (3), as well as atropisomers, racemic mixtures, and stereoisomers of any of the foregoing, and pharmaceutically acceptable salts of any of the foregoing, and labeled compounds of any of the foregoing, in which $R^1$ is selected from the group consisting of: butyl, propyl, fluoropropyl, fluorobutyl, and $FCH_2$—$CH$=$CH$—$CH_2$. $R^2$ is selected from the group consisting of: methyl, ethyl, propyl, fluoroethyl, and fluoropropyl. $R^4$ is independently selected from the group consisting of: H, methyl, ethyl, propyl, butyl, iodo, chloro, fluoro, bromo, —$CF_3$, —OH, —$OCH_3$, —$OCF_3$, —$OCH_2F$, —$OCHF_2$, —$OCH_2CH_2F$, and —$OCH_2CH_2CH_2F$. $R^9$ is H. $R^{10}$ is methyl. The variable o is 1 or 2. The variable z is 1, 2, or 3.

An embodiment of the present disclosure includes a compound according to formulae (IXa),

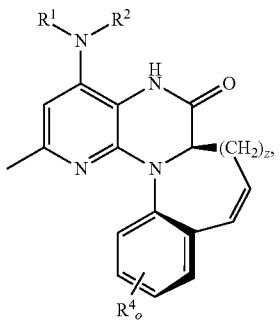

or (IXb),

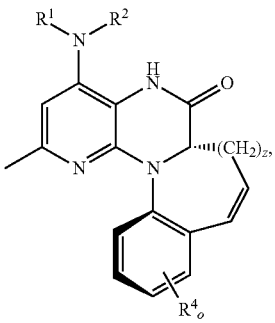

as well as atropisomers, racemic mixtures, and stereoisomers of any of the foregoing, and pharmaceutically acceptable salts of any of the foregoing, and labeled compounds of any of the foregoing, in which $R^1$, $R^2$, $R^4$, o, and z are as previously defined. Each $R^4$ can be independently selected from the other $R^4$ groups.

An embodiment of the present disclosure includes a compound according to formula (4),

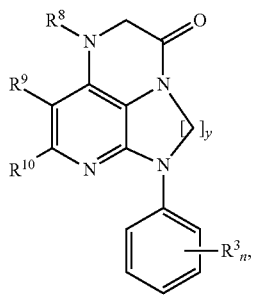

as well as atropisomers, racemic mixtures, and stereoisomers of any of the foregoing, and pharmaceutically acceptable salts of any of the foregoing, and labeled compounds of any of the foregoing, in which $R^3$ is independently selected from the group consisting of: —H, —X, alkyl, haloalkyl, —OH, —O-alkyl, —O-haloalkyl, —$NO_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl, in which n is 1, 2, or 3. Each $R^3$ can be independently selected from the other $R^3$ groups. $R^8$ is selected from the group consisting of: —H, alkyl, alkenyl, haloalkyl, haloalkenyl, and

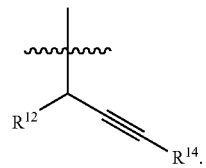

$R^9$ and $R^{10}$ are independently selected from the group consisting of: —H and alkyl. X is a halogen moiety. $R^{12}$ and $R^{14}$ are described above. The variable y is 1 or 2.

An embodiment of the present disclosure includes a compound according to formula (4), as well as atropisomers, racemic mixtures, and stereoisomers of any of the foregoing, and pharmaceutically acceptable salts of any of the foregoing, and labeled compounds of any of the foregoing, in which $R^3$ is independently selected from the group consisting of: H, methyl, ethyl, propyl, butyl, iodo, chloro, fluoro, bromo, —$CH_2F$, —$CHF_2$, —$CF_3$, —$Sn(CH_3)_3$, —OH, —$OCH_3$, —$OCF_3$, —$OCH_2F$, —$OCHF_2$, —$OCH_2CH_2F$, —$OCH_2CH_2CH_2F$, —SH, —$SCH_3$, —$SCH_2F$, —$SCHF_2$, —$SCH_2CH_2F$, —$SCH_2CH_2CH_2F$, —$SCF_3$, —$NO_2$, —$NH_2$, —$NHCH_3$, —$N(CH_3)_2$, —$N(CH_3)_3$OTf, and —$N(CH_3)_3$I. Each $R^3$ can be independently selected from the other $R^3$ groups. $R^8$ is selected from the group consisting of: H, methyl, ethyl, propyl, butyl, fluoromethyl, fluoroethyl, fluoropropyl, fluorobutyl, benzyl, $FCH_2$—$CH$=$CH$—$CH_2$, and

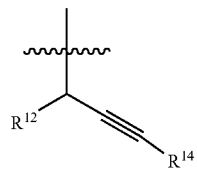

$R^9$ is H. $R^{10}$ is methyl. The variable n is 1, 2, or 3. The variable y is 1 or 2. $R^{12}$ and $R^{14}$ are described above.

An embodiment of the present disclosure includes a compound according to formula (XIV),

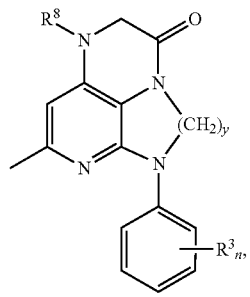

as well as atropisomers, racemic mixtures, and stereoisomers of any of the foregoing, and pharmaceutically acceptable salts of any of the foregoing, and labeled compounds of any of the foregoing, in which $R^3$, $R^8$, n, and y are as previously defined. Each $R^3$ can be independently selected from the other $R^3$ groups.

An embodiment of the present disclosure includes a compound according to formula (5),

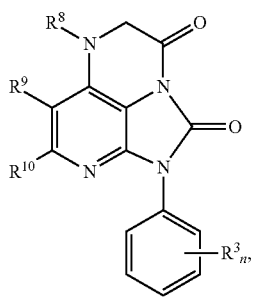

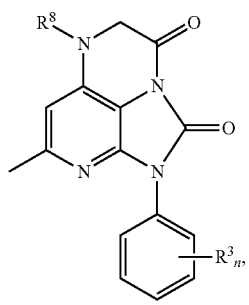

as well as atropisomers, racemic mixtures, and stereoisomers of any of the foregoing, and pharmaceutically acceptable salts of any of the foregoing, and labeled compounds of any of the foregoing, in which $R^3$ is independently selected from the group consisting of: —H, —X, alkyl, haloalkyl, —OH, —O-alkyl, —O-haloalkyl, —NO$_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl, in which n is selected from the group consisting of: 1, 2, and 3. Each $R^3$ can be independently selected from the other $R^3$ groups. $R^8$ is selected from the group consisting of: —H, alkyl, alkenyl, haloalkyl, haloalkenyl, and

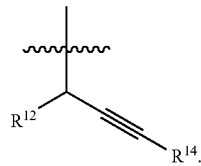

$R^9$ and $R^{10}$ are independently selected from the group consisting of: —H and alkyl. X is a halogen moiety. $R^{12}$ and $R^{14}$ are described above.

An embodiment of the present disclosure includes a compound according to formula (5), as well as atropisomers, racemic mixtures, and stereoisomers of any of the foregoing, and pharmaceutically acceptable salts of any of the foregoing, and labeled compounds of any of the foregoing, in which $R^3$ is independently selected from the group consisting of: H, methyl, ethyl, propyl, butyl, iodo, chloro, fluoro, bromo, —CH$_2$F, —CHF$_2$, —CF$_3$, —Sn(CH$_3$)$_3$, —OH, —OCH$_3$, —OCF$_3$, —OCH$_2$F, —OCHF$_2$, —OCH$_2$CH$_2$F, —OCH$_2$CH$_2$CH$_2$F, —SH, —SCH$_3$, —SCH$_2$F, —SCHF$_2$, —SCH$_2$CH$_2$F, —SCH$_2$CH$_2$CH$_2$F, —SCF$_3$, —NO$_2$, —NH$_2$, —NHCH$_3$, —N(CH$_3$)$_2$, —N(CH$_3$)$_3$OTf, and —N(CH$_3$)$_3$I. Each $R^3$ can be independently selected from the other $R^3$ groups. $R^8$ is selected from the group consisting of: H, methyl, ethyl, propyl, butyl, fluoromethyl, fluoroethyl, fluoropropyl, fluorobutyl, benzyl, FCH$_2$—CH=CH—CH$_2$, and

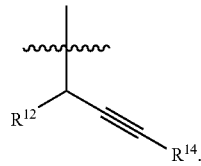

$R^9$ is H. $R^{10}$ is methyl. $R^{12}$ and $R^{14}$ are described above. The variable n is 1, 2, or 3.

An embodiment of the present disclosure includes a compound according to formulae (XV), as well as atropisomers, racemic mixtures, and stereoisomers of any of the foregoing, and pharmaceutically acceptable salts of any of the foregoing, and labeled compounds of any of the foregoing, in which $R^3$, $R^8$, and n are as previously defined. Each $R^3$ can be independently selected from the other $R^3$ groups.

As described above, embodiments of the present disclosure include labeled triamino-pyridine derivatives such as labeled compounds of formulae (1), (2), (3), (4), (5), (VI), (VII), (VIII), (IXa), (IXb), (X), (XI), (XII), (XIII), (XIV), and (XV).

The labeled triamino-pyridine derivatives can be imaged using imaging systems such as positron emission tomography (PET) imaging systems, single photon emission computed tomography (SPECT), and the like. The PET and SPECT imaging systems are known in the art. In an embodiment, the labeled triamino-pyridine derivatives includes a label can be used to detect, image, or otherwise identify the labeled triamino-pyridine derivatives, quantify the amount of labeled triamino-pyridine derivatives, determine the location of the labeled triamino-pyridine derivatives (e.g., in imaging), and combinations thereof.

In an embodiment, the labeled triamino-pyridine derivative can include a radiolabel and/or a compound including a radiolabel. In an embodiment, the label is a radiolabel. In an embodiment, the radiolabel (e.g., non-radiolabels and their radiolabel counterparts) can include, but is not limited to, F-19 (F-18), C-12 (C-11), I-127 (I-125, I-124, I-131, I-123), Cl-36 (Cl-32, Cl-33, Cl-34), and Br-80 (Br-74, Br-75, Br-76, Br-77, Br-78). It should be noted that an alternative way to represent F-18, C-11, and the like, is the following: $^{18}$F and $^{11}$C respectively, and both ways are used herein. In an embodiment, the radiolabel can be $^2$H, $^3$H, $^{11}$C, $^{13}$C, $^{14}$C, $^{32}$Cl, $^{13}$N, $^{18}$F, $^{75}$Br, $^{76}$Br, $^{123}$I, $^{124}$I, $^{125}$I, $^{131}$I. In an embodiment, the PET radiolabel can be $^{18}$F, $^{76}$Br, or $^{124}$I or $^{131}$I or combinations thereof. The SPECT isotope can include, but is not limited to, $^{123}$I, $^{125}$I, $^{131}$I, $^{99}$Tc, $^{111}$In, $^{186/188}$Re, or combinations thereof.

An embodiment of the present disclosure includes stereoisomers of triamino-pyridine derivatives including compounds according to any of the formulae previously described, which are enantiomers, diastereomers, atropisomers, conformers, racemic mixtures (racemate), and cis/trans isomers of these compounds.

An embodiment of the present disclosure includes compositions comprising triamino-pyridine derivatives or labeled triamino-pyridine derivatives, and stereoisomers of any of these, including a compound of formulae (1), (2), (3), (4), (5), (VI), (VII), (VIII), (IXa), (IXb), (X), (XI), (XII), (XIII), (XIV), and (XV) or a pharmaceutically acceptable salt thereof. An embodiment further comprises a pharmaceutically acceptable carrier.

Methods of Use

Embodiments of this disclosure include, but are not limited to: methods of imaging tissue, cells, or a host using labeled triamino-pyridine derivatives; methods of imaging an a CRF$_1$ related disease or condition as described herein, or related biological events; methods of diagnosing a $CRF_1$ related disease or condition or related biological events; methods of monitoring the progress of a $CRF_1$ related disease or condition or related biological events, and the like.

Embodiments of the present disclosure can be used to image, detect, study, monitor, evaluate, assess, and/or screen, $CRF_1$ related disease or condition or related biological events in vivo or in vitro using labeled triamino-pyridine derivatives.

In general, the labeled triamino-pyridine derivatives can be used in imaging $CRF_1$ related diseases or conditions. For example, the labeled triamino-pyridine derivative is provided or administered to a host in an amount effective to result in uptake of the labeled triamino-pyridine derivative. After an appropriate amount of time, the host is then introduced to an appropriate imaging system (e.g., PET system) for a certain amount of time. The cell, tissue, and/or organ that takes-up the labeled triamino-pyridine derivative could be detected using the imaging system.

In an embodiment, the labeled triamino-pyridine derivative may find use both in diagnosing and/or in treating $CRF_1$ related diseases or conditions. In diagnosing the presence of $CRF_1$ related diseases or conditions in a host, the labeled triamino-pyridine derivative is administered to the host in an amount effective to result in uptake of the labeled triamino-pyridine derivative. After administration of the labeled triamino-pyridine derivative, the labeled triamino-pyridine derivatives are detected using an appropriate imaging system. Embodiments of the present disclosure can non-invasively image $CRF_1$ related diseases or conditions throughout an animal or human patient.

Embodiments of the labeled triamino-pyridine derivative can also find use in a host undergoing treatment, to aid in visualizing the response of $CRF_1$ related diseases or conditions to the treatment. In this embodiment, the labeled triamino-pyridine derivative is typically visualized and sized prior to treatment, and periodically during treatment to monitor the $CRF_1$ related diseases or conditions.

Embodiments of the labeled triamino-pyridine derivative also finds use as a screening tool in vitro to select compounds for use in treating $CRF_1$ related diseases or conditions. The $CRF_1$ related diseases or conditions could be easily monitored by incubating the cells with the labeled triamino-pyridine derivative during or after incubation with one or more candidate drugs. The ability of the drug compound to affect the binding of suitably labeled triamino-pyridine derivative will confer potency of the drug.

In addition, embodiments of this disclosure include methods of treating a host using labeled triamino-pyridine derivatives, where the host has or may have a $CRF_1$ related disease or condition as described herein, or related biological events.

It should be noted that the amount effective to result in uptake of triamino-pyridine derivative or labeled triamino-pyridine derivative into the cells or tissue or organ of interest or the host will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and triamino-pyridine derivative and/or the labeled triamino-pyridine derivative of the disclosure. In certain embodiments, the packaged compositions or pharmaceutical composition includes the reaction precursors to be used to generate the triamino-pyridine derivative and/or the labeled triamino-pyridine derivative according to the present disclosure. Other packaged compositions or pharmaceutical compositions provided by the present disclosure further include indicia including at least one of: instructions for using the composition to image a host, or host samples (e.g., cells or tissues), which can be used as an indicator of conditions including, but not limited to, $CRF_1$ related diseases or conditions and biological related events. In embodiments, the kit may include instructions for using the composition or pharmaceutical composition to assess therapeutic effect of a drug protocol administered to a patient, instructions for using the composition to selectively image $CRF^1$ related diseases or conditions, and instructions for using the composition to predict metastatic potential.

Embodiments of this disclosure encompass kits that include, but are not limited to, the triamino-pyridine derivative and/or the labeled triamino-pyridine derivative and directions (written instructions for their use). The components listed above can be tailored to the particular biological event to be monitored as described herein. The kit can further include appropriate buffers and reagents known in the art for administering various combinations of the components listed above to the host cell or host organism. The triamino-pyridine derivative and/or the labeled triamino-pyridine derivative and carrier may be provided in solution or in lyophilized form. When the triamino-pyridine derivative and/or the labeled triamino-pyridine derivative and carrier of the kit are in lyophilized form, the kit may optionally contain a sterile and physiologically acceptable reconstitution medium such as water, saline, buffered saline, and the like.

Pharmaceutical Formulations and Routes of Administration

Embodiments of the present disclosure include one or more triamino-pyridine derivative and/or the labeled triamino-pyridine derivatives identified herein and formulated with one or more pharmaceutically acceptable excipients, diluents, carriers and/or adjuvants. In addition, embodiments of the present disclosure include such triamino-pyridine derivative and/or the labeled triamino-pyridine derivatives formulated with one or more pharmaceutically acceptable auxiliary substances. In particular, one or more triamino-pyridine derivative and/or the labeled triamino-pyridine derivatives can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the triamino-pyridine derivative and/or the labeled triamino-pyridine derivative is administered to the host using any means capable of resulting in the desired effect. Thus, the triamino-pyridine derivative and/or the labeled triamino-pyridine derivative can be incorporated into a variety of formulations for therapeutic administration. For example, the triamino-pyridine derivative and/or the labeled triamino-pyridine derivative can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the triamino-pyridine derivative and/or the labeled triamino-pyridine derivative can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the triamino-pyridine derivative and/or the labeled triamino-pyridine derivative can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the triamino-pyridine derivative and/or the labeled triamino-pyridine derivative can be utilized in aerosol formulation to be administered via inhalation. Embodiments of the triamino-pyridine derivative and/or the labeled triamino-pyridine derivative can be formulated into pressurized acceptable propellants such as dichlorodifluoromethane, propane, nitrogen and the like.

Furthermore, embodiments of the triamino-pyridine derivative and/or the labeled triamino-pyridine derivative can be made into suppositories by mixing with a variety of bases such as emulsifying bases or water-soluble bases. Embodiments of the triamino-pyridine derivative and/or the labeled triamino-pyridine derivative can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the triamino-pyridine derivative and/or the labeled triamino-pyridine derivative in a composition as a solution in sterile water, normal saline or another pharmaceutically acceptable carrier.

Embodiments of the triamino-pyridine derivative and/or the labeled triamino-pyridine derivative can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the triamino-pyridine derivative and/or the labeled triamino-pyridine derivative is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the triamino-pyridine derivative and/or the labeled triamino-pyridine derivative can be accomplished using any of a variety of refillable, pump systems. Pumps provide consistent, controlled release over time. In some embodiments, the triamino-pyridine derivative and/or the labeled triamino-pyridine derivative is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the triamino-pyridine derivative and/or the labeled triamino-pyridine derivative adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the triamino-pyridine derivative and/or the labeled triamino-pyridine derivative may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the triamino-pyridine derivative and/or the labeled triamino-pyridine derivative described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the triamino-pyridine derivative and/or the labeled triamino-pyridine derivative can be administered to a host in one or more doses. Those of skill will readily appreciate that dose levels can vary as a function of the specific triamino-pyridine derivative and/or the labeled triamino-pyridine derivative administered, the severity of the symptoms and the susceptibility of the subject to side effects. Preferred dosages for a given compound are readily determinable by those of skill in the art by a variety of means.

In an embodiment, multiple doses of the triamino-pyridine derivative and/or the labeled triamino-pyridine derivative are administered. The frequency of administration of the triamino-pyridine derivative and/or the labeled triamino-pyridine derivative can vary depending on any of a variety of factors, e.g., severity of the symptoms, and the like. For example, in an embodiment, the triamino-pyridine derivative and/or the labeled triamino-pyridine derivative is administered once per month, twice per month, three times per month, every other week (qow), once per week (qw), twice per week (biw), three times per week (tiw), four times per week, five times per week, six times per week, every other day (god), daily (qd), twice a day (qid), or three times a day (tid). As discussed above, in an embodiment, the triamino-pyridine derivative and/or the labeled triamino-pyridine derivative is administered continuously.

The duration of administration of the triamino-pyridine derivative and/or the labeled triamino-pyridine derivative, e.g., the period of time over which the triamino-pyridine derivative and/or the labeled triamino-pyridine derivative is administered, can vary, depending on any of a variety of factors, e.g., patient response, etc. For example, the triamino-pyridine derivative and/or the labeled triamino-pyridine derivative can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., triamino-pyridine derivative and/or the labeled triamino-pyridine derivative) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., tri-amino-pyridine derivative and/or the labeled triamino-pyridine derivative) can be administered in a single dose or in multiple doses.

Embodiments of the triamino-pyridine derivative and/or the labeled triamino-pyridine derivative can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the triamino-pyridine derivative and/or the labeled triamino-pyridine derivative. Where systemic delivery is desired, administration typically involves invasive or systemically absorbed topical or mucosal administration of pharmaceutical preparations.

The triamino-pyridine derivative and/or the labeled triamino-pyridine derivative can also be delivered to the subject by enteral administration. Enteral routes of administration include, but are not limited to, oral and rectal (e.g., using a suppository) delivery.

Methods of administration of the triamino-pyridine derivative and/or the labeled triamino-pyridine derivative through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

EXAMPLES

Example 1

Compounds disclosed herein can be represented by one of the following general structures VI-XV. The lists of substituents for the $R^1$-$R^8$ and $X^2$ groups are shown in Tables 1-10 and are described above.

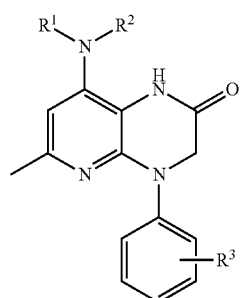

(Table 1)

VI

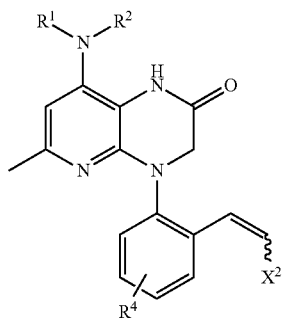

(Table 2)

VII

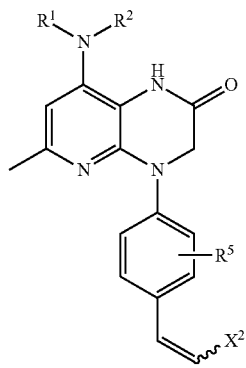

(Table 3)

VIII

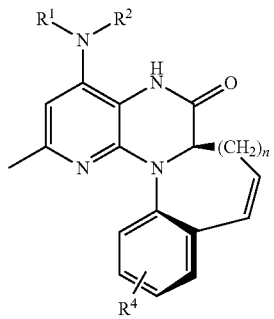

(Table 4)

IXa

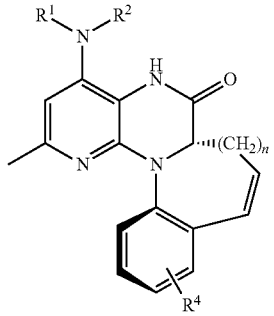

(Table 4)

IXb

X

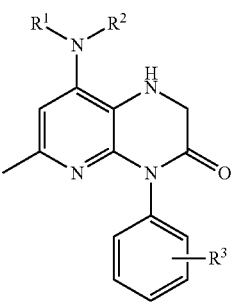

(Table 5)

XI

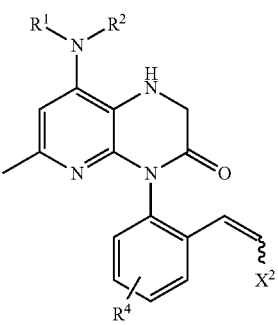

(Table 6)

XII

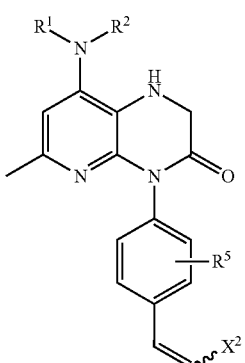

(Table 7)

XIII

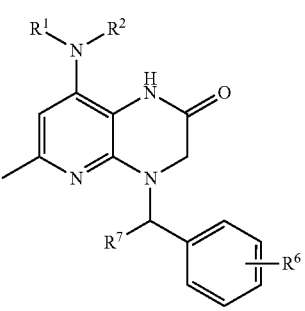

(Table 8)

XIV

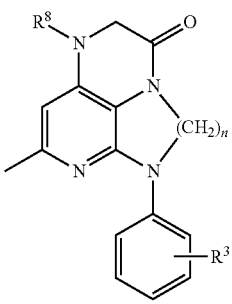

(Table 9)

XV

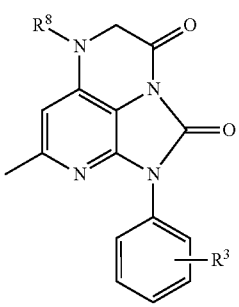

(Table 10)

Example 2

Compounds of general structure VI are shown in Table 1 and may be synthesized by the sequence shown in Scheme 1. The $R^1$—N—$R^2$ groups contained in these structures can be purchased commercially or prepared according to known literature procedures. Chen, et al. *J. Labelled. Cpd. Radiopharm.* (1999) 42:Suppl. 1:S400; Hsin, et al. *Bioorg. Med. Chem. Lett.* (2000) 10:707; Hsin, *J. Labelled Cpd. Radiopharm.* (2000) 43:899; Martarello, et al. *Nuc. Med. Biol.* (2001) 28:187; Dubowchik, et al. *Bioorg. Med. Chem. Lett.* (2004) 14:3147; Singh, et al. *Eur. J. Org. Chem.* (2007) 8:1369.

Compounds which contain a bulky ortho-substituent will have reduced rotation around the bond connecting the aniline ring to the central core and will experience atropisomerism. Eliel, et al. *Stereochemistry of Organic Compounds.* (1994) John Wiley & Sons, Inc.: NY.

Scheme 1

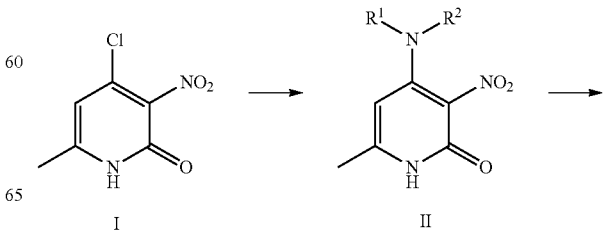

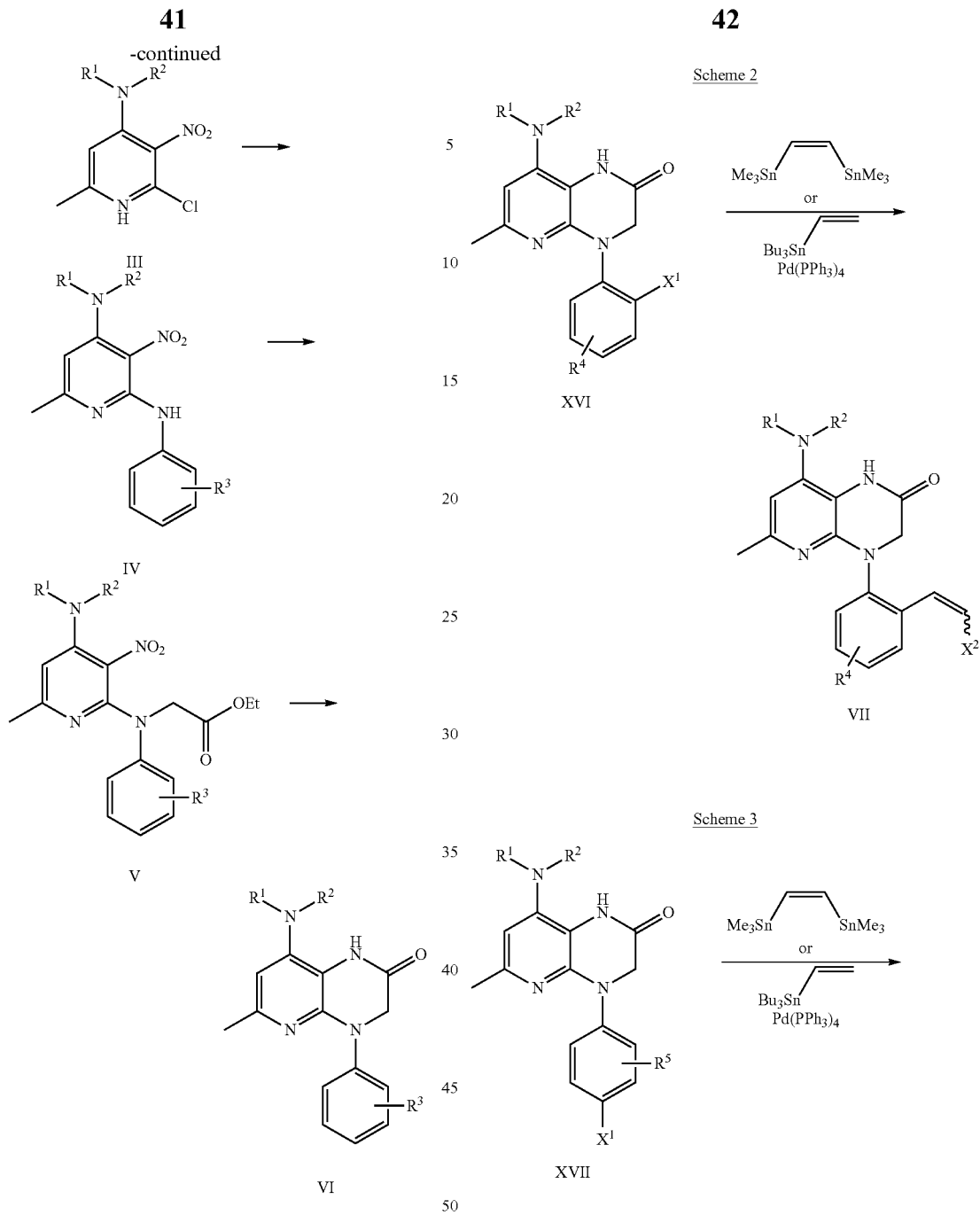

Atropisomerism can be observed by ¹H NMR (FIG. 1) due to diastereotopic splitting of the protons on the α-carbon of the acetamide group. Nelson, *J. Nuclear Magnetic Resonance Spectroscopy* (2003) Pearson Education, Inc.: Upper Saddle River, N.J. Atropisomeric compounds can be separated by chiral HPLC or chiral crystallization. Shi, et al. *J. Chromatogr. A* (2005) 1078:67; Anand, et al. *Tetrahedron* (2007) 63:5236; Erol, et al. *J. Org. Chem.* (2007) 72:2494; Vrudhula, *J. Med. Chem.* (2007) 50:1050.

Example 3

Compounds of general structure VII (Table 2) and VIII (Table 3) may be prepared as shown in Schemes 2 and 3, respectively.

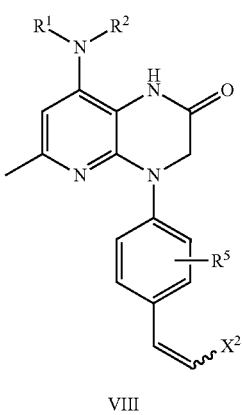

Example 4

Compounds of general structure XVI and XVII (derived from VI) which contain a halogen (Br, I) or other group suitable for coupling in the ortho- or para-positions ($X^1$) can be coupled to (Z)-1,2-bis(trimethylstannyl)ethene or tributyl(vinyl)tin (for $X^2$=H compounds) to give the vinyl compounds ($X^2$=H, $SnMe_3$) and will provide both the cis and trans isomers when $X^2$=$SnMe_3$ (Schemes 2 and 3). Mitchell, et al. *J. Organomet. Chem.* (1986) 304:257; Blough, et al. *J. Med. Chem.* (2002) 45:4029; Stehouwer, et al. *J. Med. Chem.* (2006) 49:6760. The vinyltin compounds ($X^2$=$SnMe_3$) can then be converted to the corresponding vinylhalide compounds ($X^2$=Br, I) by halo-destannylation. Stehouwer, et al. *J. Med. Chem.* (2006) 49:6760. This halo-destannylation reaction can also be used for radiolabeling. (Scheme 15). Goodman, et al. *J. Med. Chem.* (2003) 46:925; Plisson, et al. *J. Med. Chem.* (2004) 47:1122.

Example 5

The aniline ring of XVI can be linked to the central core to give compounds of general structure IX (Table 4) as shown in Scheme 4. Coupling of XVI with (Z)-3-(tri-n-butylstannyl)-2-propen-1-ol, (Z)-4-(tri-n-butylstannyl)-3-buten-1-ol, or (Z)-5-(tri-n-butylstannyl)-4-penten-1-ol, provides the intermediate alcohol XVIII which can then be converted to the tosylate (or other appropriate leaving group) XIX. Leusink, et al. *J. Organometal. Chem.* (1967) 9:285; Jung, et al. *Tetrahedron Lett.* (1982) 23:3851; Miura, et al. *J. Org. Chem.* (2003) 68:8730; Dussault, *J. Am. Chem. Soc.* (1998) 120:7133. Treatment of XIX with a strong base such as a metal hydride or metal amide will generate an enolate which will then displace the leaving group and provide compounds IX. Alternatively, XVI can be treated first with a strong base such as a metal hydride or metal amide to provide an enolate which can then be alkylated with a vinyltin-alkane containing a leaving group (halogen, alkyl sulfonate, etc.) to give XX. Subjection of XX to metal-catalyzed coupling conditions will then provide compounds IX.

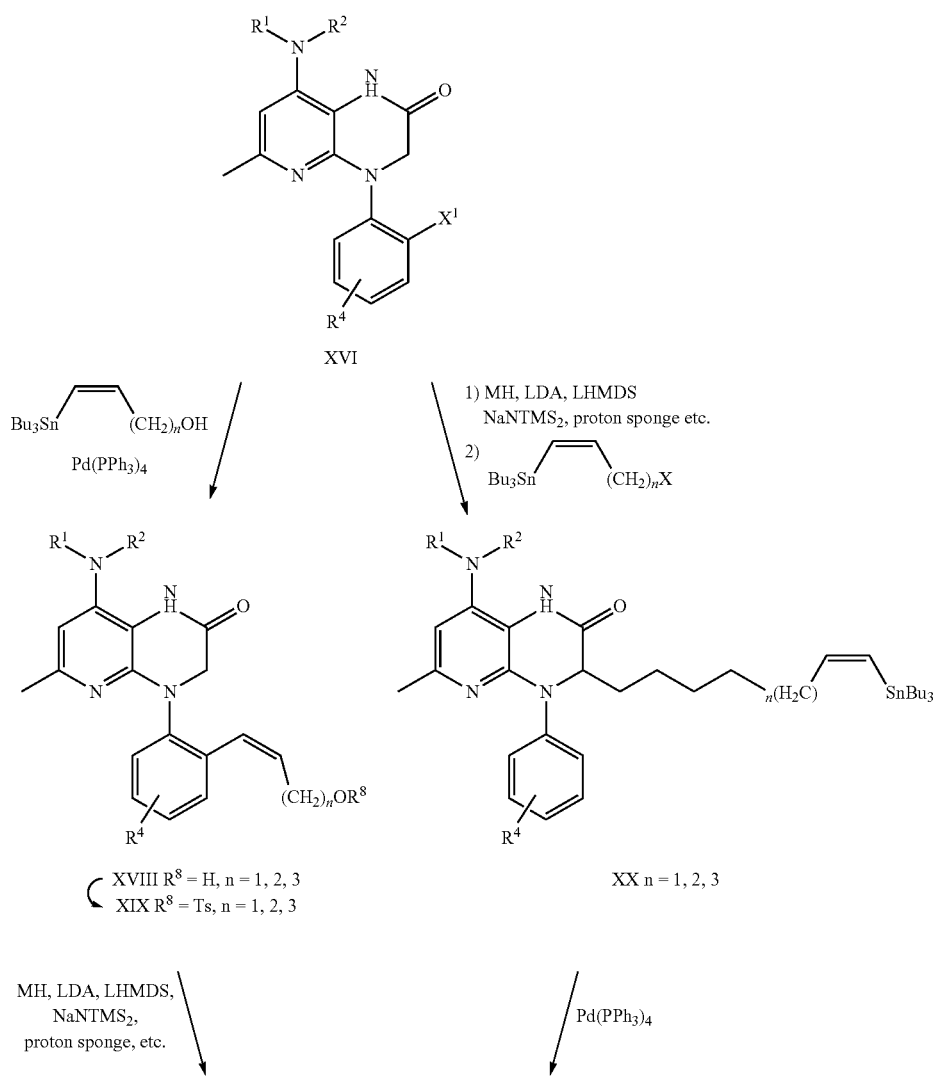

Scheme 4

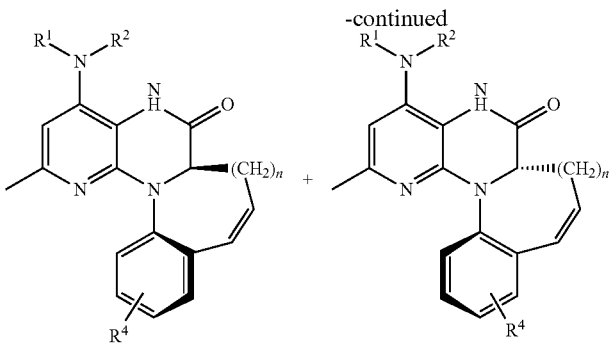

IXa    IXb n = 1, 2, 3

Example 6

Compounds of general structure X (Table 5) can be synthesized as shown in Scheme 5. Reaction of compound IV with a haloacetyl halide (chloroacetyl chloride, bromoacetyl bromide, bromoacetyl chloride, etc.) or a haloacetic anhydride (chloroacetic anhydride, bromoacetic anhydride, iodoacetic anhydride) will afford compound XXI which can then be cyclized under conditions similar to that employed to prepare VI from V (Scheme 1) to afford compounds X. Placing the carbonyl group in this position creates additional steric hindrance between the aniline ring and central core and will, therefore, produce atropisomers as mentioned above.

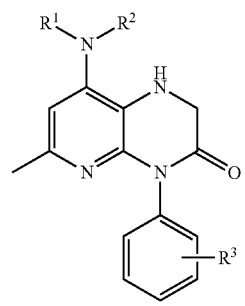

X

Example 7

Compounds of general structure XI (Table 6) and XII (Table 7) are prepared from compounds XXII and XXIII, respectively, by the same method with which compounds VII and VIII are prepared from XVI and XVII, respectively (Schemes 2 and 3).

Scheme 5

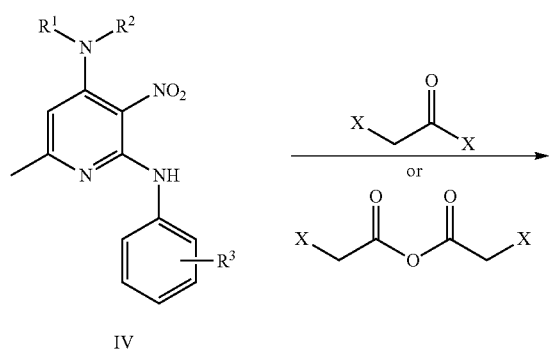

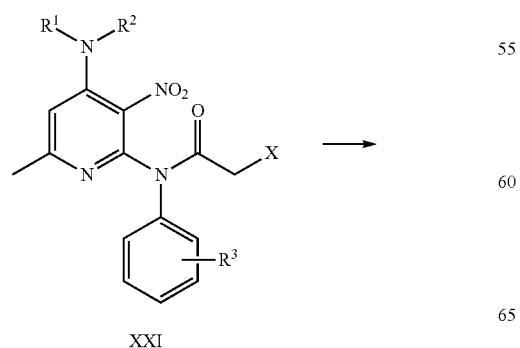

XXI

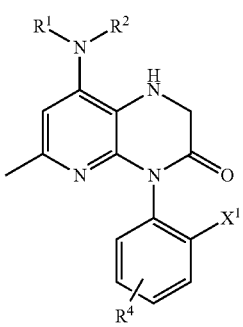

XXII

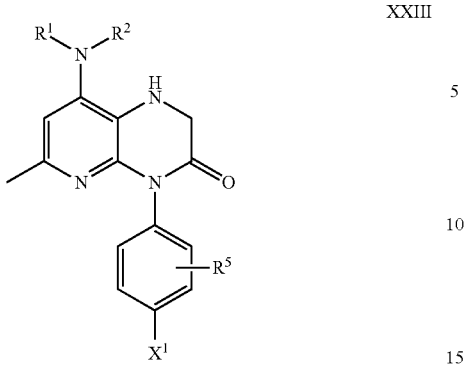

XXIII

Example 8

Compounds of general structure XIII (Table 8) are prepared as shown in Scheme 6. Reduction of III affords XXIV which can be reacted with a haloacetyl halide (chloroacetyl chloride, bromoacetyl bromide, bromoacetyl chloride, etc.) or a haloacetic anhydride (chloroacetic anhydride, bromoacetic anhydride, iodoacetic anhydride) to give compound XXV as well as compounds XXVI and XXVII (see below). Reaction of XXV with a benzyl amine derivative affords XXVIII (and also XXVI and XXVII as side products) which can be cyclized by heating in a high-boiling alcohol (including, but not limited to, n-butanol, isoamyl alcohol, cyclohexanol) in the presence of base to afford XIII. As a specific example of XIII, FIG. 2 shows the X-ray crystal structure of compound 8374.HCl (Table 8, $R^1$=Bu, $R^2$=Et, $R^6$=H, $R^7$=H).

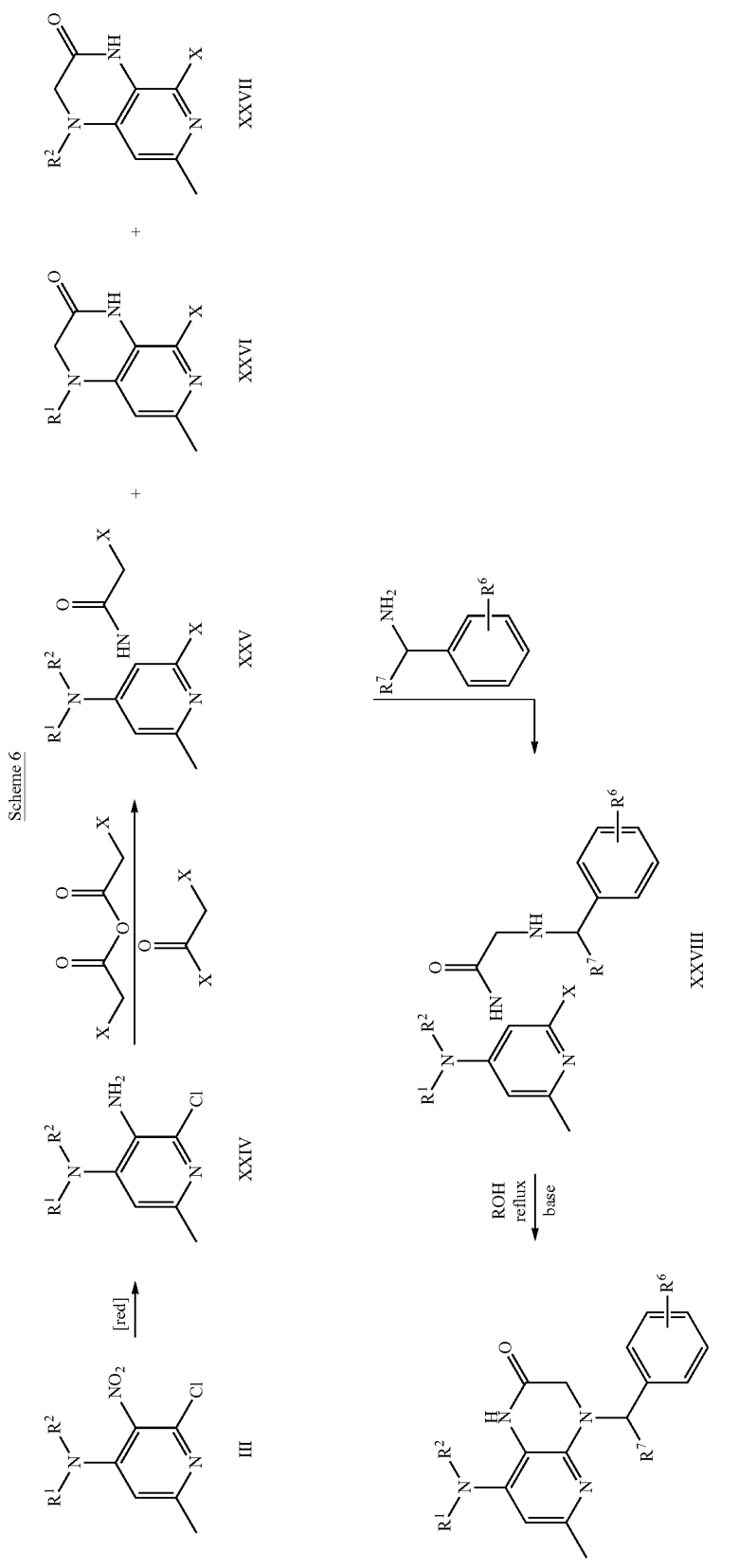

Example 9

Scheme 7 demonstrates a specific example of the synthesis of compounds of type XXVI and XXVII. Reaction of XXIX with chloroacetic anhydride and diisopropylethylamine (i-Pr₂Net) in CHCl₃ affords compound XXX in which the nitrogen lone pair can attack the chloro-acetamide group to give the proposed transient compound XXXI. A chloride anion can then attack either the butyl or ethyl group of XXXI to give compounds XXXIII and XXXII, respectively. The X-ray crystal structures of XXXII and XXXIII are shown in FIGS. 3 and 4, respectively. Compounds XXXII and XXXIII can also be prepared directly by heating XXX in an appropriate solvent in the presence of base.

Scheme 7

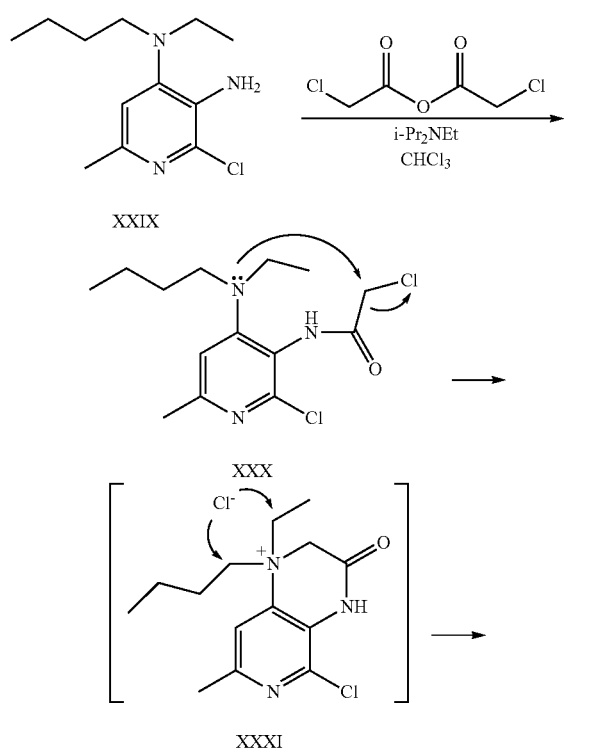

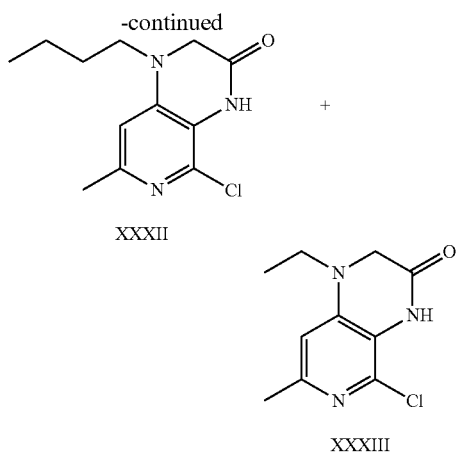

Example 10

Compounds of general structures XIV (Table 9) and XV (Table 10) can be prepared from compounds of type XXVI and XXVII as shown in Scheme 8. Reaction of XXVI/XXVII with aniline derivatives by known literature methods will provide compound XXXIV which can be reacted with a dihaloalkane (CH₂X₂, XCH₂CH₂X, etc.) or other alkane with suitable leaving groups (e.g. alkylsulfonate esters) to afford compound XIV. Guo, et al. *J. Med. Chem.* (2005) 48:5104; Gentile, et al. *Bioorg. Med. Chem. Lett.* (2007) 17:5218.

Example 11

Compound XXXIV can also be reacted with phosgene, triphosgene, diethylcarbonate, etc. to afford compound XV. Compounds XIV and XV can be N-dealkylated (R⁸) to afford compound XXXV. Guo, et al. *J. Med. Chem.* (2005) 48:5104; Beck, et al. *Bioorg. Med. Chem. Lett.* (1999) 9:967; He, et al. *J. Med. Chem.* (2000) 43:449. Alternatively, if R⁸=Bn (obtained by reacting I with N-benzylmethylamine and then carrying the product through the synthetic sequences shown above) the N-benzyl group can be removed by hydrogenolysis on Pd/C to afford XXXV. Compound XXXV can then be N-alkylated to afford additional derivatives or radiolabeled compounds (see below). Guo, et al. *J. Med. Chem.* (2005) 48:5104; Gross, et al. *J. Med. Chem.* (2005) 48:5780.

Scheme 8

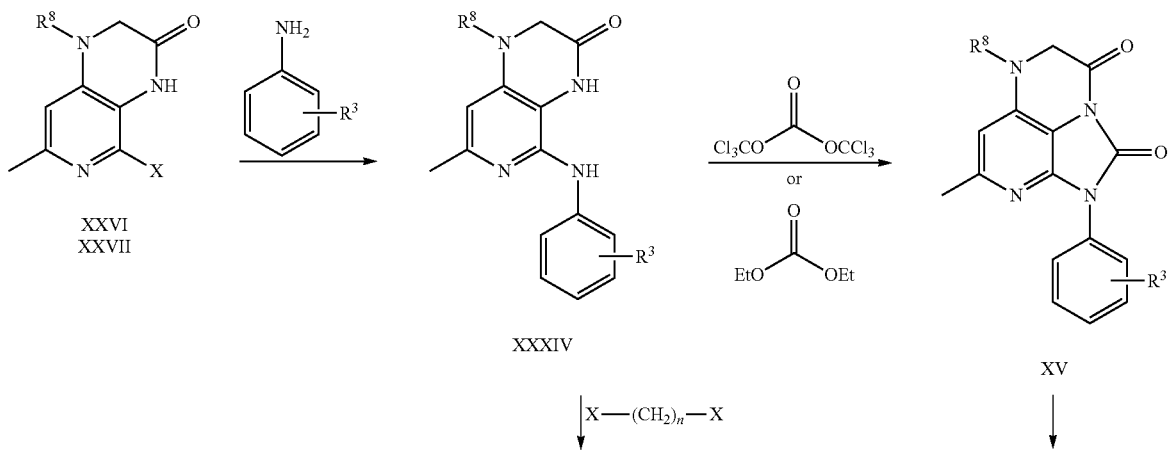

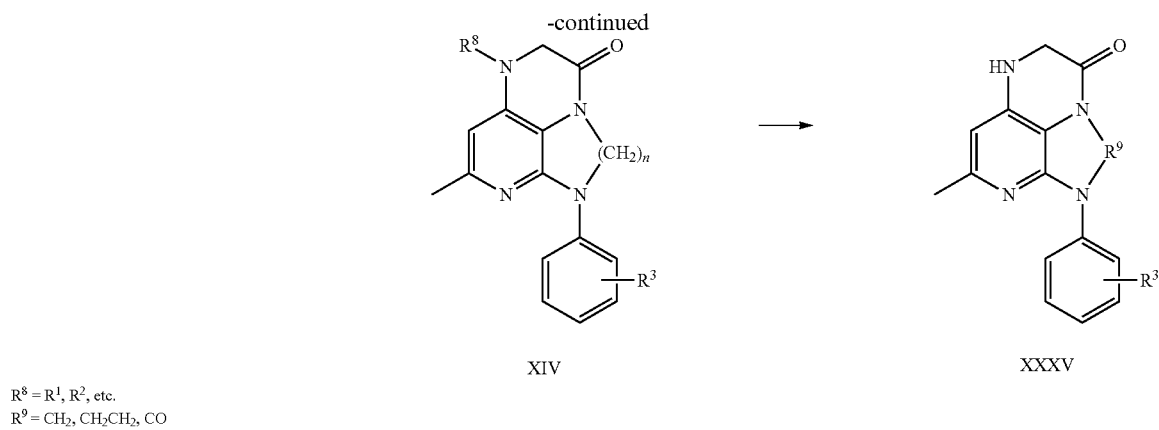

$R^8 = R^1, R^2,$ etc.
$R^9 = CH_2, CH_2CH_2, CO$

Example 12

The radiosynthetic methods for preparing these radiolabeled derivatives are summarized below. Many of the radiosyntheses can be accomplished by nucleophilic $S_N^2$ reactions such as O- and N-alkylations (Schemes 9 and 10) which are common radiolabeling methods reported in the literature. Kumar, at al. *Bioorg. Med. Chem.* (2006) 14:4029; Sullivan, *Nuc. Med. Biol.* (2007) 34:353; Scott, et al. *J. Label. Compd. Radiopharm.* (2007) 50:Supplement 1:S124; Stehouwer, et al. *J. Med. Chem.* (2005) 48:7080. Reaction with [$^{11}$C]methyl iodide or [$^{11}$C]methyl triflate allows for the introduction of a [$^{11}$C]-radiolabel while reaction with a [$^{18}$F]fluoroalkane containing a leaving group (e.g. [$^{18}$F]fluoromethyl tosylate, [$^{18}$F]fluoroethyl tosylate, [$^{18}$F]fluoroethyl brosylate, [$^{18}$F]fluoropropyl brosylate, (E/Z)-[$^{18}$F]-1-fluoro-4-tosyl-2-butene, etc.) allows for the introduction of an [$^{18}$F]-radiolabel. [$^{18}$F]Fluoromethyl derivatives can be prepared from ditosylmethane derivatives as shown in Scheme 11. Reaction of diiodomethane, diiodomethane-D$_2$, or dibromodifluoromethane with silver tosylate will afford ditosylates XXXVI which can then be reacted with $^{18}$F$^-$ to give the [$^{18}$F]-alkylating agents XXXVII. Emmons, et al. *J. Am. Chem. Soc.* (1953) 75:2257; Neal, et al. *J. Label. Compd. Radiopharm.* (2003) 46:Supplement 1:S198. Alternatively, $^{18}$FCH$_2$Br can be prepared from dibromomethane and $^{18}$FCBrF$_2$ can be prepared from dibromodifluoromethane. Eskola, et al. *J. Label. Compd. Radiopharm.* (1999) 42:Supplement 1:S543; Viljanen, *J. Label. Compd. Radiopharm.* 2003, 46, Supplement 1, S219. Compounds XXXVII can then be used as shown in Schemes 9 and 10. Compounds containing the —OCF$_2^{18}$F group can also be prepared from chlorodifluoromethoxy precursors. Hagooly, et al. *Eur. J. Org. Chem.* (2008) 17:2875.

Scheme 9

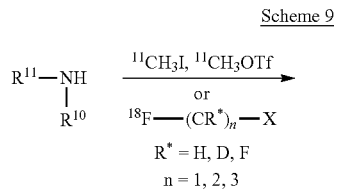

$R^* = H, D, F$
$n = 1, 2, 3$

-continued $R^{11}$—N—$R^{**}$
          |
         $R^{10}$ $R^{**} =$
$^{11}CH_3, ^{11}CD_3, CF_2{}^{18}F,$
$(CH_2)_n{}^{18}F, (CD_2)_n{}^{18}F,$
(E/Z)-$^{18}FCH_2$—CH=CH—CH$_2$
n = 1, 2, 3

Scheme 10

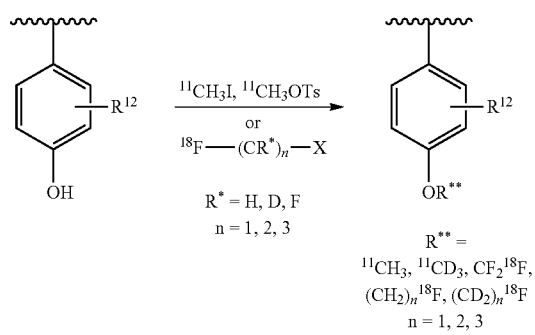

$R^* = H, D, F$
n = 1, 2, 3

$R^{**} =$
$^{11}CH_3, ^{11}CD_3, CF_2{}^{18}F,$
$(CH_2)_n{}^{18}F, (CD_2)_n{}^{18}F$
n = 1, 2, 3

Scheme 11

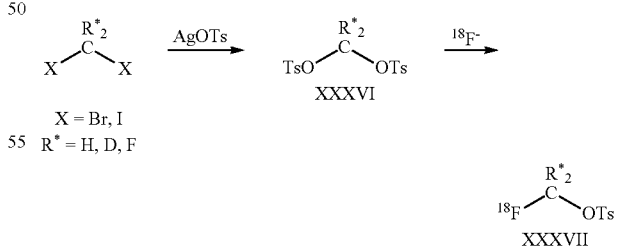

X = Br, I
$R^* = H, D, F$

Example 13

Employing $^{18}$F$^-$ as a nucleophile is another common literature method for radiolabeling. As shown in Scheme 12, displacing a leaving group (halogen, alkyl sulfonate, etc.) from an alkyl group allows for the creation of an [$^{18}$F]alkyl substituent. Kim, et al. *J. Am. Chem. Soc.* (2006) 128:16394; Hsin, et al. *Bioorg. Med. Chem. Lett.* (2000) 10:707; Hsin, et al. *J. Labelled Cpd. Radiopharm.* (2000) 43:899; Martarello, et al. *Nuc. Med. Biol.* (2001) 28:187. [$^{18}$F]Fluorination of an aromatic ring can be achieved by displacing a halide, nitro group, trialkylammonium halide or triflate, or an iodonium salt, as shown in Scheme 13. Oya, et al. *J. Med. Chem.* (2002) 45:4716; Mach, et al. *Nucl. Med. Biol.* (1993) 20:777; Kuhnast, et al. *J. Label. Compd. Radiopharm.* (2008) 51:336; Koser, et al. *J. Org. Chem.* (1980) 45:1542; Koser, et al. *J. Org. Chem.* (1980) 45:1543; Pike, et al. *J. Chem. Soc.*, Perkin Trans. 1 (1999) 245; Ross, et al. *J. Am. Chem. Soc.* (2007) 129:8018.

Scheme 12

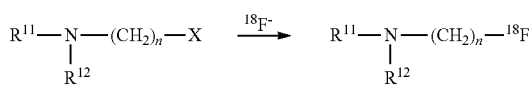

Scheme 13

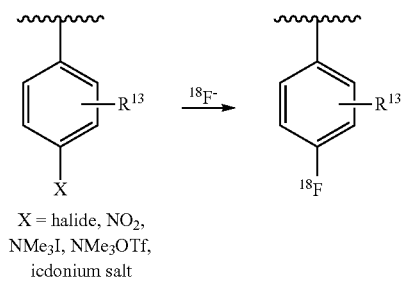

X = halide, NO$_2$,
NMe$_3$I, NMe$_3$OTf,
iodonium salt

Example 14

Coupling reactions with [$^{11}$C]methyl iodide or [$^{11}$C]methyl triflate can be employed to connect a [$^{11}$C]radiolabel to an aromatic ring as shown in Scheme 14. Suzuki, et al. *Chem. Eur. J.* (1997) 3:2039; Björkman, *J. Label. Compd. Radiopharm.* (2000) 43:1327; Karimi, et al. *J. Label. Compd. Radiopharm.* (2002) 45:423. Halodestannylation reactions with a vinyl stannane are a method of preparing radiolabeled vinyl halides and an example is shown in Scheme 15. Tamagnan, *NeuroImage* (2006) 31:T131; Plisson, *J. Med. Chem.* (2004) 47:1122; Goodman, *J. Med. Chem.* (2003) 46:925.

Scheme 14

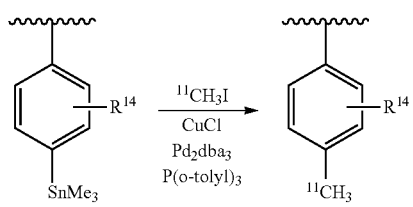

Scheme 15

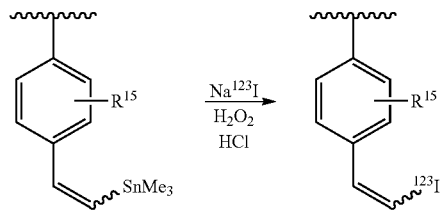

Thus, Schemes 9-15 demonstrate generation of the radiolabeled versions of the compounds listed in Tables 1-10 (excluding the radiolabeling precursors that are listed in those tables) using known literature procedures. Disclosed herein are the radiolabeling precursors (those listed in as well as those not listed in Tables 1-10) that are necessary to prepare these radiolabeled compounds (e.g. R$^1$ or R$^2$=alkyl containing a leaving group) as well as the intermediates that are necessary to prepare these radiolabeling precursors (e.g., R$^1$ or R$^2$=alkyl containing a hydroxyl group for conversion to a leaving group).

Example 15

"Click-chemistry" is the Cu(I)-catalyzed 1,3-dipolar cycloaddition of a terminal alkyne and an azide (Scheme 16) and this method has been used successfully for radio-labeling PET tracers (Schemes 17 and 18). Kolb, et al. *Angew. Chem. Int. Ed.* (2001) 40:2004; Rostovtsev, et al. *Angew. Chem. Int. Ed.* (2002) 41:2596; Kolb, et al. *Drug Discovery Today* (2003) 8:1128; Wang, et al. *Green Chem.* (2008) 10:452; Marik, et al. *Tetrahedron Lett.* (2006) 47:6681; Glaser, et al. *Bioconjugate Chem.* (2007) 18:989; Kuhnast, et al. *J. Label. Compd. Radiopharm.* (2008) 51:336; Smith, et al. *J. Med. Chem.* (2008) 51:8057.

Scheme 16

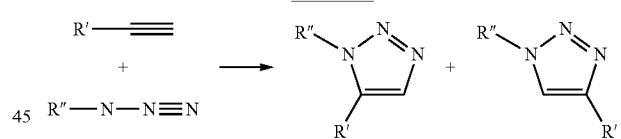

Scheme 17

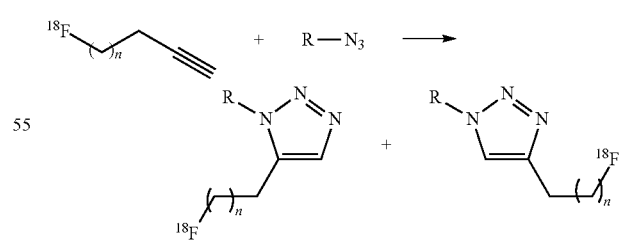

Scheme 18

-continued

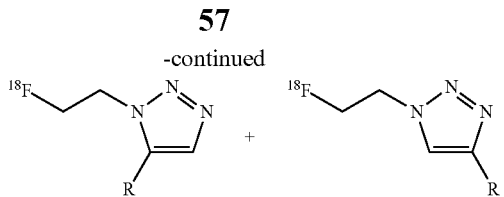

Accordingly, the compounds with general structure XXX-VIII (Scheme 19) can be reacted under click chemistry conditions to give compounds of general structures XXXIX and XXXX, where $R^{12}$=H, OH, O-alkyl, alkyl, halogen, haloalkyl, heteroalkyl; $R^{13}$=H, alkyl, haloalkyl, heteroalkyl; and where $R^1$ and $R^2$ are as defined in Tables 1-8; and the derivatives of compounds VI-XIII where $R^1$=propargyl derivatives (example: compound XXXXI, Scheme 20) and where $R^2$-$R^7$, $X^2$, n= as defined in Tables 1-8; and also the derivatives of compounds XIV and XV where $R^8$=propargyl derivatives, and $R^3$ and n are as defined in Tables 9 and 10. Furthermore, triazole products that can result from performing click-chemistry on these compounds (e.g., compounds XXXXII and XXXXIII).

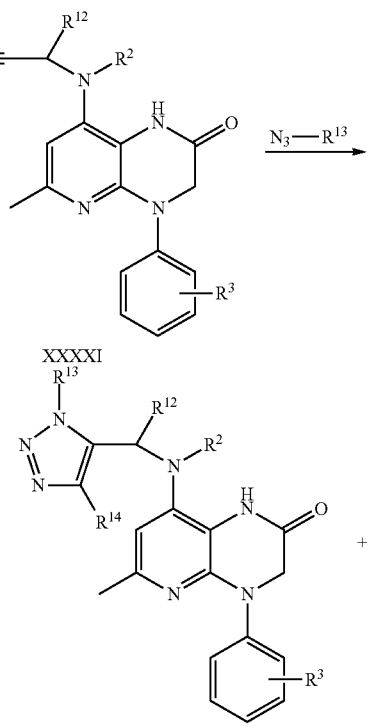

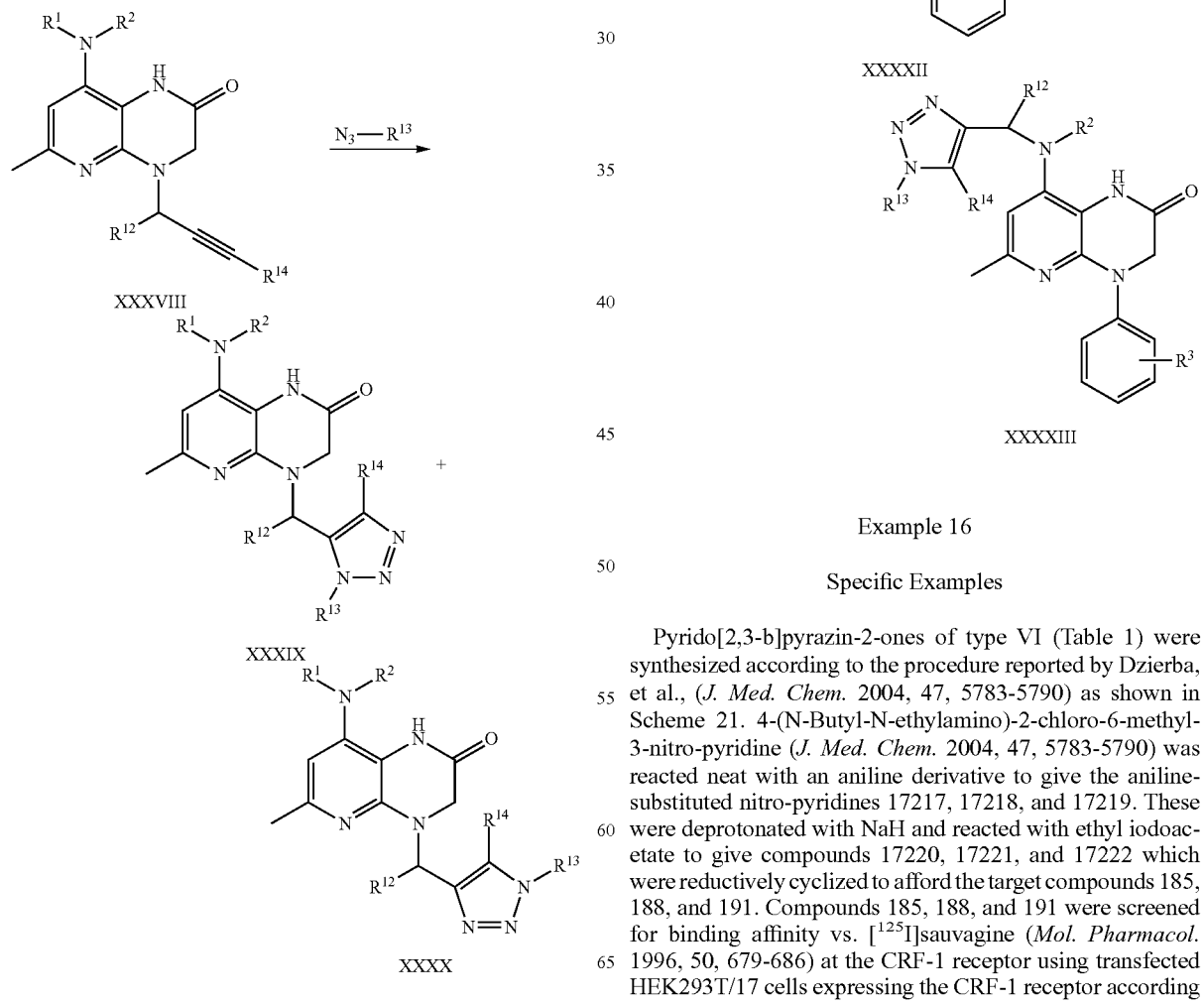

Example 16

Specific Examples

Pyrido[2,3-b]pyrazin-2-ones of type VI (Table 1) were synthesized according to the procedure reported by Dzierba, et al., (*J. Med. Chem.* 2004, 47, 5783-5790) as shown in Scheme 21. 4-(N-Butyl-N-ethylamino)-2-chloro-6-methyl-3-nitro-pyridine (*J. Med. Chem.* 2004, 47, 5783-5790) was reacted neat with an aniline derivative to give the aniline-substituted nitro-pyridines 17217, 17218, and 17219. These were deprotonated with NaH and reacted with ethyl iodoacetate to give compounds 17220, 17221, and 17222 which were reductively cyclized to afford the target compounds 185, 188, and 191. Compounds 185, 188, and 191 were screened for binding affinity vs. [$^{125}$I]sauvagine (*Mol. Pharmacol.* 1996, 50, 679-686) at the CRF-1 receptor using transfected HEK293T/17 cells expressing the CRF-1 receptor according to standard in vitro competitive binding procedures. (*Mol.*

Pharmacol. 2003, 63, 751-765; Peptides 2003, 24, 1881-1897; Peptides 2005, 26, 457-470) The binding affinities of compounds 185, 188, and 191 are shown in Table 11 along with the binding affinities of sauvagine and R121919, (Neuropsychopharmacology 2002, 27, 194-202; J. Med. Chem. 2004, 47, 4787-4798) for comparison. Compounds 185, 188, and 191 all have a high affinity for the CRF-1 receptor, only slightly reduced from that found for R121919, indicating that these compounds are potential antagonists of the CRF-1 receptor and also may potentially be employed as imaging agents.

Scheme 22 shows the conversion of bromo-compound 185 to the trimethylstannyl-compound 190, which was accomplished by reacting 185 with hexamethylditin in the presence of catalytic Pd. Compound 190 can serve as the radiolabeling precursor to prepare [$^{11}$C]191 (Scheme 14). The bulkiness of the trimethylstannyl group of 190 restricts the rotation of the aniline ring resulting in atropisomerism as demonstrated by the diastereotopic proton splitting pattern in the $^1$H NMR spectrum (FIG. 1).

Scheme 21

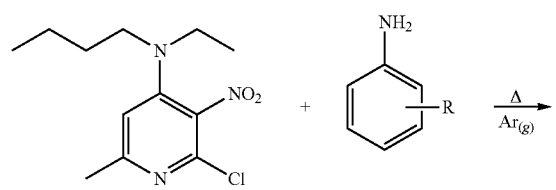

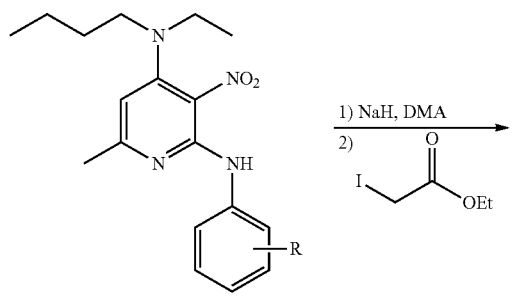

17217 R = 2-Me, 4-Me
17218 R = 2-Br, 4-Me
17219 R = 2-Me, 4-Br

17220 R = 2-Me, 4-Me
17221 R = 2-Br, 4-Me
17222 R = 2-Me, 4-Br

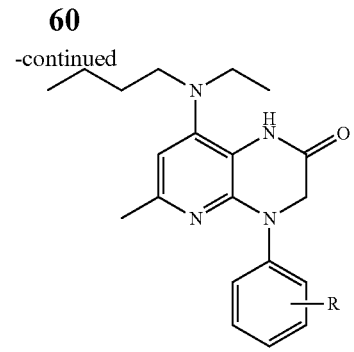

185 R = 2-Br, 4-Me
188 R = 2-Me, 4-Br
191 R = 2-Me, 4-Me

TABLE 11

| CRF-1 Receptor Binding Affinities (vs. [$^{125}$I] Sauvagine). $K_i$ (nM) | | | | |
|---|---|---|---|---|
| Sauvagine | R121919 | 185 | 188 | 191 |
| 0.45 ± 0.05 (n = 5) | 4.1 ± 0.4 (n = 10) | 6.2 ± 1.4 (n = 2) | 5.7 ± 0.3 (n = 2) | 9.1 (n = 1) |

Scheme 22

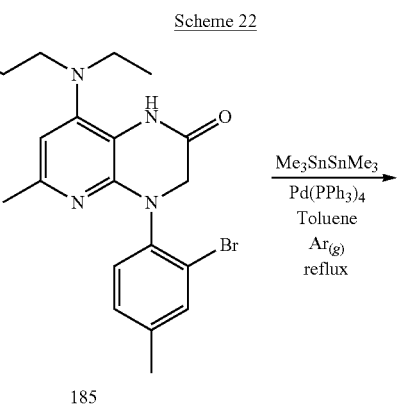

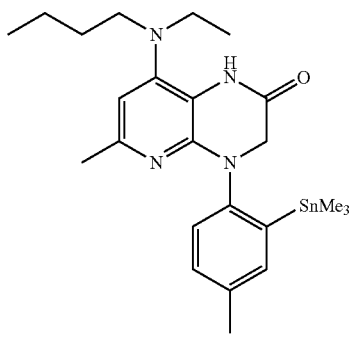

FIG. 1 illustrates the $^1$H NMR spectra (600 MHz, CDCl$_3$) of compounds 191, 185, and 190 demonstrating the existence of atropisomerism due to restricted rotation of the aniline ring.

Compounds of type XIII (Table 8) were synthesized as shown in Scheme 23. 4-(N-Butyl-N-ethylamino)-2-chloro-6-methyl-3-nitro-pyridine (J. Med. Chem. 2004, 47, 5783-5790) was reduced with SnCl$_2$ to give the substituted aminopyridine XXIX. Reaction of XXIX with chloroacetic anhydride afforded chloroacetamido-pyridine XXX along with compounds XXXII and XXXIII as side-products (see Scheme 7). Chloroacetamido-pyridine XXX was then reacted with benzylamine or a benzylamine derivative to give compounds 17223-17227 (along with compounds XXXII and XXXIII as side-products). Compounds 17223-17225 were then cyclized to compounds 8374-8376, respectively, by stirring in refluxing nBuOH in the presence of base, whereas compounds 17226 and 17227 were cyclized to compounds 8404 and 8409, respectively, by stirring in refluxing cyclohexanol in the presence of base. Compound 8374 was converted to the HCl salt by adding HCl/EtOEt to a solution of 8374 in EtOEt. The X-ray crystal structure of 8374.HCl is shown in FIG. 2.

FIG. 2 illustrates the thermal ellipsoid representation of the X-ray crystal structure of 8374.HCl.

TABLE 12

Crystal data and structure refinement for 8374•HCl.

| | |
|---|---|
| Empirical formula | $C_{21}H_{29}ClN_4O$ |
| Formula weight | 388.93 |
| Temperature | 173(2) K |
| Wavelength | 1.54178 Å |
| Crystal system | Monoclinic |
| Space group | P2(1)/c |

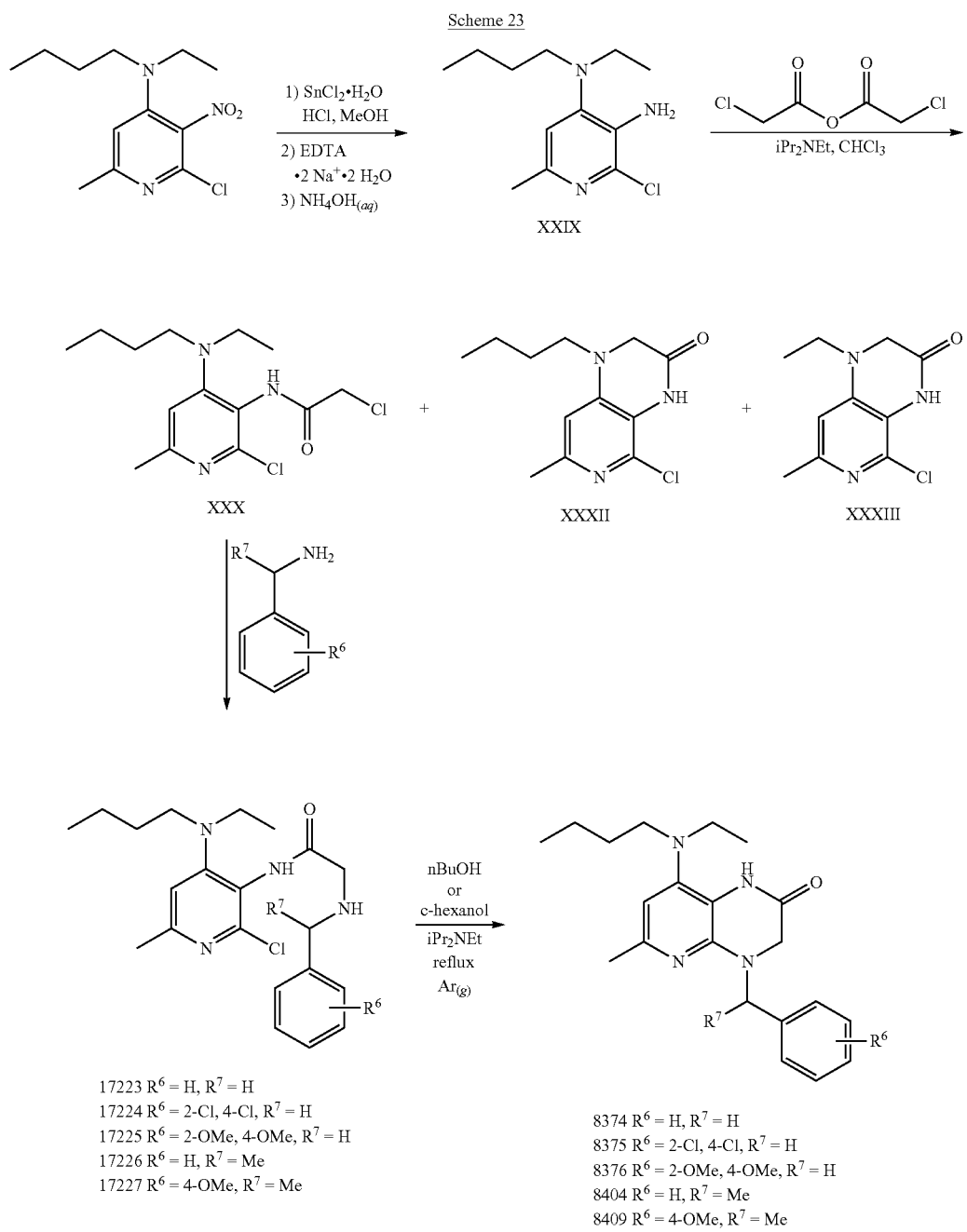

TABLE 12-continued

Crystal data and structure refinement for 8374•HCl.

| | |
|---|---|
| Unit cell dimensions | a = 11.5688(9) Å   α = 90°. |
| | b = 12.7793(11) A   β = 93.995(4)°. |
| | c = 14.2458(9) Å   γ = 90°. |
| Volume | 2101.0(3) Å$^3$ |
| Z | 4 |
| Density (calculated) | 1.230 Mg/m$^3$ |
| Absorption coefficient | 1.741 mm$^{-1}$ |
| F(000) | 832 |
| Crystal size | 0.24 × 0.19 × 0.07 mm$^3$ |
| Theta range for data collection | 3.83 to 65.21°. |
| Index ranges | −12 <= h <= 13, −13 <= k <= 14, |
| | −16 <= l <= 16 |
| Reflections collected | 9738 |
| Independent reflections | 3234 [R(int) = 0.0578] |
| Completeness to theta = 65.21° | 89.8% |
| Absorption correction | Semi-empirical from equivalents |
| Max. and min. transmission | 0.8879 and 0.6801 |
| Refinement method | Full-matrix least-squares on F$^2$ |
| Data/restraints/parameters | 3234/0/256 |
| Goodness-of-fit on F$^2$ | 1.035 |
| Final R indices [I > 2sigma(I)] | R1 = 0.0444, wR2 = 0.1113 |
| R indices (all data) | R1 = 0.0728, wR2 = 0.1331 |
| Extinction coefficient | 0.0008(2) |
| Largest diff. peak and hole | 0.310 and −0.260 e.Å$^{-3}$ |

Compounds XXXII and XXXIII can also be prepared by reacting compound XXIX with bromoacetic anhydride. The X-ray crystal structures of XXXII and XXXIII are shown in FIGS. 3 and 4, respectively, and the crystal data is shown in Tables 13 and 14, respectively.

FIG. 3 illustrates the thermal ellipsoid representation of the X-ray crystal structure of XXXII.

TABLE 13

Crystal data and structure refinement for XXXII.

| | |
|---|---|
| Empirical formula | C12 H14.35 Cl N3 O1.35 |
| Formula weight | 257.66 |
| Temperature | 173(2) K |
| Wavelength | 1.54178 Å |
| Crystal system | Triclinic |
| Space group | P-1 |
| Unit cell dimensions | a = 7.2453(17) Å   α = 69.509(14)°. |
| | b = 9.187(2) Å   β = 86.852(12)°. |
| | c = 9.997(2) Å   γ = 80.726(14)°. |
| Volume | 615.2(3) Å$^3$ |
| Z | 2 |
| Density (calculated) | 1.391 Mg/m$^3$ |
| Absorption coefficient | 2.685 mm$^{-1}$ |
| F(000) | 270 |
| Crystal size | 0.33 × 0.31 × 0.30 mm$^3$ |
| Theta range for data collection | 4.72 to 65.80°. |
| Index ranges | −8 <= h <= 8, −9 <= k <= 10, |
| | −11 <= l <= 11 |
| Reflections collected | 4412 |
| Independent reflections | 1700 [R(int) = 0.0383] |
| Completeness to theta = 65.80° | 79.7% |
| Absorption correction | Semi-empirical from equivalents |
| Max. and min. transmission | 0.4997 and 0.4711 |
| Refinement method | Full-matrix least-squares on F$^2$ |
| Data/restraints/parameters | 1700/0/166 |
| Goodness-of-fit on F$^2$ | 1.235 |
| Final R indices [I > 2sigma(I)] | R1 = 0.0751, wR2 = 0.2179 |
| R indices (all data) | R1 = 0.0949, wR2 = 0.2683 |
| Extinction coefficient | 0.011(4) |
| Largest diff. peak and hole | 0.608 and −0.566e.Å$^{-3}$ |

FIG. 4 illustrates the thermal ellipsoid representation of the X-ray crystal structure of XXXIII.

TABLE 14

Crystal data and structure refinement for XXXIII.

| | |
|---|---|
| Empirical formula | C10 H12 Cl N3 O |
| Formula weight | 225.68 |
| Temperature | 173(2) K |
| Wavelength | 1.54178 Å |
| Crystal system | Monoclinic |
| Space group | P2(1)/n |
| Unit cell dimensions | a = 6.9906(5) Å   α = 90°. |
| | b = 9.0272(7) Å   β = 101.034(4)°. |
| | c = 16.7567(11) Å   γ = 90°. |
| Volume | 1037.89(13) Å$^3$ |
| Z | 4 |
| Density (calculated) | 1.444 Mg/m$^3$ |
| Absorption coefficient | 3.072 mm$^{-1}$ |
| F(000) | 472 |
| Crystal size | 0.39 × 0.28 × 0.04 mm$^3$ |
| Theta range for data collection | 5.38 to 65.54°. |
| Index ranges | −6 <= h <= 7, −9 <= k <= 9, |
| | −17 <= l <= 19 |
| Reflections collected | 4339 |
| Independent reflections | 1476 [R(int) = 0.0235] |
| Completeness to theta = 65.54° | 82.2% |
| Absorption correction | Semi-empirical from equivalents |
| Max. and min. transmission | 0.9001 and 0.3805 |
| Refinement method | Full-matrix least-squares on F$^2$ |
| Data/restraints/parameters | 1476/0/142 |
| Goodness-of-fit on F$^2$ | 1.047 |
| Final R indices [I > 2sigma(I)] | R1 = 0.0327, wR2 = 0.0887 |
| R indices (all data) | R1 = 0.0337, wR2 = 0.0899 |
| Largest diff. peak and hole | 0.206 and −0.217 e.Å$^{-3}$ |

Experimental

General. NMR spectra were obtained on Varian Unity and Inova spectrometers at the specified frequencies. $^1$H chemical shifts are referenced to internal TMS or residual CHCl$_3$ (7.26 ppm) and $^{13}$C chemical shifts are referenced to CDCl$_3$ (77.23 ppm). Solvents were purchased from VWR and had originated from EMD or Burdick & Jackson. Anhydrous solvents (100-mL septum-capped bottles) were purchased from Aldrich. TLC plates used were EMD glass-backed Silica Gel 60 F$_{254}$, 20×20 cm, 250 μm. Preparatory TLC plates used were Analtech Uniplate Silica Gel GF 20×20 cm, 2000 μm. Silica gel used was EMD Silica Gel 60, 40-63 μm. Radial chromatography was performed with a Harrison Research Chromatotron. Semi-preparatory HPLC: Waters XTerra Prep RP$_{18}$, 5 μm, 19×100 mm+guard cartridge (19×10 mm). Analytical HPLC: Waters NovaPak 3.9×150 mm. HRMS was performed by the Emory University Mass Spectrometry Center. X-ray diffraction data collection and structure determination was performed by the Emory University X-ray Crystallography Center.

4-(2-Bromo-4-methylphenyl)-8-(butylethylamino)-6-methyl-3,4-dihydra-1H-pyrido[2,3-b]pyrazin-2-one (185). {(2-Bromo-4-methylphenyl)-[4-(butylethylamino)-6-methyl-3-nitropyridin-2-yl]amino}acetic acid ethyl ester (0.33 g, 6.50× 10$^{-4}$ mol), Fe$^0$ (0.36 g, 6.45 mmol, 9.9 equiv.), conc. HCl$_{(aq)}$ (0.85 mL, 10.2 mmol, 15.7 equiv.), EtOH (15 mL), and boiling chips were heated at reflux under Ar$_{(g)}$ for 16 h. The reaction mixture was cooled to rt, filtered through Celite, the Celite was rinsed with EtOH, and the solvent was removed from the filtrate to give a brown residue. To the residue was added CH$_2$Cl$_2$ (50 mL) and a suspension of EDTA.2 Na$^+$.2 H$_2$O (2.96 g, 7.95 mmol, 1.2 equiv. Fe$^0$) in H$_2$O (50 mL). The mixture was stirred at rt for 35 min, cooled to 0° C., and neutralized with conc. NH$_4$OH$_{(aq)}$. The layers were separated, the aqueous layer was extracted with CH$_2$Cl$_2$ (20 mL×2), and the combined CH$_2$Cl$_2$ layers were dried over MgSO$_4$. The solvent was removed to give a yellow-brown oil that was vacuum flash chromatographed on silica (40 mm h×43 mm i.d.): CH$_2$Cl$_2$ (50 mL), hexanes (50 mL), hexanes/EtOAc/NEt$_3$ v/v/v 90:8:2 (100 mL), 75:20:5 (150 mL) to afford a colorless syrup that was further purified by radial chromatography (2 mm silica): hexanes/EtOAc/NEt$_3$ v/v/v 95:4:1 (200 mL), 90:8:2 (50 mL), 75:20:5 (100 mL) to give 0.23 g (82%) of a sticky, white foam: TLC R$_f$=0.36 (silica, 75:20:5 v/v/v hexanes/EtOAc/NEt$_3$); $^1$H NMR (600 MHz, CDCl$_3$) δ 7.92 (br s, 1 H), 7.48 (s, 1 H), 7.24 (d, 1 H, J=8.4 Hz), 7.18 (d, 1 H, J=8.4 Hz), 6.35 (s, 1 H), 4.38 and 4.32 (2 overlapping br s, 2 H), 2.98 (q, 2 H, J=7.2 Hz), 2.91 (t, 2 H, J=7.2 Hz), 2.37 (s, 3 H), 2.20 (s, 3 H), 1.40 (m, 2 H), 1.29 (sextet, 2 H, J=7.2 Hz), 1.02 (t, 3 H, J=7.2 Hz), 0.90 (t, 3 H, J=7.2 Hz).

8-(Butylethylamino)-4-(2-methyl-4-bromophenyl)-6-methyl-3,4-dihydro-1H-pyrido[2,3-b]pyrazin-2-one (188). {(2-Methyl-4-bromophenyl)-[4-(butylethylamino)-6-methyl-3-nitropyridin-2-yl]amino}acetic acid ethyl ester (0.24 g, 4.73× 10$^{-4}$ mol), Fe$^0$ (0.37 g, 6.63 mmol, 14.0 equiv.), conc. HCl$_{(aq)}$ (0.60 mL, 7.2 mmol, 15.2 equiv.), EtOH (15 mL), and boiling chips were heated at reflux under Ar$_{(g)}$ for 16 h. The reaction mixture was cooled to rt, filtered through Celite, the Celite was rinsed with EtOH, and the solvent was removed from the filtrate to give a brown residue. To the residue was added CH$_2$Cl$_2$ (40 mL) and a suspension of EDTA.2 Na$^+$.2H$_2$O (2.71 g, 7.28 mmol, 1.1 equiv. Fe$^0$) in H$_2$O (40 mL). The mixture was stirred at it for 35 min, cooled to 0° C., and neutralized with conc. NH$_4$OH$_{(aq)}$. The layers were separated, the aqueous layer was extracted with CH$_2$Cl$_2$ (20 mL×2), and the combined CH$_2$Cl$_2$ layers were dried over MgSO$_4$. The solvent was removed to give a colorless syrup that was vacuum flash chromatographed on silica (40 mm h×43 mm i.d.): CH$_2$Cl$_2$ (50 mL), hexanes (50 mL), hexanes/EtOAc/NEt$_3$ v/v/v 95:4:1 (100 mL) 90:8:2 (100 mL), 75:20:5 (150 mL) to afford a colorless syrup that was further purified by radial chromatography (2 mm silica): hexanes/EtOAc/NEt$_3$ v/v/v 95:4:1 (300 mL), 90:8:2 (100 mL) to give 0.16 g (78%) of a white foam: TLC R$_f$=0.31 (silica, 75:20:5 v/v/v hexanes/EtOAc/NEt$_3$); $^1$H NMR (600 MHz, CDCl$_3$) δ 7.89 (br s, 1 H), 7.41 (s, 1 H), 7.38 (d, 1 H, J=8.4 Hz), 7.09 (d, 1 H, J=8.4 Hz), 6.36 (s, 1 H), 4.30 (br s, 2 H), 2.99 (q, 2 H, J=7.2 Hz), 2.92 (t, 2 H, J=7.2 Hz), 2.21 (s, 3 H), 2.07 (s, 3 H), 1.40 (m, 2 H), 1.30 (sextet, 2 H, J=7.2 Hz), 1.02 (t, 3 H, J=7.2 Hz), 0.90 (t, 3 H, J=7.2 Hz).

8-(Butylethylamino)-6-methyl-4-(2-trimethylstannyl-4-methylphenyl)-3,4-dihydro-1H-pyrido[2,3-b]pyrazin-2-one (190). 4-(2-Bromo-4-methylphenyl)-8-(butylethylamino)-6-methyl-3,4-dihydro-1H-pyrido[2,3-b]pyrazin-2-one (0.17 g, 3.94×10$^{-4}$ mol), hexamethylditin (0.50 g, 1.53 mmol, 3.9 equiv.), Pd(PPh$_3$)$_4$ (48 mg, 4.15×10$^{-5}$ mol, 0.1 equiv), and anhydrous toluene (25 mL) were stirred at reflux under Ar$_{(g)}$ for 16 h. The reaction mixture was cooled to rt, poured onto dry silica (40 mm h×43 mm i.d.), and eluted under vacuum: CH$_2$Cl$_2$ (50 mL), hexanes (50 mL), hexanes/EtOAc/NEt$_3$ v/v/v 95:4:1 (100 mL), 90:8:2 (100 mL), 75:20:5 (150 mL) to give an off-white foam (0.16 g). Purification by preparatory-TLC (20×20 cm, 2 mm thickness, 90:8:2 v/v/v hexanes/EtOAc/NEt$_3$×3) afforded recovered starting material (53 mg, 31%) and the trimethylstannyl target compound (86 mg) which was further purified by radial chromatography (1 mm silica): hexanes/EtOAc/NEt$_3$ v/v/v 98:1:1 (180 mL), 95:4:1 (100 mL) to afford a pure fraction (22 mg) and an impure fraction that was further purified by preparatory-TLC (20×20 cm, 2 mm thickness, 90:8:2 v/v/v hexanes/EtOAc/NEt$_3$×2). Total yield—61 mg (30%) as a white solid: TLC R$_f$=0.38 (silica, 75:20:5 v/v/v hexanes/EtOAc/NEt$_3$); $^1$H NMR (600 MHz, CDCl$_3$) δ 7.99 (br s, 1 H), 7.35 (partially resolved td, 1 H, J$_{SnH}$=24.5 Hz), 7.25 (partially resolved d, 1 H, J=1.8 Hz), 7.18 (dt, 1 H, J=8.4 Hz, J$_{SnH}$=12.6 Hz), 6.36 (s, 1 H), 4.47 (d, 1 H, J=16.2 Hz), 4.07 (d, 1 H, J=16.2 Hz), 2.96 and 2.95 (2 overlapping q, 2 H, J=7.2 Hz), 2.91 and 2.88 (2 overlapping t, 2 H, J=7.2 Hz), 2.39 (s, 3 H), 2.18 (s, 3 H), 1.36 (m, 2 H), 1.28 (sextet, 2 H, J=7.2 Hz), 1.00 (t, 3 H, J=7.2 Hz), 0.88 (t, 3 H, J=7.2 Hz), 0.02 (t, 9 H, J=27.0 Hz).

8-(Butylethylamino)-4-(2,4-dimethylphenyl)-6-methyl-3,4-dihydro-1H-pyrido[2,3-b]pyrazin-2-one (191). {(2,4-Dimethylphenyl)-[4-(butylethylamino)-6-methyl-3-nitropyridin-2-yl]amino}acetic acid ethyl ester (63 mg, 1.42×10$^{-4}$ mol), Fe$^0$ (82 mg, 1.47 mmol, 10.4 equiv.), conc. HCl$_{(aq)}$ (0.20 mL, 2.4 mmol, 16.9 equiv.), EtOH (4 mL) and boiling chips were heated at reflux under Ar$_{(g)}$ for 15 h. The reaction mixture was cooled to rt, filtered through Celite, the Celite was rinsed with EtOH, and the solvent was removed from the filtrate to give a brown oil. To the residue was added CH$_2$Cl$_2$ (10 mL) and a suspension of EDTA.2 Na$^+$.2H$_2$O (0.66 g, 1.77 mmol, 1.2 equiv. Fe$^0$) in H$_2$O (10 mL). The mixture was stirred at it for 30 min, cooled to 0° C., and neutralized with conc. NH$_4$OH$_{(aq)}$. The layers were separated, the aqueous layer was extracted with CH$_2$Cl$_2$ (5 mL×2), and the combined CH$_2$Cl$_2$ layers were dried over MgSO$_4$. The solvent was removed to give a blue-green syrup that was purified on silica Sep-Pak Classics (3 in series): CH$_2$Cl$_2$ (4 mL), hexanes (3 mL), hexanes/EtOAc/NEt$_3$ v/v/v 95:4:1 (2 mL×2), 90:8:2 (1 mL×12), 85:12:3 (1 mL×8). The desired fractions were combined and purified again on silica Sep-Pak Classics (3 in series): CH$_2$Cl$_2$ (2 mL), hexanes/EtOAc/NEt$_3$ v/v/v 95:4:1 (1 mL×25), 90:8:2 (5 mL×2) to afford 31 mg (59%) of a colorless syrup that solidified after scrapping and drying under vacuum: TLC R$_f$=0.34 (silica, 75:20:5 v/v/v hexanes/EtOAc/NEt$_3$); $^1$H NMR (600 MHz, CDCl$_3$) δ 7.93 (br s, 1 H), 7.09 (m, 3 H), 6.32 (s, 1 H), 2.11 (2 overlapping br s, 2 H), 2.99 (q, 2 H, J=7.2 Hz), 2.91 (t, 2 H, J=7.2 Hz), 2.35 (s, 3 H), 2.20 (s, 3 H), 2.08 (s, 3 H), 1.40 (m, 2 H), 1.30 (sextet, 2 H, J=7.2 Hz), 1.02 (t, 3 H, J=7.2 Hz), 0.90 (t, 3 H, J=7.2 Hz).

3-Amino-4-(N-butyl-N-ethylamino)-2-chloro-6-methylpyridine (XXIX). 4-(N-Butyl-N-ethylamino)-2-chloro-6-methyl-3-nitro-pyridine (2.26 g, 8.32 mmol) was dissolved in MeOH (150 mL) followed by addition of SnCl$_2$.2H$_2$O (11.63 g, 51.55 mmol, 6.2 equiv.) and then conc. HCl$_{(aq)}$ (11 mL, 0.13 mol, 15.6 equiv.). The reaction mixture was stirred at reflux under Ar$_{(g)}$ for 17 h, cooled, and the solvent was removed to give a faint yellow oil that was dissolved in CH$_2$Cl$_2$ (125 mL) and added to a suspension of EDTA.2 Na$^+$.2H$_2$O (23.87 g, 64.13 mmol, 1.2 equiv. Sn) in H$_2$O (125 mL). The mixture was stirred at rt for 5 min (white precipitate formed) and then cooled to 0° C. (aqueous layer pH=0). The aqueous layer was neutralized to pH=6-7 with conc. NH$_4$OH$_{(aq)}$, the mixture was filtered through Celite, and the layers were separated. The aqueous layer was extracted with CH$_2$Cl$_2$ (25 mL×3), the combined CH$_2$Cl$_2$ layers were dried over MgSO$_4$, and the solvent was removed to give a yellow oil (1.97 g) that was purified by flash column chromatography (45 g silica, 1% MeOH/CH$_2$Cl$_2$-700 mL) to afford a colorless oil (1.34 g, 67%): TLC R$_f$=0.6 (silica, 5% MeOH/CH$_2$Cl$_2$); $^1$H NMR (600 MHz, CDCl$_3$) δ 6.66 (br s, 1 H), 4.00 (br s, 2 H), 3.04 (q, 2 H, J=7.2 Hz), 2.97 (t, 2 H, J=7.5 Hz), 2.39 (s, 3 H), 1.40 (quintet, 2 H, J=7.5 Hz), 1.28 (sextet, 2 H, J=7.5 Hz), 1.01 (t, 3 H, J=7.2 Hz), 0.89 t, 3 H, J=7.5 Hz); $^{13}$C NMR (150 MHz, CDCl$_3$) δ 147.14, 146.49, 136.44, 133.14, 115.50, 50.53, 45.70, 29.29, 23.64, 20.46, 14.07, 12.26; HRMS (ESI) [MH]$^+$Calcd for C$_{12}$H$_{21}$N$_3$$^{35}$Cl: 242.1419. found: 242.1415.

4-(N-Butyl-N-ethylamino)-3-(2-chloroacetamido)-2-chloro-6-methyl-pyridine (XXX). 3-Amino-4-(N-butyl-N-ethylamino)-2-chloro-6-methyl-pyridine (XXIX) (0.46 g, 1.90 mmol), chloroacetic anhydride (1.80 g, 10.53 mmol, 5.5 equiv.), iPr$_2$NEt (0.51 mL, 2.9 mmol, 1.5 equiv.), and CHCl$_3$ (50 mL) were stirred at reflux under Ar$_{(g)}$ for 17 h. The solvent was removed to give a yellow-brown oil that was dried under vacuum (2.67 g) and then purified by vacuum flash chromatography on silica (12.5 cm h×4 cm i.d.): CH$_2$Cl$_2$ (100 mL), hexanes (50 mL), hexanes/EtOAc/NEt$_3$ v/v/v 75:20:5 (500 mL), 50:45:5 (400 mL) to afford an off-white solid (0.54 g, 89%): TLC R$_f$=0.35 (silica, 50:45:5 v/v/v hexanes/EtOAc/NEt$_3$); $^1$H NMR (600 MHz, CDCl$_3$) δ 7.80 (s, 1 H), 6.54 (s, 1 H), 4.23 (s, 2 H), 3.24 (q, 2 H, J=7.2 Hz), 3.15 (t, 2 H, J=7.2 Hz) 2.42 (s, 3 H), 1.51 (m, 2 H), 1.30 (sextet, 2 H, J=7.5 Hz), 1.14 (t, 3 H, J=7.2 Hz), 0.93 (t, 3 H, J=7.5 Hz); $^{13}$C NMR (150 MHz, CDCl$_3$) δ 165.13, 157.36, 155.81, 150.86, 115.74, 111.69, 51.01, 46.50, 42.89, 30.03, 24.46, 20.44, 14.06, 13.15; HRMS (ESI) [MH]$^+$Calcd for C$_{14}$H$_{22}$ON$_3^{35}$Cl$_2$: 318.1134. found: 318.1131.

Synthesis of compounds XXXII and XXXIII using bromoacetic anhydride. 3-Amino-4-(N-butyl-N-ethylamino)-2-chloro-6-methyl-pyridine (XXIX) (0.53 g, 2.19 mmol), bromoacetic anhydride (3.53 g, 13.58 mmol, 6.2 equiv.), iPr$_2$NEt (0.57 mL, 3.27 mmol, 1.5 equiv.), and CHCl$_3$ were stirred at reflux under Ar$_{(g)}$ for 21 h. The solvent was removed to give a brown syrup that was vacuum flash chromatographed on silica (13 cm h×4 cm i.d.): CH$_2$Cl$_2$ (150 mL), hexanes (100 mL), hexanes/EtOAc/NEt$_3$ v/v/v 90:8:2 (100 mL), 75:20:5 (400 mL), 50:45:5 (300 mL) to give an off-white solid (0.50 g) that was further purified by radial chromatography (4 mm silica): hexanes (25 mL), hexanes/EtOAc/NEt$_3$ v/v/v 95:4:1 (100 mL), 90:8:2 (250 mL), 85:12:3 (100 mL), 80:16:4 (100 mL) to afford two white solids: compound XXXII (0.18 g, 32%) and compound XXXIII (27 mg, 5%). Compound XXXII. $^1$H NMR (600 MHz, CDCl$_3$) δ 7.72 (br s, 1 H), 6.32 (s, 1 H), 4.01 (s, 2 H), 3.26 (t, 2 H, J=7.5 Hz), 2.40 (s, 3 H), 1.61 (quintet, 2 H, J=7.5 Hz) 1.41 (sextet, 2 H, J=7.5 Hz), 1.00 (t, 3 H, J=7.5 Hz); HRMS (ESI) [MH]$^+$Calcd for C$_{12}$H$_{17}$ON$_3^{35}$Cl: 254.1055. found: 254.1051. Compound XXXIII. $^1$H NMR (600 MHz, CDCl$_3$) δ 7.75 (br s, 1 H), 6.35 (s, 1 H), 3.99 (s, 2 H), 3.36 (q, 2 H, J=7.2 Hz), 2.40 (s, 3 H), 1.23 (t, 3 H, J=7.2 Hz); HRMS (ESI) [MH]$^+$Calcd for C$_{10}$H$_{13}$ON$_3^{35}$Cl: 226.0742. found: 226.0738.

4-(N-Butyl-N-ethylamino)-3-(2-(benzylamino)acetamido)-2-chloro-6-methyl-pyridine (17223). 4-(N-Butyl-N-ethylamino)-3-(2-chloroacetamido)-2-chloro-6-methyl-pyridine (XXX) (0.12 g, 3.77×10$^{-4}$ mol), benzylamine (0.25 mL, 2.29 mmol, 6.1 equiv.), iPr$_2$NEt (0.10 mL, 5.74×10$^{-4}$ mol, 1.5 equiv.) and CH$_3$CN (10 mL) were stirred at reflux under Ar$_{(g)}$ for 21 h. The solvent was removed to give a residue that was dissolved in CH$_2$Cl$_2$, poured onto dry silica (43 mm h×43 mm i.d.), and eluted under vacuum: CH$_2$Cl$_2$ (50 mL), hexanes (50 mL), hexanes/EtOAc/NEt$_3$ v/v/v 75:20:5 (100 mL), 50:45:5 (200 mL) to afford 0.11 g (75%) of a colorless syrup: $^1$H NMR (600 MHz, CDCl$_3$) δ 8.72 (br s, 1 H), 7.35 (m, 4 H), 7.30 (m, 1 H), 6.53 (s, 1 H), 3.93 (s, 2 H), 3.49 (s, 2 H), 3.22 (q, 2 H, J=7.2 Hz), 3.14 (t, 2 H, J=7.5 Hz), 2.42 (s, 3 H), 1.95 (br s, 1 H), 1.50 (m, 2 H), 1.28 (sextet, 2 H, J=7.5 Hz), 1.11 (t, 3 H, J=7.2 Hz), 0.91 (t, 3 H, J=7.5 Hz); HRMS (ESI) Calcd for C$_{21}$H$_{30}$ON$_4^{35}$Cl: 389.2103. found: 389.2099.

4-(N-Benzyl)-8-(butylethylamino)-6-methyl-3,4-dihydro-1H-pyrido[2,3-b]pyrazin-2-one (8374). 4-(N-Butyl-N-ethylamino)-3-(2-(benzylamino)acetamido)-2-chloro-6-methyl-pyridine (XXX) (0.11 g, 2.83×10$^{-4}$ mol), iPr$_2$NEt (0.10 mL, 5.74×10$^{-4}$ mol, 2 equiv), and nBuOH (40 mL) were stirred at reflux under Ar$_{(g)}$ for 64 h. The solvent was removed azeotropically with heptane to give a colorless syrup that was dissolved in CH$_2$Cl$_2$, poured onto dry silica (43 mm h×43 mm i.d.), and eluted under vacuum: CH$_2$Cl$_2$ (50 mL), hexanes (50 mL), hexanes/EtOAc/NEt$_3$ v/v/v 90:8:2 (100 mL), 75:20:5 (100 mL), 50:45:5 (200 mL) to afford 80 mg (80%) of a colorless residue: $^1$H NMR (600 MHz, CDCl$_3$) δ 7.89 (br s, 1 H), 7.37 (d, 2 H, J=7.2 Hz), 7.33 (t, 2 H, J=7.2 Hz), 7.28 (d, 1 H, J=7.2 Hz), 6.33 (s, 1 H), 4.82 (s, 2 H), 3.88 (s, 2 H), 2.92 (q, 2 H, J=71 Hz), 2.86 (t, 2 H, J=7.2 Hz), 2.37 (s, 3 H), 1.37 (m, 2 H), 1.27 (sextet, 2 H, J=7.2 Hz), 0.99 (t, 3 H, J=7.2 Hz), 0.88 (t, 3 H, J=7.2 Hz); HRMS (ESI) [MH]$^+$Calcd for C$_{21}$H$_{29}$ON$_4$: 353.2336. found: 353.2329; HPLC: t$_R$=17.2 min (Waters XTerra+guard, 70:30:0.1 v/v/v MeOH/H$_2$O/NEt$_3$, 9.2 mL/min).

4-(N-Benzyl)-8-(butylethylamino)-6-methyl-3,4-dihydro-1H-pyrido[2,3-b]pyrazin-2-one HCl salt (8374.HCl). 4-(N-Benzyl)-8-(butylethylamino)-6-methyl-3,4-dihydro-1H-pyrido[2,3-b]pyrazin-2-one (8374) (71 mg, 2.01×10$^{-4}$ mol) was dissolved in EtOEt (3 mL) and cooled to 0° C. under Ar$_{(g)}$. HCl (2.0 M in EtOEt, 0.2 mL, 0.4 mmol, 2 equiv.) was added dropwise, the mixture was stirred for 5 min, filtered, and the white solid was dried under vacuum (71 mg, 91%). X-ray quality crystals were grown by dissolving 5.6 mg of the white solid in MeOH (1 mL) and then allowing the MeOH to slowly evaporate. $^1$H NMR (600 MHz, CDCl$_3$) δ 7.81 (br s, 1 H), 7.35 (m, 5 H), 6.33 (s, 1 H), 5.39 (s, 2 H), 4.01 (s, 2 H), 3.24 (q, 2 H, J=7.2 Hz), 3.16 (t, 2 H, J=7.5 Hz), 3.07 (s, 3 H), 1.50 (m, 2 H), 1.30 (sextet, 2 H, J=7.5 Hz), 1.15 (t, 3 H, J=7.2 Hz), 0.92 (t, 3 H, J=7.2 Hz).

Compounds 8375 and 8376 were prepared in a similar manner as compound 8374, and compounds (R/S)-8404, (R)-8404, (S)-8404, and (S)-8409 were also prepared in the same manner except that cyclohexanol was used in place of nBuOH.

Compound 8375. $^1$H NMR (600 MHz, CDCl$_3$) δ 7.88 (br s, 1 H), 7.40 (m, 2 H), 7.20 (dd, 1 H, J=1.8 Hz, J=8.4 Hz), 6.34 (s, 1 H), 4.89 (s, 2 H), 3.97 (s, 2 H), 2.94 (q, 2 H, J=7.2 Hz), 2.87 (t, 2 H, J=7.2 Hz), 2.34 (s, 3 H), 1.37 (m, 2 H), 1.28 (sextet, 2 H, J=7.2 Hz), 0.99 (t, 3 H, J=7.2 Hz), 0.88 (t, 3 H, J=7.2 Hz); HRMS (ESI) [MH]$^+$Calcd for C$_{21}$H$_{27}$ON$_4^{35}$Cl$_2$: 421.1556. found: 421.1552.

Compound 8376. $^1$H NMR (600 MHz, CDCl$_3$) δ 7.87 (br s, 1 H), 7.42 (d, 1 H, J=8.4 Hz), 6.46 (m, 1 H), 6.44 (d, 1 H, J=2.4 Hz), 6.28 (s, 1 H), 4.74 (s, 2 H), 4.00 (s, 2 H), 3.82 (s, 3 H), 3.80 (s, 3 H), 2.90 (q, 2 H, J=7.2 Hz), 2.84 (t, 2 H, J=7.2 Hz), 2.37 (s, 3 H), 1.34 (m, 2 H), 1.26 (sextet, 2 H, J=7.2 Hz), 0.97 (t, 3 H, J=7.2 Hz), 0.87 (t, 3 H, J=7.2 Hz); HRMS (APCI) [MH]$^+$Calcd for C$_{23}$H$_{33}$O$_3$N$_4$: 413.2547. found: 413.2540; HPLC: t$_R$=3.5 min (XTerra+guard, 70:30:0.1 v/v/v MeOH/H$_2$O/NEt$_3$, 9.2 mL/min).

Compound (R/S)-8404. $^1$H NMR (600 MHz, CDCl$_3$) δ 7.84 (br s, 1 H), 7.41 (d, 2 H, J=7.8 Hz), 7.33 (t, 2 H, J=7.8 Hz), 7.26 (t—partially obscured by CHCl$_3$ solvent peak, 1 H), 6.31 (overlapping s+q, 2 H, J=7.2 Hz), 3.86 (d, 1 H, J=16.2 Hz), 3.54 (d, 1 H, J=16.2 Hz), 2.92 (q, 2 H, J=7.2 Hz), 2.86 (t, 2 H, J=7.2 Hz), 2.38 (s, 3 H), 1.57 (d, 3 H, J=7.2 Hz), 1.37 (m, 2 H), 1.27 (sextet, 2 H, J=7.2 Hz), 0.99 (t, 3 H, J=7.2 Hz), 0.88 (t, 3 H, J=7.2 Hz); HRMS (ESI) [MH]$^+$Calcd for C$_{22}$H$_{31}$ON$_4$: 367.2492. found: 367.2490.

Compound (R)-8404. $^1$H NMR (600 MHz, CDCl$_3$) δ 7.85 (br s, 1 H), 7.41 (d, 2 H, J=7.8 Hz), 7.33 (t, 2 H, J=7.8 Hz), 7.26 (t, 1 H, J=7.8 Hz), 6.32 (overlapping s+q, 2 H, J=7.2 Hz), 3.86 (d, 1 H, J=16.2 Hz), 3.55 (d, 1 H, J=16.2 Hz), 2.93 (q, 2 H, J=7.2 Hz), 2.87 (t, 2 H, J=7.2 Hz), 2.38 (s, 3 H), 1.57 (d, 3 H, J=7.2 Hz), 1.37 (m, 2 H), 1.27 (sextet, 2 H, J=7.2 Hz), 0.99 (t, 3 H, J=7.2 Hz), 0.88 (t, 3 H, J=7.2 Hz); HRMS (ESI) [MH]$^+$Calcd for C$_{22}$H$_{31}$ON$_4$: 367.2492. found: 367.2490.

Compound (S)-8404. $^1$H NMR (600 MHz, CDCl$_3$) δ 7.84 (br s, 1 H), 7.41 (d, 2 H, J=7.8 Hz), 7.33 (t, 2 H, J=7.8 Hz), 7.26 (t, 1 H, J=7.8 Hz), 6.31 (overlapping s+q, 2 H, J=7.2 Hz), 3.86 (d, 1 H, J=16.2 Hz), 3.54 (d, 1 H, J=16.2 Hz), 2.93 (q, 2 H, J=7.2 Hz), 2.87 (t, 2 H, J=7.2 Hz), 2.38 (s, 3 H), 1.57 (d, 3 H, J=7.2 Hz), 1.37 (m, 2 H), 1.27 (sextet, 2 H, J=7.2 Hz), 0.99 (t, 3 H, J=7.2 Hz), 0.88 (t, 3 H, J=7.2 Hz); HRMS (ESI) [MH]$^+$Calcd for $C_{22}H_{31}ON_4$: 367.2492. found: 367.2490.

Compound (S)-8409. $^1$H NMR (600 MHz, CDCl$_3$) δ 7.82 (br s, 1 H), 7.34 (d, 2 H, J=8.4 Hz), 6.86 (d, 2 H, J=8.4 Hz), 6.31 (s, 1 H), 6.25 (q, 1 H, J=7.2 Hz), 3.83 (d, 1 H, J=16.2 Hz), 3.80 (s, 3 H), 3.53 (d, 1 H, J=16.2 Hz), 2.92 (q, 2 H, J=7.2 Hz), 2.86 (t, 2 H, J=7.2 Hz), 2.38 (s, 3 H), 1.54 (d, 3 H, J=7.2 Hz), 1.37 (m, 2 H), 1.27 (sextet, 2 H, J=7.2 Hz), 0.99 (t, 3 H, J=7.2 Hz), 0.88 (t, 3 H, J=7.2 Hz).

TABLE 1

Substituent list for compounds of general structure VI.

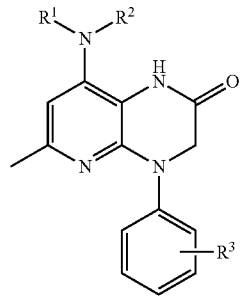

VI

| Compound # | R$^1$ = | R$^2$ = | R$^3$ = |
|---|---|---|---|
| 1 | Bu | Et | H |
| 2 | Bu | Et | 2-t-Bu |
| 3 | Bu | Et | 2-Br |
| 4 | Bu | Et | 3-Br |
| 5 | Bu | Et | 4-Br |
| 6 | Bu | Et | 2-I |
| 7 | Bu | Et | 3-I |
| 8 | Bu | Et | 4-I |
| 9 | Bu | Et | 2-SnMe$_3$ |
| 10 | Bu | Et | 3-SnMe$_3$ |
| 11 | Bu | Et | 4-SnMe$_3$ |
| 12 | Bu | Et | 2-Me |
| 13 | Bu | Et | 3-Me |
| 14 | Bu | Et | 4-Me |
| 15 | Bu | Et | 2-OH |
| 16 | Bu | Et | 3-OH |
| 17 | Bu | Et | 4-OH |
| 18 | Bu | Et | 2-OMe |
| 19 | Bu | Et | 3-OMe |
| 20 | Bu | Et | 4-OMe |
| 21 | Bu | Et | 2-OMeF |
| 22 | Bu | Et | 3-OMeF |
| 23 | Bu | Et | 4-OMeF |
| 24 | Bu | Et | 2-OCF$_3$ |
| 25 | Bu | Et | 3-OCF$_3$ |
| 26 | Bu | Et | 4-OCF$_3$ |
| 27 | Bu | Et | 2-OEtF |
| 28 | Bu | Et | 3-OEtF |
| 29 | Bu | Et | 4-OEtF |
| 30 | Bu | Et | 2-OPrF |
| 31 | Bu | Et | 3-OPrF |
| 32 | Bu | Et | 4-OPrF |
| 33 | Bu | Et | 2-SH |
| 34 | Bu | Et | 3-SH |
| 35 | Bu | Et | 4-SH |
| 36 | Bu | Et | 2-SMe |
| 37 | Bu | Et | 3-SMe |
| 38 | Bu | Et | 4-SMe |
| 39 | Bu | Et | 2-SMeF |
| 40 | Bu | Et | 3-SMeF |
| 41 | Bu | Et | 4-SMeF |
| 42 | Bu | Et | 2-SCF$_3$ |
| 43 | Bu | Et | 3-SCF$_3$ |
| 44 | Bu | Et | 4-SCF$_3$ |
| 45 | Bu | Et | 2-SEtF |
| 46 | Bu | Et | 3-SEtF |
| 47 | Bu | Et | 4-SEtF |
| 48 | Bu | Et | 2-SPrF |
| 49 | Bu | Et | 3-SPrF |
| 50 | Bu | Et | 4-SPrF |
| 51 | Bu | Et | 2-OMe, 4-OMe |
| 52 | Bu | Et | 2-Me, 5-OH |
| 53 | Bu | Et | 2-Me, 5-OMe |
| 54 | Bu | Et | 2-Me, 5-OMeF |
| 55 | Bu | Et | 2-Me, 5-OEtF |
| 56 | Bu | Et | 2-Me, 5-OPrF |
| 57 | Bu | Et | 2-Me, 4-OH |
| 58 | Bu | Et | 2-Me, 4-OMeF |
| 59 | Bu | Et | 2-Me, 4-OCF$_3$ |
| 60 | Bu | Et | 2-Me, 4-OEtF |
| 61 | Bu | Et | 2-Me, 4-OPrF |
| 62 | Bu | Et | 2-OH, 4-Me |
| 63 | Bu | Et | 2-OMe, 4-Me |
| 64 | Bu | Et | 2-OMeF, 4-Me |
| 65 | Bu | Et | 2-OCF$_3$, 4-Me |
| 66 | Bu | Et | 2-OEtF, 4-Me |
| 67 | Bu | Et | 2-OPrF, 4-Me |
| 68 | Bu | Et | 2-Cl, 4-OH |
| 69 | Bu | Et | 2-Cl, 4-OMeF |
| 70 | Bu | Et | 2-Cl, 4-OCF$_3$ |
| 71 | Bu | Et | 2-Cl, 4-OEtF |
| 72 | Bu | Et | 2-Cl, 4-OPrF |
| 73 | Bu | Et | 2-F, 4-F |
| 74 | Bu | Et | 2-Cl, 4-F |
| 75 | Bu | Et | 2-Cl, 4-NO$_2$ |
| 76 | Bu | Et | 2-Cl, 4-NH$_2$ |
| 77 | Bu | Et | 2-Cl, 4-NHMe |
| 78 | Bu | Et | 2-Cl, 4-NMe$_2$ |
| 79 | Bu | Et | 2-Cl, 4-NMe$_3$OTf |
| 80 | Bu | Et | 2-Cl, 4-NMe$_3$I |
| 81 | Bu | Et | 2-Cl, 5-F |
| 82 | Bu | Et | 2-Cl, 5-NO$_2$ |
| 83 | Bu | Et | 2-Cl, 5-NH$_2$ |
| 84 | Bu | Et | 2-Cl, 5-NHMe |
| 85 | Bu | Et | 2-Cl, 5-NMe$_2$ |
| 86 | Bu | Et | 2-Cl, 5-NMe$_3$OTf |
| 87 | Bu | Et | 2-Cl, 5-NMe$_3$I |
| 88 | Bu | Et | 2-F, 4-Cl |
| 89 | Bu | Et | 2-NO$_2$, 4-Cl |
| 90 | Bu | Et | 2-NH$_2$, 4-Cl |
| 91 | Bu | Et | 2-NHMe, 4-Cl |
| 92 | Bu | Et | 2-NMe$_2$, 4-Cl |
| 93 | Bu | Et | 2-NMe$_3$OTf, 4-Cl |
| 94 | Bu | Et | 2-NMe$_3$I, 4-Cl |
| 95 | Bu | Et | 2-F, 5-Cl |
| 96 | Bu | Et | 2-NO$_2$, 5-Cl |
| 97 | Bu | Et | 2-NH$_2$, 5-Cl |
| 98 | Bu | Et | 2-NHMe, 5-Cl |
| 99 | Bu | Et | 2-NMe$_2$, 5-Cl |
| 100 | Bu | Et | 2-NMe$_3$OTf, 5-Cl |
| 101 | Bu | Et | 2-NMe$_3$I, 5-Cl |
| 102 | Bu | Et | 2-Br, 4-F |

TABLE 1-continued

Substituent list for compounds of general structure VI.

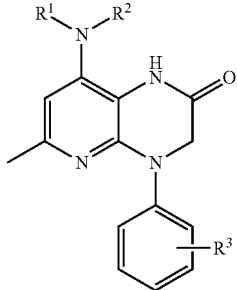

VI

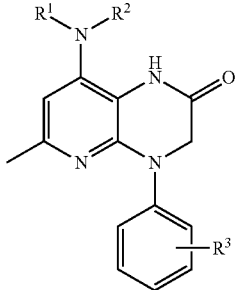

VI

| Compound # | R$^1$ = | R$^2$ = | R$^3$ = | Compound # | R$^1$ = | R$^2$ = | R$^3$ = |
|---|---|---|---|---|---|---|---|
| 103 | Bu | Et | 2-Br, 4-NO$_2$ | 161 | Bu | Et | 2-NHMe, 4-Me |
| 104 | Bu | Et | 2-Br, 4-NH$_2$ | 162 | Bu | Et | 2-NMe$_2$, 4-Me |
| 105 | Bu | Et | 2-Br, 4-NHMe | 163 | Bu | Et | 2-NMe$_3$, 4-Me |
| 106 | Bu | Et | 2-Br, 4-NMe$_2$ | 164 | Bu | Et | 2-NMe$_3$OTf, 4-Me |
| 107 | Bu | Et | 2-Br, 4-NMe$_3$OTf | 165 | Bu | Et | 2-NMe$_3$I, 4-Me |
| 108 | Bu | Et | 2-Br, 4-NMe$_3$I | 166 | Bu | Et | 2-SnMe$_3$, 4-F |
| 109 | Bu | Et | 2-Br, 5-F | 167 | Bu | Et | 2-SnMe$_3$, 5-F |
| 110 | Bu | Et | 2-Br, 5-NO$_2$ | 168 | Bu | Et | 2-F, 4-SnMe$_3$ |
| 111 | Bu | Et | 2-Br, 5-NH$_2$ | 169 | Bu | Et | 2-Br, 6-Cl, 4-F |
| 112 | Bu | Et | 2-Br, 5-NHMe | 170 | Bu | Et | 2-Br, 6-Cl, 4-NO$_2$ |
| 113 | Bu | Et | 2-Br, 5-NMe$_2$ | 171 | Bu | Et | 2-Br, 6-Cl, 4-NH$_2$ |
| 114 | Bu | Et | 2-Br, 5-NMe$_3$OTf | 172 | Bu | Et | 2-Br, 6-Cl, 4-NHMe |
| 115 | Bu | Et | 2-Br, 5-NMe$_3$I | 173 | Bu | Et | 2-Br, 6-Cl, 4-NMe$_2$ |
| 116 | Bu | Et | 2-F, 4-Br | 174 | Bu | Et | 2-Br, 6-Cl, 4-NMe$_3$OTf |
| 117 | Bu | Et | 2-NO$_2$, 4-Br | 175 | Bu | Et | 2-Br, 6-Cl, 4-NMe$_3$I |
| 118 | Bu | Et | 2-NH$_2$, 4-Br | 176 | Bu | Et | 2-Me, 6-Cl, 4-F |
| 119 | Bu | Et | 2-NHMe, 4-Br | 177 | Bu | Et | 2-SnMe$_3$, 6-Cl, 4-F |
| 120 | Bu | Et | 2-NMe$_2$, 4-Br | 178 | Bu | Et | 2-Cl, 4-Me |
| 121 | Bu | Et | 2-NMe$_3$OTf, 4-Br | 179 | Bu | Et | 2-Cl, 4-Br |
| 122 | Bu | Et | 2-NMe$_3$I, 4-Br | 180 | Bu | Et | 2-Cl, 4-SnMe$_3$ |
| 123 | Bu | Et | 2-I, 4-F | 181 | Bu | Et | 2-Br, 4-Cl |
| 124 | Bu | Et | 2-I, 4-NO$_2$ | 182 | Bu | Et | 2-SnMe$_3$, 4-Cl |
| 125 | Bu | Et | 2-I, 4-NH$_2$ | 183 | Bu | Et | 2-Me, 4-Cl |
| 126 | Bu | Et | 2-I, 4-NHMe | 184 | Bu | Et | 2-Br, 4-Br |
| 127 | Bu | Et | 2-I, 4-NMe$_2$ | 185 | Bu | Et | 2-Br, 4-Me |
| 128 | Bu | Et | 2-I, 4-NMe$_3$OTf | 186 | Bu | Et | 2-Br, 4-SnMe$_3$ |
| 129 | Bu | Et | 2-I, 4-NMe$_3$I | 187 | Bu | Et | 2-SnMe$_3$, 4-Br |
| 130 | Bu | Et | 2-F, 4-I | 188 | Bu | Et | 2-Me, 4-Br |
| 131 | Bu | Et | 2-NO$_2$, 4-I | 189 | Bu | Et | 2-Me, 4-SnMe$_3$ |
| 132 | Bu | Et | 2-NH$_2$, 4-I | 190 | Bu | Et | 2-SnMe$_3$, 4-Me |
| 133 | Bu | Et | 2-NHMe, 4-I | 191 | Bu | Et | 2-Me, 4-Me |
| 134 | Bu | Et | 2-NMe$_2$, 4-I | 192 | Bu | Et | 2-Et, 4-Br |
| 135 | Bu | Et | 2-NMe$_3$OTf, 4-I | 193 | Bu | Et | 2-Et, 4-SnMe$_3$ |
| 136 | Bu | Et | 2-NMe$_3$I, 4-I | 194 | Bu | Et | 2-Et, 4-Me |
| 137 | Bu | Et | 2-Me, 3-F | 195 | Bu | Et | 2-Me, 4-Br, 6-Me |
| 138 | Bu | Et | 2-Me, 3-NO$_2$ | 196 | Bu | Et | 2-Me, 4-SnMe$_3$, 6-Me |
| 139 | Bu | Et | 2-Me, 3-NH$_2$ | 197 | Bu | Et | 2-Et, 6-Me |
| 140 | Bu | Et | 2-Me, 3-NHMe | 198 | Bu | Et | 2-SnMe$_3$, 4-i-Pr |
| 141 | Bu | Et | 2-Me, 3-NMe$_2$ | 199 | Bu | Et | 2-Me, 4-i-Pr |
| 142 | Bu | Et | 2-Me, 3-NMe$_3$OTf | 200 | Bu | Et | 2-Br, 4-Br, 6-Br |
| 143 | Bu | Et | 2-Me, 3-NMe$_3$I | 201 | Bu | Et | 2-Br, 4-Me, 6-Br |
| 144 | Bu | Et | 2-Me, 4-F | 202 | Bu | Et | 2-Br, 4-SnMe$_3$, 6-Br |
| 145 | Bu | Et | 2-Me, 4-NO$_2$ | 203 | Bu | Et | 2-SnMe$_3$, 4-Br, 6-Br |
| 146 | Bu | Et | 2-Me, 4-NH$_2$ | 204 | Bu | Et | 2-Br, 4-Br, 6-Me |
| 147 | Bu | Et | 2-Me, 4-NHMe | 205 | Bu | Et | 2-Br, 4-CF$_3$, 6-Br |
| 148 | Bu | Et | 2-Me, 4-NMe$_2$ | 206 | Bu | Et | 2-Br, 4-Br, 6-CF$_3$ |
| 149 | Bu | Et | 2-Me, 4-NMe$_3$OTf | 207 | Bu | Et | 2-CF$_3$, 4-CF$_3$ |
| 150 | Bu | Et | 2-Me, 4-NMe$_3$I | 208 | Bu | Et | 2-Cl, 4-CF$_3$ |
| 151 | Bu | Et | 2-Me, 5-F | 209 | Bu | Et | 2-CF$_3$, 4-Cl |
| 152 | Bu | Et | 2-Me, 5-NO$_2$ | 210 | Bu | Et | 2-Br, 4-CF$_3$ |
| 153 | Bu | Et | 2-Me, 5-NH$_2$ | 211 | Bu | Et | 2-SnMe$_3$, 4-CF$_3$ |
| 154 | Bu | Et | 2-Me, 5-NHMe | 212 | Bu | Et | 2-Me, 4-CF$_3$ |
| 155 | Bu | Et | 2-Me, 5-NMe$_2$ | 213 | Bu | Et | 2-CF$_3$, 4-Br |
| 156 | Bu | Et | 2-Me, 5-NMe$_3$OTf | 214 | Bu | Et | 2-CF$_3$, 4-SnMe$_3$ |
| 157 | Bu | Et | 2-Me, 5-NMe$_3$I | 215 | Bu | Et | 2-CF$_3$, 4-Me |
| 158 | Bu | Et | 2-F, 4-Me | 216 | Bu | Et | 2-Br, 4-OH |
| 159 | Bu | Et | 2-NO$_2$, 4-Me | 217 | Bu | Et | 2-Br, 4-OMe |
| 160 | Bu | Et | 2-NH$_2$, 4-Me | 218 | Bu | Et | 2-Br, 4-OMeF |
| | | | | 219 | Bu | Et | 2-Br, 4-OCF$_3$ |
| | | | | 220 | Bu | Et | 2-Br, 4-OEtF |

TABLE 1-continued

Substituent list for compounds of general structure VI.

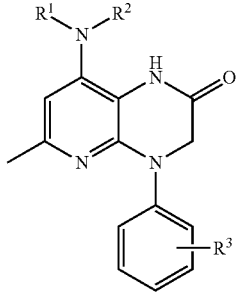

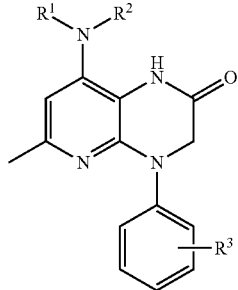

| Compound # | R¹ = | R² = | R³ = |
|---|---|---|---|
| 221 | Bu | Et | 2-Br, 4-OPrF |
| 222 | Bu | Et | 2-OH, 4-Br |
| 223 | Bu | Et | 2-OMe, 4-Br |
| 224 | Bu | Et | 2-OMeF, 4-Br |
| 225 | Bu | Et | 2-OCF$_3$, 4-Br |
| 226 | Bu | Et | 2-OEtF, 4-Br |
| 227 | Bu | Et | 2-OPrF, 4-Br |
| 228 | Bu | Et | 2-I, 4-OH |
| 229 | Bu | Et | 2-I, 4-OMe |
| 230 | Bu | Et | 2-I, 4-OMeF |
| 231 | Bu | Et | 2-I, 4-OCF$_3$ |
| 232 | Bu | Et | 2-I, 4-OEtF |
| 233 | Bu | Et | 2-I, 4-OPrF |
| 234 | Bu | Et | 2-OH, 4-I |
| 235 | Bu | Et | 2-OMe, 4-I |
| 236 | Bu | Et | 2-OMeF, 4-I |
| 237 | Bu | Et | 2-OCF$_3$, 4-I |
| 238 | Bu | Et | 2-OEtF, 4-I |
| 239 | Bu | Et | 2-OPrF, 4-I |
| 240 | Bu | Et | 2-SnMe$_3$, 4-OH |
| 241 | Bu | Et | 2-SnMe$_3$, 4-OMe |
| 242 | Bu | Et | 2-SnMe$_3$, 4-OMeF |
| 243 | Bu | Et | 2-SnMe$_3$, 4-OCF$_3$ |
| 244 | Bu | Et | 2-SnMe$_3$, 4-OEtF |
| 245 | Bu | Et | 2-SnMe$_3$, 4-OPrF |
| 246 | Bu | Et | 2-OH, 4-SnMe$_3$ |
| 247 | Bu | Et | 2-OMe, 4-SnMe$_3$ |
| 248 | Bu | Et | 2-OMeF, 4-SnMe$_3$ |
| 249 | Bu | Et | 2-OCF$_3$, 4-SnMe$_3$ |
| 250 | Bu | Et | 2-OEtF, 4-SnMe$_3$ |
| 251 | Bu | Et | 2-OPrF, 4-SnMe$_3$ |
| 252 | Pr | Pr | H |
| 253 | Pr | Pr | 2-t-Bu |
| 254 | Pr | Pr | 2-Br |
| 255 | Pr | Pr | 3-Br |
| 256 | Pr | Pr | 4-Br |
| 257 | Pr | Pr | 2-I |
| 258 | Pr | Pr | 3-I |
| 259 | Pr | Pr | 4-I |
| 260 | Pr | Pr | 2-SnMe$_3$ |
| 261 | Pr | Pr | 3-SnMe$_3$ |
| 262 | Pr | Pr | 4-SnMe$_3$ |
| 263 | Pr | Pr | 2-Me |
| 264 | Pr | Pr | 3-Me |
| 265 | Pr | Pr | 4-Me |
| 266 | Pr | Pr | 2-OH |
| 267 | Pr | Pr | 3-OH |
| 268 | Pr | Pr | 4-OH |
| 269 | Pr | Pr | 2-OMe |
| 270 | Pr | Pr | 3-OMe |
| 271 | Pr | Pr | 4-OMe |
| 272 | Pr | Pr | 2-OMeF |
| 273 | Pr | Pr | 3-OMeF |
| 274 | Pr | Pr | 4-OMeF |
| 275 | Pr | Pr | 2-OCF$_3$ |
| 276 | Pr | Pr | 3-OCF$_3$ |
| 277 | Pr | Pr | 4-OCF$_3$ |
| 278 | Pr | Pr | 2-OEtF |
| 279 | Pr | Pr | 3-OEtF |
| 280 | Pr | Pr | 4-OEtF |
| 281 | Pr | Pr | 2-OPrF |
| 282 | Pr | Pr | 3-OPrF |
| 283 | Pr | Pr | 4-OPrF |
| 284 | Pr | Pr | 2-SH |
| 285 | Pr | Pr | 3-SH |
| 286 | Pr | Pr | 4-SH |
| 287 | Pr | Pr | 2-SMe |
| 288 | Pr | Pr | 3-SMe |
| 289 | Pr | Pr | 4-SMe |
| 290 | Pr | Pr | 2-SMeF |
| 291 | Pr | Pr | 3-SMeF |
| 292 | Pr | Pr | 4-SMeF |
| 293 | Pr | Pr | 2-SCF$_3$ |
| 294 | Pr | Pr | 3-SCF$_3$ |
| 295 | Pr | Pr | 4-SCF$_3$ |
| 296 | Pr | Pr | 2-SEtF |
| 297 | Pr | Pr | 3-SEtF |
| 298 | Pr | Pr | 4-SEtF |
| 299 | Pr | Pr | 2-SPrF |
| 300 | Pr | Pr | 3-SPrF |
| 301 | Pr | Pr | 4-SPrF |
| 302 | Pr | Pr | 2-OMe, 4-OMe |
| 303 | Pr | Pr | 2-Me, 5-OH |
| 304 | Pr | Pr | 2-Me, 5-OMe |
| 305 | Pr | Pr | 2-Me, 5-OMeF |
| 306 | Pr | Pr | 2-Me, 5-OEtF |
| 307 | Pr | Pr | 2-Me, 5-OPrF |
| 308 | Pr | Pr | 2-Me, 4-OH |
| 309 | Pr | Pr | 2-Me, 4-OMe |
| 310 | Pr | Pr | 2-Me, 4-OMeF |
| 311 | Pr | Pr | 2-Me, 4-OCF$_3$ |
| 312 | Pr | Pr | 2-Me, 4-OEtF |
| 313 | Pr | Pr | 2-Me, 4-OPrF |
| 314 | Pr | Pr | 2-OH, 4-Me |
| 315 | Pr | Pr | 2-OMe, 4-Me |
| 316 | Pr | Pr | 2-OMeF, 4-Me |
| 317 | Pr | Pr | 2-OCF$_3$, 4-Me |
| 318 | Pr | Pr | 2-OEtF, 4-Me |
| 319 | Pr | Pr | 2-OPrF, 4-Me |
| 320 | Pr | Pr | 2-Cl, 4-OH |
| 321 | Pr | Pr | 2-Cl, 4-OMe |
| 322 | Pr | Pr | 2-Cl, 4-OMeF |
| 323 | Pr | Pr | 2-Cl, 4-OCF$_3$ |
| 324 | Pr | Pr | 2-Cl, 4-OEtF |
| 325 | Pr | Pr | 2-Cl, 4-OPrF |
| 326 | Pr | Pr | 2-F, 4-F |
| 327 | Pr | Pr | 2-Cl, 4-Cl |
| 328 | Pr | Pr | 2-Cl, 4-F |
| 329 | Pr | Pr | 2-Cl, 4-NO$_2$ |
| 330 | Pr | Pr | 2-Cl, 4-NH$_2$ |
| 331 | Pr | Pr | 2-Cl, 4-NHMe |
| 332 | Pr | Pr | 2-Cl, 4-NMe$_2$ |
| 333 | Pr | Pr | 2-Cl, 4-NMe$_3$OTf |
| 334 | Pr | Pr | 2-Cl, 4-NMe$_3$I |
| 335 | Pr | Pr | 2-Cl, 5-F |
| 336 | Pr | Pr | 2-Cl, 5-NO$_2$ |
| 337 | Pr | Pr | 2-Cl, 5-NH$_2$ |
| 338 | Pr | Pr | 2-Cl, 5-NHMe |
| 339 | Pr | Pr | 2-Cl, 5-NMe$_2$ |
| 340 | Pr | Pr | 2-Cl, 5-NMe$_3$OTf |

TABLE 1-continued

Substituent list for compounds of general structure VI.

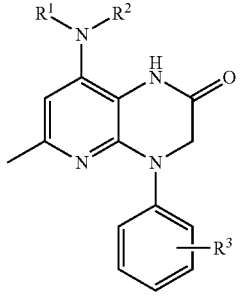

| Compound # | R¹ = | R² = | R³ = |
|---|---|---|---|
| 341 | Pr | Pr | 2-Cl, 5-NMe₃I |
| 342 | Pr | Pr | 2-F, 4-Cl |
| 343 | Pr | Pr | 2-NO₂, 4-Cl |
| 344 | Pr | Pr | 2-NH₂, 4-Cl |
| 345 | Pr | Pr | 2-NHMe, 4-Cl |
| 346 | Pr | Pr | 2-NMe₂, 4-Cl |
| 347 | Pr | Pr | 2-NMe₃OTf, 4-Cl |
| 348 | Pr | Pr | 2-NMe₃I, 4-Cl |
| 349 | Pr | Pr | 2-F, 5-Cl |
| 350 | Pr | Pr | 2-NO₂, 5-Cl |
| 351 | Pr | Pr | 2-NH₂, 5-Cl |
| 352 | Pr | Pr | 2-NHMe, 5-Cl |
| 353 | Pr | Pr | 2-NMe₂, 5-Cl |
| 354 | Pr | Pr | 2-NMe₃OTf, 5-Cl |
| 355 | Pr | Pr | 2-NMe₃I, 5-Cl |
| 356 | Pr | Pr | 2-Br, 4-F |
| 357 | Pr | Pr | 2-Br, 4-NO₂ |
| 358 | Pr | Pr | 2-Br, 4-NH₂ |
| 359 | Pr | Pr | 2-Br, 4-NHMe |
| 360 | Pr | Pr | 2-Br, 4-NMe₂ |
| 361 | Pr | Pr | 2-Br, 4-NMe₃OTf |
| 362 | Pr | Pr | 2-Br, 4-NMe₃I |
| 363 | Pr | Pr | 2-Br, 5-F |
| 364 | Pr | Pr | 2-Br, 5-NO₂ |
| 365 | Pr | Pr | 2-Br, 5-NH₂ |
| 366 | Pr | Pr | 2-Br, 5-NHMe |
| 367 | Pr | Pr | 2-Br, 5-NMe₂ |
| 368 | Pr | Pr | 2-Br, 5-NMe₃OTf |
| 369 | Pr | Pr | 2-Br, 5-NMe₃I |
| 370 | Pr | Pr | 2-F, 4-Br |
| 371 | Pr | Pr | 2-NO₂, 4-Br |
| 372 | Pr | Pr | 2-NH₂, 4-Br |
| 373 | Pr | Pr | 2-NHMe, 4-Br |
| 374 | Pr | Pr | 2-NMe₂, 4-Br |
| 375 | Pr | Pr | 2-NMe₃OTf, 4-Br |
| 376 | Pr | Pr | 2-NMe₃I, 4-Br |
| 377 | Pr | Pr | 2-I, 4-F |
| 378 | Pr | Pr | 2-I, 4-NO₂ |
| 379 | Pr | Pr | 2-I, 4-NH₂ |
| 380 | Pr | Pr | 2-I, 4-NHMe |
| 381 | Pr | Pr | 2-I, 4-NMe₂ |
| 382 | Pr | Pr | 2-I, 4-NMe₃OTf |
| 383 | Pr | Pr | 2-I, 4-NMe₃I |
| 384 | Pr | Pr | 2-F, 4-I |
| 385 | Pr | Pr | 2-NO₂, 4-I |
| 386 | Pr | Pr | 2-NH₂, 4-I |
| 387 | Pr | Pr | 2-NHMe, 4-I |
| 388 | Pr | Pr | 2-NMe₂, 4-I |
| 389 | Pr | Pr | 2-NMe₃OTf, 4-I |
| 390 | Pr | Pr | 2-NMe₃I, 4-I |
| 391 | Pr | Pr | 2-Me, 3-F |
| 392 | Pr | Pr | 2-Me, 3-NO₂ |
| 393 | Pr | Pr | 2-Me, 3-NH₂ |
| 394 | Pr | Pr | 2-Me, 3-NHMe |
| 395 | Pr | Pr | 2-Me, 3-NMe₂ |
| 396 | Pr | Pr | 2-Me, 3-NMe₃OTf |
| 397 | Pr | Pr | 2-Me, 3-NMe₃I |
| 398 | Pr | Pr | 2-Me, 4-F |
| 399 | Pr | Pr | 2-Me, 4-NO₂ |
| 400 | Pr | Pr | 2-Me, 4-NH₂ |
| 401 | Pr | Pr | 2-Me, 4-NHMe |
| 402 | Pr | Pr | 2-Me, 4-NMe₂ |
| 403 | Pr | Pr | 2-Me, 4-NMe₃OTf |
| 404 | Pr | Pr | 2-Me, 4-NMe₃I |
| 405 | Pr | Pr | 2-Me, 5-F |
| 406 | Pr | Pr | 2-Me, 5-NO₂ |
| 407 | Pr | Pr | 2-Me, 5-NH₂ |
| 408 | Pr | Pr | 2-Me, 5-NHMe |
| 409 | Pr | Pr | 2-Me, 5-NMe₂ |
| 410 | Pr | Pr | 2-Me, 5-NMe₃OTf |
| 411 | Pr | Pr | 2-Me, 5-NMe₃I |
| 412 | Pr | Pr | 2-F, 4-Me |
| 413 | Pr | Pr | 2-NO₂, 4-Me |
| 414 | Pr | Pr | 2-NH₂, 4-Me |
| 415 | Pr | Pr | 2-NHMe, 4-Me |
| 416 | Pr | Pr | 2-NMe₂, 4-Me |
| 417 | Pr | Pr | 2-NMe₃, 4-Me |
| 418 | Pr | Pr | 2-NMe₃OTf, 4-Me |
| 419 | Pr | Pr | 2-NMe₃I, 4-Me |
| 420 | Pr | Pr | 2-SnMe₃, 4-F |
| 421 | Pr | Pr | 2-SnMe3, 5-F |
| 422 | Pr | Pr | 2-F, 4-SnMe₃ |
| 423 | Pr | Pr | 2-Br, 6-Cl, 4-F |
| 424 | Pr | Pr | 2-Br, 6-Cl, 4-NO₂ |
| 425 | Pr | Pr | 2-Br, 6-Cl, 4-NH₂ |
| 426 | Pr | Pr | 2-Br, 6-Cl, 4-NHMe |
| 427 | Pr | Pr | 2-Br, 6-Cl, 4-NMe₂ |
| 428 | Pr | Pr | 2-Br, 6-Cl, 4-NMe₂OTf |
| 429 | Pr | Pr | 2-Br, 6-Cl, 4-NMe₃I |
| 430 | Pr | Pr | 2-Me, 6-Cl, 4-F |
| 431 | Pr | Pr | 2-SnMe₃, 6-Cl, 4-F |
| 432 | Pr | Pr | 2-Cl, 4-Me |
| 433 | Pr | Pr | 2-Cl, 4-Br |
| 434 | Pr | Pr | 2-Cl, 4-SnMe₃ |
| 435 | Pr | Pr | 2-Br, 4-Cl |
| 436 | Pr | Pr | 2-SnMe₃, 4-Cl |
| 437 | Pr | Pr | 2-Me, 4-Cl |
| 438 | Pr | Pr | 2-Br, 4-F |
| 439 | Pr | Pr | 2-Br, 4-Me |
| 440 | Pr | Pr | 2-Br, 4-SnMe₃ |
| 441 | Pr | Pr | 2-SnMe₃, 4-Br |
| 442 | Pr | Pr | 2-Me, 4-Br |
| 443 | Pr | Pr | 2-Me, 4-SnMe₃ |
| 444 | Pr | Pr | 2-SnMe₃, 4-Me |
| 445 | Pr | Pr | 2-Me, 4-Me |
| 446 | Pr | Pr | 2-Et, 4-Br |
| 447 | Pr | Pr | 2-Et, 4-SnMe₃ |
| 448 | Pr | Pr | 2-Et, 4-Me |
| 449 | Pr | Pr | 2-Me, 4-Me, 6-Me |
| 450 | Pr | Pr | 2-Me, 4-Br, 6-Me |
| 451 | Pr | Pr | 2-Me, 4-SnMe₃, 6-Me |
| 452 | Pr | Pr | 2-Et, 6-Me |
| 453 | Pr | Pr | 2-Br, 4-i-Pr |
| 454 | Pr | Pr | 2-SnMe₃, 4-i-Pr |
| 455 | Pr | Pr | 2-Me, 4-i-Pr |
| 456 | Pr | Pr | 2-Br, 4-Br, 6-Br |
| 457 | Pr | Pr | 2-Br, 4-Me, 6-Br |
| 458 | Pr | Pr | 2-Br, 4-SnMe₃, 6-Br |
| 459 | Pr | Pr | 2-SnMe₃, 4-Br, 6-Br |
| 460 | Pr | Pr | 2-Br, 4-Br, 6-Me |

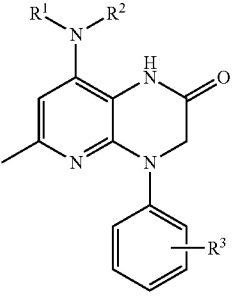

TABLE 1-continued

Substituent list for compounds of general structure VI.

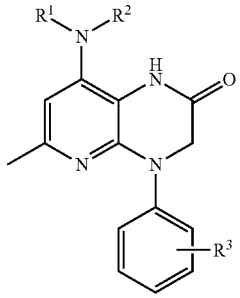

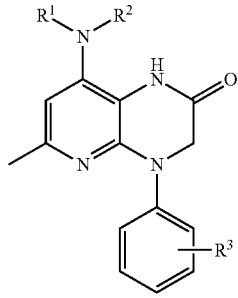

| Compound # | R¹ = | R² = | R³ = |
|---|---|---|---|
| 461 | Pr | Pr | 2-Br, 4-CF₃, 6-Br |
| 462 | Pr | Pr | 2-Br, 4-Br, 6-CF₃ |
| 463 | Pr | Pr | 2-CF₃, 4-CF₃ |
| 464 | Pr | Pr | 2-Cl, 4-CF₃ |
| 465 | Pr | Pr | 2-CF₃, 4-Cl |
| 466 | Pr | Pr | 2-Br, 4-CF₃ |
| 467 | Pr | Pr | 2-SnMe₃, 4-CF₃ |
| 468 | Pr | Pr | 2-Me, 4-CF₃ |
| 469 | Pr | Pr | 2-CF₃, 4-Br |
| 470 | Pr | Pr | 2-CF₃, 4-SnMe₃ |
| 471 | Pr | Pr | 2-CF₃, 4-Me |
| 472 | Pr | Pr | 2-Br, 4-OH |
| 473 | Pr | Pr | 2-Br, 4-OMe |
| 474 | Pr | Pr | 2-Br, 4-OMeF |
| 475 | Pr | Pr | 2-Br, 4-OCF₃ |
| 476 | Pr | Pr | 2-Br, 4-OEtF |
| 477 | Pr | Pr | 2-Br, 4-OPrF |
| 478 | Pr | Pr | 2-OH, 4-Br |
| 479 | Pr | Pr | 2-OMe, 4-Br |
| 480 | Pr | Pr | 2-OMeF, 4-Br |
| 481 | Pr | Pr | 2-OCF₃, 4-Br |
| 482 | Pr | Pr | 2-OEtF, 4-Br |
| 483 | Pr | Pr | 2-OPrF, 4-Br |
| 484 | Pr | Pr | 2-I, 4-OH |
| 485 | Pr | Pr | 2-I, 4-OMe |
| 486 | Pr | Pr | 2-I, 4-OMeF |
| 487 | Pr | Pr | 2-I, 4-OCF₃ |
| 488 | Pr | Pr | 2-I, 4-OEtF |
| 489 | Pr | Pr | 2-I, 4-OPrF |
| 490 | Pr | Pr | 2-OH, 4-I |
| 491 | Pr | Pr | 2-OMe, 4-I |
| 492 | Pr | Pr | 2-OMeF, 4-I |
| 493 | Pr | Pr | 2-OCF₃, 4-I |
| 494 | Pr | Pr | 2-OEtF, 4-I |
| 495 | Pr | Pr | 2-OPrF, 4-I |
| 496 | Pr | Pr | 2-SnMe₃, 4-OH |
| 497 | Pr | Pr | 2-SnMe₃, 4-OMe |
| 498 | Pr | Pr | 2-SnMe₃, 4-OMeF |
| 499 | Pr | Pr | 2-SnMe₃, 4-OCF₃ |
| 500 | Pr | Pr | 2-SnMe₃, 4-OEtF |
| 501 | Pr | Pr | 2-SnMe₃, 4-OPrF |
| 502 | Pr | Pr | 2-OH, 4-SnMe₃ |
| 503 | Pr | Pr | 2-OMe, 4-SnMe₃ |
| 504 | Pr | Pr | 2-OMeF, 4-SnMe₃ |
| 505 | Pr | Pr | 2-OCF₃, 4-SnMe₃ |
| 506 | Pr | Pr | 2-OEtF, 4-SnMe₃ |
| 507 | Pr | Pr | 2-OPrF, 4-SnMe₃ |
| 508 | Pr | Pr—F | H |
| 509 | Pr | Pr—F | 2-t-Bu |
| 510 | Pr | Pr—F | 2-Br |
| 511 | Pr | Pr—F | 3-Br |
| 512 | Pr | Pr—F | 4-Br |
| 513 | Pr | Pr—F | 2-I |
| 514 | Pr | Pr—F | 3-I |
| 515 | Pr | Pr—F | 4-I |
| 516 | Pr | Pr—F | 2-SnMe₃ |
| 517 | Pr | Pr—F | 3-SnMe₃ |
| 518 | Pr | Pr—F | 4-SnMe₃ |
| 519 | Pr | Pr—F | 2-Me |
| 520 | Pr | Pr—F | 3-Me |
| 521 | Pr | Pr—F | 4-Me |
| 522 | Pr | Pr—F | 2-OH |
| 523 | Pr | Pr—F | 3-OH |
| 524 | Pr | Pr—F | 4-OH |
| 525 | Pr | Pr—F | 2-OMe |
| 526 | Pr | Pr—F | 3-OMe |
| 527 | Pr | Pr—F | 4-OMe |
| 528 | Pr | Pr—F | 2-OMeF |
| 529 | Pr | Pr—F | 3-OMeF |
| 530 | Pr | Pr—F | 4-OMeF |
| 531 | Pr | Pr—F | 2-OCF₃ |
| 532 | Pr | Pr—F | 3-OCF₃ |
| 533 | Pr | Pr—F | 4-OCF₃ |
| 534 | Pr | Pr—F | 2-OEtF |
| 535 | Pr | Pr—F | 3-OEtF |
| 536 | Pr | Pr—F | 4-OEtF |
| 537 | Pr | Pr—F | 2-OPrF |
| 538 | Pr | Pr—F | 3-OPrF |
| 539 | Pr | Pr—F | 4-OPrF |
| 540 | Pr | Pr—F | 2-SH |
| 541 | Pr | Pr—F | 3-SH |
| 542 | Pr | Pr—F | 4-SH |
| 543 | Pr | Pr—F | 2-SMe |
| 544 | Pr | Pr—F | 3-SMe |
| 545 | Pr | Pr—F | 4-SMe |
| 546 | Pr | Pr—F | 2-SMeF |
| 547 | Pr | Pr—F | 3-SMeF |
| 548 | Pr | Pr—F | 4-SMeF |
| 549 | Pr | Pr—F | 2-SCF₃ |
| 550 | Pr | Pr—F | 3-SCF₃ |
| 551 | Pr | Pr—F | 4-SCF₃ |
| 552 | Pr | Pr—F | 2-SEtF |
| 553 | Pr | Pr—F | 3-SEtF |
| 554 | Pr | Pr—F | 4-SEtF |
| 555 | Pr | Pr—F | 2-SPrF |
| 556 | Pr | Pr—F | 3-SPrF |
| 557 | Pr | Pr—F | 4-SPrF |
| 558 | Pr | Pr—F | 2-OMe, 4-OMe |
| 559 | Pr | Pr—F | 2-Me, 5-OH |
| 560 | Pr | Pr—F | 2-Me, 5-OMe |
| 561 | Pr | Pr—F | 2-Me, 5-OMeF |
| 562 | Pr | Pr—F | 2-Me, 5-OEtF |
| 563 | Pr | Pr—F | 2-Me, 5-OPrF |
| 564 | Pr | Pr—F | 2-Me, 4-OH |
| 565 | Pr | Pr—F | 2-Me, 4-OMe |
| 566 | Pr | Pr—F | 2-Me, 4-OMeF |
| 567 | Pr | Pr—F | 2-Me, 4-OCF₃ |
| 568 | Pr | Pr—F | 2-Me, 4-OEtF |
| 569 | Pr | Pr—F | 2-Me, 4-OPrF |
| 570 | Pr | Pr—F | 2-OH, 4-Me |
| 571 | Pr | Pr—F | 2-OMe, 4-Me |
| 572 | Pr | Pr—F | 2-OMeF, 4-Me |
| 573 | Pr | Pr—F | 2-OCF₃, 4-Me |
| 574 | Pr | Pr—F | 2-OEtF, 4-Me |
| 575 | Pr | Pr—F | 2-OPrF, 4-Me |
| 576 | Pr | Pr—F | 2-Cl, 4-OH |
| 577 | Pr | Pr—F | 2-Cl, 4-OMe |
| 578 | Pr | Pr—F | 2-Cl, 4-OMeF |
| 579 | Pr | Pr—F | 2-Cl, 4-OCF₃ |
| 580 | Pr | Pr—F | 2-Cl, 4-OEtF |

TABLE 1-continued

Substituent list for compounds of general structure VI.

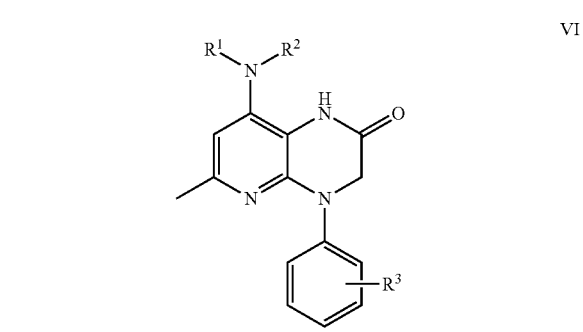

| Compound # | R¹ = | R² = | R³ = |
|---|---|---|---|
| 581 | Pr | Pr—F | 2-Cl, 4-OPrF |
| 582 | Pr | Pr—F | 2-F, 4-F |
| 583 | Pr | Pr—F | 2-Cl, 4-Cl |
| 584 | Pr | Pr—F | 2-Cl, 4-F |
| 585 | Pr | Pr—F | 2-Cl, 4-NO$_2$ |
| 586 | Pr | Pr—F | 2-Cl, 4-NH$_2$ |
| 587 | Pr | Pr—F | 2-Cl, 4-NHMe |
| 588 | Pr | Pr—F | 2-Cl, 4-NMe$_2$ |
| 589 | Pr | Pr—F | 2-Cl, 4-NMe$_3$OTf |
| 590 | Pr | Pr—F | 2-Cl, 4-NMe$_3$I |
| 591 | Pr | Pr—F | 2-Cl, 5-F |
| 592 | Pr | Pr—F | 2-Cl, 5-NO$_2$ |
| 593 | Pr | Pr—F | 2-Cl, 5-NH$_2$ |
| 594 | Pr | Pr—F | 2-Cl, 5-NHMe |
| 595 | Pr | Pr—F | 2-Cl, 5-NMe$_2$ |
| 596 | Pr | Pr—F | 2-Cl, 5-NMe$_3$OTf |
| 597 | Pr | Pr—F | 2-Cl, 5-NMe$_3$I |
| 598 | Pr | Pr—F | 2-F, 4-Cl |
| 599 | Pr | Pr—F | 2-NO$_2$, 4-Cl |
| 600 | Pr | Pr—F | 2-NH$_2$, 4-Cl |
| 601 | Pr | Pr—F | 2-NHMe, 4-Cl |
| 602 | Pr | Pr—F | 2-NMe$_2$, 4-Cl |
| 603 | Pr | Pr—F | 2-NMe$_3$OTf, 4-Cl |
| 604 | Pr | Pr—F | 2-NMe$_3$I, 4-Cl |
| 605 | Pr | Pr—F | 2-F, 5-Cl |
| 606 | Pr | Pr—F | 2-NO$_2$, 5-Cl |
| 607 | Pr | Pr—F | 2-NH$_2$, 5-Cl |
| 608 | Pr | Pr—F | 2-NHMe, 5-Cl |
| 609 | Pr | Pr—F | 2-NMe$_2$, 5-Cl |
| 610 | Pr | Pr—F | 2-NMe$_3$OTf, 5-Cl |
| 611 | Pr | Pr—F | 2-NMe$_3$I, 5-Cl |
| 612 | Pr | Pr—F | 2-Br, 4-F |
| 613 | Pr | Pr—F | 2-Br, 4-NO$_2$ |
| 614 | Pr | Pr—F | 2-Br, 4-NH$_2$ |
| 615 | Pr | Pr—F | 2-Br, 4-NHMe |
| 616 | Pr | Pr—F | 2-Br, 4-NMe$_2$ |
| 617 | Pr | Pr—F | 2-Br, 4-NMe$_3$OTf |
| 618 | Pr | Pr—F | 2-Br, 4-NMe$_3$I |
| 619 | Pr | Pr—F | 2-Br, 5-F |
| 620 | Pr | Pr—F | 2-Br, 5-NO$_2$ |
| 621 | Pr | Pr—F | 2-Br, 5-NH$_2$ |
| 622 | Pr | Pr—F | 2-Br, 5-NHMe |
| 623 | Pr | Pr—F | 2-Br, 5-NMe$_2$ |
| 624 | Pr | Pr—F | 2-Br, 5-NMe$_3$OTf |
| 625 | Pr | Pr—F | 2-Br, 5-NMe$_3$I |
| 626 | Pr | Pr—F | 2-F, 4-Br |
| 627 | Pr | Pr—F | 2-NO$_2$, 4-Br |
| 628 | Pr | Pr—F | 2-NH$_2$, 4-Br |
| 629 | Pr | Pr—F | 2-NHMe, 4-Br |
| 630 | Pr | Pr—F | 2-NMe$_2$, 4-Br |
| 631 | Pr | Pr—F | 2-NMe$_3$OTf, 4-Br |
| 632 | Pr | Pr—F | 2-NMe$_3$I, 4-Br |
| 633 | Pr | Pr—F | 2-I, 4-F |
| 634 | Pr | Pr—F | 2-I, 4-NO$_2$ |
| 635 | Pr | Pr—F | 2-I, 4-NH$_2$ |
| 636 | Pr | Pr—F | 2-I, 4-NHMe |
| 637 | Pr | Pr—F | 2-I, 4-NMe$_2$ |
| 638 | Pr | Pr—F | 2-I, 4-NMe$_3$OTf |
| 639 | Pr | Pr—F | 2-I, 4-NMe$_3$I |
| 640 | Pr | Pr—F | 2-F, 4-I |
| 641 | Pr | Pr—F | 2-NO$_2$, 4-I |
| 642 | Pr | Pr—F | 2-NH$_2$, 4-I |
| 643 | Pr | Pr—F | 2-NHMe, 4-I |
| 644 | Pr | Pr—F | 2-NMe$_2$, 4-I |
| 645 | Pr | Pr—F | 2-NMe$_3$OTf, 4-I |
| 646 | Pr | Pr—F | 2-NMe$_3$I, 4-I |
| 647 | Pr | Pr—F | 2-Me, 3-F |
| 648 | Pr | Pr—F | 2-Me, 3-NO$_2$ |
| 649 | Pr | Pr—F | 2-Me, 3-NH$_2$ |
| 650 | Pr | Pr—F | 2-Me, 3-NHMe |
| 651 | Pr | Pr—F | 2-Me, 3-NMe$_2$ |
| 652 | Pr | Pr—F | 2-Me, 3-NMe$_3$OTf |
| 653 | Pr | Pr—F | 2-Me, 3-NMe$_3$I |
| 654 | Pr | Pr—F | 2-Me, 4-F |
| 655 | Pr | Pr—F | 2-Me, 4-NO$_2$ |
| 656 | Pr | Pr—F | 2-Me, 4-NH$_2$ |
| 657 | Pr | Pr—F | 2-Me, 4-NHMe |
| 658 | Pr | Pr—F | 2-Me, 4-NMe$_2$ |
| 659 | Pr | Pr—F | 2-Me, 4-NMe$_3$OTf |
| 660 | Pr | Pr—F | 2-Me, 4-NMe$_3$I |
| 661 | Pr | Pr—F | 2-Me, 5-F |
| 662 | Pr | Pr—F | 2-Me, 5-NO$_2$ |
| 663 | Pr | Pr—F | 2-Me, 5-NH$_2$ |
| 664 | Pr | Pr—F | 2-Me, 5-NHMe |
| 665 | Pr | Pr—F | 2-Me, 5-NMe$_2$ |
| 666 | Pr | Pr—F | 2-Me, 5-NMe$_3$OTf |
| 667 | Pr | Pr—F | 2-Me, 5-NMe$_3$I |
| 668 | Pr | Pr—F | 2-F, 4-Me |
| 669 | Pr | Pr—F | 2-NO$_2$, 4-Me |
| 670 | Pr | Pr—F | 2-NH$_2$, 4-Me |
| 671 | Pr | Pr—F | 2-NHMe, 4-Me |
| 672 | Pr | Pr—F | 2-NMe$_2$, 4-Me |
| 673 | Pr | Pr—F | 2-NMe$_3$, 4-Me |
| 674 | Pr | Pr—F | 2-NMe$_3$OTf, 4-Me |
| 675 | Pr | Pr—F | 2-NMe$_3$I, 4-Me |
| 676 | Pr | Pr—F | 2-SnMe$_3$, 4-F |
| 677 | Pr | Pr—F | 2-SnMe$_3$, 5-F |
| 678 | Pr | Pr—F | 2-F, 4-SnMe$_3$ |
| 679 | Pr | Pr—F | 2-Br, 6-Cl, 4-F |
| 680 | Pr | Pr—F | 2-Br, 6-Cl, 4-NO$_2$ |
| 681 | Pr | Pr—F | 2-Br, 6-Cl, 4-NH$_2$ |
| 682 | Pr | Pr—F | 2-Br, 6-Cl, 4-NHMe |
| 683 | Pr | Pr—F | 2-Br, 6-Cl, 4-NMe$_2$ |
| 684 | Pr | Pr—F | 2-Br, 6-Cl, 4-NMe$_3$OTf |
| 685 | Pr | Pr—F | 2-Br, 6-Cl, 4-NMe$_3$I |
| 686 | Pr | Pr—F | 2-Me, 6-Cl, 4-F |
| 687 | Pr | Pr—F | 2-SnMe$_3$, 6-Cl, 4-F |
| 688 | Pr | Pr—F | 2-Cl, 4-Me |
| 689 | Pr | Pr—F | 2-Cl, 4-Br |
| 690 | Pr | Pr—F | 2-Cl, 4-SnMe$_3$ |
| 691 | Pr | Pr—F | 2-Br, 4-Cl |
| 692 | Pr | Pr—F | 2-SnMe$_3$, 4-Cl |
| 693 | Pr | Pr—F | 2-Me, 4-Cl |
| 694 | Pr | Pr—F | 2-Br, 4-I |
| 695 | Pr | Pr—F | 2-Br, 4-Me |
| 696 | Pr | Pr—F | 2-Br, 4-SnMe$_3$ |
| 697 | Pr | Pr—F | 2-SnMe$_3$, 4-Br |
| 698 | Pr | Pr—F | 2-Me, 4-Br |
| 699 | Pr | Pr—F | 2-Me, 4-SnMe$_3$ |

TABLE 1-continued

Substituent list for compounds of general structure VI.

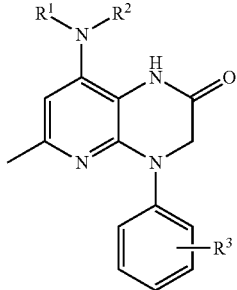

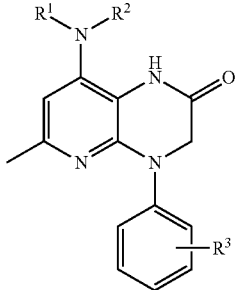

| Compound # | R¹ = | R² = | R³ = |
|---|---|---|---|
| 700 | Pr | Pr—F | 2-SnMe₃, 4-Me |
| 701 | Pr | Pr—F | 2-Me, 4-Me |
| 702 | Pr | Pr—F | 2-Et, 4-Br |
| 703 | Pr | Pr—F | 2-Et, 4-SnMe₃ |
| 704 | Pr | Pr—F | 2-Et, 4-Me |
| 705 | Pr | Pr—F | 2-Me, 4-Me, 6-Me |
| 706 | Pr | Pr—F | 2-Me, 4-Br, 6-Me |
| 707 | Pr | Pr—F | 2-Me, 4-SnMe₃, 6-Me |
| 708 | Pr | Pr—F | 2-Et, 6-Me |
| 709 | Pr | Pr—F | 2-Br, 4-i-Pr |
| 710 | Pr | Pr—F | 2-SnMe₃, 4-i-Pr |
| 711 | Pr | Pr—F | 2-Me, 4-i-Pr |
| 712 | Pr | Pr—F | 2-Br, 4-Br, 6-Br |
| 713 | Pr | Pr—F | 2-Br, 4-Me, 6-Br |
| 714 | Pr | Pr—F | 2-Br, 4-SnMe₃, 6-Br |
| 715 | Pr | Pr—F | 2-SnMe₃, 4-Br, 6-Br |
| 716 | Pr | Pr—F | 2-Br, 4-Br, 6-Me |
| 717 | Pr | Pr—F | 2-Br, 4-CF₃, 6-Br |
| 718 | Pr | Pr—F | 2-Br, 4-Br, 6-CF₃ |
| 719 | Pr | Pr—F | 2-CF₃, 4-CF₃ |
| 720 | Pr | Pr—F | 2-Cl, 4-CF₃ |
| 721 | Pr | Pr—F | 2-CF₃, 4-Cl |
| 722 | Pr | Pr—F | 2-Br, 4-CF₃ |
| 723 | Pr | Pr—F | 2-SnMe₃, 4-CF₃ |
| 724 | Pr | Pr—F | 2-Me, 4-CF₃ |
| 725 | Pr | Pr—F | 2-CF₃, 4-Br |
| 726 | Pr | Pr—F | 2-CF₃, 4-SnMe₃ |
| 727 | Pr | Pr—F | 2-CF₃, 4-Me |
| 728 | Pr | Pr—F | 2-Br, 4-OH |
| 729 | Pr | Pr—F | 2-Br, 4-OMe |
| 730 | Pr | Pr—F | 2-Br, 4-OMeF |
| 731 | Pr | Pr—F | 2-Br, 4-OCF₃ |
| 732 | Pr | Pr—F | 2-Br, 4-OEtF |
| 733 | Pr | Pr—F | 2-Br, 4-OPrF |
| 734 | Pr | Pr—F | 2-OH, 4-Br |
| 735 | Pr | Pr—F | 2-OMe, 4-Br |
| 736 | Pr | Pr—F | 2-OMeF, 4-Br |
| 737 | Pr | Pr—F | 2-OCF₃, 4-Br |
| 738 | Pr | Pr—F | 2-OEtF, 4-Br |
| 739 | Pr | Pr—F | 2-OPrF, 4-Br |
| 740 | Pr | Pr—F | 2-I, 4-OH |
| 741 | Pr | Pr—F | 2-I, 4-OMe |
| 742 | Pr | Pr—F | 2-I, 4-OMeF |
| 743 | Pr | Pr—F | 2-I, 4-OCF₃ |
| 744 | Pr | Pr—F | 2-I, 4-OEtF |
| 745 | Pr | Pr—F | 2-I, 4-OPrF |
| 746 | Pr | Pr—F | 2-OH, 4-I |
| 747 | Pr | Pr—F | 2-OMe, 4-I |
| 748 | Pr | Pr—F | 2-OMeF, 4-I |
| 749 | Pr | Pr—F | 2-OCF₃, 4-I |
| 750 | Pr | Pr—F | 2-OEtF, 4-I |
| 751 | Pr | Pr—F | 2-OPrF, 4-I |
| 752 | Pr | Pr—F | 2-SnMe₃, 4-OH |
| 753 | Pr | Pr—F | 2-SnMe₃, 4-OMe |
| 754 | Pr | Pr—F | 2-SnMe₃, 4-OMeF |
| 755 | Pr | Pr—F | 2-SnMe₃, 4-OCF₃ |
| 756 | Pr | Pr—F | 2-SnMe₃, 4-OEtF |
| 757 | Pr | Pr—F | 2-SnMe₃, 4-OPrF |
| 758 | Pr | Pr—F | 2-OH, 4-SnMe₃ |
| 759 | Pr | Pr—F | 2-OMe, 4-SnMe₃ |
| 760 | Pr | Pr—F | 2-OMeF, 4-SnMe₃ |
| 761 | Pr | Pr—F | 2-OCF₃, 4-SnMe₃ |
| 762 | Pr | Pr—F | 2-OEtF, 4-SnMe₃ |
| 763 | Pr | Pr—F | 2-OPrF, 4-SnMe₃ |
| 764 | Pr | Et—F | H |
| 765 | Pr | Et—F | 2-t-Bu |
| 766 | Pr | Et—F | 2-Br |
| 767 | Pr | Et—F | 3-Br |
| 768 | Pr | Et—F | 4-Br |
| 769 | Pr | Et—F | 2-I |
| 770 | Pr | Et—F | 3-I |
| 771 | Pr | Et—F | 4-I |
| 772 | Pr | Et—F | 2-SnMe₃ |
| 773 | Pr | Et—F | 3-SnMe₃ |
| 774 | Pr | Et—F | 4-SnMe₃ |
| 775 | Pr | Et—F | 2-Me |
| 776 | Pr | Et—F | 3-Me |
| 777 | Pr | Et—F | 4-Me |
| 778 | Pr | Et—F | 2-OH |
| 779 | Pr | Et—F | 3-OH |
| 780 | Pr | Et—F | 4-OH |
| 781 | Pr | Et—F | 2-OMe |
| 782 | Pr | Et—F | 3-OMe |
| 783 | Pr | Et—F | 4-OMe |
| 784 | Pr | Et—F | 2-OMeF |
| 785 | Pr | Et—F | 3-OMeF |
| 786 | Pr | Et—F | 4-OMeF |
| 787 | Pr | Et—F | 2-OCF₃ |
| 788 | Pr | Et—F | 3-OCF₃ |
| 789 | Pr | Et—F | 4-OCF₃ |
| 790 | Pr | Et—F | 2-OEtF |
| 791 | Pr | Et—F | 3-OEtF |
| 792 | Pr | Et—F | 4-OEtF |
| 793 | Pr | Et—F | 2-OPrF |
| 794 | Pr | Et—F | 3-OPrF |
| 795 | Pr | Et—F | 4-OPrF |
| 796 | Pr | Et—F | 2-SH |
| 797 | Pr | Et—F | 3-SH |
| 798 | Pr | Et—F | 4-SH |
| 799 | Pr | Et—F | 2-SMe |
| 800 | Pr | Et—F | 3-SMe |
| 801 | Pr | Et—F | 4-SMe |
| 802 | Pr | Et—F | 2-SMeF |
| 803 | Pr | Et—F | 3-SMeF |
| 804 | Pr | Et—F | 4-SMeF |
| 805 | Pr | Et—F | 2-SCF₃ |
| 806 | Pr | Et—F | 3-SCF₃ |
| 807 | Pr | Et—F | 4-SCF₃ |
| 808 | Pr | Et—F | 2-SEtF |
| 809 | Pr | Et—F | 3-SEtF |
| 810 | Pr | Et—F | 4-SEtF |
| 811 | Pr | Et—F | 2-SPrF |
| 812 | Pr | Et—F | 3-SPrF |
| 813 | Pr | Et—F | 4-SPrF |
| 814 | Pr | Et—F | 2-OMe, 4-OMe |
| 815 | Pr | Et—F | 2-Me, 5-OH |
| 816 | Pr | Et—F | 2-Me, 5-OMe |
| 817 | Pr | Et—F | 2-Me, 5-OMeF |
| 818 | Pr | Et—F | 2-Me, 5-OEtF |
| 819 | Pr | Et—F | 2-Me, 5-OPrF |

TABLE 1-continued

Substituent list for compounds of general structure VI.

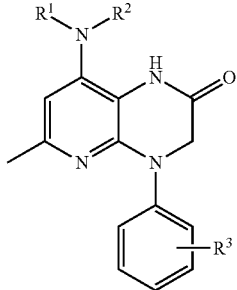

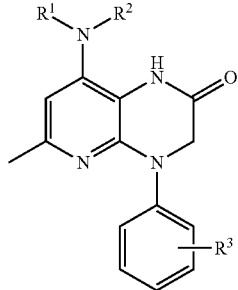

| Compound # | R¹ = | R² = | R³ = |
|---|---|---|---|
| 820 | Pr | Et—F | 2-Me, 4-OH |
| 821 | Pr | Et—F | 2-Me, 4-OMe |
| 822 | Pr | Et—F | 2-Me, 4-OMeF |
| 823 | Pr | Et—F | 2-Me, 4-OCF$_3$ |
| 824 | Pr | Et—F | 2-Me, 4-OEtF |
| 825 | Pr | Et—F | 2-Me, 4-OPrF |
| 826 | Pr | Et—F | 2-OH, 4-Me |
| 827 | Pr | Et—F | 2-OMe, 4-Me |
| 828 | Pr | Et—F | 2-OMeF, 4-Me |
| 829 | Pr | Et—F | 2-OCF$_3$, 4-Me |
| 830 | Pr | Et—F | 2-OEtF, 4-Me |
| 831 | Pr | Et—F | 2-OPrF, 4-Me |
| 832 | Pr | Et—F | 2-Cl, 4-OH |
| 833 | Pr | Et—F | 2-Cl, 4-OMe |
| 834 | Pr | Et—F | 2-Cl, 4-OMeF |
| 835 | Pr | Et—F | 2-Cl, 4-OCF$_3$ |
| 836 | Pr | Et—F | 2-Cl, 4-OEtF |
| 837 | Pr | Et—F | 2-Cl, 4-OPrF |
| 838 | Pr | Et—F | 2-F, 4-F |
| 839 | Pr | Et—F | 2-Cl, 4-Cl |
| 840 | Pr | Et—F | 2-Cl, 4-F |
| 841 | Pr | Et—F | 2-Cl, 4-NO$_2$ |
| 842 | Pr | Et—F | 2-Cl, 4-NH$_2$ |
| 843 | Pr | Et—F | 2-Cl, 4-NHMe |
| 844 | Pr | Et—F | 2-Cl, 4-NMe$_2$ |
| 845 | Pr | Et—F | 2-Cl, 4-NMe$_3$OTf |
| 846 | Pr | Et—F | 2-Cl, 4-NMe$_3$I |
| 847 | Pr | Et—F | 2-Cl, 5-F |
| 848 | Pr | Et—F | 2-Cl, 5-NO$_2$ |
| 849 | Pr | Et—F | 2-Cl, 5-NH$_2$ |
| 850 | Pr | Et—F | 2-Cl, 5-NHMe |
| 851 | Pr | Et—F | 2-Cl, 5-NMe$_2$ |
| 852 | Pr | Et—F | 2-Cl, 5-NMe$_3$OTf |
| 853 | Pr | Et—F | 2-Cl, 5-NMe$_3$I |
| 854 | Pr | Et—F | 2-F, 4-Cl |
| 855 | Pr | Et—F | 2-NO$_2$, 4-Cl |
| 856 | Pr | Et—F | 2-NH$_2$, 4-Cl |
| 857 | Pr | Et—F | 2-NHMe, 4-Cl |
| 858 | Pr | Et—F | 2-NMe$_2$, 4-Cl |
| 859 | Pr | Et—F | 2-NMe$_3$OTf, 4-Cl |
| 860 | Pr | Et—F | 2-NMe$_3$I, 4-Cl |
| 861 | Pr | Et—F | 2-F, 5-Cl |
| 862 | Pr | Et—F | 2-NO$_2$, 5-Cl |
| 863 | Pr | Et—F | 2-NH$_2$, 5-Cl |
| 864 | Pr | Et—F | 2-NHMe, 5-Cl |
| 865 | Pr | Et—F | 2-NMe$_2$, 5-Cl |
| 866 | Pr | Et—F | 2-NMe$_3$OTf, 5-Cl |
| 867 | Pr | Et—F | 2-NMe$_3$I, 5-Cl |
| 868 | Pr | Et—F | 2-Br, 4-F |
| 869 | Pr | Et—F | 2-Br, 4-NO$_2$ |
| 870 | Pr | Et—F | 2-Br, 4-NH$_2$ |
| 871 | Pr | Et—F | 2-Br, 4-NHMe |
| 872 | Pr | Et—F | 2-Br, 4-NMe$_2$ |
| 873 | Pr | Et—F | 2-Br, 4-NMe$_3$OTf |
| 874 | Pr | Et—F | 2-Br, 4-NMe$_3$I |
| 875 | Pr | Et—F | 2-Br, 5-F |
| 876 | Pr | Et—F | 2-Br, 5-NO$_2$ |
| 877 | Pr | Et—F | 2-Br, 5-NH$_2$ |
| 878 | Pr | Et—F | 2-Br, 5-NHMe |
| 879 | Pr | Et—F | 2-Br, 5-NMe$_2$ |
| 880 | Pr | Et—F | 2-Br, 5-NMe$_3$OTf |
| 881 | Pr | Et—F | 2-Br, 5-NMe$_3$I |
| 882 | Pr | Et—F | 2-F, 4-Br |
| 883 | Pr | Et—F | 2-NO$_2$, 4-Br |
| 884 | Pr | Et—F | 2-NH$_2$, 4-Br |
| 885 | Pr | Et—F | 2-NHMe, 4-Br |
| 886 | Pr | Et—F | 2-NMe$_2$, 4-Br |
| 887 | Pr | Et—F | 2-NMe$_3$OTf, 4-Br |
| 888 | Pr | Et—F | 2-NMe$_3$I, 4-Br |
| 889 | Pr | Et—F | 2-I, 4-F |
| 890 | Pr | Et—F | 2-I, 4-NO$_2$ |
| 891 | Pr | Et—F | 2-I, 4-NH$_2$ |
| 892 | Pr | Et—F | 2-I, 4-NHMe |
| 893 | Pr | Et—F | 2-I, 4-NMe$_2$ |
| 894 | Pr | Et—F | 2-I, 4-NMe$_3$OTf |
| 895 | Pr | Et—F | 2-I, 4-NMe$_3$I |
| 896 | Pr | Et—F | 2-F, 4-I |
| 897 | Pr | Et—F | 2-NO$_2$, 4-I |
| 898 | Pr | Et—F | 2-NH$_2$, 4-I |
| 899 | Pr | Et—F | 2-NHMe, 4-I |
| 900 | Pr | Et—F | 2-NMe$_2$, 4-I |
| 901 | Pr | Et—F | 2-NMe$_3$OTf, 4-I |
| 902 | Pr | Et—F | 2-NMe$_3$I, 4-I |
| 903 | Pr | Et—F | 2-Me, 3-F |
| 904 | Pr | Et—F | 2-Me, 3-NO$_2$ |
| 905 | Pr | Et—F | 2-Me, 3-NH$_2$ |
| 906 | Pr | Et—F | 2-Me, 3-NHMe |
| 907 | Pr | Et—F | 2-Me, 3-NMe$_2$ |
| 908 | Pr | Et—F | 2-Me, 3-NMe$_3$OTf |
| 909 | Pr | Et—F | 2-Me, 3-NMe$_3$I |
| 910 | Pr | Et—F | 2-Me, 4-F |
| 911 | Pr | Et—F | 2-Me, 4-NO$_2$ |
| 912 | Pr | Et—F | 2-Me, 4-NH$_2$ |
| 913 | Pr | Et—F | 2-Me, 4-NHMe |
| 914 | Pr | Et—F | 2-Me, 4-NMe$_2$ |
| 915 | Pr | Et—F | 2-Me, 4-NMe$_3$OTf |
| 916 | Pr | Et—F | 2-Me, 4-NMe$_3$I |
| 917 | Pr | Et—F | 2-Me, 5-F |
| 918 | Pr | Et—F | 2-Me, 5-NO$_2$ |
| 919 | Pr | Et—F | 2-Me, 5-NH$_2$ |
| 920 | Pr | Et—F | 2-Me, 5-NHMe |
| 921 | Pr | Et—F | 2-Me, 5-NMe$_2$ |
| 922 | Pr | Et—F | 2-Me, 5-NMe$_3$OTf |
| 923 | Pr | Et—F | 2-Me, 5-NMe$_3$I |
| 924 | Pr | Et—F | 2-F, 4-Me |
| 925 | Pr | Et—F | 2-NO$_2$, 4-Me |
| 926 | Pr | Et—F | 2-NH$_2$, 4-Me |
| 927 | Pr | Et—F | 2-NHMe, 4-Me |
| 928 | Pr | Et—F | 2-NMe$_2$, 4-Me |
| 929 | Pr | Et—F | 2-NMe$_3$, 4-Me |
| 930 | Pr | Et—F | 2-NMe$_3$OTf, 4-Me |
| 931 | Pr | Et—F | 2-NMe$_3$I, 4-Me |
| 932 | Pr | Et—F | 2-SnMe$_3$, 4-F |
| 933 | Pr | Et—F | 2-SnMe$_3$, 5-F |
| 934 | Pr | Et—F | 2-F, 4-SnMe$_3$ |
| 935 | Pr | Et—F | 2-Br, 6-Cl, 4-F |
| 936 | Pr | Et—F | 2-Br, 6-Cl, 4-NO$_2$ |
| 937 | Pr | Et—F | 2-Br, 6-Cl, 4-NH$_2$ |
| 938 | Pr | Et—F | 2-Br, 6-Cl, 4-NHMe |
| 939 | Pr | Et—F | 2-Br, 6-Cl, 4-NMe$_2$ |

TABLE 1-continued

Substituent list for compounds of general structure VI.

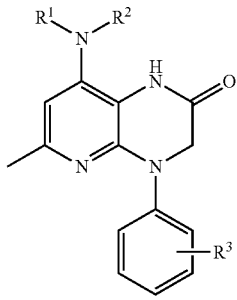

| Compound # | R¹ = | R² = | R³ = |
|---|---|---|---|
| 940 | Pr | Et—F | 2-Br, 6-Cl, 4-NMe₃OTf |
| 941 | Pr | Et—F | 2-Br, 6-Cl, 4-NMe₃I |
| 942 | Pr | Et—F | 2-Me, 6-Cl, 4-F |
| 943 | Pr | Et—F | 2-SnMe₃, 6-Cl, 4-F |
| 944 | Pr | Et—F | 2-Cl, 4-Me |
| 945 | Pr | Et—F | 2-Cl, 4-Br |
| 946 | Pr | Et—F | 2-Cl, 4-SnMe₃ |
| 947 | Pr | Et—F | 2-Br, 4-Cl |
| 948 | Pr | Et—F | 2-SnMe₃, 4-Cl |
| 949 | Pr | Et—F | 2-Me, 4-Cl |
| 950 | Pr | Et—F | 2-Br, 4-Br |
| 951 | Pr | Et—F | 2-Br, 4-Me |
| 952 | Pr | Et—F | 2-Br, 4-SnMe₃ |
| 953 | Pr | Et—F | 2-SnMe₃, 4-Br |
| 954 | Pr | Et—F | 2-Me, 4-Br |
| 955 | Pr | Et—F | 2-Me, 4-SnMe₃ |
| 956 | Pr | Et—F | 2-SnMe₃, 4-Me |
| 957 | Pr | Et—F | 2-Me, 4-Me |
| 958 | Pr | Et—F | 2-Et, 4-Br |
| 959 | Pr | Et—F | 2-Et, 4-SnMe₃ |
| 960 | Pr | Et—F | 2-Et, 4-Me |
| 961 | Pr | Et—F | 2-Me, 4-Me, 6-Me |
| 962 | Pr | Et—F | 2-Me, 4-Br, 6-Me |
| 963 | Pr | Et—F | 2-Me, 4-SnMe₃, 6-Me |
| 964 | Pr | Et—F | 2-Et, 6-Me |
| 965 | Pr | Et—F | 2-Br, 4-i-Pr |
| 966 | Pr | Et—F | 2-SnMe₃, 4-i-Pr |
| 967 | Pr | Et—F | 2-Me, 4-i-Pr |
| 968 | Pr | Et—F | 2-Br, 4-Br, 6-Br |
| 969 | Pr | Et—F | 2-Br, 4-Me, 6-Br |
| 970 | Pr | Et—F | 2-Br, 4-SnMe₃, 6-Br |
| 971 | Pr | Et—F | 2-SnMe₃, 4-Br, 6-Br |
| 972 | Pr | Et—F | 2-Br, 4-Br, 6-Me |
| 973 | Pr | Et—F | 2-Br, 4-CF₃, 6-Br |
| 974 | Pr | Et—F | 2-Br, 4-Br, 6-CF₃ |
| 975 | Pr | Et—F | 2-CF₃, 4-CF₃ |
| 976 | Pr | Et—F | 2-Cl, 4-CF₃ |
| 977 | Pr | Et—F | 2-CF₃, 4-Cl |
| 978 | Pr | Et—F | 2-Br, 4-CF₃ |
| 979 | Pr | Et—F | 2-SnMe₃, 4-CF₃ |
| 980 | Pr | Et—F | 2-Me, 4-CF₃ |
| 981 | Pr | Et—F | 2-CF₃, 4-Br |
| 982 | Pr | Et—F | 2-CF₃, 4-SnMe₃ |
| 983 | Pr | Et—F | 2-CF₃, 4-Me |
| 984 | Pr | Et—F | 2-Br, 4-OH |
| 985 | Pr | Et—F | 2-Br, 4-OMe |
| 986 | Pr | Et—F | 2-Br, 4-OMeF |
| 987 | Pr | Et—F | 2-Br, 4-OCF₃ |
| 988 | Pr | Et—F | 2-Br, 4-OEtF |
| 989 | Pr | Et—F | 2-Br, 4-OPrF |
| 990 | Pr | Et—F | 2-OH, 4-Br |
| 991 | Pr | Et—F | 2-OMe, 4-Br |
| 992 | Pr | Et—F | 2-OMeF, 4-Br |
| 993 | Pr | Et—F | 2-OCF₃, 4-Br |
| 994 | Pr | Et—F | 2-OEtF, 4-Br |
| 995 | Pr | Et—F | 2-OPrF, 4-Br |
| 996 | Pr | Et—F | 2-I, 4-OH |
| 997 | Pr | Et—F | 2-I, 4-OMe |
| 998 | Pr | Et—F | 2-I, 4-OMeF |
| 999 | Pr | Et—F | 2-I, 4-OCF₃ |

TABLE 1-continued

Substituent list for compounds of general structure VI.

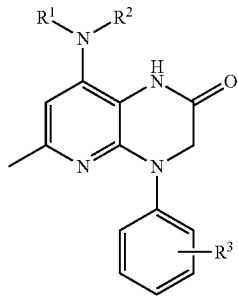

| Compound # | R¹ = | R² = | R³ = |
|---|---|---|---|
| 1000 | Pr | Et—F | 2-I, 4-OEtF |
| 1001 | Pr | Et—F | 2-I, 4-OPrF |
| 1002 | Pr | Et—F | 2-OH, 4-I |
| 1003 | Pr | Et—F | 2-OMe, 4-I |
| 1004 | Pr | Et—F | 2-OMeF, 4-I |
| 1005 | Pr | Et—F | 2-OCF₃, 4-I |
| 1006 | Pr | Et—F | 2-OEtF, 4-I |
| 1007 | Pr | Et—F | 2-OPrF, 4-I |
| 1008 | Pr | Et—F | 2-SnMe₃, 4-OH |
| 1009 | Pr | Et—F | 2-SnMe₃, 4-OMe |
| 1010 | Pr | Et—F | 2-SnMe₃, 4-OMeF |
| 1011 | Pr | Et—F | 2-SnMe₃, 4-OCF₃ |
| 1012 | Pr | Et—F | 2-SnMe₃, 4-OEtF |
| 1013 | Pr | Et—F | 2-SnMe₃, 4-OPrF |
| 1014 | Pr | Et—F | 2-OH, 4-SnMe₃ |
| 1015 | Pr | Et—F | 2-OMe, 4-SnMe₃ |
| 1016 | Pr | Et—F | 2-OMeF, 4-SnMe₃ |
| 1017 | Pr | Et—F | 2-OCF₃, 4-SnMe₃ |
| 1018 | Pr | Et—F | 2-OEtF, 4-SnMe₃ |
| 1019 | Pr | Et—F | 2-OPrF, 4-SnMe₃ |
| 1020 | Pr—F | Et | H |
| 1021 | Pr—F | Et | 2-t-Bu |
| 1022 | Pr—F | Et | 2-Br |
| 1023 | Pr—F | Et | 3-Br |
| 1024 | Pr—F | Et | 4-Br |
| 1025 | Pr—F | Et | 2-I |
| 1026 | Pr—F | Et | 3-I |
| 1027 | Pr—F | Et | 4-I |
| 1028 | Pr—F | Et | 2-SnMe₃ |
| 1029 | Pr—F | Et | 3-SnMe₃ |
| 1030 | Pr—F | Et | 4-SnMe₃ |
| 1031 | Pr—F | Et | 2-Me |
| 1032 | Pr—F | Et | 3-Me |
| 1033 | Pr—F | Et | 4-Me |
| 1034 | Pr—F | Et | 2-OH |
| 1035 | Pr—F | Et | 3-OH |
| 1036 | Pr—F | Et | 4-OH |
| 1037 | Pr—F | Et | 2-OMe |
| 1038 | Pr—F | Et | 3-OMe |
| 1039 | Pr—F | Et | 4-OMe |
| 1040 | Pr—F | Et | 2-OMeF |
| 1041 | Pr—F | Et | 3-OMeF |
| 1042 | Pr—F | Et | 4-OMeF |
| 1043 | Pr—F | Et | 2-OCF₃ |
| 1044 | Pr—F | Et | 3-OCF₃ |
| 1045 | Pr—F | Et | 4-OCF₃ |
| 1046 | Pr—F | Et | 2-OEtF |
| 1047 | Pr—F | Et | 3-OEtF |
| 1048 | Pr—F | Et | 4-OEtF |
| 1049 | Pr—F | Et | 2-OPrF |
| 1050 | Pr—F | Et | 3-OPrF |
| 1051 | Pr—F | Et | 4-OPrF |
| 1052 | Pr—F | Et | 2-SH |
| 1053 | Pr—F | Et | 3-SH |
| 1054 | Pr—F | Et | 4-SH |
| 1055 | Pr—F | Et | 2-SMe |
| 1056 | Pr—F | Et | 3-SMe |
| 1057 | Pr—F | Et | 4-SMe |
| 1058 | Pr—F | Et | 2-SMeF |
| 1059 | Pr—F | Et | 3-SMeF |

TABLE 1-continued

Substituent list for compounds of general structure VI.

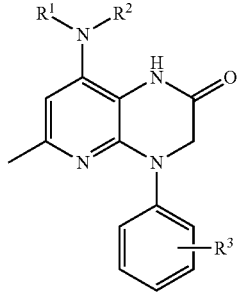

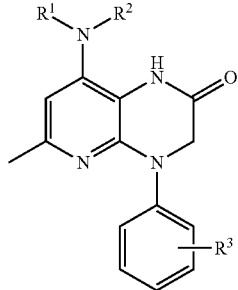

| Compound # | R¹ = | R² = | R³ = |
|---|---|---|---|
| 1060 | Pr—F | Et | 4-SMeF |
| 1061 | Pr—F | Et | 2-SCF₃ |
| 1062 | Pr—F | Et | 3-SCF₃ |
| 1063 | Pr—F | Et | 4-SCF₃ |
| 1064 | Pr—F | Et | 2-SEtF |
| 1065 | Pr—F | Et | 3-SEtF |
| 1066 | Pr—F | Et | 4-SEtF |
| 1067 | Pr—F | Et | 2-SPrF |
| 1068 | Pr—F | Et | 3-SPrF |
| 1069 | Pr—F | Et | 4-SPrF |
| 1070 | Pr—F | Et | 2-OMe, 4-OMe |
| 1071 | Pr—F | Et | 2-Me, 5-OH |
| 1072 | Pr—F | Et | 2-Me, 5-OMe |
| 1073 | Pr—F | Et | 2-Me, 5-OMeF |
| 1074 | Pr—F | Et | 2-Me, 5-OEtF |
| 1075 | Pr—F | Et | 2-Me, 5-OPrF |
| 1076 | Pr—F | Et | 2-Me, 4-OH |
| 1077 | Pr—F | Et | 2-Me, 4-OMe |
| 1078 | Pr—F | Et | 2-Me, 4-OMeF |
| 1079 | Pr—F | Et | 2-Me, 4-OCF₃ |
| 1080 | Pr—F | Et | 2-Me, 4-OEtF |
| 1081 | Pr—F | Et | 2-Me, 4-OPrF |
| 1082 | Pr—F | Et | 2-OH, 4-Me |
| 1083 | Pr—F | Et | 2-OMe, 4-Me |
| 1084 | Pr—F | Et | 2-OMeF, 4-Me |
| 1085 | Pr—F | Et | 2-OCF₃, 4-Me |
| 1086 | Pr—F | Et | 2-OEtF, 4-Me |
| 1087 | Pr—F | Et | 2-OPrF, 4-Me |
| 1088 | Pr—F | Et | 2-Cl, 4-OH |
| 1089 | Pr—F | Et | 2-Cl, 4-OMe |
| 1090 | Pr—F | Et | 2-Cl, 4-OMeF |
| 1091 | Pr—F | Et | 2-Cl, 4-OCF₃ |
| 1092 | Pr—F | Et | 2-Cl, 4-OEtF |
| 1093 | Pr—F | Et | 2-Cl, 4-OPrF |
| 1094 | Pr—F | Et | 2-F, 4-F |
| 1095 | Pr—F | Et | 2-Cl, 4-Cl |
| 1096 | Pr—F | Et | 2-Cl, 4-F |
| 1097 | Pr—F | Et | 2-Cl, 4-NO₂ |
| 1098 | Pr—F | Et | 2-Cl, 4-NH₂ |
| 1099 | Pr—F | Et | 2-Cl, 4-NHMe |
| 1100 | Pr—F | Et | 2-Cl, 4-NMe₂ |
| 1101 | Pr—F | Et | 2-Cl, 4-NMe₃OTf |
| 1102 | Pr—F | Et | 2-Cl, 4-NMe₃I |
| 1103 | Pr—F | Et | 2-Cl, 5-F |
| 1104 | Pr—F | Et | 2-Cl, 5-NO₂ |
| 1105 | Pr—F | Et | 2-Cl, 5-NH₂ |
| 1106 | Pr—F | Et | 2-Cl, 5-NHMe |
| 1107 | Pr—F | Et | 2-Cl, 5-NMe₂ |
| 1108 | Pr—F | Et | 2-Cl, 5-NMe₃OTf |
| 1109 | Pr—F | Et | 2-Cl, 5-NMe₃I |
| 1110 | Pr—F | Et | 2-F, 4-Cl |
| 1111 | Pr—F | Et | 2-NO₂, 4-Cl |
| 1112 | Pr—F | Et | 2-NH₂, 4-Cl |
| 1113 | Pr—F | Et | 2-NHMe, 4-Cl |
| 1114 | Pr—F | Et | 2-NMe₂, 4-Cl |
| 1115 | Pr—F | Et | 2-NMe₃OTf, 4-Cl |
| 1116 | Pr—F | Et | 2-NMe₃I, 4-Cl |
| 1117 | Pr—F | Et | 2-F, 5-Cl |
| 1118 | Pr—F | Et | 2-NO₂, 5-Cl |
| 1119 | Pr—F | Et | 2-NH₂, 5-Cl |
| 1120 | Pr—F | Et | 2-NHMe, 5-Cl |
| 1121 | Pr—F | Et | 2-NMe₂, 5-Cl |
| 1122 | Pr—F | Et | 2-NMe₃OTf, 5-Cl |
| 1123 | Pr—F | Et | 2-NMe₃I, 5-Cl |
| 1124 | Pr—F | Et | 2-Br, 4-F |
| 1125 | Pr—F | Et | 2-Br, 4-NO₂ |
| 1126 | Pr—F | Et | 2-Br, 4-NH₂ |
| 1127 | Pr—F | Et | 2-Br, 4-NHMe |
| 1128 | Pr—F | Et | 2-Br, 4-NMe₂ |
| 1129 | Pr—F | Et | 2-Br, 4-NMe₃OTf |
| 1130 | Pr—F | Et | 2-Br, 4-NMe₃I |
| 1131 | Pr—F | Et | 2-Br, 5-F |
| 1132 | Pr—F | Et | 2-Br, 5-NO₂ |
| 1133 | Pr—F | Et | 2-Br, 5-NH₂ |
| 1134 | Pr—F | Et | 2-Br, 5-NHMe |
| 1135 | Pr—F | Et | 2-Br, 5-NMe₂ |
| 1136 | Pr—F | Et | 2-Br, 5-NMe₃OTf |
| 1137 | Pr—F | Et | 2-Br, 5-NMe₃I |
| 1138 | Pr—F | Et | 2-F, 4-Br |
| 1139 | Pr—F | Et | 2-NO₂, 4-Br |
| 1140 | Pr—F | Et | 2-NH₂, 4-Br |
| 1141 | Pr—F | Et | 2-NHMe, 4-Br |
| 1142 | Pr—F | Et | 2-NMe₂, 4-Br |
| 1143 | Pr—F | Et | 2-NMe₃OTf, 4-Br |
| 1144 | Pr—F | Et | 2-NMe₃I, 4-Br |
| 1145 | Pr—F | Et | 2-I, 4-F |
| 1146 | Pr—F | Et | 2-I, 4-NO₂ |
| 1147 | Pr—F | Et | 2-I, 4-NH₂ |
| 1148 | Pr—F | Et | 2-I, 4-NHMe |
| 1149 | Pr—F | Et | 2-I, 4-NMe₂ |
| 1150 | Pr—F | Et | 2-I, 4-NMe₃OTf |
| 1151 | Pr—F | Et | 2-I, 4-NMe₃I |
| 1152 | Pr—F | Et | 2-F, 4-I |
| 1153 | Pr—F | Et | 2-NO₂, 4-I |
| 1154 | Pr—F | Et | 2-NH₂, 4-I |
| 1155 | Pr—F | Et | 2-NHMe, 4-I |
| 1156 | Pr—F | Et | 2-NMe₂, 4-I |
| 1157 | Pr—F | Et | 2-NMe₃OTf, 4-I |
| 1158 | Pr—F | Et | 2-NMe₃I, 4-I |
| 1159 | Pr—F | Et | 2-Me, 3-F |
| 1160 | Pr—F | Et | 2-Me, 3-NO₂ |
| 1161 | Pr—F | Et | 2-Me, 3-NH₂ |
| 1162 | Pr—F | Et | 2-Me, 3-NHMe |
| 1163 | Pr—F | Et | 2-Me, 3-NMe₂ |
| 1164 | Pr—F | Et | 2-Me, 3-NMe₃OTf |
| 1165 | Pr—F | Et | 2-Me, 3-NMe₃I |
| 1166 | Pr—F | Et | 2-Me, 4-F |
| 1167 | Pr—F | Et | 2-Me, 4-NO₂ |
| 1168 | Pr—F | Et | 2-Me, 4-NH₂ |
| 1169 | Pr—F | Et | 2-Me, 4-NHMe |
| 1170 | Pr—F | Et | 2-Me, 4-NMe₂ |
| 1171 | Pr—F | Et | 2-Me, 4-NMe₃OTf |
| 1172 | Pr—F | Et | 2-Me, 4-NMe₃I |
| 1173 | Pr—F | Et | 2-Me, 5-F |
| 1174 | Pr—F | Et | 2-Me, 5-NO₂ |
| 1175 | Pr—F | Et | 2-Me, 5-NH₂ |
| 1176 | Pr—F | Et | 2-Me, 5-NHMe |
| 1177 | Pr—F | Et | 2-Me, 5-NMe₂ |
| 1178 | Pr—F | Et | 2-Me, 5-NMe₃OTf |
| 1179 | Pr—F | Et | 2-Me, 5-NMe₃I |

TABLE 1-continued

Substituent list for compounds of general structure VI.

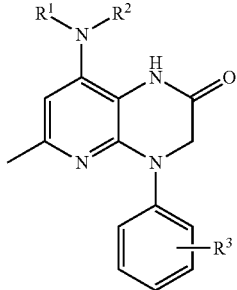

| Compound # | R¹ = | R² = | R³ = |
|---|---|---|---|
| 1180 | Pr—F | Et | 2-F, 4-Me |
| 1181 | Pr—F | Et | 2-NO₂, 4-Me |
| 1182 | Pr—F | Et | 2-NH₂, 4-Me |
| 1183 | Pr—F | Et | 2-NHMe, 4-Me |
| 1184 | Pr—F | Et | 2-NMe₂, 4-Me |
| 1185 | Pr—F | Et | 2-NMe₃, 4-Me |
| 1186 | Pr—F | Et | 2-NMe₃OTf, 4-Me |
| 1187 | Pr—F | Et | 2-NMe₃I, 4-Me |
| 1188 | Pr—F | Et | 2-SnMe₃, 4-F |
| 1189 | Pr—F | Et | 2-SnMe₃, 5-F |
| 1190 | Pr—F | Et | 2-F, 4-SnMe₃ |
| 1191 | Pr—F | Et | 2-Br, 6-Cl, 4-F |
| 1192 | Pr—F | Et | 2-Br, 6-Cl, 4-NO₂ |
| 1193 | Pr—F | Et | 2-Br, 6-Cl, 4-NH₂ |
| 1194 | Pr—F | Et | 2-Br, 6-Cl, 4-NHMe |
| 1195 | Pr—F | Et | 2-Br, 6-Cl, 4-NMe₂ |
| 1196 | Pr—F | Et | 2-Br, 6-Cl, 4-NMe₃OTf |
| 1197 | Pr—F | Et | 2-Br, 6-Cl, 4-NMe₃I |
| 1198 | Pr—F | Et | 2-Me, 6-Cl, 4-F |
| 1199 | Pr—F | Et | 2-SnMe₃, 6-Cl, 4-F |
| 1200 | Pr—F | Et | 2-Cl, 4-Me |
| 1201 | Pr—F | Et | 2-Cl, 4-Br |
| 1202 | Pr—F | Et | 2-Cl, 4-SnMe₃ |
| 1203 | Pr—F | Et | 2-Br, 4-Cl |
| 1204 | Pr—F | Et | 2-SnMe₃, 4-Cl |
| 1205 | Pr—F | Et | 2-Me, 4-Cl |
| 1206 | Pr—F | Et | 2-Br, 4-Br |
| 1207 | Pr—F | Et | 2-Br, 4-Me |
| 1208 | Pr—F | Et | 2-Br, 4-SnMe₃ |
| 1209 | Pr—F | Et | 2-SnMe₃, 4-Br |
| 1210 | Pr—F | Et | 2-Me, 4-Br |
| 1211 | Pr—F | Et | 2-Me, 4-SnMe₃ |
| 1212 | Pr—F | Et | 2-SnMe₃, 4-Me |
| 1213 | Pr—F | Et | 2-Me, 4-Me |
| 1214 | Pr—F | Et | 2-Et, 4-Br |
| 1215 | Pr—F | Et | 2-Et, 4-SnMe₃ |
| 1216 | Pr—F | Et | 2-Et, 4-Me |
| 1217 | Pr—F | Et | 2-Me, 4-Me, 6-Me |
| 1218 | Pr—F | Et | 2-Me, 4-Br, 6-Me |
| 1219 | Pr—F | Et | 2-Me, 4-SnMe₃, 6-Me |
| 1220 | Pr—F | Et | 2-Et, 6-Me |
| 1221 | Pr—F | Et | 2-Br, 4-i-Pr |
| 1222 | Pr—F | Et | 2-SnMe₃, 4-i-Pr |
| 1223 | Pr—F | Et | 2-Me, 4-i-Pr |
| 1224 | Pr—F | Et | 2-Br, 4-Br, 6-Br |
| 1225 | Pr—F | Et | 2-Br, 4-Me, 6-Br |
| 1226 | Pr—F | Et | 2-Br, 4-SnMe₃, 6-Br |
| 1227 | Pr—F | Et | 2-SnMe₃, 4-Br, 6-Br |
| 1228 | Pr—F | Et | 2-Br, 4-Br, 6-Me |
| 1229 | Pr—F | Et | 2-Br, 4-CF₃, 6-Br |
| 1230 | Pr—F | Et | 2-Br, 4-Br, 6-CF₃ |
| 1231 | Pr—F | Et | 2-CF₃, 4-CF₃ |
| 1232 | Pr—F | Et | 2-Cl, 4-CF₃ |
| 1233 | Pr—F | Et | 2-CF₃, 4-Cl |
| 1234 | Pr—F | Et | 2-Br, 4-CF₃ |
| 1235 | Pr—F | Et | 2-SnMe₃, 4-CF₃ |
| 1236 | Pr—F | Et | 2-Me, 4-CF₃ |
| 1237 | Pr—F | Et | 2-CF₃, 4-Br |
| 1238 | Pr—F | Et | 2-CF₃, 4-SnMe₃ |
| 1239 | Pr—F | Et | 2-CF₃, 4-Me |

TABLE 1-continued

Substituent list for compounds of general structure VI.

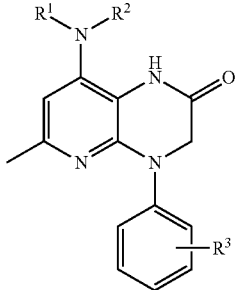

| Compound # | R¹ = | R² = | R³ = |
|---|---|---|---|
| 1240 | Pr—F | Et | 2-Br, 4-OH |
| 1241 | Pr—F | Et | 2-Br, 4-OMe |
| 1242 | Pr—F | Et | 2-Br, 4-OMeF |
| 1243 | Pr—F | Et | 2-Br, 4-OCF₃ |
| 1244 | Pr—F | Et | 2-Br, 4-OEtF |
| 1245 | Pr—F | Et | 2-Br, 4-OPrF |
| 1246 | Pr—F | Et | 2-OH, 4-Br |
| 1247 | Pr—F | Et | 2-OMe, 4-Br |
| 1248 | Pr—F | Et | 2-OMeF, 4-Br |
| 1249 | Pr—F | Et | 2-OCF₃, 4-Br |
| 1250 | Pr—F | Et | 2-OEtF, 4-Br |
| 1251 | Pr—F | Et | 2-OPrF, 4-Br |
| 1252 | Pr—F | Et | 2-I, 4-OH |
| 1253 | Pr—F | Et | 2-I, 4-OMe |
| 1254 | Pr—F | Et | 2-I, 4-OMeF |
| 1255 | Pr—F | Et | 2-I, 4-OCF₃ |
| 1256 | Pr—F | Et | 2-I, 4-OEtF |
| 1257 | Pr—F | Et | 2-I, 4-OPrF |
| 1258 | Pr—F | Et | 2-OH, 4-I |
| 1259 | Pr—F | Et | 2-OMe, 4-I |
| 1260 | Pr—F | Et | 2-OMeF, 4-I |
| 1261 | Pr—F | Et | 2-OCF₃, 4-I |
| 1262 | Pr—F | Et | 2-OEtF, 4-I |
| 1263 | Pr—F | Et | 2-OPrF, 4-I |
| 1264 | Pr—F | Et | 2-SnMe₃, 4-OH |
| 1265 | Pr—F | Et | 2-SnMe₃, 4-OMe |
| 1266 | Pr—F | Et | 2-SnMe₃, 4-OMeF |
| 1267 | Pr—F | Et | 2-SnMe₃, 4-OCF₃ |
| 1268 | Pr—F | Et | 2-SnMe₃, 4-OEtF |
| 1269 | Pr—F | Et | 2-SnMe₃, 4-OPrF |
| 1270 | Pr—F | Et | 2-OH, 4-SnMe₃ |
| 1271 | Pr—F | Et | 2-OMe, 4-SnMe₃ |
| 1272 | Pr—F | Et | 2-OMeF, 4-SnMe₃ |
| 1273 | Pr—F | Et | 2-OCF₃, 4-SnMe₃ |
| 1274 | Pr—F | Et | 2-OEtF, 4-SnMe₃ |
| 1275 | Pr—F | Et | 2-OPrF, 4-SnMe₃ |
| 1276 | Bu | Et—F | H |
| 1277 | Bu | Et—F | 2-t-Bu |
| 1278 | Bu | Et—F | 2-Br |
| 1279 | Bu | Et—F | 3-Br |
| 1280 | Bu | Et—F | 4-Br |
| 1281 | Bu | Et—F | 2-I |
| 1282 | Bu | Et—F | 3-I |
| 1283 | Bu | Et—F | 4-I |
| 1284 | Bu | Et—F | 2-SnMe₃ |
| 1285 | Bu | Et—F | 3-SnMe₃ |
| 1286 | Bu | Et—F | 4-SnMe₃ |
| 1287 | Bu | Et—F | 2-Me |
| 1288 | Bu | Et—F | 3-Me |
| 1289 | Bu | Et—F | 4-Me |
| 1290 | Bu | Et—F | 2-OH |
| 1291 | Bu | Et—F | 3-OH |
| 1292 | Bu | Et—F | 4-OH |
| 1293 | Bu | Et—F | 2-OMe |
| 1294 | Bu | Et—F | 3-OMe |
| 1295 | Bu | Et—F | 4-OMe |
| 1296 | Bu | Et—F | 2-OMeF |
| 1297 | Bu | Et—F | 3-OMeF |
| 1298 | Bu | Et—F | 4-OMeF |
| 1299 | Bu | Et—F | 2-OCF₃ |

TABLE 1-continued

Substituent list for compounds of general structure VI.

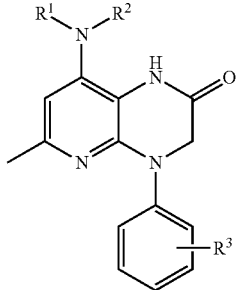

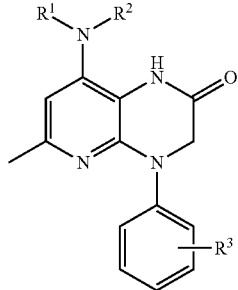

| Compound # | R¹ = | R² = | R³ = |
|---|---|---|---|
| 1300 | Bu | Et—F | 3-OCF₃ |
| 1301 | Bu | Et—F | 4-OCF₃ |
| 1302 | Bu | Et—F | 2-OEtF |
| 1303 | Bu | Et—F | 3-OEtF |
| 1304 | Bu | Et—F | 4-OEtF |
| 1305 | Bu | Et—F | 2-OPrF |
| 1306 | Bu | Et—F | 3-OPrF |
| 1307 | Bu | Et—F | 4-OPrF |
| 1308 | Bu | Et—F | 2-SH |
| 1309 | Bu | Et—F | 3-SH |
| 1310 | Bu | Et—F | 4-SH |
| 1311 | Bu | Et—F | 2-SMe |
| 1312 | Bu | Et—F | 3-SMe |
| 1313 | Bu | Et—F | 4-SMe |
| 1314 | Bu | Et—F | 2-SMeF |
| 1315 | Bu | Et—F | 3-SMeF |
| 1316 | Bu | Et—F | 4-SMeF |
| 1317 | Bu | Et—F | 2-SCF₃ |
| 1318 | Bu | Et—F | 3-SCF₃ |
| 1319 | Bu | Et—F | 4-SCF₃ |
| 1320 | Bu | Et—F | 2-SEtF |
| 1321 | Bu | Et—F | 3-SEtF |
| 1322 | Bu | Et—F | 4-SEtF |
| 1323 | Bu | Et—F | 2-SPrF |
| 1324 | Bu | Et—F | 3-SPrF |
| 1325 | Bu | Et—F | 4-SPrF |
| 1326 | Bu | Et—F | 2-OMe, 4-OMe |
| 1327 | Bu | Et—F | 2-Me, 5-OH |
| 1328 | Bu | Et—F | 2-Me, 5-OMe |
| 1329 | Bu | Et—F | 2-Me, 5-OMeF |
| 1330 | Bu | Et—F | 2-Me, 5-OEtF |
| 1331 | Bu | Et—F | 2-Me, 5-OPrF |
| 1332 | Bu | Et—F | 2-Me, 4-OH |
| 1333 | Bu | Et—F | 2-Me, 4-OMe |
| 1334 | Bu | Et—F | 2-Me, 4-OMeF |
| 1335 | Bu | Et—F | 2-Me, 4-OCF₃ |
| 1336 | Bu | Et—F | 2-Me, 4-OEtF |
| 1337 | Bu | Et—F | 2-Me, 4-OPrF |
| 1338 | Bu | Et—F | 2-OH, 4-Me |
| 1339 | Bu | Et—F | 2-OMe, 4-Me |
| 1340 | Bu | Et—F | 2-OMeF, 4-Me |
| 1341 | Bu | Et—F | 2-OCF₃, 4-Me |
| 1342 | Bu | Et—F | 2-OEtF, 4-Me |
| 1343 | Bu | Et—F | 2-OPrF, 4-Me |
| 1344 | Bu | Et—F | 2-Cl, 4-OH |
| 1345 | Bu | Et—F | 2-Cl, 4-OMe |
| 1346 | Bu | Et—F | 2-Cl, 4-OMeF |
| 1347 | Bu | Et—F | 2-Cl, 4-OCF₃ |
| 1348 | Bu | Et—F | 2-Cl, 4-OEtF |
| 1349 | Bu | Et—F | 2-Cl, 4-OPrF |
| 1350 | Bu | Et—F | 2-F, 4-F |
| 1351 | Bu | Et—F | 2-Cl, 4-Cl |
| 1352 | Bu | Et—F | 2-Cl, 4-F |
| 1353 | Bu | Et—F | 2-Cl, 4-NO₂ |
| 1354 | Bu | Et—F | 2-Cl, 4-NH₂ |
| 1355 | Bu | Et—F | 2-Cl, 4-NHMe |
| 1356 | Bu | Et—F | 2-Cl, 4-NMe₂ |
| 1357 | Bu | Et—F | 2-Cl, 4-NMe₃OTf |
| 1358 | Bu | Et—F | 2-Cl, 4-NMe₃I |
| 1359 | Bu | Et—F | 2-Cl, 5-F |
| 1360 | Bu | Et—F | 2-Cl, 5-NO₂ |
| 1361 | Bu | Et—F | 2-Cl, 5-NH₂ |
| 1362 | Bu | Et—F | 2-Cl, 5-NHMe |
| 1363 | Bu | Et—F | 2-Cl, 5-NMe₂ |
| 1364 | Bu | Et—F | 2-Cl, 5-NMe₃OTf |
| 1365 | Bu | Et—F | 2-Cl, 5-NMe₃I |
| 1366 | Bu | Et—F | 2-F, 4-Cl |
| 1367 | Bu | Et—F | 2-NO₂, 4-Cl |
| 1368 | Bu | Et—F | 2-NH₂, 4-Cl |
| 1369 | Bu | Et—F | 2-NHMe, 4-Cl |
| 1370 | Bu | Et—F | 2-NMe₂, 4-Cl |
| 1371 | Bu | Et—F | 2-NMe₃OTf, 4-Cl |
| 1372 | Bu | Et—F | 2-NMe₃I, 4-Cl |
| 1373 | Bu | Et—F | 2-F, 5-Cl |
| 1374 | Bu | Et—F | 2-NO₂, 5-Cl |
| 1375 | Bu | Et—F | 2-NH₂, 5-Cl |
| 1376 | Bu | Et—F | 2-NHMe, 5-Cl |
| 1377 | Bu | Et—F | 2-NMe₂, 5-Cl |
| 1378 | Bu | Et—F | 2-NMe₃OTf, 5-Cl |
| 1379 | Bu | Et—F | 2-NMe₃I, 5-Cl |
| 1380 | Bu | Et—F | 2-Br, 4-F |
| 1381 | Bu | Et—F | 2-Br, 4-NO₂ |
| 1382 | Bu | Et—F | 2-Br, 4-NH₂ |
| 1383 | Bu | Et—F | 2-Br, 4-NHMe |
| 1384 | Bu | Et—F | 2-Br, 4-NMe₂ |
| 1385 | Bu | Et—F | 2-Br, 4-NMe₃OTf |
| 1386 | Bu | Et—F | 2-Br, 4-NMe₃I |
| 1387 | Bu | Et—F | 2-Br, 5-F |
| 1388 | Bu | Et—F | 2-Br, 5-NO₂ |
| 1389 | Bu | Et—F | 2-Br, 5-NH₂ |
| 1390 | Bu | Et—F | 2-Br, 5-NHMe |
| 1391 | Bu | Et—F | 2-Br, 5-NMe₂ |
| 1392 | Bu | Et—F | 2-Br, 5-NMe₃OTf |
| 1393 | Bu | Et—F | 2-Br, 5-NMe₃I |
| 1394 | Bu | Et—F | 2-F, 4-Br |
| 1395 | Bu | Et—F | 2-NO₂, 4-Br |
| 1396 | Bu | Et—F | 2-NH₂, 4-Br |
| 1397 | Bu | Et—F | 2-NHMe, 4-Br |
| 1398 | Bu | Et—F | 2-NMe₂, 4-Br |
| 1399 | Bu | Et—F | 2-NMe₃OTf, 4-Br |
| 1400 | Bu | Et—F | 2-NMe₃I, 4-Br |
| 1401 | Bu | Et—F | 2-I, 4-F |
| 1402 | Bu | Et—F | 2-I, 4-NO₂ |
| 1403 | Bu | Et—F | 2-I, 4-NH₂ |
| 1404 | Bu | Et—F | 2-I, 4-NHMe |
| 1405 | Bu | Et—F | 2-I, 4-NMe₂ |
| 1406 | Bu | Et—F | 2-I, 4-NMe₃OTf |
| 1407 | Bu | Et—F | 2-I, 4-NMe₃I |
| 1408 | Bu | Et—F | 2-F, 4-I |
| 1409 | Bu | Et—F | 2-NO₂, 4-I |
| 1410 | Bu | Et—F | 2-NH₂, 4-I |
| 1411 | Bu | Et—F | 2-NHMe, 4-I |
| 1412 | Bu | Et—F | 2-NMe₂, 4-I |
| 1413 | Bu | Et—F | 2-NMe₃OTf, 4-I |
| 1414 | Bu | Et—F | 2-NMe₃I, 4-I |
| 1415 | Bu | Et—F | 2-Me, 3-F |
| 1416 | Bu | Et—F | 2-Me, 3-NO₂ |
| 1417 | Bu | Et—F | 2-Me, 3-NH₂ |
| 1418 | Bu | Et—F | 2-Me, 3-NHMe |
| 1419 | Bu | Et—F | 2-Me, 3-NMe₂ |

TABLE 1-continued

Substituent list for compounds of general structure VI.

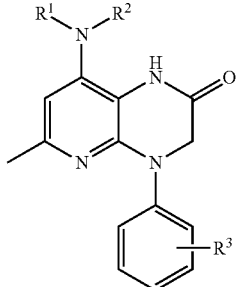
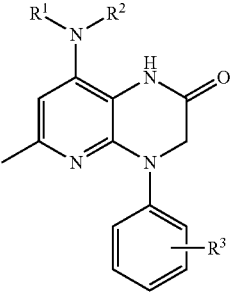

VI

| Compound # | R¹ = | R² = | R³ = |
|---|---|---|---|
| 1420 | Bu | Et—F | 2-Me, 3-NMe$_3$OTf |
| 1421 | Bu | Et—F | 2-Me, 3-NMe$_3$I |
| 1422 | Bu | Et—F | 2-Me, 4-F |
| 1423 | Bu | Et—F | 2-Me, 4-NO$_2$ |
| 1424 | Bu | Et—F | 2-Me, 4-NH$_2$ |
| 1425 | Bu | Et—F | 2-Me, 4-NHMe |
| 1426 | Bu | Et—F | 2-Me, 4-NMe$_2$ |
| 1427 | Bu | Et—F | 2-Me, 4-NMe$_3$OTf |
| 1428 | Bu | Et—F | 2-Me, 4-NMe$_3$I |
| 1429 | Bu | Et—F | 2-Me, 5-F |
| 1430 | Bu | Et—F | 2-Me, 5-NO$_2$ |
| 1431 | Bu | Et—F | 2-Me, 5-NH$_2$ |
| 1432 | Bu | Et—F | 2-Me, 5-NHMe |
| 1433 | Bu | Et—F | 2-Me, 5-NMe$_2$ |
| 1434 | Bu | Et—F | 2-Me, 5-NMe$_3$OTf |
| 1435 | Bu | Et—F | 2-Me, 5-NMe$_3$I |
| 1436 | Bu | Et—F | 2-F, 4-Me |
| 1437 | Bu | Et—F | 2-NO$_2$, 4-Me |
| 1438 | Bu | Et—F | 2-NH$_2$, 4-Me |
| 1439 | Bu | Et—F | 2-NHMe, 4-Me |
| 1440 | Bu | Et—F | 2-NMe$_2$, 4-Me |
| 1441 | Bu | Et—F | 2-NMe$_3$, 4-Me |
| 1442 | Bu | Et—F | 2-NMe$_3$OTf, 4-Me |
| 1443 | Bu | Et—F | 2-NMe$_3$I, 4-Me |
| 1444 | Bu | Et—F | 2-SnMe$_3$, 4-F |
| 1445 | Bu | Et—F | 2-SnMe$_3$, 5-F |
| 1446 | Bu | Et—F | 2-F, 4-SnMe$_3$ |
| 1447 | Bu | Et—F | 2-Br, 6-Cl, 4-F |
| 1448 | Bu | Et—F | 2-Br, 6-Cl, 4-NO$_2$ |
| 1449 | Bu | Et—F | 2-Br, 6-Cl, 4-NH$_2$ |
| 1450 | Bu | Et—F | 2-Br, 6-Cl, 4-NHMe |
| 1451 | Bu | Et—F | 2-Br, 6-Cl, 4-NMe$_2$ |
| 1452 | Bu | Et—F | 2-Br, 6-Cl, 4-NMe$_3$OTf |
| 1453 | Bu | Et—F | 2-Br, 6-Cl, 4-NMe$_3$I |
| 1454 | Bu | Et—F | 2-Me, 6-Cl, 4-F |
| 1455 | Bu | Et—F | 2-SnMe$_3$, 6-Cl, 4-F |
| 1456 | Bu | Et—F | 2-Cl, 4-Me |
| 1457 | Bu | Et—F | 2-Cl, 4-Br |
| 1458 | Bu | Et—F | 2-Cl, 4-SnMe$_3$ |
| 1459 | Bu | Et—F | 2-Br, 4-Cl |
| 1460 | Bu | Et—F | 2-SnMe$_3$, 4-Cl |
| 1461 | Bu | Et—F | 2-Me, 4-Cl |
| 1462 | Bu | Et—F | 2-Br, 4-Br |
| 1463 | Bu | Et—F | 2-Br, 4-Me |
| 1464 | Bu | Et—F | 2-Br, 4-SnMe$_3$ |
| 1465 | Bu | Et—F | 2-SnMe$_3$, 4-Br |
| 1466 | Bu | Et—F | 2-Me, 4-Br |
| 1467 | Bu | Et—F | 2-Me, 4-SnMe$_3$ |
| 1468 | Bu | Et—F | 2-SnMe$_3$, 4-Me |
| 1469 | Bu | Et—F | 2-Me, 4-Me |
| 1470 | Bu | Et—F | 2-Et, 4-Br |
| 1471 | Bu | Et—F | 2-Et, 4-SnMe$_3$ |
| 1472 | Bu | Et—F | 2-Et, 4-Me |
| 1473 | Bu | Et—F | 2-Me, 4-Me, 6-Me |
| 1474 | Bu | Et—F | 2-Me, 4-Br, 6-Me |
| 1475 | Bu | Et—F | 2-Me, 4-SnMe$_3$, 6-Me |
| 1476 | Bu | Et—F | 2-Et, 6-Me |
| 1477 | Bu | Et—F | 2-Br, 4-i-Pr |
| 1478 | Bu | Et—F | 2-SnMe$_3$, 4-i-Pr |
| 1479 | Bu | Et—F | 2-Me, 4-i-Pr |
| 1480 | Bu | Et—F | 2-Br, 4-Br, 6-Br |
| 1481 | Bu | Et—F | 2-Br, 4-Me, 6-Br |
| 1482 | Bu | Et—F | 2-Br, 4-SnMe$_3$, 6-Br |
| 1483 | Bu | Et—F | 2-SnMe$_3$, 4-Br, 6-Br |
| 1484 | Bu | Et—F | 2-Br, 4-Br, 6-Me |
| 1485 | Bu | Et—F | 2-Br, 4-CF$_3$, 6-Br |
| 1486 | Bu | Et—F | 2-Br, 4-Br, 6-CF$_3$ |
| 1487 | Bu | Et—F | 2-CF$_3$, 4-CF$_3$ |
| 1488 | Bu | Et—F | 2-Cl, 4-CF$_3$ |
| 1489 | Bu | Et—F | 2-CF$_3$, 4-Cl |
| 1490 | Bu | Et—F | 2-Br, 4-CF$_3$ |
| 1491 | Bu | Et—F | 2-SnMe$_3$, 4-CF$_3$ |
| 1492 | Bu | Et—F | 2-Me, 4-CF$_3$ |
| 1493 | Bu | Et—F | 2-CF$_3$, 4-Br |
| 1494 | Bu | Et—F | 2-CF$_3$, 4-SnMe$_3$ |
| 1495 | Bu | Et—F | 2-CF$_3$, 4-Me |
| 1496 | Bu | Et—F | 2-Br, 4-OH |
| 1497 | Bu | Et—F | 2-Br, 4-OMe |
| 1498 | Bu | Et—F | 2-Br, 4-OMeF |
| 1499 | Bu | Et—F | 2-Br, 4-OCF$_3$ |
| 1500 | Bu | Et—F | 2-Br, 4-OEtF |
| 1501 | Bu | Et—F | 2-Br, 4-OPrF |
| 1502 | Bu | Et—F | 2-OH, 4-Br |
| 1503 | Bu | Et—F | 2-OMe, 4-Br |
| 1504 | Bu | Et—F | 2-OMeF, 4-Br |
| 1505 | Bu | Et—F | 2-OCF$_3$, 4-Br |
| 1506 | Bu | Et—F | 2-OEtF, 4-Br |
| 1507 | Bu | Et—F | 2-OPrF, 4-Br |
| 1508 | Bu | Et—F | 2-I, 4-OH |
| 1509 | Bu | Et—F | 2-I, 4-OMe |
| 1510 | Bu | Et—F | 2-I, 4-OMeF |
| 1511 | Bu | Et—F | 2-I, 4-OCF$_3$ |
| 1512 | Bu | Et—F | 2-I, 4-OEtF |
| 1513 | Bu | Et—F | 2-I, 4-OPrF |
| 1514 | Bu | Et—F | 2-OH, 4-I |
| 1515 | Bu | Et—F | 2-OMe, 4-I |
| 1516 | Bu | Et—F | 2-OMeF, 4-I |
| 1517 | Bu | Et—F | 2-OCF$_3$, 4-I |
| 1518 | Bu | Et—F | 2-OEtF, 4-I |
| 1519 | Bu | Et—F | 2-OPrF, 4-I |
| 1520 | Bu | Et—F | 2-SnMe$_3$, 4-OH |
| 1521 | Bu | Et—F | 2-SnMe$_3$, 4-OMe |
| 1522 | Bu | Et—F | 2-SnMe$_3$, 4-OMeF |
| 1523 | Bu | Et—F | 2-SnMe$_3$, 4-OCF$_3$ |
| 1524 | Bu | Et—F | 2-SnMe$_3$, 4-OEtF |
| 1525 | Bu | Et—F | 2-SnMe$_3$, 4-OPrF |
| 1526 | Bu | Et—F | 2-OH, 4-SnMe$_3$ |
| 1527 | Bu | Et—F | 2-OMe, 4-SnMe$_3$ |
| 1528 | Bu | Et—F | 2-OMeF, 4-SnMe$_3$ |
| 1529 | Bu | Et—F | 2-OCF$_3$, 4-SnMe$_3$ |
| 1530 | Bu | Et—F | 2-OEtF, 4-SnMe$_3$ |
| 1531 | Bu | Et—F | 2-OPrF, 4-SnMe$_3$ |
| 1532 | Bu—F | Et | H |
| 1533 | Bu—F | Et | 2-t-Bu |
| 1534 | Bu—F | Et | 2-Br |
| 1535 | Bu—F | Et | 3-Br |
| 1536 | Bu—F | Et | 4-Br |
| 1537 | Bu—F | Et | 2-I |
| 1538 | Bu—F | Et | 3-I |
| 1539 | Bu—F | Et | 4-I |

TABLE 1-continued

Substituent list for compounds of general structure VI.

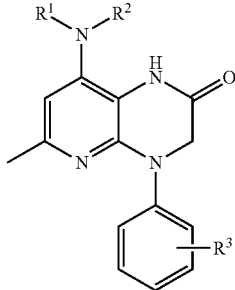

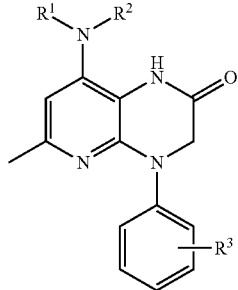

| Compound # | R¹ = | R² = | R³ = |
|---|---|---|---|
| 1540 | Bu—F | Et | 2-SnMe₃ |
| 1541 | Bu—F | Et | 3-SnMe₃ |
| 1542 | Bu—F | Et | 4-SnMe₃ |
| 1543 | Bu—F | Et | 2-Me |
| 1544 | Bu—F | Et | 3-Me |
| 1545 | Bu—F | Et | 4-Me |
| 1546 | Bu—F | Et | 2-OH |
| 1547 | Bu—F | Et | 3-OH |
| 1548 | Bu—F | Et | 4-OH |
| 1549 | Bu—F | Et | 2-OMe |
| 1550 | Bu—F | Et | 3-OMe |
| 1551 | Bu—F | Et | 4-OMe |
| 1552 | Bu—F | Et | 2-OMeF |
| 1553 | Bu—F | Et | 3-OMeF |
| 1554 | Bu—F | Et | 4-OMeF |
| 1555 | Bu—F | Et | 2-OCF₃ |
| 1556 | Bu—F | Et | 3-OCF₃ |
| 1557 | Bu—F | Et | 4-OCF₃ |
| 1558 | Bu—F | Et | 2-OEtF |
| 1559 | Bu—F | Et | 3-OEtF |
| 1560 | Bu—F | Et | 4-OEtF |
| 1561 | Bu—F | Et | 2-OPrF |
| 1562 | Bu—F | Et | 3-OPrF |
| 1563 | Bu—F | Et | 4-OPrF |
| 1564 | Bu—F | Et | 2-SH |
| 1565 | Bu—F | Et | 3-SH |
| 1566 | Bu—F | Et | 4-SH |
| 1567 | Bu—F | Et | 2-SMe |
| 1568 | Bu—F | Et | 3-SMe |
| 1569 | Bu—F | Et | 4-SMe |
| 1570 | Bu—F | Et | 2-SMeF |
| 1571 | Bu—F | Et | 3-SMeF |
| 1572 | Bu—F | Et | 4-SMeF |
| 1573 | Bu—F | Et | 2-SCF₃ |
| 1574 | Bu—F | Et | 3-SCF₃ |
| 1575 | Bu—F | Et | 4-SCF₃ |
| 1576 | Bu—F | Et | 2-SEtF |
| 1577 | Bu—F | Et | 3-SEtF |
| 1578 | Bu—F | Et | 4-SEtF |
| 1579 | Bu—F | Et | 2-SPrF |
| 1580 | Bu—F | Et | 3-SPrF |
| 1581 | Bu—F | Et | 4-SPrF |
| 1582 | Bu—F | Et | 2-OMe, 4-OMe |
| 1583 | Bu—F | Et | 2-Me, 5-OH |
| 1584 | Bu—F | Et | 2-Me, 5-OMe |
| 1585 | Bu—F | Et | 2-Me, 5-OMeF |
| 1586 | Bu—F | Et | 2-Me, 5-OEtF |
| 1587 | Bu—F | Et | 2-Me, 5-OPrF |
| 1588 | Bu—F | Et | 2-Me, 4-OH |
| 1589 | Bu—F | Et | 2-Me, 4-OMe |
| 1590 | Bu—F | Et | 2-Me, 4-OMeF |
| 1591 | Bu—F | Et | 2-Me, 4-OCF₃ |
| 1592 | Bu—F | Et | 2-Me, 4-OEtF |
| 1593 | Bu—F | Et | 2-Me, 4-OPrF |
| 1594 | Bu—F | Et | 2-OH, 4-Me |
| 1595 | Bu—F | Et | 2-OMe, 4-Me |
| 1596 | Bu—F | Et | 2-OMeF, 4-Me |
| 1597 | Bu—F | Et | 2-OCF₃, 4-Me |
| 1598 | Bu—F | Et | 2-OEtF, 4-Me |
| 1599 | Bu—F | Et | 2-OPrF, 4-Me |
| 1600 | Bu—F | Et | 2-Cl, 4-OH |
| 1601 | Bu—F | Et | 2-Cl, 4-OMe |
| 1602 | Bu—F | Et | 2-Cl, 4-OMeF |
| 1603 | Bu—F | Et | 2-Cl, 4-OCF₃ |
| 1604 | Bu—F | Et | 2-Cl, 4-OEtF |
| 1605 | Bu—F | Et | 2-Cl, 4-OPrF |
| 1606 | Bu—F | Et | 2-F, 4-F |
| 1607 | Bu—F | Et | 2-Cl, 4-Cl |
| 1608 | Bu—F | Et | 2-Cl, 4-F |
| 1609 | Bu—F | Et | 2-Cl, 4-NO₂ |
| 1610 | Bu—F | Et | 2-Cl, 4-NH₂ |
| 1611 | Bu—F | Et | 2-Cl, 4-NHMe |
| 1612 | Bu—F | Et | 2-Cl, 4-NMe₂ |
| 1613 | Bu—F | Et | 2-Cl, 4-NMe₃OTf |
| 1614 | Bu—F | Et | 2-Cl, 4-NMe₃I |
| 1615 | Bu—F | Et | 2-Cl, 5-F |
| 1616 | Bu—F | Et | 2-Cl, 5-NO₂ |
| 1617 | Bu—F | Et | 2-Cl, 5-NH₂ |
| 1618 | Bu—F | Et | 2-Cl, 5-NHMe |
| 1619 | Bu—F | Et | 2-Cl, 5-NMe₂ |
| 1620 | Bu—F | Et | 2-Cl, 5-NMe₃OTf |
| 1621 | Bu—F | Et | 2-Cl, 5-NMe₃I |
| 1622 | Bu—F | Et | 2-F, 4-Cl |
| 1623 | Bu—F | Et | 2-NO₂, 4-Cl |
| 1624 | Bu—F | Et | 2-NH₂, 4-Cl |
| 1625 | Bu—F | Et | 2-NHMe, 4-Cl |
| 1626 | Bu—F | Et | 2-NMe₂, 4-Cl |
| 1627 | Bu—F | Et | 2-NMe₃OTf, 4-Cl |
| 1628 | Bu—F | Et | 2-NMe₃I, 4-Cl |
| 1629 | Bu—F | Et | 2-F, 5-Cl |
| 1630 | Bu—F | Et | 2-NO₂, 5-Cl |
| 1631 | Bu—F | Et | 2-NH₂, 5-Cl |
| 1632 | Bu—F | Et | 2-NHMe, 5-Cl |
| 1633 | Bu—F | Et | 2-NMe₂, 5-Cl |
| 1634 | Bu—F | Et | 2-NMe₃OTf, 5-Cl |
| 1635 | Bu—F | Et | 2-NMe₃I, 5-Cl |
| 1636 | Bu—F | Et | 2-Br, 4-F |
| 1637 | Bu—F | Et | 2-Br, 4-NO₂ |
| 1638 | Bu—F | Et | 2-Br, 4-NH₂ |
| 1639 | Bu—F | Et | 2-Br, 4-NHMe |
| 1640 | Bu—F | Et | 2-Br, 4-NMe₂ |
| 1641 | Bu—F | Et | 2-Br, 4-NMe₃OTf |
| 1642 | Bu—F | Et | 2-Br, 4-NMe₃I |
| 1643 | Bu—F | Et | 2-Br, 5-F |
| 1644 | Bu—F | Et | 2-Br, 5-NO₂ |
| 1645 | Bu—F | Et | 2-Br, 5-NH₂ |
| 1646 | Bu—F | Et | 2-Br, 5-NHMe |
| 1647 | Bu—F | Et | 2-Br, 5-NMe₂ |
| 1648 | Bu—F | Et | 2-Br, 5-NMe₃OTf |
| 1649 | Bu—F | Et | 2-Br, 5-NMe₃I |
| 1650 | Bu—F | Et | 2-F, 4-Br |
| 1651 | Bu—F | Et | 2-NO₂, 4-Br |
| 1652 | Bu—F | Et | 2-NH₂, 4-Br |
| 1653 | Bu—F | Et | 2-NHMe, 4-Br |
| 1654 | Bu—F | Et | 2-NMe₂, 4-Br |
| 1655 | Bu—F | Et | 2-NMe₃OTf, 4-Br |
| 1656 | Bu—F | Et | 2-NMe₃I, 4-Br |
| 1657 | Bu—F | Et | 2-I, 4-F |
| 1658 | Bu—F | Et | 2-I, 4-NO₂ |
| 1659 | Bu—F | Et | 2-I, 4-NH₂ |

TABLE 1-continued

Substituent list for compounds of general structure VI.

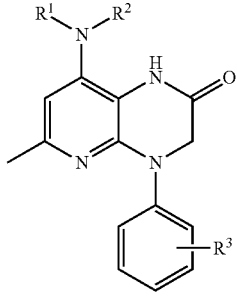

| Compound # | R¹ = | R² = | R³ = |
|---|---|---|---|
| 1660 | Bu—F | Et | 2-I, 4-NHMe |
| 1661 | Bu—F | Et | 2-I, 4-NMe$_2$ |
| 1662 | Bu—F | Et | 2-I, 4-NMe$_3$OTf |
| 1663 | Bu—F | Et | 2-I, 4-NMe$_3$I |
| 1664 | Bu—F | Et | 2-F, 4-I |
| 1665 | Bu—F | Et | 2-NO$_2$, 4-I |
| 1666 | Bu—F | Et | 2-NH$_2$, 4-I |
| 1667 | Bu—F | Et | 2-NHMe, 4-I |
| 1668 | Bu—F | Et | 2-NMe$_2$, 4-I |
| 1669 | Bu—F | Et | 2-NMe$_3$OTf, 4-I |
| 1670 | Bu—F | Et | 2-NMe$_3$I, 4-I |
| 1671 | Bu—F | Et | 2-Me, 3-F |
| 1672 | Bu—F | Et | 2-Me, 3-NO$_2$ |
| 1673 | Bu—F | Et | 2-Me, 3-NH$_2$ |
| 1674 | Bu—F | Et | 2-Me, 3-NHMe |
| 1675 | Bu—F | Et | 2-Me, 3-NMe$_2$ |
| 1676 | Bu—F | Et | 2-Me, 3-NMe$_3$OTf |
| 1677 | Bu—F | Et | 2-Me, 3-NMe3I |
| 1678 | Bu—F | Et | 2-Me, 4-F |
| 1679 | Bu—F | Et | 2-Me, 4-NO$_2$ |
| 1680 | Bu—F | Et | 2-Me, 4-NH$_2$ |
| 1681 | Bu—F | Et | 2-Me, 4-NHMe |
| 1682 | Bu—F | Et | 2-Me, 4-NMe$_2$ |
| 1683 | Bu—F | Et | 2-Me, 4-NMe$_3$OTf |
| 1684 | Bu—F | Et | 2-Me, 4-NMe$_3$I |
| 1685 | Bu—F | Et | 2-Me, 5-F |
| 1686 | Bu—F | Et | 2-Me, 5-NO$_2$ |
| 1687 | Bu—F | Et | 2-Me, 5-NH$_2$ |
| 1688 | Bu—F | Et | 2-Me, 5-NHMe |
| 1689 | Bu—F | Et | 2-Me, 5-NMe$_2$ |
| 1690 | Bu—F | Et | 2-Me, 5-NMe$_3$OTf |
| 1691 | Bu—F | Et | 2-Me, 5-NMe$_3$I |
| 1692 | Bu—F | Et | 2-F, 4-Me |
| 1693 | Bu—F | Et | 2-NO$_2$, 4-Me |
| 1694 | Bu—F | Et | 2-NH$_2$, 4-Me |
| 1695 | Bu—F | Et | 2-NHMe, 4-Me |
| 1696 | Bu—F | Et | 2-NMe$_2$, 4-Me |
| 1697 | Bu—F | Et | 2-NMe$_3$, 4-Me |
| 1698 | Bu—F | Et | 2-NMe$_3$OTf, 4-Me |
| 1699 | Bu—F | Et | 2-NMe$_3$I, 4-Me |
| 1700 | Bu—F | Et | 2-SnMe$_3$, 4-F |
| 1701 | Bu—F | Et | 2-SnMe$_3$, 5-F |
| 1702 | Bu—F | Et | 2-F, 4-SnMe$_3$ |
| 1703 | Bu—F | Et | 2-Br, 6-Cl, 4-F |
| 1704 | Bu—F | Et | 2-Br, 6-Cl, 4-NO$_2$ |
| 1705 | Bu—F | Et | 2-Br, 6-Cl, 4-NH$_2$ |
| 1706 | Bu—F | Et | 2-Br, 6-Cl, 4-NHMe |
| 1707 | Bu—F | Et | 2-Br, 6-Cl, 4-NMe$_2$ |
| 1708 | Bu—F | Et | 2-Br, 6-Cl, 4-NMe$_3$OTf |
| 1709 | Bu—F | Et | 2-Br, 6-Cl, 4-NMe$_3$I |
| 1710 | Bu—F | Et | 2-Me, 6-Cl, 4-F |
| 1711 | Bu—F | Et | 2-SnMe$_3$, 6-Cl, 4-F |
| 1712 | Bu—F | Et | 2-Cl, 4-Me |
| 1713 | Bu—F | Et | 2-Cl, 4-Br |
| 1714 | Bu—F | Et | 2-Cl, 4-SnMe$_3$ |
| 1715 | Bu—F | Et | 2-Br, 4-Cl |
| 1716 | Bu—F | Et | 2-SnMe$_3$, 4-Cl |
| 1717 | Bu—F | Et | 2-Me, 4-Cl |
| 1718 | Bu—F | Et | 2-Br, 4-Br |
| 1719 | Bu—F | Et | 2-Br, 4-Me |

TABLE 1-continued

Substituent list for compounds of general structure VI.

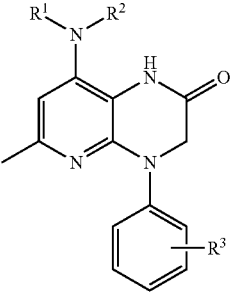

| Compound # | R¹ = | R² = | R³ = |
|---|---|---|---|
| 1720 | Bu—F | Et | 2-Br, 4-SnMe$_3$ |
| 1721 | Bu—F | Et | 2-SnMe$_3$, 4-Br |
| 1722 | Bu—F | Et | 2-Me, 4-Br |
| 1723 | Bu—F | Et | 2-Me, 4-SnMe$_3$ |
| 1724 | Bu—F | Et | 2-SnMe$_3$, 4-Me |
| 1725 | Bu—F | Et | 2-Me, 4-Me |
| 1726 | Bu—F | Et | 2-Et, 4-Br |
| 1727 | Bu—F | Et | 2-Et, 4-SnMe$_3$ |
| 1728 | Bu—F | Et | 2-Et, 4-Me |
| 1729 | Bu—F | Et | 2-Me, 4-Me, 6-Me |
| 1730 | Bu—F | Et | 2-Me, 4-Br, 6-Me |
| 1731 | Bu—F | Et | 2-Me, 4-SnMe$_3$, 6-Me |
| 1732 | Bu—F | Et | 2-Et, 6-Me |
| 1733 | Bu—F | Et | 2-Br, 4-i-Pr |
| 1734 | Bu—F | Et | 2-SnMe$_3$, 4-i-Pr |
| 1735 | Bu—F | Et | 2-Me, 4-i-Pr |
| 1736 | Bu—F | Et | 2-Br, 4-Br, 6-Br |
| 1737 | Bu—F | Et | 2-Br, 4-Me, 6-Br |
| 1738 | Bu—F | Et | 2-Br, 4-SnMe$_3$, 6-Br |
| 1739 | Bu—F | Et | 2-SnMe$_3$, 4-Br, 6-Br |
| 1740 | Bu—F | Et | 2-Br, 4-Br, 6-Me |
| 1741 | Bu—F | Et | 2-Br, 4-CF$_3$, 6-Br |
| 1742 | Bu—F | Et | 2-Br, 4-Br, 6-CF$_3$ |
| 1743 | Bu—F | Et | 2-CF$_3$, 4-CF$_3$ |
| 1744 | Bu—F | Et | 2-Cl, 4-CF$_3$ |
| 1745 | Bu—F | Et | 2-CF$_3$, 4-Cl |
| 1746 | Bu—F | Et | 2-Br, 4-CF$_3$ |
| 1747 | Bu—F | Et | 2-SnMe$_3$, 4-CF$_3$ |
| 1748 | Bu—F | Et | 2-Me, 4-CF$_3$ |
| 1749 | Bu—F | Et | 2-CF$_3$, 4-Br |
| 1750 | Bu—F | Et | 2-CF$_3$, 4-SnMe$_3$ |
| 1751 | Bu—F | Et | 2-CF$_3$, 4-Me |
| 1752 | Bu—F | Et | 2-Br, 4-OH |
| 1753 | Bu—F | Et | 2-Br, 4-OMe |
| 1754 | Bu—F | Et | 2-Br, 4-OMeF |
| 1755 | Bu—F | Et | 2-Br, 4-OCF$_3$ |
| 1756 | Bu—F | Et | 2-Br, 4-OEtF |
| 1757 | Bu—F | Et | 2-Br, 4-OPrF |
| 1758 | Bu—F | Et | 2-OH, 4-Br |
| 1759 | Bu—F | Et | 2-OMe, 4-Br |
| 1760 | Bu—F | Et | 2-OMeF, 4-Br |
| 1761 | Bu—F | Et | 2-OCF$_3$, 4-Br |
| 1762 | Bu—F | Et | 2-OEtF, 4-Br |
| 1763 | Bu—F | Et | 2-OPrF, 4-Br |
| 1764 | Bu—F | Et | 2-I, 4-OH |
| 1765 | Bu—F | Et | 2-I, 4-OMe |
| 1766 | Bu—F | Et | 2-I, 4-OMeF |
| 1767 | Bu—F | Et | 2-I, 4-OCF$_3$ |
| 1768 | Bu—F | Et | 2-I, 4-OEtF |
| 1769 | Bu—F | Et | 2-I, 4-OPrF |
| 1770 | Bu—F | Et | 2-OH, 4-I |
| 1771 | Bu—F | Et | 2-OMe, 4-I |
| 1772 | Bu—F | Et | 2-OMeF, 4-I |
| 1773 | Bu—F | Et | 2-OCF$_3$, 4-I |
| 1774 | Bu—F | Et | 2-OEtF, 4-I |
| 1775 | Bu—F | Et | 2-OPrF, 4-I |
| 1776 | Bu—F | Et | 2-SnMe$_3$, 4-OH |
| 1777 | Bu—F | Et | 2-SnMe$_3$, 4-OMe |
| 1778 | Bu—F | Et | 2-SnMe$_3$, 4-OMeF |
| 1779 | Bu—F | Et | 2-SnMe$_3$, 4-OCF$_3$ |

TABLE 1-continued

Substituent list for compounds of general structure VI.

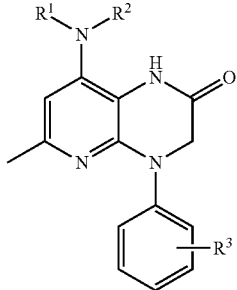

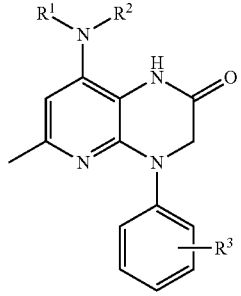

| Compound # | R¹ = | R² = | R³ = |
|---|---|---|---|
| 1780 | Bu—F | Et | 2-SnMe₃, 4-OEtF |
| 1781 | Bu—F | Et | 2-SnMe₃, 4-OPrF |
| 1782 | Bu—F | Et | 2-OH, 4-SnMe₃ |
| 1783 | Bu—F | Et | 2-OMe, 4-SnMe₃ |
| 1784 | Bu—F | Et | 2-OMeF, 4-SnMe₃ |
| 1785 | Bu—F | Et | 2-OCF₃, 4-SnMe₃ |
| 1786 | Bu—F | Et | 2-OEtF, 4-SnMe₃ |
| 1787 | Bu—F | Et | 2-OPrF, 4-SnMe₃ |
| 1788 | FCH₂—CH=CH—CH₂ | Me | H |
| 1789 | FCH₂—CH=CH—CH₂ | Me | 2-t-Bu |
| 1790 | FCH₂—CH=CH—CH₂ | Me | 2-Br |
| 1791 | FCH₂—CH=CH—CH₂ | Me | 3-Br |
| 1792 | FCH₂—CH=CH—CH₂ | Me | 4-Br |
| 1793 | FCH₂—CH=CH—CH₂ | Me | 2-I |
| 1794 | FCH₂—CH=CH—CH₂ | Me | 3-I |
| 1795 | FCH₂—CH=CH—CH₂ | Me | 4-I |
| 1796 | FCH₂—CH=CH—CH₂ | Me | 2-SnMe₃ |
| 1797 | FCH₂—CH=CH—CH₂ | Me | 3-SnMe₃ |
| 1798 | FCH₂—CH=CH—CH₂ | Me | 4-SnMe₃ |
| 1799 | FCH₂—CH=CH—CH₂ | Me | 2-Me |
| 1800 | FCH₂—CH=CH—CH₂ | Me | 3-Me |
| 1801 | FCH₂—CH=CH—CH₂ | Me | 4-Me |
| 1802 | FCH₂—CH=CH—CH₂ | Me | 2-OH |
| 1803 | FCH₂—CH=CH—CH₂ | Me | 3-OH |
| 1804 | FCH₂—CH=CH—CH₂ | Me | 4-OH |
| 1805 | FCH₂—CH=CH—CH₂ | Me | 2-OMe |
| 1806 | FCH₂—CH=CH—CH₂ | Me | 3-OMe |
| 1807 | FCH₂—CH=CH—CH₂ | Me | 4-OMe |
| 1808 | FCH₂—CH=CH—CH₂ | Me | 2-OMeF |
| 1809 | FCH₂—CH=CH—CH₂ | Me | 3-OMeF |
| 1810 | FCH₂—CH=CH—CH₂ | Me | 4-OMeF |
| 1811 | FCH₂—CH=CH—CH₂ | Me | 2-OCF₃ |
| 1812 | FCH₂—CH=CH—CH₂ | Me | 3-OCF₃ |
| 1813 | FCH₂—CH=CH—CH₂ | Me | 4-OCF₃ |
| 1814 | FCH₂—CH=CH—CH₂ | Me | 2-OEtF |
| 1815 | FCH₂—CH=CH—CH₂ | Me | 3-OEtF |
| 1816 | FCH₂—CH=CH—CH₂ | Me | 4-OEtF |
| 1817 | FCH₂—CH=CH—CH₂ | Me | 2-OPrF |
| 1818 | FCH₂—CH=CH—CH₂ | Me | 3-OPrF |
| 1819 | FCH₂—CH=CH—CH₂ | Me | 4-OPrF |
| 1820 | FCH₂—CH=CH—CH₂ | Me | 2-SH |
| 1821 | FCH₂—CH=CH—CH₂ | Me | 3-SH |
| 1822 | FCH₂—CH=CH—CH₂ | Me | 4-SH |
| 1823 | FCH₂—CH=CH—CH₂ | Me | 2-SMe |
| 1824 | FCH₂—CH=CH—CH₂ | Me | 3-SMe |
| 1825 | FCH₂—CH=CH—CH₂ | Me | 4-SMe |
| 1826 | FCH₂—CH=CH—CH₂ | Me | 2-SMeF |
| 1827 | FCH₂—CH=CH—CH₂ | Me | 3-SMeF |
| 1828 | FCH₂—CH=CH—CH₂ | Me | 4-SMeF |
| 1829 | FCH₂—CH=CH—CH₂ | Me | 2-SCF₃ |
| 1830 | FCH₂—CH=CH—CH₂ | Me | 3-SCF₃ |
| 1831 | FCH₂—CH=CH—CH₂ | Me | 4-SCF₃ |
| 1832 | FCH₂—CH=CH—CH₂ | Me | 2-SEtF |
| 1833 | FCH₂—CH=CH—CH₂ | Me | 3-SEtF |
| 1834 | FCH₂—CH=CH—CH₂ | Me | 4-SEtF |
| 1835 | FCH₂—CH=CH—CH₂ | Me | 2-SPrF |
| 1836 | FCH₂—CH=CH—CH₂ | Me | 3-SPrF |
| 1837 | FCH₂—CH=CH—CH₂ | Me | 4-SPrF |
| 1838 | FCH₂—CH=CH—CH₂ | Me | 2-OMe, 4-OMe |
| 1839 | FCH₂—CH=CH—CH₂ | Me | 2-Me, 5-OH |
| 1840 | FCH₂—CH=CH—CH₂ | Me | 2-Me, 5-OMe |
| 1841 | FCH₂—CH=CH—CH₂ | Me | 2-Me, 5-OMeF |
| 1842 | FCH₂—CH=CH—CH₂ | Me | 2-Me, 5-OEtF |
| 1843 | FCH₂—CH=CH—CH₂ | Me | 2-Me, 5-OPrF |
| 1844 | FCH₂—CH=CH—CH₂ | Me | 2-Me, 4-OH |
| 1845 | FCH₂—CH=CH—CH₂ | Me | 2-Me, 4-OMe |
| 1846 | FCH₂—CH=CH—CH₂ | Me | 2-Me, 4-OMeF |
| 1847 | FCH₂—CH=CH—CH₂ | Me | 2-Me, 4-OCF₃ |
| 1848 | FCH₂—CH=CH—CH₂ | Me | 2-Me, 4-OEtF |
| 1849 | FCH₂—CH=CH—CH₂ | Me | 2-Me, 4-OPrF |
| 1850 | FCH₂—CH=CH—CH₂ | Me | 2-OH, 4-Me |
| 1851 | FCH₂—CH=CH—CH₂ | Me | 2-OMe, 4-Me |
| 1852 | FCH₂—CH=CH—CH₂ | Me | 2-OMeF, 4-Me |
| 1853 | FCH₂—CH=CH—CH₂ | Me | 2-OCF₃, 4-Me |
| 1854 | FCH₂—CH=CH—CH₂ | Me | 2-OEtF, 4-Me |
| 1855 | FCH₂—CH=CH—CH₂ | Me | 2-OPrF, 4-Me |
| 1856 | FCH₂—CH=CH—CH₂ | Me | 2-Cl, 4-OH |
| 1857 | FCH₂—CH=CH—CH₂ | Me | 2-Cl, 4-OMe |
| 1858 | FCH₂—CH=CH—CH₂ | Me | 2-Cl, 4-OMeF |
| 1859 | FCH₂—CH=CH—CH₂ | Me | 2-Cl, 4-OCF₃ |
| 1860 | FCH₂—CH=CH—CH₂ | Me | 2-Cl, 4-OEtF |
| 1861 | FCH₂—CH=CH—CH₂ | Me | 2-Cl, 4-OPrF |
| 1862 | FCH₂—CH=CH—CH₂ | Me | 2-F, 4-F |
| 1863 | FCH₂—CH=CH—CH₂ | Me | 2-Cl, 4-Cl |
| 1864 | FCH₂—CH=CH—CH₂ | Me | 2-Cl, 4-F |
| 1865 | FCH₂—CH=CH—CH₂ | Me | 2-Cl, 4-NO₂ |
| 1866 | FCH₂—CH=CH—CH₂ | Me | 2-Cl, 4-NH₂ |
| 1867 | FCH₂—CH=CH—CH₂ | Me | 2-Cl, 4-NHMe |
| 1868 | FCH₂—CH=CH—CH₂ | Me | 2-Cl, 4-NMe₂ |
| 1869 | FCH₂—CH=CH—CH₂ | Me | 2-Cl, 4-NMe₃OTf |
| 1870 | FCH₂—CH=CH—CH₂ | Me | 2-Cl, 4-NMe₃I |
| 1871 | FCH₂—CH=CH—CH₂ | Me | 2-Cl, 5-F |
| 1872 | FCH₂—CH=CH—CH₂ | Me | 2-Cl, 5-NO₂ |
| 1873 | FCH₂—CH=CH—CH₂ | Me | 2-Cl, 5-NH₂ |
| 1874 | FCH₂—CH=CH—CH₂ | Me | 2-Cl, 5-NHMe |
| 1875 | FCH₂—CH=CH—CH₂ | Me | 2-Cl, 5-NMe₂ |
| 1876 | FCH₂—CH=CH—CH₂ | Me | 2-Cl, 5-NMe₃OTf |
| 1877 | FCH₂—CH=CH—CH₂ | Me | 2-Cl, 5-NMe₃I |
| 1878 | FCH₂—CH=CH—CH₂ | Me | 2-F, 4-Cl |
| 1879 | FCH₂—CH=CH—CH₂ | Me | 2-NO₂, 4-Cl |
| 1880 | FCH₂—CH=CH—CH₂ | Me | 2-NH₂, 4-Cl |
| 1881 | FCH₂—CH=CH—CH₂ | Me | 2-NHMe, 4-Cl |
| 1882 | FCH₂—CH=CH—CH₂ | Me | 2-NMe₂, 4-Cl |
| 1883 | FCH₂—CH=CH—CH₂ | Me | 2-NMe₃OTf, 4-Cl |
| 1884 | FCH₂—CH=CH—CH₂ | Me | 2-NMe₃I, 4-Cl |
| 1885 | FCH₂—CH=CH—CH₂ | Me | 2-F, 5-Cl |
| 1886 | FCH₂—CH=CH—CH₂ | Me | 2-NO₂, 5-Cl |
| 1887 | FCH₂—CH=CH—CH₂ | Me | 2-NH₂, 5-Cl |
| 1888 | FCH₂—CH=CH—CH₂ | Me | 2-NHMe, 5-Cl |
| 1889 | FCH₂—CH=CH—CH₂ | Me | 2-NMe₂, 5-Cl |
| 1890 | FCH₂—CH=CH—CH₂ | Me | 2-NMe₃OTf, 5-Cl |
| 1891 | FCH₂—CH=CH—CH₂ | Me | 2-NMe₃I, 5-Cl |
| 1892 | FCH₂—CH=CH—CH₂ | Me | 2-Br, 4-F |
| 1893 | FCH₂—CH=CH—CH₂ | Me | 2-Br, 4-NO₂ |
| 1894 | FCH₂—CH=CH—CH₂ | Me | 2-Br, 4-NH₂ |
| 1895 | FCH₂—CH=CH—CH₂ | Me | 2-Br, 4-NHMe |
| 1896 | FCH₂—CH=CH—CH₂ | Me | 2-Br, 4-NMe₂ |
| 1897 | FCH₂—CH=CH—CH₂ | Me | 2-Br, 4-NMe₃OTf |
| 1898 | FCH₂—CH=CH—CH₂ | Me | 2-Br, 4-NMe₃I |
| 1899 | FCH₂—CH=CH—CH₂ | Me | 2-Br, 5-F |

TABLE 1-continued

Substituent list for compounds of general structure VI.

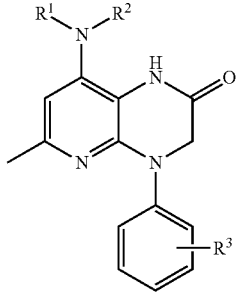

VI

| Compound # | R¹ = | R² = | R³ = |
|---|---|---|---|
| 1900 | FCH₂—CH=CH—CH₂ | Me | 2-Br, 5-NO₂ |
| 1901 | FCH₂—CH=CH—CH₂ | Me | 2-Br, 5-NH₂ |
| 1902 | FCH₂—CH=CH—CH₂ | Me | 2-Br, 5-NHMe |
| 1903 | FCH₂—CH=CH—CH₂ | Me | 2-Br, 5-NMe₂ |
| 1904 | FCH₂—CH=CH—CH₂ | Me | 2-Br, 5-NMe₃OTf |
| 1905 | FCH₂—CH=CH—CH₂ | Me | 2-Br, 5-NMe₃I |
| 1906 | FCH₂—CH=CH—CH₂ | Me | 2-F, 4-Br |
| 1907 | FCH₂—CH=CH—CH₂ | Me | 2-NO₂, 4-Br |
| 1908 | FCH₂—CH=CH—CH₂ | Me | 2-NH₂, 4-Br |
| 1909 | FCH₂—CH=CH—CH₂ | Me | 2-NHMe, 4-Br |
| 1910 | FCH₂—CH=CH—CH₂ | Me | 2-NMe₂, 4-Br |
| 1911 | FCH₂—CH=CH—CH₂ | Me | 2-NMe₃OTf, 4-Br |
| 1912 | FCH₂—CH=CH—CH₂ | Me | 2-NMe₃I, 4-Br |
| 1913 | FCH₂—CH=CH—CH₂ | Me | 2-I, 4-F |
| 1914 | FCH₂—CH=CH—CH₂ | Me | 2-I, 4-NO₂ |
| 1915 | FCH₂—CH=CH—CH₂ | Me | 2-I, 4-NH₂ |
| 1916 | FCH₂—CH=CH—CH₂ | Me | 2-I, 4-NHMe |
| 1917 | FCH₂—CH=CH—CH₂ | Me | 2-I, 4-NMe₂ |
| 1918 | FCH₂—CH=CH—CH₂ | Me | 2-I, 4-NMe₃OTf |
| 1919 | FCH₂—CH=CH—CH₂ | Me | 2-I, 4-NMe₃I |
| 1920 | FCH₂—CH=CH—CH₂ | Me | 2-F, 4-I |
| 1921 | FCH₂—CH=CH—CH₂ | Me | 2-NO₂, 4-I |
| 1922 | FCH₂—CH=CH—CH₂ | Me | 2-NH₂, 4-I |
| 1923 | FCH₂—CH=CH—CH₂ | Me | 2-NHMe, 4-I |
| 1924 | FCH₂—CH=CH—CH₂ | Me | 2-NMe₂, 4-I |
| 1925 | FCH₂—CH=CH—CH₂ | Me | 2-NMe₃OTf, 4-I |
| 1926 | FCH₂—CH=CH—CH₂ | Me | 2-NMe₃I, 4-I |
| 1927 | FCH₂—CH=CH—CH₂ | Me | 2-Me, 3-F |
| 1928 | FCH₂—CH=CH—CH₂ | Me | 2-Me, 3-NO₂ |
| 1929 | FCH₂—CH=CH—CH₂ | Me | 2-Me, 3-NH₂ |
| 1930 | FCH₂—CH=CH—CH₂ | Me | 2-Me, 3-NHMe |
| 1931 | FCH₂—CH=CH—CH₂ | Me | 2-Me, 3-NMe₂ |
| 1932 | FCH₂—CH=CH—CH₂ | Me | 2-Me, 3-NMe₃OTf |
| 1933 | FCH₂—CH=CH—CH₂ | Me | 2-Me, 3-NMe₃I |
| 1934 | FCH₂—CH=CH—CH₂ | Me | 2-Me, 4-F |
| 1935 | FCH₂—CH=CH—CH₂ | Me | 2-Me, 4-NO₂ |
| 1936 | FCH₂—CH=CH—CH₂ | Me | 2-Me, 4-NH₂ |
| 1937 | FCH₂—CH=CH—CH₂ | Me | 2-Me, 4-NHMe |
| 1938 | FCH₂—CH=CH—CH₂ | Me | 2-Me, 4-NMe₂ |
| 1939 | FCH₂—CH=CH—CH₂ | Me | 2-Me, 4-NMe₃OTf |
| 1940 | FCH₂—CH=CH—CH₂ | Me | 2-Me, 4-NMe₃I |
| 1941 | FCH₂—CH=CH—CH₂ | Me | 2-Me, 5-F |
| 1942 | FCH₂—CH=CH—CH₂ | Me | 2-Me, 5-NO₂ |
| 1943 | FCH₂—CH=CH—CH₂ | Me | 2-Me, 5-NH₂ |
| 1944 | FCH₂—CH=CH—CH₂ | Me | 2-Me, 5-NHMe |
| 1945 | FCH₂—CH=CH—CH₂ | Me | 2-Me, 5-NMe₂ |
| 1946 | FCH₂—CH=CH—CH₂ | Me | 2-Me, 5-NMe₃OTf |
| 1947 | FCH₂—CH=CH—CH₂ | Me | 2-Me, 5-NMe₃I |
| 1948 | FCH₂—CH=CH—CH₂ | Me | 2-F, 4-Me |
| 1949 | FCH₂—CH=CH—CH₂ | Me | 2-NO₂, 4-Me |
| 1950 | FCH₂—CH=CH—CH₂ | Me | 2-NH₂, 4-Me |
| 1951 | FCH₂—CH=CH—CH₂ | Me | 2-NHMe, 4-Me |
| 1952 | FCH₂—CH=CH—CH₂ | Me | 2-NMe₂, 4-Me |
| 1953 | FCH₂—CH=CH—CH₂ | Me | 2-NMe₃, 4-Me |
| 1954 | FCH₂—CH=CH—CH₂ | Me | 2-NMe₃OTf, 4-Me |
| 1955 | FCH₂—CH=CH—CH₂ | Me | 2-NMe₃I, 4-Me |
| 1956 | FCH₂—CH=CH—CH₂ | Me | 2-SnMe₃, 4-F |
| 1957 | FCH₂—CH=CH—CH₂ | Me | 2-SnMe₃, 5-F |
| 1958 | FCH₂—CH=CH—CH₂ | Me | 2-F, 4-SnMe₃ |
| 1959 | FCH₂—CH=CH—CH₂ | Me | 2-Br, 6-Cl, 4-F |
| 1960 | FCH₂—CH=CH—CH₂ | Me | 2-Br, 6-Cl, 4-NO₂ |
| 1961 | FCH₂—CH=CH—CH₂ | Me | 2-Br, 6-Cl, 4-NH₂ |
| 1962 | FCH₂—CH=CH—CH₂ | Me | 2-Br, 6-Cl, 4-NHMe |
| 1963 | FCH₂—CH=CH—CH₂ | Me | 2-Br, 6-Cl, 4-NMe₂ |
| 1964 | FCH₂—CH=CH—CH₂ | Me | 2-Br, 6-Cl, 4-NMe₃OTf |
| 1965 | FCH₂—CH=CH—CH₂ | Me | 2-Br, 6-Cl, 4-NMe₃I |
| 1966 | FCH₂—CH=CH—CH₂ | Me | 2-Me, 6-Cl, 4-F |
| 1967 | FCH₂—CH=CH—CH₂ | Me | 2-SnMe₃, 6-Cl, 4-F |
| 1968 | FCH₂—CH=CH—CH₂ | Me | 2-Cl, 4-Me |
| 1969 | FCH₂—CH=CH—CH₂ | Me | 2-Cl, 4-Br |
| 1970 | FCH₂—CH=CH—CH₂ | Me | 2-Cl, 4-SnMe₃ |
| 1971 | FCH₂—CH=CH—CH₂ | Me | 2-Br, 4-Cl |
| 1972 | FCH₂—CH=CH—CH₂ | Me | 2-SnMe₃, 4-Cl |
| 1973 | FCH₂—CH=CH—CH₂ | Me | 2-Me, 4-Cl |
| 1974 | FCH₂—CH=CH—CH₂ | Me | 2-Br, 4-Br |
| 1975 | FCH₂—CH=CH—CH₂ | Me | 2-Br, 4-Me |
| 1976 | FCH₂—CH=CH—CH₂ | Me | 2-Br, 4-SnMe₃ |
| 1977 | FCH₂—CH=CH—CH₂ | Me | 2-SnMe₃, 4-Br |
| 1978 | FCH₂—CH=CH—CH₂ | Me | 2-Me, 4-Br |
| 1979 | FCH₂—CH=CH—CH₂ | Me | 2-Me, 4-SnMe₃ |
| 1980 | FCH₂—CH=CH—CH₂ | Me | 2-SnMe₃, 4-Me |
| 1981 | FCH₂—CH=CH—CH₂ | Me | 2-Me, 4-Me |
| 1982 | FCH₂—CH=CH—CH₂ | Me | 2-Et, 4-Br |
| 1983 | FCH₂—CH=CH—CH₂ | Me | 2-Et, 4-SnMe₃ |
| 1984 | FCH₂—CH=CH—CH₂ | Me | 2-Et, 4-Me |
| 1985 | FCH₂—CH=CH—CH₂ | Me | 2-Me, 4-Me, 6-Me |
| 1986 | FCH₂—CH=CH—CH₂ | Me | 2-Me, 4-Br, 6-Me |
| 1987 | FCH₂—CH=CH—CH₂ | Me | 2-Me, 4-SnMe₃, 6-Me |
| 1988 | FCH₂—CH=CH—CH₂ | Me | 2-Et, 6-Me |
| 1989 | FCH₂—CH=CH—CH₂ | Me | 2-Br, 4-i-Pr |
| 1990 | FCH₂—CH=CH—CH₂ | Me | 2-SnMe₃, 4-i-Pr |
| 1991 | FCH₂—CH=CH—CH₂ | Me | 2-Me, 4-i-Pr |
| 1992 | FCH₂—CH=CH—CH₂ | Me | 2-Br, 4-Br, 6-Br |
| 1993 | FCH₂—CH=CH—CH₂ | Me | 2-Br, 4-Me, 6-Br |
| 1994 | FCH₂—CH=CH—CH₂ | Me | 2-Br, 4-SnMe₃, 6-Br |
| 1995 | FCH₂—CH=CH—CH₂ | Me | 2-SnMe₃, 4-Br, 6-Br |
| 1996 | FCH₂—CH=CH—CH₂ | Me | 2-Br, 4-Br, 6-Me |
| 1997 | FCH₂—CH=CH—CH₂ | Me | 2-Br, 4-CF₃, 6-Br |
| 1998 | FCH₂—CH=CH—CH₂ | Me | 2-Br, 4-Br, 6-CF₃ |
| 1999 | FCH₂—CH=CH—CH₂ | Me | 2-CF₃, 4-CF₃ |
| 2000 | FCH₂—CH=CH—CH₂ | Me | 2-Cl, 4-CF₃ |
| 2001 | FCH₂—CH=CH—CH₂ | Me | 2-CF₃, 4-Cl |
| 2002 | FCH₂—CH=CH—CH₂ | Me | 2-Br, 4-CF₃ |
| 2003 | FCH₂—CH=CH—CH₂ | Me | 2-SnMe₃, 4-CF₃ |
| 2004 | FCH₂—CH=CH—CH₂ | Me | 2-Me, 4-CF₃ |
| 2005 | FCH₂—CH=CH—CH₂ | Me | 2-CF₃, 4-Br |
| 2006 | FCH₂—CH=CH—CH₂ | Me | 2-CF₃, 4-SnMe₃ |
| 2007 | FCH₂—CH=CH—CH₂ | Me | 2-CF₃, 4-Me |
| 2008 | FCH₂—CH=CH—CH₂ | Me | 2-Br, 4-OH |
| 2009 | FCH₂—CH=CH—CH₂ | Me | 2-Br, 4-OMe |
| 2010 | FCH₂—CH=CH—CH₂ | Me | 2-Br, 4-OMeF |
| 2011 | FCH₂—CH=CH—CH₂ | Me | 2-Br, 4-OCF₃ |
| 2012 | FCH₂—CH=CH—CH₂ | Me | 2-Br, 4-OEtF |
| 2013 | FCH₂—CH=CH—CH₂ | Me | 2-Br, 4-OPrF |
| 2014 | FCH₂—CH=CH—CH₂ | Me | 2-OH, 4-Br |
| 2015 | FCH₂—CH=CH—CH₂ | Me | 2-OMe, 4-Br |
| 2016 | FCH₂—CH=CH—CH₂ | Me | 2-OMeF, 4-Br |
| 2017 | FCH₂—CH=CH—CH₂ | Me | 2-OCF₃, 4-Br |
| 2018 | FCH₂—CH=CH—CH₂ | Me | 2-OEtF, 4-Br |
| 2019 | FCH₂—CH=CH—CH₂ | Me | 2-OPrF, 4-Br |

TABLE 1-continued

Substituent list for compounds of general structure VI.


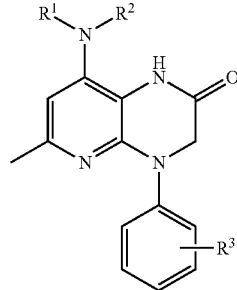

| Compound # | R$^1$ = | R$^2$ = | R$^3$ = |
|---|---|---|---|
| 2020 | FCH$_2$—CH=CH—CH$_2$ | Me | 2-I, 4-OH |
| 2021 | FCH$_2$—CH=CH—CH$_2$ | Me | 2-I, 4-OMe |
| 2022 | FCH$_2$—CH=CH—CH$_2$ | Me | 2-I, 4-OMeF |
| 2023 | FCH$_2$—CH=CH—CH$_2$ | Me | 2-I, 4-OCF$_3$ |
| 2024 | FCH$_2$—CH=CH—CH$_2$ | Me | 2-I, 4-OEtF |
| 2025 | FCH$_2$—CH=CH—CH$_2$ | Me | 2-I, 4-OPrF |
| 2026 | FCH$_2$—CH=CH—CH$_2$ | Me | 2-OH, 4-I |
| 2027 | FCH$_2$—CH=CH—CH$_2$ | Me | 2-OMe, 4-I |
| 2028 | FCH$_2$—CH=CH—CH$_2$ | Me | 2-OMeF, 4-I |
| 2029 | FCH$_2$—CH=CH—CH$_2$ | Me | 2-OCF$_3$, 4-I |
| 2030 | FCH$_2$—CH=CH—CH$_2$ | Me | 2-OEtF, 4-I |
| 2031 | FCH$_2$—CH=CH—CH$_2$ | Me | 2-OPrF, 4-I |
| 2032 | FCH$_2$—CH=CH—CH$_2$ | Me | 2-SnMe$_3$, 4-OH |
| 2033 | FCH$_2$—CH=CH—CH$_2$ | Me | 2-SnMe$_3$, 4-OMe |
| 2034 | FCH$_2$—CH=CH—CH$_2$ | Me | 2-SnMe$_3$, 4-OMeF |
| 2035 | FCH$_2$—CH=CH—CH$_2$ | Me | 2-SnMe$_3$, 4-OCF$_3$ |
| 2036 | FCH$_2$—CH=CH—CH$_2$ | Me | 2-SnMe$_3$, 4-OEtF |
| 2037 | FCH$_2$—CH=CH—CH$_2$ | Me | 2-SnMe$_3$, 4-OPrF |
| 2038 | FCH$_2$—CH=CH—CH$_2$ | Me | 2-OH, 4-SnMe$_3$ |
| 2039 | FCH$_2$—CH=CH—CH$_2$ | Me | 2-OMe, 4-SnMe$_3$ |
| 2040 | FCH$_2$—CH=CH—CH$_2$ | Me | 2-OMeF, 4-SnMe$_3$ |
| 2041 | FCH$_2$—CH=CH—CH$_2$ | Me | 2-OCF$_3$, 4-SnMe$_3$ |
| 2042 | FCH$_2$—CH=CH—CH$_2$ | Me | 2-OEtF, 4-SnMe$_3$ |
| 2043 | FCH$_2$—CH=CH—CH$_2$ | Me | 2-OPrF, 4-SnMe$_3$ |
| 2044 | FCH$_2$—CH=CH—CH$_2$ | Et | H |
| 2045 | FCH$_2$—CH=CH—CH$_2$ | Et | 2-t-Bu |
| 2046 | FCH$_2$—CH=CH—CH$_2$ | Et | 2-Br |
| 2047 | FCH$_2$—CH=CH—CH$_2$ | Et | 3-Br |
| 2048 | FCH$_2$—CH=CH—CH$_2$ | Et | 4-Br |
| 2049 | FCH$_2$—CH=CH—CH$_2$ | Et | 2-I |
| 2050 | FCH$_2$—CH=CH—CH$_2$ | Et | 3-I |
| 2051 | FCH$_2$—CH=CH—CH$_2$ | Et | 4-I |
| 2052 | FCH$_2$—CH=CH—CH$_2$ | Et | 2-SnMe$_3$ |
| 2053 | FCH$_2$—CH=CH—CH$_2$ | Et | 3-SnMe$_3$ |
| 2054 | FCH$_2$—CH=CH—CH$_2$ | Et | 4-SnMe$_3$ |
| 2055 | FCH$_2$—CH=CH—CH$_2$ | Et | 2-Me |
| 2056 | FCH$_2$—CH=CH—CH$_2$ | Et | 3-Me |
| 2057 | FCH$_2$—CH=CH—CH$_2$ | Et | 4-Me |
| 2058 | FCH$_2$—CH=CH—CH$_2$ | Et | 2-OH |
| 2059 | FCH$_2$—CH=CH—CH$_2$ | Et | 3-OH |
| 2060 | FCH$_2$—CH=CH—CH$_2$ | Et | 4-OH |
| 2061 | FCH$_2$—CH=CH—CH$_2$ | Et | 2-OMe |
| 2062 | FCH$_2$—CH=CH—CH$_2$ | Et | 3-OMe |
| 2063 | FCH$_2$—CH=CH—CH$_2$ | Et | 4-OMe |
| 2064 | FCH$_2$—CH=CH—CH$_2$ | Et | 2-OMeF |
| 2065 | FCH$_2$—CH=CH—CH$_2$ | Et | 3-OMeF |
| 2066 | FCH$_2$—CH=CH—CH$_2$ | Et | 4-OMeF |
| 2067 | FCH$_2$—CH=CH—CH$_2$ | Et | 2-OCF$_3$ |
| 2068 | FCH$_2$—CH=CH—CH$_2$ | Et | 3-OCF$_3$ |
| 2069 | FCH$_2$—CH=CH—CH$_2$ | Et | 4-OCF$_3$ |
| 2070 | FCH$_2$—CH=CH—CH$_2$ | Et | 2-OEtF |
| 2071 | FCH$_2$—CH=CH—CH$_2$ | Et | 3-OEtF |
| 2072 | FCH$_2$—CH=CH—CH$_2$ | Et | 4-OEtF |
| 2073 | FCH$_2$—CH=CH—CH$_2$ | Et | 2-OPrF |
| 2074 | FCH$_2$—CH=CH—CH$_2$ | Et | 3-OPrF |
| 2075 | FCH$_2$—CH=CH—CH$_2$ | Et | 4-OPrF |
| 2076 | FCH$_2$—CH=CH—CH$_2$ | Et | 2-SH |
| 2077 | FCH$_2$—CH=CH—CH$_2$ | Et | 3-SH |
| 2078 | FCH$_2$—CH=CH—CH$_2$ | Et | 4-SH |
| 2079 | FCH$_2$—CH=CH—CH$_2$ | Et | 2-SMe |
| 2080 | FCH$_2$—CH=CH—CH$_2$ | Et | 3-SMe |
| 2081 | FCH$_2$—CH=CH—CH$_2$ | Et | 4-SMe |
| 2082 | FCH$_2$—CH=CH—CH$_2$ | Et | 2-SMeF |
| 2083 | FCH$_2$—CH=CH—CH$_2$ | Et | 3-SMeF |
| 2084 | FCH$_2$—CH=CH—CH$_2$ | Et | 4-SMeF |
| 2085 | FCH$_2$—CH=CH—CH$_2$ | Et | 2-SCF$_3$ |
| 2086 | FCH$_2$—CH=CH—CH$_2$ | Et | 3-SCF$_3$ |
| 2087 | FCH$_2$—CH=CH—CH$_2$ | Et | 4-SCF$_3$ |
| 2088 | FCH$_2$—CH=CH—CH$_2$ | Et | 2-SEtF |
| 2089 | FCH$_2$—CH=CH—CH$_2$ | Et | 3-SEtF |
| 2090 | FCH$_2$—CH=CH—CH$_2$ | Et | 4-SEtF |
| 2091 | FCH$_2$—CH=CH—CH$_2$ | Et | 2-SPrF |
| 2092 | FCH$_2$—CH=CH—CH$_2$ | Et | 3-SPrF |
| 2093 | FCH$_2$—CH=CH—CH$_2$ | Et | 4-SPrF |
| 2094 | FCH$_2$—CH=CH—CH$_2$ | Et | 2-OMe, 4-OMe |
| 2095 | FCH$_2$—CH=CH—CH$_2$ | Et | 2-Me, 5-OH |
| 2096 | FCH$_2$—CH=CH—CH$_2$ | Et | 2-Me, 5-OMe |
| 2097 | FCH$_2$—CH=CH—CH$_2$ | Et | 2-Me, 5-OMeF |
| 2098 | FCH$_2$—CH=CH—CH$_2$ | Et | 2-Me, 5-OEtF |
| 2099 | FCH$_2$—CH=CH—CH$_2$ | Et | 2-Me, 5-OPrF |
| 2100 | FCH$_2$—CH=CH—CH$_2$ | Et | 2-Me, 4-OH |
| 2101 | FCH$_2$—CH=CH—CH$_2$ | Et | 2-Me, 4-OMe |
| 2102 | FCH$_2$—CH=CH—CH$_2$ | Et | 2-Me, 4-OMeF |
| 2103 | FCH$_2$—CH=CH—CH$_2$ | Et | 2-Me, 4-OCF$_3$ |
| 2104 | FCH$_2$—CH=CH—CH$_2$ | Et | 2-Me, 4-OEtF |
| 2105 | FCH$_2$—CH=CH—CH$_2$ | Et | 2-Me, 4-OPrF |
| 2106 | FCH$_2$—CH=CH—CH$_2$ | Et | 2-OH, 4-Me |
| 2107 | FCH$_2$—CH=CH—CH$_2$ | Et | 2-OMe, 4-Me |
| 2108 | FCH$_2$—CH=CH—CH$_2$ | Et | 2-OMeF, 4-Me |
| 2109 | FCH$_2$—CH=CH—CH$_2$ | Et | 2-OCF$_3$, 4-Me |
| 2110 | FCH$_2$—CH=CH—CH$_2$ | Et | 2-OEtF, 4-Me |
| 2111 | FCH$_2$—CH=CH—CH$_2$ | Et | 2-OPrF, 4-Me |
| 2112 | FCH$_2$—CH=CH—CH$_2$ | Et | 2-Cl, 4-OH |
| 2113 | FCH$_2$—CH=CH—CH$_2$ | Et | 2-Cl, 4-OMe |
| 2114 | FCH$_2$—CH=CH—CH$_2$ | Et | 2-Cl, 4-OMeF |
| 2115 | FCH$_2$—CH=CH—CH$_2$ | Et | 2-Cl, 4-OCF$_3$ |
| 2116 | FCH$_2$—CH=CH—CH$_2$ | Et | 2-Cl, 4-OEtF |
| 2117 | FCH$_2$—CH=CH—CH$_2$ | Et | 2-Cl, 4-OPrF |
| 2118 | FCH$_2$—CH=CH—CH$_2$ | Et | 2-F, 4-F |
| 2119 | FCH$_2$—CH=CH—CH$_2$ | Et | 2-Cl, 4-Cl |
| 2120 | FCH$_2$—CH=CH—CH$_2$ | Et | 2-Cl, 4-F |
| 2121 | FCH$_2$—CH=CH—CH$_2$ | Et | 2-Cl, 4-NO$_2$ |
| 2122 | FCH$_2$—CH=CH—CH$_2$ | Et | 2-Cl, 4-NH$_2$ |
| 2123 | FCH$_2$—CH=CH—CH$_2$ | Et | 2-Cl, 4-NHMe |
| 2124 | FCH$_2$—CH=CH—CH$_2$ | Et | 2-Cl, 4-NMe$_2$ |
| 2125 | FCH$_2$—CH=CH—CH$_2$ | Et | 2-Cl, 4-NMe$_3$OTf |
| 2126 | FCH$_2$—CH=CH—CH$_2$ | Et | 2-Cl, 4-NMe$_3$I |
| 2127 | FCH$_2$—CH=CH—CH$_2$ | Et | 2-Cl, 5-F |
| 2128 | FCH$_2$—CH=CH—CH$_2$ | Et | 2-Cl, 5-NO$_2$ |
| 2129 | FCH$_2$—CH=CH—CH$_2$ | Et | 2-Cl, 5-NH$_2$ |
| 2130 | FCH$_2$—CH=CH—CH$_2$ | Et | 2-Cl, 5-NHMe |
| 2131 | FCH$_2$—CH=CH—CH$_2$ | Et | 2-Cl, 5-NMe$_2$ |
| 2132 | FCH$_2$—CH=CH—CH$_2$ | Et | 2-Cl, 5-NMe$_3$OTf |
| 2133 | FCH$_2$—CH=CH—CH$_2$ | Et | 2-Cl, 5-NMe$_3$I |
| 2134 | FCH$_2$—CH=CH—CH$_2$ | Et | 2-F, 4-Cl |
| 2135 | FCH$_2$—CH=CH—CH$_2$ | Et | 2-NO$_2$, 4-Cl |
| 2136 | FCH$_2$—CH=CH—CH$_2$ | Et | 2-NH$_2$, 4-Cl |
| 2137 | FCH$_2$—CH=CH—CH$_2$ | Et | 2-NHMe, 4-Cl |
| 2138 | FCH$_2$—CH=CH—CH$_2$ | Et | 2-NMe$_2$, 4-Cl |
| 2139 | FCH$_2$—CH=CH—CH$_2$ | Et | 2-NMe$_3$OTf, 4-Cl |

TABLE 1-continued

Substituent list for compounds of general structure VI.

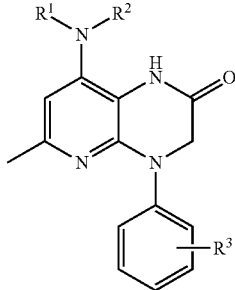

| Compound # | R¹ = | R² = | R³ = |
|---|---|---|---|
| 2140 | FCH₂—CH=CH—CH₂ | Et | 2-NMe₃I, 4-Cl |
| 2141 | FCH₂—CH=CH—CH₂ | Et | 2-F, 5-Cl |
| 2142 | FCH₂—CH=CH—CH₂ | Et | 2-NO₂, 5-Cl |
| 2143 | FCH₂—CH=CH—CH₂ | Et | 2-NH₂, 5-Cl |
| 2144 | FCH₂—CH=CH—CH₂ | Et | 2-NHMe, 5-Cl |
| 2145 | FCH₂—CH=CH—CH₂ | Et | 2-NMe₂, 5-Cl |
| 2146 | FCH₂—CH=CH—CH₂ | Et | 2-NMe₃OTf, 5-Cl |
| 2147 | FCH₂—CH=CH—CH₂ | Et | 2-NMe₃I, 5-Cl |
| 2148 | FCH₂—CH=CH—CH₂ | Et | 2-Br, 4-F |
| 2149 | FCH₂—CH=CH—CH₂ | Et | 2-Br, 4-NO₂ |
| 2150 | FCH₂—CH=CH—CH₂ | Et | 2-Br, 4-NH₂ |
| 2151 | FCH₂—CH=CH—CH₂ | Et | 2-Br, 4-NHMe |
| 2152 | FCH₂—CH=CH—CH₂ | Et | 2-Br, 4-NMe₂ |
| 2153 | FCH₂—CH=CH—CH₂ | Et | 2-Br, 4-NMe₃OTf |
| 2154 | FCH₂—CH=CH—CH₂ | Et | 2-Br, 4-NMe₃I |
| 2155 | FCH₂—CH=CH—CH₂ | Et | 2-Br, 5-F |
| 2156 | FCH₂—CH=CH—CH₂ | Et | 2-Br, 5-NO₂ |
| 2157 | FCH₂—CH=CH—CH₂ | Et | 2-Br, 5-NH₂ |
| 2158 | FCH₂—CH=CH—CH₂ | Et | 2-Br, 5-NHMe |
| 2159 | FCH₂—CH=CH—CH₂ | Et | 2-Br, 5-NMe₂ |
| 2160 | FCH₂—CH=CH—CH₂ | Et | 2-Br, 5-NMe₃OTf |
| 2161 | FCH₂—CH=CH—CH₂ | Et | 2-Br, 5-NMe₃I |
| 2162 | FCH₂—CH=CH—CH₂ | Et | 2-F, 4-Br |
| 2163 | FCH₂—CH=CH—CH₂ | Et | 2-NO₂, 4-Br |
| 2164 | FCH₂—CH=CH—CH₂ | Et | 2-NH₂, 4-Br |
| 2165 | FCH₂—CH=CH—CH₂ | Et | 2-NHMe, 4-Br |
| 2166 | FCH₂—CH=CH—CH₂ | Et | 2-NMe₂, 4-Br |
| 2167 | FCH₂—CH=CH—CH₂ | Et | 2-NMe₃OTf, 4-Br |
| 2168 | FCH₂—CH=CH—CH₂ | Et | 2-NMe₃I, 4-Br |
| 2169 | FCH₂—CH=CH—CH₂ | Et | 2-I, 4-F |
| 2170 | FCH₂—CH=CH—CH₂ | Et | 2-I, 4-NO₂ |
| 2171 | FCH₂—CH=CH—CH₂ | Et | 2-I, 4-NH₂ |
| 2172 | FCH₂—CH=CH—CH₂ | Et | 2-I, 4-NHMe |
| 2173 | FCH₂—CH=CH—CH₂ | Et | 2-I, 4-NMe₂ |
| 2174 | FCH₂—CH=CH—CH₂ | Et | 2-I, 4-NMe₃OTf |
| 2175 | FCH₂—CH=CH—CH₂ | Et | 2-I, 4-NMe₃I |
| 2176 | FCH₂—CH=CH—CH₂ | Et | 2-F, 4-I |
| 2177 | FCH₂—CH=CH—CH₂ | Et | 2-NO₂, 4-I |
| 2178 | FCH₂—CH=CH—CH₂ | Et | 2-NH₂, 4-I |
| 2179 | FCH₂—CH=CH—CH₂ | Et | 2-NHMe, 4-I |
| 2180 | FCH₂—CH=CH—CH₂ | Et | 2-NMe₂, 4-I |
| 2181 | FCH₂—CH=CH—CH₂ | Et | 2-NMe₃OTf, 4-I |
| 2182 | FCH₂—CH=CH—CH₂ | Et | 2-NMe₃I, 4-I |
| 2183 | FCH₂—CH=CH—CH₂ | Et | 2-Me, 3-F |
| 2184 | FCH₂—CH=CH—CH₂ | Et | 2-Me, 3-NO₂ |
| 2185 | FCH₂—CH=CH—CH₂ | Et | 2-Me, 3-NH₂ |
| 2186 | FCH₂—CH=CH—CH₂ | Et | 2-Me, 3-NHMe |
| 2187 | FCH₂—CH=CH—CH₂ | Et | 2-Me, 3-NMe₂ |
| 2188 | FCH₂—CH=CH—CH₂ | Et | 2-Me, 3-NMe₃OTf |
| 2189 | FCH₂—CH=CH—CH₂ | Et | 2-Me, 3-NMe₃I |
| 2190 | FCH₂—CH=CH—CH₂ | Et | 2-Me, 4-F |
| 2191 | FCH₂—CH=CH—CH₂ | Et | 2-Me, 4-NO₂ |
| 2192 | FCH₂—CH=CH—CH₂ | Et | 2-Me, 4-NH₂ |
| 2193 | FCH₂—CH=CH—CH₂ | Et | 2-Me, 4-NHMe |
| 2194 | FCH₂—CH=CH—CH₂ | Et | 2-Me, 4-NMe₂ |
| 2195 | FCH₂—CH=CH—CH₂ | Et | 2-Me, 4-NMe₃OTf |
| 2196 | FCH₂—CH=CH—CH₂ | Et | 2-Me, 4-NMe₃I |
| 2197 | FCH₂—CH=CH—CH₂ | Et | 2-Me, 5-F |
| 2198 | FCH₂—CH=CH—CH₂ | Et | 2-Me, 5-NO₂ |
| 2199 | FCH₂—CH=CH—CH₂ | Et | 2-Me, 5-NH₂ |

TABLE 1-continued

Substituent list for compounds of general structure VI.

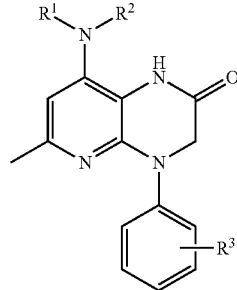

| Compound # | R¹ = | R² = | R³ = |
|---|---|---|---|
| 2200 | FCH₂—CH=CH—CH₂ | Et | 2-Me, 5-NHMe |
| 2201 | FCH₂—CH=CH—CH₂ | Et | 2-Me, 5-NMe₂ |
| 2202 | FCH₂—CH=CH—CH₂ | Et | 2-Me, 5-NMe₃OTf |
| 2203 | FCH₂—CH=CH—CH₂ | Et | 2-Me, 5-NMe₃I |
| 2204 | FCH₂—CH=CH—CH₂ | Et | 2-F, 4-Me |
| 2205 | FCH₂—CH=CH—CH₂ | Et | 2-NO₂, 4-Me |
| 2206 | FCH₂—CH=CH—CH₂ | Et | 2-NH₂, 4-Me |
| 2207 | FCH₂—CH=CH—CH₂ | Et | 2-NHMe, 4-Me |
| 2208 | FCH₂—CH=CH—CH₂ | Et | 2-NMe₂, 4-Me |
| 2209 | FCH₂—CH=CH—CH₂ | Et | 2-NMe₃, 4-Me |
| 2210 | FCH₂—CH=CH—CH₂ | Et | 2-NMe₃OTf, 4-Me |
| 2211 | FCH₂—CH=CH—CH₂ | Et | 2-NMe₃I, 4-Me |
| 2212 | FCH₂—CH=CH—CH₂ | Et | 2-SnMe₃, 4-F |
| 2213 | FCH₂—CH=CH—CH₂ | Et | 2-SnMe₃, 5-F |
| 2214 | FCH₂—CH=CH—CH₂ | Et | 2-F, 4-SnMe₃ |
| 2215 | FCH₂—CH=CH—CH₂ | Et | 2-Br, 6-Cl, 4-F |
| 2216 | FCH₂—CH=CH—CH₂ | Et | 2-Br, 6-Cl, 4-NO₂ |
| 2217 | FCH₂—CH=CH—CH₂ | Et | 2-Br, 6-Cl, 4-NH₂ |
| 2218 | FCH₂—CH=CH—CH₂ | Et | 2-Br, 6-Cl, 4-NHMe |
| 2219 | FCH₂—CH=CH—CH₂ | Et | 2-Br, 6-Cl, 4-NMe₂ |
| 2220 | FCH₂—CH=CH—CH₂ | Et | 2-Br, 6-Cl, 4-NMe₃OTf |
| 2221 | FCH₂—CH=CH—CH₂ | Et | 2-Br, 6-Cl, 4-NMe₃I |
| 2222 | FCH₂—CH=CH—CH₂ | Et | 2-Me, 6-Cl, 4-F |
| 2223 | FCH₂—CH=CH—CH₂ | Et | 2-SnMe₃, 6-Cl, 4-F |
| 2224 | FCH₂—CH=CH—CH₂ | Et | 2-Cl, 4-Me |
| 2225 | FCH₂—CH=CH—CH₂ | Et | 2-Cl, 4-Br |
| 2226 | FCH₂—CH=CH—CH₂ | Et | 2-Cl, 4-SnMe₃ |
| 2227 | FCH₂—CH=CH—CH₂ | Et | 2-Br, 4-Cl |
| 2228 | FCH₂—CH=CH—CH₂ | Et | 2-SnMe₃, 4-Cl |
| 2229 | FCH₂—CH=CH—CH₂ | Et | 2-Me, 4-Cl |
| 2230 | FCH₂—CH=CH—CH₂ | Et | 2-Br, 4-Br |
| 2231 | FCH₂—CH=CH—CH₂ | Et | 2-Br, 4-Me |
| 2232 | FCH₂—CH=CH—CH₂ | Et | 2-Br, 4-SnMe₃ |
| 2233 | FCH₂—CH=CH—CH₂ | Et | 2-SnMe₃, 4-Me |
| 2234 | FCH₂—CH=CH—CH₂ | Et | 2-Me, 4-Br |
| 2235 | FCH₂—CH=CH—CH₂ | Et | 2-Me, 4-SnMe₃ |
| 2236 | FCH₂—CH=CH—CH₂ | Et | 2-SnMe₃, 4-Me |
| 2237 | FCH₂—CH=CH—CH₂ | Et | 2-Me, 4-Me |
| 2238 | FCH₂—CH=CH—CH₂ | Et | 2-Et, 4-Br |
| 2239 | FCH₂—CH=CH—CH₂ | Et | 2-Et, 4-SnMe₃ |
| 2240 | FCH₂—CH=CH—CH₂ | Et | 2-Et, 4-Me |
| 2241 | FCH₂—CH=CH—CH₂ | Et | 2-Me, 4-Me, 6-Me |
| 2242 | FCH₂—CH=CH—CH₂ | Et | 2-Me, 4-Br, 6-Me |
| 2243 | FCH₂—CH=CH—CH₂ | Et | 2-Me, 4-SnMe₃, 6-Me |
| 2244 | FCH₂—CH=CH—CH₂ | Et | 2-Et, 6-Me |
| 2245 | FCH₂—CH=CH—CH₂ | Et | 2-Br, 4-i-Pr |
| 2246 | FCH₂—CH=CH—CH₂ | Et | 2-SnMe₃, 4-i-Pr |
| 2247 | FCH₂—CH=CH—CH₂ | Et | 2-Me, 4-i-Pr |
| 2248 | FCH₂—CH=CH—CH₂ | Et | 2-Br, 4-Br, 6-Br |
| 2249 | FCH₂—CH=CH—CH₂ | Et | 2-Br, 4-Me, 6-Br |
| 2250 | FCH₂—CH=CH—CH₂ | Et | 2-Br, 4-SnMe₃, 6-Br |
| 2251 | FCH₂—CH=CH—CH₂ | Et | 2-SnMe₃, 4-Br, 6-Br |
| 2252 | FCH₂—CH=CH—CH₂ | Et | 2-Br, 4-Br, 6-Me |
| 2253 | FCH₂—CH=CH—CH₂ | Et | 2-Br, 4-CF₃, 6-Br |
| 2254 | FCH₂—CH=CH—CH₂ | Et | 2-Br, 4-Br, 6-CF₃ |
| 2255 | FCH₂—CH=CH—CH₂ | Et | 2-CF₃, 4-CF₃ |
| 2256 | FCH₂—CH=CH—CH₂ | Et | 2-Cl, 4-CF₃ |
| 2257 | FCH₂—CH=CH—CH₂ | Et | 2-CF₃, 4-Cl |
| 2258 | FCH₂—CH=CH—CH₂ | Et | 2-Br, 4-CF₃ |
| 2259 | FCH₂—CH=CH—CH₂ | Et | 2-SnMe₃, 4-CF₃ |

TABLE 1-continued

Substituent list for compounds of general structure VI.


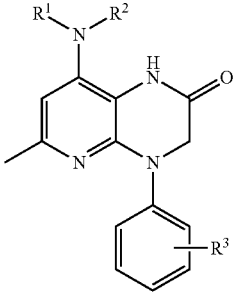

| Compound # | R¹ = | R² = | R³ = |
|---|---|---|---|
| 2260 | FCH₂—CH=CH—CH₂ | Et | 2-Me, 4-CF₃ |
| 2261 | FCH₂—CH=CH—CH₂ | Et | 2-CF₃, 4-Br |
| 2262 | FCH₂—CH=CH—CH₂ | Et | 2-CF₃, 4-SnMe₃ |
| 2263 | FCH₂—CH=CH—CH₂ | Et | 2-CF₃, 4-Me |
| 2264 | FCH₂—CH=CH—CH₂ | Et | 2-Br, 4-OH |
| 2265 | FCH₂—CH=CH—CH₂ | Et | 2-Br, 4-OMe |
| 2266 | FCH₂—CH=CH—CH₂ | Et | 2-Br, 4-OMeF |
| 2267 | FCH₂—CH=CH—CH₂ | Et | 2-Br, 4-OCF₃ |
| 2268 | FCH₂—CH=CH—CH₂ | Et | 2-Br, 4-OEtF |
| 2269 | FCH₂—CH=CH—CH₂ | Et | 2-Br, 4-OPrF |
| 2270 | FCH₂—CH=CH—CH₂ | Et | 2-OH, 4-Br |
| 2271 | FCH₂—CH=CH—CH₂ | Et | 2-OMe, 4-Br |
| 2272 | FCH₂—CH=CH—CH₂ | Et | 2-OMeF, 4-Br |
| 2273 | FCH₂—CH=CH—CH₂ | Et | 2-OCF₃, 4-Br |
| 2274 | FCH₂—CH=CH—CH₂ | Et | 2-OEtF, 4-Br |
| 2275 | FCH₂—CH=CH—CH₂ | Et | 2-OPrF, 4-Br |
| 2276 | FCH₂—CH=CH—CH₂ | Et | 2-I, 4-OH |
| 2276 | FCH₂—CH=CH—CH₂ | Et | 2-I, 4-OMe |
| 2278 | FCH₂—CH=CH—CH₂ | Et | 2-I, 4-OMeF |
| 2279 | FCH₂—CH=CH—CH₂ | Et | 2-I, 4-OCF₃ |
| 2280 | FCH₂—CH=CH—CH₂ | Et | 2-I, 4-OEtF |
| 2281 | FCH₂—CH=CH—CH₂ | Et | 2-I, 4-OPrF |
| 2282 | FCH₂—CH=CH—CH₂ | Et | 2-OH, 4-I |
| 2283 | FCH₂—CH=CH—CH₂ | Et | 2-OMe, 4-I |
| 2284 | FCH₂—CH=CH—CH₂ | Et | 2-OMeF, 4-I |
| 2285 | FCH₂—CH=CH—CH₂ | Et | 2-OCF₃, 4-I |
| 2286 | FCH₂—CH=CH—CH₂ | Et | 2-OEtF, 4-I |
| 2287 | FCH₂—CH=CH—CH₂ | Et | 2-OPrF, 4-I |
| 2288 | FCH₂—CH=CH—CH₂ | Et | 2-SnMe₃, 4-OH |
| 2289 | FCH₂—CH=CH—CH₂ | Et | 2-SnMe₃, 4-OMe |
| 2290 | FCH₂—CH=CH—CH₂ | Et | 2-SnMe₃, 4-OMeF |
| 2291 | FCH₂—CH=CH—CH₂ | Et | 2-SnMe₃, 4-OCF₃ |
| 2292 | FCH₂—CH=CH—CH₂ | Et | 2-SnMe₃, 4-OEtF |
| 2293 | FCH₂—CH=CH—CH₂ | Et | 2-SnMe₃, 4-OPrF |
| 2294 | FCH₂—CH=CH—CH₂ | Et | 2-OH, 4-SnMe₃ |
| 2295 | FCH₂—CH=CH—CH₂ | Et | 2-OMe, 4-SnMe₃ |
| 2296 | FCH₂—CH=CH—CH₂ | Et | 2-OMeF, 4-SnMe₃ |
| 2297 | FCH₂—CH=CH—CH₂ | Et | 2-OCF₃, 4-SnMe₃ |
| 2298 | FCH₂—CH=CH—CH₂ | Et | 2-OEtF, 4-SnMe₃ |
| 2299 | FCH₂—CH=CH—CH₂ | Et | 2-OPrF, 4-SnMe₃ |
| 2300 | FCH₂—CH=CH—CH₂ | Et—F | H |
| 2301 | FCH₂—CH=CH—CH₂ | Et—F | 2-t-Bu |
| 2302 | FCH₂—CH=CH—CH₂ | Et—F | 2-Br |
| 2303 | FCH₂—CH=CH—CH₂ | Et—F | 3-Br |
| 2304 | FCH₂—CH=CH—CH₂ | Et—F | 4-Br |
| 2305 | FCH₂—CH=CH—CH₂ | Et—F | 2-I |
| 2306 | FCH₂—CH=CH—CH₂ | Et—F | 3-I |
| 2307 | FCH₂—CH=CH—CH₂ | Et—F | 4-I |
| 2308 | FCH₂—CH=CH—CH₂ | Et—F | 2-SnMe₃ |
| 2309 | FCH₂—CH=CH—CH₂ | Et—F | 3-SnMe₃ |
| 2310 | FCH₂—CH=CH—CH₂ | Et—F | 4-SnMe₃ |
| 2311 | FCH₂—CH=CH—CH₂ | Et—F | 2-Me |
| 2312 | FCH₂—CH=CH—CH₂ | Et—F | 3-Me |
| 2313 | FCH₂—CH=CH—CH₂ | Et—F | 4-Me |
| 2314 | FCH₂—CH=CH—CH₂ | Et—F | 2-OH |
| 2315 | FCH₂—CH=CH—CH₂ | Et—F | 3-OH |
| 2316 | FCH₂—CH=CH—CH₂ | Et—F | 4-OH |
| 2317 | FCH₂—CH=CH—CH₂ | Et—F | 2-OMe |
| 2318 | FCH₂—CH=CH—CH₂ | Et—F | 3-OMe |
| 2319 | FCH₂—CH=CH—CH₂ | Et—F | 4-OMe |
| 2320 | FCH₂—CH=CH—CH₂ | Et—F | 2-OMeF |
| 2321 | FCH₂—CH=CH—CH₂ | Et—F | 3-OMeF |
| 2322 | FCH₂—CH=CH—CH₂ | Et—F | 4-OMeF |
| 2323 | FCH₂—CH=CH—CH₂ | Et—F | 2-OCF₃ |
| 2324 | FCH₂—CH=CH—CH₂ | Et—F | 3-OCF₃ |
| 2325 | FCH₂—CH=CH—CH₂ | Et—F | 4-OCF₃ |
| 2326 | FCH₂—CH=CH—CH₂ | Et—F | 2-OEtF |
| 2327 | FCH₂—CH=CH—CH₂ | Et—F | 3-OEtF |
| 2328 | FCH₂—CH=CH—CH₂ | Et—F | 4-OEtF |
| 2329 | FCH₂—CH=CH—CH₂ | Et—F | 2-OPrF |
| 2330 | FCH₂—CH=CH—CH₂ | Et—F | 3-OPrF |
| 2331 | FCH₂—CH=CH—CH₂ | Et—F | 4-OPrF |
| 2332 | FCH₂—CH=CH—CH₂ | Et—F | 2-SH |
| 2333 | FCH₂—CH=CH—CH₂ | Et—F | 3-SH |
| 2334 | FCH₂—CH=CH—CH₂ | Et—F | 4-SH |
| 2335 | FCH₂—CH=CH—CH₂ | Et—F | 2-SMe |
| 2336 | FCH₂—CH=CH—CH₂ | Et—F | 3-SMe |
| 2337 | FCH₂—CH=CH—CH₂ | Et—F | 4-SMe |
| 2338 | FCH₂—CH=CH—CH₂ | Et—F | 2-SMeF |
| 2339 | FCH₂—CH=CH—CH₂ | Et—F | 3-SMeF |
| 2340 | FCH₂—CH=CH—CH₂ | Et—F | 4-SMeF |
| 2341 | FCH₂—CH=CH—CH₂ | Et—F | 2-SCF₃ |
| 2342 | FCH₂—CH=CH—CH₂ | Et—F | 3-SCF₃ |
| 2343 | FCH₂—CH=CH—CH₂ | Et—F | 4-SCF₃ |
| 2344 | FCH₂—CH=CH—CH₂ | Et—F | 2-SEtF |
| 2345 | FCH₂—CH=CH—CH₂ | Et—F | 3-SEtF |
| 2346 | FCH₂—CH=CH—CH₂ | Et—F | 4-SEtF |
| 2347 | FCH₂—CH=CH—CH₂ | Et—F | 2-SPrF |
| 2348 | FCH₂—CH=CH—CH₂ | Et—F | 3-SPrF |
| 2349 | FCH₂—CH=CH—CH₂ | Et—F | 4-SPrF |
| 2350 | FCH₂—CH=CH—CH₂ | Et—F | 2-OMe, 4-OMe |
| 2351 | FCH₂—CH=CH—CH₂ | Et—F | 2-Me, 5-OH |
| 2352 | FCH₂—CH=CH—CH₂ | Et—F | 2-Me, 5-OMe |
| 2353 | FCH₂—CH=CH—CH₂ | Et—F | 2-Me, 5-OMeF |
| 2354 | FCH₂—CH=CH—CH₂ | Et—F | 2-Me, 5-OEtF |
| 2355 | FCH₂—CH=CH—CH₂ | Et—F | 2-Me, 5-OPrF |
| 2356 | FCH₂—CH=CH—CH₂ | Et—F | 2-Me, 4-OH |
| 2357 | FCH₂—CH=CH—CH₂ | Et—F | 2-Me, 4-OMe |
| 2358 | FCH₂—CH=CH—CH₂ | Et—F | 2-Me, 4-OMeF |
| 2359 | FCH₂—CH=CH—CH₂ | Et—F | 2-Me, 4-OCF₃ |
| 2360 | FCH₂—CH=CH—CH₂ | Et—F | 2-Me, 4-OEtF |
| 2361 | FCH₂—CH=CH—CH₂ | Et—F | 2-Me, 4-OPrF |
| 2362 | FCH₂—CH=CH—CH₂ | Et—F | 2-OH, 4-Me |
| 2363 | FCH₂—CH=CH—CH₂ | Et—F | 2-OMe, 4-Me |
| 2364 | FCH₂—CH=CH—CH₂ | Et—F | 2-OMeF, 4-Me |
| 2365 | FCH₂—CH=CH—CH₂ | Et—F | 2-OCF₃, 4-Me |
| 2366 | FCH₂—CH=CH—CH₂ | Et—F | 2-OEtF, 4-Me |
| 2367 | FCH₂—CH=CH—CH₂ | Et—F | 2-OPrF, 4-Me |
| 2368 | FCH₂—CH=CH—CH₂ | Et—F | 2-Cl, 4-OH |
| 2369 | FCH₂—CH=CH—CH₂ | Et—F | 2-Cl, 4-OMe |
| 2370 | FCH₂—CH=CH—CH₂ | Et—F | 2-Cl, 4-OMeF |
| 2371 | FCH₂—CH=CH—CH₂ | Et—F | 2-Cl, 4-OCF₃ |
| 2372 | FCH₂—CH=CH—CH₂ | Et—F | 2-Cl, 4-OEtF |
| 2373 | FCH₂—CH=CH—CH₂ | Et—F | 2-Cl, 4-OPrF |
| 2374 | FCH₂—CH=CH—CH₂ | Et—F | 2-F, 4-F |
| 2375 | FCH₂—CH=CH—CH₂ | Et—F | 2-Cl, 4-Cl |
| 2376 | FCH₂—CH=CH—CH₂ | Et—F | 2-Cl, 4-F |
| 2377 | FCH₂—CH=CH—CH₂ | Et—F | 2-Cl, 4-NO₂ |
| 2378 | FCH₂—CH=CH—CH₂ | Et—F | 2-Cl, 4-NH₂ |
| 2379 | FCH₂—CH=CH—CH₂ | Et—F | 2-Cl, 4-NHMe |

TABLE 1-continued

Substituent list for compounds of general structure VI.

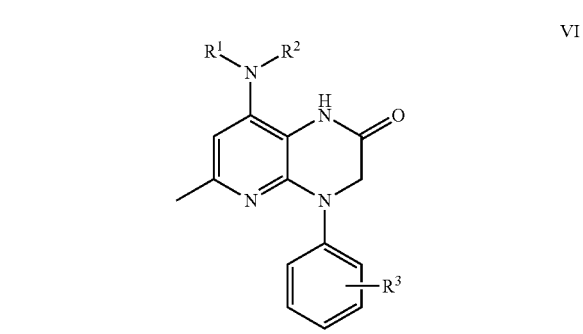

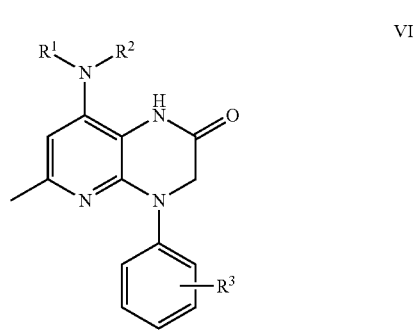

| Compound # | R¹ = | R² = | R³ = |
|---|---|---|---|
| 2380 | FCH₂—CH=CH—CH₂ | Et—F | 2-Cl, 4-NMe₂ |
| 2381 | FCH₂—CH=CH—CH₂ | Et—F | 2-Cl, 4-NMe₃OTf |
| 2382 | FCH₂—CH=CH—CH₂ | Et—F | 2-Cl, 4-NMe₃I |
| 2383 | FCH₂—CH=CH—CH₂ | Et—F | 2-Cl, 5-F |
| 2384 | FCH₂—CH=CH—CH₂ | Et—F | 2-Cl, 5-NO₂ |
| 2385 | FCH₂—CH=CH—CH₂ | Et—F | 2-Cl, 5-NH₂ |
| 2386 | FCH₂—CH=CH—CH₂ | Et—F | 2-Cl, 5-NHMe |
| 2387 | FCH₂—CH=CH—CH₂ | Et—F | 2-Cl, 5-NMe₂ |
| 2388 | FCH₂—CH=CH—CH₂ | Et—F | 2-Cl, 5-NMe₃OTf |
| 2389 | FCH₂—CH=CH—CH₂ | Et—F | 2-Cl, 5-NMe₃I |
| 2390 | FCH₂—CH=CH—CH₂ | Et—F | 2-F, 4-Cl |
| 2391 | FCH₂—CH=CH—CH₂ | Et—F | 2-NO₂, 4-Cl |
| 2392 | FCH₂—CH=CH—CH₂ | Et—F | 2-NH₂, 4-Cl |
| 2393 | FCH₂—CH=CH—CH₂ | Et—F | 2-NHMe, 4-Cl |
| 2394 | FCH₂—CH=CH—CH₂ | Et—F | 2-NMe₂, 4-Cl |
| 2395 | FCH₂—CH=CH—CH₂ | Et—F | 2-NMe₃OTf, 4-Cl |
| 2396 | FCH₂—CH=CH—CH₂ | Et—F | 2-NMe₃I, 4-Cl |
| 2397 | FCH₂—CH=CH—CH₂ | Et—F | 2-F, 5-Cl |
| 2398 | FCH₂—CH=CH—CH₂ | Et—F | 2-NO₂, 5-Cl |
| 2399 | FCH₂—CH=CH—CH₂ | Et—F | 2-NH₂, 5-Cl |
| 2400 | FCH₂—CH=CH—CH₂ | Et—F | 2-NHMe, 5-Cl |
| 2401 | FCH₂—CH=CH—CH₂ | Et—F | 2-NMe₂, 5-Cl |
| 2402 | FCH₂—CH=CH—CH₂ | Et—F | 2-NMe₃OTf, 5-Cl |
| 2403 | FCH₂—CH=CH—CH₂ | Et—F | 2-NMe₃I, 5-Cl |
| 2404 | FCH₂—CH=CH—CH₂ | Et—F | 2-Br, 4-F |
| 2405 | FCH₂—CH=CH—CH₂ | Et—F | 2-Br, 4-NO₂ |
| 2406 | FCH₂—CH=CH—CH₂ | Et—F | 2-Br, 4-NH₂ |
| 2407 | FCH₂—CH=CH—CH₂ | Et—F | 2-Br, 4-NHMe |
| 2408 | FCH₂—CH=CH—CH₂ | Et—F | 2-Br, 4-NMe₂ |
| 2409 | FCH₂—CH=CH—CH₂ | Et—F | 2-Br, 4-NMe₃OTf |
| 2410 | FCH₂—CH=CH—CH₂ | Et—F | 2-Br, 4-NMe₃I |
| 2411 | FCH₂—CH=CH—CH₂ | Et—F | 2-Br, 5-F |
| 2412 | FCH₂—CH=CH—CH₂ | Et—F | 2-Br, 5-NO₂ |
| 2413 | FCH₂—CH=CH—CH₂ | Et—F | 2-Br, 5-NH₂ |
| 2414 | FCH₂—CH=CH—CH₂ | Et—F | 2-Br, 5-NHMe |
| 2415 | FCH₂—CH=CH—CH₂ | Et—F | 2-Br, 5-NMe₂ |
| 2416 | FCH₂—CH=CH—CH₂ | Et—F | 2-Br, 5-NMe₃OTf |
| 2417 | FCH₂—CH=CH—CH₂ | Et—F | 2-Br, 5-NMe₃I |
| 2418 | FCH₂—CH=CH—CH₂ | Et—F | 2-F, 4-Br |
| 2419 | FCH₂—CH=CH—CH₂ | Et—F | 2-NO₂, 4-Br |
| 2420 | FCH₂—CH=CH—CH₂ | Et—F | 2-NH₂, 4-Br |
| 2421 | FCH₂—CH=CH—CH₂ | Et—F | 2-NHMe, 4-Br |
| 2422 | FCH₂—CH=CH—CH₂ | Et—F | 2-NMe₂, 4-Br |
| 2423 | FCH₂—CH=CH—CH₂ | Et—F | 2-NMe₃OTf, 4-Br |
| 2424 | FCH₂—CH=CH—CH₂ | Et—F | 2-NMe₃I, 4-Br |
| 2425 | FCH₂—CH=CH—CH₂ | Et—F | 2-I, 4-F |
| 2426 | FCH₂—CH=CH—CH₂ | Et—F | 2-I, 4-NO₂ |
| 2427 | FCH₂—CH=CH—CH₂ | Et—F | 2-I, 4-NH₂ |
| 2428 | FCH₂—CH=CH—CH₂ | Et—F | 2-I, 4-NHMe |
| 2429 | FCH₂—CH=CH—CH₂ | Et—F | 2-I, 4-NMe₂ |
| 2430 | FCH₂—CH=CH—CH₂ | Et—F | 2-I, 4-NMe₃OTf |
| 2431 | FCH₂—CH=CH—CH₂ | Et—F | 2-I, 4-NMe₃I |
| 2432 | FCH₂—CH=CH—CH₂ | Et—F | 2-F, 4-I |
| 2433 | FCH₂—CH=CH—CH₂ | Et—F | 2-NO₂, 4-I |
| 2434 | FCH₂—CH=CH—CH₂ | Et—F | 2-NH₂, 4-I |
| 2435 | FCH₂—CH=CH—CH₂ | Et—F | 2-NHMe, 4-I |
| 2436 | FCH₂—CH=CH—CH₂ | Et—F | 2-NMe₂, 4-I |
| 2437 | FCH₂—CH=CH—CH₂ | Et—F | 2-NMe₃OTf, 4-I |
| 2438 | FCH₂—CH=CH—CH₂ | Et—F | 2-NMe₃I, 4-I |
| 2439 | FCH₂—CH=CH—CH₂ | Et—F | 2-Me, 3-F |
| 2440 | FCH₂—CH=CH—CH₂ | Et—F | 2-Me, 3-NO₂ |
| 2441 | FCH₂—CH=CH—CH₂ | Et—F | 2-Me, 3-NH₂ |
| 2442 | FCH₂—CH=CH—CH₂ | Et—F | 2-Me, 3-NHMe |
| 2443 | FCH₂—CH=CH—CH₂ | Et—F | 2-Me, 3-NMe₂ |
| 2444 | FCH₂—CH=CH—CH₂ | Et—F | 2-Me, 3-NMe₃OTf |
| 2445 | FCH₂—CH=CH—CH₂ | Et—F | 2-Me, 3-NMe₃I |
| 2446 | FCH₂—CH=CH—CH₂ | Et—F | 2-Me, 4-F |
| 2447 | FCH₂—CH=CH—CH₂ | Et—F | 2-Me, 4-NO₂ |
| 2448 | FCH₂—CH=CH—CH₂ | Et—F | 2-Me, 4-NH₂ |
| 2449 | FCH₂—CH=CH—CH₂ | Et—F | 2-Me, 4-NHMe |
| 2450 | FCH₂—CH=CH—CH₂ | Et—F | 2-Me, 4-NMe₂ |
| 2451 | FCH₂—CH=CH—CH₂ | Et—F | 2-Me, 4-NMe₃OTf |
| 2452 | FCH₂—CH=CH—CH₂ | Et—F | 2-Me, 4-NMe₃I |
| 2453 | FCH₂—CH=CH—CH₂ | Et—F | 2-Me, 5-F |
| 2454 | FCH₂—CH=CH—CH₂ | Et—F | 2-Me, 5-NO₂ |
| 2455 | FCH₂—CH=CH—CH₂ | Et—F | 2-Me, 5-NH₂ |
| 2456 | FCH₂—CH=CH—CH₂ | Et—F | 2-Me, 5-NHMe |
| 2457 | FCH₂—CH=CH—CH₂ | Et—F | 2-Me, 5-NMe₂ |
| 2458 | FCH₂—CH=CH—CH₂ | Et—F | 2-Me, 5-NMe₃OTf |
| 2459 | FCH₂—CH=CH—CH₂ | Et—F | 2-Me, 5-NMe₃I |
| 2460 | FCH₂—CH=CH—CH₂ | Et—F | 2-F, 4-Me |
| 2461 | FCH₂—CH=CH—CH₂ | Et—F | 2-NO₂, 4-Me |
| 2462 | FCH₂—CH=CH—CH₂ | Et—F | 2-NH₂, 4-Me |
| 2463 | FCH₂—CH=CH—CH₂ | Et—F | 2-NHMe, 4-Me |
| 2464 | FCH₂—CH=CH—CH₂ | Et—F | 2-NMe₂, 4-Me |
| 2465 | FCH₂—CH=CH—CH₂ | Et—F | 2-NMe₃, 4-Me |
| 2466 | FCH₂—CH=CH—CH₂ | Et—F | 2-NMe₃OTf, 4-Me |
| 2467 | FCH₂—CH=CH—CH₂ | Et—F | 2-NMe₃I, 4-Me |
| 2468 | FCH₂—CH=CH—CH₂ | Et—F | 2-SnMe₃, 4-F |
| 2469 | FCH₂—CH=CH—CH₂ | Et—F | 2-SnMe₃, 4-Me |
| 2470 | FCH₂—CH=CH—CH₂ | Et—F | 2-F, 4-SnMe₃ |
| 2471 | FCH₂—CH=CH—CH₂ | Et—F | 2-Br, 6-Cl, 4-F |
| 2472 | FCH₂—CH=CH—CH₂ | Et—F | 2-Br, 6-Cl, 4-NO₂ |
| 2473 | FCH₂—CH=CH—CH₂ | Et—F | 2-Br, 6-Cl, 4-NH₂ |
| 2474 | FCH₂—CH=CH—CH₂ | Et—F | 2-Br, 6-Cl, 4-NHMe |
| 2475 | FCH₂—CH=CH—CH₂ | Et—F | 2-Br, 6-Cl, 4-NMe₂ |
| 2476 | FCH₂—CH=CH—CH₂ | Et—F | 2-Br, 6-Cl, 4-NMe₃OTf |
| 2477 | FCH₂—CH=CH—CH₂ | Et—F | 2-Br, 6-Cl, 4-NMe₃I |
| 2478 | FCH₂—CH=CH—CH₂ | Et—F | 2-Me, 6-Cl, 4-F |
| 2479 | FCH₂—CH=CH—CH₂ | Et—F | 2-SnMe₃, 6-Cl, 4-F |
| 2480 | FCH₂—CH=CH—CH₂ | Et—F | 2-Cl, 4-Me |
| 2481 | FCH₂—CH=CH—CH₂ | Et—F | 2-Cl, 4-Br |
| 2482 | FCH₂—CH=CH—CH₂ | Et—F | 2-Cl, 4-SnMe₃ |
| 2483 | FCH₂—CH=CH—CH₂ | Et—F | 2-Br, 4-Cl |
| 2484 | FCH₂—CH=CH—CH₂ | Et—F | 2-SnMe₃, 4-Cl |
| 2485 | FCH₂—CH=CH—CH₂ | Et—F | 2-Me, 4-Cl |
| 2486 | FCH₂—CH=CH—CH₂ | Et—F | 2-Br, 4-Br |
| 2487 | FCH₂—CH=CH—CH₂ | Et—F | 2-Br, 4-Me |
| 2488 | FCH₂—CH=CH—CH₂ | Et—F | 2-Br, 4-SnMe₃ |
| 2489 | FCH₂—CH=CH—CH₂ | Et—F | 2-SnMe₃, 4-Br |
| 2490 | FCH₂—CH=CH—CH₂ | Et—F | 2-Me, 4-Br |
| 2491 | FCH₂—CH=CH—CH₂ | Et—F | 2-Me, 4-SnMe₃ |
| 2492 | FCH₂—CH=CH—CH₂ | Et—F | 2-SnMe₃, 4-Me |
| 2493 | FCH₂—CH=CH—CH₂ | Et—F | 2-Me, 4-Me |
| 2494 | FCH₂—CH=CH—CH₂ | Et—F | 2-Et, 4-Br |
| 2495 | FCH₂—CH=CH—CH₂ | Et—F | 2-Et, 4-SnMe₃ |
| 2496 | FCH₂—CH=CH—CH₂ | Et—F | 2-Et, 4-Me |
| 2497 | FCH₂—CH=CH—CH₂ | Et—F | 2-Me, 4-Me, 6-Me |
| 2498 | FCH₂—CH=CH—CH₂ | Et—F | 2-Me, 4-Br, 6-Me |
| 2499 | FCH₂—CH=CH—CH₂ | Et—F | 2-Me, 4-SnMe₃, 6-Me |

TABLE 1-continued
Substituent list for compounds of general structure VI.

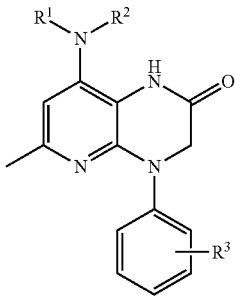

| Compound # | R¹ = | R² = | R³ = |
|---|---|---|---|
| 2500 | FCH₂—CH=CH—CH₂ | Et—F | 2-Et, 6-Me |
| 2501 | FCH₂—CH=CH—CH₂ | Et—F | 2-Br, 4-i-Pr |
| 2502 | FCH₂—CH=CH—CH₂ | Et—F | 2-SnMe₃, 4-i-Pr |
| 2503 | FCH₂—CH=CH—CH₂ | Et—F | 2-Me, 4-i-Pr |
| 2504 | FCH₂—CH=CH—CH₂ | Et—F | 2-Br, 4-Br, 6-Br |
| 2505 | FCH₂—CH=CH—CH₂ | Et—F | 2-Br, 4-Me, 6-Br |
| 2506 | FCH₂—CH=CH—CH₂ | Et—F | 2-Br, 4-SnMe₃, 6-Br |
| 2507 | FCH₂—CH=CH—CH₂ | Et—F | 2-SnMe₃, 4-Br, 6-Br |
| 2508 | FCH₂—CH=CH—CH₂ | Et—F | 2-Br, 4-Br, 6-Me |
| 2509 | FCH₂—CH=CH—CH₂ | Et—F | 2-Br, 4-CF₃, 6-Br |
| 2510 | FCH₂—CH=CH—CH₂ | Et—F | 2-Br, 4-Br, 6-CF₃ |
| 2511 | FCH₂—CH=CH—CH₂ | Et—F | 2-CF₃, 4-CF₃ |
| 2512 | FCH₂—CH=CH—CH₂ | Et—F | 2-Cl, 4-CF₃ |
| 2513 | FCH₂—CH=CH—CH₂ | Et—F | 2-CF₃, 4-Cl |
| 2514 | FCH₂—CH=CH—CH₂ | Et—F | 2-Br, 4-CF₃ |
| 2515 | FCH₂—CH=CH—CH₂ | Et—F | 2-SnMe₃, 4-CF₃ |
| 2516 | FCH₂—CH=CH—CH₂ | Et—F | 2-Me, 4-CF₃ |
| 2517 | FCH₂—CH=CH—CH₂ | Et—F | 2-CF₃, 4-Br |
| 2518 | FCH₂—CH=CH—CH₂ | Et—F | 2-CF₃, 4-SnMe₃ |
| 2519 | FCH₂—CH=CH—CH₂ | Et—F | 2-CF₃, 4-Me |
| 2520 | FCH₂—CH=CH—CH₂ | Et—F | 2-Br, 4-OH |
| 2521 | FCH₂—CH=CH—CH₂ | Et—F | 2-Br, 4-OMe |
| 2522 | FCH₂—CH=CH—CH₂ | Et—F | 2-Br, 4-OMeF |
| 2523 | FCH₂—CH=CH—CH₂ | Et—F | 2-Br, 4-OCF₃ |
| 2524 | FCH₂—CH=CH—CH₂ | Et—F | 2-Br, 4-OEtF |
| 2525 | FCH₂—CH=CH—CH₂ | Et—F | 2-Br, 4-OPrF |
| 2526 | FCH₂—CH=CH—CH₂ | Et—F | 2-OH, 4-Br |
| 2527 | FCH₂—CH=CH—CH₂ | Et—F | 2-OMe, 4-Br |
| 2528 | FCH₂—CH=CH—CH₂ | Et—F | 2-OMeF, 4-Br |
| 2529 | FCH₂—CH=CH—CH₂ | Et—F | 2-OCF₃, 4-Br |
| 2530 | FCH₂—CH=CH—CH₂ | Et—F | 2-OEtF, 4-Br |
| 2531 | FCH₂—CH=CH—CH₂ | Et—F | 2-OPrF, 4-Br |
| 2532 | FCH₂—CH=CH—CH₂ | Et—F | 2-I, 4-OH |
| 2533 | FCH₂—CH=CH—CH₂ | Et—F | 2-I, 4-OMe |
| 2534 | FCH₂—CH=CH—CH₂ | Et—F | 2-I, 4-OMeF |
| 2535 | FCH₂—CH=CH—CH₂ | Et—F | 2-I, 4-OCF₃ |
| 2536 | FCH₂—CH=CH—CH₂ | Et—F | 2-I, 4-OEtF |
| 2537 | FCH₂—CH=CH—CH₂ | Et—F | 2-I, 4-OPrF |
| 2538 | FCH₂—CH=CH—CH₂ | Et—F | 2-OH, 4-I |
| 2539 | FCH₂—CH=CH—CH₂ | Et—F | 2-OMe, 4-I |
| 2540 | FCH₂—CH=CH—CH₂ | Et—F | 2-OMeF, 4-I |
| 2541 | FCH₂—CH=CH—CH₂ | Et—F | 2-OCF₃, 4-I |
| 2542 | FCH₂—CH=CH—CH₂ | Et—F | 2-OEtF, 4-I |
| 2543 | FCH₂—CH=CH—CH₂ | Et—F | 2-OPrF, 4-I |
| 2544 | FCH₂—CH=CH—CH₂ | Et—F | 2-SnMe₃, 4-OH |
| 2545 | FCH₂—CH=CH—CH₂ | Et—F | 2-SnMe₃, 4-OMe |
| 2546 | FCH₂—CH=CH—CH₂ | Et—F | 2-SnMe₃, 4-OMeF |
| 2547 | FCH₂—CH=CH—CH₂ | Et—F | 2-SnMe₃, 4-OCF₃ |
| 2548 | FCH₂—CH=CH—CH₂ | Et—F | 2-SnMe₃, 4-OEtF |
| 2549 | FCH₂—CH=CH—CH₂ | Et—F | 2-SnMe₃, 4-OPrF |
| 2550 | FCH₂—CH=CH—CH₂ | Et—F | 2-OH, 4-SnMe₃ |
| 2551 | FCH₂—CH=CH—CH₂ | Et—F | 2-OMe, 4-SnMe₃ |
| 2552 | FCH₂—CH=CH—CH₂ | Et—F | 2-OMeF, 4-SnMe₃ |
| 2553 | FCH₂—CH=CH—CH₂ | Et—F | 2-OCF₃, 4-SnMe₃ |
| 2554 | FCH₂—CH=CH—CH₂ | Et—F | 2-OEtF, 4-SnMe₃ |
| 2555 | FCH₂—CH=CH—CH₂ | Et—F | 2-OPrF, 4-SnMe₃ |

TABLE 2
Substituent list for compounds of general structure VII.

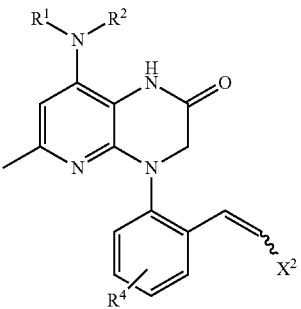

| Compound # | R¹ = | R² = | R⁴ = | X² = |
|---|---|---|---|---|
| 2556 | Bu | Et | H | H |
| 2557 | Bu | Et | H | SnMe₃ |
| 2558 | Bu | Et | H | Br |
| 2559 | Bu | Et | H | I |
| 2560 | Bu | Et | 4-F | H |
| 2561 | Bu | Et | 4-F | SnMe₃ |
| 2562 | Bu | Et | 4-F | Br |
| 2563 | Bu | Et | 4-F | I |
| 2564 | Bu | Et | 5-F | H |
| 2565 | Bu | Et | 5-F | SnMe₃ |
| 2566 | Bu | Et | 5-F | Br |
| 2567 | Bu | Et | 5-F | I |
| 2568 | Bu | Et | 4-Cl | H |
| 2569 | Bu | Et | 4-Cl | SnMe₃ |
| 2570 | Bu | Et | 4-Cl | Br |
| 2571 | Bu | Et | 4-Cl | I |
| 2572 | Bu | Et | 4-Br | H |
| 2573 | Bu | Et | 4-Br | SnMe₃ |
| 2574 | Bu | Et | 4-Br | Br |
| 2575 | Bu | Et | 4-Br | I |
| 2576 | Bu | Et | 4-Me | H |
| 2577 | Bu | Et | 4-Me | SnMe₃ |
| 2578 | Bu | Et | 4-Me | Br |
| 2579 | Bu | Et | 4-Me | I |
| 2580 | Bu | Et | 4-CF₃ | H |
| 2581 | Bu | Et | 4-CF₃ | SnMe₃ |
| 2582 | Bu | Et | 4-CF₃ | Br |
| 2583 | Bu | Et | 4-CF₃ | I |
| 2584 | Bu | Et | 4-OH | H |
| 2585 | Bu | Et | 4-OH | SnMe₃ |
| 2586 | Bu | Et | 4-OH | Br |
| 2587 | Bu | Et | 4-OH | 1 |
| 2588 | Bu | Et | 4-OMe | H |
| 2589 | Bu | Et | 4-OMe | SnMe₃ |
| 2590 | Bu | Et | 4-OMe | Br |
| 2591 | Bu | Et | 4-OMe | I |
| 2592 | Bu | Et | 4-OMeF | H |
| 2593 | Bu | Et | 4-OMeF | SnMe₃ |
| 2594 | Bu | Et | 4-OMeF | Br |
| 2595 | Bu | Et | 4-OMeF | I |
| 2596 | Bu | Et | 4-OCF₃ | H |
| 2597 | Bu | Et | 4-OCF₃ | SnMe₃ |
| 2598 | Bu | Et | 4-OCF₃ | Br |
| 2599 | Bu | Et | 4-OCF₃ | I |
| 2600 | Bu | Et | 4-OEtF | H |
| 2601 | Bu | Et | 4-OEtF | SnMe₃ |
| 2602 | Bu | Et | 4-OEtF | Br |
| 2603 | Bu | Et | 4-OEtF | I |
| 2604 | Bu | Et | 4-OPrF | H |
| 2605 | Bu | Et | 4-OPrF | SnMe₃ |
| 2606 | Bu | Et | 4-OPrF | Br |
| 2607 | Bu | Et | 4-OPrF | I |
| 2608 | Bu | Et | 4-i-Pr | H |
| 2609 | Bu | Et | 4-i-Pr | SnMe₃ |
| 2610 | Bu | Et | 4-i-Pr | Br |
| 2611 | Bu | Et | 4-i-Pr | I |
| 2612 | Bu | Et | 2-Br, 4-CF₃ | H |
| 2613 | Bu | Et | 2-Br, 4-CF₃ | SnMe₃ |
| 2614 | Bu | Et | 2-Br, 4-CF₃ | Br |

TABLE 2-continued

Substituent list for compounds of general structure VII.

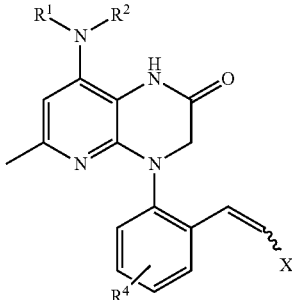

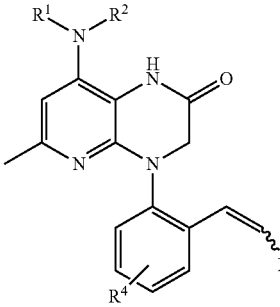

| Compound # | R¹ = | R² = | R⁴ = | X² = |
|---|---|---|---|---|
| 2615 | Bu | Et | 2-Br, 4-CF₃ | I |
| 2616 | Bu | Et | 2-CF₃, 4-Br | H |
| 2617 | Bu | Et | 2-CF₃, 4-Br | SnMe₃ |
| 2618 | Bu | Et | 2-CF₃, 4-Br | Br |
| 2619 | Bu | Et | 2-CF₃, 4-Br | I |
| 2620 | Bu | Et | 2-Br, 4-Br | H |
| 2621 | Bu | Et | 2-Br, 4-Br | SnMe₃ |
| 2622 | Bu | Et | 2-Br, 4-Br | Br |
| 2623 | Bu | Et | 2-Br, 4-Br | I |
| 2624 | Bu | Et | 2-Br, 4-Me | H |
| 2625 | Bu | Et | 2-Br, 4-Me | SnMe₃ |
| 2626 | Bu | Et | 2-Br, 4-Me | Br |
| 2627 | Bu | Et | 2-Br, 4-Me | I |
| 2628 | Pr | Pr | H | H |
| 2629 | Pr | Pr | H | SnMe₃ |
| 2630 | Pr | Pr | H | Br |
| 2631 | Pr | Pr | H | I |
| 2632 | Pr | Pr | 4-F | H |
| 2633 | Pr | Pr | 4-F | SnMe₃ |
| 2634 | Pr | Pr | 4-F | Br |
| 2635 | Pr | Pr | 4-F | I |
| 2636 | Pr | Pr | 5-F | H |
| 2637 | Pr | Pr | 5-F | SnMe₃ |
| 2638 | Pr | Pr | 5-F | Br |
| 2639 | Pr | Pr | 5-F | I |
| 2640 | Pr | Pr | 4-Cl | H |
| 2641 | Pr | Pr | 4-Cl | SnMe₃ |
| 2642 | Pr | Pr | 4-Cl | Br |
| 2643 | Pr | Pr | 4-Cl | I |
| 2644 | Pr | Pr | 4-Br | H |
| 2645 | Pr | Pr | 4-Br | SnMe₃ |
| 2646 | Pr | Pr | 4-Br | Br |
| 2647 | Pr | Pr | 4-Br | I |
| 2648 | Pr | Pr | 4-Me | H |
| 2649 | Pr | Pr | 4-Me | SnMe₃ |
| 2650 | Pr | Pr | 4-Me | Br |
| 2651 | Pr | Pr | 4-Me | I |
| 2652 | Pr | Pr | 4-CF₃ | H |
| 2653 | Pr | Pr | 4-CF₃ | SnMe₃ |
| 2654 | Pr | Pr | 4-CF₃ | Br |
| 2655 | Pr | Pr | 4-CF₃ | I |
| 2656 | Pr | Pr | 4-OH | H |
| 2657 | Pr | Pr | 4-OH | SnMe₃ |
| 2658 | Pr | Pr | 4-OH | Br |
| 2659 | Pr | Pr | 4-OH | I |
| 2660 | Pr | Pr | 4-OMe | H |
| 2661 | Pr | Pr | 4-OMe | SnMe₃ |
| 2662 | Pr | Pr | 4-OMe | Br |
| 2663 | Pr | Pr | 4-OMe | I |
| 2664 | Pr | Pr | 4-OMeF | H |
| 2665 | Pr | Pr | 4-OMeF | SnMe₃ |
| 2666 | Pr | Pr | 4-OMeF | Br |
| 2667 | Pr | Pr | 4-OMeF | I |
| 2668 | Pr | Pr | 4-OCF₃ | H |
| 2669 | Pr | Pr | 4-OCF₃ | SnMe₃ |
| 2670 | Pr | Pr | 4-OCF₃ | Br |
| 2671 | Pr | Pr | 4-OCF₃ | I |
| 2672 | Pr | Pr | 4-OEtF | H |
| 2673 | Pr | Pr | 4-OEtF | SnMe₃ |
| 2674 | Pr | Pr | 4-OEtF | Br |
| 2675 | Pr | Pr | 4-OEtF | I |
| 2676 | Pr | Pr | 4-OPrF | H |
| 2677 | Pr | Pr | 4-OPrF | SnMe₃ |
| 2678 | Pr | Pr | 4-OPrF | Br |
| 2679 | Pr | Pr | 4-OPrF | I |
| 2680 | Pr | Pr | 4-i-Pr | H |
| 2681 | Pr | Pr | 4-i-Pr | SnMe₃ |
| 2682 | Pr | Pr | 4-i-Pr | Br |
| 2683 | Pr | Pr | 4-i-Pr | I |
| 2684 | Pr | Pr | 2-Br, 4-CF₃ | H |
| 2685 | Pr | Pr | 2-Br, 4-CF₃ | SnMe₃ |
| 2686 | Pr | Pr | 2-Br, 4-CF₃ | Br |
| 2687 | Pr | Pr | 2-Br, 4-CF₃ | I |
| 2688 | Pr | Pr | 2-CF₃, 4-Br | H |
| 2689 | Pr | Pr | 2-CF₃, 4-Br | SnMe₃ |
| 2690 | Pr | Pr | 2-CF₃, 4-Br | Br |
| 2691 | Pr | Pr | 2-CF₃, 4-Br | I |
| 2692 | Pr | Pr | 2-Br, 4-Br | H |
| 2693 | Pr | Pr | 2-Br, 4-Br | SnMe₃ |
| 2694 | Pr | Pr | 2-Br, 4-Br | Br |
| 2695 | Pr | Pr | 2-Br, 4-Br | I |
| 2696 | Pr | Pr | 2-Br, 4-Me | H |
| 2697 | Pr | Pr | 2-Br, 4-Me | SnMe₃ |
| 2698 | Pr | Pr | 2-Br, 4-Me | Br |
| 2699 | Pr | Pr | 2-Br, 4-Me | I |
| 2700 | Pr | Pr—F | H | H |
| 2701 | Pr | Pr—F | H | SnMe₃ |
| 2702 | Pr | Pr—F | H | Br |
| 2703 | Pr | Pr—F | H | I |
| 2704 | Pr | Pr—F | 4-F | H |
| 2705 | Pr | Pr—F | 4-F | SnMe₃ |
| 2706 | Pr | Pr—F | 4-F | Br |
| 2707 | Pr | Pr—F | 4-F | I |
| 2708 | Pr | Pr—F | 5-F | H |
| 2709 | Pr | Pr—F | 5-F | SnMe₃ |
| 2710 | Pr | Pr—F | 5-F | Br |
| 2711 | Pr | Pr—F | 5-F | I |
| 2712 | Pr | Pr—F | 4-Cl | H |
| 2713 | Pr | Pr—F | 4-Cl | SnMe₃ |
| 2714 | Pr | Pr—F | 4-Cl | Br |
| 2715 | Pr | Pr—F | 4-Cl | I |
| 2716 | Pr | Pr—F | 4-Br | H |
| 2717 | Pr | Pr—F | 4-Br | SnMe₃ |
| 2718 | Pr | Pr—F | 4-Br | Br |
| 2719 | Pr | Pr—F | 4-Br | I |
| 2720 | Pr | Pr—F | 4-Me | H |
| 2721 | Pr | Pr—F | 4-Me | SnMe₃ |
| 2722 | Pr | Pr—F | 4-Me | Br |
| 2723 | Pr | Pr—F | 4-Me | I |
| 2724 | Pr | Pr—F | 4-CF₃ | H |
| 2725 | Pr | Pr—F | 4-CF₃ | SnMe₃ |
| 2726 | Pr | Pr—F | 4-CF₃ | Br |
| 2727 | Pr | Pr—F | 4-CF₃ | I |
| 2728 | Pr | Pr—F | 4-OH | H |
| 2729 | Pr | Pr—F | 4-OH | SnMe₃ |
| 2730 | Pr | Pr—F | 4-OH | Br |
| 2731 | Pr | Pr—F | 4-OH | I |
| 2732 | Pr | Pr—F | 4-OMe | H |

TABLE 2-continued

Substituent list for compounds of general structure VII.

| Compound # | R¹ = | R² = | R⁴ = | X² = |
|---|---|---|---|---|
| 2733 | Pr | Pr—F | 4-OMe | SnMe₃ |
| 2734 | Pr | Pr—F | 4-OMe | Br |
| 2735 | Pr | Pr—F | 4-OMe | I |
| 2736 | Pr | Pr—F | 4-OMeF | H |
| 2737 | Pr | Pr—F | 4-OMeF | SnMe₃ |
| 2738 | Pr | Pr—F | 4-OMeF | Br |
| 2739 | Pr | Pr—F | 4-OMeF | I |
| 2740 | Pr | Pr—F | 4-OCF₃ | H |
| 2741 | Pr | Pr—F | 4-OCF₃ | SnMe₃ |
| 2742 | Pr | Pr—F | 4-OCF₃ | Br |
| 2743 | Pr | Pr—F | 4-OCF₃ | I |
| 2744 | Pr | Pr—F | 4-OEtF | H |
| 2745 | Pr | Pr—F | 4-OEtF | SnMe₃ |
| 2746 | Pr | Pr—F | 4-OEtF | Br |
| 2747 | Pr | Pr—F | 4-OEtF | I |
| 2748 | Pr | Pr—F | 4-OPrF | H |
| 2749 | Pr | Pr—F | 4-OPrF | SnMe₃ |
| 2750 | Pr | Pr—F | 4-OPrF | Br |
| 2751 | Pr | Pr—F | 4-OPrF | I |
| 2752 | Pr | Pr—F | 4-i-Pr | H |
| 2753 | Pr | Pr—F | 4-i-Pr | SnMe₃ |
| 2754 | Pr | Pr—F | 4-i-Pr | Br |
| 2755 | Pr | Pr—F | 4-I-Pr | I |
| 2756 | Pr | Pr—F | 2-Br, 4-CF₃ | H |
| 2757 | Pr | Pr—F | 2-Br, 4-CF₃ | SnMe₃ |
| 2758 | Pr | Pr—F | 2-Br, 4-CF₃ | Br |
| 2759 | Pr | Pr—F | 2-Br, 4-CF₃ | I |
| 2760 | Pr | Pr—F | 2-CF₃, 4-Br | H |
| 2761 | Pr | Pr—F | 2-CF₃, 4-Br | SnMe₃ |
| 2762 | Pr | Pr—F | 2-CF₃, 4-Br | Br |
| 2763 | Pr | Pr—F | 2-CF₃, 4-Br | I |
| 2764 | Pr | Pr—F | 2-Br, 4-Br | H |
| 2765 | Pr | Pr—F | 2-Br, 4-Br | SnMe₃ |
| 2766 | Pr | Pr—F | 2-Br, 4-Br | Br |
| 2767 | Pr | Pr—F | 2-Br, 4-Br | I |
| 2768 | Pr | Pr—F | 2-Br, 4-Me | H |
| 2769 | Pr | Pr—F | 2-Br, 4-Me | SnMe₃ |
| 2770 | Pr | Pr—F | 2-Br, 4-Me | Br |
| 2771 | Pr | Pr—F | 2-Br, 4-Me | I |
| 2772 | Pr | Et—F | H | H |
| 2773 | Pr | Et—F | H | SnMe₃ |
| 2774 | Pr | Et—F | H | Br |
| 2775 | Pr | Et—F | H | I |
| 2776 | Pr | Et—F | 4-F | H |
| 2777 | Pr | Et—F | 4-F | SnMe₃ |
| 2778 | Pr | Et—F | 4-F | Br |
| 2779 | Pr | Et—F | 4-F | I |
| 2780 | Pr | Et—F | 5-F | H |
| 2781 | Pr | Et—F | 5-F | SnMe₃ |
| 2782 | Pr | Et—F | 5-F | Br |
| 2783 | Pr | Et—F | 5-F | I |
| 2784 | Pr | Et—F | 4-Cl | H |
| 2785 | Pr | Et—F | 4-Cl | SnMe₃ |
| 2786 | Pr | Et—F | 4-Cl | Br |
| 2787 | Pr | Et—F | 4-Cl | I |
| 2788 | Pr | Et—F | 4-Br | H |
| 2789 | Pr | Et—F | 4-Br | SnMe₃ |
| 2790 | Pr | Et—F | 4-Br | Br |
| 2791 | Pr | Et—F | 4-Br | I |
| 2792 | Pr | Et—F | 4-Me | H |
| 2793 | Pr | Et—F | 4-Me | SnMe₃ |
| 2794 | Pr | Et—F | 4-Me | Br |
| 2795 | Pr | Et—F | 4-Me | I |
| 2796 | Pr | Et—F | 4-CF₃ | H |
| 2797 | Pr | Et—F | 4-CF₃ | SnMe₃ |
| 2798 | Pr | Et—F | 4-CF₃ | Br |
| 2799 | Pr | Et—F | 4-CF₃ | I |
| 2800 | Pr | Et—F | 4-OH | H |
| 2801 | Pr | Et—F | 4-OH | SnMe₃ |
| 2802 | Pr | Et—F | 4-OH | Br |
| 2803 | Pr | Et—F | 4-OH | I |
| 2804 | Pr | Et—F | 4-OMe | H |
| 2805 | Pr | Et—F | 4-OMe | SnMe₃ |
| 2806 | Pr | Et—F | 4-OMe | Br |
| 2807 | Pr | Et—F | 4-OMe | I |
| 2808 | Pr | Et—F | 4-OMeF | H |
| 2809 | Pr | Et—F | 4-OMeF | SnMe₃ |
| 2810 | Pr | Et—F | 4-OMeF | Br |
| 2811 | Pr | Et—F | 4-OMeF | I |
| 2812 | Pr | Et—F | 4-OCF₃ | H |
| 2813 | Pr | Et—F | 4-OCF₃ | SnMe₃ |
| 2814 | Pr | Et—F | 4-OCF₃ | Br |
| 2815 | Pr | Et—F | 4-OCF₃ | I |
| 2816 | Pr | Et—F | 4-OEtF | H |
| 2817 | Pr | Et—F | 4-OEtF | SnMe₃ |
| 2818 | Pr | Et—F | 4-OEtF | Br |
| 2819 | Pr | Et—F | 4-OEtF | I |
| 2820 | Pr | Et—F | 4-OPrF | H |
| 2821 | Pr | Et—F | 4-OPrF | SnMe₃ |
| 2822 | Pr | Et—F | 4-OPrF | Br |
| 2823 | Pr | Et—F | 4-OPrF | I |
| 2824 | Pr | Et—F | 4-i-Pr | H |
| 2825 | Pr | Et—F | 4-i-Pr | SnMe₃ |
| 2826 | Pr | Et—F | 4-i-Pr | Br |
| 2827 | Pr | Et—F | 4-i-Pr | I |
| 2828 | Pr | Et—F | 2-Br, 4-CF₃ | H |
| 2829 | Pr | Et—F | 2-Br, 4-CF₃ | SnMe₃ |
| 2830 | Pr | Et—F | 2-Br, 4-CF₃ | Br |
| 2831 | Pr | Et—F | 2-Br, 4-CF₃ | I |
| 2832 | Pr | Et—F | 2-CF₃, 4-Br | H |
| 2833 | Pr | Et—F | 2-CF₃, 4-Br | SnMe₃ |
| 2834 | Pr | Et—F | 2-CF₃, 4-Br | Br |
| 2835 | Pr | Et—F | 2-CF₃, 4-Br | I |
| 2836 | Pr | Et—F | 2-Br, 4-Br | H |
| 2837 | Pr | Et—F | 2-Br, 4-Br | SnMe₃ |
| 2838 | Pr | Et—F | 2-Br, 4-Br | Br |
| 2839 | Pr | Et—F | 2-Br, 4-Br | I |
| 2840 | Pr | Et—F | 2-Br, 4-Me | H |
| 2841 | Pr | Et—F | 2-Br, 4-Me | SnMe₃ |
| 2842 | Pr | Et—F | 2-Br, 4-Me | Br |
| 2843 | Pr | Et—F | 2-Br, 4-Me | I |
| 2844 | Pr—F | Et | H | H |
| 2845 | Pr—F | Et | H | SnMe₃ |
| 2846 | Pr—F | Et | H | Br |
| 2847 | Pr—F | Et | H | I |
| 2848 | Pr—F | Et | 4-F | H |
| 2849 | Pr—F | Et | 4-F | SnMe₃ |
| 2850 | Pr—F | Et | 4-F | Br |

TABLE 2-continued

Substituent list for compounds of general structure VII.

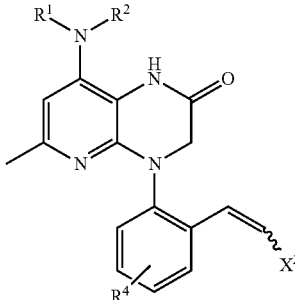

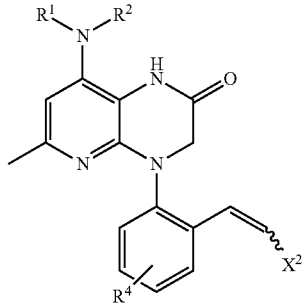

| Compound # | R¹ = | R² = | R⁴ = | X² = |
|---|---|---|---|---|
| 2851 | Pr—F | Et | 4-F | I |
| 2852 | Pr—F | Et | 5-F | H |
| 2853 | Pr—F | Et | 5-F | SnMe₃ |
| 2854 | Pr—F | Et | 5-F | Br |
| 2855 | Pr—F | Et | 5-F | I |
| 2856 | Pr—F | Et | 4-Cl | H |
| 2857 | Pr—F | Et | 4-Cl | SnMe₃ |
| 2858 | Pr—F | Et | 4-Cl | Br |
| 2859 | Pr—F | Et | 4-Cl | I |
| 2860 | Pr—F | Et | 4-Br | H |
| 2861 | Pr—F | Et | 4-Br | SnMe₃ |
| 2862 | Pr—F | Et | 4-Br | Br |
| 2863 | Pr—F | Et | 4-Br | I |
| 2864 | Pr—F | Et | 4-Me | H |
| 2865 | Pr—F | Et | 4-Me | SnMe₃ |
| 2866 | Pr—F | Et | 4-Me | Br |
| 2867 | Pr—F | Et | 4-Me | I |
| 2868 | Pr—F | Et | 4-CF₃ | H |
| 2869 | Pr—F | Et | 4-CF₃ | SnMe₃ |
| 2870 | Pr—F | Et | 4-CF₃ | Br |
| 2871 | Pr—F | Et | 4-CF₃ | I |
| 2872 | Pr—F | Et | 4-OH | H |
| 2873 | Pr—F | Et | 4-OH | SnMe₃ |
| 2874 | Pr—F | Et | 4-OH | Br |
| 2875 | Pr—F | Et | 4-OH | I |
| 2876 | Pr—F | Et | 4-OMe | H |
| 2877 | Pr—F | Et | 4-OMe | SnMe₃ |
| 2878 | Pr—F | Et | 4-OMe | Br |
| 2879 | Pr—F | Et | 4-OMe | I |
| 2880 | Pr—F | Et | 4-OMeF | H |
| 2881 | Pr—F | Et | 4-OMeF | SnMe₃ |
| 2882 | Pr—F | Et | 4-OMeF | Br |
| 2883 | Pr—F | Et | 4-OMeF | I |
| 2884 | Pr—F | Et | 4-OCF₃ | H |
| 2885 | Pr—F | Et | 4-OCF₃ | SnMe₃ |
| 2886 | Pr—F | Et | 4-OCF₃ | Br |
| 2887 | Pr—F | Et | 4-OCF₃ | 1 |
| 2888 | Pr—F | Et | 4-OEtF | H |
| 2889 | Pr—F | Et | 4-OEtF | SnMe₃ |
| 2890 | Pr—F | Et | 4-OEtF | Br |
| 2891 | Pr—F | Et | 4-OEtF | I |
| 2892 | Pr—F | Et | 4-OPrF | H |
| 2893 | Pr—F | Et | 4-OPrF | SnMe₃ |
| 2894 | Pr—F | Et | 4-OPrF | Br |
| 2895 | Pr—F | Et | 4-OPrF | I |
| 2896 | Pr—F | Et | 4-i-Pr | H |
| 2897 | Pr—F | Et | 4-i-Pr | SnMe₃ |
| 2898 | Pr—F | Et | 4-i-Pr | Br |
| 2899 | Pr—F | Et | 4-i-Pr | I |
| 2900 | Pr—F | Et | 2-Br, 4-CF₃ | H |
| 2901 | Pr—F | Et | 2-Br, 4-CF₃ | SnMe₃ |
| 2902 | Pr—F | Et | 2-Br, 4-CF₃ | Br |
| 2903 | Pr—F | Et | 2-Br, 4-CF₃ | I |
| 2904 | Pr—F | Et | 2-CF₃, 4-Br | H |
| 2905 | Pr—F | Et | 2-CF₃, 4-Br | SnMe₃ |
| 2906 | Pr—F | Et | 2-CF₃, 4-Br | Br |
| 2907 | Pr—F | Et | 2-CF₃, 4-Br | I |
| 2908 | Pr—F | Et | 2-Br, 4-Br | H |
| 2909 | Pr—F | Et | 2-Br, 4-Br | SnMe₃ |
| 2910 | Pr—F | Et | 2-Br, 4-Br | Br |
| 2911 | Pr—F | Et | 2-Br, 4-Br | I |
| 2912 | Pr—F | Et | 2-Br, 4-Me | H |
| 2913 | Pr—F | Et | 2-Br, 4-Me | SnMe₃ |
| 2914 | Pr—F | Et | 2-Br, 4-Me | Br |
| 2915 | Pr—F | Et | 2-Br, 4-Me | I |
| 2916 | Bu | Et—F | H | H |
| 2917 | Bu | Et—F | H | SnMe₃ |
| 2918 | Bu | Et—F | H | Br |
| 2919 | Bu | Et—F | H | I |
| 2920 | Bu | Et—F | 4-F | H |
| 2921 | Bu | Et—F | 4-F | SnMe₃ |
| 2922 | Bu | Et—F | 4-F | Br |
| 2923 | Bu | Et—F | 4-F | I |
| 2924 | Bu | Et—F | 5-F | H |
| 2925 | Bu | Et—F | 5-F | SnMe₃ |
| 2926 | Bu | Et—F | 5-F | Br |
| 2927 | Bu | Et—F | 5-F | I |
| 2928 | Bu | Et—F | 4-Cl | H |
| 2929 | Bu | Et—F | 4-Cl | SnMe₃ |
| 2930 | Bu | Et—F | 4-Cl | Br |
| 2931 | Bu | Et—F | 4-Cl | I |
| 2932 | Bu | Et—F | 4-Br | H |
| 2933 | Bu | Et—F | 4-Br | SnMe₃ |
| 2934 | Bu | Et—F | 4-Br | Br |
| 2935 | Bu | Et—F | 4-Br | I |
| 2936 | Bu | Et—F | 4-Me | H |
| 2937 | Bu | Et—F | 4-Me | SnMe₃ |
| 2938 | Bu | Et—F | 4-Me | Br |
| 2939 | Bu | Et—F | 4-Me | I |
| 2940 | Bu | Et—F | 4-CF₃ | H |
| 2941 | Bu | Et—F | 4-CF₃ | SnMe₃ |
| 2942 | Bu | Et—F | 4-CF₃ | Br |
| 2943 | Bu | Et—F | 4-CF₃ | 1 |
| 2944 | Bu | Et—F | 4-OH | H |
| 2945 | Bu | Et—F | 4-OH | SnMe₃ |
| 2946 | Bu | Et—F | 4-OH | Br |
| 2947 | Bu | Et—F | 4-OH | I |
| 2948 | Bu | Et—F | 4-OMe | H |
| 2949 | Bu | Et—F | 4-OMe | SnMe₃ |
| 2950 | Bu | Et—F | 4-OMe | Br |
| 2951 | Bu | Et—F | 4-OMe | I |
| 2952 | Bu | Et—F | 4-OMeF | H |
| 2953 | Bu | Et—F | 4-OMeF | SnMe₃ |
| 2954 | Bu | Et—F | 4-OMeF | Br |
| 2955 | Bu | Et—F | 4-OMeF | I |
| 2956 | Bu | Et—F | 4-OCF₃ | H |
| 2957 | Bu | Et—F | 4-OCF₃ | SnMe₃ |
| 2958 | Bu | Et—F | 4-OCF₃ | Br |
| 2959 | Bu | Et—F | 4-OCF₃ | I |
| 2960 | Bu | Et—F | 4-OEtF | H |
| 2961 | Bu | Et—F | 4-OEtF | SnMe₃ |
| 2962 | Bu | Et—F | 4-OEtF | Br |
| 2963 | Bu | Et—F | 4-OEtF | I |
| 2964 | Bu | Et—F | 4-OPrF | H |
| 2965 | Bu | Et—F | 4-OPrF | SnMe₃ |
| 2966 | Bu | Et—F | 4-OPrF | Br |
| 2967 | Bu | Et—F | 4-OPrF | I |
| 2968 | Bu | Et—F | 4-i-Pr | H |

TABLE 2-continued

Substituent list for compounds of general structure VII.

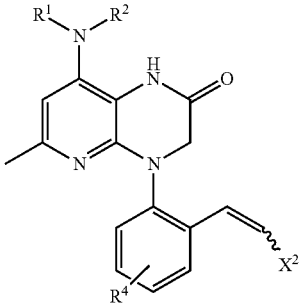 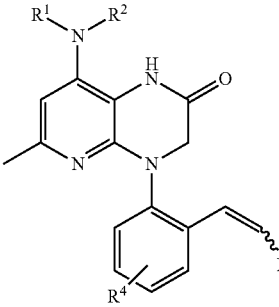

| Compound # | R¹ = | R² = | R⁴ = | X² = | Compound # | R¹ = | R² = | R⁴ = | X² = |
|---|---|---|---|---|---|---|---|---|---|
| 2969 | Bu | Et—F | 4-i-Pr | SnMe₃ | 3028 | Bu—F | Et | 4-OCF₃ | H |
| 2970 | Bu | Et—F | 4-i-Pr | Br | 3029 | Bu—F | Et | 4-OCF₃ | SnMe₃ |
| 2971 | Bu | Et—F | 4-i-Pr | I | 3030 | Bu—F | Et | 4-OCF₃ | Br |
| 2972 | Bu | Et—F | 2-Br, 4-CF₃ | H | 3031 | Bu—F | Et | 4-OCF₃ | I |
| 2973 | Bu | Et—F | 2-Br, 4-CF₃ | SnMe₃ | 3032 | Bu—F | Et | 4-OEtF | H |
| 2974 | Bu | Et—F | 2-Br, 4-CF₃ | Br | 3033 | Bu—F | Et | 4-OEtF | SnMe₃ |
| 2975 | Bu | Et—F | 2-Br, 4-CF₃ | I | 3034 | Bu—F | Et | 4-OEtF | Br |
| 2976 | Bu | Et—F | 2-CF₃, 4-Br | H | 3035 | Bu—F | Et | 4-OEtF | I |
| 2977 | Bu | Et—F | 2-CF₃, 4-Br | SnMe₃ | 3036 | Bu—F | Et | 4-OPrF | H |
| 2978 | Bu | Et—F | 2-CF₃, 4-Br | Br | 3037 | Bu—F | Et | 4-OPrF | SnMe₃ |
| 2979 | Bu | Et—F | 2-CF₃, 4-Br | I | 3038 | Bu—F | Et | 4-OPrF | Br |
| 2980 | Bu | Et—F | 2-Br, 4-Br | H | 3039 | Bu—F | Et | 4-OPrF | I |
| 2981 | Bu | Et—F | 2-Br, 4-Br | SnMe₃ | 3040 | Bu—F | Et | 4-i-Pr | H |
| 2982 | Bu | Et—F | 2-Br, 4-Br | Br | 3041 | Bu—F | Et | 4-i-Pr | SnMe₃ |
| 2983 | Bu | Et—F | 2-Br, 4-Br | I | 3042 | Bu—F | Et | 4-i-Pr | Br |
| 2984 | Bu | Et—F | 2-Br, 4-Me | H | 3043 | Bu—F | Et | 4-i-Pr | I |
| 2985 | Bu | Et—F | 2-Br, 4-Me | SnMe₃ | 3044 | Bu—F | Et | 2-Br, 4-CF₃ | H |
| 2986 | Bu | Et—F | 2-Br, 4-Me | Br | 3045 | Bu—F | Et | 2-Br, 4-CF₃ | SnMe₃ |
| 2987 | Bu | Et—F | 2-Br, 4-Me | I | 3046 | Bu—F | Et | 2-Br, 4-CF₃ | Br |
| 2988 | Bu—F | Et | H | H | 3047 | Bu—F | Et | 2-Br, 4-CF₃ | I |
| 2989 | Bu—F | Et | H | SnMe₃ | 3048 | Bu—F | Et | 2-CF₃, 4-Br | H |
| 2990 | Bu—F | Et | H | Br | 3049 | Bu—F | Et | 2-CF₃, 4-Br | SnMe₃ |
| 2991 | Bu—F | Et | H | I | 3050 | Bu—F | Et | 2-CF₃, 4-Br | Br |
| 2992 | Bu—F | Et | 4-F | H | 3051 | Bu—F | Et | 2-CF₃, 4-Br | I |
| 2993 | Bu—F | Et | 4-F | SnMe₃ | 3052 | Bu—F | Et | 2-Br, 4-Br | H |
| 2994 | Bu—F | Et | 4-F | Br | 3053 | Bu—F | Et | 2-Br, 4-Br | SnMe₃ |
| 2995 | Bu—F | Et | 4-F | I | 3054 | Bu—F | Et | 2-Br, 4-Br | Br |
| 2996 | Bu—F | Et | 5-F | H | 3055 | Bu—F | Et | 2-Br, 4-Br | 1 |
| 2997 | Bu—F | Et | 5-F | SnMe₃ | 3056 | Bu—F | Et | 2-Br, 4-Me | H |
| 2998 | Bu—F | Et | 5-F | Br | 3057 | Bu—F | Et | 2-Br, 4-Me | SnMe₃ |
| 2999 | Bu—F | Et | 5-F | 1 | 3058 | Bu—F | Et | 2-Br, 4-Me | Br |
| 3000 | Bu—F | Et | 4-Cl | H | 3059 | Bu—F | Et | 2-Br, 4-Me | I |
| 3001 | Bu—F | Et | 4-Cl | SnMe₃ | 3060 | FCH₂—CH=CH—CH₂ | Me | H | H |
| 3002 | Bu—F | Et | 4-Cl | Br | 3061 | FCH₂—CH=CH—CH₂ | Me | H | SnMe₃ |
| 3003 | Bu—F | Et | 4-Cl | I | 3062 | FCH₂—CH=CH—CH₂ | Me | H | Br |
| 3004 | Bu—F | Et | 4-Br | H | 3063 | FCH₂—CH=CH—CH₂ | Me | H | I |
| 3005 | Bu—F | Et | 4-Br | SnMe₃ | 3064 | FCH₂—CH=CH—CH₂ | Me | 4-F | H |
| 3006 | Bu—F | Et | 4-Br | Br | 3065 | FCH₂—CH=CH—CH₂ | Me | 4-F | SnMe₃ |
| 3007 | Bu—F | Et | 4-Br | I | 3066 | FCH₂—CH=CH—CH₂ | Me | 4-F | Br |
| 3008 | Bu—F | Et | 4-Me | H | 3067 | FCH₂—CH=CH—CH₂ | Me | 4-F | I |
| 3009 | Bu—F | Et | 4-Me | SnMe₃ | 3068 | FCH₂—CH=CH—CH₂ | Me | 5-F | H |
| 3010 | Bu—F | Et | 4-Me | Br | 3069 | FCH₂—CH=CH—CH₂ | Me | 5-F | SnMe₃ |
| 3011 | Bu—F | Et | 4-Me | I | 3070 | FCH₂—CH=CH—CH₂ | Me | 5-F | Br |
| 3012 | Bu—F | Et | 4-CF₃ | H | 3071 | FCH₂—CH=CH—CH₂ | Me | 5-F | I |
| 3013 | Bu—F | Et | 4-CF₃ | SnMe₃ | 3072 | FCH₂—CH=CH—CH₂ | Me | 4-Cl | H |
| 3014 | Bu—F | Et | 4-CF₃ | Br | 3073 | FCH₂—CH=CH—CH₂ | Me | 4-Cl | SnMe₃ |
| 3015 | Bu—F | Et | 4-CF₃ | I | 3074 | FCH₂—CH=CH—CH₂ | Me | 4-Cl | Br |
| 3016 | Bu—F | Et | 4-OH | H | 3075 | FCH₂—CH=CH—CH₂ | Me | 4-Cl | I |
| 3017 | Bu—F | Et | 4-OH | SnMe₃ | 3076 | FCH₂—CH=CH—CH₂ | Me | 4-Br | H |
| 3018 | Bu—F | Et | 4-OH | Br | 3077 | FCH₂—CH=CH—CH₂ | Me | 4-Br | SnMe₃ |
| 3019 | Bu—F | Et | 4-OH | I | 3078 | FCH₂—CH=CH—CH₂ | Me | 4-Br | Br |
| 3020 | Bu—F | Et | 4-OMe | H | 3079 | FCH₂—CH=CH—CH₂ | Me | 4-Br | I |
| 3021 | Bu—F | Et | 4-OMe | SnMe₃ | 3080 | FCH₂—CH=CH—CH₂ | Me | 4-Me | H |
| 3022 | Bu—F | Et | 4-OMe | Br | 3081 | FCH₂—CH=CH—CH₂ | Me | 4-Me | SnMe₃ |
| 3023 | Bu—F | Et | 4-OMe | I | 3082 | FCH₂—CH=CH—CH₂ | Me | 4-Me | Br |
| 3024 | Bu—F | Et | 4-OMeF | H | 3083 | FCH₂—CH=CH—CH₂ | Me | 4-Me | I |
| 3025 | Bu—F | Et | 4-OMeF | SnMe₃ | 3084 | FCH₂—CH=CH—CH₂ | Me | 4-CF₃ | H |
| 3026 | Bu—F | Et | 4-OMeF | Br | 3085 | FCH₂—CH=CH—CH₂ | Me | 4-CF₃ | SnMe₃ |
| 3027 | Bu—F | Et | 4-OMeF | I | 3086 | FCH₂—CH=CH—CH₂ | Me | 4-CF₃ | Br |

TABLE 2-continued

Substituent list for compounds of general structure VII.

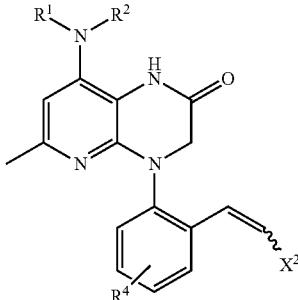

| Compound # | R¹ = | R² = | R⁴ = | X² = |
|---|---|---|---|---|
| 3087 | FCH₂—CH=CH—CH₂ | Me | 4-CF₃ | I |
| 3088 | FCH₂—CH=CH—CH₂ | Me | 4-OH | H |
| 3089 | FCH₂—CH=CH—CH₂ | Me | 4-OH | SnMe₃ |
| 3090 | FCH₂—CH=CH—CH₂ | Me | 4-OH | Br |
| 3091 | FCH₂—CH=CH—CH₂ | Me | 4-OH | I |
| 3092 | FCH₂—CH=CH—CH₂ | Me | 4-OMe | H |
| 3093 | FCH₂—CH=CH—CH₂ | Me | 4-OMe | SnMe₃ |
| 3094 | FCH₂—CH=CH—CH₂ | Me | 4-OMe | Br |
| 3095 | FCH₂—CH=CH—CH₂ | Me | 4-OMe | I |
| 3096 | FCH₂—CH=CH—CH₂ | Me | 4-OMeF | H |
| 3097 | FCH₂—CH=CH—CH₂ | Me | 4-OMeF | SnMe₃ |
| 3098 | FCH₂—CH=CH—CH₂ | Me | 4-OMeF | Br |
| 3099 | FCH₂—CH=CH—CH₂ | Me | 4-OMeF | I |
| 3100 | FCH₂—CH=CH—CH₂ | Me | 4-OCF₃ | H |
| 3101 | FCH₂—CH=CH—CH₂ | Me | 4-OCF₃ | SnMe₃ |
| 3102 | FCH₂—CH=CH—CH₂ | Me | 4-OCF₃ | Br |
| 3103 | FCH₂—CH=CH—CH₂ | Me | 4-OCF₃ | I |
| 3104 | FCH₂—CH=CH—CH₂ | Me | 4-OEtF | H |
| 3105 | FCH₂—CH=CH—CH₂ | Me | 4-OEtF | SnMe₃ |
| 3106 | FCH₂—CH=CH—CH₂ | Me | 4-OEtF | Br |
| 3107 | FCH₂—CH=CH—CH₂ | Me | 4-OEtF | I |
| 3108 | FCH₂—CH=CH—CH₂ | Me | 4-OPrF | H |
| 3109 | FCH₂—CH=CH—CH₂ | Me | 4-OPrF | SnMe₃ |
| 3110 | FCH₂—CH=CH—CH₂ | Me | 4-OPrF | Br |
| 3111 | FCH₂—CH=CH—CH₂ | Me | 4-OPrF | I |
| 3112 | FCH₂—CH=CH—CH₂ | Me | 4-i-Pr | H |
| 3113 | FCH₂—CH=CH—CH₂ | Me | 4-i-Pr | SnMe₃ |
| 3114 | FCH₂—CH=CH—CH₂ | Me | 4-i-Pr | Br |
| 3115 | FCH₂—CH=CH—CH₂ | Me | 4-i-Pr | I |
| 3116 | FCH₂—CH=CH—CH₂ | Me | 2-Br, 4-CF₃ | H |
| 3117 | FCH₂—CH=CH—CH₂ | Me | 2-Br, 4-CF₃ | SnMe₃ |
| 3118 | FCH₂—CH=CH—CH₂ | Me | 2-Br, 4-CF₃ | Br |
| 3119 | FCH₂—CH=CH—CH₂ | Me | 2-Br, 4-CF₃ | I |
| 3120 | FCH₂—CH=CH—CH₂ | Me | 2-CF₃, 4-Br | H |
| 3121 | FCH₂—CH=CH—CH₂ | Me | 2-CF₃, 4-Br | SnMe₃ |
| 3122 | FCH₂—CH=CH—CH₂ | Me | 2-CF₃, 4-Br | Br |
| 3123 | FCH₂—CH=CH—CH₂ | Me | 2-CF₃, 4-Br | I |
| 3124 | FCH₂—CH=CH—CH₂ | Me | 2-Br, 4-Br | H |
| 3125 | FCH₂—CH=CH—CH₂ | Me | 2-Br, 4-Br | SnMe₃ |
| 3126 | FCH₂—CH=CH—CH₂ | Me | 2-Br, 4-Br | Br |
| 3127 | FCH₂—CH=CH—CH₂ | Me | 2-Br, 4-Br | I |
| 3128 | FCH₂—CH=CH—CH₂ | Me | 2-Br, 4-Me | H |
| 3129 | FCH₂—CH=CH—CH₂ | Me | 2-Br, 4-Me | SnMe₃ |
| 3130 | FCH₂—CH=CH—CH₂ | Me | 2-Br, 4-Me | Br |
| 3131 | FCH₂—CH=CH—CH₂ | Me | 2-Br, 4-Me | I |
| 3132 | FCH₂—CH=CH—CH₂ | Et | H | H |
| 3133 | FCH₂—CH=CH—CH₂ | Et | H | SnMe₃ |
| 3134 | FCH₂—CH=CH—CH₂ | Et | H | Br |
| 3135 | FCH₂—CH=CH—CH₂ | Et | H | I |
| 3136 | FCH₂—CH=CH—CH₂ | Et | 4-F | H |
| 3137 | FCH₂—CH=CH—CH₂ | Et | 4-F | SnMe₃ |
| 3138 | FCH₂—CH=CH—CH₂ | Et | 4-F | Br |
| 3139 | FCH₂—CH=CH—CH₂ | Et | 4-F | I |
| 3140 | FCH₂—CH=CH—CH₂ | Et | 5-F | H |
| 3141 | FCH₂—CH=CH—CH₂ | Et | 5-F | SnMe₃ |
| 3142 | FCH₂—CH=CH—CH₂ | Et | 5-F | Br |
| 3143 | FCH₂—CH=CH—CH₂ | Et | 5-F | I |
| 3144 | FCH₂—CH=CH—CH₂ | Et | 4-Cl | H |
| 3145 | FCH₂—CH=CH—CH₂ | Et | 4-Cl | SnMe₃ |

TABLE 2-continued

Substituent list for compounds of general structure VII.

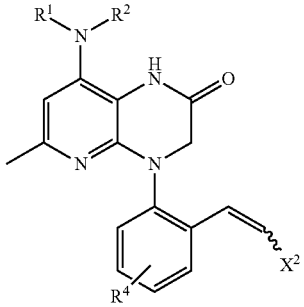

| Compound # | R¹ = | R² = | R⁴ = | X² = |
|---|---|---|---|---|
| 3146 | FCH₂—CH=CH—CH₂ | Et | 4-Cl | Br |
| 3147 | FCH₂—CH=CH—CH₂ | Et | 4-Cl | I |
| 3148 | FCH₂—CH=CH—CH₂ | Et | 4-Br | H |
| 3149 | FCH₂—CH=CH—CH₂ | Et | 4-Br | SnMe₃ |
| 3150 | FCH₂—CH=CH—CH₂ | Et | 4-Br | Br |
| 3151 | FCH₂—CH=CH—CH₂ | Et | 4-Br | I |
| 3152 | FCH₂—CH=CH—CH₂ | Et | 4-Me | H |
| 3153 | FCH₂—CH=CH—CH₂ | Et | 4-Me | SnMe₃ |
| 3154 | FCH₂—CH=CH—CH₂ | Et | 4-Me | Br |
| 3155 | FCH₂—CH=CH—CH₂ | Et | 4-Me | I |
| 3156 | FCH₂—CH=CH—CH₂ | Et | 4-CF₃ | H |
| 3157 | FCH₂—CH=CH—CH₂ | Et | 4-CF₃ | SnMe₃ |
| 3158 | FCH₂—CH=CH—CH₂ | Et | 4-CF₃ | Br |
| 3159 | FCH₂—CH=CH—CH₂ | Et | 4-CF₃ | I |
| 3160 | FCH₂—CH=CH—CH₂ | Et | 4-OH | H |
| 3161 | FCH₂—CH=CH—CH₂ | Et | 4-OH | SnMe₃ |
| 3162 | FCH₂—CH=CH—CH₂ | Et | 4-OH | Br |
| 3163 | FCH₂—CH=CH—CH₂ | Et | 4-OH | I |
| 3164 | FCH₂—CH=CH—CH₂ | Et | 4-OMe | H |
| 3165 | FCH₂—CH=CH—CH₂ | Et | 4-OMe | SnMe₃ |
| 3166 | FCH₂—CH=CH—CH₂ | Et | 4-OMe | Br |
| 3167 | FCH₂—CH=CH—CH₂ | Et | 4-OMe | I |
| 3168 | FCH₂—CH=CH—CH₂ | Et | 4-OMeF | H |
| 3169 | FCH₂—CH=CH—CH₂ | Et | 4-OMeF | SnMe₃ |
| 3170 | FCH₂—CH=CH—CH₂ | Et | 4-OMeF | Br |
| 3171 | FCH₂—CH=CH—CH₂ | Et | 4-OMeF | I |
| 3172 | FCH₂—CH=CH—CH₂ | Et | 4-OCF₃ | H |
| 3173 | FCH₂—CH=CH—CH₂ | Et | 4-OCF₃ | SnMe₃ |
| 3174 | FCH₂—CH=CH—CH₂ | Et | 4-OCF₃ | Br |
| 3175 | FCH₂—CH=CH—CH₂ | Et | 4-OCF₃ | I |
| 3176 | FCH₂—CH=CH—CH₂ | Et | 4-OEtF | H |
| 3177 | FCH₂—CH=CH—CH₂ | Et | 4-OEtF | SnMe₃ |
| 3178 | FCH₂—CH=CH—CH₂ | Et | 4-OEtF | Br |
| 3179 | FCH₂—CH=CH—CH₂ | Et | 4-OEtF | I |
| 3180 | FCH₂—CH=CH—CH₂ | Et | 4-OPrF | H |
| 3181 | FCH₂—CH=CH—CH₂ | Et | 4-OPrF | SnMe₃ |
| 3182 | FCH₂—CH=CH—CH₂ | Et | 4-OPrF | Br |
| 3183 | FCH₂—CH=CH—CH₂ | Et | 4-OPrF | I |
| 3184 | FCH₂—CH=CH—CH₂ | Et | 4-i-Pr | H |
| 3185 | FCH₂—CH=CH—CH₂ | Et | 4-i-Pr | SnMe₃ |
| 3186 | FCH₂—CH=CH—CH₂ | Et | 4-i-Pr | Br |
| 3187 | FCH₂—CH=CH—CH₂ | Et | 4-i-Pr | I |
| 3188 | FCH₂—CH=CH—CH₂ | Et | 2-Br, 4-CF₃ | H |
| 3189 | FCH₂—CH=CH—CH₂ | Et | 2-Br, 4-CF₃ | SnMe₃ |
| 3190 | FCH₂—CH=CH—CH₂ | Et | 2-Br, 4-CF₃ | Br |
| 3191 | FCH₂—CH=CH—CH₂ | Et | 2-Br, 4-CF₃ | I |
| 3192 | FCH₂—CH=CH—CH₂ | Et | 2-CF₃, 4-Br | H |
| 3193 | FCH₂—CH=CH—CH₂ | Et | 2-CF₃, 4-Br | SnMe₃ |
| 3194 | FCH₂—CH=CH—CH₂ | Et | 2-CF₃, 4-Br | Br |
| 3195 | FCH₂—CH=CH—CH₂ | Et | 2-CF₃, 4-Br | I |
| 3196 | FCH₂—CH=CH—CH₂ | Et | 2-Br, 4-Br | H |
| 3197 | FCH₂—CH=CH—CH₂ | Et | 2-Br, 4-Br | SnMe₃ |
| 3198 | FCH₂—CH=CH—CH₂ | Et | 2-Br, 4-Br | Br |
| 3199 | FCH₂—CH=CH—CH₂ | Et | 2-Br, 4-Br | I |
| 3200 | FCH₂—CH=CH—CH₂ | Et | 2-Br, 4-Me | H |
| 3201 | FCH₂—CH=CH—CH₂ | Et | 2-Br, 4-Me | SnMe₃ |
| 3202 | FCH₂—CH=CH—CH₂ | Et | 2-Br, 4-Me | Br |
| 3203 | FCH₂—CH=CH—CH₂ | Et | 2-Br, 4-Me | I |
| 3204 | FCH₂—CH=CH—CH₂ | Et—F | H | H |

TABLE 2-continued

Substituent list for compounds of general structure VII.

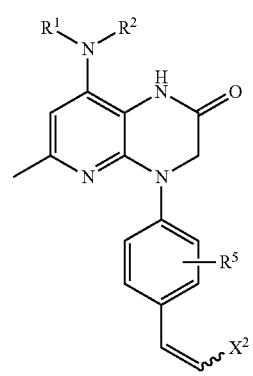

VII

| Compound # | R¹ = | R² = | R⁴ = | X² = |
|---|---|---|---|---|
| 3205 | FCH$_2$—CH=CH—CH$_2$ | Et—F | H | SnMe$_3$ |
| 3206 | FCH$_2$—CH=CH—CH$_2$ | Et—F | H | Br |
| 3207 | FCH$_2$—CH=CH—CH$_2$ | Et—F | H | I |
| 3208 | FCH$_2$—CH=CH—CH$_2$ | Et—F | 4-F | H |
| 3209 | FCH$_2$—CH=CH—CH$_2$ | Et—F | 4-F | SnMe$_3$ |
| 3210 | FCH$_2$—CH=CH—CH$_2$ | Et—F | 4-F | Br |
| 3211 | FCH$_2$—CH=CH—CH$_2$ | Et—F | 4-F | I |
| 3212 | FCH$_2$—CH=CH—CH$_2$ | Et—F | 5-F | H |
| 3213 | FCH$_2$—CH=CH—CH$_2$ | Et—F | 5-F | SnMe$_3$ |
| 3214 | FCH$_2$—CH=CH—CH$_2$ | Et—F | 5-F | Br |
| 3215 | FCH$_2$—CH=CH—CH$_2$ | Et—F | 5-F | I |
| 3216 | FCH$_2$—CH=CH—CH$_2$ | Et—F | 4-Cl | H |
| 3217 | FCH$_2$—CH=CH—CH$_2$ | Et—F | 4-Cl | SnMe$_3$ |
| 3218 | FCH$_2$—CH=CH—CH$_2$ | Et—F | 4-Cl | Br |
| 3219 | FCH$_2$—CH=CH—CH$_2$ | Et—F | 4-Cl | I |
| 3220 | FCH$_2$—CH=CH—CH$_2$ | Et—F | 4-Br | H |
| 3221 | FCH$_2$—CH=CH—CH$_2$ | Et—F | 4-Br | SnMe$_3$ |
| 3222 | FCH$_2$—CH=CH—CH$_2$ | Et—F | 4-Br | Br |
| 3223 | FCH$_2$—CH=CH—CH$_2$ | Et—F | 4-Br | I |
| 3224 | FCH$_2$—CH=CH—CH$_2$ | Et—F | 4-Me | H |
| 3225 | FCH$_2$—CH=CH—CH$_2$ | Et—F | 4-Me | SnMe$_3$ |
| 3226 | FCH$_2$—CH=CH—CH$_2$ | Et—F | 4-Me | Br |
| 3227 | FCH$_2$—CH=CH—CH$_2$ | Et—F | 4-Me | I |
| 3228 | FCH$_2$—CH=CH—CH$_2$ | Et—F | 4-CF$_3$ | H |
| 3229 | FCH$_2$—CH=CH—CH$_2$ | Et—F | 4-CF$_3$ | SnMe$_3$ |
| 3230 | FCH$_2$—CH=CH—CH$_2$ | Et—F | 4-CF$_3$ | Br |
| 3231 | FCH$_2$—CH=CH—CH$_2$ | Et—F | 4-CF$_3$ | I |
| 3232 | FCH$_2$—CH=CH—CH$_2$ | Et—F | 4-OH | H |
| 3233 | FCH$_2$—CH=CH—CH$_2$ | Et—F | 4-OH | SnMe$_3$ |
| 3234 | FCH$_2$—CH=CH—CH$_2$ | Et—F | 4-OH | Br |
| 3235 | FCH$_2$—CH=CH—CH$_2$ | Et—F | 4-OH | I |
| 3236 | FCH$_2$—CH=CH—CH$_2$ | Et—F | 4-OMe | H |
| 3237 | FCH$_2$—CH=CH—CH$_2$ | Et—F | 4-OMe | SnMe$_3$ |
| 3238 | FCH$_2$—CH=CH—CH$_2$ | Et—F | 4-OMe | Br |
| 3239 | FCH$_2$—CH=CH—CH$_2$ | Et—F | 4-OMe | I |
| 3240 | FCH$_2$—CH=CH—CH$_2$ | Et—F | 4-OMeF | H |
| 3241 | FCH$_2$—CH=CH—CH$_2$ | Et—F | 4-OMeF | SnMe$_3$ |
| 3242 | FCH$_2$—CH=CH—CH$_2$ | Et—F | 4-OMeF | Br |
| 3243 | FCH$_2$—CH=CH—CH$_2$ | Et—F | 4-OMeF | I |
| 3244 | FCH$_2$—CH=CH—CH$_2$ | Et—F | 4-OCF$_3$ | H |
| 3245 | FCH$_2$—CH=CH—CH$_2$ | Et—F | 4-OCF$_3$ | SnMe$_3$ |
| 3246 | FCH$_2$—CH=CH—CH$_2$ | Et—F | 4-OCF$_3$ | Br |
| 3247 | FCH$_2$—CH=CH—CH$_2$ | Et—F | 4-OCF$_3$ | I |
| 3248 | FCH$_2$—CH=CH—CH$_2$ | Et—F | 4-OEtF | H |
| 3249 | FCH$_2$—CH=CH—CH$_2$ | Et—F | 4-OEtF | SnMe$_3$ |
| 3250 | FCH$_2$—CH=CH—CH$_2$ | Et—F | 4-OEtF | Br |
| 3251 | FCH$_2$—CH=CH—CH$_2$ | Et—F | 4-OEtF | I |
| 3252 | FCH$_2$—CH=CH—CH$_2$ | Et—F | 4-OPrF | H |
| 3253 | FCH$_2$—CH=CH—CH$_2$ | Et—F | 4-OPrF | SnMe$_3$ |
| 3254 | FCH$_2$—CH=CH—CH$_2$ | Et—F | 4-OPrF | Br |
| 3255 | FCH$_2$—CH=CH—CH$_2$ | Et—F | 4-OPrF | I |
| 3256 | FCH$_2$—CH=CH—CH$_2$ | Et—F | 4-i-Pr | H |
| 3257 | FCH$_2$—CH=CH—CH$_2$ | Et—F | 4-i-Pr | SnMe$_3$ |
| 3258 | FCH$_2$—CH=CH—CH$_2$ | Et—F | 4-i-Pr | Br |
| 3259 | FCH$_2$—CH=CH—CH$_2$ | Et—F | 4-i-Pr | I |
| 3260 | FCH$_2$—CH=CH—CH$_2$ | Et—F | 2-Br, 4-CF$_3$ | H |
| 3261 | FCH$_2$—CH=CH—CH$_2$ | Et—F | 2-Br, 4-CF$_3$ | SnMe$_3$ |
| 3262 | FCH$_2$—CH=CH—CH$_2$ | Et—F | 2-Br, 4-CF$_3$ | Br |
| 3263 | FCH$_2$—CH=CH—CH$_2$ | Et—F | 2-Br, 4-CF$_3$ | I |
| 3264 | FCH$_2$—CH=CH—CH$_2$ | Et—F | 2-CF$_3$, 4-Br | H |
| 3265 | FCH$_2$—CH=CH—CH$_2$ | Et—F | 2-CF$_3$, 4-Br | SnMe$_3$ |
| 3266 | FCH$_2$—CH=CH—CH$_2$ | Et—F | 2-CF$_3$, 4-Br | Br |
| 3267 | FCH$_2$—CH=CH—CH$_2$ | Et—F | 2-CF$_3$, 4-Br | I |
| 3268 | FCH$_2$—CH=CH—CH$_2$ | Et—F | 2-Br, 4-Br | H |
| 3269 | FCH$_2$—CH=CH—CH$_2$ | Et—F | 2-Br, 4-Br | SnMe$_3$ |
| 3270 | FCH$_2$—CH=CH—CH$_2$ | Et—F | 2-Br, 4-Br | Br |
| 3271 | FCH$_2$—CH=CH—CH$_2$ | Et—F | 2-Br, 4-Br | I |
| 3272 | FCH$_2$—CH=CH—CH$_2$ | Et—F | 2-Br, 4-Me | H |
| 3273 | FCH$_2$—CH=CH—CH$_2$ | Et—F | 2-Br, 4-Me | SnMe$_3$ |
| 3274 | FCH$_2$—CH=CH—CH$_2$ | Et—F | 2-Br, 4-Me | Br |
| 3275 | FCH$_2$—CH=CH—CH$_2$ | Et—F | 2-Br, 4-Me | I |

TABLE 3

Substituent list for compounds of general structure VIII.

VIII

| Compound # | R¹ = | R² = | R⁵ = | X² = |
|---|---|---|---|---|
| 3276 | Bu | Et | H | H |
| 3277 | Bu | Et | H | SnMe$_3$ |
| 3278 | Bu | Et | H | Br |
| 3279 | Bu | Et | H | I |
| 3280 | Bu | Et | 2-F | H |
| 3281 | Bu | Et | 2-F | SnMe$_3$ |
| 3282 | Bu | Et | 2-F | Br |
| 3283 | Bu | Et | 2-F | I |
| 3284 | Bu | Et | 2-Cl | H |
| 3285 | Bu | Et | 2-Cl | SnMe$_3$ |
| 3286 | Bu | Et | 2-Cl | Br |
| 3287 | Bu | Et | 2-Cl | I |
| 3288 | Bu | Et | 2-Br | H |
| 3289 | Bu | Et | 2-Br | SnMe$_3$ |
| 3290 | Bu | Et | 2-Br | Br |
| 3291 | Bu | Et | 2-Br | I |
| 3292 | Bu | Et | 2-Me | H |
| 3293 | Bu | Et | 2-Me | SnMe$_3$ |
| 3294 | Bu | Et | 2-Me | Br |

TABLE 3-continued

Substituent list for compounds of general structure VIII.

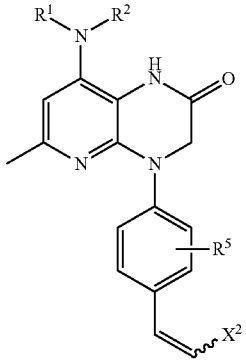

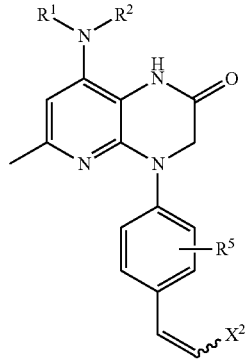

| Compound # | R¹ = | R² = | R⁵ = | X² = | Compound # | R¹ = | R² = | R⁵ = | X² = |
| --- | --- | --- | --- | --- | --- | --- | --- | --- | --- |
| 3295 | Bu | Et | 2-Me | I | 3352 | Pr | Pr | 2-Br | H |
| 3296 | Bu | Et | 2-Et | H | 3353 | Pr | Pr | 2-Br | SnMe₃ |
| 3297 | Bu | Et | 2-Et | SnMe₃ | 3354 | Pr | Pr | 2-Br | Br |
| 3298 | Bu | Et | 2-Et | Br | 3355 | Pr | Pr | 2-Br | I |
| 3299 | Bu | Et | 2-Et | I | 3356 | Pr | Pr | 2-Me | H |
| 3300 | Bu | Et | 2-Me, 6-Me | H | 3357 | Pr | Pr | 2-Me | SnMe₃ |
| 3301 | Bu | Et | 2-Me, 6-Me | SnMe₃ | 3358 | Pr | Pr | 2-Me | Br |
| 3302 | Bu | Et | 2-Me, 6-Me | Br | 3359 | Pr | Pr | 2-Me | I |
| 3303 | Bu | Et | 2-Me, 6-Me | I | 3360 | Pr | Pr | 2-Et | H |
| 3304 | Bu | Et | 2-OH | H | 3361 | Pr | Pr | 2-Et | SnMe₃ |
| 3305 | Bu | Et | 2-OH | SnMe₃ | 3362 | Pr | Pr | 2-Et | Br |
| 3306 | Bu | Et | 2-OH | Br | 3363 | Pr | Pr | 2-Et | I |
| 3307 | Bu | Et | 2-OH | I | 3364 | Pr | Pr | 2-Me, 6-Me | H |
| 3308 | Bu | Et | 2-OMe | H | 3365 | Pr | Pr | 2-Me, 6-Me | SnMe₃ |
| 3309 | Bu | Et | 2-OMe | SnMe₃ | 3366 | Pr | Pr | 2-Me, 6-Me | Br |
| 3310 | Bu | Et | 2-OMe | Br | 3367 | Pr | Pr | 2-Me, 6-Me | I |
| 3311 | Bu | Et | 2-OMe | I | 3368 | Pr | Pr | 2-OH | H |
| 3312 | Bu | Et | 2-OMeF | H | 3369 | Pr | Pr | 2-OH | SnMe₃ |
| 3313 | Bu | Et | 2-OMeF | SnMe₃ | 3370 | Pr | Pr | 2-OH | Br |
| 3314 | Bu | Et | 2-OMeF | Br | 3371 | Pr | Pr | 2-OH | I |
| 3315 | Bu | Et | 2-OMeF | I | 3372 | Pr | Pr | 2-OMe | H |
| 3316 | Bu | Et | 2-OCF₃ | H | 3373 | Pr | Pr | 2-OMe | SnMe₃ |
| 3317 | Bu | Et | 2-OCF₃ | SnMe₃ | 3374 | Pr | Pr | 2-OMe | Br |
| 3318 | Bu | Et | 2-OCF₃ | Br | 3375 | Pr | Pr | 2-OMe | I |
| 3319 | Bu | Et | 2-OCF₃ | I | 3376 | Pr | Pr | 2-OMeF | H |
| 3320 | Bu | Et | 2-OEtF | H | 3377 | Pr | Pr | 2-OMeF | SnMe₃ |
| 3321 | Bu | Et | 2-OEtF | SnMe₃ | 3378 | Pr | Pr | 2-OMeF | Br |
| 3322 | Bu | Et | 2-OEtF | Br | 3379 | Pr | Pr | 2-OMeF | I |
| 3323 | Bu | Et | 2-OEtF | I | 3380 | Pr | Pr | 2-OCF₃ | H |
| 3324 | Bu | Et | 2-OPrF | H | 3381 | Pr | Pr | 2-OCF₃ | SnMe₃ |
| 3325 | Bu | Et | 2-OPrF | SnMe₃ | 3382 | Pr | Pr | 2-OCF₃ | Br |
| 3326 | Bu | Et | 2-OPrF | Br | 3383 | Pr | Pr | 2-OCF₃ | I |
| 3327 | Bu | Et | 2-OPrF | I | 3384 | Pr | Pr | 2-OEtF | H |
| 3328 | Bu | Et | 2-CF₃ | H | 3385 | Pr | Pr | 2-OEtF | SnMe₃ |
| 3329 | Bu | Et | 2-CF₃ | SnMe₃ | 3386 | Pr | Pr | 2-OEtF | Br |
| 3330 | Bu | Et | 2-CF₃ | Br | 3387 | Pr | Pr | 2-OEtF | I |
| 3331 | Bu | Et | 2-CF₃ | I | 3388 | Pr | Pr | 2-OPrF | H |
| 3332 | Bu | Et | 2-Br, 6-CF₃ | H | 3389 | Pr | Pr | 2-OPrF | SnMe₃ |
| 3333 | Bu | Et | 2-Br, 6-CF₃ | SnMe₃ | 3390 | Pr | Pr | 2-OPrF | Br |
| 3334 | Bu | Et | 2-Br, 6-CF₃ | Br | 3391 | Pr | Pr | 2-OPrF | I |
| 3335 | Bu | Et | 2-Br, 6-CF₃ | I | 3392 | Pr | Pr | 2-CF₃ | H |
| 3336 | Bu | Et | 2-Br, 6-Br | H | 3393 | Pr | Pr | 2-CF₃ | SnMe₃ |
| 3337 | Bu | Et | 2-Br, 6-Br | SnMe₃ | 3394 | Pr | Pr | 2-CF₃ | Br |
| 3338 | Bu | Et | 2-Br, 6-Br | Br | 3395 | Pr | Pr | 2-CF₃ | I |
| 3339 | Bu | Et | 2-Br, 6-Br | I | 3396 | Pr | Pr | 2-Br, 6-CF₃ | H |
| 3340 | Pr | Pr | H | H | 3397 | Pr | Pr | 2-Br, 6-CF₃ | SnMe₃ |
| 3341 | Pr | Pr | H | SnMe₃ | 3398 | Pr | Pr | 2-Br, 6-CF₃ | Br |
| 3342 | Pr | Pr | H | Br | 3399 | Pr | Pr | 2-Br, 6-CF₃ | I |
| 3343 | Pr | Pr | H | I | 3400 | Pr | Pr | 2-Br, 6-Br | H |
| 3344 | Pr | Pr | 2-F | H | 3401 | Pr | Pr | 2-Br, 6-Br | SnMe₃ |
| 3345 | Pr | Pr | 2-F | SnMe₃ | 3402 | Pr | Pr | 2-Br, 6-Br | Br |
| 3346 | Pr | Pr | 2-F | Br | 3403 | Pr | Pr | 2-Br, 6-Br | I |
| 3347 | Pr | Pr | 2-F | I | 3404 | Pr | Pr—F | H | H |
| 3348 | Pr | Pr | 2-Cl | H | 3405 | Pr | Pr—F | H | SnMe₃ |
| 3349 | Pr | Pr | 2-Cl | SnMe₃ | 3406 | Pr | Pr—F | H | Br |
| 3350 | Pr | Pr | 2-Cl | Br | 3407 | Pr | Pr—F | H | I |
| 3351 | Pr | Pr | 2-Cl | I | 3408 | Pr | Pr—F | 2-F | H |

TABLE 3-continued

Substituent list for compounds of general structure VIII.

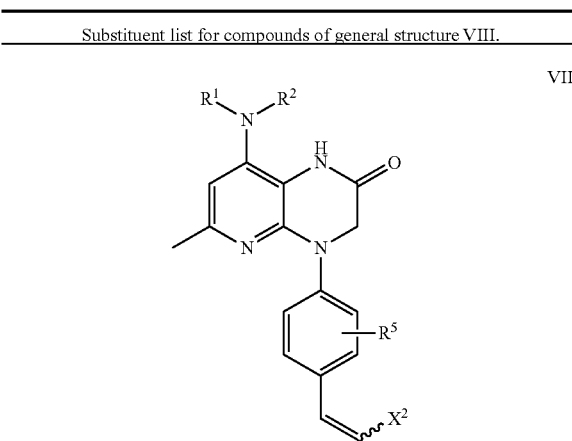

| Compound # | R¹ = | R² = | R⁵ = | X² = |
|---|---|---|---|---|
| 3409 | Pr | Pr—F | 2-F | SnMe₃ |
| 3410 | Pr | Pr—F | 2-F | Br |
| 3411 | Pr | Pr—F | 2-F | I |
| 3412 | Pr | Pr—F | 2-Cl | H |
| 3413 | Pr | Pr—F | 2-Cl | SnMe₃ |
| 3414 | Pr | Pr—F | 2-Cl | Br |
| 3415 | Pr | Pr—F | 2-Cl | I |
| 3416 | Pr | Pr—F | 2-Br | H |
| 3417 | Pr | Pr—F | 2-Br | SnMe₃ |
| 3418 | Pr | Pr—F | 2-Br | Br |
| 3419 | Pr | Pr—F | 2-Br | I |
| 3420 | Pr | Pr—F | 2-Me | H |
| 3421 | Pr | Pr—F | 2-Me | SnMe₃ |
| 3422 | Pr | Pr—F | 2-Me | Br |
| 3423 | Pr | Pr—F | 2-Me | I |
| 3424 | Pr | Pr—F | 2-Et | H |
| 3425 | Pr | Pr—F | 2-Et | SnMe₃ |
| 3426 | Pr | Pr—F | 2-Et | Br |
| 3427 | Pr | Pr—F | 2-Et | I |
| 3428 | Pr | Pr—F | 2-Me, 6-Me | H |
| 3429 | Pr | Pr—F | 2-Me, 6-Me | SnMe₃ |
| 3430 | Pr | Pr—F | 2-Me, 6-Me | Br |
| 3431 | Pr | Pr—F | 2-Me, 6-Me | I |
| 3432 | Pr | Pr—F | 2-OH | H |
| 3433 | Pr | Pr—F | 2-OH | SnMe₃ |
| 3434 | Pr | Pr—F | 2-OH | Br |
| 3435 | Pr | Pr—F | 2-OH | I |
| 3436 | Pr | Pr—F | 2-OMe | H |
| 3437 | Pr | Pr—F | 2-OMe | SnMe₃ |
| 3438 | Pr | Pr—F | 2-OMe | Br |
| 3439 | Pr | Pr—F | 2-OMe | I |
| 3440 | Pr | Pr—F | 2-OMeF | H |
| 3441 | Pr | Pr—F | 2-OMeF | SnMe₃ |
| 3442 | Pr | Pr—F | 2-OMeF | Br |
| 3443 | Pr | Pr—F | 2-OMeF | I |
| 3444 | Pr | Pr—F | 2-OCF₃ | H |
| 3445 | Pr | Pr—F | 2-OCF₃ | SnMe³ |
| 3446 | Pr | Pr—F | 2-OCF₃ | Br |
| 3447 | Pr | Pr—F | 2-OCF₃ | I |
| 3448 | Pr | Pr—F | 2-OEtF | H |
| 3449 | Pr | Pr—F | 2-OEtF | SnMe³ |
| 3450 | Pr | Pr—F | 2-OEtF | Br |
| 3451 | Pr | Pr—F | 2-OEtF | I |
| 3452 | Pr | Pr—F | 2-OPrF | H |
| 3453 | Pr | Pr—F | 2-OPrF | SnMe³ |
| 3454 | Pr | Pr—F | 2-OPrF | Br |
| 3455 | Pr | Pr—F | 2-OPrF | I |
| 3456 | Pr | Pr—F | 2-CF₃ | H |
| 3457 | Pr | Pr—F | 2-CF₃ | SnMe³ |
| 3458 | Pr | Pr—F | 2-CF₃ | Br |
| 3459 | Pr | Pr—F | 2-CF₃ | I |
| 3460 | Pr | Pr—F | 2-Br, 6-CF₃ | H |
| 3461 | Pr | Pr—F | 2-Br, 6-CF₃ | SnMe³ |
| 3462 | Pr | Pr—F | 2-Br, 6-CF₃ | Br |
| 3463 | Pr | Pr—F | 2-Br, 6-CF₃ | I |
| 3464 | Pr | Pr—F | 2-Br, 6-Br | H |
| 3465 | Pr | Pr—F | 2-Br, 6-Br | SnMe³ |
| 3466 | Pr | Pr—F | 2-Br, 6-Br | Br |
| 3467 | Pr | Pr—F | 2-Br, 6-Br | I |
| 3468 | Pr | Et—F | H | H |
| 3469 | Pr | Et—F | H | SnMe₃ |
| 3470 | Pr | Et—F | H | Br |
| 3471 | Pr | Et—F | H | I |
| 3472 | Pr | Et—F | 2-F | H |
| 3473 | Pr | Et—F | 2-F | SnMe₃ |
| 3474 | Pr | Et—F | 2-F | Br |
| 3475 | Pr | Et—F | 2-F | I |
| 3476 | Pr | Et—F | 2-Cl | H |
| 3477 | Pr | Et—F | 2-Cl | SnMe₃ |
| 3478 | Pr | Et—F | 2-Cl | Br |
| 3479 | Pr | Et—F | 2-Cl | I |
| 3480 | Pr | Et—F | 2-Br | H |
| 3481 | Pr | Et—F | 2-Br | SnMe₃ |
| 3482 | Pr | Et—F | 2-Br | Br |
| 3483 | Pr | Et—F | 2-Br | I |
| 3484 | Pr | Et—F | 2-Me | H |
| 3485 | Pr | Et—F | 2-Me | SnMe₃ |
| 3486 | Pr | Et—F | 2-Me | Br |
| 3487 | Pr | Et—F | 2-Me | I |
| 3488 | Pr | Et—F | 2-Et | H |
| 3489 | Pr | Et—F | 2-Et | SnMe₃ |
| 3490 | Pr | Et—F | 2-Et | Br |
| 3491 | Pr | Et—F | 2-Et | I |
| 3492 | Pr | Et—F | 2-Me, 6-Me | H |
| 3493 | Pr | Et—F | 2-Me, 6-Me | SnMe₃ |
| 3494 | Pr | Et—F | 2-Me, 6-Me | Br |
| 3495 | Pr | Et—F | 2-Me, 6-Me | I |
| 3496 | Pr | Et—F | 2-OH | H |
| 3497 | Pr | Et—F | 2-OH | SnMe₃ |
| 3498 | Pr | Et—F | 2-OH | Br |
| 3499 | Pr | Et—F | 2-OH | I |
| 3500 | Pr | Et—F | 2-OMe | H |
| 3501 | Pr | Et—F | 2-OMe | SnMe₃ |
| 3502 | Pr | Et—F | 2-OMe | Br |
| 3503 | Pr | Et—F | 2-OMe | I |
| 3504 | Pr | Et—F | 2-OMeF | H |
| 3505 | Pr | Et—F | 2-OMeF | SnMe₃ |
| 3506 | Pr | Et—F | 2-OMeF | Br |
| 3507 | Pr | Et—F | 2-OMeF | I |
| 3508 | Pr | Et—F | 2-OCF₃ | H |
| 3509 | Pr | Et—F | 2-OCF₃ | SnMe₃ |
| 3510 | Pr | Et—F | 2-OCF₃ | Br |
| 3511 | Pr | Et—F | 2-OCF₃ | I |
| 3512 | Pr | Et—F | 2-OEtF | H |
| 3513 | Pr | Et—F | 2-OEtF | SnMe₃ |
| 3514 | Pr | Et—F | 2-OEtF | Br |
| 3515 | Pr | Et—F | 2-OEtF | I |
| 3516 | Pr | Et—F | 2-OPrF | H |
| 3517 | Pr | Et—F | 2-OPrF | SnMe₃ |
| 3518 | Pr | Et—F | 2-OPrF | Br |
| 3519 | Pr | Et—F | 2-OPrF | I |
| 3520 | Pr | Et—F | 2-CF₃ | H |
| 3521 | Pr | Et—F | 2-CF₃ | SnMe₃ |
| 3522 | Pr | Et—F | 2-CF₃ | Br |

TABLE 3-continued

Substituent list for compounds of general structure VIII.

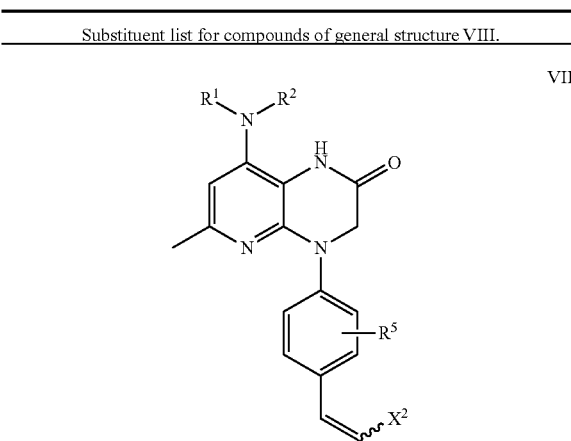

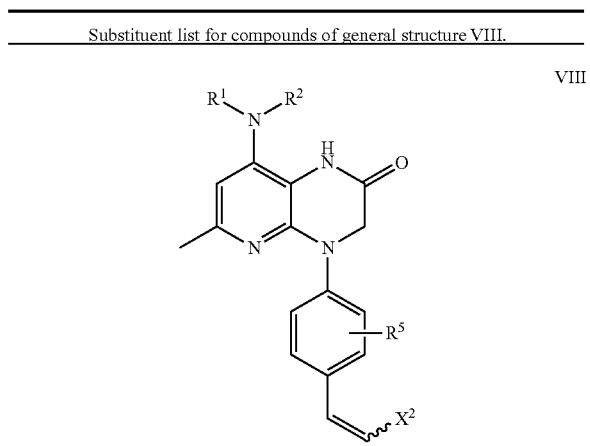

| Compound # | R¹ = | R² = | R⁵ = | X² = |
|---|---|---|---|---|
| 3523 | Pr | Et—F | 2-CF₃ | I |
| 3524 | Pr | Et—F | 2-Br, 6-CF₃ | H |
| 3525 | Pr | Et—F | 2-Br, 6-CF₃ | SnMe₃ |
| 3526 | Pr | Et—F | 2-Br, 6-CF₃ | Br |
| 3527 | Pr | Et—F | 2-Br, 6-CF₃ | I |
| 3528 | Pr | Et—F | 2-Br, 6-Br | H |
| 3529 | Pr | Et—F | 2-Br, 6-Br | SnMe₃ |
| 3530 | Pr | Et—F | 2-Br, 6-Br | Br |
| 3531 | Pr | Et—F | 2-Br, 6-Br | I |
| 3532 | Pr—F | Et | H | H |
| 3533 | Pr—F | Et | H | SnMe₃ |
| 3534 | Pr—F | Et | H | Br |
| 3535 | Pr—F | Et | H | I |
| 3536 | Pr—F | Et | 2-F | H |
| 3537 | Pr—F | Et | 2-F | SnMe₃ |
| 3538 | Pr—F | Et | 2-F | Br |
| 3539 | Pr—F | Et | 2-F | I |
| 3540 | Pr—F | Et | 2-Cl | H |
| 3541 | Pr—F | Et | 2-Cl | SnMe₃ |
| 3542 | Pr—F | Et | 2-Cl | Br |
| 3543 | Pr—F | Et | 2-Cl | I |
| 3544 | Pr—F | Et | 2-Br | H |
| 3545 | Pr—F | Et | 2-Br | SnMe₃ |
| 3546 | Pr—F | Et | 2-Br | Br |
| 3547 | Pr—F | Et | 2-Br | I |
| 3548 | Pr—F | Et | 2-Me | H |
| 3549 | Pr—F | Et | 2-Me | SnMe₃ |
| 3550 | Pr—F | Et | 2-Me | Br |
| 3551 | Pr—F | Et | 2-Me | I |
| 3552 | Pr—F | Et | 2-Et | H |
| 3553 | Pr—F | Et | 2-Et | SnMe₃ |
| 3554 | Pr—F | Et | 2-Et | Br |
| 3555 | Pr—F | Et | 2-Et | I |
| 3556 | Pr—F | Et | 2-Me, 6-Me | H |
| 3557 | Pr—F | Et | 2-Me, 6-Me | SnMe₃ |
| 3558 | Pr—F | Et | 2-Me, 6-Me | Br |
| 3559 | Pr—F | Et | 2-Me, 6-Me | I |
| 3560 | Pr—F | Et | 2-OH | H |
| 3561 | Pr—F | Et | 2-OH | SnMe₃ |
| 3562 | Pr—F | Et | 2-OH | Br |
| 3563 | Pr—F | Et | 2-OH | I |
| 3564 | Pr—F | Et | 2-OMe | H |
| 3565 | Pr—F | Et | 2-OMe | SnMe₃ |
| 3566 | Pr—F | Et | 2-OMe | Br |
| 3567 | Pr—F | Et | 2-OMe | I |
| 3568 | Pr—F | Et | 2-OMeF | H |
| 3569 | Pr—F | Et | 2-OMeF | SnMe₃ |
| 3570 | Pr—F | Et | 2-OMeF | Br |
| 3571 | Pr—F | Et | 2-OMeF | I |
| 3572 | Pr—F | Et | 2-OCF₃ | H |
| 3573 | Pr—F | Et | 2-OCF₃ | SnMe₃ |
| 3574 | Pr—F | Et | 2-OCF₃ | Br |
| 3575 | Pr—F | Et | 2-OCF₃ | I |
| 3576 | Pr—F | Et | 2-OEtF | H |
| 3577 | Pr—F | Et | 2-OEtF | SnMe₃ |
| 3578 | Pr—F | Et | 2-OEtF | Br |
| 3579 | Pr—F | Et | 2-OEtF | I |
| 3580 | Pr—F | Et | 2-OPrF | H |
| 3581 | Pr—F | Et | 2-OPrF | SnMe₃ |
| 3582 | Pr—F | Et | 2-OPrF | Br |
| 3583 | Pr—F | Et | 2-OPrF | I |
| 3584 | Pr—F | Et | 2-CF₃ | H |
| 3585 | Pr—F | Et | 2-CF₃ | SnMe₃ |
| 3586 | Pr—F | Et | 2-CF₃ | Br |
| 3587 | Pr—F | Et | 2-CF₃ | I |
| 3588 | Pr—F | Et | 2-Br, 6-CF₃ | H |
| 3589 | Pr—F | Et | 2-Br, 6-CF₃ | SnMe₃ |
| 3590 | Pr—F | Et | 2-Br, 6-CF₃ | Br |
| 3591 | Pr—F | Et | 2-Br, 6-CF₃ | I |
| 3592 | Pr—F | Et | 2-Br, 6-Br | H |
| 3593 | Pr—F | Et | 2-Br, 6-Br | SnMe₃ |
| 3594 | Pr—F | Et | 2-Br, 6-Br | Br |
| 3595 | Pr—F | Et | 2-Br, 6-Br | I |
| 3596 | Bu | Et—F | H | H |
| 3597 | Bu | Et—F | H | SnMe₃ |
| 3598 | Bu | Et—F | H | Br |
| 3599 | Bu | Et—F | H | I |
| 3600 | Bu | Et—F | 2-F | H |
| 3601 | Bu | Et—F | 2-F | SnMe₃ |
| 3602 | Bu | Et—F | 2-F | Br |
| 3603 | Bu | Et—F | 2-F | I |
| 3604 | Bu | Et—F | 2-Cl | H |
| 3605 | Bu | Et—F | 2-Cl | SnMe₃ |
| 3606 | Bu | Et—F | 2-Cl | Br |
| 3607 | Bu | Et—F | 2-Cl | I |
| 3608 | Bu | Et—F | 2-Br | H |
| 3609 | Bu | Et—F | 2-Br | SnMe₃ |
| 3610 | Bu | Et—F | 2-Br | Br |
| 3611 | Bu | Et—F | 2-Br | I |
| 3612 | Bu | Et—F | 2-Me | H |
| 3613 | Bu | Et—F | 2-Me | SnMe₃ |
| 3614 | Bu | Et—F | 2-Me | Br |
| 3615 | Bu | Et—F | 2-Me | I |
| 3616 | Bu | Et—F | 2-Et | H |
| 3617 | Bu | Et—F | 2-Et | SnMe₃ |
| 3618 | Bu | Et—F | 2-Et | Br |
| 3619 | Bu | Et—F | 2-Et | I |
| 3620 | Bu | Et—F | 2-Me, 6-Me | H |
| 3621 | Bu | Et—F | 2-Me, 6-Me | SnMe₃ |
| 3622 | Bu | Et—F | 2-Me, 6-Me | Br |
| 3623 | Bu | Et—F | 2-Me, 6-Me | I |
| 3624 | Bu | Et—F | 2-OH | H |
| 3625 | Bu | Et—F | 2-OH | SnMe₃ |
| 3626 | Bu | Et—F | 2-OH | Br |
| 3627 | Bu | Et—F | 2-OH | I |
| 3628 | Bu | Et—F | 2-OMe | H |
| 3629 | Bu | Et—F | 2-OMe | SnMe₃ |
| 3630 | Bu | Et—F | 2-OMe | Br |
| 3631 | Bu | Et—F | 2-OMe | I |
| 3632 | Bu | Et—F | 2-OMeF | H |
| 3633 | Bu | Et—F | 2-OMeF | SnMe₃ |
| 3634 | Bu | Et—F | 2-OMeF | Br |
| 3635 | Bu | Et—F | 2-OMeF | I |
| 3636 | Bu | Et—F | 2-OCF₃ | H |

TABLE 3-continued

Substituent list for compounds of general structure VIII.

| Compound # | R¹ = | R² = | R⁵ = | X² = |
|---|---|---|---|---|
| 3637 | Bu | Et—F | 2-OCF$_3$ | SnMe$_3$ |
| 3638 | Bu | Et—F | 2-OCF$_3$ | Br |
| 3639 | Bu | Et—F | 2-OCF$_3$ | I |
| 3640 | Bu | Et—F | 2-OEtF | H |
| 3641 | Bu | Et—F | 2-OEtF | SnMe$_3$ |
| 3642 | Bu | Et—F | 2-OEtF | Br |
| 3643 | Bu | Et—F | 2-OEtF | I |
| 3644 | Bu | Et—F | 2-OPrF | H |
| 3645 | Bu | Et—F | 2-OPrF | SnMe$_3$ |
| 3646 | Bu | Et—F | 2-OPrF | Br |
| 3647 | Bu | Et—F | 2-OPrF | I |
| 3648 | Bu | Et—F | 2-CF$_3$ | H |
| 3649 | Bu | Et—F | 2-CF$_3$ | SnMe$_3$ |
| 3650 | Bu | Et—F | 2-CF$_3$ | Br |
| 3651 | Bu | Et—F | 2-CF$_3$ | I |
| 3652 | Bu | Et—F | 2-Br, 6-CF$_3$ | H |
| 3653 | Bu | Et—F | 2-Br, 6-CF$_3$ | SnMe$_3$ |
| 3654 | Bu | Et—F | 2-Br, 6-CF$_3$ | Br |
| 3655 | Bu | Et—F | 2-Br, 6-CF$_3$ | I |
| 3656 | Bu | Et—F | 2-Br, 6-Br | H |
| 3657 | Bu | Et—F | 2-Br, 6-Br | SnMe$_3$ |
| 3658 | Bu | Et—F | 2-Br, 6-Br | Br |
| 3659 | Bu | Et—F | 2-Br, 6-Br | I |
| 3660 | Bu—F | Et | H | H |
| 3661 | Bu—F | Et | H | SnMe$_3$ |
| 3662 | Bu—F | Et | H | Br |
| 3663 | Bu—F | Et | H | I |
| 3664 | Bu—F | Et | 2-F | H |
| 3665 | Bu—F | Et | 2-F | SnMe$_3$ |
| 3666 | Bu—F | Et | 2-F | Br |
| 3667 | Bu—F | Et | 2-F | I |
| 3668 | Bu—F | Et | 2-Cl | H |
| 3669 | Bu—F | Et | 2-Cl | SnMe$_3$ |
| 3670 | Bu—F | Et | 2-Cl | Br |
| 3671 | Bu—F | Et | 2-Cl | I |
| 3672 | Bu—F | Et | 2-Br | H |
| 3673 | Bu—F | Et | 2-Br | SnMe$_3$ |
| 3674 | Bu—F | Et | 2-Br | Br |
| 3675 | Bu—F | Et | 2-Br | I |
| 3676 | Bu—F | Et | 2-Me | H |
| 3677 | Bu—F | Et | 2-Me | SnMe$_3$ |
| 3678 | Bu—F | Et | 2-Me | Br |
| 3679 | Bu—F | Et | 2-Me | I |
| 3680 | Bu—F | Et | 2-Et | H |
| 3681 | Bu—F | Et | 2-Et | SnMe$_3$ |
| 3682 | Bu—F | Et | 2-Et | Br |
| 3683 | Bu—F | Et | 2-Et | I |
| 3684 | Bu—F | Et | 2-Me, 6-Me | H |
| 3685 | Bu—F | Et | 2-Me, 6-Me | SnMe$_3$ |
| 3686 | Bu—F | Et | 2-Me, 6-Me | Br |
| 3687 | Bu—F | Et | 2-Me, 6-Me | I |
| 3688 | Bu—F | Et | 2-OH | H |
| 3689 | Bu—F | Et | 2-OH | SnMe$_3$ |
| 3690 | Bu—F | Et | 2-OH | Br |
| 3691 | Bu—F | Et | 2-OH | I |
| 3692 | Bu—F | Et | 2-OMe | H |
| 3693 | Bu—F | Et | 2-OMe | SnMe$_3$ |
| 3694 | Bu—F | Et | 2-OMe | Br |
| 3695 | Bu—F | Et | 2-OMe | I |
| 3696 | Bu—F | Et | 2-OMeF | H |
| 3697 | Bu—F | Et | 2-OMeF | SnMe$_3$ |
| 3698 | Bu—F | Et | 2-OMeF | Br |
| 3699 | Bu—F | Et | 2-OMeF | I |
| 3700 | Bu—F | Et | 2-OCF$_3$ | H |
| 3701 | Bu—F | Et | 2-OCF$_3$ | SnMe$_3$ |
| 3702 | Bu—F | Et | 2-OCF$_3$ | Br |
| 3703 | Bu—F | Et | 2-OCF$_3$ | I |
| 3704 | Bu—F | Et | 2-OEtF | H |
| 3705 | Bu—F | Et | 2-OEtF | SnMe$_3$ |
| 3706 | Bu—F | Et | 2-OEtF | Br |
| 3707 | Bu—F | Et | 2-OEtF | I |
| 3708 | Bu—F | Et | 2-OPrF | H |
| 3709 | Bu—F | Et | 2-OPrF | SnMe$_3$ |
| 3710 | Bu—F | Et | 2-OPrF | Br |
| 3711 | Bu—F | Et | 2-OPrF | I |
| 3712 | Bu—F | Et | 2-CF$_3$ | H |
| 3713 | Bu—F | Et | 2-CF$_3$ | SnMe$_3$ |
| 3714 | Bu—F | Et | 2-CF$_3$ | Br |
| 3715 | Bu—F | Et | 2-CF$_3$ | 1 |
| 3716 | Bu—F | Et | 2-Br, 6-CF$_3$ | H |
| 3717 | Bu—F | Et | 2-Br, 6-CF$_3$ | SnMe$_3$ |
| 3718 | Bu—F | Et | 2-Br, 6-CF$_3$ | Br |
| 3719 | Bu—F | Et | 2-Br, 6-CF$_3$ | I |
| 3720 | Bu—F | Et | 2-Br, 6-Br | H |
| 3721 | Bu—F | Et | 2-Br, 6-Br | SnMe$_3$ |
| 3722 | Bu—F | Et | 2-Br, 6-Br | Br |
| 3723 | Bu—F | Et | 2-Br, 6-Br | I |
| 3724 | FCH$_2$—CH=CH—CH$_2$ | Me | H | H |
| 3725 | FCH$_2$—CH=CH—CH$_2$ | Me | H | SnMe$_3$ |
| 3726 | FCH$_2$—CH=CH—CH$_2$ | Me | H | Br |
| 3727 | FCH$_2$—CH=CH—CH$_2$ | Me | H | I |
| 3728 | FCH$_2$—CH=CH—CH$_2$ | Me | 2-F | H |
| 3729 | FCH$_2$—CH=CH—CH$_2$ | Me | 2-F | SnMe$_3$ |
| 3730 | FCH$_2$—CH=CH—CH$_2$ | Me | 2-F | Br |
| 3731 | FCH$_2$—CH=CH—CH$_2$ | Me | 2-F | I |
| 3732 | FCH$_2$—CH=CH—CH$_2$ | Me | 2-Cl | H |
| 3733 | FCH$_2$—CH=CH—CH$_2$ | Me | 2-Cl | SnMe$_3$ |
| 3734 | FCH$_2$—CH=CH—CH$_2$ | Me | 2-Cl | Br |
| 3735 | FCH$_2$—CH=CH—CH$_2$ | Me | 2-Cl | I |
| 3736 | FCH$_2$—CH=CH—CH$_2$ | Me | 2-Br | H |
| 3737 | FCH$_2$—CH=CH—CH$_2$ | Me | 2-Br | SnMe$_3$ |
| 3738 | FCH$_2$—CH=CH—CH$_2$ | Me | 2-Br | Br |
| 3739 | FCH$_2$—CH=CH—CH$_2$ | Me | 2-Br | I |
| 3740 | FCH$_2$—CH=CH—CH$_2$ | Me | 2-Me | H |
| 3741 | FCH$_2$—CH=CH—CH$_2$ | Me | 2-Me | SnMe$_3$ |
| 3742 | FCH$_2$—CH=CH—CH$_2$ | Me | 2-Me | Br |
| 3743 | FCH$_2$—CH=CH—CH$_2$ | Me | 2-Me | I |
| 3744 | FCH$_2$—CH=CH—CH$_2$ | Me | 2-Et | H |
| 3745 | FCH$_2$—CH=CH—CH$_2$ | Me | 2-Et | SnMe$_3$ |
| 3746 | FCH$_2$—CH=CH—CH$_2$ | Me | 2-Et | Br |
| 3747 | FCH$_2$—CH=CH—CH$_2$ | Me | 2-Et | I |
| 3748 | FCH$_2$—CH=CH—CH$_2$ | Me | 2-Me, 6-Me | H |
| 3749 | FCH$_2$—CH=CH—CH$_2$ | Me | 2-Me, 6-Me | SnMe$_3$ |
| 3750 | FCH$_2$—CH=CH—CH$_2$ | Me | 2-Me, 6-Me | Br |

TABLE 3-continued

Substituent list for compounds of general structure VIII.

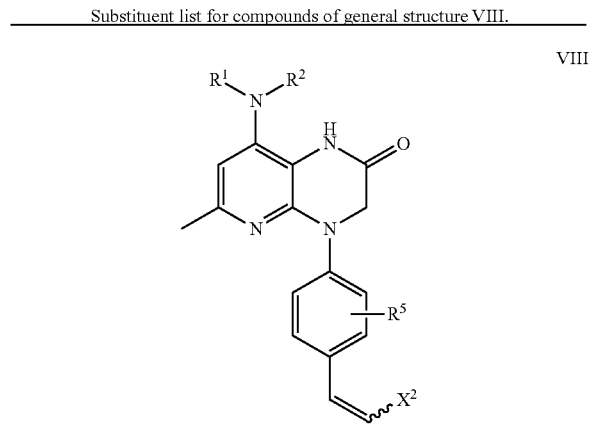

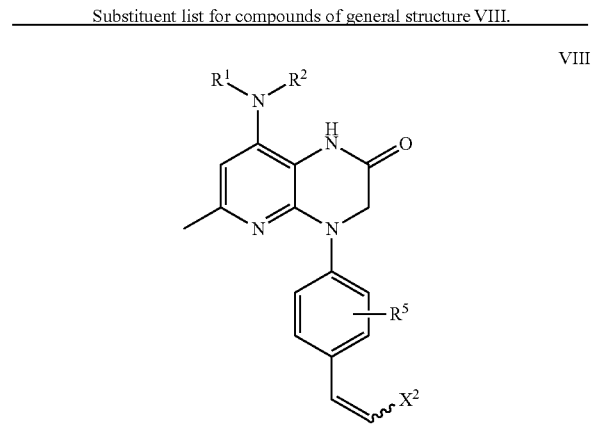

| Compound # | R¹ = | R² = | R⁵ = | X² = |
|---|---|---|---|---|
| 3751 | FCH₂—CH=CH—CH₂ | Me | 2-Me, 6-Me | I |
| 3752 | FCH₂—CH=CH—CH₂ | Me | 2-OH | H |
| 3753 | FCH₂—CH=CH—CH₂ | Me | 2-OH | SnMe₃ |
| 3754 | FCH₂—CH=CH—CH₂ | Me | 2-OH | Br |
| 3755 | FCH₂—CH=CH—CH₂ | Me | 2-OH | I |
| 3756 | FCH₂—CH=CH—CH₂ | Me | 2-OMe | H |
| 3757 | FCH₂—CH=CH—CH₂ | Me | 2-OMe | SnMe₃ |
| 3758 | FCH₂—CH=CH—CH₂ | Me | 2-OMe | Br |
| 3759 | FCH₂—CH=CH—CH₂ | Me | 2-OMe | I |
| 3760 | FCH₂—CH=CH—CH₂ | Me | 2-OMeF | H |
| 3761 | FCH₂—CH=CH—CH₂ | Me | 2-OMeF | SnMe₃ |
| 3762 | FCH₂—CH=CH—CH₂ | Me | 2-OMeF | Br |
| 3763 | FCH₂—CH=CH—CH₂ | Me | 2-OMeF | I |
| 3764 | FCH₂—CH=CH—CH₂ | Me | 2-OCF₃ | H |
| 3765 | FCH₂—CH=CH—CH₂ | Me | 2-OCF₃ | SnMe₃ |
| 3766 | FCH₂—CH=CH—CH₂ | Me | 2-OCF₃ | Br |
| 3767 | FCH₂—CH=CH—CH₂ | Me | 2-OCF₃ | I |
| 3768 | FCH₂—CH=CH—CH₂ | Me | 2-OEtF | H |
| 3769 | FCH₂—CH=CH—CH₂ | Me | 2-OEtF | SnMe₃ |
| 3770 | FCH₂—CH=CH—CH₂ | Me | 2-OEtF | Br |
| 3771 | FCH₂—CH=CH—CH₂ | Me | 2-OEtF | I |
| 3772 | FCH₂—CH=CH—CH₂ | Me | 2-OPrF | H |
| 3773 | FCH₂—CH=CH—CH₂ | Me | 2-OPrF | SnMe₃ |
| 3774 | FCH₂—CH=CH—CH₂ | Me | 2-OPrF | Br |
| 3775 | FCH₂—CH=CH—CH₂ | Me | 2-OPrF | I |
| 3776 | FCH₂—CH=CH—CH₂ | Me | 2-CF₃ | H |
| 3777 | FCH₂—CH=CH—CH₂ | Me | 2-CF₃ | SnMe₃ |
| 3778 | FCH₂—CH=CH—CH₂ | Me | 2-CF₃ | Br |
| 3779 | FCH₂—CH=CH—CH₂ | Me | 2-CF₃ | I |
| 3780 | FCH₂—CH=CH—CH₂ | Me | 2-Br, 6-CF₃ | H |
| 3781 | FCH₂—CH=CH—CH₂ | Me | 2-Br, 6-CF₃ | SnMe₃ |
| 3782 | FCH₂—CH=CH—CH₂ | Me | 2-Br, 6-CF₃ | Br |
| 3783 | FCH₂—CH=CH—CH₂ | Me | 2-Br, 6-CF₃ | I |
| 3784 | FCH₂—CH=CH—CH₂ | Me | 2-Br, 6-Br | H |
| 3785 | FCH₂—CH=CH—CH₂ | Me | 2-Br, 6-Br | SnMe₃ |
| 3786 | FCH₂—CH=CH—CH₂ | Me | 2-Br, 6-Br | Br |
| 3787 | FCH₂—CH=CH—CH₂ | Me | 2-Br, 6-Br | I |
| 3788 | FCH₂—CH=CH—CH₂ | Et | H | H |
| 3789 | FCH₂—CH=CH—CH₂ | Et | H | SnMe₃ |
| 3790 | FCH₂—CH=CH—CH₂ | Et | H | Br |
| 3791 | FCH₂—CH=CH—CH₂ | Et | H | I |
| 3792 | FCH₂—CH=CH—CH₂ | Et | 2-F | H |
| 3793 | FCH₂—CH=CH—CH₂ | Et | 2-F | SnMe₃ |
| 3794 | FCH₂—CH=CH—CH₂ | Et | 2-F | Br |
| 3795 | FCH₂—CH=CH—CH₂ | Et | 2-F | I |
| 3796 | FCH₂—CH=CH—CH₂ | Et | 2-Cl | H |
| 3797 | FCH₂—CH=CH—CH₂ | Et | 2-Cl | SnMe₃ |
| 3798 | FCH₂—CH=CH—CH₂ | Et | 2-Cl | Br |
| 3799 | FCH₂—CH=CH—CH₂ | Et | 2-Cl | I |
| 3800 | FCH₂—CH=CH—CH₂ | Et | 2-Br | H |
| 3801 | FCH₂—CH=CH—CH₂ | Et | 2-Br | SnMe₃ |
| 3802 | FCH₂—CH=CH—CH₂ | Et | 2-Br | Br |
| 3803 | FCH₂—CH=CH—CH₂ | Et | 2-Br | I |
| 3804 | FCH₂—CH=CH—CH₂ | Et | 2-Me | H |
| 3805 | FCH₂—CH=CH—CH₂ | Et | 2-Me | SnMe₃ |
| 3806 | FCH₂—CH=CH—CH₂ | Et | 2-Me | Br |
| 3807 | FCH₂—CH=CH—CH₂ | Et | 2-Me | I |
| 3808 | FCH₂—CH=CH—CH₂ | Et | 2-Et | H |
| 3809 | FCH₂—CH=CH—CH₂ | Et | 2-Et | SnMe₃ |
| 3810 | FCH₂—CH=CH—CH₂ | Et | 2-Et | Br |
| 3811 | FCH₂—CH=CH—CH₂ | Et | 2-Et | I |
| 3812 | FCH₂—CH=CH—CH₂ | Et | 2-Me, 6-Me | H |
| 3813 | FCH₂—CH=CH—CH₂ | Et | 2-Me, 6-Me | SnMe₃ |
| 3814 | FCH₂—CH=CH—CH₂ | Et | 2-Me, 6-Me | Br |
| 3815 | FCH₂—CH=CH—CH₂ | Et | 2-Me, 6-Me | I |
| 3816 | FCH₂—CH=CH—CH₂ | Et | 2-OH | H |
| 3817 | FCH₂—CH=CH—CH₂ | Et | 2-OH | SnMe₃ |
| 3818 | FCH₂—CH=CH—CH₂ | Et | 2-OH | Br |
| 3819 | FCH₂—CH=CH—CH₂ | Et | 2-OH | I |
| 3820 | FCH₂—CH=CH—CH₂ | Et | 2-OMe | H |
| 3821 | FCH₂—CH=CH—CH₂ | Et | 2-OMe | SnMe₃ |
| 3822 | FCH₂—CH=CH—CH₂ | Et | 2-OMe | Br |
| 3823 | FCH₂—CH=CH—CH₂ | Et | 2-OMe | I |
| 3824 | FCH₂—CH=CH—CH₂ | Et | 2-OMeF | H |
| 3825 | FCH₂—CH=CH—CH₂ | Et | 2-OMeF | SnMe₃ |
| 3826 | FCH₂—CH=CH—CH₂ | Et | 2-OMeF | Br |
| 3827 | FCH₂—CH=CH—CH₂ | Et | 2-OMeF | I |
| 3828 | FCH₂—CH=CH—CH₂ | Et | 2-OCF₃ | H |
| 3829 | FCH₂—CH=CH—CH₂ | Et | 2-OCF₃ | SnMe₃ |
| 3830 | FCH₂—CH=CH—CH₂ | Et | 2-OCF₃ | Br |
| 3831 | FCH₂—CH=CH—CH₂ | Et | 2-OCF₃ | I |
| 3832 | FCH₂—CH=CH—CH₂ | Et | 2-OEtF | H |
| 3833 | FCH₂—CH=CH—CH₂ | Et | 2-OEtF | SnMe₃ |
| 3834 | FCH₂—CH=CH—CH₂ | Et | 2-OEtF | Br |
| 3835 | FCH₂—CH=CH—CH₂ | Et | 2-OEtF | I |
| 3836 | FCH₂—CH=CH—CH₂ | Et | 2-OPrF | H |
| 3837 | FCH₂—CH=CH—CH₂ | Et | 2-OPrF | SnMe₃ |
| 3838 | FCH₂—CH=CH—CH₂ | Et | 2-OPrF | Br |
| 3839 | FCH₂—CH=CH—CH₂ | Et | 2-OPrF | I |
| 3840 | FCH₂—CH=CH—CH₂ | Et | 2-CF₃ | H |
| 3841 | FCH₂—CH=CH—CH₂ | Et | 2-CF₃ | SnMe₃ |
| 3842 | FCH₂—CH=CH—CH₂ | Et | 2-CF₃ | Br |
| 3843 | FCH₂—CH=CH—CH₂ | Et | 2-CF₃ | I |
| 3844 | FCH₂—CH=CH—CH₂ | Et | 2-Br, 6-CF₃ | H |
| 3845 | FCH₂—CH=CH—CH₂ | Et | 2-Br, 6-CF₃ | SnMe₃ |
| 3846 | FCH₂—CH=CH—CH₂ | Et | 2-Br, 6-CF₃ | Br |
| 3847 | FCH₂—CH=CH—CH₂ | Et | 2-Br, 6-CF₃ | I |
| 3848 | FCH₂—CH=CH—CH₂ | Et | 2-Br, 6-Br | H |
| 3849 | FCH₂—CH=CH—CH₂ | Et | 2-Br, 6-Br | SnMe₃ |
| 3850 | FCH₂—CH=CH—CH₂ | Et | 2-Br, 6-Br | Br |
| 3851 | FCH₂—CH=CH—CH₂ | Et | 2-Br, 6-Br | I |
| 3852 | FCH₂—CH=CH—CH₂ | Et—F | H | H |
| 3853 | FCH₂—CH=CH—CH₂ | Et—F | H | SnMe₃ |
| 3854 | FCH₂—CH=CH—CH₂ | Et—F | H | Br |
| 3855 | FCH₂—CH=CH—CH₂ | Et—F | H | I |
| 3856 | FCH₂—CH=CH—CH₂ | Et—F | 2-F | H |
| 3857 | FCH₂—CH=CH—CH₂ | Et—F | 2-F | SnMe₃ |
| 3858 | FCH₂—CH=CH—CH₂ | Et—F | 2-F | Br |
| 3859 | FCH₂—CH=CH—CH₂ | Et—F | 2-F | I |
| 3860 | FCH₂—CH=CH—CH₂ | Et—F | 2-Cl | H |
| 3861 | FCH₂—CH=CH—CH₂ | Et—F | 2-Cl | SnMe₃ |
| 3862 | FCH₂—CH=CH—CH₂ | Et—F | 2-Cl | Br |
| 3863 | FCH₂—CH=CH—CH₂ | Et—F | 2-Cl | I |
| 3864 | FCH₂—CH=CH—CH₂ | Et—F | 2-Br | H |

TABLE 3-continued

Substituent list for compounds of general structure VIII.

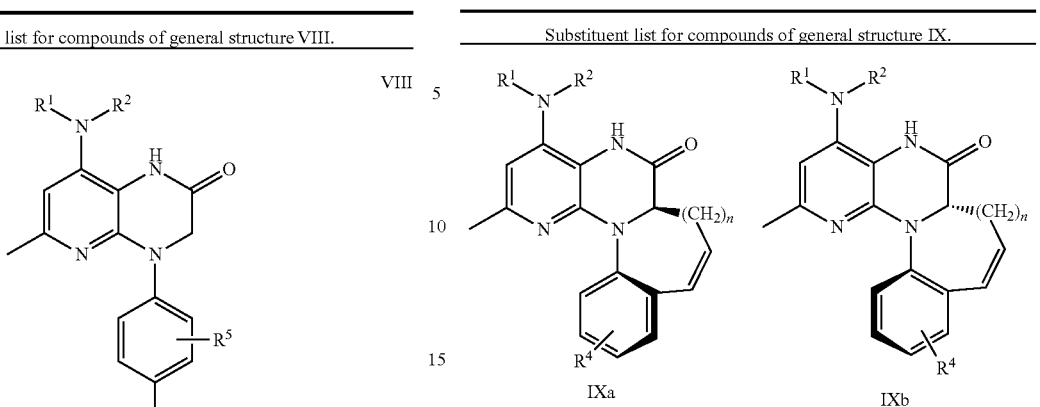

VIII

| Compound # | R¹ = | R² = | R⁵ = | X² = |
|---|---|---|---|---|
| 3865 | FCH₂—CH=CH—CH₂ | Et—F | 2-Br | SnMe₃ |
| 3866 | FCH₂—CH=CH—CH₂ | Et—F | 2-Br | Br |
| 3867 | FCH₂—CH=CH—CH₂ | Et—F | 2-Br | I |
| 3868 | FCH₂—CH=CH—CH₂ | Et—F | 2-Me | H |
| 3869 | FCH₂—CH=CH—CH₂ | Et—F | 2-Me | SnMe₃ |
| 3870 | FCH₂—CH=CH—CH₂ | Et—F | 2-Me | Br |
| 3871 | FCH₂—CH=CH—CH₂ | Et—F | 2-Me | I |
| 3872 | FCH₂—CH=CH—CH₂ | Et—F | 2-Et | H |
| 3873 | FCH₂—CH=CH—CH₂ | Et—F | 2-Et | SnMe₃ |
| 3874 | FCH₂—CH=CH—CH₂ | Et—F | 2-Et | Br |
| 3875 | FCH₂—CH=CH—CH₂ | Et—F | 2-Et | I |
| 3876 | FCH₂—CH=CH—CH₂ | Et—F | 2-Me, 6-Me | H |
| 3877 | FCH₂—CH=CH—CH₂ | Et—F | 2-Me, 6-Me | SnMe₃ |
| 3878 | FCH₂—CH=CH—CH₂ | Et—F | 2-Me, 6-Me | Br |
| 3879 | FCH₂—CH=CH—CH₂ | Et—F | 2-Me, 6-Me | I |
| 3880 | FCH₂—CH=CH—CH₂ | Et—F | 2-OH | H |
| 3881 | FCH₂—CH=CH—CH₂ | Et—F | 2-OH | SnMe₃ |
| 3882 | FCH₂—CH=CH—CH₂ | Et—F | 2-OH | Br |
| 3883 | FCH₂—CH=CH—CH₂ | Et—F | 2-OH | I |
| 3884 | FCH₂—CH=CH—CH₂ | Et—F | 2-OMe | H |
| 3885 | FCH₂—CH=CH—CH₂ | Et—F | 2-OMe | SnMe₃ |
| 3886 | FCH₂—CH=CH—CH₂ | Et—F | 2-OMe | Br |
| 3887 | FCH₂—CH=CH—CH₂ | Et—F | 2-OMe | I |
| 3888 | FCH₂—CH=CH—CH₂ | Et—F | 2-OMeF | H |
| 3889 | FCH₂—CH=CH—CH₂ | Et—F | 2-OMeF | SnMe₃ |
| 3890 | FCH₂—CH=CH—CH₂ | Et—F | 2-OMeF | Br |
| 3891 | FCH₂—CH=CH—CH₂ | Et—F | 2-OMeF | I |
| 3892 | FCH₂—CH=CH—CH₂ | Et—F | 2-OCF₃ | H |
| 3893 | FCH₂—CH=CH—CH₂ | Et—F | 2-OCF₃ | SnMe₃ |
| 3894 | FCH₂—CH=CH—CH₂ | Et—F | 2-OCF₃ | Br |
| 3895 | FCH₂—CH=CH—CH₂ | Et—F | 2-OCF₃ | I |
| 3896 | FCH₂—CH=CH—CH₂ | Et—F | 2-OEtF | H |
| 3897 | FCH₂—CH=CH—CH₂ | Et—F | 2-OEtF | SnMe₃ |
| 3898 | FCH₂—CH=CH—CH₂ | Et—F | 2-OEtF | Br |
| 3899 | FCH₂—CH=CH—CH₂ | Et—F | 2-OEtF | I |
| 3900 | FCH₂—CH=CH—CH₂ | Et—F | 2-OPrF | H |
| 3901 | FCH₂—CH=CH—CH₂ | Et—F | 2-OPrF | SnMe₃ |
| 3902 | FCH₂—CH=CH—CH₂ | Et—F | 2-OPrF | Br |
| 3903 | FCH₂—CH=CH—CH₂ | Et—F | 2-OPrF | I |
| 3904 | FCH₂—CH=CH—CH₂ | Et—F | 2-CF₃ | H |
| 3905 | FCH₂—CH=CH—CH₂ | Et—F | 2-CF₃ | SnMe₃ |
| 3906 | FCH₂—CH=CH—CH₂ | Et—F | 2-CF₃ | Br |
| 3907 | FCH₂—CH=CH—CH₂ | Et—F | 2-CF₃ | I |
| 3908 | FCH₂—CH=CH—CH₂ | Et—F | 2-Br, 6-CF₃ | H |
| 3909 | FCH₂—CH=CH—CH₂ | Et—F | 2-Br, 6-CF₃ | SnMe₃ |
| 3910 | FCH₂—CH=CH—CH₂ | Et—F | 2-Br, 6-CF₃ | Br |
| 3911 | FCH₂—CH=CH—CH₂ | Et—F | 2-Br, 6-CF₃ | I |
| 3912 | FCH₂—CH=CH—CH₂ | Et—F | 2-Br, 6-Br | H |
| 3913 | FCH₂—CH=CH—CH₂ | Et—F | 2-Br, 6-Br | SnMe₃ |
| 3914 | FCH₂—CH=CH—CH₂ | Et—F | 2-Br, 6-Br | Br |
| 3915 | FCH₂—CH=CH—CH₂ | Et—F | 2-Br, 6-Br | I |

TABLE 4

Substituent list for compounds of general structure IX.

| Compound # | R¹ = | R² = | R⁴ = | n = |
|---|---|---|---|---|
| 3916 | Bu | Et | H | 1 |
| 3917 | Bu | Et | H | 2 |
| 3918 | Bu | Et | H | 3 |
| 3919 | Bu | Et | 4-F | 1 |
| 3920 | Bu | Et | 4-F | 2 |
| 3921 | Bu | Et | 4-F | 3 |
| 3922 | Bu | Et | 5-F | 1 |
| 3923 | Bu | Et | 5-F | 2 |
| 3924 | Bu | Et | 5-F | 3 |
| 3925 | Bu | Et | 4-Cl | 1 |
| 3926 | Bu | Et | 4-Cl | 2 |
| 3927 | Bu | Et | 4-Cl | 3 |
| 3928 | Bu | Et | 4-Br | 1 |
| 3929 | Bu | Et | 4-Br | 2 |
| 3930 | Bu | Et | 4-Br | 3 |
| 3931 | Bu | Et | 4-Me | 1 |
| 3932 | Bu | Et | 4-Me | 2 |
| 3933 | Bu | Et | 4-Me | 3 |
| 3934 | Bu | Et | 4-CF₃ | 1 |
| 3935 | Bu | Et | 4-CF₃ | 2 |
| 3936 | Bu | Et | 4-CF₃ | 3 |
| 3937 | Bu | Et | 4-OH | 1 |
| 3938 | Bu | Et | 4-OH | 2 |
| 3939 | Bu | Et | 4-OH | 3 |
| 3940 | Bu | Et | 4-OMe | 1 |
| 3941 | Bu | Et | 4-OMe | 2 |
| 3942 | Bu | Et | 4-OMe | 3 |
| 3943 | Bu | Et | 4-OMeF | 1 |
| 3944 | Bu | Et | 4-OMeF | 2 |
| 3945 | Bu | Et | 4-OMeF | 3 |
| 3946 | Bu | Et | 4-OCF₃ | 1 |
| 3947 | Bu | Et | 4-OCF₃ | 2 |
| 3948 | Bu | Et | 4-OCF₃ | 3 |
| 3949 | Bu | Et | 4-OEtF | 1 |
| 3950 | Bu | Et | 4-OEtF | 2 |
| 3951 | Bu | Et | 4-OEtF | 3 |
| 3952 | Bu | Et | 4-OPrF | 1 |
| 3953 | Bu | Et | 4-OPrF | 2 |
| 3954 | Bu | Et | 4-OPrF | 3 |
| 3955 | Bu | Et | 4-i-Pr | 1 |
| 3956 | Bu | Et | 4-i-Pr | 2 |
| 3957 | Bu | Et | 4-i-Pr | 3 |
| 3958 | Bu | Et | 2-Br, 4-CF₃ | 1 |
| 3959 | Bu | Et | 2-Br, 4-CF₃ | 2 |
| 3960 | Bu | Et | 2-Br, 4-CF₃ | 3 |
| 3961 | Bu | Et | 2-CF₃, 4-Br | 1 |
| 3962 | Bu | Et | 2-CF₃, 4-Br | 2 |
| 3963 | Bu | Et | 2-CF₃, 4-Br | 3 |
| 3964 | Bu | Et | 2-Br, 4-Br | 1 |
| 3965 | Bu | Et | 2-Br, 4-Br | 2 |
| 3966 | Bu | Et | 2-Br, 4-Br | 3 |
| 3967 | Bu | Et | 2-Br, 4-Me | 1 |
| 3968 | Bu | Et | 2-Br, 4-Me | 2 |
| 3969 | Bu | Et | 2-Br, 4-Me | 3 |
| 3970 | Pr | Pr | H | 1 |
| 3971 | Pr | Pr | H | 2 |
| 3972 | Pr | Pr | H | 3 |
| 3973 | Pr | Pr | 4-F | 1 |

TABLE 4-continued

Substituent list for compounds of general structure IX.

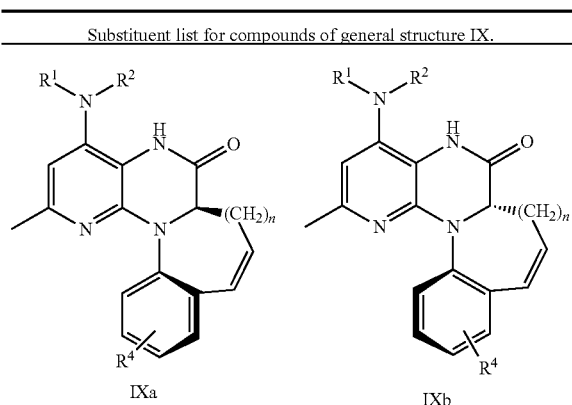

IXa IXb

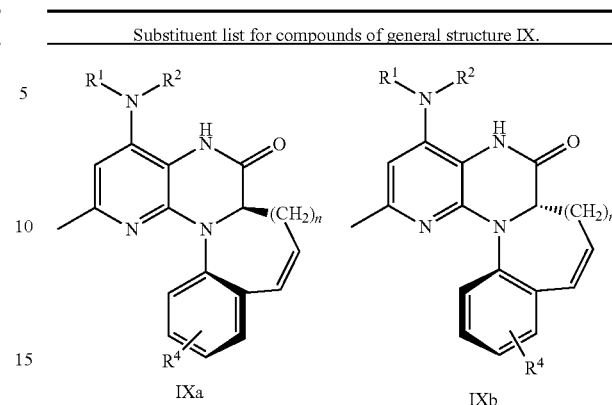

IXa IXb

| Compound # | R¹ = | R² = | R⁴ = | n = |
|---|---|---|---|---|
| 3974 | Pr | Pr | 4-F | 2 |
| 3975 | Pr | Pr | 4-F | 3 |
| 3976 | Pr | Pr | 5-F | 1 |
| 3977 | Pr | Pr | 5-F | 2 |
| 3978 | Pr | Pr | 5-F | 3 |
| 3979 | Pr | Pr | 4-Cl | 1 |
| 3980 | Pr | Pr | 4-Cl | 2 |
| 3981 | Pr | Pr | 4-Cl | 3 |
| 3982 | Pr | Pr | 4-Br | 1 |
| 3983 | Pr | Pr | 4-Br | 2 |
| 3984 | Pr | Pr | 4-Br | 3 |
| 3985 | Pr | Pr | 4-Me | 1 |
| 3986 | Pr | Pr | 4-Me | 2 |
| 3987 | Pr | Pr | 4-Me | 3 |
| 3988 | Pr | Pr | 4-CF₃ | 1 |
| 3989 | Pr | Pr | 4-CF₃ | 2 |
| 3990 | Pr | Pr | 4-CF₃ | 3 |
| 3991 | Pr | Pr | 4-OH | 1 |
| 3992 | Pr | Pr | 4-OH | 2 |
| 3993 | Pr | Pr | 4-OH | 3 |
| 3994 | Pr | Pr | 4-OMe | 1 |
| 3995 | Pr | Pr | 4-OMe | 2 |
| 3996 | Pr | Pr | 4-OMe | 3 |
| 3997 | Pr | Pr | 4-OMeF | 1 |
| 3998 | Pr | Pr | 4-OMeF | 2 |
| 3999 | Pr | Pr | 4-OMeF | 3 |
| 4000 | Pr | Pr | 4-OCF₃ | 1 |
| 4001 | Pr | Pr | 4-OCF₃ | 2 |
| 4002 | Pr | Pr | 4-OCF₃ | 3 |
| 4003 | Pr | Pr | 4-OEtF | 1 |
| 4004 | Pr | Pr | 4-OEtF | 2 |
| 4005 | Pr | Pr | 4-OEtF | 3 |
| 4006 | Pr | Pr | 4-OPrF | 1 |
| 4007 | Pr | Pr | 4-OPrF | 2 |
| 4008 | Pr | Pr | 4-OPrF | 3 |
| 4009 | Pr | Pr | 4-i-Pr | 1 |
| 4010 | Pr | Pr | 4-i-Pr | 2 |
| 4011 | Pr | Pr | 4-i-Pr | 3 |
| 4012 | Pr | Pr | 2-Br, 4-CF₃ | 1 |
| 4013 | Pr | Pr | 2-Br, 4-CF₃ | 2 |
| 4014 | Pr | Pr | 2-Br, 4-CF₃ | 3 |
| 4015 | Pr | Pr | 2-CF₃, 4-Br | 1 |
| 4016 | Pr | Pr | 2-CF₃, 4-Br | 2 |
| 4017 | Pr | Pr | 2-CF₃, 4-Br | 3 |
| 4018 | Pr | Pr | 2-Br, 4-Br | 1 |
| 4019 | Pr | Pr | 2-Br, 4-Br | 2 |
| 4020 | Pr | Pr | 2-Br, 4-Br | 3 |
| 4021 | Pr | Pr | 2-Br, 4-Me | 1 |
| 4022 | Pr | Pr | 2-Br, 4-Me | 2 |
| 4023 | Pr | Pr | 2-Br, 4-Me | 3 |
| 4024 | Pr | Pr—F | H | 1 |
| 4025 | Pr | Pr—F | H | 2 |
| 4026 | Pr | Pr—F | H | 3 |
| 4027 | Pr | Pr—F | 4-F | 1 |
| 4028 | Pr | Pr—F | 4-F | 2 |
| 4029 | Pr | Pr—F | 4-F | 3 |
| 4030 | Pr | Pr—F | 5-F | 1 |
| 4031 | Pr | Pr—F | 5-F | 2 |
| 4032 | Pr | Pr—F | 5-F | 3 |
| 4033 | Pr | Pr—F | 4-Cl | 1 |
| 4034 | Pr | Pr—F | 4-Cl | 2 |
| 4035 | Pr | Pr—F | 4-Cl | 3 |
| 4036 | Pr | Pr—F | 4-Br | 1 |
| 4037 | Pr | Pr—F | 4-Br | 2 |
| 4038 | Pr | Pr—F | 4-Br | 3 |
| 4039 | Pr | Pr—F | 4-Me | 1 |
| 4040 | Pr | Pr—F | 4-Me | 2 |
| 4041 | Pr | Pr—F | 4-Me | 3 |
| 4042 | Pr | Pr—F | 4-CF₃ | 1 |
| 4043 | Pr | Pr—F | 4-CF₃ | 2 |
| 4044 | Pr | Pr—F | 4-CF₃ | 3 |
| 4045 | Pr | Pr—F | 4-OH | 1 |
| 4046 | Pr | Pr—F | 4-OH | 2 |
| 4047 | Pr | Pr—F | 4-OH | 3 |
| 4048 | Pr | Pr—F | 4-OMe | 1 |
| 4049 | Pr | Pr—F | 4-OMe | 2 |
| 4050 | Pr | Pr—F | 4-OMe | 3 |
| 4051 | Pr | Pr—F | 4-OMeF | 1 |
| 4052 | Pr | Pr—F | 4-OMeF | 2 |
| 4053 | Pr | Pr—F | 4-OMeF | 3 |
| 4054 | Pr | Pr—F | 4-OCF₃ | 1 |
| 4055 | Pr | Pr—F | 4-OCF₃ | 2 |
| 4056 | Pr | Pr—F | 4-OCF₃ | 3 |
| 4057 | Pr | Pr—F | 4-OEtF | 1 |
| 4058 | Pr | Pr—F | 4-OEtF | 2 |
| 4059 | Pr | Pr—F | 4-OEtF | 3 |
| 4060 | Pr | Pr—F | 4-OPrF | 1 |
| 4061 | Pr | Pr—F | 4-OPrF | 2 |
| 4062 | Pr | Pr—F | 4-OPrF | 3 |
| 4063 | Pr | Pr—F | 4-i-Pr | 1 |
| 4064 | Pr | Pr—F | 4-i-Pr | 2 |
| 4065 | Pr | Pr—F | 4-i-Pr | 3 |
| 4066 | Pr | Pr—F | 2-Br, 4-CF₃ | 1 |
| 4067 | Pr | Pr—F | 2-Br, 4-CF₃ | 2 |
| 4068 | Pr | Pr—F | 2-Br, 4-CF₃ | 3 |
| 4069 | Pr | Pr—F | 2-CF₃, 4-Br | 1 |
| 4070 | Pr | Pr—F | 2-CF₃, 4-Br | 2 |
| 4071 | Pr | Pr—F | 2-CF₃, 4-Br | 3 |
| 4072 | Pr | Pr—F | 2-Br, 4-Br | 1 |
| 4073 | Pr | Pr—F | 2-Br, 4-Br | 2 |
| 4074 | Pr | Pr—F | 2-Br, 4-Br | 3 |
| 4075 | Pr | Pr—F | 2-Br, 4-Me | 1 |
| 4076 | Pr | Pr—F | 2-Br, 4-Me | 2 |
| 4077 | Pr | Pr—F | 2-Br, 4-Me | 3 |
| 4078 | Pr | Et—F | H | 1 |
| 4079 | Pr | Et—F | H | 2 |
| 4080 | Pr | Et—F | H | 3 |
| 4081 | Pr | Et—F | 4-F | 1 |
| 4082 | Pr | Et—F | 4-F | 2 |
| 4083 | Pr | Et—F | 4-F | 3 |
| 4084 | Pr | Et—F | 5-F | 1 |
| 4085 | Pr | Et—F | 5-F | 2 |
| 4086 | Pr | Et—F | 5-F | 3 |
| 4087 | Pr | Et—F | 4-Cl | 1 |
| 4088 | Pr | Et—F | 4-Cl | 2 |
| 4089 | Pr | Et—F | 4-Cl | 3 |

TABLE 4-continued

Substituent list for compounds of general structure IX.

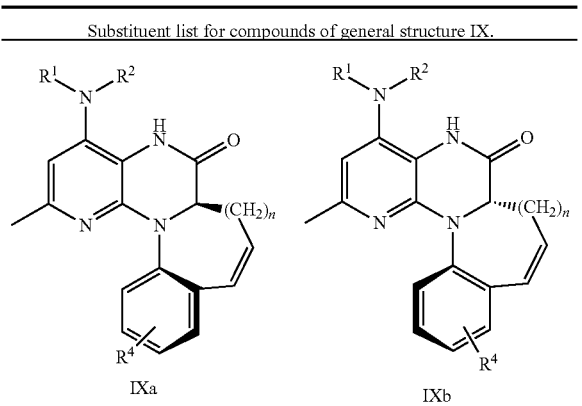

IXa    IXb

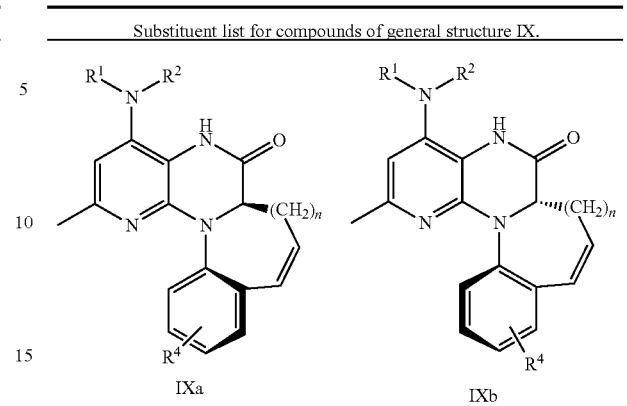

IXa    IXb

| Compound # | R¹ = | R² = | R⁴ = | n = |
|---|---|---|---|---|
| 4090 | Pr | Et—F | 4-Br | 1 |
| 4091 | Pr | Et—F | 4-Br | 2 |
| 4092 | Pr | Et—F | 4-Br | 3 |
| 4093 | Pr | Et—F | 4-Me | 1 |
| 4094 | Pr | Et—F | 4-Me | 2 |
| 4095 | Pr | Et—F | 4-Me | 3 |
| 4096 | Pr | Et—F | 4-CF₃ | 1 |
| 4097 | Pr | Et—F | 4-CF₃ | 2 |
| 4098 | Pr | Et—F | 4-CF₃ | 3 |
| 4099 | Pr | Et—F | 4-OH | 1 |
| 4100 | Pr | Et—F | 4-OH | 2 |
| 4101 | Pr | Et—F | 4-OH | 3 |
| 4102 | Pr | Et—F | 4-OMe | 1 |
| 4103 | Pr | Et—F | 4-OMe | 2 |
| 4104 | Pr | Et—F | 4-OMe | 3 |
| 4105 | Pr | Et—F | 4-OMeF | 1 |
| 4106 | Pr | Et—F | 4-OMeF | 2 |
| 4107 | Pr | Et—F | 4-OMeF | 3 |
| 4108 | Pr | Et—F | 4-OCF₃ | 1 |
| 4109 | Pr | Et—F | 4-OCF₃ | 2 |
| 4110 | Pr | Et—F | 4-OCF₃ | 3 |
| 4111 | Pr | Et—F | 4-OEtF | 1 |
| 4112 | Pr | Et—F | 4-OEtF | 2 |
| 4113 | Pr | Et—F | 4-OEtF | 3 |
| 4114 | Pr | Et—F | 4-OPrF | 1 |
| 4115 | Pr | Et—F | 4-OPrF | 2 |
| 4116 | Pr | Et—F | 4-OPrF | 3 |
| 4117 | Pr | Et—F | 4-i-Pr | 1 |
| 4118 | Pr | Et—F | 4-i-Pr | 2 |
| 4119 | Pr | Et—F | 4-i-Pr | 3 |
| 4120 | Pr | Et—F | 2-Br, 4-CF₃ | 1 |
| 4121 | Pr | Et—F | 2-Br, 4-CF₃ | 2 |
| 4122 | Pr | Et—F | 2-Br, 4-CF₃ | 3 |
| 4123 | Pr | Et—F | 2-CF₃, 4-Br | 1 |
| 4124 | Pr | Et—F | 2-CF₃, 4-Br | 2 |
| 4125 | Pr | Et—F | 2-CF₃, 4-Br | 3 |
| 4126 | Pr | Et—F | 2-Br, 4-Br | 1 |
| 4127 | Pr | Et—F | 2-Br, 4-Br | 2 |
| 4128 | Pr | Et—F | 2-Br, 4-Br | 3 |
| 4129 | Pr | Et—F | 2-Br, 4-Me | 1 |
| 4130 | Pr | Et—F | 2-Br, 4-Me | 2 |
| 4131 | Pr | Et—F | 2-Br, 4-Me | 3 |
| 4132 | Pr—F | Et | H | 1 |
| 4133 | Pr—F | Et | H | 2 |
| 4134 | Pr—F | Et | H | 3 |
| 4135 | Pr—F | Et | 4-F | 1 |
| 4136 | Pr—F | Et | 4-F | 2 |
| 4137 | Pr—F | Et | 4-F | 3 |
| 4138 | Pr—F | Et | 5-F | 1 |
| 4139 | Pr—F | Et | 5-F | 2 |
| 4140 | Pr—F | Et | 5-F | 3 |
| 4141 | Pr—F | Et | 4-Cl | 1 |
| 4142 | Pr—F | Et | 4-Cl | 2 |
| 4143 | Pr—F | Et | 4-Cl | 3 |
| 4144 | Pr—F | Et | 4-Br | 1 |
| 4145 | Pr—F | Et | 4-Br | 2 |
| 4146 | Pr—F | Et | 4-Br | 3 |
| 4147 | Pr—F | Et | 4-Me | 1 |
| 4148 | Pr—F | Et | 4-Me | 2 |
| 4149 | Pr—F | Et | 4-Me | 3 |
| 4150 | Pr—F | Et | 4-CF₃ | 1 |
| 4151 | Pr—F | Et | 4-CF₃ | 2 |
| 4152 | Pr—F | Et | 4-CF₃ | 3 |
| 4153 | Pr—F | Et | 4-OH | 1 |
| 4154 | Pr—F | Et | 4-OH | 2 |
| 4155 | Pr—F | Et | 4-OH | 3 |
| 4156 | Pr—F | Et | 4-OMe | 1 |
| 4157 | Pr—F | Et | 4-OMe | 2 |
| 4158 | Pr—F | Et | 4-OMe | 3 |
| 4159 | Pr—F | Et | 4-OMeF | 1 |
| 4160 | Pr—F | Et | 4-OMeF | 2 |
| 4161 | Pr—F | Et | 4-OMeF | 3 |
| 4162 | Pr—F | Et | 4-OCF₃ | 1 |
| 4163 | Pr—F | Et | 4-OCF₃ | 2 |
| 4164 | Pr—F | Et | 4-OCF₃ | 3 |
| 4165 | Pr—F | Et | 4-OEtF | 1 |
| 4166 | Pr—F | Et | 4-OEtF | 2 |
| 4167 | Pr—F | Et | 4-OEtF | 3 |
| 4168 | Pr—F | Et | 4-OPrF | 1 |
| 4169 | Pr—F | Et | 4-OPrF | 2 |
| 4170 | Pr—F | Et | 4-OPrF | 3 |
| 4171 | Pr—F | Et | 4-i-Pr | 1 |
| 4172 | Pr—F | Et | 4-i-Pr | 2 |
| 4173 | Pr—F | Et | 4-i-Pr | 3 |
| 4174 | Pr—F | Et | 2-Br, 4-CF₃ | 1 |
| 4175 | Pr—F | Et | 2-Br, 4-CF₃ | 2 |
| 4176 | Pr—F | Et | 2-Br, 4-CF₃ | 3 |
| 4177 | Pr—F | Et | 2-CF₃, 4-Br | 1 |
| 4178 | Pr—F | Et | 2-CF₃, 4-Br | 2 |
| 4179 | Pr—F | Et | 2-CF₃, 4-Br | 3 |
| 4180 | Pr—F | Et | 2-Br, 4-Br | 1 |
| 4181 | Pr—F | Et | 2-Br, 4-Br | 2 |
| 4182 | Pr—F | Et | 2-Br, 4-Br | 3 |
| 4183 | Pr—F | Et | 2-Br, 4-Me | 1 |
| 4184 | Pr—F | Et | 2-Br, 4-Me | 2 |
| 4185 | Pr—F | Et | 2-Br, 4-Me | 3 |
| 4186 | Bu | Et—F | H | 1 |
| 4187 | Bu | Et—F | H | 2 |
| 4188 | Bu | Et—F | H | 3 |
| 4189 | Bu | Et—F | 4-F | 1 |
| 4190 | Bu | Et—F | 4-F | 2 |
| 4191 | Bu | Et—F | 4-F | 3 |
| 4192 | Bu | Et—F | 5-F | 1 |
| 4193 | Bu | Et—F | 5-F | 2 |
| 4194 | Bu | Et—F | 5-F | 3 |
| 4195 | Bu | Et—F | 4-Cl | 1 |
| 4196 | Bu | Et—F | 4-Cl | 2 |
| 4197 | Bu | Et—F | 4-Cl | 3 |
| 4198 | Bu | Et—F | 4-Br | 1 |
| 4199 | Bu | Et—F | 4-Br | 2 |
| 4200 | Bu | Et—F | 4-Br | 3 |
| 4201 | Bu | Et—F | 4-Me | 1 |
| 4202 | Bu | Et—F | 4-Me | 2 |
| 4203 | Bu | Et—F | 4-Me | 3 |
| 4204 | Bu | Et—F | 4-CF₃ | 1 |
| 4205 | Bu | Et—F | 4-CF₃ | 2 |

TABLE 4-continued

Substituent list for compounds of general structure IX.

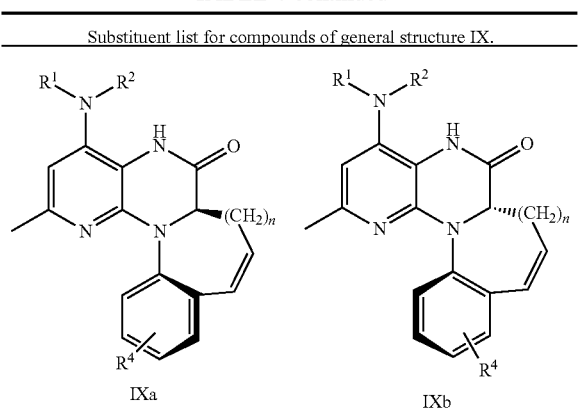

IXa  IXb

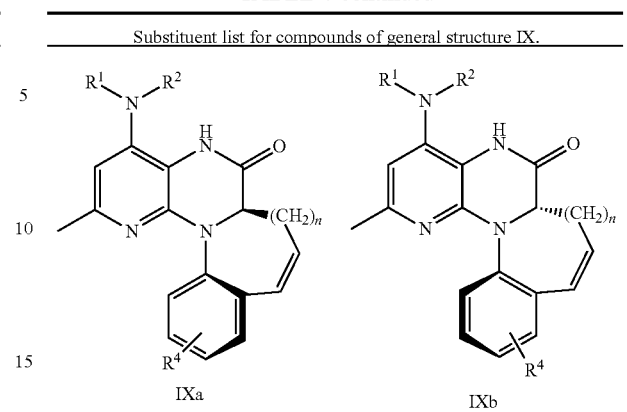

IXa  IXb

| Compound # | R¹ = | R² = | R⁴ = | n = |
|---|---|---|---|---|
| 4206 | Bu | Et—F | 4-CF₃ | 3 |
| 4207 | Bu | Et—F | 4-OH | 1 |
| 4208 | Bu | Et—F | 4-OH | 2 |
| 4209 | Bu | Et—F | 4-OH | 3 |
| 4210 | Bu | Et—F | 4-OMe | 1 |
| 4211 | Bu | Et—F | 4-OMe | 2 |
| 4212 | Bu | Et—F | 4-OMe | 3 |
| 4213 | Bu | Et—F | 4-OMeF | 1 |
| 4214 | Bu | Et—F | 4-OMeF | 2 |
| 4215 | Bu | Et—F | 4-OMeF | 3 |
| 4216 | Bu | Et—F | 4-OCF₃ | 1 |
| 4217 | Bu | Et—F | 4-OCF₃ | 2 |
| 4218 | Bu | Et—F | 4-OCF₃ | 3 |
| 4219 | Bu | Et—F | 4-OEtF | 1 |
| 4220 | Bu | Et—F | 4-OEtF | 2 |
| 4221 | Bu | Et—F | 4-OEtF | 3 |
| 4222 | Bu | Et—F | 4-OPrF | 1 |
| 4223 | Bu | Et—F | 4-OPrF | 2 |
| 4224 | Bu | Et—F | 4-OPrF | 3 |
| 4225 | Bu | Et—F | 4-i-Pr | 1 |
| 4226 | Bu | Et—F | 4-i-Pr | 2 |
| 4227 | Bu | Et—F | 4-i-Pr | 3 |
| 4228 | Bu | Et—F | 2-Br, 4-CF₃ | 1 |
| 4229 | Bu | Et—F | 2-Br, 4-CF₃ | 2 |
| 4230 | Bu | Et—F | 2-Br, 4-CF₃ | 3 |
| 4231 | Bu | Et—F | 2-CF₃, 4-Br | 1 |
| 4232 | Bu | Et—F | 2-CF₃, 4-Br | 2 |
| 4233 | Bu | Et—F | 2-CF₃, 4-Br | 3 |
| 4234 | Bu | Et—F | 2-Br, 4-Br | 1 |
| 4235 | Bu | Et—F | 2-Br, 4-Br | 2 |
| 4236 | Bu | Et—F | 2-Br, 4-Br | 3 |
| 4237 | Bu | Et—F | 2-Br, 4-Me | 1 |
| 4238 | Bu | Et—F | 2-Br, 4-Me | 2 |
| 4239 | Bu | Et—F | 2-Br, 4-Me | 3 |
| 4240 | Bu—F | Et | H | 1 |
| 4241 | Bu—F | Et | H | 2 |
| 4242 | Bu—F | Et | H | 3 |
| 4243 | Bu—F | Et | 4-F | 1 |
| 4244 | Bu—F | Et | 4-F | 2 |
| 4245 | Bu—F | Et | 4-F | 3 |
| 4246 | Bu—F | Et | 5-F | 1 |
| 4247 | Bu—F | Et | 5-F | 2 |
| 4248 | Bu—F | Et | 5-F | 3 |
| 4249 | Bu—F | Et | 4-Cl | 1 |
| 4250 | Bu—F | Et | 4-Cl | 2 |
| 4251 | Bu—F | Et | 4-Cl | 3 |
| 4252 | Bu—F | Et | 4-Br | 1 |
| 4253 | Bu—F | Et | 4-Br | 2 |
| 4254 | Bu—F | Et | 4-Br | 3 |
| 4255 | Bu—F | Et | 4-Me | 1 |
| 4256 | Bu—F | Et | 4-Me | 2 |
| 4257 | Bu—F | Et | 4-Me | 3 |
| 4258 | Bu—F | Et | 4-CF₃ | 1 |
| 4259 | Bu—F | Et | 4-CF₃ | 2 |
| 4260 | Bu—F | Et | 4-CF₃ | 3 |
| 4261 | Bu—F | Et | 4-OH | 1 |
| 4262 | Bu—F | Et | 4-OH | 2 |
| 4263 | Bu—F | Et | 4-OH | 3 |
| 4264 | Bu—F | Et | 4-OMe | 1 |
| 4265 | Bu—F | Et | 4-OMe | 2 |
| 4266 | Bu—F | Et | 4-OMe | 3 |
| 4267 | Bu—F | Et | 4-OMeF | 1 |
| 4268 | Bu—F | Et | 4-OMeF | 2 |
| 4269 | Bu—F | Et | 4-OMeF | 3 |
| 4270 | Bu—F | Et | 4-OCF₃ | 1 |
| 4271 | Bu—F | Et | 4-OCF₃ | 2 |
| 4272 | Bu—F | Et | 4-OCF₃ | 3 |
| 4273 | Bu—F | Et | 4-OEtF | 1 |
| 4274 | Bu—F | Et | 4-OEtF | 2 |
| 4275 | Bu—F | Et | 4-OEtF | 3 |
| 4276 | Bu—F | Et | 4-OPrF | 1 |
| 4277 | Bu—F | Et | 4-OPrF | 2 |
| 4278 | Bu—F | Et | 4-OPrF | 3 |
| 4279 | Bu—F | Et | 4-i-Pr | 1 |
| 4280 | Bu—F | Et | 4-i-Pr | 2 |
| 4281 | Bu—F | Et | 4-i-Pr | 3 |
| 4282 | Bu—F | Et | 2-Br, 4-CF₃ | 1 |
| 4283 | Bu—F | Et | 2-Br, 4-CF₃ | 2 |
| 4284 | Bu—F | Et | 2-Br, 4-CF₃ | 3 |
| 4285 | Bu—F | Et | 2-CF₃, 4-Br | 1 |
| 4286 | Bu—F | Et | 2-CF₃, 4-Br | 2 |
| 4287 | Bu—F | Et | 2-CF₃, 4-Br | 3 |
| 4288 | Bu—F | Et | 2-Br, 4-Br | 1 |
| 4289 | Bu—F | Et | 2-Br, 4-Br | 2 |
| 4290 | Bu—F | Et | 2-Br, 4-Br | 3 |
| 4291 | Bu—F | Et | 2-Br, 4-Me | 1 |
| 4292 | Bu—F | Et | 2-Br, 4-Me | 2 |
| 4293 | Bu—F | Et | 2-Br, 4-Me | 3 |
| 4294 | FCH₂—CH=CH—CH₂ | Me | H | 1 |
| 4295 | FCH₂—CH=CH—CH₂ | Me | H | 2 |
| 4296 | FCH₂—CH=CH—CH₂ | Me | H | 3 |
| 4297 | FCH₂—CH=CH—CH₂ | Me | 4-F | 1 |
| 4298 | FCH₂—CH=CH—CH₂ | Me | 4-F | 2 |
| 4299 | FCH₂—CH=CH—CH₂ | Me | 4-F | 3 |
| 4300 | FCH₂—CH=CH—CH₂ | Me | 5-F | 1 |
| 4301 | FCH₂—CH=CH—CH₂ | Me | 5-F | 2 |
| 4302 | FCH₂—CH=CH—CH₂ | Me | 5-F | 3 |
| 4303 | FCH₂—CH=CH—CH₂ | Me | 4-Cl | 1 |
| 4304 | FCH₂—CH=CH—CH₂ | Me | 4-Cl | 2 |
| 4305 | FCH₂—CH=CH—CH₂ | Me | 4-Cl | 3 |
| 4306 | FCH₂—CH=CH—CH₂ | Me | 4-Br | 1 |
| 4307 | FCH₂—CH=CH—CH₂ | Me | 4-Br | 2 |
| 4308 | FCH₂—CH=CH—CH₂ | Me | 4-Br | 3 |
| 4309 | FCH₂—CH=CH—CH₂ | Me | 4-Me | 1 |
| 4310 | FCH₂—CH=CH—CH₂ | Me | 4-Me | 2 |
| 4311 | FCH₂—CH=CH—CH₂ | Me | 4-Me | 3 |
| 4312 | FCH₂—CH=CH—CH₂ | Me | 4-CF₃ | 1 |
| 4313 | FCH₂—CH=CH—CH₂ | Me | 4-CF₃ | 2 |
| 4314 | FCH₂—CH=CH—CH₂ | Me | 4-CF₃ | 3 |
| 4315 | FCH₂—CH=CH—CH₂ | Me | 4-OH | 1 |
| 4316 | FCH₂—CH=CH—CH₂ | Me | 4-OH | 2 |
| 4317 | FCH₂—CH=CH—CH₂ | Me | 4-OH | 3 |
| 4318 | FCH₂—CH=CH—CH₂ | Me | 4-OMe | 1 |
| 4319 | FCH₂—CH=CH—CH₂ | Me | 4-OMe | 2 |
| 4320 | FCH₂—CH=CH—CH₂ | Me | 4-OMe | 3 |
| 4321 | FCH₂—CH=CH—CH₂ | Me | 4-OMeF | 1 |

TABLE 4-continued

Substituent list for compounds of general structure IX.

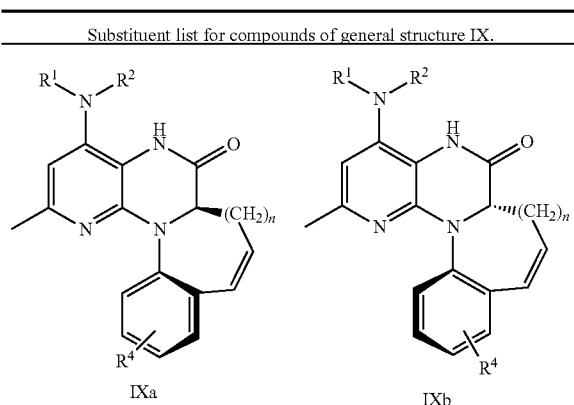

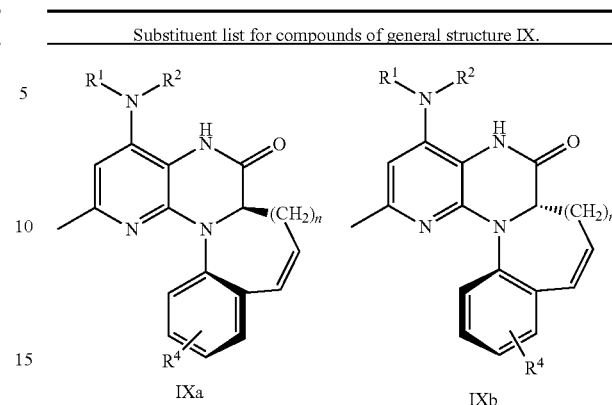

| Compound # | R¹ = | R² = | R⁴ = | n = |
|---|---|---|---|---|
| 4322 | FCH₂—CH=CH—CH₂ | Me | 4-OMeF | 2 |
| 4323 | FCH₂—CH=CH—CH₂ | Me | 4-OMeF | 3 |
| 4324 | FCH₂—CH=CH—CH₂ | Me | 4-OCF₃ | 1 |
| 4325 | FCH₂—CH=CH—CH₂ | Me | 4-OCF₃ | 2 |
| 4326 | FCH₂—CH=CH—CH₂ | Me | 4-OCF₃ | 3 |
| 4327 | FCH₂—CH=CH—CH₂ | Me | 4-OEtF | 1 |
| 4328 | FCH₂—CH=CH—CH₂ | Me | 4-OEtF | 2 |
| 4329 | FCH₂—CH=CH—CH₂ | Me | 4-OEtF | 3 |
| 4330 | FCH₂—CH=CH—CH₂ | Me | 4-OPrF | 1 |
| 4331 | FCH₂—CH=CH—CH₂ | Me | 4-OPrF | 2 |
| 4332 | FCH₂—CH=CH—CH₂ | Me | 4-OPrF | 3 |
| 4333 | FCH₂—CH=CH—CH₂ | Me | 4-i-Pr | 1 |
| 4334 | FCH₂—CH=CH—CH₂ | Me | 4-i-Pr | 2 |
| 4335 | FCH₂—CH=CH—CH₂ | Me | 4-i-Pr | 3 |
| 4336 | FCH₂—CH=CH—CH₂ | Me | 2-Br, 4-CF₃ | 1 |
| 4337 | FCH₂—CH=CH—CH₂ | Me | 2-Br, 4-CF₃ | 2 |
| 4338 | FCH₂—CH=CH—CH₂ | Me | 2-Br, 4-CF₃ | 3 |
| 4339 | FCH₂—CH=CH—CH₂ | Me | 2-CF₃, 4-Br | 1 |
| 4340 | FCH₂—CH=CH—CH₂ | Me | 2-CF₃, 4-Br | 2 |
| 4341 | FCH₂—CH=CH—CH₂ | Me | 2-CF₃, 4-Br | 3 |
| 4342 | FCH₂—CH=CH—CH₂ | Me | 2-Br, 4-Br | 1 |
| 4343 | FCH₂—CH=CH—CH₂ | Me | 2-Br, 4-Br | 2 |
| 4344 | FCH₂—CH=CH—CH₂ | Me | 2-Br, 4-Br | 3 |
| 4345 | FCH₂—CH=CH—CH₂ | Me | 2-Br, 4-Me | 1 |
| 4346 | FCH₂—CH=CH—CH₂ | Me | 2-Br, 4-Me | 2 |
| 4347 | FCH₂—CH=CH—CH₂ | Me | 2-Br, 4-Me | 3 |
| 4348 | FCH₂—CH=CH—CH₂ | Et | H | 1 |
| 4349 | FCH₂—CH=CH—CH₂ | Et | H | 2 |
| 4350 | FCH₂—CH=CH—CH₂ | Et | H | 3 |
| 4351 | FCH₂—CH=CH—CH₂ | Et | 4-F | 1 |
| 4352 | FCH₂—CH=CH—CH₂ | Et | 4-F | 2 |
| 4353 | FCH₂—CH=CH—CH₂ | Et | 4-F | 3 |
| 4354 | FCH₂—CH=CH—CH₂ | Et | 5-F | 1 |
| 4355 | FCH₂—CH=CH—CH₂ | Et | 5-F | 2 |
| 4356 | FCH₂—CH=CH—CH₂ | Et | 5-F | 3 |
| 4357 | FCH₂—CH=CH—CH₂ | Et | 4-Cl | 1 |
| 4358 | FCH₂—CH=CH—CH₂ | Et | 4-Cl | 2 |
| 4359 | FCH₂—CH=CH—CH₂ | Et | 4-Cl | 3 |
| 4360 | FCH₂—CH=CH—CH₂ | Et | 4-Br | 1 |
| 4361 | FCH₂—CH=CH—CH₂ | Et | 4-Br | 2 |
| 4362 | FCH₂—CH=CH—CH₂ | Et | 4-Br | 3 |
| 4363 | FCH₂—CH=CH—CH₂ | Et | 4-Me | 1 |
| 4364 | FCH₂—CH=CH—CH₂ | Et | 4-Me | 2 |
| 4365 | FCH₂—CH=CH—CH₂ | Et | 4-Me | 3 |
| 4366 | FCH₂—CH=CH—CH₂ | Et | 4-CF₃ | 1 |
| 4367 | FCH₂—CH=CH—CH₂ | Et | 4-CF₃ | 2 |
| 4368 | FCH₂—CH=CH—CH₂ | Et | 4-CF₃ | 3 |
| 4369 | FCH₂—CH=CH—CH₂ | Et | 4-OH | 1 |
| 4370 | FCH₂—CH=CH—CH₂ | Et | 4-OH | 2 |
| 4371 | FCH₂—CH=CH—CH₂ | Et | 4-OH | 3 |
| 4372 | FCH₂—CH=CH—CH₂ | Et | 4-OMe | 1 |
| 4373 | FCH₂—CH=CH—CH₂ | Et | 4-OMe | 2 |
| 4374 | FCH₂—CH=CH—CH₂ | Et | 4-OMe | 3 |
| 4375 | FCH₂—CH=CH—CH₂ | Et | 4-OMeF | 1 |
| 4376 | FCH₂—CH=CH—CH₂ | Et | 4-OMeF | 2 |
| 4377 | FCH₂—CH=CH—CH₂ | Et | 4-OMeF | 3 |
| 4378 | FCH₂—CH=CH—CH₂ | Et | 4-OCF₃ | 1 |
| 4379 | FCH₂—CH=CH—CH₂ | Et | 4-OCF₃ | 2 |
| 4380 | FCH₂—CH=CH—CH₂ | Et | 4-OCF₃ | 3 |
| 4381 | FCH₂—CH=CH—CH₂ | Et | 4-OEtF | 1 |
| 4382 | FCH₂—CH=CH—CH₂ | Et | 4-OEtF | 2 |
| 4383 | FCH₂—CH=CH—CH₂ | Et | 4-OEtF | 3 |
| 4384 | FCH₂—CH=CH—CH₂ | Et | 4-OPrF | 1 |
| 4385 | FCH₂—CH=CH—CH₂ | Et | 4-OPrF | 2 |
| 4386 | FCH₂—CH=CH—CH₂ | Et | 4-OPrF | 3 |
| 4387 | FCH₂—CH=CH—CH₂ | Et | 4-i-Pr | 1 |
| 4388 | FCH₂—CH=CH—CH₂ | Et | 4-i-Pr | 2 |
| 4389 | FCH₂—CH=CH—CH₂ | Et | 4-i-Pr | 3 |
| 4390 | FCH₂—CH=CH—CH₂ | Et | 2-Br, 4-CF₃ | 1 |
| 4391 | FCH₂—CH=CH—CH₂ | Et | 2-Br, 4-CF₃ | 2 |
| 4392 | FCH₂—CH=CH—CH₂ | Et | 2-Br, 4-CF₃ | 3 |
| 4393 | FCH₂—CH=CH—CH₂ | Et | 2-CF₃, 4-Br | 1 |
| 4394 | FCH₂—CH=CH—CH₂ | Et | 2-CF₃, 4-Br | 2 |
| 4395 | FCH₂—CH=CH—CH₂ | Et | 2-CF₃, 4-Br | 3 |
| 4396 | FCH₂—CH=CH—CH₂ | Et | 2-Br, 4-Br | 1 |
| 4397 | FCH₂—CH=CH—CH₂ | Et | 2-Br, 4-Br | 2 |
| 4398 | FCH₂—CH=CH—CH₂ | Et | 2-Br, 4-Br | 3 |
| 4399 | FCH₂—CH=CH—CH₂ | Et | 2-Br, 4-Me | 1 |
| 4400 | FCH₂—CH=CH—CH₂ | Et | 2-Br, 4-Me | 2 |
| 4401 | FCH₂—CH=CH—CH₂ | Et | 2-Br, 4-Me | 3 |
| 4402 | FCH₂—CH=CH—CH₂ | Et—F | H | 1 |
| 4403 | FCH₂—CH=CH—CH₂ | Et—F | H | 2 |
| 4404 | FCH₂—CH=CH—CH₂ | Et—F | H | 3 |
| 4405 | FCH₂—CH=CH—CH₂ | Et—F | 4-F | 1 |
| 4406 | FCH₂—CH=CH—CH₂ | Et—F | 4-F | 2 |
| 4407 | FCH₂—CH=CH—CH₂ | Et—F | 4-F | 3 |
| 4408 | FCH₂—CH=CH—CH₂ | Et—F | 5-F | 1 |
| 4409 | FCH₂—CH=CH—CH₂ | Et—F | 5-F | 2 |
| 4410 | FCH₂—CH=CH—CH₂ | Et—F | 5-F | 3 |
| 4411 | FCH₂—CH=CH—CH₂ | Et—F | 4-Cl | 1 |
| 4412 | FCH₂—CH=CH—CH₂ | Et—F | 4-Cl | 2 |
| 4413 | FCH₂—CH=CH—CH₂ | Et—F | 4-Cl | 3 |
| 4414 | FCH₂—CH=CH—CH₂ | Et—F | 4-Br | 1 |
| 4415 | FCH₂—CH=CH—CH₂ | Et—F | 4-Br | 2 |
| 4416 | FCH₂—CH=CH—CH₂ | Et—F | 4-Br | 3 |
| 4417 | FCH₂—CH=CH—CH₂ | Et—F | 4-Me | 1 |
| 4418 | FCH₂—CH=CH—CH₂ | Et—F | 4-Me | 2 |
| 4419 | FCH₂—CH=CH—CH₂ | Et—F | 4-Me | 3 |
| 4420 | FCH₂—CH=CH—CH₂ | Et—F | 4-CF₃ | 1 |
| 4421 | FCH₂—CH=CH—CH₂ | Et—F | 4-CF₃ | 2 |
| 4422 | FCH₂—CH=CH—CH₂ | Et—F | 4-CF₃ | 3 |
| 4423 | FCH₂—CH=CH—CH₂ | Et—F | 4-OH | 1 |
| 4424 | FCH₂—CH=CH—CH₂ | Et—F | 4-OH | 2 |
| 4425 | FCH₂—CH=CH—CH₂ | Et—F | 4-OH | 3 |
| 4426 | FCH₂—CH=CH—CH₂ | Et—F | 4-OMe | 1 |
| 4427 | FCH₂—CH=CH—CH₂ | Et—F | 4-OMe | 2 |
| 4428 | FCH₂—CH=CH—CH₂ | Et—F | 4-OMe | 3 |
| 4429 | FCH₂—CH=CH—CH₂ | Et—F | 4-OMeF | 1 |
| 4430 | FCH₂—CH=CH—CH₂ | Et—F | 4-OMeF | 2 |
| 4431 | FCH₂—CH=CH—CH₂ | Et—F | 4-OMeF | 3 |
| 4432 | FCH₂—CH=CH—CH₂ | Et—F | 4-OCF₃ | 1 |
| 4433 | FCH₂—CH=CH—CH₂ | Et—F | 4-OCF₃ | 2 |
| 4434 | FCH₂—CH=CH—CH₂ | Et—F | 4-OCF₃ | 3 |
| 4435 | FCH₂—CH=CH—CH₂ | Et—F | 4-OEtF | 1 |
| 4436 | FCH₂—CH=CH—CH₂ | Et—F | 4-OEtF | 2 |
| 4437 | FCH₂—CH=CH—CH₂ | Et—F | 4-OEtF | 3 |

TABLE 4-continued

Substituent list for compounds of general structure IX.

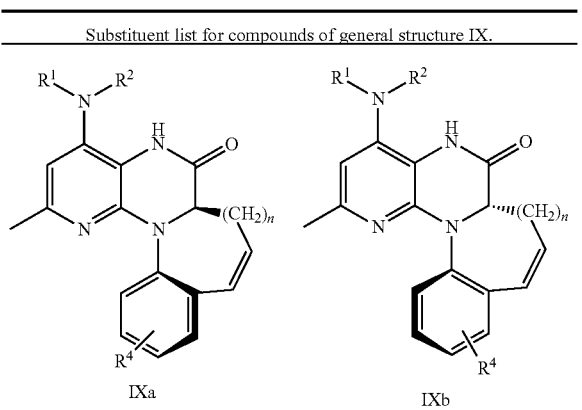

IXa IXb

| Compound # | R¹ = | R² = | R⁴ = | n = |
|---|---|---|---|---|
| 4438 | FCH₂—CH=CH—CH₂ | Et—F | 4-OPrF | 1 |
| 4439 | FCH₂—CH=CH—CH₂ | Et—F | 4-OPrF | 2 |
| 4440 | FCH₂—CH=CH—CH₂ | Et—F | 4-OPrF | 3 |
| 4441 | FCH₂—CH=CH—CH₂ | Et—F | 4-i-Pr | 1 |
| 4442 | FCH₂—CH=CH—CH₂ | Et—F | 4-i-Pr | 2 |
| 4443 | FCH₂—CH=CH—CH₂ | Et—F | 4-i-Pr | 3 |
| 4444 | FCH₂—CH=CH—CH₂ | Et—F | 2-Br, 4-CF₃ | 1 |
| 4445 | FCH₂—CH=CH—CH₂ | Et—F | 2-Br, 4-CF₃ | 2 |
| 4446 | FCH₂—CH=CH—CH₂ | Et—F | 2-Br, 4-CF₃ | 3 |
| 4447 | FCH₂—CH=CH—CH₂ | Et—F | 2-CF₃, 4-Br | 1 |
| 4448 | FCH₂—CH=CH—CH₂ | Et—F | 2-CF₃, 4-Br | 2 |
| 4449 | FCH₂—CH=CH—CH₂ | Et—F | 2-CF₃, 4-Br | 3 |
| 4450 | FCH₂—CH=CH—CH₂ | Et—F | 2-Br, 4-Br | 1 |
| 4451 | FCH₂—CH=CH—CH₂ | Et—F | 2-Br, 4-Br | 2 |
| 4452 | FCH₂—CH=CH—CH₂ | Et—F | 2-Br, 4-Br | 3 |
| 4453 | FCH₂—CH=CH—CH₂ | Et—F | 2-Br, 4-Me | 1 |
| 4454 | FCH₂—CH=CH—CH₂ | Et—F | 2-Br, 4-Me | 2 |
| 4455 | FCH₂—CH=CH—CH₂ | Et—F | 2-Br, 4-Me | 3 |

TABLE 5

Substituent list for compounds of general structure X.

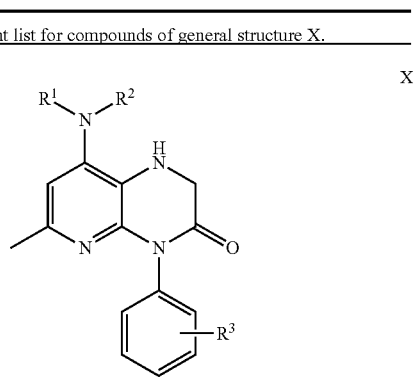

| Compound # | R¹ = | R² = | R³ = |
|---|---|---|---|
| 4456 | Bu | Et | H |
| 4457 | Bu | Et | 2-t-Bu |
| 4458 | Bu | Et | 2-Br |
| 4459 | Bu | Et | 3-Br |
| 4460 | Bu | Et | 4-Br |
| 4461 | Bu | Et | 2-I |
| 4462 | Bu | Et | 3-I |
| 4463 | Bu | Et | 4-I |
| 4464 | Bu | Et | 2-SnMe₃ |
| 4465 | Bu | Et | 3-SnMe₃ |
| 4466 | Bu | Et | 4-SnMe₃ |
| 4467 | Bu | Et | 2-Me |
| 4468 | Bu | Et | 3-Me |
| 4469 | Bu | Et | 4-Me |
| 4470 | Bu | Et | 2-OH |

TABLE 5-continued

Substituent list for compounds of general structure X.

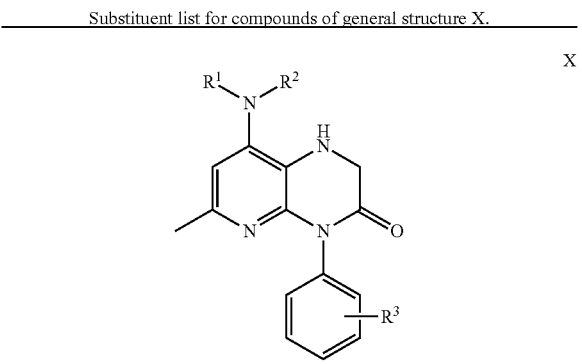

| Compound # | R¹ = | R² = | R³ = |
|---|---|---|---|
| 4471 | Bu | Et | 3-OH |
| 4472 | Bu | Et | 4-OH |
| 4473 | Bu | Et | 2-OMe |
| 4474 | Bu | Et | 3-OMe |
| 4475 | Bu | Et | 4-OMe |
| 4476 | Bu | Et | 2-OMeF |
| 4477 | Bu | Et | 3-OMeF |
| 4478 | Bu | Et | 4-OMeF |
| 4479 | Bu | Et | 2-OCF₃ |
| 4480 | Bu | Et | 3-OCF₃ |
| 4481 | Bu | Et | 4-OCF₃ |
| 4482 | Bu | Et | 2-OEtF |
| 4483 | Bu | Et | 3-OEtF |
| 4484 | Bu | Et | 4-OEtF |
| 4485 | Bu | Et | 2-OPrF |
| 4486 | Bu | Et | 3-OPrF |
| 4487 | Bu | Et | 4-OPrF |
| 4488 | Bu | Et | 2-SH |
| 4489 | Bu | Et | 3-SH |
| 4490 | Bu | Et | 4-SH |
| 4491 | Bu | Et | 2-SMe |
| 4492 | Bu | Et | 3-SMe |
| 4493 | Bu | Et | 4-SMe |
| 4494 | Bu | Et | 2-SMeF |
| 4495 | Bu | Et | 3-SMeF |
| 4496 | Bu | Et | 4-SMeF |
| 4497 | Bu | Et | 2-SCF₃ |
| 4498 | Bu | Et | 3-SCF₃ |
| 4499 | Bu | Et | 4-SCF₃ |
| 4500 | Bu | Et | 2-SEtF |
| 4501 | Bu | Et | 3-SEtF |
| 4502 | Bu | Et | 4-SEtF |
| 4503 | Bu | Et | 2-SPrF |
| 4504 | Bu | Et | 3-SPrF |
| 4505 | Bu | Et | 4-SPrF |
| 4506 | Bu | Et | 2-OMe, 4-OMe |
| 4507 | Bu | Et | 2-Me, 5-OH |
| 4508 | Bu | Et | 2-Me, 5-OMe |
| 4509 | Bu | Et | 2-Me, 5-OMeF |
| 4510 | Bu | Et | 2-Me, 5-OEtF |
| 4511 | Bu | Et | 2-Me, 5-OPrF |
| 4512 | Bu | Et | 2-Me, 4-OH |
| 4513 | Bu | Et | 2-Me, 4-OMe |
| 4514 | Bu | Et | 2-Me, 4-OMeF |
| 4515 | Bu | Et | 2-Me, 4-OCF₃ |
| 4516 | Bu | Et | 2-Me, 4-OEtF |
| 4517 | Bu | Et | 2-Me, 4-OPrF |
| 4518 | Bu | Et | 2-OH, 4-Me |
| 4519 | Bu | Et | 2-OMe, 4-Me |
| 4520 | Bu | Et | 2-OMeF, 4-Me |
| 4521 | Bu | Et | 2-OCF₃, 4-Me |
| 4522 | Bu | Et | 2-OEtF, 4-Me |
| 4523 | Bu | Et | 2-OPrF, 4-Me |
| 4524 | Bu | Et | 2-Cl, 4-OH |
| 4525 | Bu | Et | 2-Cl, 4-OMe |
| 4526 | Bu | Et | 2-Cl, 4-OMeF |
| 4527 | Bu | Et | 2-Cl, 4-OCF₃ |
| 4528 | Bu | Et | 2-Cl, 4-OEtF |
| 4529 | Bu | Et | 2-Cl, 4-OPrF |
| 4530 | Bu | Et | 2-F, 4-F |

TABLE 5-continued

Substituent list for compounds of general structure X.

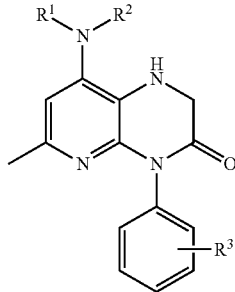

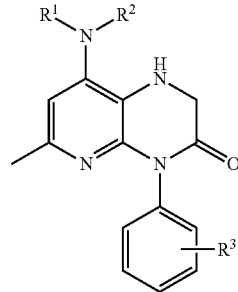

| Compound # | R¹ = | R² = | R³ = |
|---|---|---|---|
| 4531 | Bu | Et | 2-Cl, 4-Cl |
| 4532 | Bu | Et | 2-Cl, 4-F |
| 4533 | Bu | Et | 2-Cl, 4-NO₂ |
| 4534 | Bu | Et | 2-Cl, 4-NH₂ |
| 4535 | Bu | Et | 2-Cl, 4-NHMe |
| 4536 | Bu | Et | 2-Cl, 4-NMe₂ |
| 4537 | Bu | Et | 2-Cl, 4-NMe₃OTf |
| 4538 | Bu | Et | 2-Cl, 4-NMe₃I |
| 4539 | Bu | Et | 2-Cl, 5-F |
| 4540 | Bu | Et | 2-Cl, 5-NO₂ |
| 4541 | Bu | Et | 2-Cl, 5-NH₂ |
| 4542 | Bu | Et | 2-Cl, 5-NHMe |
| 4543 | Bu | Et | 2-Cl, 5-NMe₂ |
| 4544 | Bu | Et | 2-Cl, 5-NMe₃OTf |
| 4545 | Bu | Et | 2-Cl, 5-NMe₃I |
| 4546 | Bu | Et | 2-F, 4-Cl |
| 4547 | Bu | Et | 2-NO₂, 4-Cl |
| 4548 | Bu | Et | 2-NH₂, 4-Cl |
| 4549 | Bu | Et | 2-NHMe, 4-Cl |
| 4550 | Bu | Et | 2-NMe₂, 4-Cl |
| 4551 | Bu | Et | 2-NMe₃OTf, 4-Cl |
| 4552 | Bu | Et | 2-NMe₃I, 4-Cl |
| 4553 | Bu | Et | 2-F, 5-Cl |
| 4554 | Bu | Et | 2-NO₂, 5-Cl |
| 4555 | Bu | Et | 2-NH₂, 5-Cl |
| 4556 | Bu | Et | 2-NHMe, 5-Cl |
| 4557 | Bu | Et | 2-NMe₂, 5-Cl |
| 4558 | Bu | Et | 2-NMe₃OTf, 5-Cl |
| 4559 | Bu | Et | 2-NMe₃I, 5-Cl |
| 4560 | Bu | Et | 2-Br, 4-F |
| 4561 | Bu | Et | 2-Br, 4-NO₂ |
| 4562 | Bu | Et | 2-Br, 4-NH₂ |
| 4563 | Bu | Et | 2-Br, 4-NHMe |
| 4564 | Bu | Et | 2-Br, 4-NMe₂ |
| 4565 | Bu | Et | 2-Br, 4-NMe₃OTf |
| 4566 | Bu | Et | 2-Br, 4-NMe₃I |
| 4567 | Bu | Et | 2-Br, 5-F |
| 4568 | Bu | Et | 2-Br, 5-NO₂ |
| 4569 | Bu | Et | 2-Br, 5-NH₂ |
| 4570 | Bu | Et | 2-Br, 5-NHMe |
| 4571 | Bu | Et | 2-Br, 5-NMe₂ |
| 4572 | Bu | Et | 2-Br, 5-NMe₃OTf |
| 4573 | Bu | Et | 2-Br, 5-NMe₃I |
| 4574 | Bu | Et | 2-F, 4-Br |
| 4575 | Bu | Et | 2-NO₂, 4-Br |
| 4576 | Bu | Et | 2-NH₂, 4-Br |
| 4577 | Bu | Et | 2-NHMe, 4-Br |
| 4578 | Bu | Et | 2-NMe₂, 4-Br |
| 4579 | Bu | Et | 2-NMe₃OTf, 4-Br |
| 4580 | Bu | Et | 2-NMe₃I, 4-Br |
| 4581 | Bu | Et | 2-I, 4-F |
| 4582 | Bu | Et | 2-I, 4-NO₂ |
| 4583 | Bu | Et | 2-I, 4-NH₂ |
| 4584 | Bu | Et | 2-I, 4-NHMe |
| 4585 | Bu | Et | 2-I, 4-NMe₂ |
| 4586 | Bu | Et | 2-I, 4-NMe₃OTf |
| 4587 | Bu | Et | 2-I, 4-NMe₃I |
| 4588 | Bu | Et | 2-F, 4-I |
| 4589 | Bu | Et | 2-NO₂, 4-I |
| 4590 | Bu | Et | 2-NH₂, 4-I |
| 4591 | Bu | Et | 2-NHMe, 4-I |
| 4592 | Bu | Et | 2-NMe₂, 4-I |
| 4593 | Bu | Et | 2-NMe₃OTf, 4-I |
| 4594 | Bu | Et | 2-NMe₃I, 4-I |
| 4595 | Bu | Et | 2-Me, 3-F |
| 4596 | Bu | Et | 2-Me, 3-NO₂ |
| 4597 | Bu | Et | 2-Me, 3-NH₂ |
| 4598 | Bu | Et | 2-Me, 3-NHMe |
| 4599 | Bu | Et | 2-Me, 3-NMe₂ |
| 4600 | Bu | Et | 2-Me, 3-NMe₃OTf |
| 4601 | Bu | Et | 2-Me, 3-NMe₃I |
| 4602 | Bu | Et | 2-Me, 4-F |
| 4603 | Bu | Et | 2-Me, 4-NO₂ |
| 4604 | Bu | Et | 2-Me, 4-NH₂ |
| 4605 | Bu | Et | 2-Me, 4-NHMe |
| 4606 | Bu | Et | 2-Me, 4-NMe₂ |
| 4607 | Bu | Et | 2-Me, 4-NMe₃OTf |
| 4608 | Bu | Et | 2-Me, 4-NMe₃I |
| 4609 | Bu | Et | 2-Me, 5-F |
| 4610 | Bu | Et | 2-Me, 5-NO₂ |
| 4611 | Bu | Et | 2-Me, 5-NH₂ |
| 4612 | Bu | Et | 2-Me, 5-NHMe |
| 4613 | Bu | Et | 2-Me, 5-NMe₂ |
| 4614 | Bu | Et | 2-Me, 5-NMe₃OTf |
| 4615 | Bu | Et | 2-Me, 5-NMe₃I |
| 4616 | Bu | Et | 2-F, 4-Me |
| 4617 | Bu | Et | 2-NO₂, 4-Me |
| 4618 | Bu | Et | 2-NH₂, 4-Me |
| 4619 | Bu | Et | 2-NHMe, 4-Me |
| 4620 | Bu | Et | 2-NMe₂, 4-Me |
| 4621 | Bu | Et | 2-NMe₃, 4-Me |
| 4622 | Bu | Et | 2-NMe₃OTf, 4-Me |
| 4623 | Bu | Et | 2-NMe₃I, 4-Me |
| 4624 | Bu | Et | 2-SnMe₃, 4-F |
| 4625 | Bu | Et | 2-SnMe₃, 5-F |
| 4626 | Bu | Et | 2-F, 4-SnMe₃ |
| 4627 | Bu | Et | 2-Br, 6-Cl, 4-F |
| 4628 | Bu | Et | 2-Br, 6-Cl, 4-NO₂ |
| 4629 | Bu | Et | 2-Br, 6-Cl, 4-NH₂ |
| 4630 | Bu | Et | 2-Br, 6-Cl, 4-NHMe |
| 4631 | Bu | Et | 2-Br, 6-Cl, 4-NMe₂ |
| 4632 | Bu | Et | 2-Br, 6-Cl, 4-NMe₃OTf |
| 4633 | Bu | Et | 2-Br, 6-Cl, 4-NMe₃I |
| 4634 | Bu | Et | 2-Me, 6-Cl, 4-F |
| 4635 | Bu | Et | 2-SnMe₃, 6-Cl, 4-F |
| 4636 | Bu | Et | 2-Cl, 4-Me |
| 4637 | Bu | Et | 2-Cl, 4-Br |
| 4638 | Bu | Et | 2-Cl, 4-SnMe₃ |
| 4639 | Bu | Et | 2-Br, 4-Cl |
| 4640 | Bu | Et | 2-SnMe₃, 4-Cl |
| 4641 | Bu | Et | 2-Me, 4-Cl |
| 4642 | Bu | Et | 2-Br, 4-Br |
| 4643 | Bu | Et | 2-Br, 4-Me |
| 4644 | Bu | Et | 2-Br, 4-SnMe₃ |
| 4645 | Bu | Et | 2-SnMe₃, 4-Br |
| 4646 | Bu | Et | 2-Me, 4-Br |
| 4647 | Bu | Et | 2-Me, 4-SnMe₃ |
| 4648 | Bu | Et | 2-SnMe₃, 4-Me |
| 4649 | Bu | Et | 2-Me, 4-Me |
| 4650 | Bu | Et | 2-Et, 4-Br |

TABLE 5-continued

Substituent list for compounds of general structure X.

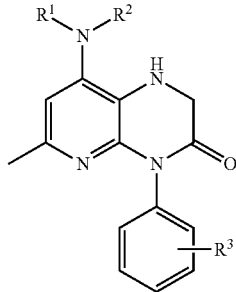

| Compound # | R¹ = | R² = | R³ = |
|---|---|---|---|
| 4651 | Bu | Et | 2-Et, 4-SnMe₃ |
| 4652 | Bu | Et | 2-Et, 4-Me |
| 4653 | Bu | Et | 2-Me, 4-Me, 6-Me |
| 4654 | Bu | Et | 2-Me, 4-Br, 6-Me |
| 4655 | Bu | Et | 2-Me, 4-SnMe₃, 6-Me |
| 4656 | Bu | Et | 2-Et, 6-Me |
| 4657 | Bu | Et | 2-Br, 4-i-Pr |
| 4658 | Bu | Et | 2-SnMe₃, 4-i-Pr |
| 4659 | Bu | Et | 2-Me, 4-i-Pr |
| 4660 | Bu | Et | 2-Br, 4-Br, 6-Br |
| 4661 | Bu | Et | 2-Br, 4-Me, 6-Br |
| 4662 | Bu | Et | 2-Br, 4-SnMe₃, 6-Br |
| 4663 | Bu | Et | 2-SnMe₃, 4-Br, 6-Br |
| 4664 | Bu | Et | 2-Br, 4-Br, 6-Me |
| 4665 | Bu | Et | 2-Br, 4-CF₃, 6-Br |
| 4666 | Bu | Et | 2-Br, 4-Br, 6- |
| 4667 | Bu | Et | 2-CF₃, 4-CF₃ |
| 4668 | Bu | Et | 2-Cl, 4-CF₃ |
| 4669 | Bu | Et | 2-CF₃, 4-Cl |
| 4670 | Bu | Et | 2-Br, 4-CF₃ |
| 4671 | Bu | Et | 2-SnMe₃, 4-CF₃ |
| 4672 | Bu | Et | 2-Me, 4-CF₃ |
| 4673 | Bu | Et | 2-CF₃, 4-Br |
| 4674 | Bu | Et | 2-CF₃, 4-SnMe₃ |
| 4675 | Bu | Et | 2-CF₃, 4-Me |
| 4676 | Bu | Et | 2-Br, 4-OH |
| 4677 | Bu | Et | 2-Br, 4-OMe |
| 4678 | Bu | Et | 2-Br, 4-OMeF |
| 4679 | Bu | Et | 2-Br, 4-OCF₃ |
| 4680 | Bu | Et | 2-Br, 4-OEtF |
| 4681 | Bu | Et | 2-Br, 4-OPrF |
| 4682 | Bu | Et | 2-OH, 4-Br |
| 4683 | Bu | Et | 2-OMe, 4-Br |
| 4684 | Bu | Et | 2-OMeF, 4-Br |
| 4685 | Bu | Et | 2-OCF₃, 4-Br |
| 4686 | Bu | Et | 2-OEtF, 4-Br |
| 4687 | Bu | Et | 2-OPrF, 4-Br |
| 4688 | Bu | Et | 2-I, 4-OH |
| 4689 | Bu | Et | 2-I, 4-OMe |
| 4690 | Bu | Et | 2-I, 4-OMeF |
| 4691 | Bu | Et | 2-I, 4-OCF₃ |
| 4692 | Bu | Et | 2-I, 4-OEtF |
| 4693 | Bu | Et | 2-I, 4-OPrF |
| 4694 | Bu | Et | 2-OH, 4-I |
| 4695 | Bu | Et | 2-OMe, 4-I |
| 4696 | Bu | Et | 2-OMeF, 4-I |
| 4697 | Bu | Et | 2-OCF₃, 4-I |
| 4698 | Bu | Et | 2-OEtF, 4-I |
| 4699 | Bu | Et | 2-OPrF, 4-I |
| 4700 | Bu | Et | 2-SnMe₃, 4-OH |
| 4701 | Bu | Et | 2-SnMe₃, 4-OMe |
| 4702 | Bu | Et | 2-SnMe₃, 4-OMeF |
| 4703 | Bu | Et | 2-SnMe₃, 4-OCF₃ |
| 4704 | Bu | Et | 2-SnMe₃, 4-OEtF |
| 4705 | Bu | Et | 2-SnMe₃, 4-OPrF |
| 4706 | Bu | Et | 2-OH, 4-SnMe₃ |
| 4707 | Bu | Et | 2-OMe, 4-SnMe₃ |
| 4708 | Bu | Et | 2-OMeF, 4-SnMe₃ |
| 4709 | Bu | Et | 2-OCF3, 4-SnMe₃ |
| 4710 | Pr | Pr | H |

TABLE 5-continued

Substituent list for compounds of general structure X.

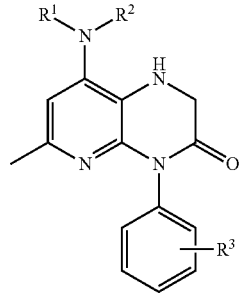

| Compound # | R¹ = | R² = | R³ = |
|---|---|---|---|
| 4711 | Pr | Pr | 2-t-Bu |
| 4712 | Pr | Pr | 2-Br |
| 4713 | Pr | Pr | 3-Br |
| 4714 | Pr | Pr | 4-Br |
| 4715 | Pr | Pr | 2-I |
| 4716 | Pr | Pr | 3-I |
| 4717 | Pr | Pr | 4-I |
| 4718 | Pr | Pr | 2-SnMe₃ |
| 4719 | Pr | Pr | 3-SnMe₃ |
| 4720 | Pr | Pr | 4-SnMe₃ |
| 4721 | Pr | Pr | 2-Me |
| 4722 | Pr | Pr | 3-Me |
| 4723 | Pr | Pr | 4-Me |
| 4724 | Pr | Pr | 2-OH |
| 4725 | Pr | Pr | 3-OH |
| 4726 | Pr | Pr | 4-OH |
| 4727 | Pr | Pr | 2-OMe |
| 4728 | Pr | Pr | 3-OMe |
| 4729 | Pr | Pr | 4-OMe |
| 4730 | Pr | Pr | 2-OMeF |
| 4731 | Pr | Pr | 3-OMeF |
| 4732 | Pr | Pr | 4-OMeF |
| 4733 | Pr | Pr | 2-OCF₃ |
| 4734 | Pr | Pr | 3-OCF₃ |
| 4735 | Pr | Pr | 4-OCF₃ |
| 4736 | Pr | Pr | 2-OEtF |
| 4737 | Pr | Pr | 3-OEtF |
| 4738 | Pr | Pr | 4-OEtF |
| 4739 | Pr | Pr | 2-OPrF |
| 4740 | Pr | Pr | 3-OPrF |
| 4741 | Pr | Pr | 4-OPrF |
| 4742 | Pr | Pr | 2-SH |
| 4743 | Pr | Pr | 3-SH |
| 4744 | Pr | Pr | 4-SH |
| 4745 | Pr | Pr | 2-SMe |
| 4746 | Pr | Pr | 3-SMe |
| 4747 | Pr | Pr | 4-SMe |
| 4748 | Pr | Pr | 2-SMeF |
| 4749 | Pr | Pr | 3-SMeF |
| 4750 | Pr | Pr | 4-SMeF |
| 4751 | Pr | Pr | 2-SCF₃ |
| 4752 | Pr | Pr | 3-SCF₃ |
| 4753 | Pr | Pr | 4-SCF₃ |
| 4754 | Pr | Pr | 2-SEtF |
| 4755 | Pr | Pr | 3-SEtF |
| 4756 | Pr | Pr | 4-SEtF |
| 4757 | Pr | Pr | 2-SPrF |
| 4758 | Pr | Pr | 3-SPrF |
| 4759 | Pr | Pr | 4-SPrF |
| 4760 | Pr | Pr | 2-OMe, 4-OMe |
| 4761 | Pr | Pr | 2-Me, 5-OH |
| 4762 | Pr | Pr | 2-Me, 5-OMe |
| 4763 | Pr | Pr | 2-Me, 5-OMeF |
| 4764 | Pr | Pr | 2-Me, 5-OEtF |
| 4765 | Pr | Pr | 2-Me, 5-OPrF |
| 4766 | Pr | Pr | 2-Me, 4-OH |
| 4767 | Pr | Pr | 2-Me, 4-OMe |
| 4768 | Pr | Pr | 2-Me, 4-OMeF |
| 4769 | Pr | Pr | 2-Me, 4-OCF₃ |
| 4770 | Pr | Pr | 2-Me, 4-OEtF |

TABLE 5-continued

Substituent list for compounds of general structure X.

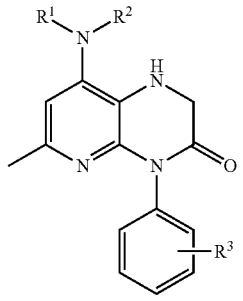

| Compound # | R¹ = | R² = | R³ = |
|---|---|---|---|
| 4771 | Pr | Pr | 2-Me, 4-OPrF |
| 4772 | Pr | Pr | 2-OH, 4-Me |
| 4773 | Pr | Pr | 2-OMe, 4-Me |
| 4774 | Pr | Pr | 2-OMeF, 4-Me |
| 4775 | Pr | Pr | 2-OCF$_3$, 4-Me |
| 4776 | Pr | Pr | 2-OEtF, 4-Me |
| 4777 | Pr | Pr | 2-OPrF, 4-Me |
| 4778 | Pr | Pr | 2-Cl, 4-OH |
| 4779 | Pr | Pr | 2-Cl, 4-OMe |
| 4780 | Pr | Pr | 2-Cl, 4-OMeF |
| 4781 | Pr | Pr | 2-Cl, 4-OCF$_3$ |
| 4782 | Pr | Pr | 2-Cl, 4-OEtF |
| 4783 | Pr | Pr | 2-Cl, 4-OPrF |
| 4784 | Pr | Pr | 2-F, 4-F |
| 4785 | Pr | Pr | 2-Cl, 4-Cl |
| 4786 | Pr | Pr | 2-Cl, 4-F |
| 4787 | Pr | Pr | 2-Cl, 4-NO$_2$ |
| 4788 | Pr | Pr | 2-Cl, 4-NH$_2$ |
| 4789 | Pr | Pr | 2-Cl, 4-NHMe |
| 4790 | Pr | Pr | 2-Cl, 4-NMe$_2$ |
| 4791 | Pr | Pr | 2-Cl, 4-NMe$_3$OTf |
| 4792 | Pr | Pr | 2-Cl, 4-NMe$_3$I |
| 4793 | Pr | Pr | 2-Cl, 5-F |
| 4794 | Pr | Pr | 2-Cl, 5-NO$_2$ |
| 4795 | Pr | Pr | 2-Cl, 5-NH$_2$ |
| 4796 | Pr | Pr | 2-Cl, 5-NHMe |
| 4797 | Pr | Pr | 2-Cl, 5-NMe$_2$ |
| 4798 | Pr | Pr | 2-Cl, 5-NMe$_3$OTf |
| 4799 | Pr | Pr | 2-Cl, 5- NMe$_3$I |
| 4800 | Pr | Pr | 2-F, 4-Cl |
| 4801 | Pr | Pr | 2-NO$_2$, 4-Cl |
| 4802 | Pr | Pr | 2-NH$_2$, 4-Cl |
| 4803 | Pr | Pr | 2-NHMe, 4-Cl |
| 4804 | Pr | Pr | 2-NMe$_2$, 4-Cl |
| 4805 | Pr | Pr | 2-NMe$_3$OTf, 4-Cl |
| 4806 | Pr | Pr | 2-NMe$_3$I, 4-Cl |
| 4807 | Pr | Pr | 2-F, 5-Cl |
| 4808 | Pr | Pr | 2-NO$_2$, 5-Cl |
| 4809 | Pr | Pr | 2-NH$_2$, 5-Cl |
| 4810 | Pr | Pr | 2-NHMe, 5-Cl |
| 4811 | Pr | Pr | 2-NMe$_2$, 5-Cl |
| 4812 | Pr | Pr | 2-NMe$_3$OTf, 5-Cl |
| 4813 | Pr | Pr | 2-NMe$_3$I, 5-Cl |
| 4814 | Pr | Pr | 2-Br, 4-F |
| 4815 | Pr | Pr | 2-Br, 4-NO$_2$ |
| 4816 | Pr | Pr | 2-Br, 4-NH$_2$ |
| 4817 | Pr | Pr | 2-Br, 4-NHMe |
| 4818 | Pr | Pr | 2-Br, 4-NMe$_2$ |
| 4819 | Pr | Pr | 2-Br, 4-NMe$_3$OTf |
| 4820 | Pr | Pr | 2-Br, 4-NMe$_3$I |
| 4821 | Pr | Pr | 2-Br, 5-F |
| 4822 | Pr | Pr | 2-Br, 5-NO$_2$ |
| 4823 | Pr | Pr | 2-Br, 5-NH$_2$ |
| 4824 | Pr | Pr | 2-Br, 5-NHMe |
| 4825 | Pr | Pr | 2-Br, 5-NMe$_2$ |
| 4826 | Pr | Pr | 2-Br, 5-NMe$_3$OTf |
| 4827 | Pr | Pr | 2-Br, 5-NMe$_3$I |
| 4828 | Pr | Pr | 2-F, 4-Br |
| 4829 | Pr | Pr | 2-NO$_2$, 4-Br |
| 4830 | Pr | Pr | 2-NH$_2$, 4-Br |

TABLE 5-continued

Substituent list for compounds of general structure X.

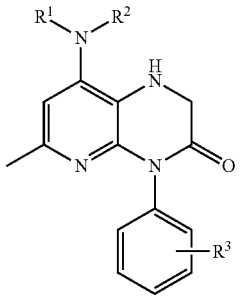

| Compound # | R¹ = | R² = | R³ = |
|---|---|---|---|
| 4831 | Pr | Pr | 2-NHMe, 4-Br |
| 4832 | Pr | Pr | 2-NMe$_2$, 4-Br |
| 4833 | Pr | Pr | 2-NMe$_3$OTf, 4-Br |
| 4834 | Pr | Pr | 2-NMe$_3$I, 4-Br |
| 4835 | Pr | Pr | 2-I, 4-F |
| 4836 | Pr | Pr | 2-I, 4-NO$_2$ |
| 4837 | Pr | Pr | 2-I, 4-NH$_2$ |
| 4838 | Pr | Pr | 2-I, 4-NHMe |
| 4839 | Pr | Pr | 2-I, 4-NMe$_2$ |
| 4840 | Pr | Pr | 2-I, 4-NMe$_3$OTf |
| 4841 | Pr | Pr | 2-I, 4-NMe$_3$I |
| 4842 | Pr | Pr | 2-F, 4-I |
| 4843 | Pr | Pr | 2-NO$_2$, 4-I |
| 4844 | Pr | Pr | 2-NH$_2$, 4-I |
| 4845 | Pr | Pr | 2-NHMe, 4-I |
| 4846 | Pr | Pr | 2-NMe$_2$, 4-I |
| 4847 | Pr | Pr | 2-NMe$_3$OTf, 4-I |
| 4848 | Pr | Pr | 2-NMe$_3$I, 4-I |
| 4849 | Pr | Pr | 2-Me, 3-F |
| 4850 | Pr | Pr | 2-Me, 3-NO$_2$ |
| 4851 | Pr | Pr | 2-Me, 3-NH$_2$ |
| 4852 | Pr | Pr | 2-Me, 3-NHMe |
| 4853 | Pr | Pr | 2-Me, 3-NMe$_2$ |
| 4854 | Pr | Pr | 2-Me, 3-NMe$_3$OTf |
| 4855 | Pr | Pr | 2-Me, 3-NMe$_3$I |
| 4856 | Pr | Pr | 2-Me, 4-F |
| 4857 | Pr | Pr | 2-Me, 4-NO$_2$ |
| 4858 | Pr | Pr | 2-Me, 4-NH$_2$ |
| 4859 | Pr | Pr | 2-Me, 4-NHMe |
| 4860 | Pr | Pr | 2-Me, 4-NMe$_2$ |
| 4861 | Pr | Pr | 2-Me, 4-NMe$_3$OTf |
| 4862 | Pr | Pr | 2-Me, 4-NMe$_3$I |
| 4863 | Pr | Pr | 2-Me, 5-F |
| 4864 | Pr | Pr | 2-Me, 5-NO$_2$ |
| 4865 | Pr | Pr | 2-Me, 5-NH$_2$ |
| 4866 | Pr | Pr | 2-Me, 5-NHMe |
| 4867 | Pr | Pr | 2-Me, 5-NMe$_2$ |
| 4868 | Pr | Pr | 2-Me, 5-NMe$_3$OTf |
| 4869 | Pr | Pr | 2-Me, 5-NMe$_3$I |
| 4870 | Pr | Pr | 2-F, 4-Me |
| 4871 | Pr | Pr | 2-NO$_2$, 4-Me |
| 4872 | Pr | Pr | 2-NH$_2$, 4-Me |
| 4873 | Pr | Pr | 2-NHMe, 4-Me |
| 4874 | Pr | Pr | 2-NMe$_2$, 4-Me |
| 4875 | Pr | Pr | 2-NMe$_3$, 4-Me |
| 4876 | Pr | Pr | 2-NMe$_3$OTf, 4-Me |
| 4877 | Pr | Pr | 2-NMe$_3$I, 4-Me |
| 4878 | Pr | Pr | 2-SnMe$_3$, 4-F |
| 4879 | Pr | Pr | 2-SnMe$_3$, 5-F |
| 4880 | Pr | Pr | 2-F, 4-SnMe$_3$ |
| 4881 | Pr | Pr | 2-Br, 6-Cl, 4-F |
| 4882 | Pr | Pr | 2-Br, 6-Cl, 4-NO$_2$ |
| 4883 | Pr | Pr | 2-Br, 6-Cl, 4-NH$_2$ |
| 4884 | Pr | Pr | 2-Br, 6-Cl, 4-NHMe |
| 4885 | Pr | Pr | 2-Br, 6-Cl, 4-NMe$_2$ |
| 4886 | Pr | Pr | 2-Br, 6-Cl, 4-NMe$_3$OTf |
| 4887 | Pr | Pr | 2-Br, 6-Cl, 4-NMe$_3$I |
| 4888 | Pr | Pr | 2-Me, 6-Cl, 4-F |
| 4889 | Pr | Pr | 2-SnMe$_3$, 6-Cl, 4-F |
| 4890 | Pr | Pr | 2-Cl, 4-Me |

TABLE 5-continued

Substituent list for compounds of general structure X.


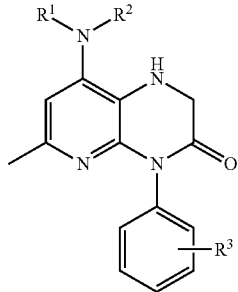

| Compound # | R¹ = | R² = | R³ = |
|---|---|---|---|
| 4891 | Pr | Pr | 2-Cl, 4-Br |
| 4892 | Pr | Pr | 2-Cl, 4-SnMe₃ |
| 4893 | Pr | Pr | 2-Br, 4-Cl |
| 4894 | Pr | Pr | 2-SnMe₃, 4-Cl |
| 4895 | Pr | Pr | 2-Me, 4-Cl |
| 4896 | Pr | Pr | 2-Br, 4-Br |
| 4897 | Pr | Pr | 2-Br, 4-Me |
| 4898 | Pr | Pr | 2-Br, 4-SnMe₃ |
| 4899 | Pr | Pr | 2-SnMe₃, 4-Br |
| 4900 | Pr | Pr | 2-Me, 4-Br |
| 4901 | Pr | Pr | 2-Me, 4-SnMe₃ |
| 4902 | Pr | Pr | 2-SnMe₃, 4-Me |
| 4903 | Pr | Pr | 2-Me, 4-Me |
| 4904 | Pr | Pr | 2-Et, 4-Br |
| 4905 | Pr | Pr | 2-Et, 4-SnMe₃ |
| 4906 | Pr | Pr | 2-Et, 4-Me |
| 4907 | Pr | Pr | 2-Me, 4-Me, 6-Me |
| 4908 | Pr | Pr | 2-Me, 4-Br, 6-Me |
| 4909 | Pr | Pr | 2-Me, 4-SnMe₃, 6-Me |
| 4910 | Pr | Pr | 2-Et, 6-Me |
| 4911 | Pr | Pr | 2-Br, 4-i-Pr |
| 4912 | Pr | Pr | 2-SnMe₃, 4-i-Pr |
| 4913 | Pr | Pr | 2-Me, 4-i-Pr |
| 4914 | Pr | Pr | 2-Br, 4-Br, 6-Br |
| 4915 | Pr | Pr | 2-Br, 4-Me, 6-Br |
| 4916 | Pr | Pr | 2-Br, 4-SnMe₃, 6-Br |
| 4917 | Pr | Pr | 2-SnMe₃, 4,6-Br |
| 4918 | Pr | Pr | 2-Br, 4-Br, 6-Me |
| 4919 | Pr | Pr | 2-Br, 4-CF₃, 6-Br |
| 4920 | Pr | Pr | 2-Br, 4-Br, 6-CF₃ |
| 4921 | Pr | Pr | 2-CF₃, 4-CF₃ |
| 4922 | Pr | Pr | 2-Cl, 4-CF₃ |
| 4923 | Pr | Pr | 2-CF₃, 4-Cl |
| 4924 | Pr | Pr | 2-Br, 4-CF₃ |
| 4925 | Pr | Pr | 2-SnMe₃, 4-CF₃ |
| 4926 | Pr | Pr | 2-Me, 4-CF₃ |
| 4927 | Pr | Pr | 2-CF₃, 4-Br |
| 4928 | Pr | Pr | 2-CF₃, 4-SnMe₃ |
| 4929 | Pr | Pr | 2-CF₃, 4-Me |
| 4930 | Pr | Pr | 2-Br, 4-OH |
| 4931 | Pr | Pr | 2-Br, 4-OMe |
| 4932 | Pr | Pr | 2-Br, 4-OMeF |
| 4933 | Pr | Pr | 2-Br, 4-OCF₃ |
| 4934 | Pr | Pr | 2-Br, 4-OEtF |
| 4935 | Pr | Pr | 2-Br, 4-OPrF |
| 4936 | Pr | Pr | 2-OH, 4-Br |
| 4937 | Pr | Pr | 2-OMe, 4-Br |
| 4938 | Pr | Pr | 2-OMeF, 4-Br |
| 4939 | Pr | Pr | 2-OCF₃, 4-Br |
| 4940 | Pr | Pr | 2-OEtF, 4-Br |
| 4941 | Pr | Pr | 2-OPrF, 4-Br |
| 4942 | Pr | Pr | 2-I, 4-OH |
| 4943 | Pr | Pr | 2-I, 4-OMe |
| 4944 | Pr | Pr | 2-I, 4-OMeF |
| 4945 | Pr | Pr | 2-I, 4-OCF₃ |
| 4946 | Pr | Pr | 2-I, 4-OEtF |
| 4947 | Pr | Pr | 2-I, 4-OPrF |
| 4948 | Pr | Pr | 2-OH, 4-I |
| 4949 | Pr | Pr | 2-OMe, 4-I |
| 4950 | Pr | Pr | 2-OMeF, 4-I |
| 4951 | Pr | Pr | 2-OCF₃, 4-I |
| 4952 | Pr | Pr | 2-OEtF, 4-I |
| 4953 | Pr | Pr | 2-OPrF, 4-I |
| 4954 | Pr | Pr | 2-SnMe₃, 4-OH |
| 4955 | Pr | Pr | 2-SnMe₃, 4-OMe |
| 4956 | Pr | Pr | 2-SnMe₃, 4-OMeF |
| 4957 | Pr | Pr | 2-SnMe₃, 4-OCF₃ |
| 4958 | Pr | Pr | 2-SnMe₃, 4-OEtF |
| 4959 | Pr | Pr | 2-SnMe₃, 4-OPrF |
| 4960 | Pr | Pr | 2-OH, 4-SnMe₃ |
| 4961 | Pr | Pr | 2-OMe, 4-SnMe₃ |
| 4962 | Pr | Pr | 2-OMeF, 4-SnMe₃ |
| 4963 | Pr | Pr | 2-OCF₃, 4-SnMe₃ |
| 4964 | Pr | Pr | 2-OEtF, 4-SnMe₃ |
| 4965 | Pr | Pr | 2-OPrF, 4-SnMe₃ |
| 4966 | Pr | Pr—F | H |
| 4967 | Pr | Pr—F | 2-t-Bu |
| 4968 | Pr | Pr—F | 2-Br |
| 4969 | Pr | Pr—F | 3-Br |
| 4970 | Pr | Pr—F | 4-Br |
| 4971 | Pr | Pr—F | 2-I |
| 4972 | Pr | Pr—F | 3-I |
| 4973 | Pr | Pr—F | 4-I |
| 4974 | Pr | Pr—F | 2-SnMe₃ |
| 4975 | Pr | Pr—F | 3-SnMe₃ |
| 4976 | Pr | Pr—F | 4-SnMe₃ |
| 4977 | Pr | Pr—F | 2-Me |
| 4978 | Pr | Pr—F | 3-Me |
| 4979 | Pr | Pr—F | 4-Me |
| 4980 | Pr | Pr—F | 2-OH |
| 4981 | Pr | Pr—F | 3-OH |
| 4982 | Pr | Pr—F | 4-OH |
| 4983 | Pr | Pr—F | 2-OMe |
| 4984 | Pr | Pr—F | 3-OMe |
| 4985 | Pr | Pr—F | 4-OMe |
| 4986 | Pr | Pr—F | 2-OMeF |
| 4987 | Pr | Pr—F | 3-OMeF |
| 4988 | Pr | Pr—F | 4-OMeF |
| 4989 | Pr | Pr—F | 2-OCF₃ |
| 4990 | Pr | Pr—F | 3-OCF₃ |
| 4991 | Pr | Pr—F | 4-OCF₃ |
| 4992 | Pr | Pr—F | 2-OEtF |
| 4993 | Pr | Pr—F | 3-OEtF |
| 4994 | Pr | Pr—F | 4-OEtF |
| 4995 | Pr | Pr—F | 2-OPrF |
| 4996 | Pr | Pr—F | 3-OPrF |
| 4997 | Pr | Pr—F | 4-OPrF |
| 4998 | Pr | Pr—F | 2-SH |
| 4999 | Pr | Pr—F | 3-SH |
| 5000 | Pr | Pr—F | 4-SH |
| 5001 | Pr | Pr—F | 2-SMe |
| 5002 | Pr | Pr—F | 3-SMe |
| 5003 | Pr | Pr—F | 4-SMe |
| 5004 | Pr | Pr—F | 2-SMeF |
| 5005 | Pr | Pr—F | 3-SMeF |
| 5006 | Pr | Pr—F | 4-SMeF |
| 5007 | Pr | Pr—F | 2-SCF₃ |
| 5008 | Pr | Pr—F | 3-SCF₃ |
| 5009 | Pr | Pr—F | 4-SCF₃ |
| 5010 | Pr | Pr—F | 2-SEtF |

TABLE 5-continued

Substituent list for compounds of general structure X.

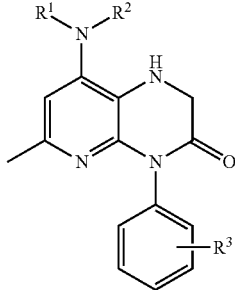

| Compound # | R¹ = | R² = | R³ = |
|---|---|---|---|
| 5011 | Pr | Pr—F | 3-SEtF |
| 5012 | Pr | Pr—F | 4-SEtF |
| 5013 | Pr | Pr—F | 2-SPrF |
| 5014 | Pr | Pr—F | 3-SPrF |
| 5015 | Pr | Pr—F | 4-SPrF |
| 5016 | Pr | Pr—F | 2-OMe, 4-OMe |
| 5017 | Pr | Pr—F | 2-Me, 5-OH |
| 5018 | Pr | Pr—F | 2-Me, 5-OMe |
| 5019 | Pr | Pr—F | 2-Me, 5-OMeF |
| 5020 | Pr | Pr—F | 2-Me, 5-OEtF |
| 5021 | Pr | Pr—F | 2-Me, 5-OPrF |
| 5022 | Pr | Pr—F | 2-Me, 4-OH |
| 5023 | Pr | Pr—F | 2-Me, 4-OMe |
| 5024 | Pr | Pr—F | 2-Me, 4-OMeF |
| 5025 | Pr | Pr—F | 2-Me, 4-OCF$_3$ |
| 5026 | Pr | Pr—F | 2-Me, 4-OEtF |
| 5027 | Pr | Pr—F | 2-Me, 4-OPrF |
| 5028 | Pr | Pr—F | 2-OH, 4-Me |
| 5029 | Pr | Pr—F | 2-OMe, 4-Me |
| 5030 | Pr | Pr—F | 2-OMeF, 4-Me |
| 5031 | Pr | Pr—F | 2-OCF$_3$, 4-Me |
| 5032 | Pr | Pr—F | 2-OEtF, 4-Me |
| 5033 | Pr | Pr—F | 2-OPrF, 4-Me |
| 5034 | Pr | Pr—F | 2-Cl, 4-OH |
| 5035 | Pr | Pr—F | 2-Cl, 4-OMe |
| 5036 | Pr | Pr—F | 2-Cl, 4-OMeF |
| 5037 | Pr | Pr—F | 2-Cl, 4-OCF$_3$ |
| 5038 | Pr | Pr—F | 2-Cl, 4-OEtF |
| 5039 | Pr | Pr—F | 2-Cl, 4-OPrF |
| 5040 | Pr | Pr—F | 2-F, 4-F |
| 5041 | Pr | Pr—F | 2-Cl, 4-Cl |
| 5042 | Pr | Pr—F | 2-Cl, 4-F |
| 5043 | Pr | Pr—F | 2-Cl, 4-NO$_2$ |
| 5044 | Pr | Pr—F | 2-Cl, 4-NH$_2$ |
| 5045 | Pr | Pr—F | 2-Cl, 4-NHMe |
| 5046 | Pr | Pr—F | 2-Cl, 4-NMe$_2$ |
| 5047 | Pr | Pr—F | 2-Cl, 4-NMe$_3$OTf |
| 5048 | Pr | Pr—F | 2-Cl, 4-NMe$_3$I |
| 5049 | Pr | Pr—F | 2-Cl, 5-F |
| 5050 | Pr | Pr—F | 2-Cl, 5-NO$_2$ |
| 5051 | Pr | Pr—F | 2-Cl, 5-NH$_2$ |
| 5052 | Pr | Pr—F | 2-Cl, 5-NHMe |
| 5053 | Pr | Pr—F | 2-Cl, 5-NMe$_2$ |
| 5054 | Pr | Pr—F | 2-Cl, 5-NMe$_3$OTf |
| 5055 | Pr | Pr—F | 2-Cl, 5-NMe$_3$I |
| 5056 | Pr | Pr—F | 2-F, 4-Cl |
| 5057 | Pr | Pr—F | 2-NO$_2$, 4-Cl |
| 5058 | Pr | Pr—F | 2-NH$_2$, 4-Cl |
| 5059 | Pr | Pr—F | 2-NHMe, 4-Cl |
| 5060 | Pr | Pr—F | 2-NMe$_2$, 4-Cl |
| 5061 | Pr | Pr—F | 2-NMe$_3$OTf, 4-Cl |
| 5062 | Pr | Pr—F | 2-NMe$_3$I, 4-Cl |
| 5063 | Pr | Pr—F | 2-F, 5-Cl |
| 5064 | Pr | Pr—F | 2-NO$_2$, 5-Cl |
| 5065 | Pr | Pr—F | 2-NH$_2$, 5-Cl |
| 5066 | Pr | Pr—F | 2-NHMe, 5-Cl |
| 5067 | Pr | Pr—F | 2-NMe$_2$, 5-Cl |
| 5068 | Pr | Pr—F | 2-NMe$_3$OTf, 5-Cl |
| 5069 | Pr | Pr—F | 2-NMe$_3$I, 5-Cl |
| 5070 | Pr | Pr—F | 2-Br, 4-F |

TABLE 5-continued

Substituent list for compounds of general structure X.

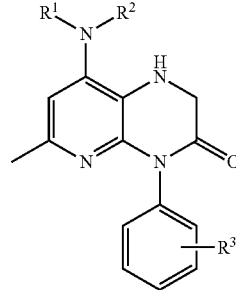

| Compound # | R¹ = | R² = | R³ = |
|---|---|---|---|
| 5071 | Pr | Pr—F | 2-Br, 4-NO$_2$ |
| 5072 | Pr | Pr—F | 2-Br, 4-NH$_2$ |
| 5073 | Pr | Pr—F | 2-Br, 4-NHMe |
| 5074 | Pr | Pr—F | 2-Br, 4-NMe$_2$ |
| 5075 | Pr | Pr—F | 2-Br, 4-NMe$_3$OTf |
| 5076 | Pr | Pr—F | 2-Br, 4-NMe$_3$I |
| 5077 | Pr | Pr—F | 2-Br, 5-F |
| 5078 | Pr | Pr—F | 2-Br, 5-NO$_2$ |
| 5079 | Pr | Pr—F | 2-Br, 5-NH$_2$ |
| 5080 | Pr | Pr—F | 2-Br, 5-NHMe |
| 5081 | Pr | Pr—F | 2-Br, 5-NMe$_2$ |
| 5082 | Pr | Pr—F | 2-Br, 5-NMe$_3$OTf |
| 5083 | Pr | Pr—F | 2-Br, 5-NMe$_3$I |
| 5084 | Pr | Pr—F | 2-F, 4-Br |
| 5085 | Pr | Pr—F | 2-NO$_2$, 4-Br |
| 5086 | Pr | Pr—F | 2-NH$_2$, 4-Br |
| 5087 | Pr | Pr—F | 2-NHMe, 4-Br |
| 5088 | Pr | Pr—F | 2-NMe$_2$, 4-Br |
| 5089 | Pr | Pr—F | 2-NMe$_3$OTf, 4-Br |
| 5090 | Pr | Pr—F | 2-NMe$_3$I, 4-Br |
| 5091 | Pr | Pr—F | 2-I, 4-F |
| 5092 | Pr | Pr—F | 2-I, 4-NO$_2$ |
| 5093 | Pr | Pr—F | 2-I, 4-NH$_2$ |
| 5094 | Pr | Pr—F | 2-I, 4-NHMe |
| 5095 | Pr | Pr—F | 2-I, 4-NMe$_2$ |
| 5096 | Pr | Pr—F | 2-I, 4-NMe$_3$OTf |
| 5097 | Pr | Pr—F | 2-I, 4-NMe$_3$I |
| 5098 | Pr | Pr—F | 2-F, 4-I |
| 5099 | Pr | Pr—F | 2-NO$_2$, 4-I |
| 5100 | Pr | Pr—F | 2-NH$_2$, 4-I |
| 5101 | Pr | Pr—F | 2-NHMe, 4-I |
| 5102 | Pr | Pr—F | 2-NMe$_2$, 4-I |
| 5103 | Pr | Pr—F | 2-NMe$_3$OTf, 4-I |
| 5104 | Pr | Pr—F | 2-NMe$_3$I, 4-I |
| 5105 | Pr | Pr—F | 2-Me, 3-F |
| 5106 | Pr | Pr—F | 2-Me, 3-NO$_2$ |
| 5107 | Pr | Pr—F | 2-Me, 3-NH$_2$ |
| 5108 | Pr | Pr—F | 2-Me, 3-NHMe |
| 5109 | Pr | Pr—F | 2-Me, 3-NMe$_2$ |
| 5110 | Pr | Pr—F | 2-Me, 3-NMe$_3$OTf |
| 5111 | Pr | Pr—F | 2-Me, 3-NMe$_3$I |
| 5112 | Pr | Pr—F | 2-Me, 4-F |
| 5113 | Pr | Pr—F | 2-Me, 4-NO$_2$ |
| 5114 | Pr | Pr—F | 2-Me, 4-NH$_2$ |
| 5115 | Pr | Pr—F | 2-Me, 4-NHMe |
| 5116 | Pr | Pr—F | 2-Me, 4-NMe$_2$ |
| 5117 | Pr | Pr—F | 2-Me, 4-NMe$_3$OTf |
| 5118 | Pr | Pr—F | 2-Me, 4-NMe$_3$I |
| 5119 | Pr | Pr—F | 2-Me, 5-F |
| 5120 | Pr | Pr—F | 2-Me, 5-NO$_2$ |
| 5121 | Pr | Pr—F | 2-Me, 5-NH$_2$ |
| 5122 | Pr | Pr—F | 2-Me, 5-NHMe |
| 5123 | Pr | Pr—F | 2-Me, 5-NMe$_2$ |
| 5124 | Pr | Pr—F | 2-Me, 5-NMe$_3$OTf |
| 5125 | Pr | Pr—F | 2-Me, 5-NMe$_3$I |
| 5126 | Pr | Pr—F | 2-F, 4-Me |
| 5127 | Pr | Pr—F | 2-NO$_2$, 4-Me |
| 5128 | Pr | Pr—F | 2-NH$_2$, 4-Me |
| 5129 | Pr | Pr—F | 2-NHMe, 4-Me |
| 5130 | Pr | Pr—F | 2-NMe$_2$, 4-Me |

TABLE 5-continued

Substituent list for compounds of general structure X.

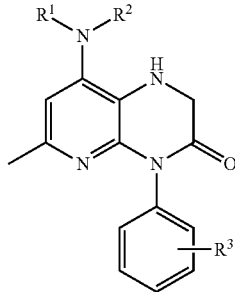

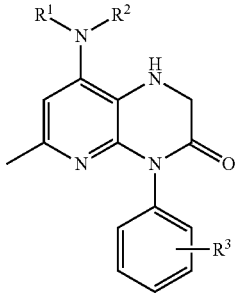

| Compound # | R¹ = | R² = | R³ = |
|---|---|---|---|
| 5131 | Pr | Pr—F | 2-NMe₂, 4-Me |
| 5132 | Pr | Pr—F | 2-NMe₃OTf, 4-Me |
| 5133 | Pr | Pr—F | 2-NMe₃I, 4-Me |
| 5134 | Pr | Pr—F | 2-SnMe₃, 4-F |
| 5135 | Pr | Pr—F | 2-SnMe₃, 5-F |
| 5136 | Pr | Pr—F | 2-F, 4-SnMe₃ |
| 5137 | Pr | Pr—F | 2-Br, 6-Cl, 4-F |
| 5138 | Pr | Pr—F | 2-Br, 6-Cl, 4-NO₂ |
| 5139 | Pr | Pr—F | 2-Br, 6-Cl, 4-NH₂ |
| 5140 | Pr | Pr—F | 2-Br, 6-Cl, 4-NHMe |
| 5141 | Pr | Pr—F | 2-Br, 6-Cl, 4-NMe₂ |
| 5142 | Pr | Pr—F | 2-Br, 6-Cl, 4-NMe₃OTf |
| 5143 | Pr | Pr—F | 2-Br, 6-Cl, 4-NMe₃I |
| 5144 | Pr | Pr—F | 2-Me, 6-Cl, 4-F |
| 5145 | Pr | Pr—F | 2-SnMe₃, 6-Cl, 4-F |
| 5146 | Pr | Pr—F | 2-Cl, 4-Me |
| 5147 | Pr | Pr—F | 2-Cl, 4-Br |
| 5148 | Pr | Pr—F | 2-Cl, 4-SnMe₃ |
| 5149 | Pr | Pr—F | 2-Br, 4-Cl |
| 5150 | Pr | Pr—F | 2-SnMe₃, 4-Cl |
| 5151 | Pr | Pr—F | 2-Me, 4-Cl |
| 5152 | Pr | Pr—F | 2-Br, 4-Br |
| 5153 | Pr | Pr—F | 2-Br, 4-Me |
| 5154 | Pr | Pr—F | 2-Br, 4-SnMe₃ |
| 5155 | Pr | Pr—F | 2-SnMe₃, 4-Br |
| 5156 | Pr | Pr—F | 2-Me, 4-Br |
| 5157 | Pr | Pr—F | 2-Me, 4-SnMe₃ |
| 5158 | Pr | Pr—F | 2-SnMe₃, 4-Me |
| 5159 | Pr | Pr—F | 2-Me, 4-Me |
| 5160 | Pr | Pr—F | 2-Et, 4-Br |
| 5161 | Pr | Pr—F | 2-Et, 4-SnMe₃ |
| 5162 | Pr | Pr—F | 2-Et, 4-Me |
| 5163 | Pr | Pr—F | 2-Me, 4-Me, 6-Me |
| 5164 | Pr | Pr—F | 2-Me, 4-Br, 6-Me |
| 5165 | Pr | Pr—F | 2-Me, 4-SnMe₃, 6-Me |
| 5166 | Pr | Pr—F | 2-Et, 6-Me |
| 5167 | Pr | Pr—F | 2-Br, 4-i-Pr |
| 5168 | Pr | Pr—F | 2-SnMe₃, 4-i-Pr |
| 5169 | Pr | Pr—F | 2-Me, 4-i-Pr |
| 5170 | Pr | Pr—F | 2-Br, 4-Br, 6-Br |
| 5171 | Pr | Pr—F | 2-Br, 4-Me, 6-Br |
| 5172 | Pr | Pr—F | 2-Br, 4-SnMe₃, 6-Br |
| 5173 | Pr | Pr—F | 2-SnMe₃, 4-Br, 6-Br |
| 5174 | Pr | Pr—F | 2-Br, 4-Br, 6-Me |
| 5175 | Pr | Pr—F | 2-Br, 4-CF₃, 6-Br |
| 5176 | Pr | Pr—F | 2-Br, 4-Br, 6-CF₃ |
| 5177 | Pr | Pr—F | 2-CF₃, 4-CF₃ |
| 5178 | Pr | Pr—F | 2-Cl, 4-CF₃ |
| 5179 | Pr | Pr—F | 2-CF₃, 4-Cl |
| 5180 | Pr | Pr—F | 2-Br, 4-CF₃ |
| 5181 | Pr | Pr—F | 2-SnMe₃, 4-CF₃ |
| 5182 | Pr | Pr—F | 2-Me, 4-CF₃ |
| 5183 | Pr | Pr—F | 2-CF₃, 4-Br |
| 5184 | Pr | Pr—F | 2-CF₃, 4-SnMe₃ |
| 5185 | Pr | Pr—F | 2-CF₃, 4-Me |
| 5186 | Pr | Pr—F | 2-Br, 4-OH |
| 5187 | Pr | Pr—F | 2-Br, 4-OMe |
| 5188 | Pr | Pr—F | 2-Br, 4-OMeF |
| 5189 | Pr | Pr—F | 2-Br, 4-OCF₃ |
| 5190 | Pr | Pr—F | 2-Br, 4-OEtF |
| 5191 | Pr | Pr—F | 2-Br, 4-OPrF |
| 5192 | Pr | Pr—F | 2-OH, 4-Br |
| 5193 | Pr | Pr—F | 2-OMe, 4-Br |
| 5194 | Pr | Pr—F | 2-OMeF, 4-Br |
| 5195 | Pr | Pr—F | 2-OCF₃, 4-Br |
| 5196 | Pr | Pr—F | 2-OEtF, 4-Br |
| 5197 | Pr | Pr—F | 2-OPrF, 4-Br |
| 5198 | Pr | Pr—F | 2-I, 4-OH |
| 5199 | Pr | Pr—F | 2-I, 4-OMe |
| 5200 | Pr | Pr—F | 2-I, 4-OMeF |
| 5201 | Pr | Pr—F | 2-I, 4-OCF₃ |
| 5202 | Pr | Pr—F | 2-I, 4-OEtF |
| 5203 | Pr | Pr—F | 2-I, 4-OPrF |
| 5204 | Pr | Pr—F | 2-OH, 4-I |
| 5205 | Pr | Pr—F | 2-OMe, 4-I |
| 5206 | Pr | Pr—F | 2-OMeF, 4-I |
| 5207 | Pr | Pr—F | 2-OCF₃, 4-I |
| 5208 | Pr | Pr—F | 2-OEtF, 4-I |
| 5209 | Pr | Pr—F | 2-OPrF, 4-I |
| 5210 | Pr | Pr—F | 2-SnMe₃, 4-OH |
| 5211 | Pr | Pr—F | 2-SnMe₃, 4-OMe |
| 5212 | Pr | Pr—F | 2-SnMe₃, 4-OMeF |
| 5213 | Pr | Pr—F | 2-SnMe₃, 4-OCF₃ |
| 5214 | Pr | Pr—F | 2-SnMe₃, 4-OEtF |
| 5215 | Pr | Pr—F | 2-SnMe₃, 4-OPrF |
| 5216 | Pr | Pr—F | 2-OH, 4-SnMe₃ |
| 5217 | Pr | Pr—F | 2-OMe, 4-SnMe₃ |
| 5218 | Pr | Pr—F | 2-OMeF, 4-SnMe₃ |
| 5219 | Pr | Pr—F | 2-OCF₃, 4-SnMe₃ |
| 5220 | Pr | Pr—F | 2-OEtF, 4-SnMe₃ |
| 5221 | Pr | Pr—F | 2-OPrF, 4-SnMe₃ |
| 5222 | Pr | Et—F | H |
| 5223 | Pr | Et—F | 2-t-Bu |
| 5224 | Pr | Et—F | 2-Br |
| 5225 | Pr | Et—F | 3-Br |
| 5226 | Pr | Et—F | 4-Br |
| 5227 | Pr | Et—F | 2-I |
| 5228 | Pr | Et—F | 3-I |
| 5229 | Pr | Et—F | 4-I |
| 5230 | Pr | Et—F | 2-SnMe₃ |
| 5231 | Pr | Et—F | 3-SnMe₃ |
| 5232 | Pr | Et—F | 4-SnMe₃ |
| 5233 | Pr | Et—F | 2-Me |
| 5234 | Pr | Et—F | 3-Me |
| 5235 | Pr | Et—F | 4-Me |
| 5236 | Pr | Et—F | 2-OH |
| 5237 | Pr | Et—F | 3-OH |
| 5238 | Pr | Et—F | 4-OH |
| 5239 | Pr | Et—F | 2-OMe |
| 5240 | Pr | Et—F | 3-OMe |
| 5241 | Pr | Et—F | 4-OMe |
| 5242 | Pr | Et—F | 2-OMeF |
| 5243 | Pr | Et—F | 3-OMeF |
| 5244 | Pr | Et—F | 4-OMeF |
| 5245 | Pr | Et—F | 2-OCF₃ |
| 5246 | Pr | Et—F | 3-OCF₃ |
| 5247 | Pr | Et—F | 4-OCF₃ |
| 5248 | Pr | Et—F | 2-OEtF |
| 5249 | Pr | Et—F | 3-OEtF |
| 5250 | Pr | Et—F | 4-OEtF |

TABLE 5-continued

Substituent list for compounds of general structure X.

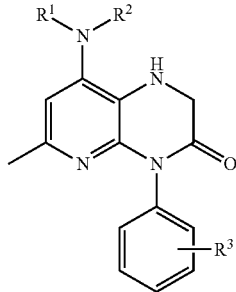

| Compound # | R¹ = | R² = | R³ = |
|---|---|---|---|
| 5251 | Pr | Et—F | 2-OPrF |
| 5252 | Pr | Et—F | 3-OPrF |
| 5253 | Pr | Et—F | 4-OPrF |
| 5254 | Pr | Et—F | 2-SH |
| 5255 | Pr | Et—F | 3-SH |
| 5256 | Pr | Et—F | 4-SH |
| 5257 | Pr | Et—F | 2-SMe |
| 5258 | Pr | Et—F | 3-SMe |
| 5259 | Pr | Et—F | 4-SMe |
| 5260 | Pr | Et—F | 2-SMeF |
| 5261 | Pr | Et—F | 3-SMeF |
| 5262 | Pr | Et—F | 4-SMeF |
| 5263 | Pr | Et—F | 2-SCF₃ |
| 5264 | Pr | Et—F | 3-SCF₃ |
| 5265 | Pr | Et—F | 4-SCF₃ |
| 5266 | Pr | Et—F | 2-SEtF |
| 5267 | Pr | Et—F | 3-SEtF |
| 5268 | Pr | Et—F | 4-SEtF |
| 5269 | Pr | Et—F | 2-SPrF |
| 5270 | Pr | Et—F | 3-SPrF |
| 5271 | Pr | Et—F | 4-SPrF |
| 5272 | Pr | Et—F | 2-OMe, 4-OMe |
| 5273 | Pr | Et—F | 2-Me, 5-OH |
| 5274 | Pr | Et—F | 2-Me, 5-OMe |
| 5275 | Pr | Et—F | 2-Me, 5-OMeF |
| 5276 | Pr | Et—F | 2-Me, 5-OEtF |
| 5277 | Pr | Et—F | 2-Me, 5-OPrF |
| 5278 | Pr | Et—F | 2-Me, 4-OH |
| 5279 | Pr | Et—F | 2-Me, 4-OMe |
| 5280 | Pr | Et—F | 2-Me, 4-OMeF |
| 5281 | Pr | Et—F | 2-Me, 4-OCF₃ |
| 5282 | Pr | Et—F | 2-Me, 4-OEtF |
| 5283 | Pr | Et—F | 2-Me, 4-OPrF |
| 5284 | Pr | Et—F | 2-OH, 4-Me |
| 5285 | Pr | Et—F | 2-OMe, 4-Me |
| 5286 | Pr | Et—F | 2-OMeF, 4-Me |
| 5287 | Pr | Et—F | 2-OCF₃, 4-Me |
| 5288 | Pr | Et—F | 2-OEtF, 4-Me |
| 5289 | Pr | Et—F | 2-OPrF, 4-Me |
| 5290 | Pr | Et—F | 2-Cl, 4-OH |
| 5291 | Pr | Et—F | 2-Cl, 4-OMe |
| 5292 | Pr | Et—F | 2-Cl, 4-OMeF |
| 5293 | Pr | Et—F | 2-Cl, 4-OCF₃ |
| 5294 | Pr | Et—F | 2-Cl, 4-OEtF |
| 5295 | Pr | Et—F | 2-Cl, 4-OPrF |
| 5296 | Pr | Et—F | 2-F, 4-F |
| 5297 | Pr | Et—F | 2-Cl, 4-Cl |
| 5298 | Pr | Et—F | 2-Cl, 4-F |
| 5299 | Pr | Et—F | 2-Cl, 4-NO₂ |
| 5300 | Pr | Et—F | 2-Cl, 4-NH₂ |
| 5301 | Pr | Et—F | 2-Cl, 4-NHMe |
| 5302 | Pr | Et—F | 2-Cl, 4-NMe₂ |
| 5303 | Pr | Et—F | 2-Cl, 4-NMe₃OTf |
| 5304 | Pr | Et—F | 2-Cl, 4-NMe₃I |
| 5305 | Pr | Et—F | 2-Cl, 5-F |
| 5306 | Pr | Et—F | 2-Cl, 5-NO₂ |
| 5307 | Pr | Et—F | 2-Cl, 5-NH₂ |
| 5308 | Pr | Et—F | 2-Cl, 5-NHMe |
| 5309 | Pr | Et—F | 2-Cl, 5-NMe₂ |
| 5310 | Pr | Et—F | 2-Cl, 5-NMe₃OTf |

TABLE 5-continued

Substituent list for compounds of general structure X.

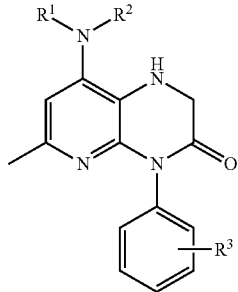

| Compound # | R¹ = | R² = | R³ = |
|---|---|---|---|
| 5311 | Pr | Et—F | 2-Cl, 5-NMe₃I |
| 5312 | Pr | Et—F | 2-F, 4-Cl |
| 5313 | Pr | Et—F | 2-NO₂, 4-Cl |
| 5314 | Pr | Et—F | 2-NH₂, 4-Cl |
| 5315 | Pr | Et—F | 2-NHMe, 4-Cl |
| 5316 | Pr | Et—F | 2-NMe₂, 4-Cl |
| 5317 | Pr | Et—F | 2-NMe₃OTf, 4-Cl |
| 5318 | Pr | Et—F | 2-NMe₃I, 4-Cl |
| 5319 | Pr | Et—F | 2-F, 5-Cl |
| 5320 | Pr | Et—F | 2-NO₂, 5-Cl |
| 5321 | Pr | Et—F | 2-NH₂, 5-Cl |
| 5322 | Pr | Et—F | 2-NHMe, 5-Cl |
| 5323 | Pr | Et—F | 2-NMe₂, 5-Cl |
| 5324 | Pr | Et—F | 2-NMe₃OTf, 5-Cl |
| 5325 | Pr | Et—F | 2-NMe₃I, 5-Cl |
| 5326 | Pr | Et—F | 2-Br, 4-F |
| 5327 | Pr | Et—F | 2-Br, 4-NO₂ |
| 5328 | Pr | Et—F | 2-Br, 4-NH₂ |
| 5329 | Pr | Et—F | 2-Br, 4-NHMe |
| 5330 | Pr | Et—F | 2-Br, 4-NMe₂ |
| 5331 | Pr | Et—F | 2-Br, 4-NMe₃OTf |
| 5332 | Pr | Et—F | 2-Br, 4-NMe₃I |
| 5333 | Pr | Et—F | 2-Br, 5-F |
| 5334 | Pr | Et—F | 2-Br, 5-NO₂ |
| 5335 | Pr | Et—F | 2-Br, 5-NH₂ |
| 5336 | Pr | Et—F | 2-Br, 5-NHMe |
| 5337 | Pr | Et—F | 2-Br, 5-NMe₂ |
| 5338 | Pr | Et—F | 2-Br, 5-NMe₃OTf |
| 5339 | Pr | Et—F | 2-Br, 5-NMe₃I |
| 5340 | Pr | Et—F | 2-F, 4-Br |
| 5341 | Pr | Et—F | 2-NO₂, 4-Br |
| 5342 | Pr | Et—F | 2-NH₂, 4-Br |
| 5343 | Pr | Et—F | 2-NHMe, 4-Br |
| 5344 | Pr | Et—F | 2-NMe₂, 4-Br |
| 5345 | Pr | Et—F | 2-NMe₃OTf, 4-Br |
| 5346 | Pr | Et—F | 2-NMe₃I, 4-Br |
| 5347 | Pr | Et—F | 2-I, 4-F |
| 5348 | Pr | Et—F | 2-I, 4-NO₂ |
| 5349 | Pr | Et—F | 2-I, 4-NH₂ |
| 5350 | Pr | Et—F | 2-I, 4-NHMe |
| 5351 | Pr | Et—F | 2-I, 4-NMe₂ |
| 5352 | Pr | Et—F | 2-I, 4-NMe₃OTf |
| 5353 | Pr | Et—F | 2-I, 4-NMe₃I |
| 5354 | Pr | Et—F | 2-F, 4-I |
| 5355 | Pr | Et—F | 2-NO₂, 4-I |
| 5356 | Pr | Et—F | 2-NH₂, 4-I |
| 5357 | Pr | Et—F | 2-NHMe, 4-I |
| 5358 | Pr | Et—F | 2-NMe₂, 4-I |
| 5359 | Pr | Et—F | 2-NMe₃OTf, 4-I |
| 5360 | Pr | Et—F | 2-NMe₃I, 4-I |
| 5361 | Pr | Et—F | 2-Me, 3-F |
| 5362 | Pr | Et—F | 2-Me, 3-NO₂ |
| 5363 | Pr | Et—F | 2-Me, 3-NH₂ |
| 5364 | Pr | Et—F | 2-Me, 3-NHMe |
| 5365 | Pr | Et—F | 2-Me, 3-NMe₂ |
| 5366 | Pr | Et—F | 2-Me, 3-NMe₃OTf |
| 5367 | Pr | Et—F | 2-Me, 3-NMe₃I |
| 5368 | Pr | Et—F | 2-Me, 4-F |
| 5369 | Pr | Et—F | 2-Me, 4-NO₂ |
| 5370 | Pr | Et—F | 2-Me, 4-NH₂ |

TABLE 5-continued

Substituent list for compounds of general structure X.

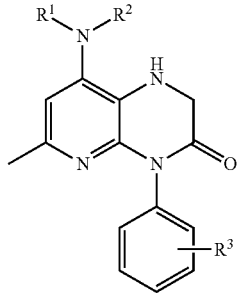

| Compound # | R¹ = | R² = | R³ = |
|---|---|---|---|
| 5371 | Pr | Et—F | 2-Me, 4-NHMe |
| 5372 | Pr | Et—F | 2-Me, 4-NMe₂ |
| 5373 | Pr | Et—F | 2-Me, 4-NMe₃OTf |
| 5374 | Pr | Et—F | 2-Me, 4-NMe₃I |
| 5375 | Pr | Et—F | 2-Me, 5-F |
| 5376 | Pr | Et—F | 2-Me, 5-NO₂ |
| 5377 | Pr | Et—F | 2-Me, 5-NH₂ |
| 5378 | Pr | Et—F | 2-Me, 5-NHMe |
| 5379 | Pr | Et—F | 2-Me, 5-NMe₂ |
| 5380 | Pr | Et—F | NMe₃OTf |
| 5381 | Pr | Et—F | 2-Me, 5-NMe₃I |
| 5382 | Pr | Et—F | 2-F, 4-Me |
| 5383 | Pr | Et—F | 2-NO₂, 4-Me |
| 5384 | Pr | Et—F | 2-NH₂, 4-Me |
| 5385 | Pr | Et—F | 2-NHMe, 4-Me |
| 5386 | Pr | Et—F | 2-NMe₂, 4-Me |
| 5387 | Pr | Et—F | 2-NMe₃, 4-Me |
| 5388 | Pr | Et—F | 2-NMe₃OTf, 4-Me |
| 5389 | Pr | Et—F | 2-NMe₃I, 4-Me |
| 5390 | Pr | Et—F | 2-SnMe₃, 4-F |
| 5391 | Pr | Et—F | 2-SnMe₃, 5-F |
| 5392 | Pr | Et—F | 2-F, 4-SnMe₃ |
| 5393 | Pr | Et—F | 2-Br, 6-Cl, 4-F |
| 5394 | Pr | Et—F | 2-Br, 6-Cl, 4-NO₂ |
| 5395 | Pr | Et—F | 2-Br, 6-Cl, 4-NH₂ |
| 5396 | Pr | Et—F | 2-Br, 6-Cl, 4-NHMe |
| 5397 | Pr | Et—F | 2-Br, 6-Cl, 4-NMe₂ |
| 5398 | Pr | Et—F | 2-Br, 6-Cl, 4-NMe₃OTf |
| 5399 | Pr | Et—F | 2-Br, 6-Cl, 4-NMe₃I |
| 5400 | Pr | Et—F | 2-Me, 6-Cl, 4-F |
| 5401 | Pr | Et—F | 2-SnMe₃, 6-Cl, 4-F |
| 5402 | Pr | Et—F | 2-Cl, 4-Me |
| 5403 | Pr | Et—F | 2-Cl, 4-Br |
| 5404 | Pr | Et—F | 2-Cl, 4-SnMe₃ |
| 5405 | Pr | Et—F | 2-Br, 4-Cl |
| 5406 | Pr | Et—F | 2-SnMe₃, 4-Cl |
| 5407 | Pr | Et—F | 2-Me, 4-Cl |
| 5408 | Pr | Et—F | 2-Br, 4-Br |
| 5409 | Pr | Et—F | 2-Br, 4-Me |
| 5410 | Pr | Et—F | 2-Br, 4-SnMe₃ |
| 5411 | Pr | Et—F | 2-SnMe₃, 4-Br |
| 5412 | Pr | Et—F | 2-Me, 4-Br |
| 5413 | Pr | Et—F | 2-Me, 4-SnMe₃ |
| 5414 | Pr | Et—F | 2-SnMe₃, 4-Me |
| 5415 | Pr | Et—F | 2-Me, 4-Me |
| 5416 | Pr | Et—F | 2-Et, 4-Br |
| 5417 | Pr | Et—F | 2-Et, 4-SnMe₃ |
| 5418 | Pr | Et—F | 2-Et, 4-Me |
| 5419 | Pr | Et—F | 2-Me, 4-Me, 6-Me |
| 5420 | Pr | Et—F | 2-Me, 4-Br, 6-Me |
| 5421 | Pr | Et—F | 2-Me, 4-SnMe₃, 6-Me |
| 5422 | Pr | Et—F | 2-Et, 6-Me |
| 5423 | Pr | Et—F | 2-Br, 4-i-Pr |
| 5424 | Pr | Et—F | 2-SnMe₃, 4-i-Pr |
| 5425 | Pr | Et—F | 2-Me, 4-i-Pr |
| 5426 | Pr | Et—F | 2-Br, 4-Br, 6-Br |
| 5427 | Pr | Et—F | 2-Br, 4-Me, 6-Br |
| 5428 | Pr | Et—F | 2-Br, 4-SnMe₃, 6-Br |
| 5429 | Pr | Et—F | 2-SnMe₃, 4-Br, 6-Br |
| 5430 | Pr | Et—F | 2-Br, 4-Br, 6-Me |

TABLE 5-continued

Substituent list for compounds of general structure X.

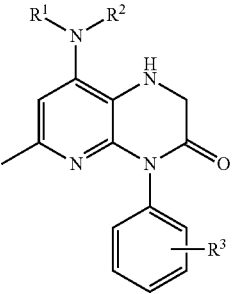

| Compound # | R¹ = | R² = | R³ = |
|---|---|---|---|
| 5431 | Pr | Et—F | 2-Br, 4-CF₃, 6-Br |
| 5432 | Pr | Et—F | 2-Br, 4-Br, 6-CF₃ |
| 5433 | Pr | Et—F | 2-CF₃, 4-CF₃ |
| 5434 | Pr | Et—F | 2-Cl, 4-CF₃ |
| 5435 | Pr | Et—F | 2-CF₃, 4-Cl |
| 5436 | Pr | Et—F | 2-Br, 4-CF₃ |
| 5437 | Pr | Et—F | 2-SnMe₃, 4-CF₃ |
| 5438 | Pr | Et—F | 2-Me, 4-CF₃ |
| 5439 | Pr | Et—F | 2-CF₃, 4-Br |
| 5440 | Pr | Et—F | 2-CF₃, 4-SnMe₃ |
| 5441 | Pr | Et—F | 2-CF₃, 4-Me |
| 5442 | Pr | Et—F | 2-Br, 4-OH |
| 5443 | Pr | Et—F | 2-Br, 4-OMe |
| 5444 | Pr | Et—F | 2-Br, 4-OMeF |
| 5445 | Pr | Et—F | 2-Br, 4-OCF₃ |
| 5446 | Pr | Et—F | 2-Br, 4-OEtF |
| 5447 | Pr | Et—F | 2-Br, 4-OPrF |
| 5448 | Pr | Et—F | 2-OH, 4-Br |
| 5449 | Pr | Et—F | 2-OMe, 4-Br |
| 5450 | Pr | Et—F | 2-OMeF, 4-Br |
| 5451 | Pr | Et—F | 2-OCF₃, 4-Br |
| 5452 | Pr | Et—F | 2-OEtF, 4-Br |
| 5453 | Pr | Et—F | 2-OPrF, 4-Br |
| 5454 | Pr | Et—F | 2-I, 4-OH |
| 5455 | Pr | Et—F | 2-I, 4-OMe |
| 5456 | Pr | Et—F | 2-I, 4-OMeF |
| 5457 | Pr | Et—F | 2-I, 4-OCF₃ |
| 5458 | Pr | Et—F | 2-I, 4-OEtF |
| 5459 | Pr | Et—F | 2-I, 4-OPrF |
| 5460 | Pr | Et—F | 2-OH, 4-I |
| 5461 | Pr | Et—F | 2-OMe, 4-I |
| 5462 | Pr | Et—F | 2-OMeF, 4-I |
| 5463 | Pr | Et—F | 2-OCF₃, 4-I |
| 5464 | Pr | Et—F | 2-OEtF, 4-I |
| 5465 | Pr | Et—F | 2-OPrF, 4-I |
| 5466 | Pr | Et—F | 2-SnMe₃, 4-OH |
| 5467 | Pr | Et—F | 2-SnMe₃, 4-OMe |
| 5468 | Pr | Et—F | 2-SnMe₃, 4-OMeF |
| 5469 | Pr | Et—F | 2-SnMe₃, 4-OCF |
| 5470 | Pr | Et—F | 2-SnMe₃, 4-OEtF |
| 5471 | Pr | Et—F | 2-SnMe₃, 4-OPrF |
| 5472 | Pr | Et—F | 2-OH, 4-SnMe₃ |
| 5473 | Pr | Et—F | 2-OMe, 4-SnMe₃ |
| 5474 | Pr | Et—F | 2-OMeF, 4-SnMe₃ |
| 5475 | Pr | Et—F | 2-OCF₃, 4-SnMe₃ |
| 5476 | Pr | Et—F | 2-OEtF, 4-SnMe₃ |
| 5477 | Pr | Et—F | 2-OPrF, 4-SnMe₃ |
| 5478 | Pr—F | Et | H |
| 5479 | Pr—F | Et | 2-t-Bu |
| 5480 | Pr—F | Et | 2-Br |
| 5481 | Pr—F | Et | 3-Br |
| 5482 | Pr—F | Et | 4-Br |
| 5483 | Pr—F | Et | 2-I |
| 5484 | Pr—F | Et | 3-I |
| 5485 | Pr—F | Et | 4-I |
| 5486 | Pr—F | Et | 2-SnMe₃ |
| 5487 | Pr—F | Et | 3-SnMe₃ |
| 5488 | Pr—F | Et | 4-SnMe₃ |
| 5489 | Pr—F | Et | 2-Me |
| 5490 | Pr—F | Et | 3-Me |

TABLE 5-continued

Substituent list for compounds of general structure X.

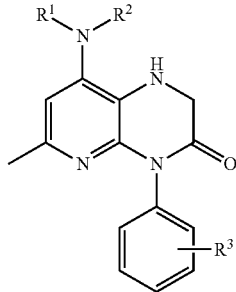

| Compound # | R¹ = | R² = | R³ = |
|---|---|---|---|
| 5491 | Pr—F | Et | 4-Me |
| 5492 | Pr—F | Et | 2-OH |
| 5493 | Pr—F | Et | 3-OH |
| 5494 | Pr—F | Et | 4-OH |
| 5495 | Pr—F | Et | 2-OMe |
| 5496 | Pr—F | Et | 3-OMe |
| 5497 | Pr—F | Et | 4-OMe |
| 5498 | Pr—F | Et | 2-OMeF |
| 5499 | Pr—F | Et | 3-OMeF |
| 5500 | Pr—F | Et | 4-OMeF |
| 5501 | Pr—F | Et | 2-OCF₃ |
| 5502 | Pr—F | Et | 3-OCF₃ |
| 5503 | Pr—F | Et | 4-OCF₃ |
| 5504 | Pr—F | Et | 2-OEtF |
| 5505 | Pr—F | Et | 3-OEtF |
| 5506 | Pr—F | Et | 4-OEtF |
| 5507 | Pr—F | Et | 2-OPrF |
| 5508 | Pr—F | Et | 3-OPrF |
| 5509 | Pr—F | Et | 4-OPrF |
| 5510 | Pr—F | Et | 2-SH |
| 5511 | Pr—F | Et | 3-SH |
| 5512 | Pr—F | Et | 4-SH |
| 5513 | Pr—F | Et | 2-SMe |
| 5514 | Pr—F | Et | 3-SMe |
| 5515 | Pr—F | Et | 4-SMe |
| 5516 | Pr—F | Et | 2-SMeF |
| 5517 | Pr—F | Et | 3-SMeF |
| 5518 | Pr—F | Et | 4-SMeF |
| 5519 | Pr—F | Et | 2-SCF₃ |
| 5520 | Pr—F | Et | 3-SCF₃ |
| 5521 | Pr—F | Et | 4-SCF₃ |
| 5522 | Pr—F | Et | 2-SEtF |
| 5523 | Pr—F | Et | 3-SEtF |
| 5524 | Pr—F | Et | 4-SEtF |
| 5525 | Pr—F | Et | 2-SPrF |
| 5526 | Pr—F | Et | 3-SPrF |
| 5527 | Pr—F | Et | 4-SPrF |
| 5528 | Pr—F | Et | 2-OMe, 4-OMe |
| 5529 | Pr—F | Et | 2-Me, 5-OH |
| 5530 | Pr—F | Et | 2-Me, 5-OMe |
| 5531 | Pr—F | Et | 2-Me, 5-OMeF |
| 5532 | Pr—F | Et | 2-Me, 5-OEtF |
| 5533 | Pr—F | Et | 2-Me, 5-OPrF |
| 5534 | Pr—F | Et | 2-Me, 4-OH |
| 5535 | Pr—F | Et | 2-Me, 4-OMe |
| 5536 | Pr—F | Et | 2-Me, 4-OMeF |
| 5537 | Pr—F | Et | 2-Me, 4-OCF₃ |
| 5538 | Pr—F | Et | 2-Me, 4-OEtF |
| 5539 | Pr—F | Et | 2-Me, 4-OPrF |
| 5540 | Pr—F | Et | 2-OH, 4-Me |
| 5541 | Pr—F | Et | 2-OMe, 4-Me |
| 5542 | Pr—F | Et | 2-OMeF, 4-Me |
| 5543 | Pr—F | Et | 2-OCF₃, 4-Me |
| 5544 | Pr—F | Et | 2-OEtF, 4-Me |
| 5545 | Pr—F | Et | 2-OPrF, 4-Me |
| 5546 | Pr—F | Et | 2-Cl, 4-OH |
| 5547 | Pr—F | Et | 2-Cl, 4-OMe |
| 5548 | Pr—F | Et | 2-Cl, 4-OMeF |
| 5549 | Pr—F | Et | 2-Cl, 4-OCF₃ |
| 5550 | Pr—F | Et | 2-Cl, 4-OEtF |

TABLE 5-continued

Substituent list for compounds of general structure X.

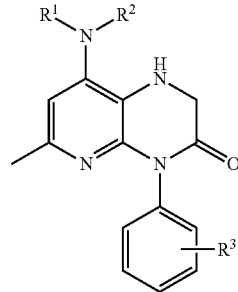

| Compound # | R¹ = | R² = | R³ = |
|---|---|---|---|
| 5551 | Pr—F | Et | 2-Cl, 4-OPrF |
| 5552 | Pr—F | Et | 2-F, 4-F |
| 5553 | Pr—F | Et | 2-Cl, 4-Cl |
| 5554 | Pr—F | Et | 2-Cl, 4-F |
| 5555 | Pr—F | Et | 2-Cl, 4-NO₂ |
| 5556 | Pr—F | Et | 2-Cl, 4-NH₂ |
| 5557 | Pr—F | Et | 2-Cl, 4-NHMe |
| 5558 | Pr—F | Et | 2-Cl, 4-NMe₂ |
| 5559 | Pr—F | Et | 2-Cl, 4-NMe₃OTf |
| 5560 | Pr—F | Et | 2-Cl, 4-NMe₃I |
| 5561 | Pr—F | Et | 2-Cl, 5-F |
| 5562 | Pr—F | Et | 2-Cl, 5-NO₂ |
| 5563 | Pr—F | Et | 2-Cl, 5-NH₂ |
| 5564 | Pr—F | Et | 2-Cl, 5-NHMe |
| 5565 | Pr—F | Et | 2-Cl, 5-NMe₂ |
| 5566 | Pr—F | Et | 2-Cl, 5-NMe₃OTf |
| 5567 | Pr—F | Et | 2-Cl, 5-NMe₃I |
| 5568 | Pr—F | Et | 2-F, 4-Cl |
| 5569 | Pr—F | Et | 2-NO₂, 4-Cl |
| 5570 | Pr—F | Et | 2-NH₂, 4-Cl |
| 5571 | Pr—F | Et | 2-NHMe, 4-Cl |
| 5572 | Pr—F | Et | 2-NMe₂, 4-Cl |
| 5573 | Pr—F | Et | 2-NMe₃OTf, 4-Cl |
| 5574 | Pr—F | Et | 2-NMe₃I, 4-Cl |
| 5575 | Pr—F | Et | 2-F, 5-Cl |
| 5576 | Pr—F | Et | 2-NO₂, 5-Cl |
| 5577 | Pr—F | Et | 2-NH₂, 5-Cl |
| 5578 | Pr—F | Et | 2-NHMe, 5-Cl |
| 5579 | Pr—F | Et | 2-NMe₂, 5-Cl |
| 5580 | Pr—F | Et | 2-NMe₃OTf, 5-Cl |
| 5581 | Pr—F | Et | 2-NMe₃I, 5-Cl |
| 5582 | Pr—F | Et | 2-Br, 4-F |
| 5583 | Pr—F | Et | 2-Br, 4-NO₂ |
| 5584 | Pr—F | Et | 2-Br, 4-NH₂ |
| 5585 | Pr—F | Et | 2-Br, 4-NHMe |
| 5586 | Pr—F | Et | 2-Br, 4-NMe₂ |
| 5587 | Pr—F | Et | 2-Br, 4-NMe₃OTf |
| 5588 | Pr—F | Et | 2-Br, 4-NMe₃I |
| 5589 | Pr—F | Et | 2-Br, 5-F |
| 5590 | Pr—F | Et | 2-Br, 5-NO₂ |
| 5591 | Pr—F | Et | 2-Br, 5-NH₂ |
| 5592 | Pr—F | Et | 2-Br, 5-NHMe |
| 5593 | Pr—F | Et | 2-Br, 5-NMe₂ |
| 5594 | Pr—F | Et | 2-Br, 5-NMe₃OTf |
| 5595 | Pr—F | Et | 2-Br, 5-NMe₃I |
| 5596 | Pr—F | Et | 2-F, 4-Br |
| 5597 | Pr—F | Et | 2-NO₂, 4-Br |
| 5598 | Pr—F | Et | 2-NH₂, 4-Br |
| 5599 | Pr—F | Et | 2-NHMe, 4-Br |
| 5600 | Pr—F | Et | 2-NMe₂, 4-Br |
| 5601 | Pr—F | Et | 2-NMe₃OTf, 4-Br |
| 5602 | Pr—F | Et | 2-NMe₃I, 4-Br |
| 5603 | Pr—F | Et | 2-I, 4-F |
| 5604 | Pr—F | Et | 2-I, 4-NO₂ |
| 5605 | Pr—F | Et | 2-I, 4-NH₂ |
| 5606 | Pr—F | Et | 2-I, 4-NHMe |
| 5607 | Pr—F | Et | 2-I, 4-NMe₂ |
| 5608 | Pr—F | Et | 2-I, 4-NMe₃OTf |
| 5609 | Pr—F | Et | 2-I, 4-NMe₃I |
| 5610 | Pr—F | Et | 2-F, 4-I |

TABLE 5-continued

Substituent list for compounds of general structure X.

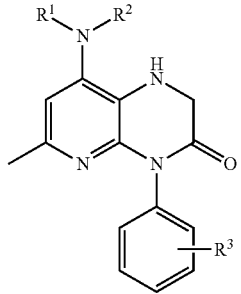

| Compound # | R¹ = | R² = | R³ = |
|---|---|---|---|
| 5611 | Pr—F | Et | 2-NO$_2$, 4-I |
| 5612 | Pr—F | Et | 2-NH$_2$, 4-I |
| 5613 | Pr—F | Et | 2-NHMe, 4-I |
| 5614 | Pr—F | Et | 2-NMe$_2$, 4-I |
| 5615 | Pr—F | Et | 2-NMe$_3$OTf, 4-I |
| 5616 | Pr—F | Et | 2-NMe$_3$I, 4-I |
| 5617 | Pr—F | Et | 2-Me, 3-F |
| 5618 | Pr—F | Et | 2-Me, 3-NO$_2$ |
| 5619 | Pr—F | Et | 2-Me, 3-NH$_2$ |
| 5620 | Pr—F | Et | 2-Me, 3-NHMe |
| 5621 | Pr—F | Et | 2-Me, 3-NMe$_2$ |
| 5622 | Pr—F | Et | 2-Me, 3-NMe$_3$OTf |
| 5623 | Pr—F | Et | 2-Me, 3-NMe$_3$I |
| 5624 | Pr—F | Et | 2-Me, 4-F |
| 5625 | Pr—F | Et | 2-Me, 4-NO$_2$ |
| 5626 | Pr—F | Et | 2-Me, 4-NH$_2$ |
| 5627 | Pr—F | Et | 2-Me, 4-NHMe |
| 5628 | Pr—F | Et | 2-Me, 4-NMe$_2$ |
| 5629 | Pr—F | Et | 2-Me, 4-NMe$_3$OTf |
| 5630 | Pr—F | Et | 2-Me, 4-NMe$_3$I |
| 5631 | Pr—F | Et | 2-Me, 5-F |
| 5632 | Pr—F | Et | 2-Me, 5-NO$_2$ |
| 5633 | Pr—F | Et | 2-Me, 5-NH$_2$ |
| 5634 | Pr—F | Et | 2-Me, 5-NHMe |
| 5635 | Pr—F | Et | 2-Me, 5-NMe$_2$ |
| 5636 | Pr—F | Et | 2-Me, 5-NMe$_3$OTf |
| 5637 | Pr—F | Et | 2-Me, 5-NMe$_3$I |
| 5638 | Pr—F | Et | 2-F, 4-Me |
| 5639 | Pr—F | Et | 2-NO$_2$, 4-Me |
| 5640 | Pr—F | Et | 2-NH$_2$, 4-Me |
| 5641 | Pr—F | Et | 2-NHMe, 4-Me |
| 5642 | Pr—F | Et | 2-NMe$_2$, 4-Me |
| 5643 | Pr—F | Et | 2-NMe$_3$, 4-Me |
| 5644 | Pr—F | Et | 2-NMe$_3$OTf, 4-Me |
| 5645 | Pr—F | Et | 2-NMe$_3$I, 4-Me |
| 5646 | Pr—F | Et | 2-SnMe$_3$, 4-F |
| 5647 | Pr—F | Et | 2-SnMe$_3$, 5-F |
| 5648 | Pr—F | Et | 2-F, 4-SnMe$_3$ |
| 5649 | Pr—F | Et | 2-Br, 6-Cl, 4-F |
| 5650 | Pr—F | Et | 2-Br, 6-Cl, 4-NO$_2$ |
| 5651 | Pr—F | Et | 2-Br, 6-Cl, 4-NH$_2$ |
| 5652 | Pr—F | Et | 2-Br, 6-Cl, 4-NHMe |
| 5653 | Pr—F | Et | 2-Br, 6-Cl, 4-NMe$_2$ |
| 5654 | Pr—F | Et | 2-Br, 6-Cl, 4-NMe$_3$OTf |
| 5655 | Pr—F | Et | 2-Br, 6-Cl, 4-NMe$_3$I |
| 5656 | Pr—F | Et | 2-Me, 6-Cl, 4-F |
| 5657 | Pr—F | Et | 2-SnMe$_3$, 6-Cl, 4-F |
| 5658 | Pr—F | Et | 2-Cl, 4-Me |
| 5659 | Pr—F | Et | 2-Cl, 4-Br |
| 5660 | Pr—F | Et | 2-Cl, 4-SnMe$_3$ |
| 5661 | Pr—F | Et | 2-Br, 4-Cl |
| 5662 | Pr—F | Et | 2-SnMe$_3$, 4-Cl |
| 5663 | Pr—F | Et | 2-Me, 4-Cl |
| 5664 | Pr—F | Et | 2-Br, 4-Br |
| 5665 | Pr—F | Et | 2-Br, 4-Me |
| 5666 | Pr—F | Et | 2-Br, 4-SnMe$_3$ |
| 5667 | Pr—F | Et | 2-SnMe$_3$, 4-Br |
| 5668 | Pr—F | Et | 2-Me, 4-Br |
| 5669 | Pr—F | Et | 2-Me, 4-SnMe$_3$ |
| 5670 | Pr—F | Et | 2-SnMe$_3$, 4-Me |

TABLE 5-continued

Substituent list for compounds of general structure X.

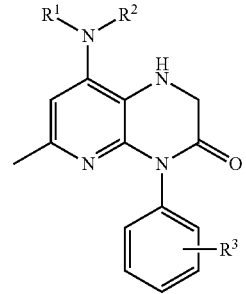

| Compound # | R¹ = | R² = | R³ = |
|---|---|---|---|
| 5671 | Pr—F | Et | 2-Me, 4-Me |
| 5672 | Pr—F | Et | 2-Et, 4-Br |
| 5673 | Pr—F | Et | 2-Et, 4-SnMe$_3$ |
| 5674 | Pr—F | Et | 2-Et, 4-Me |
| 5675 | Pr—F | Et | 2-Me, 4-Me, 6-Me |
| 5676 | Pr—F | Et | 2-Me, 4-Br, 6-Me |
| 5677 | Pr—F | Et | 2-Me, 4-SnMe$_3$, 6-Me |
| 5678 | Pr—F | Et | 2-Et, 6-Me |
| 5679 | Pr—F | Et | 2-Br, 4-i-Pr |
| 5680 | Pr—F | Et | 2-SnMe$_3$, 4-i-Pr |
| 5681 | Pr—F | Et | 2-Me, 4-i-Pr |
| 5682 | Pr—F | Et | 2-Br, 4-Br, 6-Br |
| 5683 | Pr—F | Et | 2-Br, 4-Me, 6-Br |
| 5684 | Pr—F | Et | 2-Br, 4-SnMe$_3$, 6-Br |
| 5685 | Pr—F | Et | 2-SnMe$_3$, 4-Br, 6-Br |
| 5686 | Pr—F | Et | 2-Br, 4-Br, 6-Me |
| 5687 | Pr—F | Et | 2-Br, 4-CF$_3$, 6-Br |
| 5688 | Pr—F | Et | 2-Br, 4-Br, 6-CF$_3$ |
| 5689 | Pr—F | Et | 2-CF$_3$, 4-CF$_3$ |
| 5690 | Pr—F | Et | 2-Cl, 4-CF$_3$ |
| 5691 | Pr—F | Et | 2-CF$_3$, 4-Cl |
| 5692 | Pr—F | Et | 2-Br, 4-CF$_3$ |
| 5693 | Pr—F | Et | 2-SnMe$_3$, 4-CF$_3$ |
| 5694 | Pr—F | Et | 2-Me, 4-CF$_3$ |
| 5695 | Pr—F | Et | 2-CF$_3$, 4-Br |
| 5696 | Pr—F | Et | 2-CF$_3$, 4-SnMe$_3$ |
| 5697 | Pr—F | Et | 2-CF$_3$, 4-Me |
| 5698 | Pr—F | Et | 2-Br, 4-OH |
| 5699 | Pr—F | Et | 2-Br, 4-OMe |
| 5700 | Pr—F | Et | 2-Br, 4-OMeF |
| 5701 | Pr—F | Et | 2-Br, 4-OCF$_3$ |
| 5702 | Pr—F | Et | 2-Br, 4-OEtF |
| 5703 | Pr—F | Et | 2-Br, 4-OPrF |
| 5704 | Pr—F | Et | 2-OH, 4-Br |
| 5705 | Pr—F | Et | 2-OMe, 4-Br |
| 5706 | Pr—F | Et | 2-OMeF, 4-Br |
| 5707 | Pr—F | Et | 2-OCF$_3$, 4-Br |
| 5708 | Pr—F | Et | 2-OEtF, 4-Br |
| 5709 | Pr—F | Et | 2-OPrF, 4-Br |
| 5710 | Pr—F | Et | 2-I, 4-OH |
| 5711 | Pr—F | Et | 2-I, 4-OMe |
| 5712 | Pr—F | Et | 2-I, 4-OMeF |
| 5713 | Pr—F | Et | 2-I, 4-OCF$_3$ |
| 5714 | Pr—F | Et | 2-I, 4-OEtF |
| 5715 | Pr—F | Et | 2-I, 4-OPrF |
| 5716 | Pr—F | Et | 2-OH, 4-I |
| 5717 | Pr—F | Et | 2-OMe, 4-I |
| 5718 | Pr—F | Et | 2-OMeF, 4-I |
| 5719 | Pr—F | Et | 2-OCF$_3$, 4-I |
| 5720 | Pr—F | Et | 2-OEtF, 4-I |
| 5721 | Pr—F | Et | 2-OPrF, 4-I |
| 5722 | Pr—F | Et | 2-SnMe$_3$, 4-OH |
| 5723 | Pr—F | Et | 2-SnMe$_3$, 4-OMe |
| 5724 | Pr—F | Et | 2-SnMe$_3$, 4-OMeF |
| 5725 | Pr—F | Et | 2-SnMe$_3$, 4-OCF$_3$ |
| 5726 | Pr—F | Et | 2-SnMe$_3$, 4-OEtF |
| 5727 | Pr—F | Et | 2-SnMe$_3$, 4-OPrF |
| 5728 | Pr—F | Et | 2-OH, 4-SnMe$_3$ |
| 5729 | Pr—F | Et | 2-OMe, 4-SnMe$_3$ |
| 5730 | Pr—F | Et | 2-OMeF, 4-SnMe$_3$ |

TABLE 5-continued

Substituent list for compounds of general structure X.

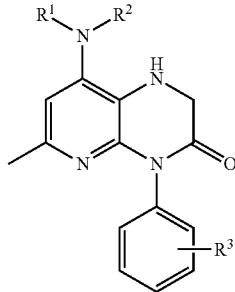

| Compound # | R¹ = | R² = | R³ = |
|---|---|---|---|
| 5731 | Pr—F | Et | 2-OCF3, 4-SnMe₃ |
| 5732 | Pr—F | Et | 2-OEtF, 4-SnMe₃ |
| 5733 | Pr—F | Et | 2-OPrF, 4-SnMe₃ |
| 5734 | Bu | Et—F | H |
| 5735 | Bu | Et—F | 2-t-Bu |
| 5736 | Bu | Et—F | 2-Br |
| 5737 | Bu | Et—F | 3-Br |
| 5738 | Bu | Et—F | 4-Br |
| 5739 | Bu | Et—F | 2-I |
| 5740 | Bu | Et—F | 3-I |
| 5741 | Bu | Et—F | 4-I |
| 5742 | Bu | Et—F | 2-SnMe₃ |
| 5743 | Bu | Et—F | 3-SnMe₃ |
| 5744 | Bu | Et—F | 4-SnMe₃ |
| 5745 | Bu | Et—F | 2-Me |
| 5746 | Bu | Et—F | 3-Me |
| 5747 | Bu | Et—F | 4-Me |
| 5748 | Bu | Et—F | 2-OH |
| 5749 | Bu | Et—F | 3-OH |
| 5750 | Bu | Et—F | 4-OH |
| 5751 | Bu | Et—F | 2-OMe |
| 5752 | Bu | Et—F | 3-OMe |
| 5753 | Bu | Et—F | 4-OMe |
| 5754 | Bu | Et—F | 2-OMeF |
| 5755 | Bu | Et—F | 3-OMeF |
| 5756 | Bu | Et—F | 4-OMeF |
| 5757 | Bu | Et—F | 2-OCF₃ |
| 5758 | Bu | Et—F | 3-OCF₃ |
| 5759 | Bu | Et—F | 4-OCF₃ |
| 5760 | Bu | Et—F | 2-OEtF |
| 5761 | Bu | Et—F | 3-OEtF |
| 5762 | Bu | Et—F | 4-OEtF |
| 5763 | Bu | Et—F | 2-OPrF |
| 5764 | Bu | Et—F | 3-OPrF |
| 5765 | Bu | Et—F | 4-OPrF |
| 5766 | Bu | Et—F | 2-SH |
| 5767 | Bu | Et—F | 3-SH |
| 5768 | Bu | Et—F | 4-SH |
| 5769 | Bu | Et—F | 2-SMe |
| 5770 | Bu | Et—F | 3-SMe |
| 5771 | Bu | Et—F | 4-SMe |
| 5772 | Bu | Et—F | 2-SMeF |
| 5773 | Bu | Et—F | 3-SMeF |
| 5774 | Bu | Et—F | 4-SMeF |
| 5775 | Bu | Et—F | 2-SCF₃ |
| 5776 | Bu | Et—F | 3-SCF₃ |
| 5777 | Bu | Et—F | 4-SCF₃ |
| 5778 | Bu | Et—F | 2-SEtF |
| 5779 | Bu | Et—F | 3-SEtF |
| 5780 | Bu | Et—F | 4-SEtF |
| 5781 | Bu | Et—F | 2-SPrF |
| 5782 | Bu | Et—F | 3-SPrF |
| 5783 | Bu | Et—F | 4-SPrF |
| 5784 | Bu | Et—F | 2-OMe, 4-OMe |
| 5785 | Bu | Et—F | 2-Me, 5-OH |
| 5786 | Bu | Et—F | 2-Me, 5-OMe |
| 5787 | Bu | Et—F | 2-Me, 5-OMeF |
| 5788 | Bu | Et—F | 2-Me, 5-OEtF |
| 5789 | Bu | Et—F | 2-Me, 5-OPrF |
| 5790 | Bu | Et—F | 2-Me, 4-OH |

TABLE 5-continued

Substituent list for compounds of general structure X.

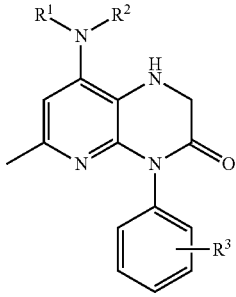

| Compound # | R¹ = | R² = | R³ = |
|---|---|---|---|
| 5791 | Bu | Et—F | 2-Me, 4-OMe |
| 5792 | Bu | Et—F | 2-Me, 4-OMeF |
| 5793 | Bu | Et—F | 2-Me, 4-OCF₃ |
| 5794 | Bu | Et—F | 2-Me, 4-OEtF |
| 5795 | Bu | Et—F | 2-Me, 4-OPrF |
| 5796 | Bu | Et—F | 2-OH, 4-Me |
| 5797 | Bu | Et—F | 2-OMe, 4-Me |
| 5798 | Bu | Et—F | 2-OMeF, 4-Me |
| 5799 | Bu | Et—F | 2-OCF₃, 4-Me |
| 5800 | Bu | Et—F | 2-OEtF, 4-Me |
| 5801 | Bu | Et—F | 2-OPrF, 4-Me |
| 5802 | Bu | Et—F | 2-Cl, 4-OH |
| 5803 | Bu | Et—F | 2-Cl, 4-OMe |
| 5804 | Bu | Et—F | 2-Cl, 4-OMeF |
| 5805 | Bu | Et—F | 2-Cl, 4-OCF₃ |
| 5806 | Bu | Et—F | 2-Cl, 4-OEtF |
| 5807 | Bu | Et—F | 2-Cl, 4-OPrF |
| 5808 | Bu | Et—F | 2-F, 4-F |
| 5809 | Bu | Et—F | 2-Cl, 4-Cl |
| 5810 | Bu | Et—F | 2-Cl, 4-F |
| 5811 | Bu | Et—F | 2-Cl, 4-NO₂ |
| 5812 | Bu | Et—F | 2-Cl, 4-NH₂ |
| 5813 | Bu | Et—F | 2-Cl, 4-NHMe |
| 5814 | Bu | Et—F | 2-Cl, 4-NMe₂ |
| 5815 | Bu | Et—F | 2-Cl, 4-NMe₃OTf |
| 5816 | Bu | Et—F | 2-Cl, 4-NMe₃I |
| 5817 | Bu | Et—F | 2-Cl, 5-F |
| 5818 | Bu | Et—F | 2-Cl, 5-NO₂ |
| 5819 | Bu | Et—F | 2-Cl, 5-NH₂ |
| 5820 | Bu | Et—F | 2-Cl, 5-NHMe |
| 5821 | Bu | Et—F | 2-Cl, 5-NMe₂ |
| 5822 | Bu | Et—F | 2-Cl, 5-NMe₃OTf |
| 5823 | Bu | Et—F | 2-Cl, 5- NMe₃I |
| 5824 | Bu | Et—F | 2-F, 4-Cl |
| 5825 | Bu | Et—F | 2-NO₂, 4-Cl |
| 5826 | Bu | Et—F | 2-NH₂, 4-Cl |
| 5827 | Bu | Et—F | 2-NHMe, 4-Cl |
| 5828 | Bu | Et—F | 2-NMe₂, 4-C |
| 5829 | Bu | Et—F | 2-NMe₃OTf, 4-Cl |
| 5830 | Bu | Et—F | 2-NMe₃I, 4-Cl |
| 5831 | Bu | Et—F | 2-F, 5-Cl |
| 5832 | Bu | Et—F | 2-NO₂, 5-Cl |
| 5833 | Bu | Et—F | 2-NH₂, 5-Cl |
| 5834 | Bu | Et—F | 2-NHMe, 5-Cl |
| 5835 | Bu | Et—F | 2-NMe₂, 5-Cl |
| 5836 | Bu | Et—F | 2-NMe₃OTf, 5-Cl |
| 5837 | Bu | Et—F | 2-NMe₃I, 5-Cl |
| 5838 | Bu | Et—F | 2-Br, 4-F |
| 5839 | Bu | Et—F | 2-Br, 4-NO₂ |
| 5840 | Bu | Et—F | 2-Br, 4-NH₂ |
| 5841 | Bu | Et—F | 2-Br, 4-NHMe |
| 5842 | Bu | Et—F | 2-Br, 4-NMe₂ |
| 5843 | Bu | Et—F | 2-Br, 4-NMe₃OTf |
| 5844 | Bu | Et—F | 2-Br, 4-NMe₃I |
| 5845 | Bu | Et—F | 2-Br, 5-F |
| 5846 | Bu | Et—F | 2-Br, 5-NO₂ |
| 5847 | Bu | Et—F | 2-Br, 5-NH₂ |
| 5848 | Bu | Et—F | 2-Br, 5-NHMe |
| 5849 | Bu | Et—F | 2-Br, 5-NMe₂ |
| 5850 | Bu | Et—F | 2-Br, 5-NMe₃OTf |

TABLE 5-continued

Substituent list for compounds of general structure X.

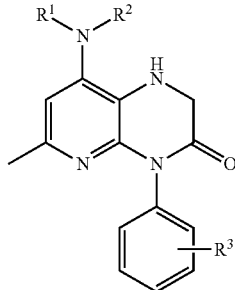

| Compound # | R¹ = | R² = | R³ = |
|---|---|---|---|
| 5851 | Bu | Et—F | 2-Br, 5-NMe₃I |
| 5852 | Bu | Et—F | 2-F, 4-Br |
| 5853 | Bu | Et—F | 2-NO₂, 4-Br |
| 5854 | Bu | Et—F | 2-NH₂, 4-Br |
| 5855 | Bu | Et—F | 2-NHMe, 4-Br |
| 5856 | Bu | Et—F | 2-NMe₂, 4-Br |
| 5857 | Bu | Et—F | 2-NMe₃OTf, 4-Br |
| 5858 | Bu | Et—F | 2-NMe₃I, 4-Br |
| 5859 | Bu | Et—F | 2-I, 4-F |
| 5860 | Bu | Et—F | 2-I, 4-NO₂ |
| 5861 | Bu | Et—F | 2-I, 4-NH₂ |
| 5862 | Bu | Et—F | 2-I, 4-NHMe |
| 5863 | Bu | Et—F | 2-I, 4-NMe₂ |
| 5864 | Bu | Et—F | 2-I, 4-NMe₃OTf |
| 5865 | Bu | Et—F | 2-I, 4-NMe₃I |
| 5866 | Bu | Et—F | 2-F, 4-I |
| 5867 | Bu | Et—F | 2-NO₂, 4-I |
| 5868 | Bu | Et—F | 2-NH₂, 4-I |
| 5869 | Bu | Et—F | 2-NHMe, 4-I |
| 5870 | Bu | Et—F | 2-NMe₂, 4-I |
| 5871 | Bu | Et—F | 2-NMe₃OTf, 4-I |
| 5872 | Bu | Et—F | 2-NMe₃I, 4-I |
| 5873 | flu | Et—F | 2-Me, 3-F |
| 5874 | Bu | Et—F | 2-Me, 3-NO₂ |
| 5875 | Bu | Et—F | 2-Me, 3-NH₂ |
| 5876 | Bu | Et—F | 2-Me, 3-NHMe |
| 5877 | Bu | Et—F | 2-Me, 3-NMe₂ |
| 5878 | Bu | Et—F | 2-Me, 3-NMe₃OTf |
| 5879 | Bu | Et—F | 2-Me, 3-NMe₃I |
| 5880 | Bu | Et—F | 2-Me, 4-F |
| 5881 | Bu | Et—F | 2-Me, 4-NO₂ |
| 5882 | Bu | Et—F | 2-Me, 4-NH₂ |
| 5883 | Bu | Et—F | 2-Me, 4-NHMe |
| 5884 | Bu | Et—F | 2-Me, 4-NMe₂ |
| 5885 | Bu | Et—F | 2-Me, 4-NMe₃OTf |
| 5886 | Bu | Et—F | 2-Me, 4-NMe₃I |
| 5887 | Bu | Et—F | 2-Me, 5-F |
| 5888 | Bu | Et—F | 2-Me, 5-NO₂ |
| 5889 | Bu | Et—F | 2-Me, 5-NH₂ |
| 5890 | Bu | Et—F | 2-Me, 5-NHMe |
| 5891 | Bu | Et—F | 2-Me, 5-NMe₂ |
| 5892 | Bu | Et—F | 2-Me, 5-NMe₃OTf |
| 5893 | Bu | Et—F | 2-Me, 5-NMe₃I |
| 5894 | Bu | Et—F | 2-F, 4-Me |
| 5895 | Bu | Et—F | 2-NO₂, 4-Me |
| 5896 | Bu | Et—F | 2-NH₂, 4-Me |
| 5897 | Bu | Et—F | 2-NHMe, 4-Me |
| 5898 | Bu | Et—F | 2-NMe₂, 4-Me |
| 5899 | Bu | Et—F | 2-NMe₃, 4-Me |
| 5900 | Bu | Et—F | 2-NMe₃OTf, 4-Me |
| 5901 | Bu | Et—F | 2-NMe₃I, 4-Me |
| 5902 | Bu | Et—F | 2-SnMe₃, 4-F |
| 5903 | Bu | Et—F | 2-SnMe₃, 5-F |
| 5904 | Bu | Et—F | 2-F, 4-SnMe₃ |
| 5905 | Bu | Et—F | 2-Br, 6-Cl, 4-F |
| 5906 | Bu | Et—F | 2-Br, 6-Cl, 4-NO₂ |
| 5907 | Bu | Et—F | 2-Br, 6-Cl, 4-NH₂ |
| 5908 | Bu | Et—F | 2-Br, 6-Cl, 4-NHMe |
| 5909 | Bu | Et—F | 2-Br, 6-Cl, 4-NMe₂ |
| 5910 | Bu | Et—F | 2-Br, 6-Cl, 4-NMe₃OTf |

TABLE 5-continued

Substituent list for compounds of general structure X.

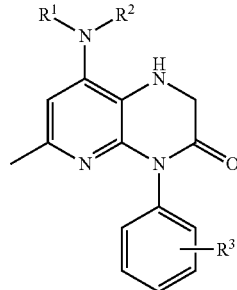

| Compound # | R¹ = | R² = | R³ = |
|---|---|---|---|
| 5911 | Bu | Et—F | 2-Br, 6-Cl, 4-NMe₃I |
| 5912 | Bu | Et—F | 2-Me, 6-Cl, 4-F |
| 5913 | Bu | Et—F | 2-SnMe₃, 6-Cl, 4-F |
| 5914 | Bu | Et—F | 2-Cl, 4-Me |
| 5915 | Bu | Et—F | 2-Cl, 4-Br |
| 5916 | Bu | Et—F | 2-Cl, 4-SnMe₃ |
| 5917 | Bu | Et—F | 2-Br, 4-Cl |
| 5918 | Bu | Et—F | 2-SnMe₃, 4-Cl |
| 5919 | Bu | Et—F | 2-Me, 4-Cl |
| 5920 | Bu | Et—F | 2-Br, 4-Br |
| 5921 | Bu | Et—F | 2-Br, 4-Me |
| 5922 | Bu | Et—F | 2-Br, 4-SnMe₃ |
| 5923 | Bu | Et—F | 2-SnMe₃, 4-Br |
| 5924 | Bu | Et—F | 2-Me, 4-Br |
| 5925 | Bu | Et—F | 2-Me, 4-SnMe₃ |
| 5926 | Bu | Et—F | 2-SnMe₃, 4-Me |
| 5927 | Bu | Et—F | 2-Me, 4-Me |
| 5928 | Bu | Et—F | 2-Et, 4-Br |
| 5929 | Bu | Et—F | 2-Et, 4-SnMe₃ |
| 5930 | Bu | Et—F | 2-Et, 4-Me |
| 5931 | Bu | Et—F | 2-Me, 4-Me, 6-Me |
| 5932 | Bu | Et—F | 2-Me, 4-Br, 6-Me |
| 5933 | Bu | Et—F | 2-Me, 4-SnMe₃, 6-Me |
| 5934 | Bu | Et—F | 2-Et, 6-Me |
| 5935 | Bu | Et—F | 2-Br, 4-i-Pr |
| 5936 | Bu | Et—F | 2-SnMe₃, 4-i-Pr |
| 5937 | Bu | Et—F | 2-Me, 4-i-Pr |
| 5938 | Bu | Et—F | 2-Br, 4-Br, 6-Br |
| 5939 | Bu | Et—F | 2-Br, 4-Me, 6-Br |
| 5940 | Bu | Et—F | 2-Br, 4-SnMe₃, 6-Br |
| 5941 | Bu | Et—F | 2-SnMe₃, 4-Br, 6-Br |
| 5942 | Bu | Et—F | 2-Br, 4-Br, 6-Me |
| 5943 | Bu | Et—F | 2-Br, 4-CF₃, 6-Br |
| 5944 | Bu | Et—F | 2-Br, 4-Br, 6-CF₃ |
| 5945 | Bu | Et—F | 2-CF₃, 4-CF₃ |
| 5946 | Bu | Et—F | 2-Cl, 4-CF₃ |
| 5947 | Bu | Et—F | 2-CF₃, 4-Cl |
| 5948 | Bu | Et—F | 2-Br, 4-CF₃ |
| 5949 | Bu | Et—F | 2-SnMe₃, 4-CF₃ |
| 5950 | Bu | Et—F | 2-Me, 4-CF₃ |
| 5951 | Bu | Et—F | 2-CF₃, 4-Br |
| 5952 | Bu | Et—F | 2-CF₃, 4-SnMe₃ |
| 5953 | Bu | Et—F | 2-CF₃, 4-Me |
| 5954 | Bu | Et—F | 2-Br, 4-OH |
| 5955 | Bu | Et—F | 2-Br, 4-OMe |
| 5956 | Bu | Et—F | 2-Br, 4-OMeF |
| 5957 | Bu | Et—F | 2-Br, 4-OCF₃ |
| 5958 | Bu | Et—F | 2-Br, 4-OEtF |
| 5959 | Bu | Et—F | 2-Br, 4-OPrF |
| 5960 | Bu | Et—F | 2-OH, 4-Br |
| 5961 | Bu | Et—F | 2-OMe, 4-Br |
| 5962 | Bu | Et—F | 2-OMeF, 4-Br |
| 5963 | Bu | Et—F | 2-OCF₃, 4-Br |
| 5964 | Bu | Et—F | 2-OEtF, 4-Br |
| 5965 | Bu | Et—F | 2-OPrF, 4-Br |
| 5966 | Bu | Et—F | 2-I, 4-OH |
| 5967 | Bu | Et—F | 2-I, 4-OMe |
| 5968 | Bu | Et—F | 2-I, 4-OMeF |
| 5969 | Bu | Et—F | 2-I, 4-OCF₃ |
| 5970 | Bu | Et—F | 2-I, 4-OEtF |

TABLE 5-continued

Substituent list for compounds of general structure X.

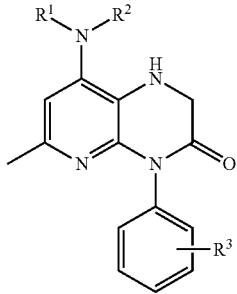

| Compound # | R¹ = | R² = | R³ = |
|---|---|---|---|
| 5971 | Bu | Et—F | 2-I, 4-OPrF |
| 5972 | Bu | Et—F | 2-OH, 4-I |
| 5973 | Bu | Et—F | 2-OMe, 4-I |
| 5974 | Bu | Et—F | 2-OMeF, 4-I |
| 5975 | Bu | Et—F | 2-OCF₃, 4-I |
| 5976 | Bu | Et—F | 2-OEtF, 4-I |
| 5977 | Bu | Et—F | 2-OPrF, 4-I |
| 5978 | Bu | Et—F | 2-SnMe₃, 4-OH |
| 5979 | Bu | Et—F | 2-SnMe₃, 4-OMe |
| 5980 | Bu | Et—F | 2-SnMe₃, 4-OMeF |
| 5981 | Bu | Et—F | 2-SnMe₃, 4-OCF₃ |
| 5982 | Bu | Et—F | 2-SnMe₃, 4-OEtF |
| 5983 | Bu | Et—F | 2-SnMe₃, 4-OPrF |
| 5984 | Bu | Et—F | 2-OH, 4-SnMe₃ |
| 5985 | Bu | Et—F | 2-OMe, 4-SnMe₃ |
| 5986 | Bu | Et—F | 2-OMeF, 4-SnMe₃ |
| 5987 | Bu | Et—F | 2-OCF₃, 4-SnMe₃ |
| 5988 | Bu | Et—F | 2-OEtF, 4-SnMe₃ |
| 5989 | Bu | Et—F | 2-OPrF, 4-SnMe₃ |
| 5990 | Bu—F | Et | H |
| 5991 | Bu—F | Et | 2-t-Bu |
| 5992 | Bu—F | Et | 2-Br |
| 5993 | Bu—F | Et | 3-Br |
| 5994 | Bu—F | Et | 4-Br |
| 5995 | Bu—F | Et | 2-I |
| 5996 | Bu—F | Et | 3-I |
| 5997 | Bu—F | Et | 4-I |
| 5998 | Bu—F | Et | 2-SnMe₃ |
| 5999 | Bu—F | Et | 3-SnMe₃ |
| 6000 | Bu—F | Et | 4-SnMe₃ |
| 6001 | Bu—F | Et | 2-Me |
| 6002 | Bu—F | Et | 3-Me |
| 6003 | Bu—F | Et | 4-Me |
| 6004 | Bu—F | Et | 2-OH |
| 6005 | Bu—F | Et | 3-OH |
| 6006 | Bu—F | Et | 4-OH |
| 6007 | Bu—F | Et | 2-OMe |
| 6008 | Bu—F | Et | 3-OMe |
| 6009 | Bu—F | Et | 4-OMe |
| 6010 | Bu—F | Et | 2-OMeF |
| 6011 | Bu—F | Et | 3-OMeF |
| 6012 | Bu—F | Et | 4-OMeF |
| 6013 | Bu—F | Et | 2-OCF₃ |
| 6014 | Bu—F | Et | 3-OCF₃ |
| 6015 | Bu—F | Et | 4-OCF₃ |
| 6016 | Bu—F | Et | 2-OEtF |
| 6017 | Bu—F | Et | 3-OEtF |
| 6018 | Bu—F | Et | 4-OEtF |
| 6019 | Bu—F | Et | 2-OPrF |
| 6020 | Bu—F | Et | 3-OPrF |
| 6021 | Bu—F | Et | 4-OPrF |
| 6022 | Bu—F | Et | 2-SH |
| 6023 | Bu—F | Et | 3-SH |
| 6024 | Bu—F | Et | 4-SH |
| 6025 | Bu—F | Et | 2-SMe |
| 6026 | Bu—F | Et | 3-SMe |
| 6027 | Bu—F | Et | 4-SMe |
| 6028 | Bu—F | Et | 2-SMeF |
| 6029 | Bu—F | Et | 3-SMeF |
| 6030 | Bu—F | Et | 4-SMeF |

TABLE 5-continued

Substituent list for compounds of general structure X.

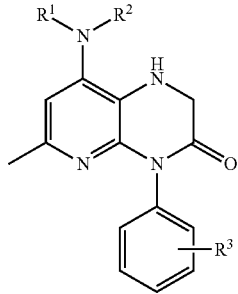

| Compound # | R¹ = | R² = | R³ = |
|---|---|---|---|
| 6031 | Bu—F | Et | 2-SCF₃ |
| 6032 | Bu—F | Et | 3-SCF₃ |
| 6033 | Bu—F | Et | 4-SCF₃ |
| 6034 | Bu—F | Et | 2-SEtF |
| 6035 | Bu—F | Et | 3-SEtF |
| 6036 | Bu—F | Et | 4-SEtF |
| 6037 | Bu—F | Et | 2-SPrF |
| 6038 | Bu—F | Et | 3-SPrF |
| 6039 | Bu—F | Et | 4-SPrF |
| 6040 | Bu—F | Et | 2-OMe, 4-OMe |
| 6041 | Bu—F | Et | 2-Me, 5-OH |
| 6042 | Bu—F | Et | 2-Me, 5-OMe |
| 6043 | Bu—F | Et | 2-Me, 5-OMeF |
| 6044 | Bu—F | Et | 2-Me, 5-OEtF |
| 6045 | Bu—F | Et | 2-Me, 5-OPrF |
| 6046 | Bu—F | Et | 2-Me, 4-OH |
| 6047 | Bu—F | Et | 2-Me, 4-OMe |
| 6048 | Bu—F | Et | 2-Me, 4-OMeF |
| 6049 | Bu—F | Et | 2-Me, 4-OCF₃ |
| 6050 | Bu—F | Et | 2-Me, 4-OEtF |
| 6051 | Bu—F | Et | 2-Me, 4-OPrF |
| 6052 | Bu—F | Et | 2-OH, 4-Me |
| 6053 | Bu—F | Et | 2-OMe, 4-Me |
| 6054 | Bu—F | Et | 2-OMeF, 4-Me |
| 6055 | Bu—F | Et | 2-OCF₃, 4-Me |
| 6056 | Bu—F | Et | 2-OEtF, 4-Me |
| 6057 | Bu—F | Et | 2-OPrF, 4-Me |
| 6058 | Bu—F | Et | 2-Cl, 4-OH |
| 6059 | Bu—F | Et | 2-Cl, 4-OMe |
| 6060 | Bu—F | Et | 2-Cl, 4-OMeF |
| 6061 | Bu—F | Et | 2-Cl, 4-OCF₃ |
| 6062 | Bu—F | Et | 2-Cl, 4-OEtF |
| 6063 | Bu—F | Et | 2-Cl, 4-OPrF |
| 6064 | Bu—F | Et | 2-F, 4-F |
| 6065 | Bu—F | Et | 2-Cl, 4-Cl |
| 6066 | Bu—F | Et | 2-Cl, 4-F |
| 6067 | Bu—F | Et | 2-Cl, 4-NO₂ |
| 6068 | Bu—F | Et | 2-Cl, 4-NH₂ |
| 6069 | Bu—F | Et | 2-Cl, 4-NHMe |
| 6070 | Bu—F | Et | 2-Cl, 4-NMe₂ |
| 6071 | Bu—F | Et | 2-Cl, 4-NMe₃OTf |
| 6072 | Bu—F | Et | 2-Cl, 4-NMe₃I |
| 6073 | Bu—F | Et | 2-Cl, 5-F |
| 6074 | Bu—F | Et | 2-Cl, 5-NO₂ |
| 6075 | Bu—F | Et | 2-Cl, 5-NH₂ |
| 6076 | Bu—F | Et | 2-Cl, 5-NHMe |
| 6077 | Bu—F | Et | 2-Cl, 5-NMe₂ |
| 6078 | Bu—F | Et | 2-Cl, 5-NMe₃OTf |
| 6079 | Bu—F | Et | 2-Cl, 5- NMe₃I |
| 6080 | Bu—F | Et | 2-F, 4-Cl |
| 6081 | Bu—F | Et | 2-NO₂, 4-Cl |
| 6082 | Bu—F | Et | 2-NH₂, 4-Cl |
| 6083 | Bu—F | Et | 2-NHMe, 4-Cl |
| 6084 | Bu—F | Et | 2-NMe₂, 4-Cl |
| 6085 | Bu—F | Et | 2-NMe₃OTf, 4-Cl |
| 6086 | Bu—F | Et | 2-NMe₃I, 4-Cl |
| 6087 | Bu—F | Et | 2-F, 5-Cl |
| 6088 | Bu—F | Et | 2-NO₂, 5-Cl |
| 6089 | Bu—F | Et | 2-NH₂, 5-Cl |
| 6090 | Bu—F | Et | 2-NHMe, 5-Cl |

TABLE 5-continued

Substituent list for compounds of general structure X.

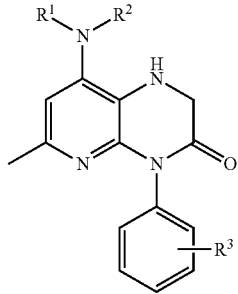

| Compound # | R¹ = | R² = | R³ = |
|---|---|---|---|
| 6091 | Bu—F | Et | 2-NMe₂, 5-Cl |
| 6092 | Bu—F | Et | 2-NMe₃OTf, 5-Cl |
| 6093 | Bu—F | Et | 2-NMe₃I, 5-Cl |
| 6094 | Bu—F | Et | 2-Br, 4-F |
| 6095 | Bu—F | Et | 2-Br, 4-NO₂ |
| 6096 | Bu—F | Et | 2-Br, 4-NH₂ |
| 6097 | Bu—F | Et | 2-Br, 4-NHMe |
| 6098 | Bu—F | Et | 2-Br, 4-NMe₂ |
| 6099 | Bu—F | Et | 2-Br, 4-NMe₃OTf |
| 6100 | Bu—F | Et | 2-Br, 4-NMe₃I |
| 6101 | Bu—F | Et | 2-Br, 5-F |
| 6102 | Bu—F | Et | 2-Br, 5-NO₂ |
| 6103 | Bu—F | Et | 2-Br, 5-NH₂ |
| 6104 | Bu—F | Et | 2-Br, 5-NHMe |
| 6105 | Bu—F | Et | 2-Br, 5-NMe₂ |
| 6106 | Bu—F | Et | 2-Br, 5-NMe₃OTf |
| 6107 | Bu—F | Et | 2-Br, 5-NMe₃I |
| 6108 | Bu—F | Et | 2-F, 4-Br |
| 6109 | Bu—F | Et | 2-NO₂, 4-Br |
| 6110 | Bu—F | Et | 2-NH₂, 4-Br |
| 6111 | Bu—F | Et | 2-NHMe, 4-Br |
| 6112 | Bu—F | Et | 2-NMe₂, 4-Br |
| 6113 | Bu—F | Et | 2-NMe₃OTf, 4-Br |
| 6114 | Bu—F | Et | 2-NMe₃I, 4-Br |
| 6115 | Bu—F | Et | 2-I, 4-F |
| 6116 | Bu—F | Et | 2-I, 4-NO₂ |
| 6117 | Bu—F | Et | 2-I, 4-NH₂ |
| 6118 | Bu—F | Et | 2-I, 4-NHMe |
| 6119 | Bu—F | Et | 2-I, 4-NMe₂ |
| 6120 | Bu—F | Et | 2-I, 4-NMe₃OTf |
| 6121 | Bu—F | Et | 2-I, 4-NMe₃I |
| 6122 | Bu—F | Et | 2-F, 4-I |
| 6123 | Bu—F | Et | 2-NO₂, 4-I |
| 6124 | Bu—F | Et | 2-NH₂, 4-I |
| 6125 | Bu—F | Et | 2-NHMe, 4-I |
| 6126 | Bu—F | Et | 2-NMe₂, 4-I |
| 6127 | Bu—F | Et | 2-NMe₃OTf, 4-I |
| 6128 | Bu—F | Et | 2-NMe₃I, 4-I |
| 6129 | Bu—F | Et | 2-Me, 3-F |
| 6130 | Bu—F | Et | 2-Me, 3-NO₂ |
| 6131 | Bu—F | Et | 2-Me, 3-NH₂ |
| 6132 | Bu—F | Et | 2-Me, 3-NHMe |
| 6133 | Bu—F | Et | 2-Me, 3-NMe₂ |
| 6134 | Bu—F | Et | 2-Me, 3-NMe₃OTf |
| 6135 | Bu—F | Et | 2-Me, 3-NMe₃I |
| 6136 | Bu—F | Et | 2-Me, 4-F |
| 6137 | Bu—F | Et | 2-Me, 4-NO₂ |
| 6138 | Bu—F | Et | 2-Me, 4-NH₂ |
| 6139 | Bu—F | Et | 2-Me, 4-NHMe |
| 6140 | Bu—F | Et | 2-Me, 4-NMe₂ |
| 6141 | Bu—F | Et | 2-Me, 4-NMe₃OTf |
| 6142 | Bu—F | Et | 2-Me, 4-NMe₃I |
| 6143 | Bu—F | Et | 2-Me, 5-F |
| 6144 | Bu—F | Et | 2-Me, 5-NO₂ |
| 6145 | Bu—F | Et | 2-Me, 5-NH₂ |
| 6146 | Bu—F | Et | 2-Me, 5-NHMe |
| 6147 | Bu—F | Et | 2-Me, 5-NMe₂ |
| 6148 | Bu—F | Et | 2-Me, 5-NMe₃OTf |
| 6149 | Bu—F | Et | 2-Me, 5-NMe₃I |
| 6150 | Bu—F | Et | 2-F, 4-Me |

TABLE 5-continued

Substituent list for compounds of general structure X.

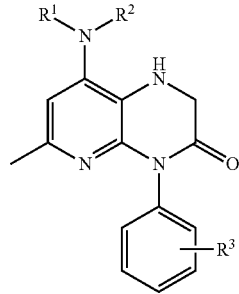

| Compound # | R¹ = | R² = | R³ = |
|---|---|---|---|
| 6151 | Bu—F | Et | 2-NO₂, 4-Me |
| 6152 | Bu—F | Et | 2-NH₂, 4-Me |
| 6153 | Bu—F | Et | 2-NHMe, 4-Me |
| 6154 | Bu—F | Et | 2-NMe₂, 4-Me |
| 6155 | Bu—F | Et | 2-NMe₃, 4-Me |
| 6156 | Bu—F | Et | 2-NMe₃OTf, 4-Me |
| 6157 | Bu—F | Et | 2-NMe₃I, 4-Me |
| 6158 | Bu—F | Et | 2-SnMe₃, 4-F |
| 6159 | Bu—F | Et | 2-SnMe₃, 5-F |
| 6160 | Bu—F | Et | 2-F, 4-SnMe₃ |
| 6161 | Bu—F | Et | 2-Br, 6-Cl, 4-F |
| 6162 | Bu—F | Et | 2-Br, 6-Cl, 4-NO₂ |
| 6163 | Bu—F | Et | 2-Br, 6-Cl, 4-NH₂ |
| 6164 | Bu—F | Et | 2-Br, 6-Cl, 4-NHMe |
| 6165 | Bu—F | Et | 2-Br, 6-Cl, 4-NMe₂ |
| 6166 | Bu—F | Et | 2-Br, 6-Cl, 4-NMe₃OTf |
| 6167 | Bu—F | Et | 2-Br, 6-Cl, 4-NMe₃I |
| 6168 | Bu—F | Et | 2-Me, 6-Cl, 4-F |
| 6169 | Bu—F | Et | 2-SnMe₃, 6-Cl, 4-F |
| 6170 | Bu—F | Et | 2-Cl, 4-Me |
| 6171 | Bu—F | Et | 2-Cl, 4-Br |
| 6172 | Bu—F | Et | 2-Cl, 4- SnMe₃ |
| 6173 | Bu—F | Et | 2-Br, 4-Cl |
| 6174 | Bu—F | Et | 2-SnMe₃, 4-Cl |
| 6175 | Bu—F | Et | 2-Me, 4-Cl |
| 6176 | Bu—F | Et | 2-Br, 4-F |
| 6177 | Bu—F | Et | 2-Br, 4-Me |
| 6178 | Bu—F | Et | 2-Br, 4-SnMe₃ |
| 6179 | Bu—F | Et | 2-SnMe3, 4-Br |
| 6180 | Bu—F | Et | 2-Me, 4-Br |
| 6181 | Bu—F | Et | 2-Me, 4-SnMe3 |
| 6182 | Bu—F | Et | 2-SnMe3, 4-Me |
| 6183 | Bu—F | Et | 2-Me, 4-Me |
| 6184 | Bu—F | Et | 2-Et, 4-Br |
| 6185 | Bu—F | Et | 2-Et, 4-SnMe₃ |
| 6186 | Bu—F | Et | 2-Et, 4-Me |
| 6187 | Bu—F | Et | 2-Me, 4-Me, 6-Me |
| 6188 | Bu—F | Et | 2-Me, 4-Br, 6-Me |
| 6189 | Bu—F | Et | 2-Me, 4-SnMe₃, 6-Me |
| 6190 | Bu—F | Et | 2-Et, 6-Me |
| 6191 | Bu—F | Et | 2-Br, 4-i-Pr |
| 6192 | Bu—F | Et | 2-SnMe₃, 4-i-Pr |
| 6193 | Bu—F | Et | 2-Me, 4-i-Pr |
| 6194 | Bu—F | Et | 2-Br, 4-Br, 6-Br |
| 6195 | Bu—F | Et | 2-Br, 4-Me, 6-Br |
| 6196 | Bu—F | Et | 2-Br, 4-SnMe₃, 6-Br |
| 6197 | Bu—F | Et | 2-SnMe₃, 4-Br, 6-Br |
| 6198 | Bu—F | Et | 2-Br, 4-Br, 6-Me |
| 6199 | Bu—F | Et | 2-Br, 4-CF₃, 6-Br |
| 6200 | Bu—F | Et | 2-Br, 4-Br, 6-CF₃ |
| 6201 | Bu—F | Et | 2-CF₃, 4-CF₃ |
| 6202 | Bu—F | Et | 2-Cl, 4-CF₃ |
| 6203 | Bu—F | Et | 2-CF₃, 4-Cl |
| 6204 | Bu—F | Et | 2-Br, 4-CF₃ |
| 6205 | Bu—F | Et | 2-SnMe₃, 4-CF₃ |
| 6206 | Bu—F | Et | 2-Me, 4-CF₃ |
| 6207 | Bu—F | Et | 2-CF₃, 4-Br |
| 6208 | Bu—F | Et | 2-CF₃, 4-SnMe₃ |
| 6209 | Bu—F | Et | 2-CF₃, 4-Me |
| 6210 | Bu—F | Et | 2-Br, 4-OH |

TABLE 5-continued

Substituent list for compounds of general structure X.

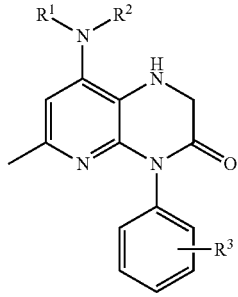

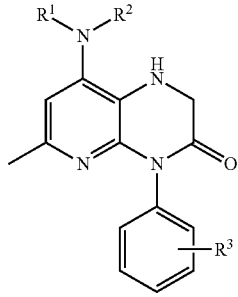

| Compound # | R¹ = | R² = | R³ = |
|---|---|---|---|
| 6211 | Bu—F | Et | 2-Br, 4-OMe |
| 6212 | Bu—F | Et | 2-Br, 4-OMeF |
| 6213 | Bu—F | Et | 2-Br, 4-OCF$_3$ |
| 6214 | Bu—F | Et | 2-Br, 4-OEtF |
| 6215 | Bu—F | Et | 2-Br, 4-OPrF |
| 6216 | Bu—F | Et | 2-OH, 4-Br |
| 6217 | Bu—F | Et | 2-OMe, 4-Br |
| 6218 | Bu—F | Et | 2-OMeF, 4-Br |
| 6219 | Bu—F | Et | 2-OCF$_3$, 4-Br |
| 6220 | Bu—F | Et | 2-OEtF, 4-Br |
| 6221 | Bu—F | Et | 2-OPrF, 4-Br |
| 6222 | Bu—F | Et | 2-I, 4-OH |
| 6223 | Bu—F | Et | 2-I, 4-OMe |
| 6224 | Bu—F | Et | 2-I, 4-OMeF |
| 6225 | Bu—F | Et | 2-I, 4-OCF$_3$ |
| 6226 | Bu—F | Et | 2-I, 4-OEtF |
| 6227 | Bu—F | Et | 2-I, 4-OPrF |
| 6228 | Bu—F | Et | 2-OH, 4-I |
| 6229 | Bu—F | Et | 2-OMe, 4-I |
| 6230 | Bu—F | Et | 2-OMeF, 4-I |
| 6231 | Bu—F | Et | 2-OCF$_3$, 4-I |
| 6232 | Bu—F | Et | 2-OEtF, 4-I |
| 6233 | Bu—F | Et | 2-OPrF, 4-I |
| 6234 | Bu—F | Et | 2-SnMe$_3$, 4-OH |
| 6235 | Bu—F | Et | 2-SnMe$_3$, 4-OMe |
| 6236 | Bu—F | Et | 2-SnMe$_3$, 4-OMeF |
| 6237 | Bu—F | Et | 2-SnMe$_3$, 4-OCF$_3$ |
| 6238 | Bu—F | Et | 2-SnMe$_3$, 4-OEtF |
| 6239 | Bu—F | Et | 2-SnMe$_3$, 4-OPrF |
| 6240 | Bu—F | Et | 2-OH, 4-SnMe$_3$ |
| 6241 | Bu—F | Et | 2-OMe, 4-SnMe$_3$ |
| 6242 | Bu—F | Et | 2-OMeF, 4-SnMe$_3$ |
| 6243 | Bu—F | Et | 2-OCF$_3$, 4-SnMe$_3$ |
| 6244 | Bu—F | Et | 2-OEtF, 4-SnMe$_3$ |
| 6245 | Bu—F | Et | 2-OPrF, 4-SnMe$_3$ |
| 6246 | FCH$_2$—CH=CH—CH$_2$ | Me | H |
| 6247 | FCH$_2$—CH=CH—CH$_2$ | Me | 2-t-Bu |
| 6248 | FCH$_2$—CH=CH—CH$_2$ | Me | 2-Br |
| 6249 | FCH$_2$—CH=CH—CH$_2$ | Me | 3-Br |
| 6250 | FCH$_2$—CH=CH—CH$_2$ | Me | 4-Br |
| 6251 | FCH$_2$—CH=CH—CH$_2$ | Me | 2-I |
| 6252 | FCH$_2$—CH=CH—CH$_2$ | Me | 3-I |
| 6253 | FCH$_2$—CH=CH—CH$_2$ | Me | 4-I |
| 6254 | FCH$_2$—CH=CH—CH$_2$ | Me | 2-SnMe$_3$ |
| 6255 | FCH$_2$—CH=CH—CH$_2$ | Me | 3-SnMe$_3$ |
| 6256 | FCH$_2$—CH=CH—CH$_2$ | Me | 4-SnMe$_3$ |
| 6257 | FCH$_2$—CH=CH—CH$_2$ | Me | 2-Me |
| 6258 | FCH$_2$—CH=CH—CH$_2$ | Me | 3-Me |
| 6259 | FCH$_2$—CH=CH—CH$_2$ | Me | 4-Me |
| 6260 | FCH$_2$—CH=CH—CH$_2$ | Me | 2-OH |
| 6261 | FCH$_2$—CH=CH—CH$_2$ | Me | 3-OH |
| 6262 | FCH$_2$—CH=CH—CH$_2$ | Me | 4-OH |
| 6263 | FCH$_2$—CH=CH—CH$_2$ | Me | 2-OMe |
| 6264 | FCH$_2$—CH=CH—CH$_2$ | Me | 3-OMe |
| 6265 | FCH$_2$—CH=CH—CH$_2$ | Me | 4-OMe |
| 6266 | FCH$_2$—CH=CH—CH$_2$ | Me | 2-OMeF |
| 6267 | FCH$_2$—CH=CH—CH$_2$ | Me | 3-OMeF |
| 6268 | FCH$_2$—CH=CH—CH$_2$ | Me | 4-OMeF |
| 6269 | FCH$_2$—CH=CH—CH$_2$ | Me | 2-OCF$_3$ |
| 6270 | FCH$_2$—CH=CH—CH$_2$ | Me | 3-OCF$_3$ |
| 6271 | FCH$_2$—CH=CH—CH$_2$ | Me | 4-OCF$_3$ |
| 6272 | FCH$_2$—CH=CH—CH$_2$ | Me | 2-OEtF |
| 6273 | FCH$_2$—CH=CH—CH$_2$ | Me | 3-OEtF |
| 6274 | FCH$_2$—CH=CH—CH$_2$ | Me | 4-OEtF |
| 6275 | FCH$_2$—CH=CH—CH$_2$ | Me | 2-OPrF |
| 6276 | FCH$_2$—CH=CH—CH$_2$ | Me | 3-OPrF |
| 6277 | FCH$_2$—CH=CH—CH$_2$ | Me | 4-OPrF |
| 6278 | FCH$_2$—CH=CH—CH$_2$ | Me | 2-SH |
| 6279 | FCH$_2$—CH=CH—CH$_2$ | Me | 3-SH |
| 6280 | FCH$_2$—CH=CH—CH$_2$ | Me | 4-SH |
| 6281 | FCH$_2$—CH=CH—CH$_2$ | Me | 2-SMe |
| 6282 | FCH$_2$—CH=CH—CH$_2$ | Me | 3-SMe |
| 6283 | FCH$_2$—CH=CH—CH$_2$ | Me | 4-SMe |
| 6284 | FCH$_2$—CH=CH—CH$_2$ | Me | 2-SMeF |
| 6285 | FCH$_2$—CH=CH—CH$_2$ | Me | 3-SMeF |
| 6286 | FCH$_2$—CH=CH—CH$_2$ | Me | 4-SMeF |
| 6287 | FCH$_2$—CH=CH—CH$_2$ | Me | 2-SCF$_3$ |
| 6288 | FCH$_2$—CH=CH—CH$_2$ | Me | 3-SCF$_3$ |
| 6289 | FCH$_2$—CH=CH—CH$_2$ | Me | 4-SCF$_3$ |
| 6290 | FCH$_2$—CH=CH—CH$_2$ | Me | 2-SEtF |
| 6291 | FCH$_2$—CH=CH—CH$_2$ | Me | 3-SEtF |
| 6292 | FCH$_2$—CH=CH—CH$_2$ | Me | 4-SEtF |
| 6293 | FCH$_2$—CH=CH—CH$_2$ | Me | 2-SPrF |
| 6294 | FCH$_2$—CH=CH—CH$_2$ | Me | 3-SPrF |
| 6295 | FCH$_2$—CH=CH—CH$_2$ | Me | 4-SPrF |
| 6296 | FCH$_2$—CH=CH—CH$_2$ | Me | 2-OMe, 4-OMe |
| 6297 | FCH$_2$—CH=CH—CH$_2$ | Me | 2-Me, 5-OH |
| 6298 | FCH$_2$—CH=CH—CH$_2$ | Me | 2-Me, 5-OMe |
| 6299 | FCH$_2$—CH=CH—CH$_2$ | Me | 2-Me, 5-OMeF |
| 6300 | FCH$_2$—CH=CH—CH$_2$ | Me | 2-Me, 5-OEtF |
| 6301 | FCH$_2$—CH=CH—CH$_2$ | Me | 2-Me, 5-OPrF |
| 6302 | FCH$_2$—CH=CH—CH$_2$ | Me | 2-Me, 4-OH |
| 6303 | FCH$_2$—CH=CH—CH$_2$ | Me | 2-Me, 4-OMe |
| 6304 | FCH$_2$—CH=CH—CH$_2$ | Me | 2-Me, 4-OMeF |
| 6305 | FCH$_2$—CH=CH—CH$_2$ | Me | 2-Me, 4-OCF$_3$ |
| 6306 | FCH$_2$—CH=CH—CH$_2$ | Me | 2-Me, 4-OEtF |
| 6307 | FCH$_2$—CH=CH—CH$_2$ | Me | 2-Me, 4-OPrF |
| 6308 | FCH$_2$—CH=CH—CH$_2$ | Me | 2-OH, 4-Me |
| 6309 | FCH$_2$—CH=CH—CH$_2$ | Me | 2-OMe, 4-Me |
| 6310 | FCH$_2$—CH=CH—CH$_2$ | Me | 2-OMeF, 4-Me |
| 6311 | FCH$_2$—CH=CH—CH$_2$ | Me | 2-OCF$_3$, 4-Me |
| 6312 | FCH$_2$—CH=CH—CH$_2$ | Me | 2-OEtF, 4-Me |
| 6313 | FCH$_2$—CH=CH—CH$_2$ | Me | 2-OPrF, 4-Me |
| 6314 | FCH$_2$—CH=CH—CH$_2$ | Me | 2-Cl, 4-OH |
| 6315 | FCH$_2$—CH=CH—CH$_2$ | Me | 2-Cl, 4-OMe |
| 6316 | FCH$_2$—CH=CH—CH$_2$ | Me | 2-Cl, 4-OMeF |
| 6317 | FCH$_2$—CH=CH—CH$_2$ | Me | 2-Cl, 4-OCF$_3$ |
| 6318 | FCH$_2$—CH=CH—CH$_2$ | Me | 2-Cl, 4-OEtF |
| 6319 | FCH$_2$—CH=CH—CH$_2$ | Me | 2-Cl, 4-OPrF |
| 6320 | FCH$_2$—CH=CH—CH$_2$ | Me | 2-F, 4-F |
| 6321 | FCH$_2$—CH=CH—CH$_2$ | Me | 2-Cl, 4-Cl |
| 6322 | FCH$_2$—CH=CH—CH$_2$ | Me | 2-Cl, 4-F |
| 6323 | FCH$_2$—CH=CH—CH$_2$ | Me | 2-Cl, 4-NO$_2$ |
| 6324 | FCH$_2$—CH=CH—CH$_2$ | Me | 2-Cl, 4-NH$_2$ |
| 6325 | FCH$_2$—CH=CH—CH$_2$ | Me | 2-Cl, 4-NHMe |
| 6326 | FCH$_2$—CH=CH—CH$_2$ | Me | 2-Cl, 4-NMe$_2$ |
| 6327 | FCH$_2$—CH=CH—CH$_2$ | Me | 2-Cl, 4-NMe$_3$OTf |
| 6328 | FCH$_2$—CH=CH—CH$_2$ | Me | 2-Cl, 4-NMe$_3$I |
| 6329 | FCH$_2$—CH=CH—CH$_2$ | Me | 2-Cl, 5-F |
| 6330 | FCH$_2$—CH=CH—CH$_2$ | Me | 2-Cl, 5-NO$_2$ |

TABLE 5-continued

Substituent list for compounds of general structure X.

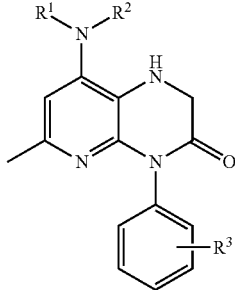
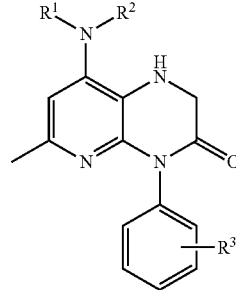

| Compound # | R¹ = | R² = | R³ = |
|---|---|---|---|
| 6331 | FCH$_2$—CH=CH—CH$_2$ | Me | 2-Cl, 5-NH$_2$ |
| 6332 | FCH$_2$—CH=CH—CH$_2$ | Me | 2-Cl, 5-NHMe |
| 6333 | FCH$_2$—CH=CH—CH$_2$ | Me | 2-Cl, 5-NMe$_2$ |
| 6334 | FCH$_2$—CH=CH—CH$_2$ | Me | 2-Cl, 5-NMe$_3$OTf |
| 6335 | FCH$_2$—CH=CH—CH$_2$ | Me | 2-Cl, 5- NMe$_3$I |
| 6336 | FCH$_2$—CH=CH—CH$_2$ | Me | 2-F, 4-Cl |
| 6337 | FCH$_2$—CH=CH—CH$_2$ | Me | 2-NO$_2$, 4-Cl |
| 6338 | FCH$_2$—CH=CH—CH$_2$ | Me | 2-NH$_2$, 4-Cl |
| 6339 | FCH$_2$—CH=CH—CH$_2$ | Me | 2-NHMe, 4-Cl |
| 6340 | FCH$_2$—CH=CH—CH$_2$ | Me | 2-NMe$_2$, 4-Cl |
| 6341 | FCH$_2$—CH=CH—CH$_2$ | Me | 2-NMe$_3$OTf, 4-Cl |
| 6342 | FCH$_2$—CH=CH—CH$_2$ | Me | 2-NMe$_3$I, 4-Cl |
| 6343 | FCH$_2$—CH=CH—CH$_2$ | Me | 2-F, 5-Cl |
| 6344 | FCH$_2$—CH=CH—CH$_2$ | Me | 2-NO$_2$, 5-Cl |
| 6345 | FCH$_2$—CH=CH—CH$_2$ | Me | 2-NH$_2$, 5-Cl |
| 6346 | FCH$_2$—CH=CH—CH$_2$ | Me | 2-NHMe, 5-Cl |
| 6347 | FCH$_2$—CH=CH—CH$_2$ | Me | 2-NMe$_2$, 5-Cl |
| 6348 | FCH$_2$—CH=CH—CH$_2$ | Me | 2-NMe$_3$OTf, 5-Cl |
| 6349 | FCH$_2$—CH=CH—CH$_2$ | Me | 2-NMe$_3$I, 5-Cl |
| 6350 | FCH$_2$—CH=CH—CH$_2$ | Me | 2-Br, 4-F |
| 6351 | FCH$_2$—CH=CH—CH$_2$ | Me | 2-Br, 4-NO$_2$ |
| 6352 | FCH$_2$—CH=CH—CH$_2$ | Me | 2-Br, 4-NH$_2$ |
| 6353 | FCH$_2$—CH=CH—CH$_2$ | Me | 2-Br, 4-NHMe |
| 6354 | FCH$_2$—CH=CH—CH$_2$ | Me | 2-Br, 4-NMe$_2$ |
| 6355 | FCH$_2$—CH=CH—CH$_2$ | Me | 2-Br, 4-NMe$_3$OTf |
| 6356 | FCH$_2$—CH=CH—CH$_2$ | Me | 2-Br, 4-NMe$_3$I |
| 6357 | FCH$_2$—CH=CH—CH$_2$ | Me | 2-Br, 5-F |
| 6358 | FCH$_2$—CH=CH—CH$_2$ | Me | 2-Br, 5-NO$_2$ |
| 6359 | FCH$_2$—CH=CH—CH$_2$ | Me | 2-Br, 5-NH$_2$ |
| 6360 | FCH$_2$—CH=CH—CH$_2$ | Me | 2-Br, 5-NHMe |
| 6361 | FCH$_2$—CH=CH—CH$_2$ | Me | 2-Br, 5-NMe$_2$ |
| 6362 | FCH$_2$—CH=CH—CH$_2$ | Me | 2-Br, 5-NMe$_3$OTf |
| 6363 | FCH$_2$—CH=CH—CH$_2$ | Me | 2-Br, 5-NMe$_3$I |
| 6364 | FCH$_2$—CH=CH—CH$_2$ | Me | 2-F, 4-Br |
| 6365 | FCH$_2$—CH=CH—CH$_2$ | Me | 2-NO$_2$, 4-Br |
| 6366 | FCH$_2$—CH=CH—CH$_2$ | Me | 2-NH$_2$, 4-Br |
| 6367 | FCH$_2$—CH=CH—CH$_2$ | Me | 2-NHMe, 4-Br |
| 6368 | FCH$_2$—CH=CH—CH$_2$ | Me | 2-NMe$_2$, 4-Br |
| 6369 | FCH$_2$—CH=CH—CH$_2$ | Me | 2-NMe$_3$OTf, 4-Br |
| 6370 | FCH$_2$—CH=CH—CH$_2$ | Me | 2-NMe$_3$I, 4-Br |
| 6371 | FCH$_2$—CH=CH—CH$_2$ | Me | 2-I, 4-F |
| 6372 | FCH$_2$—CH=CH—CH$_2$ | Me | 2-I, 4-NO$_2$ |
| 6373 | FCH$_2$—CH=CH—CH$_2$ | Me | 2-I, 4-NH$_2$ |
| 6374 | FCH$_2$—CH=CH—CH$_2$ | Me | 2-I, 4-NHMe |
| 6375 | FCH$_2$—CH=CH—CH$_2$ | Me | 2-I, 4-NMe$_2$ |
| 6376 | FCH$_2$—CH=CH—CH$_2$ | Me | 2-I, 4-NMe$_3$OTf |
| 6377 | FCH$_2$—CH=CH—CH$_2$ | Me | 2-I, 4-NMe$_3$I |
| 6378 | FCH$_2$—CH=CH—CH$_2$ | Me | 2-F, 4-I |
| 6379 | FCH$_2$—CH=CH—CH$_2$ | Me | 2-NO$_2$, 4-I |
| 6380 | FCH$_2$—CH=CH—CH$_2$ | Me | 2-NH$_2$, 4-I |
| 6381 | FCH$_2$—CH=CH—CH$_2$ | Me | 2-NHMe, 4-I |
| 6382 | FCH$_2$—CH=CH—CH$_2$ | Me | 2-NMe$_2$, 4-I |
| 6383 | FCH$_2$—CH=CH—CH$_2$ | Me | 2-NMe$_3$OTf, 4-I |
| 6384 | FCH$_2$—CH=CH—CH$_2$ | Me | 2-NMe$_3$I, 4-I |
| 6385 | FCH$_2$—CH=CH—CH$_2$ | Me | 2-Me, 3-F |
| 6386 | FCH$_2$—CH=CH—CH$_2$ | Me | 2-Me, 3-NO$_2$ |
| 6387 | FCH$_2$—CH=CH—CH$_2$ | Me | 2-Me, 3-NH$_2$ |
| 6388 | FCH$_2$—CH=CH—CH$_2$ | Me | 2-Me, 3-NHMe |
| 6389 | FCH$_2$—CH=CH—CH$_2$ | Me | 2-Me, 3-NMe$_2$ |
| 6390 | FCH$_2$—CH=CH—CH$_2$ | Me | 2-Me, 3-NMe$_3$OTf |
| 6391 | FCH$_2$—CH=CH—CH$_2$ | Me | 2-Me, 3-NMe$_3$I |
| 6392 | FCH$_2$—CH=CH—CH$_2$ | Me | 2-Me, 4-F |
| 6393 | FCH$_2$—CH=CH—CH$_2$ | Me | 2-Me, 4-NO$_2$ |
| 6394 | FCH$_2$—CH=CH—CH$_2$ | Me | 2-Me, 4-NH$_2$ |
| 6395 | FCH$_2$—CH=CH—CH$_2$ | Me | 2-Me, 4-NHMe |
| 6396 | FCH$_2$—CH=CH—CH$_2$ | Me | 2-Me, 4-NMe$_2$ |
| 6397 | FCH$_2$—CH=CH—CH$_2$ | Me | 2-Me, 4-NMe$_3$OTf |
| 6398 | FCH$_2$—CH=CH—CH$_2$ | Me | 2-Me, 4-NMe$_3$I |
| 6399 | FCH$_2$—CH=CH—CH$_2$ | Me | 2-Me, 5-F |
| 6400 | FCH$_2$—CH=CH—CH$_2$ | Me | 2-Me, 5-NO$_2$ |
| 6401 | FCH$_2$—CH=CH—CH$_2$ | Me | 2-Me, 5-NH$_2$ |
| 6402 | FCH$_2$—CH=CH—CH$_2$ | Me | 2-Me, 5-NHMe |
| 6403 | FCH$_2$—CH=CH—CH$_2$ | Me | 2-Me, 5-NMe$_2$ |
| 6404 | FCH$_2$—CH=CH—CH$_2$ | Me | 2-Me, 5-NMe$_3$OTf |
| 6405 | FCH$_2$—CH=CH—CH$_2$ | Me | 2-Me, 5-NMe$_3$I |
| 6406 | FCH$_2$—CH=CH—CH$_2$ | Me | 2-F, 4-Me |
| 6407 | FCH$_2$—CH=CH—CH$_2$ | Me | 2-NO$_2$, 4-Me |
| 6408 | FCH$_2$—CH=CH—CH$_2$ | Me | 2-NH$_2$, 4-Me |
| 6409 | FCH$_2$—CH=CH—CH$_2$ | Me | 2-NHMe, 4-Me |
| 6410 | FCH$_2$—CH=CH—CH$_2$ | Me | 2-NMe$_2$, 4-Me |
| 6411 | FCH$_2$—CH=CH—CH$_2$ | Me | 2-NMe$_3$, 4-Me |
| 6412 | FCH$_2$—CH=CH—CH$_2$ | Me | 2-NMe$_3$OTf, 4-Me |
| 6413 | FCH$_2$—CH=CH—CH$_2$ | Me | 2-NMe$_3$I, 4-Me |
| 6414 | FCH$_2$—CH=CH—CH$_2$ | Me | 2-SnMe$_3$, 4-F |
| 6415 | FCH$_2$—CH=CH—CH$_2$ | Me | 2-SnMe$_3$, 5-F |
| 6416 | FCH$_2$—CH=CH—CH$_2$ | Me | 2-F, 4-SnMe$_3$ |
| 6417 | FCH$_2$—CH=CH—CH$_2$ | Me | 2-Br, 6-Cl, 4-F |
| 6418 | FCH$_2$—CH=CH—CH$_2$ | Me | 2-Br, 6-Cl, 4-NO$_2$ |
| 6419 | FCH$_2$—CH=CH—CH$_2$ | Me | 2-Br, 6-Cl, 4-NH$_2$ |
| 6420 | FCH$_2$—CH=CH—CH$_2$ | Me | 2-Br, 6-Cl, 4-NHMe |
| 6421 | FCH$_2$—CH=CH—CH$_2$ | Me | 2-Br, 6-Cl, 4-NMe$_2$ |
| 6422 | FCH$_2$—CH=CH—CH$_2$ | Me | 2-Br, 6-Cl, 4-NMe$_3$OTf |
| 6423 | FCH$_2$—CH=CH—CH$_2$ | Me | 2-Br, 6-Cl, 4-NMe$_3$I |
| 6424 | FCH$_2$—CH=CH—CH$_2$ | Me | 2-Me, 6-Cl, 4-F |
| 6425 | FCH$_2$—CH=CH—CH$_2$ | Me | 2-SnMe$_3$, 6-Cl,4-F |
| 6426 | FCH$_2$—CH=CH—CH$_2$ | Me | 2-Cl, 4-Me |
| 6427 | FCH$_2$—CH=CH—CH$_2$ | Me | 2-Cl, 4-Br |
| 6428 | FCH$_2$—CH=CH—CH$_2$ | Me | 2-Cl, 4-SnMe$_3$ |
| 6429 | FCH$_2$—CH=CH—CH$_2$ | Me | 2-Br, 4-Cl |
| 6430 | FCH$_2$—CH=CH—CH$_2$ | Me | 2-SnMe$_3$, 4-Cl |
| 6431 | FCH$_2$—CH=CH—CH$_2$ | Me | 2-Me, 4-Cl |
| 6432 | FCH$_2$—CH=CH—CH$_2$ | Me | 2-Br, 4-Br |
| 6433 | FCH$_2$—CH=CH—CH$_2$ | Me | 2-Br, 4-Me |
| 6434 | FCH$_2$—CH=CH—CH$_2$ | Me | 2-Br, 4-SnMe$_3$ |
| 6435 | FCH$_2$—CH=CH—CH$_2$ | Me | 2-SnMe$_3$, 4-Br |
| 6436 | FCH$_2$—CH=CH—CH$_2$ | Me | 2-Me, 4-Br |
| 6437 | FCH$_2$—CH=CH—CH$_2$ | Me | 2-Me, 4-SnMe$_3$ |
| 6438 | FCH$_2$—CH=CH—CH$_2$ | Me | 2-SnMe$_3$, 4-Me |
| 6439 | FCH$_2$—CH=CH—CH$_2$ | Me | 2-Me, 4-Me |
| 6440 | FCH$_2$—CH=CH—CH$_2$ | Me | 2-Et, 4-Br |
| 6441 | FCH$_2$—CH=CH—CH$_2$ | Me | 2-Et, 4-SnMe$_3$ |
| 6442 | FCH$_2$—CH=CH—CH$_2$ | Me | 2-Et, 4-Me |
| 6443 | FCH$_2$—CH=CH—CH$_2$ | Me | 2-Me, 4-Me, 6-Me |
| 6444 | FCH$_2$—CH=CH—CH$_2$ | Me | 2-Me, 4-Br, 6-Me |
| 6445 | FCH$_2$—CH=CH—CH$_2$ | Me | 2-Me, 4-SnMe$_3$, 6-Me |
| 6446 | FCH$_2$—CH=CH—CH$_2$ | Me | 2-Et, 6-Me |
| 6447 | FCH$_2$—CH=CH—CH$_2$ | Me | 2-Br, 4-i-Pr |
| 6448 | FCH$_2$—CH=CH—CH$_2$ | Me | 2-SnMe$_3$, 4-i-Pr |
| 6449 | FCH$_2$—CH=CH—CH$_2$ | Me | 2-Me, 4-i-Pr |
| 6450 | FCH$_2$—CH=CH—CH$_2$ | Me | 2-Br, 4-Br, 6-Br |

TABLE 5-continued

Substituent list for compounds of general structure X.

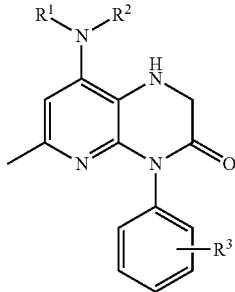

| Compound # | R¹ = | R² = | R³ = |
|---|---|---|---|
| 6451 | FCH$_2$—CH=CH—CH$_2$ | Me | 2-Br, 4-Me, 6-Br |
| 6452 | FCH$_2$—CH=CH—CH$_2$ | Me | 2-Br, 4-SnMe$_3$, 6-Br |
| 6453 | FCH$_2$—CH=CH—CH$_2$ | Me | 2-SnMe$_3$, 4-Br, 6-Br |
| 6454 | FCH$_2$—CH=CH—CH$_2$ | Me | 2-Br, 4-Br, 6-Me |
| 6455 | FCH$_2$—CH=CH—CH$_2$ | Me | 2-Br, 4-CF$_3$, 6-Br |
| 6456 | FCH$_2$—CH=CH—CH$_2$ | Me | 2-Br, 4-Br, 6-CF$_3$ |
| 6457 | FCH$_2$—CH=CH—CH$_2$ | Me | 2-CF$_3$, 4-CF$_3$ |
| 6458 | FCH$_2$—CH=CH—CH$_2$ | Me | 2-Cl, 4-CF$_3$ |
| 6459 | FCH$_2$—CH=CH—CH$_2$ | Me | 2-CF$_3$, 4-Cl |
| 6460 | FCH$_2$—CH=CH—CH$_2$ | Me | 2-Br, 4-CF$_3$ |
| 6461 | FCH$_2$—CH=CH—CH$_2$ | Me | 2-SnMe$_3$, 4-CF$_3$ |
| 6462 | FCH$_2$—CH=CH—CH$_2$ | Me | 2-Me, 4-CF$_3$ |
| 6463 | FCH$_2$—CH=CH—CH$_2$ | Me | 2-CF$_3$, 4-Br |
| 6464 | FCH$_2$—CH=CH—CH$_2$ | Me | 2-CF$_3$, 4-SnMe$_3$ |
| 6465 | FCH$_2$—CH=CH—CH$_2$ | Me | 2-CF$_3$, 4-Me |
| 6466 | FCH$_2$—CH=CH—CH$_2$ | Me | 2-Br, 4-OH |
| 6467 | FCH$_2$—CH=CH—CH$_2$ | Me | 2-Br, 4-OMe |
| 6468 | FCH$_2$—CH=CH—CH$_2$ | Me | 2-Br, 4-OMeF |
| 6469 | FCH$_2$—CH=CH—CH$_2$ | Me | 2-Br, 4-OCF$_3$ |
| 6470 | FCH$_2$—CH=CH—CH$_2$ | Me | 2-Br, 4-OEtF |
| 6471 | FCH$_2$—CH=CH—CH$_2$ | Me | 2-Br, 4-OPrF |
| 6472 | FCH$_2$—CH=CH—CH$_2$ | Me | 2-OH, 4-Br |
| 6473 | FCH$_2$—CH=CH—CH$_2$ | Me | 2-OMe, 4-Br |
| 6474 | FCH$_2$—CH=CH—CH$_2$ | Me | 2-OMeF, 4-Br |
| 6475 | FCH$_2$—CH=CH—CH$_2$ | Me | 2-OCF$_3$, 4-Br |
| 6476 | FCH$_2$—CH=CH—CH$_2$ | Me | 2-OEtF, 4-Br |
| 6477 | FCH$_2$—CH=CH—CH$_2$ | Me | 2-OPrF, 4-Br |
| 6478 | FCH$_2$—CH=CH—CH$_2$ | Me | 2-I, 4-OH |
| 6479 | FCH$_2$—CH=CH—CH$_2$ | Me | 2-I, 4-OMe |
| 6480 | FCH$_2$—CH=CH—CH$_2$ | Me | 2-I, 4-OMeF |
| 6481 | FCH$_2$—CH=CH—CH$_2$ | Me | 2-I, 4-OCF$_3$ |
| 6482 | FCH$_2$—CH=CH—CH$_2$ | Me | 2-I, 4-OEtF |
| 6483 | FCH$_2$—CH=CH—CH$_2$ | Me | 2-I, 4-OPrF |
| 6484 | FCH$_2$—CH=CH—CH$_2$ | Me | 2-OH, 4-I |
| 6485 | FCH$_2$—CH=CH—CH$_2$ | Me | 2-OMe, 4-I |
| 6486 | FCH$_2$—CH=CH—CH$_2$ | Me | 2-OMeF, 4-I |
| 6487 | FCH$_2$—CH=CH—CH$_2$ | Me | 2-OCF$_3$, 4-I |
| 6488 | FCH$_2$—CH=CH—CH$_2$ | Me | 2-OEtF, 4-I |
| 6489 | FCH$_2$—CH=CH—CH$_2$ | Me | 2-OPrF, 4-I |
| 6490 | FCH$_2$—CH=CH—CH$_2$ | Me | 2-SnMe$_3$, 4-OH |
| 6491 | FCH$_2$—CH=CH—CH$_2$ | Me | 2-SnMe$_3$, 4-OMe |
| 6492 | FCH$_2$—CH=CH—CH$_2$ | Me | 2-SnMe$_3$, 4-OMeF |
| 6493 | FCH$_2$—CH=CH—CH$_2$ | Me | 2-SnMe$_3$, 4-OCF$_3$ |
| 6494 | FCH$_2$—CH=CH—CH$_2$ | Me | 2-SnMe$_3$, 4-OEtF |
| 6495 | FCH$_2$—CH=CH—CH$_2$ | Me | 2-SnMe$_3$, 4-OPrF |
| 6496 | FCH$_2$—CH=CH—CH$_2$ | Me | 2-OH, 4-SnMe$_3$ |
| 6497 | FCH$_2$—CH=CH—CH$_2$ | Me | 2-OMe, 4-SnMe$_3$ |
| 6498 | FCH$_2$—CH=CH—CH$_2$ | Me | 2-OMeF, 4-SnMe$_3$ |
| 6499 | FCH$_2$—CH=CH—CH$_2$ | Me | 2-OCF$_3$, 4-SnMe$_3$ |
| 6500 | FCH$_2$—CH=CH—CH$_2$ | Me | 2-OEtF, 4-SnMe$_3$ |
| 6501 | FCH$_2$—CH=CH—CH$_2$ | Me | 2-OPrF, 4-SnMe$_3$ |
| 6502 | FCH$_2$—CH=CH—CH$_2$ | Et | H |
| 6503 | FCH$_2$—CH=CH—CH$_2$ | Et | 2-t-Bu |
| 6504 | FCH$_2$—CH=CH—CH$_2$ | Et | 2-Br |
| 6505 | FCH$_2$—CH=CH—CH$_2$ | Et | 3-Br |
| 6506 | FCH$_2$—CH=CH—CH$_2$ | Et | 4-Br |
| 6507 | FCH$_2$—CH=CH—CH$_2$ | Et | 2-I |
| 6508 | FCH$_2$—CH=CH—CH$_2$ | Et | 3-I |
| 6509 | FCH$_2$—CH=CH—CH$_2$ | Et | 4-I |
| 6510 | FCH$_2$—CH=CH—CH$_2$ | Et | 2-SnMe$_3$ |
| 6511 | FCH$_2$—CH=CH—CH$_2$ | Et | 3-SnMe$_3$ |
| 6512 | FCH$_2$—CH=CH—CH$_2$ | Et | 4-SnMe$_3$ |
| 6513 | FCH$_2$—CH=CH—CH$_2$ | Et | 2-Me |
| 6514 | FCH$_2$—CH=CH—CH$_2$ | Et | 3-Me |
| 6515 | FCH$_2$—CH=CH—CH$_2$ | Et | 4-Me |
| 6516 | FCH$_2$—CH=CH—CH$_2$ | Et | 2-OH |
| 6517 | FCH$_2$—CH=CH—CH$_2$ | Et | 3-OH |
| 6518 | FCH$_2$—CH=CH—CH$_2$ | Et | 4-OH |
| 6519 | FCH$_2$—CH=CH—CH$_2$ | Et | 2-OMe |
| 6520 | FCH$_2$—CH=CH—CH$_2$ | Et | 3-OMe |
| 6521 | FCH$_2$—CH=CH—CH$_2$ | Et | 4-OMe |
| 6522 | FCH$_2$—CH=CH—CH$_2$ | Et | 2-OMeF |
| 6523 | FCH$_2$—CH=CH—CH$_2$ | Et | 3-OMeF |
| 6524 | FCH$_2$—CH=CH—CH$_2$ | Et | 4-OMeF |
| 6525 | FCH$_2$—CH=CH—CH$_2$ | Et | 2-OCF$_3$ |
| 6526 | FCH$_2$—CH=CH—CH$_2$ | Et | 3-OCF$_3$ |
| 6527 | FCH$_2$—CH=CH—CH$_2$ | Et | 4-OCF$_3$ |
| 6528 | FCH$_2$—CH=CH—CH$_2$ | Et | 2-OEtF |
| 6529 | FCH$_2$—CH=CH—CH$_2$ | Et | 3-OEtF |
| 6530 | FCH$_2$—CH=CH—CH$_2$ | Et | 4-OEtF |
| 6531 | FCH$_2$—CH=CH—CH$_2$ | Et | 2-OPrF |
| 6532 | FCH$_2$—CH=CH—CH$_2$ | Et | 3-OPrF |
| 6533 | FCH$_2$—CH=CH—CH$_2$ | Et | 4-OPrF |
| 6534 | FCH$_2$—CH=CH—CH$_2$ | Et | 2-SH |
| 6535 | FCH$_2$—CH=CH—CH$_2$ | Et | 3-SH |
| 6536 | FCH$_2$—CH=CH—CH$_2$ | Et | 4-SH |
| 6537 | FCH$_2$—CH=CH—CH$_2$ | Et | 2-SMe |
| 6538 | FCH$_2$—CH=CH—CH$_2$ | Et | 3-SMe |
| 6539 | FCH$_2$—CH=CH—CH$_2$ | Et | 4-SMe |
| 6540 | FCH$_2$—CH=CH—CH$_2$ | Et | 2-SMeF |
| 6541 | FCH$_2$—CH=CH—CH$_2$ | Et | 3-SMeF |
| 6542 | FCH$_2$—CH=CH—CH$_2$ | Et | 4-SMeF |
| 6543 | FCH$_2$—CH=CH—CH$_2$ | Et | 2-SCF$_3$ |
| 6544 | FCH$_2$—CH=CH—CH$_2$ | Et | 3-SCF$_3$ |
| 6545 | FCH$_2$—CH=CH—CH$_2$ | Et | 4-SCF$_3$ |
| 6546 | FCH$_2$—CH=CH—CH$_2$ | Et | 2-SEtF |
| 6547 | FCH$_2$—CH=CH—CH$_2$ | Et | 3-SEtF |
| 6548 | FCH$_2$—CH=CH—CH$_2$ | Et | 4-SEtF |
| 6549 | FCH$_2$—CH=CH—CH$_2$ | Et | 2-SPrF |
| 6550 | FCH$_2$—CH=CH—CH$_2$ | Et | 3-SPrF |
| 6551 | FCH$_2$—CH=CH—CH$_2$ | Et | 4-SPrF |
| 6552 | FCH$_2$—CH=CH—CH$_2$ | Et | 2-OMe, 4-OMe |
| 6553 | FCH$_2$—CH=CH—CH$_2$ | Et | 2-Me, 5-OH |
| 6554 | FCH$_2$—CH=CH—CH$_2$ | Et | 2-Me, 5-OMe |
| 6555 | FCH$_2$—CH=CH—CH$_2$ | Et | 2-Me, 5-OMeF |
| 6556 | FCH$_2$—CH=CH—CH$_2$ | Et | 2-Me, 5-OEtF |
| 6557 | FCH$_2$—CH=CH—CH$_2$ | Et | 2-Me, 5-OPrF |
| 6558 | FCH$_2$—CH=CH—CH$_2$ | Et | 2-Me, 4-OH |
| 6559 | FCH$_2$—CH=CH—CH$_2$ | Et | 2-Me, 4-OMe |
| 6560 | FCH$_2$—CH=CH—CH$_2$ | Et | 2-Me, 4-OMeF |
| 6561 | FCH$_2$—CH=CH—CH$_2$ | Et | 2-Me, 4-OCF$_3$ |
| 6562 | FCH$_2$—CH=CH—CH$_2$ | Et | 2-Me, 4-OEtF |
| 6563 | FCH$_2$—CH=CH—CH$_2$ | Et | 2-Me, 4-OPrF |
| 6564 | FCH$_2$—CH=CH—CH$_2$ | Et | 2-OH, 4-Me |
| 6565 | FCH$_2$—CH=CH—CH$_2$ | Et | 2-OMe, 4-Me |
| 6566 | FCH$_2$—CH=CH—CH$_2$ | Et | 2-OMeF, 4-Me |
| 6567 | FCH$_2$—CH=CH—CH$_2$ | Et | 2-OCF$_3$, 4-Me |
| 6568 | FCH$_2$—CH=CH—CH$_2$ | Et | 2-OEtF, 4-Me |
| 6569 | FCH$_2$—CH=CH—CH$_2$ | Et | 2-OPrF, 4-Me |
| 6570 | FCH$_2$—CH=CH—CH$_2$ | Et | 2-Cl, 4-OH |

TABLE 5-continued

Substituent list for compounds of general structure X.

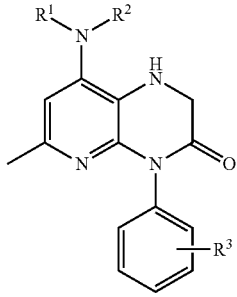

| Compound # | R¹ = | R² = | R³ = |
|---|---|---|---|
| 6571 | FCH₂—CH=CH—CH₂ | Et | 2-Cl, 4-OMe |
| 6572 | FCH₂—CH=CH—CH₂ | Et | 2-Cl, 4-OMeF |
| 6573 | FCH₂—CH=CH—CH₂ | Et | 2-Cl, 4-OCF₃ |
| 6574 | FCH₂—CH=CH—CH₂ | Et | 2-Cl, 4-OEtF |
| 6575 | FCH₂—CH=CH—CH₂ | Et | 2-Cl, 4-OPrF |
| 6576 | FCH₂—CH=CH—CH₂ | Et | 2-F, 4-F |
| 6577 | FCH₂—CH=CH—CH₂ | Et | 2-Cl, 4-Cl |
| 6578 | FCH₂—CH=CH—CH₂ | Et | 2-Cl, 4-F |
| 6579 | FCH₂—CH=CH—CH₂ | Et | 2-Cl, 4-NO₂ |
| 6580 | FCH₂—CH=CH—CH₂ | Et | 2-Cl, 4-NH₂ |
| 6581 | FCH₂—CH=CH—CH₂ | Et | 2-Cl, 4-NHMe |
| 6582 | FCH₂—CH=CH—CH₂ | Et | 2-Cl, 4-NMe₂ |
| 6583 | FCH₂—CH=CH—CH₂ | Et | 2-Cl, 4-NMe₃OTf |
| 6584 | FCH₂—CH=CH—CH₂ | Et | 2-Cl, 4-NMe₃I |
| 6585 | FCH₂—CH=CH—CH₂ | Et | 2-Cl, 5-F |
| 6586 | FCH₂—CH=CH—CH₂ | Et | 2-Cl, 5-NO₂ |
| 6587 | FCH₂—CH=CH—CH₂ | Et | 2-Cl, 5-NH₂ |
| 6588 | FCH₂—CH=CH—CH₂ | Et | 2-Cl, 5-NHMe |
| 6589 | FCH₂—CH=CH—CH₂ | Et | 2-Cl, 5-NMe₂ |
| 6590 | FCH₂—CH=CH—CH₂ | Et | 2-Cl, 5-NMe₃OTf |
| 6591 | FCH₂—CH=CH—CH₂ | Et | 2-Cl, 5-NMe₃I |
| 6592 | FCH₂—CH=CH—CH₂ | Et | 2-F, 4-Cl |
| 6593 | FCH₂—CH=CH—CH₂ | Et | 2-NO₂, 4-Cl |
| 6594 | FCH₂—CH=CH—CH₂ | Et | 2-NH₂, 4-Cl |
| 6595 | FCH₂—CH=CH—CH₂ | Et | 2-NHMe, 4-Cl |
| 6596 | FCH₂—CH=CH—CH₂ | Et | 2-NMe₂, 4-Cl |
| 6597 | FCH₂—CH=CH—CH₂ | Et | 2-NMe₃OTf, 4-Cl |
| 6598 | FCH₂—CH=CH—CH₂ | Et | 2-NMe₃I, 4-Cl |
| 6599 | FCH₂—CH=CH—CH₂ | Et | 2-F, 5-Cl |
| 6600 | FCH₂—CH=CH—CH₂ | Et | 2-NO₂, 5-Cl |
| 6601 | FCH₂—CH=CH—CH₂ | Et | 2-NH₂, 5-Cl |
| 6602 | FCH₂—CH=CH—CH₂ | Et | 2-NHMe, 5-Cl |
| 6603 | FCH₂—CH=CH—CH₂ | Et | 2-NMe₂, 5-Cl |
| 6604 | FCH₂—CH=CH—CH₂ | Et | 2-NMe₃OTf, 5-Cl |
| 6605 | FCH₂—CH=CH—CH₂ | Et | 2-NMe₃I, 5-Cl |
| 6606 | FCH₂—CH=CH—CH₂ | Et | 2-Br, 4-F |
| 6607 | FCH₂—CH=CH—CH₂ | Et | 2-Br, 4-NO₂ |
| 6608 | FCH₂—CH=CH—CH₂ | Et | 2-Br, 4-NH₂ |
| 6609 | FCH₂—CH=CH—CH₂ | Et | 2-Br, 4-NHMe |
| 6610 | FCH₂—CH=CH—CH₂ | Et | 2-Br, 4-NMe₂ |
| 6611 | FCH₂—CH=CH—CH₂ | Et | 2-Br, 4-NMe₃OTf |
| 6612 | FCH₂—CH=CH—CH₂ | Et | 2-Br, 4-NMe₃I |
| 6613 | FCH₂—CH=CH—CH₂ | Et | 2-Br, 5-F |
| 6614 | FCH₂—CH=CH—CH₂ | Et | 2-Br, 5-NO₂ |
| 6615 | FCH₂—CH=CH—CH₂ | Et | 2-Br, 5-NH₂ |
| 6616 | FCH₂—CH=CH—CH₂ | Et | 2-Br, 5-NHMe |
| 6617 | FCH₂—CH=CH—CH₂ | Et | 2-Br, 5-NMe₂ |
| 6618 | FCH₂—CH=CH—CH₂ | Et | 2-Br, 5-NMe₃OTf |
| 6619 | FCH₂—CH=CH—CH₂ | Et | 2-Br, 5-NMe₃I |
| 6620 | FCH₂—CH=CH—CH₂ | Et | 2-F, 4-Br |
| 6621 | FCH₂—CH=CH—CH₂ | Et | 2-NO₂, 4-Br |
| 6622 | FCH₂—CH=CH—CH₂ | Et | 2-NH₂, 4-Br |
| 6623 | FCH₂—CH=CH—CH₂ | Et | 2-NHMe, 4-Br |
| 6624 | FCH₂—CH=CH—CH₂ | Et | 2-NMe₂, 4-Br |
| 6625 | FCH₂—CH=CH—CH₂ | Et | 2-NMe₃OTf, 4-Br |
| 6626 | FCH₂—CH=CH—CH₂ | Et | 2-NMe₃I, 4-Br |
| 6627 | FCH₂—CH=CH—CH₂ | Et | 2-I, 4-F |
| 6628 | FCH₂—CH=CH—CH₂ | Et | 2-I, 4-NO₂ |
| 6629 | FCH₂—CH=CH—CH₂ | Et | 2-I, 4-NH₂ |
| 6630 | FCH₂—CH=CH—CH₂ | Et | 2-I, 4-NHMe |

TABLE 5-continued

Substituent list for compounds of general structure X.

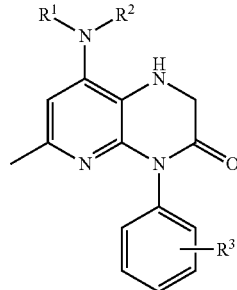

| Compound # | R¹ = | R² = | R³ = |
|---|---|---|---|
| 6631 | FCH₂—CH=CH—CH₂ | Et | 2-I, 4-NMe₂ |
| 6632 | FCH₂—CH=CH—CH₂ | Et | 2-I, 4-NMe₃OTf |
| 6633 | FCH₂—CH=CH—CH₂ | Et | 2-I, 4-NMe₃I |
| 6634 | FCH₂—CH=CH—CH₂ | Et | 2-F, 4-I |
| 6635 | FCH₂—CH=CH—CH₂ | Et | 2-NO₂, 4-I |
| 6636 | FCH₂—CH=CH—CH₂ | Et | 2-NH₂, 4-I |
| 6637 | FCH₂—CH=CH—CH₂ | Et | 2-NHMe, 4-I |
| 6638 | FCH₂—CH=CH—CH₂ | Et | 2-NMe₂, 4-I |
| 6639 | FCH₂—CH=CH—CH₂ | Et | 2-NMe₃OTf, 4-I |
| 6640 | FCH₂—CH=CH—CH₂ | Et | 2-NMe₃I, 4-I |
| 6641 | FCH₂—CH=CH—CH₂ | Et | 2-Me, 3-F |
| 6642 | FCH₂—CH=CH—CH₂ | Et | 2-Me, 3-NO₂ |
| 6643 | FCH₂—CH=CH—CH₂ | Et | 2-Me, 3-NH₂ |
| 6644 | FCH₂—CH=CH—CH₂ | Et | 2-Me, 3-NHMe |
| 6645 | FCH₂—CH=CH—CH₂ | Et | 2-Me, 3-NMe₂ |
| 6646 | FCH₂—CH=CH—CH₂ | Et | 2-Me, 3-NMe₃OTf |
| 6647 | FCH₂—CH=CH—CH₂ | Et | 2-Me, 3-NMe₃I |
| 6648 | FCH₂—CH=CH—CH₂ | Et | 2-Me, 4-F |
| 6649 | FCH₂—CH=CH—CH₂ | Et | 2-Me, 4-NO₂ |
| 6650 | FCH₂—CH=CH—CH₂ | Et | 2-Me, 4-NH₂ |
| 6651 | FCH₂—CH=CH—CH₂ | Et | 2-Me, 4-NHMe |
| 6652 | FCH₂—CH=CH—CH₂ | Et | 2-Me, 4-NMe₂ |
| 6653 | FCH₂—CH=CH—CH₂ | Et | 2-Me, 4-NMe₃OTf |
| 6654 | FCH₂—CH=CH—CH₂ | Et | 2-Me, 4-NMe₃I |
| 6655 | FCH₂—CH=CH—CH₂ | Et | 2-Me, 5-F |
| 6656 | FCH₂—CH=CH—CH₂ | Et | 2-Me, 5-NO₂ |
| 6657 | FCH₂—CH=CH—CH₂ | Et | 2-Me, 5-NH₂ |
| 6658 | FCH₂—CH=CH—CH₂ | Et | 2-Me, 5-NHMe |
| 6659 | FCH₂—CH=CH—CH₂ | Et | 2-Me, 5-NMe₂ |
| 6660 | FCH₂—CH=CH—CH₂ | Et | 2-Me, 5-NMe₃OTf |
| 6661 | FCH₂—CH=CH—CH₂ | Et | 2-Me, 5-NMe₃I |
| 6662 | FCH₂—CH=CH—CH₂ | Et | 2-F, 4-Me |
| 6663 | FCH₂—CH=CH—CH₂ | Et | 2-NO₂, 4-Me |
| 6664 | FCH₂—CH=CH—CH₂ | Et | 2-NH₂, 4-Me |
| 6665 | FCH₂—CH=CH—CH₂ | Et | 2-NHMe, 4-Me |
| 6666 | FCH₂—CH=CH—CH₂ | Et | 2-NMe₂, 4-Me |
| 6667 | FCH₂—CH=CH—CH₂ | Et | 2-NMe₃, 4-Me |
| 6668 | FCH₂—CH=CH—CH₂ | Et | 2-NMe₃OTf, 4-Me |
| 6669 | FCH₂—CH=CH—CH₂ | Et | 2-NMe₃I, 4-Me |
| 6670 | FCH₂—CH=CH—CH₂ | Et | 2-SnMe₃, 4-F |
| 6671 | FCH₂—CH=CH—CH₂ | Et | 2-SnMe₃, 5-F |
| 6672 | FCH₂—CH=CH—CH₂ | Et | 2-F, 4-SnMe₃ |
| 6673 | FCH₂—CH=CH—CH₂ | Et | 2-Br, 6-Cl, 4-F |
| 6674 | FCH₂—CH=CH—CH₂ | Et | 2-Br, 6-Cl, 4-NO₂ |
| 6675 | FCH₂—CH=CH—CH₂ | Et | 2-Br, 6-Cl, 4-NH₂ |
| 6676 | FCH₂—CH=CH—CH₂ | Et | 2-Br, 6-Cl, 4-NHMe |
| 6677 | FCH₂—CH=CH—CH₂ | Et | 2-Br, 6-Cl, 4-NMe₂ |
| 6678 | FCH₂—CH=CH—CH₂ | Et | 2-Br, 6-Cl, 4-NMe₃OTf |
| 6679 | FCH₂—CH=CH—CH₂ | Et | 2-Br, 6-Cl, 4-NMe₃I |
| 6680 | FCH₂—CH=CH—CH₂ | Et | 2-Me, 6-Cl, 4-F |
| 6681 | FCH₂—CH=CH—CH₂ | Et | 2-SnMe₃, 6-Cl, 4-F |
| 6682 | FCH₂—CH=CH—CH₂ | Et | 2-Cl, 4-Me |
| 6683 | FCH₂—CH=CH—CH₂ | Et | 2-Cl, 4-Br |
| 6684 | FCH₂—CH=CH—CH₂ | Et | 2-Cl, 4-SnMe₃ |
| 6685 | FCH₂—CH=CH—CH₂ | Et | 2-Br, 4-Cl |
| 6686 | FCH₂—CH=CH—CH₂ | Et | 2-SnMe₃, 4-Cl |
| 6687 | FCH₂—CH=CH—CH₂ | Et | 2-Me, 4-Cl |
| 6688 | FCH₂—CH=CH—CH₂ | Et | 2-Br, 4-Br |
| 6689 | FCH₂—CH=CH—CH₂ | Et | 2-Br, 4-Me |
| 6690 | FCH₂—CH=CH—CH₂ | Et | 2-Br, 4-SnMe₃ |

TABLE 5-continued

Substituent list for compounds of general structure X.

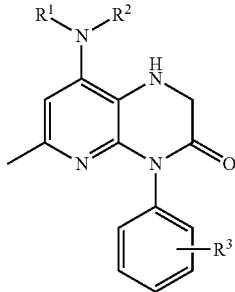

| Compound # | R¹ = | R² = | R³ = |
|---|---|---|---|
| 6691 | FCH₂—CH=CH—CH₂ | Et | 2-SnMe₃, 4-Br |
| 6692 | FCH₂—CH=CH—CH₂ | Et | 2-Me, 4-Br |
| 6693 | FCH₂—CH=CH—CH₂ | Et | 2-Me, 4-SnMe₃ |
| 6694 | FCH₂—CH=CH—CH₂ | Et | 2-SnMe₃, 4-Me |
| 6695 | FCH₂—CH=CH—CH₂ | Et | 2-Me, 4-Me |
| 6696 | FCH₂—CH=CH—CH₂ | Et | 2-Et, 4-Br |
| 6697 | FCH₂—CH=CH—CH₂ | Et | 2-Et, 4-SnMe₃ |
| 6698 | FCH₂—CH=CH—CH₂ | Et | 2-Et, 4-Me |
| 6699 | FCH₂—CH=CH—CH₂ | Et | 2-Me, 4-Me, 6-Me |
| 6700 | FCH₂—CH=CH—CH₂ | Et | 2-Me, 4-Br, 6-Me |
| 6701 | FCH₂—CH=CH—CH₂ | Et | 2-Me, 4-SnMe₃, 6-Me |
| 6702 | FCH₂—CH=CH—CH₂ | Et | 2-Et, 6-Me |
| 6703 | FCH₂—CH=CH—CH₂ | Et | 2-Br, 4-i-Pr |
| 6704 | FCH₂—CH=CH—CH₂ | Et | 2-SnMe₃, 4-i-Pr |
| 6705 | FCH₂—CH=CH—CH₂ | Et | 2-Me, 4-i-Pr |
| 6706 | FCH₂—CH=CH—CH₂ | Et | 2-Br, 4-Br, 6-Br |
| 6707 | FCH₂—CH=CH—CH₂ | Et | 2-Br, 4-Me, 6-Br |
| 6708 | FCH₂—CH=CH—CH₂ | Et | 2-Br, 4-SnMe₃, 6-Br |
| 6709 | FCH₂—CH=CH—CH₂ | Et | 2-SnMe₃, 4-Br, 6-Br |
| 6710 | FCH₂—CH=CH—CH₂ | Et | 2-Br, 4-Br, 6-Me |
| 6711 | FCH₂—CH=CH—CH₂ | Et | 2-Br, 4-CF₃, 6-Br |
| 6712 | FCH₂—CH=CH—CH₂ | Et | 2-Br, 4-Br₃, 6-CF₃ |
| 6713 | FCH₂—CH=CH—CH₂ | Et | 2-CF₃, 4-CF₃ |
| 6714 | FCH₂—CH=CH—CH₂ | Et | 2-Cl, 4-CF₃ |
| 6715 | FCH₂—CH=CH—CH₂ | Et | 2-CF₃, 4-Cl |
| 6716 | FCH₂—CH=CH—CH₂ | Et | 2-Br, 4-CF₃ |
| 6717 | FCH₂—CH=CH—CH₂ | Et | 2-SnMe₃, 4-CF₃ |
| 6718 | FCH₂—CH=CH—CH₂ | Et | 2-Me, 4-CF₃ |
| 6719 | FCH₂—CH=CH—CH₂ | Et | 2-CF₃, 4-Br |
| 6720 | FCH₂—CH=CH—CH₂ | Et | 2-CF₃, 4-SnMe₃ |
| 6721 | FCH₂—CH=CH—CH₂ | Et | 2-CF₃, 4-Me |
| 6722 | FCH₂—CH=CH—CH₂ | Et | 2-Br, 4-OH |
| 6723 | FCH₂—CH=CH—CH₂ | Et | 2-Br, 4-OMe |
| 6724 | FCH₂—CH=CH—CH₂ | Et | 2-Br, 4-OMeF |
| 6725 | FCH₂—CH=CH—CH₂ | Et | 2-Br, 4-OCF₃ |
| 6726 | FCH₂—CH=CH—CH₂ | Et | 2-Br, 4-OEtF |
| 6727 | FCH₂—CH=CH—CH₂ | Et | 2-Br, 4-OPrF |
| 6728 | FCH₂—CH=CH—CH₂ | Et | 2-OH, 4-Br |
| 6729 | FCH₂—CH=CH—CH₂ | Et | 2-OMe, 4-Br |
| 6730 | FCH₂—CH=CH—CH₂ | Et | 2-OMeF, 4-Br |
| 6731 | FCH₂—CH=CH—CH₂ | Et | 2-OCF₃, 4-Br |
| 6732 | FCH₂—CH=CH—CH₂ | Et | 2-OEtF, 4-Br |
| 6733 | FCH₂—CH=CH—CH₂ | Et | 2-OPrF, 4-Br |
| 6734 | FCH₂—CH=CH—CH₂ | Et | 2-I, 4-OH |
| 6735 | FCH₂—CH=CH—CH₂ | Et | 2-I, 4-OMe |
| 6736 | FCH₂—CH=CH—CH₂ | Et | 2-I, 4-OMeF |
| 6737 | FCH₂—CH=CH—CH₂ | Et | 2-I, 4-OCF₃ |
| 6738 | FCH₂—CH=CH—CH₂ | Et | 2-I, 4-OEtF |
| 6739 | FCH₂—CH=CH—CH₂ | Et | 2-I, 4-OPrF |
| 6740 | FCH₂—CH=CH—CH₂ | Et | 2-OH, 4-I |
| 6741 | FCH₂—CH=CH—CH₂ | Et | 2-OMe, 4-I |
| 6742 | FCH₂—CH=CH—CH₂ | Et | 2-OMeF, 4-I |
| 6743 | FCH₂—CH=CH—CH₂ | Et | 2-OCF₃, 4-I |
| 6744 | FCH₂—CH=CH—CH₂ | Et | 2-OEtF, 4-I |
| 6745 | FCH₂—CH=CH—CH₂ | Et | 2-OPrF, 4-I |
| 6746 | FCH₂—CH=CH—CH₂ | Et | 2-SnMe₃, 4-OH |
| 6747 | FCH₂—CH=CH—CH₂ | Et | 2-SnMe₃, 4-OMe |
| 6748 | FCH₂—CH=CH—CH₂ | Et | 2-SnMe₃, 4-OMeF |
| 6749 | FCH₂—CH=CH—CH₂ | Et | 2-SnMe₃, 4-OCF₃ |
| 6750 | FCH₂—CH=CH—CH₂ | Et | 2-SnMe₃, 4-OEtF |
| 6751 | FCH₂—CH=CH—CH₂ | Et | 2-SnMe₃, 4-OPrF |
| 6752 | FCH₂—CH=CH—CH₂ | Et | 2-OH, 4-SnMe₃ |
| 6753 | FCH₂—CH=CH—CH₂ | Et | 2-OMe, 4-SnMe₃ |
| 6754 | FCH₂—CH=CH—CH₂ | Et | 2-OMeF, 4-SnMe₃ |
| 6755 | FCH₂—CH=CH—CH₂ | Et | 2-OCF₃, 4-SnMe₃ |
| 6756 | FCH₂—CH=CH—CH₂ | Et | 2-OEtF, 4-SnMe₃ |
| 6757 | FCH₂—CH=CH—CH₂ | Et | 2-OPrF, 4-SnMe₃ |
| 6758 | FCH₂—CH=CH—CH₂ | Et—F | H |
| 6759 | FCH₂—CH=CH—CH₂ | Et—F | 2-t-Bu |
| 6760 | FCH₂—CH=CH—CH₂ | Et—F | 2-Br |
| 6761 | FCH₂—CH=CH—CH₂ | Et—F | 3-Br |
| 6762 | FCH₂—CH=CH—CH₂ | Et—F | 4-Br |
| 6763 | FCH₂—CH=CH—CH₂ | Et—F | 2-I |
| 6764 | FCH₂—CH=CH—CH₂ | Et—F | 3-I |
| 6765 | FCH₂—CH=CH—CH₂ | Et—F | 4-I |
| 6766 | FCH₂—CH=CH—CH₂ | Et—F | 2-SnMe₃ |
| 6767 | FCH₂—CH=CH—CH₂ | Et—F | 3-SnMe₃ |
| 6768 | FCH₂—CH=CH—CH₂ | Et—F | 4-SnMe₃ |
| 6769 | FCH₂—CH=CH—CH₂ | Et—F | 2-Me |
| 6770 | FCH₂—CH=CH—CH₂ | Et—F | 3-Me |
| 6771 | FCH₂—CH=CH—CH₂ | Et—F | 4-Me |
| 6772 | FCH₂—CH=CH—CH₂ | Et—F | 2-OH |
| 6773 | FCH₂—CH=CH—CH₂ | Et—F | 3-OH |
| 6774 | FCH₂—CH=CH—CH₂ | Et—F | 4-OH |
| 6775 | FCH₂—CH=CH—CH₂ | Et—F | 2-OMe |
| 6776 | FCH₂—CH=CH—CH₂ | Et—F | 3-OMe |
| 6777 | FCH₂—CH=CH—CH₂ | Et—F | 4-OMe |
| 6778 | FCH₂—CH=CH—CH₂ | Et—F | 2-OMeF |
| 6779 | FCH₂—CH=CH—CH₂ | Et—F | 3-OMeF |
| 6780 | FCH₂—CH=CH—CH₂ | Et—F | 4-OMeF |
| 6781 | FCH₂—CH=CH—CH₂ | Et—F | 2-OCF₃ |
| 6782 | FCH₂—CH=CH—CH₂ | Et—F | 3-OCF₃ |
| 6783 | FCH₂—CH=CH—CH₂ | Et—F | 4-OCF₃ |
| 6784 | FCH₂—CH=CH—CH₂ | Et—F | 2-OEtF |
| 6785 | FCH₂—CH=CH—CH₂ | Et—F | 3-OEtF |
| 6786 | FCH₂—CH=CH—CH₂ | Et—F | 4-OEtF |
| 6787 | FCH₂—CH=CH—CH₂ | Et—F | 2-OPrF |
| 6788 | FCH₂—CH=CH—CH₂ | Et—F | 3-OPrF |
| 6789 | FCH₂—CH=CH—CH₂ | Et—F | 4-OPrF |
| 6790 | FCH₂—CH=CH—CH₂ | Et—F | 2-SH |
| 6791 | FCH₂—CH=CH—CH₂ | Et—F | 3-SH |
| 6792 | FCH₂—CH=CH—CH₂ | Et—F | 4-SH |
| 6793 | FCH₂—CH=CH—CH₂ | Et—F | 2-SMe |
| 6794 | FCH₂—CH=CH—CH₂ | Et—F | 3-SMe |
| 6795 | FCH₂—CH=CH—CH₂ | Et—F | 4-SMe |
| 6796 | FCH₂—CH=CH—CH₂ | Et—F | 2-SMeF |
| 6797 | FCH₂—CH=CH—CH₂ | Et—F | 3-SMeF |
| 6798 | FCH₂—CH=CH—CH₂ | Et—F | 4-SMeF |
| 6799 | FCH₂—CH=CH—CH₂ | Et—F | 2-SCF₃ |
| 6800 | FCH₂—CH=CH—CH₂ | Et—F | 3-SCF₃ |
| 6801 | FCH₂—CH=CH—CH₂ | Et—F | 4-SCF₃ |
| 6802 | FCH₂—CH=CH—CH₂ | Et—F | 2-SEtF |
| 6803 | FCH₂—CH=CH—CH₂ | Et—F | 3-SEtF |
| 6804 | FCH₂—CH=CH—CH₂ | Et—F | 4-SEtF |
| 6805 | FCH₂—CH=CH—CH₂ | Et—F | 2-SPrF |
| 6806 | FCH₂—CH=CH—CH₂ | Et—F | 3-SPrF |
| 6807 | FCH₂—CH=CH—CH₂ | Et—F | 4-SPrF |
| 6808 | FCH₂—CH=CH—CH₂ | Et—F | 2-OMe, 4-OMe |
| 6809 | FCH₂—CH=CH—CH₂ | Et—F | 2-Me, 5-OH |
| 6810 | FCH₂—CH=CH—CH₂ | Et—F | 2-Me, 5-OMe |

TABLE 5-continued

Substituent list for compounds of general structure X.

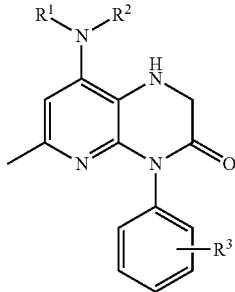
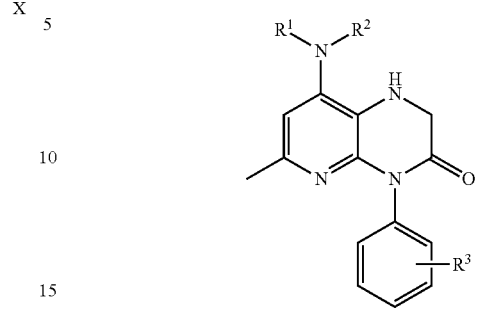

| Compound # | R¹ = | R² = | R³ = |
|---|---|---|---|
| 6811 | FCH₂—CH=CH—CH₂ | Et—F | 2-Me, 5-OMeF |
| 6812 | FCH₂—CH=CH—CH₂ | Et—F | 2-Me, 5-OEtF |
| 6813 | FCH₂—CH=CH—CH₂ | Et—F | 2-Me, 5-OPrF |
| 6814 | FCH₂—CH=CH—CH₂ | Et—F | 2-Me, 4-OH |
| 6815 | FCH₂—CH=CH—CH₂ | Et—F | 2-Me, 4-OMe |
| 6816 | FCH₂—CH=CH—CH₂ | Et—F | 2-Me, 4-OMeF |
| 6817 | FCH₂—CH=CH—CH₂ | Et—F | 2-Me, 4-OCF₃ |
| 6818 | FCH₂—CH=CH—CH₂ | Et—F | 2-Me, 4-OEtF |
| 6819 | FCH₂—CH=CH—CH₂ | Et—F | 2-Me, 4-OPrF |
| 6820 | FCH₂—CH=CH—CH₂ | Et—F | 2-OH, 4-Me |
| 6821 | FCH₂—CH=CH—CH₂ | Et—F | 2-OMe, 4-Me |
| 6822 | FCH₂—CH=CH—CH₂ | Et—F | 2-OMeF, 4-Me |
| 6823 | FCH₂—CH=CH—CH₂ | Et—F | 2-OCF₃, 4-Me |
| 6824 | FCH₂—CH=CH—CH₂ | Et—F | 2-OEtF, 4-Me |
| 6825 | FCH₂—CH=CH—CH₂ | Et—F | 2-OPrF, 4-Me |
| 6826 | FCH₂—CH=CH—CH₂ | Et—F | 2-Cl, 4-OH |
| 6827 | FCH₂—CH=CH—CH₂ | Et—F | 2-Cl, 4-OMe |
| 6828 | FCH₂—CH=CH—CH₂ | Et—F | 2-Cl, 4-OMeF |
| 6829 | FCH₂—CH=CH—CH₂ | Et—F | 2-Cl, 4-OCF₃ |
| 6830 | FCH₂—CH=CH—CH₂ | Et—F | 2-Cl, 4-OEtF |
| 6831 | FCH₂—CH=CH—CH₂ | Et—F | 2-Cl, 4-OPrF |
| 6832 | FCH₂—CH=CH—CH₂ | Et—F | 2-F, 4-F |
| 6833 | FCH₂—CH=CH—CH₂ | Et—F | 2-Cl, 4-Cl |
| 6834 | FCH₂—CH=CH—CH₂ | Et—F | 2-Cl, 4-F |
| 6835 | FCH₂—CH=CH—CH₂ | Et—F | 2-Cl, 4-NO₂ |
| 6836 | FCH₂—CH=CH—CH₂ | Et—F | 2-Cl, 4-NH₂ |
| 6837 | FCH₂—CH=CH—CH₂ | Et—F | 2-Cl, 4-NHMe |
| 6838 | FCH₂—CH=CH—CH₂ | Et—F | 2-Cl, 4-NMe₂ |
| 6839 | FCH₂—CH=CH—CH₂ | Et—F | 2-Cl, 4-NMe₃OTf |
| 6840 | FCH₂—CH=CH—CH₂ | Et—F | 2-Cl, 4-NMe₃I |
| 6841 | FCH₂—CH=CH—CH₂ | Et—F | 2-Cl, 5-F |
| 6842 | FCH₂—CH=CH—CH₂ | Et—F | 2-Cl, 5-NO₂ |
| 6843 | FCH₂—CH=CH—CH₂ | Et—F | 2-Cl, 5-NH₂ |
| 6844 | FCH₂—CH=CH—CH₂ | Et—F | 2-Cl, 5-NHMe |
| 6845 | FCH₂—CH=CH—CH₂ | Et—F | 2-Cl, 5-NMe₂ |
| 6846 | FCH₂—CH=CH—CH₂ | Et—F | 2-Cl, 5-NMe₃OTf |
| 6847 | FCH₂—CH=CH—CH₂ | Et—F | 2-Cl, 5-NMe₃I |
| 6848 | FCH₂—CH=CH—CH₂ | Et—F | 2-F, 4-Cl |
| 6849 | FCH₂—CH=CH—CH₂ | Et—F | 2-NO₂, 4-Cl |
| 6850 | FCH₂—CH=CH—CH₂ | Et—F | 2-NH₂, 4-Cl |
| 6851 | FCH₂—CH=CH—CH₂ | Et—F | 2-NHMe, 4-Cl |
| 6852 | FCH₂—CH=CH—CH₂ | Et—F | 2-NMe₂, 4-Cl |
| 6853 | FCH₂—CH=CH—CH₂ | Et—F | 2-NMe₃OTf, 4-Cl |
| 6854 | FCH₂—CH=CH—CH₂ | Et—F | 2-NMe₃I, 4-Cl |
| 6855 | FCH₂—CH=CH—CH₂ | Et—F | 2-F, 5-Cl |
| 6856 | FCH₂—CH=CH—CH₂ | Et—F | 2-NO₂, 5-Cl |
| 6857 | FCH₂—CH=CH—CH₂ | Et—F | 2-NH₂, 5-Cl |
| 6858 | FCH₂—CH=CH—CH₂ | Et—F | 2-NHMe, 5-Cl |
| 6859 | FCH₂—CH=CH—CH₂ | Et—F | 2-NMe₂, 5-Cl |
| 6860 | FCH₂—CH=CH—CH₂ | Et—F | 2-NMe₃OTf, 5-Cl |
| 6861 | FCH₂—CH=CH—CH₂ | Et—F | 2-NMe₃I, 5-Cl |
| 6862 | FCH₂—CH=CH—CH₂ | Et—F | 2-Br, 4-F |
| 6863 | FCH₂—CH=CH—CH₂ | Et—F | 2-Br, 4-NO₂ |
| 6864 | FCH₂—CH=CH—CH₂ | Et—F | 2-Br, 4-NH₂ |
| 6865 | FCH₂—CH=CH—CH₂ | Et—F | 2-Br, 4-NHMe |
| 6866 | FCH₂—CH=CH—CH₂ | Et—F | 2-Br, 4-NMe₂ |
| 6867 | FCH₂—CH=CH—CH₂ | Et—F | 2-Br, 4-NMe₃OTf |
| 6868 | FCH₂—CH=CH—CH₂ | Et—F | 2-Br, 4-NMe₃I |
| 6869 | FCH₂—CH=CH—CH₂ | Et—F | 2-Br, 5-F |
| 6870 | FCH₂—CH=CH—CH₂ | Et—F | 2-Br, 5-NO₂ |
| 6871 | FCH₂—CH=CH—CH₂ | Et—F | 2-Br, 5-NH₂ |
| 6872 | FCH₂—CH=CH—CH₂ | Et—F | 2-Br, 5-NHMe |
| 6873 | FCH₂—CH=CH—CH₂ | Et—F | 2-Br, 5-NMe₂ |
| 6874 | FCH₂—CH=CH—CH₂ | Et—F | 2-Br, 5-NMe₃OTf |
| 6875 | FCH₂—CH=CH—CH₂ | Et—F | 2-Br, 5-NMe₃I |
| 6876 | FCH₂—CH=CH—CH₂ | Et—F | 2-F, 4-Br |
| 6877 | FCH₂—CH=CH—CH₂ | Et—F | 2-NO₂, 4-Br |
| 6878 | FCH₂—CH=CH—CH₂ | Et—F | 2-NH₂, 4-Br |
| 6879 | FCH₂—CH=CH—CH₂ | Et—F | 2-NHMe, 4-Br |
| 6880 | FCH₂—CH=CH—CH₂ | Et—F | 2-NMe₂, 4-Br |
| 6881 | FCH₂—CH=CH—CH₂ | Et—F | 2-NMe₃OTf, 4-Br |
| 6882 | FCH₂—CH=CH—CH₂ | Et—F | 2-NMe₃I, 4-Br |
| 6883 | FCH₂—CH=CH—CH₂ | Et—F | 2-I, 4-F |
| 6884 | FCH₂—CH=CH—CH₂ | Et—F | 2-I, 4-NO₂ |
| 6885 | FCH₂—CH=CH—CH₂ | Et—F | 2-I, 4-NH₂ |
| 6886 | FCH₂—CH=CH—CH₂ | Et—F | 2-I, 4-NHMe |
| 6887 | FCH₂—CH=CH—CH₂ | Et—F | 2-I, 4-NMe₂ |
| 6888 | FCH₂—CH=CH—CH₂ | Et—F | 2-I, 4-NMe₃OTf |
| 6889 | FCH₂—CH=CH—CH₂ | Et—F | 2-I, 4-NMe₃I |
| 6890 | FCH₂—CH=CH—CH₂ | Et—F | 2-F, 4-I |
| 6891 | FCH₂—CH=CH—CH₂ | Et—F | 2-NO₂, 4-I |
| 6892 | FCH₂—CH=CH—CH₂ | Et—F | 2-NH₂, 4-I |
| 6893 | FCH₂—CH=CH—CH₂ | Et—F | 2-NHMe, 4-I |
| 6894 | FCH₂—CH=CH—CH₂ | Et—F | 2-NMe₂, 4-I |
| 6895 | FCH₂—CH=CH—CH₂ | Et—F | 2-NMe₃OTf, 4-I |
| 6896 | FCH₂—CH=CH—CH₂ | Et—F | 2-NMe₃I, 4-I |
| 6897 | FCH₂—CH=CH—CH₂ | Et—F | 2-Me, 3-F |
| 6898 | FCH₂—CH=CH—CH₂ | Et—F | 2-Me, 3-NO₂ |
| 6899 | FCH₂—CH=CH—CH₂ | Et—F | 2-Me, 3-NH₂ |
| 6900 | FCH₂—CH=CH—CH₂ | Et—F | 2-Me, 3-NHMe |
| 6901 | FCH₂—CH=CH—CH₂ | Et—F | 2-Me, 3-NMe₂ |
| 6902 | FCH₂—CH=CH—CH₂ | Et—F | 2-Me, 3-NMe₃OTf |
| 6903 | FCH₂—CH=CH—CH₂ | Et—F | 2-Me, 3-NMe₃I |
| 6904 | FCH₂—CH=CH—CH₂ | Et—F | 2-Me, 4-F |
| 6905 | FCH₂—CH=CH—CH₂ | Et—F | 2-Me, 4-NO₂ |
| 6906 | FCH₂—CH=CH—CH₂ | Et—F | 2-Me, 4-NH₂ |
| 6907 | FCH₂—CH=CH—CH₂ | Et—F | 2-Me, 4-NHMe |
| 6908 | FCH₂—CH=CH—CH₂ | Et—F | 2-Me, 4-NMe₂ |
| 6909 | FCH₂—CH=CH—CH₂ | Et—F | 2-Me, 4-NMe₃OTf |
| 6910 | FCH₂—CH=CH—CH₂ | Et—F | 2-Me, 4-NMe₃I |
| 6911 | FCH₂—CH=CH—CH₂ | Et—F | 2-Me, 5-F |
| 6912 | FCH₂—CH=CH—CH₂ | Et—F | 2-Me, 5-NO₂ |
| 6913 | FCH₂—CH=CH—CH₂ | Et—F | 2-Me, 5-NH₂ |
| 6914 | FCH₂—CH=CH—CH₂ | Et—F | 2-Me, 5-NHMe |
| 6915 | FCH₂—CH=CH—CH₂ | Et—F | 2-Me, 5-NMe₂ |
| 6916 | FCH₂—CH=CH—CH₂ | Et—F | 2-Me, 5-NMe₃OTf |
| 6917 | FCH₂—CH=CH—CH₂ | Et—F | 2-Me, 5-NMe₃I |
| 6918 | FCH₂—CH=CH—CH₂ | Et—F | 2-F, 4-Me |
| 6919 | FCH₂—CH=CH—CH₂ | Et—F | 2-NO₂, 4-Me |
| 6920 | FCH₂—CH=CH—CH₂ | Et—F | 2-NH₂, 4-Me |
| 6921 | FCH₂—CH=CH—CH₂ | Et—F | 2-NHMe, 4-Me |
| 6922 | FCH₂—CH=CH—CH₂ | Et—F | 2-NMe₂, 4-Me |
| 6923 | FCH₂—CH=CH—CH₂ | Et—F | 2-NMe₃, 4-Me |
| 6924 | FCH₂—CH=CH—CH₂ | Et—F | 2-NMe₃OTf, 4-Me |
| 6925 | FCH₂—CH=CH—CH₂ | Et—F | 2-NMe₃I, 4-Me |
| 6926 | FCH₂—CH=CH—CH₂ | Et—F | 2-SnMe₃, 4-F |
| 6927 | FCH₂—CH=CH—CH₂ | Et—F | 2-SnMe₃, 5-F |
| 6928 | FCH₂—CH=CH—CH₂ | Et—F | 2-F, 4-SnMe₃ |
| 6929 | FCH₂—CH=CH—CH₂ | Et—F | 2-Br, 6-Cl, 4-F |
| 6930 | FCH₂—CH=CH—CH₂ | Et—F | 2-Br, 6-Cl, 4-NO₂ |

TABLE 5-continued

Substituent list for compounds of general structure X.

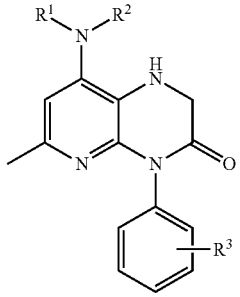

| Compound # | R¹ = | R² = | R³ = |
|---|---|---|---|
| 6931 | FCH₂—CH=CH—CH₂ | Et—F | 2-Br, 6-Cl, 4-NH₂ |
| 6932 | FCH₂—CH=CH—CH₂ | Et—F | 2-Br, 6-Cl, 4-NHMe |
| 6933 | FCH₂—CH=CH—CH₂ | Et—F | 2-Br, 6-Cl, 4-NMe₂ |
| 6934 | FCH₂—CH=CH—CH₂ | Et—F | 2-Br, 6-Cl, 4-NMe₃OTf |
| 6935 | FCH₂—CH=CH—CH₂ | Et—F | 2-Br, 6-Cl, 4-NMe₃I |
| 6936 | FCH₂—CH=CH—CH₂ | Et—F | 2-Me, 6-Cl, 4-F |
| 6937 | FCH₂—CH=CH—CH₂ | Et—F | 2-SnMe₃, 6-Cl, 4-F |
| 6938 | FCH₂—CH=CH—CH₂ | Et—F | 2-Cl, 4-Me |
| 6939 | FCH₂—CH=CH—CH₂ | Et—F | 2-Cl, 4-Br |
| 6940 | FCH₂—CH=CH—CH₂ | Et—F | 2-Cl, 4-SnMe₃ |
| 6941 | FCH₂—CH=CH—CH₂ | Et—F | 2-Br, 4-Cl |
| 6942 | FCH₂—CH=CH—CH₂ | Et—F | 2-SnMe₃, 4-Cl |
| 6943 | FCH₂—CH=CH—CH₂ | Et—F | 2-Me, 4-Cl |
| 6944 | FCH₂—CH=CH—CH₂ | Et—F | 2-Br, 4-Br |
| 6945 | FCH₂—CH=CH—CH₂ | Et—F | 2-Br, 4-Me |
| 6946 | FCH₂—CH=CH—CH₂ | Et—F | 2-Br, 4-SnMe₃ |
| 6947 | FCH₂—CH=CH—CH₂ | Et—F | 2-SnMe₃, 4-Br |
| 6948 | FCH₂—CH=CH—CH₂ | Et—F | 2-Me, 4-Br |
| 6949 | FCH₂—CH=CH—CH₂ | Et—F | 2-Me, 4-SnMe₃ |
| 6950 | FCH₂—CH=CH—CH₂ | Et—F | 2-SnMe₃, 4-Me |
| 6951 | FCH₂—CH=CH—CH₂ | Et—F | 2-Me, 4-Me |
| 6952 | FCH₂—CH=CH—CH₂ | Et—F | 2-Et, 4-Br |
| 6953 | FCH₂—CH=CH—CH₂ | Et—F | 2-Et, 4-SnMe₃ |
| 6954 | FCH₂—CH=CH—CH₂ | Et—F | 2-Et, 4-Me |
| 6955 | FCH₂—CH=CH—CH₂ | Et—F | 2-Me, 4-Me, 6-Me |
| 6956 | FCH₂—CH=CH—CH₂ | Et—F | 2-Me, 4-Br, 6-Me |
| 6957 | FCH₂—CH=CH—CH₂ | Et—F | 2-Me, 4-SnMe₃, 6-Me |
| 6958 | FCH₂—CH=CH—CH₂ | Et—F | 2-Et, 6-Me |
| 6959 | FCH₂—CH=CH—CH₂ | Et—F | 2-Br, 4-i-Pr |
| 6960 | FCH₂—CH=CH—CH₂ | Et—F | 2-SnMe₃, 4-i-Pr |
| 6961 | FCH₂—CH=CH—CH₂ | Et—F | 2-Me, 4-i-Pr |
| 6962 | FCH₂—CH=CH—CH₂ | Et—F | 2-Br, 4-Br, 6-Br |
| 6963 | FCH₂—CH=CH—CH₂ | Et—F | 2-Br, 4-Me, 6-Br |
| 6964 | FCH₂—CH=CH—CH₂ | Et—F | 2-Br, 4-SnMe₃, 6-Br |
| 6965 | FCH₂—CH=CH—CH₂ | Et—F | 2-SnMe₃, 4-Br, 6-Br |
| 6966 | FCH₂—CH=CH—CH₂ | Et—F | 2-Br, 4-Br, 6-Me |
| 6967 | FCH₂—CH=CH—CH₂ | Et—F | 2-Br, 4-CF₃, 6-Br |
| 6968 | FCH₂—CH=CH—CH₂ | Et—F | 2-Br, 4-Br, 6-CF₃ |
| 6969 | FCH₂—CH=CH—CH₂ | Et—F | 2-CF₃, 4-CF₃ |
| 6970 | FCH₂—CH=CH—CH₂ | Et—F | 2-Cl, 4-CF₃ |
| 6971 | FCH₂—CH=CH—CH₂ | Et—F | 2-CF₃, 4-Cl |
| 6972 | FCH₂—CH=CH—CH₂ | Et—F | 2-Br, 4-CF₃ |
| 6973 | FCH₂—CH=CH—CH₂ | Et—F | 2-SnMe₃, 4-CF₃ |
| 6974 | FCH₂—CH=CH—CH₂ | Et—F | 2-Me, 4-CF₃ |
| 6975 | FCH₂—CH=CH—CH₂ | Et—F | 2-CF₃, 4-Br |
| 6976 | FCH₂—CH=CH—CH₂ | Et—F | 2-CF₃, 4-SnMe₃ |
| 6977 | FCH₂—CH=CH—CH₂ | Et—F | 2-CF₃, 4-Me |
| 6978 | FCH₂—CH=CH—CH₂ | Et—F | 2-Br, 4-OH |
| 6979 | FCH₂—CH=CH—CH₂ | Et—F | 2-Br, 4-OMe |
| 6980 | FCH₂—CH=CH—CH₂ | Et—F | 2-Br, 4-OMeF |
| 6981 | FCH₂—CH=CH—CH₂ | Et—F | 2-Br, 4-OCF₃ |
| 6982 | FCH₂—CH=CH—CH₂ | Et—F | 2-Br, 4-OEtF |
| 6983 | FCH₂—CH=CH—CH₂ | Et—F | 2-Br, 4-OPrF |
| 6984 | FCH₂—CH=CH—CH₂ | Et—F | 2-OH, 4-Br |
| 6985 | FCH₂—CH=CH—CH₂ | Et—F | 2-OMe, 4-Br |
| 6986 | FCH₂—CH=CH—CH₂ | Et—F | 2-OMeF, 4-Br |
| 6987 | FCH₂—CH=CH—CH₂ | Et—F | 2-OCF₃, 4-Br |
| 6988 | FCH₂—CH=CH—CH₂ | Et—F | 2-OEtF, 4-Br |
| 6989 | FCH₂—CH=CH—CH₂ | Et—F | 2-OPrF, 4-Br |
| 6990 | FCH₂—CH=CH—CH₂ | Et—F | 2-I, 4-OH |

TABLE 5-continued

Substituent list for compounds of general structure X.

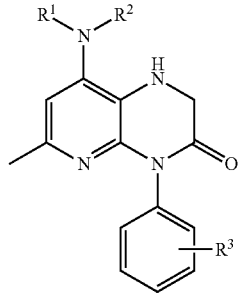

| Compound # | R¹ = | R² = | R³ = |
|---|---|---|---|
| 6991 | FCH₂—CH=CH—CH₂ | Et—F | 2-I, 4-OMe |
| 6992 | FCH₂—CH=CH—CH₂ | Et—F | 2-I, 4-OMeF |
| 6993 | FCH₂—CH=CH—CH₂ | Et—F | 2-I, 4-OCF₃ |
| 6994 | FCH₂—CH=CH—CH₂ | Et—F | 2-I, 4-OEtF |
| 6995 | FCH₂—CH=CH—CH₂ | Et—F | 2-I, 4-OPrF |
| 6996 | FCH₂—CH=CH—CH₂ | Et—F | 2-OH, 4-I |
| 6997 | FCH₂—CH=CH—CH₂ | Et—F | 2-OMe, 4-I |
| 6998 | FCH₂—CH=CH—CH₂ | Et—F | 2-OMeF, 4-I |
| 6999 | FCH₂—CH=CH—CH₂ | Et—F | 2-OCF₃, 4-I |
| 7000 | FCH₂—CH=CH—CH₂ | Et—F | 2-OEtF, 4-I |
| 7001 | FCH₂—CH=CH—CH₂ | Et—F | 2-OPrF, 4-I |
| 7002 | FCH₂—CH=CH—CH₂ | Et—F | 2-SnMe₃, 4-OH |
| 7003 | FCH₂—CH=CH—CH₂ | Et—F | 2-SnMe₃, 4-OMe |
| 7004 | FCH₂—CH=CH—CH₂ | Et—F | 2-SnMe₃, 4-OMeF |
| 7005 | FCH₂—CH=CH—CH₂ | Et—F | 2-SnMe₃, 4-OCF₃ |
| 7006 | FCH₂—CH=CH—CH₂ | Et—F | 2-SnMe₃, 4-OEtF |
| 7007 | FCH₂—CH=CH—CH₂ | Et—F | 2-SnMe₃, 4-OPrF |
| 7008 | FCH₂—CH=CH—CH₂ | Et—F | 2-OH, 4-SnMe₃ |
| 7009 | FCH₂—CH=CH—CH₂ | Et—F | 2-OMe, 4-SnMe₃ |
| 7010 | FCH₂—CH=CH—CH₂ | Et—F | 2-OMeF, 4-SnMe₃ |
| 7011 | FCH₂—CH=CH—CH₂ | Et—F | 2-OCF₃, 4-SnMe₃ |
| 7012 | FCH₂—CH=CH—CH₂ | Et—F | 2-OEtF, 4-SnMe₃ |
| 7013 | FCH₂—CH=CH—CH₂ | Et—F | 2-OPrF, 4-SnMe₃ |

TABLE 6

Substituent list for compounds of general structure XI.

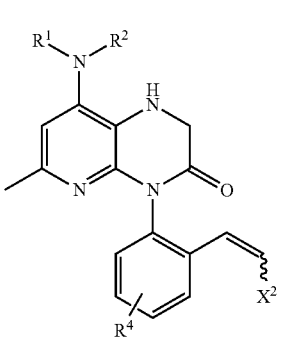

| Compound # | R¹ = | R² = | R⁴ = | X² = |
|---|---|---|---|---|
| 7014 | Bu | Et | H | H |
| 7015 | Bu | Et | H | SnMe₃ |
| 7016 | Bu | Et | H | Br |
| 7017 | Bu | Et | H | I |
| 7018 | Bu | Et | 4-F | H |
| 7019 | Bu | Et | 4-F | SnMe₃ |
| 7020 | Bu | Et | 4-F | Br |
| 7021 | Bu | Et | 4-F | I |
| 7022 | Bu | Et | 5-F | H |
| 7023 | Bu | Et | 5-F | SnMe₃ |
| 7024 | Bu | Et | 5-F | Br |
| 7025 | Bu | Et | 5-F | I |
| 7026 | Bu | Et | 4-Cl | H |

TABLE 6-continued

Substituent list for compounds of general structure XI.

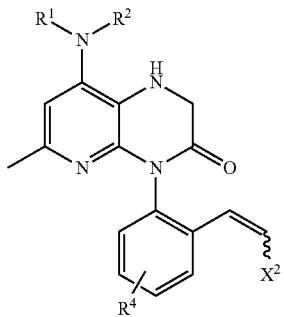
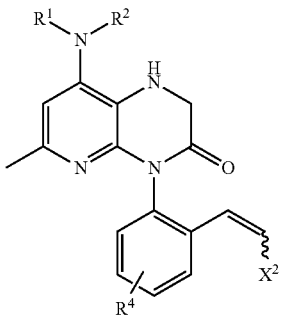

| Compound # | R¹ = | R² = | R⁴ = | X² = | Compound # | R¹ = | R² = | R⁴ = | X² = |
|---|---|---|---|---|---|---|---|---|---|
| 7027 | Bu | Et | 4-Cl | SnMe₃ | 7086 | Pr | Pr | H | H |
| 7028 | Bu | Et | 4-Cl | Br | 7087 | Pr | Pr | H | SnMe₃ |
| 7029 | Bu | Et | 4-Cl | I | 7088 | Pr | Pr | H | Br |
| 7030 | Bu | Et | 4-Br | H | 7089 | Pr | Pr | H | I |
| 7031 | Bu | Et | 4-Br | SnMe₃ | 7090 | Pr | Pr | 4-F | H |
| 7032 | Bu | Et | 4-Br | Br | 7091 | Pr | Pr | 4-F | SnMe₃ |
| 7033 | Bu | Et | 4-Br | I | 7092 | Pr | Pr | 4-F | Br |
| 7034 | Bu | Et | 4-Me | H | 7093 | Pr | Pr | 4-F | I |
| 7035 | Bu | Et | 4-Me | SnMe₃ | 7094 | Pr | Pr | 5-F | H |
| 7036 | Bu | Et | 4-Me | Br | 7095 | Pr | Pr | 5-F | SnMe₃ |
| 7037 | Bu | Et | 4-Me | I | 7096 | Pr | Pr | 5-F | Br |
| 7038 | Bu | Et | 4-CF₃ | H | 7097 | Pr | Pr | 5-F | I |
| 7039 | Bu | Et | 4-CF₃ | SnMe₃ | 7098 | Pr | Pr | 4-Cl | H |
| 7040 | Bu | Et | 4-CF₃ | Br | 7099 | Pr | Pr | 4-Cl | SnMe₃ |
| 7041 | Bu | Et | 4-CF₃ | I | 7100 | Pr | Pr | 4-Cl | Br |
| 7042 | Bu | Et | 4-OH | H | 7101 | Pr | Pr | 4-Cl | I |
| 7043 | Bu | Et | 4-OH | SnMe₃ | 7102 | Pr | Pr | 4-Br | H |
| 7044 | Bu | Et | 4-OH | Br | 7103 | Pr | Pr | 4-Br | SnMe₃ |
| 7045 | Bu | Et | 4-OH | I | 7104 | Pr | Pr | 4-Br | Br |
| 7046 | Bu | Et | 4-OMe | H | 7105 | Pr | Pr | 4-Br | I |
| 7047 | Bu | Et | 4-OMe | SnMe₃ | 7106 | Pr | Pr | 4-Me | H |
| 7048 | Bu | Et | 4-OMe | Br | 7107 | Pr | Pr | 4-Me | SnMe₃ |
| 7049 | Bu | Et | 4-OMe | I | 7108 | Pr | Pr | 4-Me | Br |
| 7050 | Bu | Et | 4-OMeF | H | 7109 | Pr | Pr | 4-Me | I |
| 7051 | Bu | Et | 4-OMeF | SnMe₃ | 7110 | Pr | Pr | 4-CF₃ | H |
| 7052 | Bu | Et | 4-OMeF | Br | 7111 | Pr | Pr | 4-CF₃ | SnMe₃ |
| 7053 | Bu | Et | 4-OMeF | I | 7112 | Pr | Pr | 4-CF₃ | Br |
| 7054 | Bu | Et | 4-OCF₃ | H | 7113 | Pr | Pr | 4-CF₃ | I |
| 7055 | Bu | Et | 4-OCF₃ | SnMe₃ | 7114 | Pr | Pr | 4-OH | H |
| 7056 | Bu | Et | 4-OCF₃ | Br | 7115 | Pr | Pr | 4-OH | SnMe₃ |
| 7057 | Bu | Et | 4-OCF₃ | I | 7116 | Pr | Pr | 4-OH | Br |
| 7058 | Bu | Et | 4-OEtF | H | 7117 | Pr | Pr | 4-OH | I |
| 7059 | Bu | Et | 4-OEtF | SnMe₃ | 7118 | Pr | Pr | 4-OMe | H |
| 7060 | Bu | Et | 4-OEtF | Br | 7119 | Pr | Pr | 4-OMe | SnMe₃ |
| 7061 | Bu | Et | 4-OEtF | I | 7120 | Pr | Pr | 4-OMe | Br |
| 7062 | Bu | Et | 4-OPrF | H | 7121 | Pr | Pr | 4-OMe | I |
| 7063 | Bu | Et | 4-OPrF | SnMe₃ | 7122 | Pr | Pr | 4-OMeF | H |
| 7064 | Bu | Et | 4-OPrF | Br | 7123 | Pr | Pr | 4-OMeF | SnMe₃ |
| 7065 | Bu | Et | 4-OPrF | I | 7124 | Pr | Pr | 4-OMeF | Br |
| 7066 | Bu | Et | 4-i-Pr | H | 7125 | Pr | Pr | 4-OMeF | I |
| 7067 | Bu | Et | 4-i-Pr | SnMe₃ | 7126 | Pr | Pr | 4-OCF₃ | H |
| 7068 | Bu | Et | 4-i-Pr | Br | 7127 | Pr | Pr | 4-OCF₃ | SnMe₃ |
| 7069 | Bu | Et | 4-i-Pr | I | 7128 | Pr | Pr | 4-OCF₃ | Br |
| 7070 | Bu | Et | 2-Br, 4-CF₃ | H | 7129 | Pr | Pr | 4-OCF₃ | I |
| 7071 | Bu | Et | 2-Br, 4-CF₃ | SnMe₃ | 7130 | Pr | Pr | 4-OEtF | H |
| 7072 | Bu | Et | 2-Br, 4-CF₃ | Br | 7131 | Pr | Pr | 4-OEtF | SnMe₃ |
| 7073 | Bu | Et | 2-Br, 4-CF₃ | I | 7132 | Pr | Pr | 4-OEtF | Br |
| 7074 | Bu | Et | 2-CF₃, 4-Br | H | 7133 | Pr | Pr | 4-OEtF | I |
| 7075 | Bu | Et | 2-CF₃, 4-Br | SnMe₃ | 7134 | Pr | Pr | 4-OPrF | H |
| 7076 | Bu | Et | 2-CF₃, 4-Br | Br | 7135 | Pr | Pr | 4-OPrF | SnMe₃ |
| 7077 | Bu | Et | 2-CF₃, 4-Br | I | 7136 | Pr | Pr | 4-OPrF | Br |
| 7078 | Bu | Et | 2-Br, 4-Br | H | 7137 | Pr | Pr | 4-OPrF | I |
| 7079 | Bu | Et | 2-Br, 4-Br | SnMe₃ | 7138 | Pr | Pr | 4-i-Pr | H |
| 7080 | Bu | Et | 2-Br, 4-Br | Br | 7139 | Pr | Pr | 4-i-Pr | SnMe₃ |
| 7081 | Bu | Et | 2-Br, 4-Br | I | 7140 | Pr | Pr | 4-i-Pr | Br |
| 7082 | Bu | Et | 2-Br, 4-Me | H | 7141 | Pr | Pr | 4-i-Pr | I |
| 7083 | Bu | Et | 2-Br, 4-Me | SnMe₃ | 7142 | Pr | Pr | 2-Br, 4-CF₃ | H |
| 7084 | Bu | Et | 2-Br, 4-Me | Br | 7143 | Pr | Pr | 2-Br, 4-CF₃ | SnMe₃ |
| 7085 | Bu | Et | 2-Br, 4-Me | I | 7144 | Pr | Pr | 2-Br, 4-CF₃ | Br |

TABLE 6-continued

Substituent list for compounds of general structure XI.

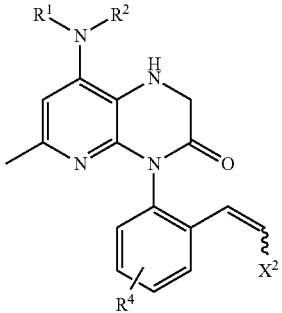
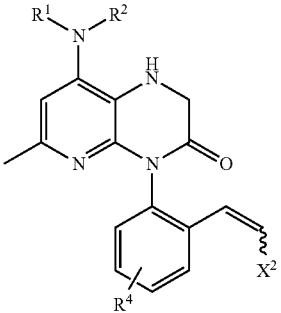

| Compound # | R¹ = | R² = | R⁴ = | X² = | Compound # | R¹ = | R² = | R⁴ = | X² = |
|---|---|---|---|---|---|---|---|---|---|
| 7145 | Pr | Pr | 2-Br, 4-CF₃ | I | 7204 | Pr | Pr—F | 4-OEtF | Br |
| 7146 | Pr | Pr | 2-CF₃, 4-Br | H | 7205 | Pr | Pr—F | 4-OEtF | I |
| 7147 | Pr | Pr | 2-CF₃, 4-Br | SnMe₃ | 7206 | Pr | Pr—F | 4-OPrF | H |
| 7148 | Pr | Pr | 2-CF₃, 4-Br | Br | 7207 | Pr | Pr—F | 4-OPrF | SnMe₃ |
| 7149 | Pr | Pr | 2-CF₃, 4-Br | I | 7208 | Pr | Pr—F | 4-OPrF | Br |
| 7150 | Pr | Pr | 2-Br, 4-Br | H | 7209 | Pr | Pr—F | 4-OPrF | I |
| 7151 | Pr | Pr | 2-Br, 4-Br | SnMe₃ | 7210 | Pr | Pr—F | 4-i-Pr | H |
| 7152 | Pr | Pr | 2-Br, 4-Br | Br | 7211 | Pr | Pr—F | 4-i-Pr | SnMe₃ |
| 7153 | Pr | Pr | 2-Br, 4-Br | I | 7212 | Pr | Pr—F | 4-i-Pr | Br |
| 7154 | Pr | Pr | 2-Br, 4-Me | H | 7213 | Pr | Pr—F | 4-i-Pr | I |
| 7155 | Pr | Pr | 2-Br, 4-Me | SnMe₃ | 7214 | Pr | Pr—F | 2-Br, 4-CF₃ | H |
| 7156 | Pr | Pr | 2-Br, 4-Me | Br | 7215 | Pr | Pr—F | 2-Br, 4-CF₃ | SnMe₃ |
| 7157 | Pr | Pr | 2-Br, 4-Me | I | 7216 | Pr | Pr—F | 2-Br, 4-CF₃ | Br |
| 7158 | Pr | Pr—F | H | H | 7217 | Pr | Pr—F | 2-Br, 4-CF₃ | I |
| 7159 | Pr | Pr—F | H | SnMe₃ | 7218 | Pr | Pr—F | 2-CF₃, 4-Br | H |
| 7160 | Pr | Pr—F | H | Br | 7219 | Pr | Pr—F | 2-CF₃, 4-Br | SnMe₃ |
| 7161 | Pr | Pr—F | H | I | 7220 | Pr | Pr—F | 2-CF₃, 4-Br | Br |
| 7162 | Pr | Pr—F | 4-F | H | 7221 | Pr | Pr—F | 2-CF₃, 4-Br | I |
| 7163 | Pr | Pr—F | 4-F | SnMe₃ | 7222 | Pr | Pr—F | 2-Br, 4-Br | H |
| 7164 | Pr | Pr—F | 4-F | Br | 7223 | Pr | Pr—F | 2-Br, 4-Br | SnMe₃ |
| 7165 | Pr | Pr—F | 4-F | I | 7224 | Pr | Pr—F | 2-Br, 4-Br | Br |
| 7166 | Pr | Pr—F | 5-F | H | 7225 | Pr | Pr—F | 2-Br, 4-Br | I |
| 7167 | Pr | Pr—F | 5-F | SnMe₃ | 7226 | Pr | Pr—F | 2-Br, 4-Me | H |
| 7168 | Pr | Pr—F | 5-F | Br | 7227 | Pr | Pr—F | 2-Br, 4-Me | SnMe₃ |
| 7169 | Pr | Pr—F | 5-F | I | 7228 | Pr | Pr—F | 2-Br, 4-Me | Br |
| 7170 | Pr | Pr—F | 4-Cl | H | 7229 | Pr | Pr—F | 2-Br, 4-Me | I |
| 7171 | Pr | Pr—F | 4-Cl | SnMe₃ | 7230 | Pr | Et—F | H | H |
| 7172 | Pr | Pr—F | 4-Cl | Br | 7231 | Pr | Et—F | H | SnMe₃ |
| 7173 | Pr | Pr—F | 4-Cl | I | 7232 | Pr | Et—F | H | Br |
| 7174 | Pr | Pr—F | 4-Br | H | 7233 | Pr | Et—F | H | I |
| 7175 | Pr | Pr—F | 4-Br | SnMe₃ | 7234 | Pr | Et—F | 4-F | H |
| 7176 | Pr | Pr—F | 4-Br | Br | 7235 | Pr | Et—F | 4-F | SnMe₃ |
| 7177 | Pr | Pr—F | 4-Br | I | 7236 | Pr | Et—F | 4-F | Br |
| 7178 | Pr | Pr—F | 4-Me | H | 7237 | Pr | Et—F | 4-F | I |
| 7179 | Pr | Pr—F | 4-Me | SnMe₃ | 7238 | Pr | Et—F | 5-F | H |
| 7180 | Pr | Pr—F | 4-Me | Br | 7239 | Pr | Et—F | 5-F | SnMe₃ |
| 7181 | Pr | Pr—F | 4-Me | I | 7240 | Pr | Et—F | 5-F | Br |
| 7182 | Pr | Pr—F | 4-CF₃ | H | 7241 | Pr | Et—F | 5-F | I |
| 7183 | Pr | Pr—F | 4-CF₃ | SnMe₃ | 7242 | Pr | Et—F | 4-Cl | H |
| 7184 | Pr | Pr—F | 4-CF₃ | Br | 7243 | Pr | Et—F | 4-Cl | SnMe₃ |
| 7185 | Pr | Pr—F | 4-CF₃ | I | 7244 | Pr | Et—F | 4-Cl | Br |
| 7186 | Pr | Pr—F | 4-OH | H | 7245 | Pr | Et—F | 4-Cl | I |
| 7187 | Pr | Pr—F | 4-OH | SnMe₃ | 7246 | Pr | Et—F | 4-Br | H |
| 7188 | Pr | Pr—F | 4-OH | Br | 7247 | Pr | Et—F | 4-Br | SnMe₃ |
| 7189 | Pr | Pr—F | 4-OH | I | 7248 | Pr | Et—F | 4-Br | Br |
| 7190 | Pr | Pr—F | 4-OMe | H | 7249 | Pr | Et—F | 4-Br | I |
| 7191 | Pr | Pr—F | 4-OMe | SnMe₃ | 7250 | Pr | Et—F | 4-Me | H |
| 7192 | Pr | Pr—F | 4-OMe | Br | 7251 | Pr | Et—F | 4-Me | SnMe₃ |
| 7193 | Pr | Pr—F | 4-OMe | I | 7252 | Pr | Et—F | 4-Me | Br |
| 7194 | Pr | Pr—F | 4-OMeF | H | 7253 | Pr | Et—F | 4-Me | I |
| 7195 | Pr | Pr—F | 4-OMeF | SnMe₃ | 7254 | Pr | Et—F | 4-CF₃ | H |
| 7196 | Pr | Pr—F | 4-OMeF | Br | 7255 | Pr | Et—F | 4-CF₃ | SnMe₃ |
| 7197 | Pr | Pr—F | 4-OMeF | I | 7256 | Pr | Et—F | 4-CF₃ | Br |
| 7198 | Pr | Pr—F | 4-OCF₃ | H | 7257 | Pr | Et—F | 4-CF₃ | I |
| 7199 | Pr | Pr—F | 4-OCF₃ | SnMe₃ | 7258 | Pr | Et—F | 4-OH | H |
| 7200 | Pr | Pr—F | 4-OCF₃ | Br | 7259 | Pr | Et—F | 4-OH | SnMe₃ |
| 7201 | Pr | Pr—F | 4-OCF₃ | I | 7260 | Pr | Et—F | 4-OH | Br |
| 7202 | Pr | Pr—F | 4-OEtF | H | 7261 | Pr | Et—F | 4-OH | I |
| 7203 | Pr | Pr—F | 4-OEtF | SnMe₃ | 7262 | Pr | Et—F | 4-OMe | H |

TABLE 6-continued

Substituent list for compounds of general structure XI.

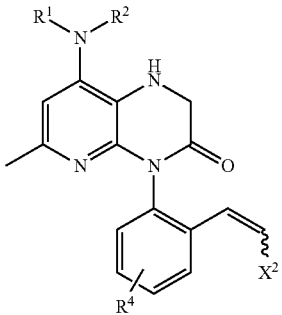

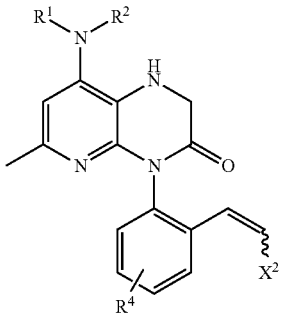

| Compound # | R$^1$ = | R$^2$ = | R$^4$ = | X$^2$ = | Compound # | R$^1$ = | R$^2$ = | R$^4$ = | X$^2$ = |
|---|---|---|---|---|---|---|---|---|---|
| 7263 | Pr | Et—F | 4-OMe | SnMe$_3$ | 7322 | Pr—F | Et | 4-Me | H |
| 7264 | Pr | Et—F | 4-OMe | Br | 7323 | Pr—F | Et | 4-Me | SnMe$_3$ |
| 7265 | Pr | Et—F | 4-OMe | I | 7324 | Pr—F | Et | 4-Me | Br |
| 7266 | Pr | Et—F | 4-OMeF | H | 7325 | Pr—F | Et | 4-Me | I |
| 7267 | Pr | Et—F | 4-OMeF | SnMe$_3$ | 7326 | Pr—F | Et | 4-CF$_3$ | H |
| 7268 | Pr | Et—F | 4-OMeF | Br | 7327 | Pr—F | Et | 4-CF$_3$ | SnMe$_3$ |
| 7269 | Pr | Et—F | 4-OMeF | I | 7328 | Pr—F | Et | 4-CF$_3$ | Br |
| 7270 | Pr | Et—F | 4-OCF$_3$ | H | 7329 | Pr—F | Et | 4-CF$_3$ | I |
| 7271 | Pr | Et—F | 4-OCF$_3$ | SnMe$_3$ | 7330 | Pr—F | Et | 4-OH | H |
| 7272 | Pr | Et—F | 4-OCF$_3$ | Br | 7331 | Pr—F | Et | 4-OH | SnMe$_3$ |
| 7273 | Pr | Et—F | 4-OCF$_3$ | I | 7332 | Pr—F | Et | 4-OH | Br |
| 7274 | Pr | Et—F | 4-OEtF | H | 7333 | Pr—F | Et | 4-OH | I |
| 7275 | Pr | Et—F | 4-OEtF | SnMe$_3$ | 7334 | Pr—F | Et | 4-OMe | H |
| 7276 | Pr | Et—F | 4-OEtF | Br | 7335 | Pr—F | Et | 4-OMe | SnMe$_3$ |
| 7277 | Pr | Et—F | 4-OEtF | I | 7336 | Pr—F | Et | 4-OMe | Br |
| 7278 | Pr | Et—F | 4-OPrF | H | 7337 | Pr—F | Et | 4-OMe | I |
| 7279 | Pr | Et—F | 4-OPrF | SnMe$_3$ | 7338 | Pr—F | Et | 4-OMeF | H |
| 7280 | Pr | Et—F | 4-OPrF | Br | 7339 | Pr—F | Et | 4-OMeF | SnMe$_3$ |
| 7281 | Pr | Et—F | 4-OPrF | I | 7340 | Pr—F | Et | 4-OMeF | Br |
| 7282 | Pr | Et—F | 4-i-Pr | H | 7341 | Pr—F | Et | 4-OMeF | I |
| 7283 | Pr | Et—F | 4-i-Pr | SnMe$_3$ | 7342 | Pr—F | Et | 4-OCF$_3$ | H |
| 7284 | Pr | Et—F | 4-i-Pr | Br | 7343 | Pr—F | Et | 4-OCF$_3$ | SnMe$_3$ |
| 7285 | Pr | Et—F | 4-i-Pr | I | 7344 | Pr—F | Et | 4-OCF$_3$ | Br |
| 7286 | Pr | Et—F | 2-Br, 4-CF$_3$ | H | 7345 | Pr—F | Et | 4-OCF$_3$ | I |
| 7287 | Pr | Et—F | 2-Br, 4-CF$_3$ | SnMe$_3$ | 7346 | Pr—F | Et | 4-OEtF | H |
| 7288 | Pr | Et—F | 2-Br, 4-CF$_3$ | Br | 7347 | Pr—F | Et | 4-OEtF | SnMe$_3$ |
| 7289 | Pr | Et—F | 2-Br, 4-CF$_3$ | I | 7348 | Pr—F | Et | 4-OEtF | Br |
| 7290 | Pr | Et—F | 2-CF$_3$, 4-Br | H | 7349 | Pr—F | Et | 4-OEtF | I |
| 7291 | Pr | Et—F | 2-CF$_3$, 4-Br | SnMe$_3$ | 7350 | Pr—F | Et | 4-OPrF | H |
| 7292 | Pr | Et—F | 2-CF$_3$, 4-Br | Br | 7351 | Pr—F | Et | 4-OPrF | SnMe$_3$ |
| 7293 | Pr | Et—F | 2-CF$_3$, 4-Br | I | 7352 | Pr—F | Et | 4-OPrF | Br |
| 7294 | Pr | Et—F | 2-Br, 4-Br | H | 7353 | Pr—F | Et | 4-OPrF | I |
| 7295 | Pr | Et—F | 2-Br, 4-Br | SnMe$_3$ | 7354 | Pr—F | Et | 4-i-Pr | H |
| 7296 | Pr | Et—F | 2-Br, 4-Br | Br | 7355 | Pr—F | Et | 4-i-Pr | SnMe$_3$ |
| 7297 | Pr | Et—F | 2-Br, 4-Br | I | 7356 | Pr—F | Et | 4-i-Pr | Br |
| 7298 | Pr | Et—F | 2-Br, 4-Me | H | 7357 | Pr—F | Et | 4-i-Pr | I |
| 7299 | Pr | Et—F | 2-Br, 4-Me | SnMe$_3$ | 7358 | Pr—F | Et | 2-Br, 4-CF$_3$ | H |
| 7300 | Pr | Et—F | 2-Br, 4-Me | Br | 7359 | Pr—F | Et | 2-Br, 4-CF$_3$ | SnMe$_3$ |
| 7301 | Pr | Et—F | 2-Br, 4-Me | I | 7360 | Pr—F | Et | 2-Br, 4-CF$_3$ | Br |
| 7302 | Pr—F | Et | H | H | 7361 | Pr—F | Et | 2-Br, 4-CF$_3$ | I |
| 7303 | Pr—F | Et | H | SnMe$_3$ | 7362 | Pr—F | Et | 2-CF$_3$, 4-Br | H |
| 7304 | Pr—F | Et | H | Br | 7363 | Pr—F | Et | 2-CF$_3$, 4-Br | SnMe$_3$ |
| 7305 | Pr—F | Et | H | I | 7364 | Pr—F | Et | 2-CF$_3$, 4-Br | Br |
| 7306 | Pr—F | Et | 4-F | H | 7365 | Pr—F | Et | 2-CF$_3$, 4-Br | I |
| 7307 | Pr—F | Et | 4-F | SnMe$_3$ | 7366 | Pr—F | Et | 2-Br, 4-Br | H |
| 7308 | Pr—F | Et | 4-F | Br | 7367 | Pr—F | Et | 2-Br, 4-Br | SnMe$_3$ |
| 7309 | Pr—F | Et | 4-F | I | 7368 | Pr—F | Et | 2-Br, 4-Br | Br |
| 7310 | Pr—F | Et | 5-F | H | 7369 | Pr—F | Et | 2-Br, 4-Br | I |
| 7311 | Pr—F | Et | 5-F | SnMe$_3$ | 7370 | Pr—F | Et | 2-Br, 4-Me | H |
| 7312 | Pr—F | Et | 5-F | Br | 7371 | Pr—F | Et | 2-Br, 4-Me | SnMe$_3$ |
| 7313 | Pr—F | Et | 5-F | I | 7372 | Pr—F | Et | 2-Br, 4-Me | Br |
| 7314 | Pr—F | Et | 4-Cl | H | 7373 | Pr—F | Et | 2-Br, 4-Me | I |
| 7315 | Pr—F | Et | 4-Cl | SnMe$_3$ | 7374 | Bu | Et—F | H | H |
| 7316 | Pr—F | Et | 4-Cl | Br | 7375 | Bu | Et—F | H | SnMe$_3$ |
| 7317 | Pr—F | Et | 4-Cl | I | 7376 | Bu | Et—F | H | Br |
| 7318 | Pr—F | Et | 4-Br | H | 7377 | Bu | Et—F | H | I |
| 7319 | Pr—F | Et | 4-Br | SnMe$_3$ | 7378 | Bu | Et—F | 4-F | H |
| 7320 | Pr—F | Et | 4-Br | Br | 7379 | Bu | Et—F | 4-F | SnMe$_3$ |
| 7321 | Pr—F | Et | 4-Br | I | 7380 | Bu | Et—F | 4-F | Br |

TABLE 6-continued

Substituent list for compounds of general structure XI.

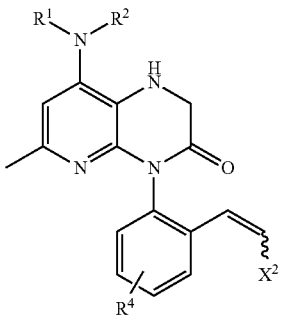
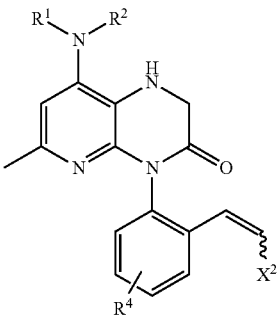

| Compound # | R¹ = | R² = | R⁴ = | X² = | Compound # | R¹ = | R² = | R⁴ = | X² = |
|---|---|---|---|---|---|---|---|---|---|
| 7381 | Bu | Et—F | 4-F | I | 7440 | Bu | Et—F | 2-Br, 4-Br | Br |
| 7382 | Bu | Et—F | 5-F | H | 7441 | Bu | Et—F | 2-Br, 4-Br | I |
| 7383 | Bu | Et—F | 5-F | SnMe$_3$ | 7442 | Bu | Et—F | 2-Br, 4-Me | H |
| 7384 | Bu | Et—F | 5-F | Br | 7443 | Bu | Et—F | 2-Br, 4-Me | SnMe$_3$ |
| 7385 | Bu | Et—F | 5-F | I | 7444 | Bu | Et—F | 2-Br, 4-Me | Br |
| 7386 | Bu | Et—F | 4-Cl | H | 7445 | Bu | Et—F | 2-Br, 4-Me | I |
| 7387 | Bu | Et—F | 4-Cl | SnMe$_3$ | 7446 | Bu—F | Et | H | H |
| 7388 | Bu | Et—F | 4-Cl | Br | 7447 | Bu—F | Et | H | SnMe$_3$ |
| 7389 | Bu | Et—F | 4-Cl | I | 7448 | Bu—F | Et | H | Br |
| 7390 | Bu | Et—F | 4-Br | H | 7449 | Bu—F | Et | H | I |
| 7391 | Bu | Et—F | 4-Br | SnMe$_3$ | 7450 | Bu—F | Et | 4-F | H |
| 7392 | Bu | Et—F | 4-Br | Br | 7451 | Bu—F | Et | 4-F | SnMe$_3$ |
| 7393 | Bu | Et—F | 4-Br | I | 7452 | Bu—F | Et | 4-F | Br |
| 7394 | Bu | Et—F | 4-Me | H | 7453 | Bu—F | Et | 4-F | I |
| 7395 | Bu | Et—F | 4-Me | SnMe$_3$ | 7454 | Bu—F | Et | 5-F | H |
| 7396 | Bu | Et—F | 4-Me | Br | 7455 | Bu—F | Et | 5-F | SnMe$_3$ |
| 7397 | Bu | Et—F | 4-Me | I | 7456 | Bu—F | Et | 5-F | Br |
| 7398 | Bu | Et—F | 4-CF$_3$ | H | 7457 | Bu—F | Et | 5-F | I |
| 7399 | Bu | Et—F | 4-CF$_3$ | SnMe$_3$ | 7458 | Bu—F | Et | 4-Cl | H |
| 7400 | Bu | Et—F | 4-CF$_3$ | Br | 7459 | Bu—F | Et | 4-Cl | SnMe$_3$ |
| 7401 | Bu | Et—F | 4-CF$_3$ | I | 7460 | Bu—F | Et | 4-Cl | Br |
| 7402 | Bu | Et—F | 4-OH | H | 7461 | Bu—F | Et | 4-Cl | I |
| 7403 | Bu | Et—F | 4-OH | SnMe$_3$ | 7462 | Bu—F | Et | 4-Br | H |
| 7404 | Bu | Et—F | 4-OH | Br | 7463 | Bu—F | Et | 4-Br | SnMe$_3$ |
| 7405 | Bu | Et—F | 4-OH | I | 7464 | Bu—F | Et | 4-Br | Br |
| 7406 | Bu | Et—F | 4-OMe | H | 7465 | Bu—F | Et | 4-Br | I |
| 7407 | Bu | Et—F | 4-OMe | SnMe$_3$ | 7466 | Bu—F | Et | 4-Me | H |
| 7408 | Bu | Et—F | 4-OMe | Br | 7467 | Bu—F | Et | 4-Me | SnMe$_3$ |
| 7409 | Bu | Et—F | 4-OMe | I | 7468 | Bu—F | Et | 4-Me | Br |
| 7410 | Bu | Et—F | 4-OMeF | H | 7469 | Bu—F | Et | 4-Me | I |
| 7411 | Bu | Et—F | 4-OMeF | SnMe$_3$ | 7470 | Bu—F | Et | 4-CF$_3$ | H |
| 7412 | Bu | Et—F | 4-OMeF | Br | 7471 | Bu—F | Et | 4-CF$_3$ | SnMe$_3$ |
| 7413 | Bu | Et—F | 4-OMeF | I | 7472 | Bu—F | Et | 4-CF$_3$ | Br |
| 7414 | Bu | Et—F | 4-OCF$_3$ | H | 7473 | Bu—F | Et | 4-CF$_3$ | I |
| 7415 | Bu | Et—F | 4-OCF$_3$ | SnMe$_3$ | 7474 | Bu—F | Et | 4-OH | H |
| 7416 | Bu | Et—F | 4-OCF$_3$ | Br | 7475 | Bu—F | Et | 4-OH | SnMe$_3$ |
| 7417 | Bu | Et—F | 4-OCF$_3$ | I | 7476 | Bu—F | Et | 4-OH | Br |
| 7418 | Bu | Et—F | 4-OEtF | H | 7477 | Bu—F | Et | 4-OH | I |
| 7419 | Bu | Et—F | 4-OEtF | SnMe$_3$ | 7478 | Bu—F | Et | 4-OMe | H |
| 7420 | Bu | Et—F | 4-OEtF | Br | 7479 | Bu—F | Et | 4-OMe | SnMe$_3$ |
| 7421 | Bu | Et—F | 4-OEtF | I | 7480 | Bu—F | Et | 4-OMe | Br |
| 7422 | Bu | Et—F | 4-OPrF | H | 7481 | Bu—F | Et | 4-OMe | I |
| 7423 | Bu | Et—F | 4-OPrF | SnMe$_3$ | 7482 | Bu—F | Et | 4-OMeF | H |
| 7424 | Bu | Et—F | 4-OPrF | Br | 7483 | Bu—F | Et | 4-OMeF | SnMe$_3$ |
| 7425 | Bu | Et—F | 4-OPrF | I | 7484 | Bu—F | Et | 4-OMeF | Br |
| 7426 | Bu | Et—F | 4-i-Pr | H | 7485 | Bu—F | Et | 4-OMeF | I |
| 7427 | Bu | Et—F | 4-i-Pr | SnMe$_3$ | 7486 | Bu—F | Et | 4-OCF$_3$ | H |
| 7428 | Bu | Et—F | 4-i-Pr | Br | 7487 | Bu—F | Et | 4-OCF$_3$ | SnMe$_3$ |
| 7429 | Bu | Et—F | 4-i-Pr | I | 7488 | Bu—F | Et | 4-OCF$_3$ | Br |
| 7430 | Bu | Et—F | 2-Br, 4-CF$_3$ | H | 7489 | Bu—F | Et | 4-OCF$_3$ | I |
| 7431 | Bu | Et—F | 2-Br, 4-CF$_3$ | SnMe$_3$ | 7490 | Bu—F | Et | 4-OetF | H |
| 7432 | Bu | Et—F | 2-Br, 4-CF$_3$ | Br | 7491 | Bu—F | Et | 4-OetF | SnMe$_3$ |
| 7433 | Bu | Et—F | 2-Br, 4-CF$_3$ | I | 7492 | Bu—F | Et | 4-OetF | Br |
| 7434 | Bu | Et—F | 2-CF$_3$, 4-Br | H | 7493 | Bu—F | Et | 4-OetF | I |
| 7435 | Bu | Et—F | 2-CF$_3$, 4-Br | SnMe$_3$ | 7494 | Bu—F | Et | 4-OPrF | H |
| 7436 | Bu | Et—F | 2-CF$_3$, 4-Br | Br | 7495 | Bu—F | Et | 4-OPrF | SnMe$_3$ |
| 7437 | Bu | Et—F | 2-CF$_3$, 4-Br | I | 7496 | Bu—F | Et | 4-OPrF | Br |
| 7438 | Bu | Et—F | 2-Br, 4-Br | H | 7497 | Bu—F | Et | 4-OPrF | I |
| 7439 | Bu | Et—F | 2-Br, 4-Br | SnMe$_3$ | 7498 | Bu—F | Et | 4-i-Pr | H |

TABLE 6-continued

Substituent list for compounds of general structure XI.

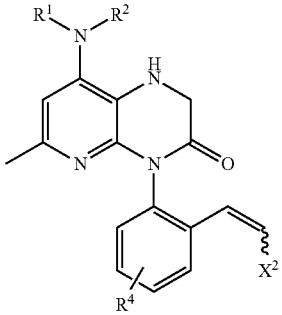

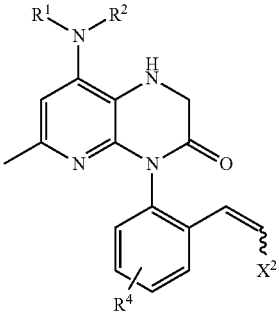

| Compound # | R¹ = | R² = | R⁴ = | X² = |
|---|---|---|---|---|
| 7499 | Bu—F | Et | 4-i-Pr | SnMe₃ |
| 7500 | Bu—F | Et | 4-i-Pr | Br |
| 7501 | Bu—F | Et | 4-i-Pr | I |
| 7502 | Bu—F | Et | 2-Br, 4-CF₃ | H |
| 7503 | Bu—F | Et | 2-Br, 4-CF₃ | SnMe₃ |
| 7504 | Bu—F | Et | 2-Br, 4-CF₃ | Br |
| 7505 | Bu—F | Et | 2-Br, 4-CF₃ | I |
| 7506 | Bu—F | Et | 2-CF₃, 4-Br | H |
| 7507 | Bu—F | Et | 2-CF₃, 4-Br | SnMe₃ |
| 7508 | Bu—F | Et | 2-CF₃, 4-Br | Br |
| 7509 | Bu—F | Et | 2-CF₃, 4-Br | I |
| 7510 | Bu—F | Et | 2-Br, 4-Br | H |
| 7511 | Bu—F | Et | 2-Br, 4-Br | SnMe₃ |
| 7512 | Bu—F | Et | 2-Br, 4-Br | Br |
| 7513 | Bu—F | Et | 2-Br, 4-Br | I |
| 7514 | Bu—F | Et | 2-Br, 4-Me | H |
| 7515 | Bu—F | Et | 2-Br, 4-Me | SnMe₃ |
| 7516 | Bu—F | Et | 2-Br, 4-Me | Br |
| 7517 | Bu—F | Et | 2-Br, 4-Me | I |
| 7518 | FCH₂—CH=CH—CH₂ | Me | H | H |
| 7519 | FCH₂—CH=CH—CH₂ | Me | H | SnMe₃ |
| 7520 | FCH₂—CH=CH—CH₂ | Me | H | Br |
| 7521 | FCH₂—CH=CH—CH₂ | Me | H | I |
| 7522 | FCH₂—CH=CH—CH₂ | Me | 4-F | H |
| 7523 | FCH₂—CH=CH—CH₂ | Me | 4-F | SnMe₃ |
| 7524 | FCH₂—CH=CH—CH₂ | Me | 4-F | Br |
| 7525 | FCH₂—CH=CH—CH₂ | Me | 4-F | I |
| 7526 | FCH₂—CH=CH—CH₂ | Me | 5-F | H |
| 7527 | FCH₂—CH=CH—CH₂ | Me | 5-F | SnMe₃ |
| 7528 | FCH₂—CH=CH—CH₂ | Me | 5-F | Br |
| 7529 | FCH₂—CH=CH—CH₂ | Me | 5-F | I |
| 7530 | FCH₂—CH=CH—CH₂ | Me | 4-Cl | H |
| 7531 | FCH₂—CH=CH—CH₂ | Me | 4-Cl | SnMe₃ |
| 7532 | FCH₂—CH=CH—CH₂ | Me | 4-Cl | Br |
| 7533 | FCH₂—CH=CH—CH₂ | Me | 4-Cl | I |
| 7534 | FCH₂—CH=CH—CH₂ | Me | 4-Br | H |
| 7535 | FCH₂—CH=CH—CH₂ | Me | 4-Br | SnMe₃ |
| 7536 | FCH₂—CH=CH—CH₂ | Me | 4-Br | Br |
| 7537 | FCH₂—CH=CH—CH₂ | Me | 4-Br | I |
| 7538 | FCH₂—CH=CH—CH₂ | Me | 4-Me | H |
| 7539 | FCH₂—CH=CH—CH₂ | Me | 4-Me | SnMe₃ |
| 7540 | FCH₂—CH=CH—CH₂ | Me | 4-Me | Br |
| 7541 | FCH₂—CH=CH—CH₂ | Me | 4-Me | I |
| 7542 | FCH₂—CH=CH—CH₂ | Me | 4-CF₃ | H |
| 7543 | FCH₂—CH=CH—CH₂ | Me | 4-CF₃ | SnMe₃ |
| 7544 | FCH₂—CH=CH—CH₂ | Me | 4-CF₃ | Br |
| 7545 | FCH₂—CH=CH—CH₂ | Me | 4-CF₃ | I |
| 7546 | FCH₂—CH=CH—CH₂ | Me | 4-OH | H |
| 7547 | FCH₂—CH=CH—CH₂ | Me | 4-OH | SnMe₃ |
| 7548 | FCH₂—CH=CH—CH₂ | Me | 4-OH | Br |
| 7549 | FCH₂—CH=CH—CH₂ | Me | 4-OH | I |
| 7550 | FCH₂—CH=CH—CH₂ | Me | 4-OMe | H |
| 7551 | FCH₂—CH=CH—CH₂ | Me | 4-OMe | SnMe₃ |
| 7552 | FCH₂—CH=CH—CH₂ | Me | 4-OMe | Br |
| 7553 | FCH₂—CH=CH—CH₂ | Me | 4-OMe | I |
| 7554 | FCH₂—CH=CH—CH₂ | Me | 4-OMeF | H |
| 7555 | FCH₂—CH=CH—CH₂ | Me | 4-OMeF | SnMe₃ |
| 7556 | FCH₂—CH=CH—CH₂ | Me | 4-OMeF | Br |
| 7557 | FCH₂—CH=CH—CH₂ | Me | 4-OMeF | I |
| 7558 | FCH₂—CH=CH—CH₂ | Me | 4-OCF₃ | H |
| 7559 | FCH₂—CH=CH—CH₂ | Me | 4-OCF₃ | SnMe₃ |
| 7560 | FCH₂—CH=CH—CH₂ | Me | 4-OCF₃ | Br |
| 7561 | FCH₂—CH=CH—CH₂ | Me | 4-OCF₃ | I |
| 7562 | FCH₂—CH=CH—CH₂ | Me | 4-OEtF | H |
| 7563 | FCH₂—CH=CH—CH₂ | Me | 4-OEtF | SnMe₃ |
| 7564 | FCH₂—CH=CH—CH₂ | Me | 4-OEtF | Br |
| 7565 | FCH₂—CH=CH—CH₂ | Me | 4-OEtF | I |
| 7566 | FCH₂—CH=CH—CH₂ | Me | 4-OPrF | H |
| 7567 | FCH₂—CH=CH—CH₂ | Me | 4-OPrF | SnMe₃ |
| 7568 | FCH₂—CH=CH—CH₂ | Me | 4-OPrF | Br |
| 7569 | FCH₂—CH=CH—CH₂ | Me | 4-OPrF | I |
| 7570 | FCH₂—CH=CH—CH₂ | Me | 4-i-Pr | H |
| 7571 | FCH₂—CH=CH—CH₂ | Me | 4-i-Pr | SnMe₃ |
| 7572 | FCH₂—CH=CH—CH₂ | Me | 4-i-Pr | Br |
| 7573 | FCH₂—CH=CH—CH₂ | Me | 4-i-Pr | I |
| 7574 | FCH₂—CH=CH—CH₂ | Me | 2-Br, 4-CF₃ | H |
| 7575 | FCH₂—CH=CH—CH₂ | Me | 2-Br, 4-CF₃ | SnMe₃ |
| 7576 | FCH₂—CH=CH—CH₂ | Me | 2-Br, 4-CF₃ | Br |
| 7577 | FCH₂—CH=CH—CH₂ | Me | 2-Br, 4-CF₃ | I |
| 7578 | FCH₂—CH=CH—CH₂ | Me | 2-CF₃, 4-Br | H |
| 7579 | FCH₂—CH=CH—CH₂ | Me | 2-CF₃, 4-Br | SnMe₃ |
| 7580 | FCH₂—CH=CH—CH₂ | Me | 2-CF₃, 4-Br | Br |
| 7581 | FCH₂—CH=CH—CH₂ | Me | 2-CF₃, 4-Br | I |
| 7582 | FCH₂—CH=CH—CH₂ | Me | 2-Br, 4-Br | H |
| 7583 | FCH₂—CH=CH—CH₂ | Me | 2-Br, 4-Br | SnMe₃ |
| 7584 | FCH₂—CH=CH—CH₂ | Me | 2-Br, 4-Br | Br |
| 7585 | FCH₂—CH=CH—CH₂ | Me | 2-Br, 4-Br | I |
| 7586 | FCH₂—CH=CH—CH₂ | Me | 2-Br, 4-Me | H |
| 7587 | FCH₂—CH=CH—CH₂ | Me | 2-Br, 4-Me | SnMe₃ |
| 7588 | FCH₂—CH=CH—CH₂ | Me | 2-Br, 4-Me | Br |
| 7589 | FCH₂—CH=CH—CH₂ | Me | 2-Br, 4-Me | I |
| 7590 | FCH₂—CH=CH—CH₂ | Et | H | H |
| 7591 | FCH₂—CH=CH—CH₂ | Et | H | SnMe₃ |
| 7592 | FCH₂—CH=CH—CH₂ | Et | H | Br |
| 7593 | FCH₂—CH=CH—CH₂ | Et | H | I |
| 7594 | FCH₂—CH=CH—CH₂ | Et | 4-F | H |
| 7595 | FCH₂—CH=CH—CH₂ | Et | 4-F | SnMe₃ |
| 7596 | FCH₂—CH=CH—CH₂ | Et | 4-F | Br |
| 7597 | FCH₂—CH=CH—CH₂ | Et | 4-F | I |
| 7598 | FCH₂—CH=CH—CH₂ | Et | 5-F | H |
| 7599 | FCH₂—CH=CH—CH₂ | Et | 5-F | SnMe₃ |
| 7600 | FCH₂—CH=CH—CH₂ | Et | 5-F | Br |
| 7601 | FCH₂—CH=CH—CH₂ | Et | 5-F | I |
| 7602 | FCH₂—CH=CH—CH₂ | Et | 4-Cl | H |
| 7603 | FCH₂—CH=CH—CH₂ | Et | 4-Cl | SnMe₃ |
| 7604 | FCH₂—CH=CH—CH₂ | Et | 4-Cl | Br |
| 7605 | FCH₂—CH=CH—CH₂ | Et | 4-Cl | I |
| 7606 | FCH₂—CH=CH—CH₂ | Et | 4-Br | H |
| 7607 | FCH₂—CH=CH—CH₂ | Et | 4-Br | SnMe₃ |
| 7608 | FCH₂—CH=CH—CH₂ | Et | 4-Br | Br |
| 7609 | FCH₂—CH=CH—CH₂ | Et | 4-Br | I |
| 7610 | FCH₂—CH=CH—CH₂ | Et | 4-Me | H |
| 7611 | FCH₂—CH=CH—CH₂ | Et | 4-Me | SnMe₃ |
| 7612 | FCH₂—CH=CH—CH₂ | Et | 4-Me | Br |
| 7613 | FCH₂—CH=CH—CH₂ | Et | 4-Me | I |
| 7614 | FCH₂—CH=CH—CH₂ | Et | 4-CF₃ | H |
| 7615 | FCH₂—CH=CH—CH₂ | Et | 4-CF₃ | SnMe₃ |
| 7616 | FCH₂—CH=CH—CH₂ | Et | 4-CF₃ | Br |

TABLE 6-continued

Substituent list for compounds of general structure XI.

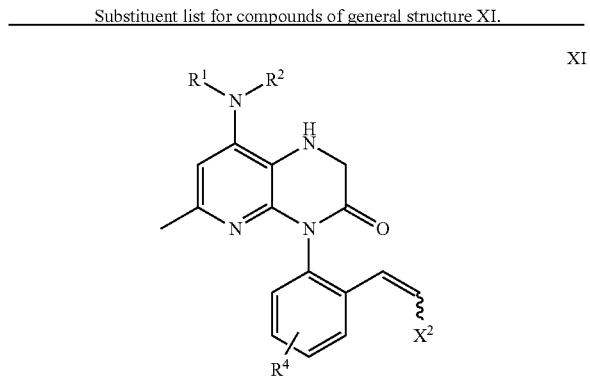

| Compound # | R$^1$ = | R$^2$ = | R$^4$ = | X$^2$ = |
|---|---|---|---|---|
| 7617 | FCH$_2$—CH=CH—CH$_2$ | Et | 4-CF$_3$ | I |
| 7618 | FCH$_2$—CH=CH—CH$_2$ | Et | 4-OH | H |
| 7619 | FCH$_2$—CH=CH—CH$_2$ | Et | 4-OH | SnMe$_3$ |
| 7620 | FCH$_2$—CH=CH—CH$_2$ | Et | 4-OH | Br |
| 7621 | FCH$_2$—CH=CH—CH$_2$ | Et | 4-OH | I |
| 7622 | FCH$_2$—CH=CH—CH$_2$ | Et | 4-OMe | H |
| 7623 | FCH$_2$—CH=CH—CH$_2$ | Et | 4-OMe | SnMe$_3$ |
| 7624 | FCH$_2$—CH=CH—CH$_2$ | Et | 4-OMe | Br |
| 7625 | FCH$_2$—CH=CH—CH$_2$ | Et | 4-OMe | I |
| 7626 | FCH$_2$—CH=CH—CH$_2$ | Et | 4-OMeF | H |
| 7627 | FCH$_2$—CH=CH—CH$_2$ | Et | 4-OMeF | SnMe$_3$ |
| 7628 | FCH$_2$—CH=CH—CH$_2$ | Et | 4-OMeF | Br |
| 7629 | FCH$_2$—CH=CH—CH$_2$ | Et | 4-OMeF | I |
| 7630 | FCH$_2$—CH=CH—CH$_2$ | Et | 4-OCF$_3$ | H |
| 7631 | FCH$_2$—CH=CH—CH$_2$ | Et | 4-OCF$_3$ | SnMe$_3$ |
| 7632 | FCH$_2$—CH=CH—CH$_2$ | Et | 4-OCF$_3$ | Br |
| 7633 | FCH$_2$—CH=CH—CH$_2$ | Et | 4-OCF$_3$ | I |
| 7634 | FCH$_2$—CH=CH—CH$_2$ | Et | 4-OEtF | H |
| 7635 | FCH$_2$—CH=CH—CH$_2$ | Et | 4-OEtF | SnMe$_3$ |
| 7636 | FCH$_2$—CH=CH—CH$_2$ | Et | 4-OEtF | Br |
| 7637 | FCH$_2$—CH=CH—CH$_2$ | Et | 4-OEtF | I |
| 7638 | FCH$_2$—CH=CH—CH$_2$ | Et | 4-OPrF | H |
| 7639 | FCH$_2$—CH=CH—CH$_2$ | Et | 4-OPrF | SnMe$_3$ |
| 7640 | FCH$_2$—CH=CH—CH$_2$ | Et | 4-OPrF | Br |
| 7641 | FCH$_2$—CH=CH—CH$_2$ | Et | 4-OPrF | I |
| 7642 | FCH$_2$—CH=CH—CH$_2$ | Et | 4-i-Pr | H |
| 7643 | FCH$_2$—CH=CH—CH$_2$ | Et | 4-i-Pr | SnMe$_3$ |
| 7644 | FCH$_2$—CH=CH—CH$_2$ | Et | 4-i-Pr | Br |
| 7645 | FCH$_2$—CH=CH—CH$_2$ | Et | 4-i-Pr | I |
| 7646 | FCH$_2$—CH=CH—CH$_2$ | Et | 2-Br, 4-CF$_3$ | H |
| 7647 | FCH$_2$—CH=CH—CH$_2$ | Et | 2-Br, 4-CF$_3$ | SnMe$_3$ |
| 7648 | FCH$_2$—CH=CH—CH$_2$ | Et | 2-Br, 4-CF$_3$ | Br |
| 7649 | FCH$_2$—CH=CH—CH$_2$ | Et | 2-Br, 4-CF$_3$ | I |
| 7650 | FCH$_2$—CH=CH—CH$_2$ | Et | 2-CF$_3$, 4-Br | H |
| 7651 | FCH$_2$—CH=CH—CH$_2$ | Et | 2-CF$_3$, 4-Br | SnMe$_3$ |
| 7652 | FCH$_2$—CH=CH—CH$_2$ | Et | 2-CF$_3$, 4-Br | Br |
| 7653 | FCH$_2$—CH=CH—CH$_2$ | Et | 2-CF$_3$, 4-Br | I |
| 7654 | FCH$_2$—CH=CH—CH$_2$ | Et | 2-Br, 4-Br | H |
| 7655 | FCH$_2$—CH=CH—CH$_2$ | Et | 2-Br, 4-Br | SnMe$_3$ |
| 7656 | FCH$_2$—CH=CH—CH$_2$ | Et | 2-Br, 4-Br | Br |
| 7657 | FCH$_2$—CH=CH—CH$_2$ | Et | 2-Br, 4-Br | I |
| 7658 | FCH$_2$—CH=CH—CH$_2$ | Et | 2-Br, 4-Me | H |
| 7659 | FCH$_2$—CH=CH—CH$_2$ | Et | 2-Br, 4-Me | SnMe$_3$ |
| 7660 | FCH$_2$—CH=CH—CH$_2$ | Et | 2-Br, 4-Me | Br |
| 7661 | FCH$_2$—CH=CH—CH$_2$ | Et | 2-Br, 4-Me | I |
| 7662 | FCH$_2$—CH=CH—CH$_2$ | Et—F | H | H |
| 7663 | FCH$_2$—CH=CH—CH$_2$ | Et—F | H | SnMe$_3$ |
| 7664 | FCH$_2$—CH=CH—CH$_2$ | Et—F | H | Br |
| 7665 | FCH$_2$—CH=CH—CH$_2$ | Et—F | H | I |
| 7666 | FCH$_2$—CH=CH—CH$_2$ | Et—F | 4-F | H |
| 7667 | FCH$_2$—CH=CH—CH$_2$ | Et—F | 4-F | SnMe$_3$ |
| 7668 | FCH$_2$—CH=CH—CH$_2$ | Et—F | 4-F | Br |
| 7669 | FCH$_2$—CH=CH—CH$_2$ | Et—F | 4-F | I |
| 7670 | FCH$_2$—CH=CH—CH$_2$ | Et—F | 5-F | H |
| 7671 | FCH$_2$—CH=CH—CH$_2$ | Et—F | 5-F | SnMe$_3$ |
| 7672 | FCH$_2$—CH=CH—CH$_2$ | Et—F | 5-F | Br |
| 7673 | FCH$_2$—CH=CH—CH$_2$ | Et—F | 5-F | I |
| 7674 | FCH$_2$—CH=CH—CH$_2$ | Et—F | 4-Cl | H |
| 7675 | FCH$_2$—CH=CH—CH$_2$ | Et—F | 4-Cl | SnMe$_3$ |
| 7676 | FCH$_2$—CH=CH—CH$_2$ | Et—F | 4-Cl | Br |
| 7677 | FCH$_2$—CH=CH—CH$_2$ | Et—F | 4-Cl | I |
| 7678 | FCH$_2$—CH=CH—CH$_2$ | Et—F | 4-Br | H |
| 7679 | FCH$_2$—CH=CH—CH$_2$ | Et—F | 4-Br | SnMe$_3$ |
| 7680 | FCH$_2$—CH=CH—CH$_2$ | Et—F | 4-Br | Br |
| 7681 | FCH$_2$—CH=CH—CH$_2$ | Et—F | 4-Br | I |
| 7682 | FCH$_2$—CH=CH—CH$_2$ | Et—F | 4-Me | H |
| 7683 | FCH$_2$—CH=CH—CH$_2$ | Et—F | 4-Me | SnMe$_3$ |
| 7684 | FCH$_2$—CH=CH—CH$_2$ | Et—F | 4-Me | Br |
| 7685 | FCH$_2$—CH=CH—CH$_2$ | Et—F | 4-Me | I |
| 7686 | FCH$_2$—CH=CH—CH$_2$ | Et—F | 4-CF$_3$ | H |
| 7687 | FCH$_2$—CH=CH—CH$_2$ | Et—F | 4-CF$_3$ | SnMe$_3$ |
| 7688 | FCH$_2$—CH=CH—CH$_2$ | Et—F | 4-CF$_3$ | Br |
| 7689 | FCH$_2$—CH=CH—CH$_2$ | Et—F | 4-CF$_3$ | I |
| 7690 | FCH$_2$—CH=CH—CH$_2$ | Et—F | 4-OH | H |
| 7691 | FCH$_2$—CH=CH—CH$_2$ | Et—F | 4-OH | SnMe$_3$ |
| 7692 | FCH$_2$—CH=CH—CH$_2$ | Et—F | 4-OH | Br |
| 7693 | FCH$_2$—CH=CH—CH$_2$ | Et—F | 4-OH | I |
| 7694 | FCH$_2$—CH=CH—CH$_2$ | Et—F | 4-OMe | H |
| 7695 | FCH$_2$—CH=CH—CH$_2$ | Et—F | 4-OMe | SnMe$_3$ |
| 7696 | FCH$_2$—CH=CH—CH$_2$ | Et—F | 4-OMe | Br |
| 7697 | FCH$_2$—CH=CH—CH$_2$ | Et—F | 4-OMe | I |
| 7698 | FCH$_2$—CH=CH—CH$_2$ | Et—F | 4-OMeF | H |
| 7699 | FCH$_2$—CH=CH—CH$_2$ | Et—F | 4-OMeF | SnMe$_3$ |
| 7700 | FCH$_2$—CH=CH—CH$_2$ | Et—F | 4-OMeF | Br |
| 7701 | FCH$_2$—CH=CH—CH$_2$ | Et—F | 4-OMeF | I |
| 7702 | FCH$_2$—CH=CH—CH$_2$ | Et—F | 4-OCF$_3$ | H |
| 7703 | FCH$_2$—CH=CH—CH$_2$ | Et—F | 4-OCF$_3$ | SnMe$_3$ |
| 7704 | FCH$_2$—CH=CH—CH$_2$ | Et—F | 4-OCF$_3$ | Br |
| 7705 | FCH$_2$—CH=CH—CH$_2$ | Et—F | 4-OCF$_3$ | I |
| 7706 | FCH$_2$—CH=CH—CH$_2$ | Et—F | 4-OEtF | H |
| 7707 | FCH$_2$—CH=CH—CH$_2$ | Et—F | 4-OEtF | SnMe$_3$ |
| 7708 | FCH$_2$—CH=CH—CH$_2$ | Et—F | 4-OEtF | Br |
| 7709 | FCH$_2$—CH=CH—CH$_2$ | Et—F | 4-OEtF | I |
| 7710 | FCH$_2$—CH=CH—CH$_2$ | Et—F | 4-OPrF | H |
| 7711 | FCH$_2$—CH=CH—CH$_2$ | Et—F | 4-OPrF | SnMe$_3$ |
| 7712 | FCH$_2$—CH=CH—CH$_2$ | Et—F | 4-OPrF | Br |
| 7713 | FCH$_2$—CH=CH—CH$_2$ | Et—F | 4-OPrF | I |
| 7714 | FCH$_2$—CH=CH—CH$_2$ | Et—F | 4-i-Pr | H |
| 7715 | FCH$_2$—CH=CH—CH$_2$ | Et—F | 4-i-Pr | SnMe$_3$ |
| 7716 | FCH$_2$—CH=CH—CH$_2$ | Et—F | 4-i-Pr | Br |
| 7717 | FCH$_2$—CH=CH—CH$_2$ | Et—F | 4-i-Pr | I |
| 7718 | FCH$_2$—CH=CH—CH$_2$ | Et—F | 2-Br, 4-CF$_3$ | H |
| 7719 | FCH$_2$—CH=CH—CH$_2$ | Et—F | 2-Br, 4-CF$_3$ | SnMe$_3$ |
| 7720 | FCH$_2$—CH=CH—CH$_2$ | Et—F | 2-Br, 4-CF$_3$ | Br |
| 7721 | FCH$_2$—CH=CH—CH$_2$ | Et—F | 2-Br, 4-CF$_3$ | I |
| 7722 | FCH$_2$—CH=CH—CH$_2$ | Et—F | 2-CF$_3$, 4-Br | H |
| 7723 | FCH$_2$—CH=CH—CH$_2$ | Et—F | 2-CF$_3$, 4-Br | SnMe$_3$ |
| 7724 | FCH$_2$—CH=CH—CH$_2$ | Et—F | 2-CF$_3$, 4-Br | Br |
| 7725 | FCH$_2$—CH=CH—CH$_2$ | Et—F | 2-CF$_3$, 4-Br | I |
| 7726 | FCH$_2$—CH=CH—CH$_2$ | Et—F | 2-Br, 4-Br | H |
| 7727 | FCH$_2$—CH=CH—CH$_2$ | Et—F | 2-Br, 4-Br | SnMe$_3$ |
| 7728 | FCH$_2$—CH=CH—CH$_2$ | Et—F | 2-Br, 4-Br | Br |
| 7729 | FCH$_2$—CH=CH—CH$_2$ | Et—F | 2-Br, 4-Br | I |
| 7730 | FCH$_2$—CH=CH—CH$_2$ | Et—F | 2-Br, 4-Me | H |
| 7731 | FCH$_2$—CH=CH—CH$_2$ | Et—F | 2-Br, 4-Me | SnMe$_3$ |
| 7732 | FCH$_2$—CH=CH—CH$_2$ | Et—F | 2-Br, 4-Me | Br |
| 7733 | FCH$_2$—CH=CH—CH$_2$ | Et—F | 2-Br, 4-Me | I |

TABLE 7

Substituent list for compounds of general structure XII.

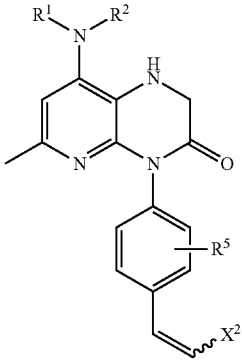

| Compound # | R¹ = | R² = | R⁵ = | X² = |
|---|---|---|---|---|
| 7734 | Bu | Et | H | H |
| 7735 | Bu | Et | H | SnMe₃ |
| 7736 | Bu | Et | H | Br |
| 7737 | Bu | Et | H | I |
| 7738 | Bu | Et | 2-F | H |
| 7739 | Bu | Et | 2-F | SnMe₃ |
| 7740 | Bu | Et | 2-F | Br |
| 7741 | Bu | Et | 2-F | I |
| 7742 | Bu | Et | 2-Cl | H |
| 7743 | Bu | Et | 2-Cl | SnMe₃ |
| 7744 | Bu | Et | 2-Cl | Br |
| 7745 | Bu | Et | 2-Cl | I |
| 7746 | Bu | Et | 2-Br | H |
| 7747 | Bu | Et | 2-Br | SnMe₃ |
| 7748 | Bu | Et | 2-Br | Br |
| 7749 | Bu | Et | 2-Br | I |
| 7750 | Bu | Et | 2-Me | H |
| 7751 | Bu | Et | 2-Me | SnMe₃ |
| 7752 | Bu | Et | 2-Me | Br |
| 7753 | Bu | Et | 2-Me | I |
| 7754 | Bu | Et | 2-Et | H |
| 7755 | Bu | Et | 2-Et | SnMe₃ |
| 7756 | Bu | Et | 2-Et | Br |
| 7757 | Bu | Et | 2-Et | I |
| 7758 | Bu | Et | 2-Me, 6-Me | H |
| 7759 | Bu | Et | 2-Me, 6-Me | SnMe₃ |
| 7760 | Bu | Et | 2-Me, 6-Me | Br |
| 7761 | Bu | Et | 2-Me, 6-Me | I |
| 7762 | Bu | Et | 2-OH | H |
| 7763 | Bu | Et | 2-OH | SnMe₃ |
| 7764 | Bu | Et | 2-OH | Br |
| 7765 | Bu | Et | 2-OH | I |
| 7766 | Bu | Et | 2-OMe | H |
| 7767 | Bu | Et | 2-OMe | SnMe₃ |
| 7768 | Bu | Et | 2-OMe | Br |
| 7769 | Bu | Et | 2-OMe | I |
| 7770 | Bu | Et | 2-OMeF | H |
| 7771 | Bu | Et | 2-OMeF | SnMe₃ |
| 7772 | Bu | Et | 2-OMeF | Br |
| 7773 | Bu | Et | 2-OMeF | I |
| 7774 | Bu | Et | 2-OCF₃ | H |
| 7775 | Bu | Et | 2-OCF₃ | SnMe₃ |
| 7776 | Bu | Et | 2-OCF₃ | Br |
| 7777 | Bu | Et | 2-OCF₃ | I |
| 7778 | Bu | Et | 2-OEtF | H |
| 7779 | Bu | Et | 2-OEtF | SnMe₃ |
| 7780 | Bu | Et | 2-OEtF | Br |
| 7781 | Bu | Et | 2-OEtF | I |
| 7782 | Bu | Et | 2-OPrF | H |
| 7783 | Bu | Et | 2-OPrF | SnMe₃ |
| 7784 | Bu | Et | 2-OPrF | Br |
| 7785 | Bu | Et | 2-OPrF | I |
| 7786 | Bu | Et | 2-CF₃ | H |
| 7787 | Eu | Et | 2-CF₃ | SnMe₃ |
| 7788 | Bu | Et | 2-CF₃ | Br |
| 7789 | Bu | Et | 2-CF₃ | I |
| 7790 | Bu | Et | 2-Br, 6-CF₃ | H |
| 7791 | Bu | Et | 2-Br, 6-CF₃ | SnMe₃ |
| 7792 | Bu | Et | 2-Br, 6-CF₃ | Br |
| 7793 | Bu | Et | 2-Br, 6-CF₃ | I |
| 7794 | Bu | Et | 2-Br, 6-Br | H |
| 7795 | Bu | Et | 2-Br, 6-Br | SnMe₃ |
| 7796 | Bu | Et | 2-Br, 6-Br | Br |
| 7797 | Bu | Et | 2-Br, 6-Br | I |
| 7798 | Pr | Pr | H | H |
| 7799 | Pr | Pr | H | SnMe₃ |
| 7800 | Pr | Pr | H | Br |
| 7801 | Pr | Pr | H | I |
| 7802 | Pr | Pr | 2-F | H |
| 7803 | Pr | Pr | 2-F | SnMe₃ |
| 7804 | Pr | Pr | 2-F | Br |
| 7805 | Pr | Pr | 2-F | I |
| 7806 | Pr | Pr | 2-Cl | H |
| 7807 | Pr | Pr | 2-Cl | SnMe₃ |
| 7808 | Pr | Pr | 2-Cl | Br |
| 7809 | Pr | Pr | 2-Cl | I |
| 7810 | Pr | Pr | 2-Br | H |
| 7811 | Pr | Pr | 2-Br | SnMe₃ |
| 7812 | Pr | Pr | 2-Br | Br |
| 7813 | Pr | Pr | 2-Br | I |
| 7814 | Pr | Pr | 2-Me | H |
| 7815 | Pr | Pr | 2-Me | SnMe₃ |
| 7816 | Pr | Pr | 2-Me | Br |
| 7817 | Pr | Pr | 2-Me | I |
| 7818 | Pr | Pr | 2-Et | H |
| 7819 | Pr | Pr | 2-Et | SnMe₃ |
| 7820 | Pr | Pr | 2-Et | Br |
| 7821 | Pr | Pr | 2-Et | I |
| 7822 | Pr | Pr | 2-Me, 6-Me | H |
| 7823 | Pr | Pr | 2-Me, 6-Me | SnMe₃ |
| 7824 | Pr | Pr | 2-Me, 6-Me | Br |
| 7825 | Pr | Pr | 2-Me, 6-Me | I |
| 7826 | Pr | Pr | 2-OH | H |
| 7827 | Pr | Pr | 2-OH | SnMe₃ |
| 7828 | Pr | Pr | 2-OH | Br |
| 7829 | Pr | Pr | 2-OH | I |
| 7830 | Pr | Pr | 2-OMe | H |
| 7831 | Pr | Pr | 2-OMe | SnMe₃ |
| 7832 | Pr | Pr | 2-OMe | Br |
| 7833 | Pr | Pr | 2-OMe | I |
| 7834 | Pr | Pr | 2-OMeF | H |
| 7835 | Pr | Pr | 2-OMeF | SnMe₃ |
| 7836 | Pr | Pr | 2-OMeF | Br |
| 7837 | Pr | Pr | 2-OMeF | I |
| 7838 | Pr | Pr | 2-OCF₃ | H |
| 7839 | Pr | Pr | 2-OCF₃ | SnMe₃ |
| 7840 | Pr | Pr | 2-OCF₃ | Br |
| 7841 | Pr | Pr | 2-OCF₃ | I |
| 7842 | Pr | Pr | 2-OEtF | H |
| 7843 | Pr | Pr | 2-OEtF | SnMe₃ |
| 7844 | Pr | Pr | 2-OEtF | Br |
| 7845 | Pr | Pr | 2-OEtF | I |
| 7846 | Pr | Pr | 2-OPrF | H |
| 7847 | Pr | Pr | 2-OPrF | SnMe₃ |

TABLE 7-continued

Substituent list for compounds of general structure XII.

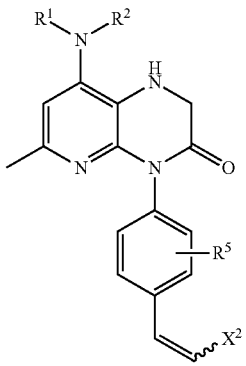

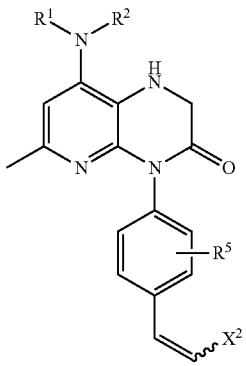

| Compound # | R¹ = | R² = | R⁵ = | X² = |
|---|---|---|---|---|
| 7848 | Pr | Pr | 2-OPrF | Br |
| 7849 | Pr | Pr | 2-OPrF | I |
| 7850 | Pr | Pr | 2-CF₃ | H |
| 7851 | Pr | Pr | 2-CF₃ | SnMe₃ |
| 7852 | Pr | Pr | 2-CF₃ | Br |
| 7853 | Pr | Pr | 2-CF₃ | I |
| 7854 | Pr | Pr | 2-Br, 6-CF₃ | H |
| 7855 | Pr | Pr | 2-Br, 6-CF₃ | SnMe₃ |
| 7856 | Pr | Pr | 2-Br, 6-CF₃ | Br |
| 7857 | Pr | Pr | 2-Br, 6-CF₃ | I |
| 7858 | Pr | Pr | 2-Br, 6-Br | H |
| 7859 | Pr | Pr | 2-Br, 6-Br | SnMe₃ |
| 7860 | Pr | Pr | 2-Br, 6-Br | Br |
| 7861 | Pr | Pr | 2-Br, 6-Br | I |
| 7862 | Pr | Pr—F | H | H |
| 7863 | Pr | Pr—F | H | SnMe₃ |
| 7864 | Pr | Pr—F | H | Br |
| 7865 | Pr | Pr—F | H | I |
| 7866 | Pr | Pr—F | 2-F | H |
| 7867 | Pr | Pr—F | 2-F | SnMe₃ |
| 7868 | Pr | Pr—F | 2-F | Br |
| 7869 | Pr | Pr—F | 2-F | I |
| 7870 | Pr | Pr—F | 2-Cl | H |
| 7871 | Pr | Pr—F | 2-Cl | SnMe₃ |
| 7872 | Pr | Pr—F | 2-Cl | Br |
| 7873 | Pr | Pr—F | 2-Cl | I |
| 7874 | Pr | Pr—F | 2-Br | H |
| 7875 | Pr | Pr—F | 2-Br | SnMe₃ |
| 7876 | Pr | Pr—F | 2-Br | Br |
| 7877 | Pr | Pr—F | 2-Br | I |
| 7878 | Pr | Pr—F | 2-Me | H |
| 7879 | Pr | Pr—F | 2-Me | SnMe₃ |
| 7880 | Pr | Pr—F | 2-Me | Br |
| 7881 | Pr | Pr—F | 2-Me | I |
| 7882 | Pr | Pr—F | 2-Et | H |
| 7883 | Pr | Pr—F | 2-Et | SnMe₃ |
| 7884 | Pr | Pr—F | 2-Et | Br |
| 7885 | Pr | Pr—F | 2-Et | I |
| 7886 | Pr | Pr—F | 2-Me, 6-Me | H |
| 7887 | Pr | Pr—F | 2-Me, 6-Me | SnMe₃ |
| 7888 | Pr | Pr—F | 2-Me, 6-Me | Br |
| 7889 | Pr | Pr—F | 2-Me, 6-Me | I |
| 7890 | Pr | Pr—F | 2-OH | H |
| 7891 | Pr | Pr—F | 2-OH | SnMe₃ |
| 7892 | Pr | Pr—F | 2-OH | Br |
| 7893 | Pr | Pr—F | 2-OH | I |
| 7894 | Pr | Pr—F | 2-OMe | H |
| 7895 | Pr | Pr—F | 2-OMe | SnMe₃ |
| 7896 | Pr | Pr—F | 2-OMe | Br |
| 7897 | Pr | Pr—F | 2-OMe | I |
| 7898 | Pr | Pr—F | 2-OMeF | H |
| 7899 | Pr | Pr—F | 2-OMeF | SnMe₃ |
| 7900 | Pr | Pr—F | 2-OMeF | Br |
| 7901 | Pr | Pr—F | 2-OMeF | I |
| 7902 | Pr | Pr—F | 2-OCF₃ | H |
| 7903 | Pr | Pr—F | 2-OCF₃ | SnMe₃ |
| 7904 | Pr | Pr—F | 2-OCF₃ | Br |
| 7905 | Pr | Pr—F | 2-OCF₃ | I |
| 7906 | Pr | Pr—F | 2-OEtF | H |
| 7907 | Pr | Pr F | 2-OEtF | SnMe₃ |
| 7908 | Pr | Pr—F | 2-OEtF | Br |
| 7909 | Pr | Pr—F | 2-OEtF | I |
| 7910 | Pr | Pr—F | 2-OPrF | H |
| 7911 | Pr | Pr—F | 2-OPrF | SnMe₃ |
| 7912 | Pr | Pr—F | 2-OPrF | Br |
| 7913 | Pr | Pr—F | 2-OPrF | I |
| 7914 | Pr | Pr—F | 2-CF₃ | H |
| 7915 | Pr | Pr—F | 2-CF₃ | SnMe₃ |
| 7916 | Pr | Pr—F | 2-CF₃ | Br |
| 7917 | Pr | Pr—F | 2-CF₃ | I |
| 7918 | Pr | Pr—F | 2-Br, 6-CF₃ | H |
| 7919 | Pr | Pr—F | 2-Br, 6-CF₃ | SnMe₃ |
| 7920 | Pr | Pr—F | 2-Br, 6-CF₃ | Br |
| 7921 | Pr | Pr—F | 2-Br, 6-CF₃ | I |
| 7922 | Pr | Pr—F | 2-Br, 6-Br | H |
| 7923 | Pr | Pr—F | 2-Br, 6-Br | SnMe₃ |
| 7924 | Pr | Pr—F | 2-Br, 6-Br | Br |
| 7925 | Pr | Pr—F | 2-Br, 6-Br | I |
| 7926 | Pr | Et—F | H | H |
| 7927 | Pr | Et—F | H | SnMe₃ |
| 7928 | Pr | Et—F | H | Br |
| 7929 | Pr | Et—F | H | I |
| 7930 | Pr | Et—F | 2-F | H |
| 7931 | Pr | Et—F | 2-F | SnMe₃ |
| 7932 | Pr | Et—F | 2-F | Br |
| 7933 | Pr | Et—F | 2-F | I |
| 7934 | Pr | Et—F | 2-Cl | H |
| 7935 | Pr | Et—F | 2-Cl | SnMe₃ |
| 7936 | Pr | Et—F | 2-Cl | Br |
| 7937 | Pr | Et—F | 2-Cl | I |
| 7938 | Pr | Et—F | 2-Br | H |
| 7939 | Pr | Et—F | 2-Br | SnMe₃ |
| 7940 | Pr | Et—F | 2-Br | Br |
| 7941 | Pr | Et—F | 2-Br | I |
| 7942 | Pr | Et—F | 2-Me | H |
| 7943 | Pr | Et—F | 2-Me | SnMe₃ |
| 7944 | Pr | Et—F | 2-Me | Br |
| 7945 | Pr | Et—F | 2-Me | I |
| 7946 | Pr | Et—F | 2-Et | H |
| 7947 | Pr | Et—F | 2-Et | SnMe₃ |
| 7948 | Pr | Et—F | 2-Et | Br |
| 7949 | Pr | Et—F | 2-Et | I |
| 7950 | Pr | Et—F | 2-Me, 6-Me | H |
| 7951 | Pr | Et—F | 2-Me, 6-Me | SnMe₃ |
| 7952 | Pr | Et—F | 2-Me, 6-Me | Br |
| 7953 | Pr | Et—F | 2-Me, 6-Me | I |
| 7954 | Pr | Et—F | 2-OH | H |
| 7955 | Pr | Et—F | 2-OH | SnMe₃ |
| 7956 | Pr | Et—F | 2-OH | Br |
| 7957 | Pr | Et—F | 2-OH | I |
| 7958 | Pr | Et—F | 2-OMe | H |
| 7959 | Pr | Et—F | 2-OMe | SnMe₃ |
| 7960 | Pr | Et—F | 2-OMe | Br |
| 7961 | Pr | Et—F | 2-OMe | I |

TABLE 7-continued

Substituent list for compounds of general structure XII.

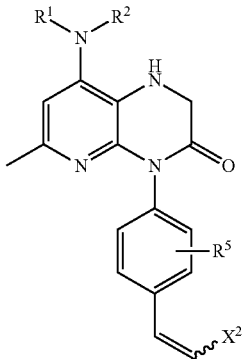

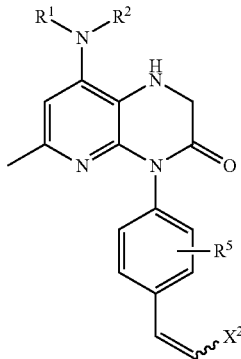

| Compound # | $R^1$ = | $R^2$ = | $R^5$ = | $X^2$ = |
|---|---|---|---|---|
| 7962 | Pr | Et—F | 2-OMeF | H |
| 7963 | Pr | Et—F | 2-OMeF | SnMe$_3$ |
| 7964 | Pr | Et—F | 2-OMeF | Br |
| 7965 | Pr | Et—F | 2-OMeF | I |
| 7966 | Pr | Et—F | 2-OCF$_3$ | H |
| 7967 | Pr | Et—F | 2-OCF$_3$ | SnMe$_3$ |
| 7968 | Pr | Et—F | 2-OCF$_3$ | Br |
| 7969 | Pr | Et—F | 2-OCF$_3$ | I |
| 7970 | Pr | Et—F | 2-OEtF | H |
| 7971 | Pr | Et—F | 2-OEtF | SnMe$_3$ |
| 7972 | Pr | Et—F | 2-OEtF | Br |
| 7973 | Pr | Et—F | 2-OEtF | I |
| 7974 | Pr | Et—F | 2-OPrF | H |
| 7975 | Pr | Et—F | 2-OPrF | SnMe$_3$ |
| 7976 | Pr | Et—F | 2-OPrF | Br |
| 7977 | Pr | Et—F | 2-OPrF | I |
| 7978 | Pr | Et—F | 2-CF$_3$ | H |
| 7979 | Pr | Et—F | 2-CF$_3$ | SnMe$_3$ |
| 7980 | Pr | Et—F | 2-CF$_3$ | Br |
| 7981 | Pr | Et—F | 2-CF$_3$ | I |
| 7982 | Pr | Et—F | 2-Br, 6-CF$_3$ | H |
| 7983 | Pr | Et—F | 2-Br, 6-CF$_3$ | SnMe$_3$ |
| 7984 | Pr | Et—F | 2-Br, 6-CF$_3$ | Br |
| 7985 | Pr | Et—F | 2-Br, 6-CF$_3$ | I |
| 7986 | Pr | Et—F | 2-Br, 6-Br | H |
| 7987 | Pr | Et—F | 2-Br, 6-Br | SnMe$_3$ |
| 7988 | Pr | Et—F | 2-Br, 6-Br | Br |
| 7989 | Pr | Et—F | 2-Br, 6-Br | I |
| 7990 | Pr—F | Et | H | H |
| 7991 | Pr—F | Et | H | SnMe$_3$ |
| 7992 | Pr—F | Et | H | Br |
| 7993 | Pr—F | Et | H | I |
| 7994 | Pr—F | Et | 2-F | H |
| 7995 | Pr—F | Et | 2-F | SnMe$_3$ |
| 7996 | Pr—F | Et | 2-F | Br |
| 7997 | Pr—F | Et | 2-F | I |
| 7998 | Pr—F | Et | 2-Cl | H |
| 7999 | Pr—F | Et | 2-Cl | SnMe$_3$ |
| 8000 | Pr—F | Et | 2-Cl | Br |
| 8001 | Pr—F | Et | 2-Cl | I |
| 8002 | Pr—F | Et | 2-Br | H |
| 8003 | Pr—F | Et | 2-Br | SnMe$_3$ |
| 8004 | Pr—F | Et | 2-Br | Br |
| 8005 | Pr—F | Et | 2-Br | I |
| 8006 | Pr—F | Et | 2-Me | H |
| 8007 | Pr—F | Et | 2-Me | SnMe$_3$ |
| 8008 | Pr—F | Et | 2-Me | Br |
| 8009 | Pr—F | Et | 2-Me | I |
| 8010 | Pr—F | Et | 2-Et | H |
| 8011 | Pr—F | Et | 2-Et | SnMe$_3$ |
| 8012 | Pr—F | Et | 2-Et | Br |
| 8013 | Pr—F | Et | 2-Et | I |
| 8014 | Pr—F | Et | 2-Me, 6-Me | H |
| 8015 | Pr—F | Et | 2-Me, 6-Me | SnMe$_3$ |
| 8016 | Pr—F | Et | 2-Me, 6-Me | Br |
| 8017 | Pr—F | Et | 2-Me, 6-Me | I |
| 8018 | Pr—F | Et | 2-OH | H |
| 8019 | Pr—F | Et | 2-OH | SnMe$_3$ |
| 8020 | Pr—F | Et | 2-OH | Br |
| 8021 | Pr—F | Et | 2-OH | I |
| 8022 | Pr—F | Et | 2-OMe | H |
| 8023 | Pr—F | Et | 2-OMe | SnMe$_3$ |
| 8024 | Pr—F | Et | 2-OMe | Br |
| 8025 | Pr—F | Et | 2-OMe | I |
| 8026 | Pr—F | Et | 2-OMeF | H |
| 8027 | Pr—F | Et | 2-OMeF | SnMe$_3$ |
| 8028 | Pr—F | Et | 2-OMeF | Br |
| 8029 | Pr—F | Et | 2-OMeF | I |
| 8030 | Pr—F | Et | 2-OCF$_3$ | H |
| 8031 | Pr—F | Et | 2-OCF$_3$ | SnMe$_3$ |
| 8032 | Pr—F | Et | 2-OCF$_3$ | Br |
| 8033 | Pr—F | Et | 2-OCF$_3$ | I |
| 8034 | Pr—F | Et | 2-OEtF | H |
| 8035 | Pr—F | Et | 2-OEtF | SnMe$_3$ |
| 8036 | Pr—F | Et | 2-OEtF | Br |
| 8037 | Pr—F | Et | 2-OEtF | I |
| 8038 | Pr—F | Et | 2-OPrF | H |
| 8039 | Pr—F | Et | 2-OPrF | SnMe$_3$ |
| 8040 | Pr—F | Et | 2-OPrF | Br |
| 8041 | Pr—F | Et | 2-OPrF | I |
| 8042 | Pr—F | Et | 2-CF$_3$ | H |
| 8043 | Pr—F | Et | 2-CF$_3$ | SnMe$_3$ |
| 8044 | Pr—F | Et | 2-CF$_3$ | Br |
| 8045 | Pr—F | Et | 2-CF$_3$ | I |
| 8046 | Pr—F | Et | 2-Br, 6-CF$_3$ | H |
| 8047 | Pr—F | Et | 2-Br, 6-CF$_3$ | SnMe$_3$ |
| 8048 | Pr—F | Et | 2-Br, 6-CF$_3$ | Br |
| 8049 | Pr—F | Et | 2-Br, 6-CF$_3$ | I |
| 8050 | Pr—F | Et | 2-Br, 6-Br | H |
| 8051 | Pr—F | Et | 2-Br, 6-Br | SnMe$_3$ |
| 8052 | Pr—F | Et | 2-Br, 6-Br | Br |
| 8053 | Pr—F | Et | 2-Br, 6-Br | I |
| 8054 | Bu | Et—F | H | H |
| 8055 | Bu | Et—F | H | SnMe$_3$ |
| 8056 | Bu | Et—F | H | Br |
| 8057 | Bu | Et—F | H | I |
| 8058 | Bu | Et—F | 2-F | H |
| 8059 | Bu | Et—F | 2-F | SnMe$_3$ |
| 8060 | Bu | Et—F | 2-F | Br |
| 8061 | Bu | Et—F | 2-F | I |
| 8062 | Bu | Et—F | 2-Cl | H |
| 8063 | Bu | Et—F | 2-Cl | SnMe$_3$ |
| 8064 | Bu | Et—F | 2-Cl | Br |
| 8065 | Bu | Et—F | 2-Cl | I |
| 8066 | Bu | Et—F | 2-Br | H |
| 8067 | Bu | Et—F | 2-Br | SnMe$_3$ |
| 8068 | Bu | Et—F | 2-Br | Br |
| 8069 | Bu | Et—F | 2-Br | I |
| 8070 | Bu | Et—F | 2-Me | H |
| 8071 | Bu | Et—F | 2-Me | SnMe$_3$ |
| 8072 | Bu | Et—F | 2-Me | Br |
| 8073 | Bu | Et—F | 2-Me | I |
| 8074 | Bu | Et—F | 2-Et | H |
| 8075 | Bu | Et—F | 2-Et | SnMe$_3$ |

TABLE 7-continued

Substituent list for compounds of general structure XII.

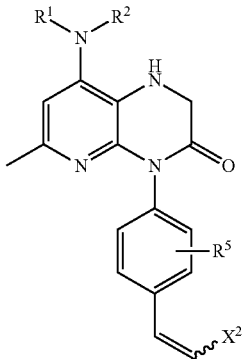

XII

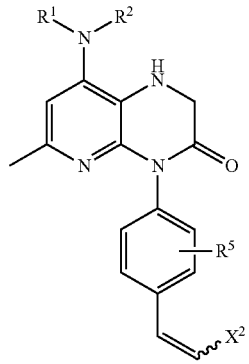

XII

| Compound # | R¹ = | R² = | R⁵ = | X² = |
|---|---|---|---|---|
| 8076 | Bu | Et—F | 2-Et | Br |
| 8077 | Bu | Et—F | 2-Et | I |
| 8078 | Bu | Et—F | 2-Me, 6-Me | H |
| 8079 | Bu | Et—F | 2-Me, 6-Me | SnMe₃ |
| 8080 | Bu | Et—F | 2-Me, 6-Me | Br |
| 8081 | Bu | Et—F | 2-Me, 6-Me | I |
| 8082 | Bu | Et—F | 2-OH | H |
| 8083 | Bu | Et—F | 2-OH | SnMe₃ |
| 8084 | Bu | Et—F | 2-OH | Br |
| 8085 | Bu | Et—F | 2-OH | I |
| 8086 | Bu | Et—F | 2-OMe | H |
| 8087 | Bu | Et—F | 2-OMe | SnMe₃ |
| 8088 | Bu | Et—F | 2-OMe | Br |
| 8089 | Bu | Et—F | 2-OMe | I |
| 8090 | Bu | Et—F | 2-OMeF | H |
| 8091 | Bu | Et—F | 2-OMeF | SnMe₃ |
| 8092 | Bu | Et—F | 2-OMeF | Br |
| 8093 | Bu | Et—F | 2-OMeF | I |
| 8094 | Bu | Et—F | 2-OCF₃ | H |
| 8095 | Bu | Et—F | 2-OCF₃ | SnMe₃ |
| 8096 | Bu | Et—F | 2-OCF₃ | Br |
| 8097 | Bu | Et—F | 2-OCF₃ | I |
| 8098 | Bu | Et—F | 2-OEtF | H |
| 8099 | Bu | Et—F | 2-OEtF | SnMe₃ |
| 8100 | Bu | Et—F | 2-OEtF | Br |
| 8101 | Bu | Et—F | 2-OEtF | I |
| 8102 | Bu | Et—F | 2-OPrF | H |
| 8103 | Bu | Et—F | 2-OPrF | SnMe₃ |
| 8104 | Bu | Et—F | 2-OPrF | Br |
| 8105 | Bu | Et—F | 2-OPrF | I |
| 8106 | Bu | Et—F | 2-CF₃ | H |
| 8107 | Bu | Et—F | 2-CF₃ | SnMe₃ |
| 8108 | Bu | Et—F | 2-CF₃ | Br |
| 8109 | Bu | Et—F | 2-CF₃ | I |
| 8110 | Bu | Et—F | 2-Br, 6-CF₃ | H |
| 8111 | Bu | Et—F | 2-Br, 6-CF₃ | SnMe₃ |
| 8112 | Bu | Et—F | 2-Br, 6-CF₃ | Br |
| 8113 | Bu | Et—F | 2-Br, 6-CF₃ | I |
| 8114 | Bu | Et—F | 2-Br, 6-Br | H |
| 8115 | Bu | Et—F | 2-Br, 6-Br | SnMe₃ |
| 8116 | Bu | Et—F | 2-Br, 6-Br | Br |
| 8117 | Bu | Et—F | 2-Br, 6-Br | I |
| 8118 | Bu—F | Et | H | H |
| 8119 | Bu—F | Et | H | SnMe₃ |
| 8120 | Bu—F | Et | H | Br |
| 8121 | Bu—F | Et | H | I |
| 8122 | Bu—F | Et | 2-F | H |
| 8123 | Bu—F | Et | 2-F | SnMe₃ |
| 8124 | Bu—F | Et | 2-F | Br |
| 8125 | Bu—F | Et | 2-F | I |
| 8126 | Bu—F | Et | 2-Cl | H |
| 8127 | Bu—F | Et | 2-Cl | SnMe₃ |
| 8128 | Bu—F | Et | 2-Cl | Br |
| 8129 | Bu—F | Et | 2-Cl | I |
| 8130 | Bu—F | Et | 2-Br | H |
| 8131 | Bu—F | Et | 2-Br | SnMe₃ |
| 8132 | Bu—F | Et | 2-Br | Br |
| 8133 | Bu—F | Et | 2-Br | I |
| 8134 | Bu—F | Et | 2-Me | H |
| 8135 | Bu—F | Et | 2-Me | SnMe₃ |
| 8136 | Bu—F | Et | 2-Me | Br |
| 8137 | Bu—F | Et | 2-Me | I |
| 8138 | Bu—F | Et | 2-Et | H |
| 8139 | Bu—F | Et | 2-Et | SnMe₃ |
| 8140 | Bu—F | Et | 2-Et | Br |
| 8141 | Bu—F | Et | 2-Et | I |
| 8142 | Bu—F | Et | 2-Me, 6-Me | H |
| 8143 | Bu—F | Et | 2-Me, 6-Me | SnMe₃ |
| 8144 | Bu—F | Et | 2-Me, 6-Me | Br |
| 8145 | Bu—F | Et | 2-Me, 6-Me | I |
| 8146 | Bu—F | Et | 2-OH | H |
| 8147 | Bu—F | Et | 2-OH | SnMe₃ |
| 8148 | Bu—F | Et | 2-OH | Br |
| 8149 | Bu—F | Et | 2-OH | I |
| 8150 | Bu—F | Et | 2-OMe | H |
| 8151 | Bu—F | Et | 2-OMe | SnMe₃ |
| 8152 | Bu—F | Et | 2-OMe | Br |
| 8153 | Bu—F | Et | 2-OMe | I |
| 8154 | Bu—F | Et | 2-OMeF | H |
| 8155 | Bu—F | Et | 2-OMeF | SnMe₃ |
| 8156 | Bu—F | Et | 2-OMeF | Br |
| 8157 | Bu—F | Et | 2-OMeF | I |
| 8158 | Bu—F | Et | 2-OCF₃ | H |
| 8159 | Bu—F | Et | 2-OCF₃ | SnMe₃ |
| 8160 | Bu—F | Et | 2-OCF₃ | Br |
| 8161 | Bu—F | Et | 2-OCF₃ | I |
| 8162 | Bu—F | Et | 2-OEtF | H |
| 8163 | Bu—F | Et | 2-OEtF | SnMe₃ |
| 8164 | Bu—F | Et | 2-OEtF | Br |
| 8165 | Bu—F | Et | 2-OEtF | I |
| 8166 | Bu—F | Et | 2-OPrF | H |
| 8167 | Bu—F | Et | 2-OPrF | SnMe₃ |
| 8168 | Bu—F | Et | 2-OPrF | Br |
| 8169 | Bu—F | Et | 2-OPrF | I |
| 8170 | Bu—F | Et | 2-CF₃ | H |
| 8171 | Bu—F | Et | 2-CF₃ | SnMe₃ |
| 8172 | Bu—F | Et | 2-CF₃ | Br |
| 8173 | Bu—F | Et | 2-CF₃ | I |
| 8174 | Bu—F | Et | 2-Br, 6-CF₃ | H |
| 8175 | Bu—F | Et | 2-Br, 6-CF₃ | SnMe₃ |
| 8176 | Bu—F | Et | 2-Br, 6-CF₃ | Br |
| 8177 | Bu—F | Et | 2-Br, 6-CF₃ | I |
| 8178 | Bu—F | Et | 2-Br, 6-Br | H |
| 8179 | Bu—F | Et | 2-Br, 6-Br | SnMe₃ |
| 8180 | Bu—F | Et | 2-Br, 6-Br | Br |
| 8181 | Bu—F | Et | 2-Br, 6-Br | I |
| 8182 | FCH₂—CH=CH—CH₂ | Me | H | H |
| 8183 | FCH₂—CH=CH—CH₂ | Me | H | SnMe₃ |
| 8184 | FCH₂—CH=CH—CH₂ | Me | H | Br |
| 8185 | FCH₂—CH=CH—CH₂ | Me | H | I |
| 8186 | FCH₂—CH=CH—CH₂ | Me | 2-F | H |
| 8187 | FCH₂—CH=CH—CH₂ | Me | 2-F | SnMe₃ |
| 8188 | FCH₂—CH=CH—CH₂ | Me | 2-F | Br |
| 8189 | FCH₂—CH=CH—CH₂ | Me | 2-F | I |

TABLE 7-continued

Substituent list for compounds of general structure XII.

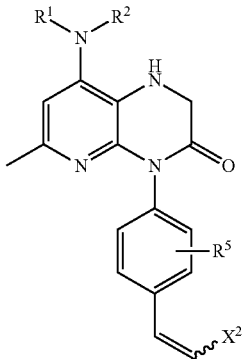 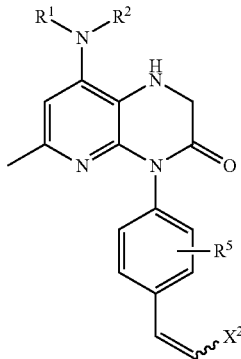

XII

| Compound # | R¹ = | R² = | R⁵ = | X² = |
|---|---|---|---|---|
| 8190 | FCH₂—CH=CH—CH₂ | Me | 2-Cl | H |
| 8191 | FCH₂—CH=CH—CH₂ | Me | 2-Cl | SnMe₃ |
| 8192 | FCH₂—CH=CH—CH₂ | Me | 2-Cl | Br |
| 8193 | FCH₂—CH=CH—CH₂ | Me | 2-Cl | I |
| 8194 | FCH₂—CH=CH—CH₂ | Me | 2-Br | H |
| 8195 | FCH₂—CH=CH—CH₂ | Me | 2-Br | SnMe₃ |
| 8196 | FCH₂—CH=CH—CH₂ | Me | 2-Br | Br |
| 8197 | FCH₂—CH=CH—CH₂ | Me | 2-Br | I |
| 8198 | FCH₂—CH=CH—CH₂ | Me | 2-Me | H |
| 8199 | FCH₂—CH=CH—CH₂ | Me | 2-Me | SnMe₃ |
| 8200 | FCH₂—CH=CH—CH₂ | Me | 2-Me | Br |
| 8201 | FCH₂—CH=CH—CH₂ | Me | 2-Me | I |
| 8202 | FCH₂—CH=CH—CH₂ | Me | 2-Et | H |
| 8203 | FCH₂—CH=CH—CH₂ | Me | 2-Et | SnMe₃ |
| 8204 | FCH₂—CH=CH—CH₂ | Me | 2-Et | Br |
| 8205 | FCH₂—CH=CH—CH₂ | Me | 2-Et | I |
| 8206 | FCH₂—CH=CH—CH₂ | Me | 2-Me, 6-Me | H |
| 8207 | FCH₂—CH=CH—CH₂ | Me | 2-Me, 6-Me | SnMe₃ |
| 8208 | FCH₂—CH=CH—CH₂ | Me | 2-Me, 6-Me | Br |
| 8209 | FCH₂—CH=CH—CH₂ | Me | 2-Me, 6-Me | I |
| 8210 | FCH₂—CH=CH—CH₂ | Me | 2-OH | H |
| 8211 | FCH₂—CH=CH—CH₂ | Me | 2-OH | SnMe₃ |
| 8212 | FCH₂—CH=CH—CH₂ | Me | 2-OH | Br |
| 8213 | FCH₂—CH=CH—CH₂ | Me | 2-OH | I |
| 8214 | FCH₂—CH=CH—CH₂ | Me | 2-OMe | H |
| 8215 | FCH₂—CH=CH—CH₂ | Me | 2-OMe | SnMe₃ |
| 8216 | FCH₂—CH=CH—CH₂ | Me | 2-OMe | Br |
| 8217 | FCH₂—CH=CH—CH₂ | Me | 2-OMe | I |
| 8218 | FCH₂—CH=CH—CH₂ | Me | 2-OMeF | H |
| 8219 | FCH₂—CH=CH—CH₂ | Me | 2-OMeF | SnMe₃ |
| 8220 | FCH₂—CH=CH—CH₂ | Me | 2-OMeF | Br |
| 8221 | FCH₂—CH=CH—CH₂ | Me | 2-OMeF | I |
| 8222 | FCH₂—CH=CH—CH₂ | Me | 2-OCF₃ | H |
| 8223 | FCH₂—CH=CH—CH₂ | Me | 2-OCF₃ | SnMe₃ |
| 8224 | FCH₂—CH=CH—CH₂ | Me | 2-OCF₃ | Br |
| 8225 | FCH₂—CH=CH—CH₂ | Me | 2-OCF₃ | I |
| 8226 | FCH₂—CH=CH—CH₂ | Me | 2-OEtF | H |
| 8227 | FCH₂—CH=CH—CH₂ | Me | 2-OEtF | SnMe₃ |
| 8228 | FCH₂—CH=CH—CH₂ | Me | 2-OEtF | Br |
| 8229 | FCH₂—CH=CH—CH₂ | Me | 2-OEtF | I |
| 8230 | FCH₂—CH=CH—CH₂ | Me | 2-OPrF | H |
| 8231 | FCH₂—CH=CH—CH₂ | Me | 2-OPrF | SnMe₃ |
| 8232 | FCH₂—CH=CH—CH₂ | Me | 2-OPrF | Br |
| 8233 | FCH₂—CH=CH—CH₂ | Me | 2-OPrF | I |
| 8234 | FCH₂—CH=CH—CH₂ | Me | 2-CF₃ | H |
| 8235 | FCH₂—CH=CH—CH₂ | Me | 2-CF₃ | SnMe₃ |
| 8236 | FCH₂—CH=CH—CH₂ | Me | 2-CF₃ | Br |
| 8237 | FCH₂—CH=CH—CH₂ | Me | 2-CF₃ | I |
| 8238 | FCH₂—CH=CH—CH₂ | Me | 2-Br, 6-CF₃ | H |
| 8239 | FCH₂—CH=CH—CH₂ | Me | 2-Br, 6-CF₃ | SnMe₃ |
| 8240 | FCH₂—CH=CH—CH₂ | Me | 2-Br, 6-CF₃ | Br |
| 8241 | FCH₂—CH=CH—CH₂ | Me | 2-Br, 6-CF₃ | I |
| 8242 | FCH₂—CH=CH—CH₂ | Me | 2-Br, 6-Br | H |
| 8243 | FCH₂—CH=CH—CH₂ | Me | 2-Br, 6-Br | SnMe₃ |
| 8244 | FCH₂—CH=CH—CH₂ | Me | 2-Br, 6-Br | Br |
| 8245 | FCH₂—CH=CH—CH₂ | Me | 2-Br, 6-Br | I |
| 8246 | FCH₂—CH=CH—CH₂ | Et | H | H |
| 8247 | FCH₂—CH=CH—CH₂ | Et | H | SnMe₃ |
| 8248 | FCH₂—CH=CH—CH₂ | Et | H | Br |
| 8249 | FCH₂—CH=CH—CH₂ | Et | H | I |
| 8250 | FCH₂—CH=CH—CH₂ | Et | 2-F | H |
| 8251 | FCH₂—CH=CH—CH₂ | Et | 2-F | SnMe₃ |
| 8252 | FCH₂—CH=CH—CH₂ | Et | 2-F | Br |
| 8253 | FCH₂—CH=CH—CH₂ | Et | 2-F | I |
| 8254 | FCH₂—CH=CH—CH₂ | Et | 2-Cl | H |
| 8255 | FCH₂—CH=CH—CH₂ | Et | 2-Cl | SnMe₃ |
| 8256 | FCH₂—CH=CH—CH₂ | Et | 2-Cl | Br |
| 8257 | FCH₂—CH=CH—CH₂ | Et | 2-Cl | I |
| 8258 | FCH₂—CH=CH—CH₂ | Et | 2-Br | H |
| 8259 | FCH₂—CH=CH—CH₂ | Et | 2-Br | SnMe₃ |
| 8260 | FCH₂—CH=CH—CH₂ | Et | 2-Br | Br |
| 8261 | FCH₂—CH=CH—CH₂ | Et | 2-Br | I |
| 8262 | FCH₂—CH=CH—CH₂ | Et | 2-Me | H |
| 8263 | FCH₂—CH=CH—CH₂ | Et | 2-Me | SnMe₃ |
| 8264 | FCH₂—CH=CH—CH₂ | Et | 2-Me | Br |
| 8265 | FCH₂—CH=CH—CH₂ | Et | 2-Me | I |
| 8266 | FCH₂—CH=CH—CH₂ | Et | 2-Et | H |
| 8267 | FCH₂—CH=CH—CH₂ | Et | 2-Et | SnMe₃ |
| 8268 | FCH₂—CH=CH—CH₂ | Et | 2-Et | Br |
| 8269 | FCH₂—CH=CH—CH₂ | Et | 2-Et | I |
| 8270 | FCH₂—CH=CH—CH₂ | Et | 2-Me, 6-Me | H |
| 8271 | FCH₂—CH=CH—CH₂ | Et | 2-Me, 6-Me | SnMe₃ |
| 8272 | FCH₂—CH=CH—CH₂ | Et | 2-Me, 6-Me | Br |
| 8273 | FCH₂—CH=CH—CH₂ | Et | 2-Me, 6-Me | I |
| 8274 | FCH₂—CH=CH—CH₂ | Et | 2-OH | H |
| 8275 | FCH₂—CH=CH—CH₂ | Et | 2-OH | SnMe₃ |
| 8276 | FCH₂—CH=CH—CH₂ | Et | 2-OH | Br |
| 8277 | FCH₂—CH=CH—CH₂ | Et | 2-OH | I |
| 8278 | FCH₂—CH=CH—CH₂ | Et | 2-OMe | H |
| 8279 | FCH₂—CH=CH—CH₂ | Et | 2-OMe | SnMe₃ |
| 8280 | FCH₂—CH=CH—CH₂ | Et | 2-OMe | Br |
| 8281 | FCH₂—CH=CH—CH₂ | Et | 2-OMe | I |
| 8282 | FCH₂—CH=CH—CH₂ | Et | 2-OMeF | H |
| 8283 | FCH₂—CH=CH—CH₂ | Et | 2-OMeF | SnMe₃ |
| 8284 | FCH₂—CH=CH—CH₂ | Et | 2-OMeF | Br |
| 8285 | FCH₂—CH=CH—CH₂ | Et | 2-OMeF | I |
| 8286 | FCH₂—CH=CH—CH₂ | Et | 2-OCF₃ | H |
| 8287 | FCH₂—CH=CH—CH₂ | Et | 2-OCF₃ | SnMe₃ |
| 8288 | FCH₂—CH=CH—CH₂ | Et | 2-OCF₃ | Br |
| 8289 | FCH₂—CH=CH—CH₂ | Et | 2-OCF₃ | I |
| 8290 | FCH₂—CH=CH—CH₂ | Et | 2-OEtF | H |
| 8291 | FCH₂—CH=CH—CH₂ | Et | 2-OEtF | SnMe₃ |
| 8292 | FCH₂—CH=CH—CH₂ | Et | 2-OEtF | Br |
| 8293 | FCH₂—CH=CH—CH₂ | Et | 2-OEtF | I |
| 8294 | FCH₂—CH=CH—CH₂ | Et | 2-OPrF | H |
| 8295 | FCH₂—CH=CH—CH₂ | Et | 2-OPrF | SnMe₃ |
| 8296 | FCH₂—CH=CH—CH₂ | Et | 2-OPrF | Br |
| 8297 | FCH₂—CH=CH—CH₂ | Et | 2-OPrF | I |
| 8298 | FCH₂—CH=CH—CH₂ | Et | 2-CF₃ | H |
| 8299 | FCH₂—CH=CH—CH₂ | Et | 2-CF₃ | SnMe₃ |
| 8300 | FCH₂—CH=CH—CH₂ | Et | 2-CF₃ | Br |
| 8301 | FCH₂—CH=CH—CH₂ | Et | 2-CF₃ | I |
| 8302 | FCH₂—CH=CH—CH₂ | Et | 2-Br, 6-CF₃ | H |
| 8303 | FCH₂—CH=CH—CH₂ | Et | 2-Br, 6-CF₃ | SnMe₃ |

TABLE 7-continued

Substituent list for compounds of general structure XII.

Structure XII: A pyrido-pyrazinone bicyclic core with $R^1R^2N$- substituent at one position, a methyl group, and an N-aryl substituent bearing $R^5$ on the phenyl ring and a vinyl-$X^2$ group.

| Compound # | $R^1 =$ | $R^2 =$ | $R^5 =$ | $X^2 =$ |
|---|---|---|---|---|
| 8304 | FCH$_2$—CH=CH—CH$_2$ | Et | 2-Br, 6-CF$_3$ | Br |
| 8305 | FCH$_2$—CH=CH—CH$_2$ | Et | 2-Br, 6-CF$_3$ | I |
| 8306 | FCH$_2$—CH=CH—CH$_2$ | Et | 2-Br, 6-Br | H |
| 8307 | FCH$_2$—CH=CH—CH$_2$ | Et | 2-Br, 6-Br | SnMe$_3$ |
| 8308 | FCH$_2$—CH=CH—CH$_2$ | Et | 2-Br, 6-Br | Br |
| 8309 | FCH$_2$—CH=CH—CH$_2$ | Et | 2-Br, 6-Br | I |
| 8310 | FCH$_2$—CH=CH—CH$_2$ | Et—F | H | H |
| 8311 | FCH$_2$—CH=CH—CH$_2$ | Et—F | H | SnMe$_3$ |
| 8312 | FCH$_2$—CH=CH—CH$_2$ | Et—F | H | Br |
| 8313 | FCH$_2$—CH=CH—CH$_2$ | Et—F | H | I |
| 8314 | FCH$_2$—CH=CH—CH$_2$ | Et—F | 2-F | H |
| 8315 | FCH$_2$—CH=CH—CH$_2$ | Et—F | 2-F | SnMe$_3$ |
| 8316 | FCH$_2$—CH=CH—CH$_2$ | Et—F | 2-F | Br |
| 8317 | FCH$_2$—CH=CH—CH$_2$ | Et—F | 2-F | I |
| 8318 | FCH$_2$—CH=CH—CH$_2$ | Et—F | 2-Cl | H |
| 8319 | FCH$_2$—CH=CH—CH$_2$ | Et—F | 2-Cl | SnMe$_3$ |
| 8320 | FCH$_2$—CH=CH—CH$_2$ | Et—F | 2-Cl | Br |
| 8321 | FCH$_2$—CH=CH—CH$_2$ | Et—F | 2-Cl | I |
| 8322 | FCH$_2$—CH=CH—CH$_2$ | Et—F | 2-Br | H |
| 8323 | FCH$_2$—CH=CH—CH$_2$ | Et—F | 2-Br | SnMe$_3$ |
| 8324 | FCH$_2$—CH=CH—CH$_2$ | Et—F | 2-Br | Br |
| 8325 | FCH$_2$—CH=CH—CH$_2$ | Et—F | 2-Br | I |
| 8326 | FCH$_2$—CH=CH—CH$_2$ | Et—F | 2-Me | H |
| 8327 | FCH$_2$—CH=CH—CH$_2$ | Et—F | 2-Me | SnMe$_3$ |
| 8328 | FCH$_2$—CH=CH—CH$_2$ | Et—F | 2-Me | Br |
| 8329 | FCH$_2$—CH=CH—CH$_2$ | Et—F | 2-Me | I |
| 8330 | FCH$_2$—CH=CH—CH$_2$ | Et—F | 2-Et | H |
| 8331 | FCH$_2$—CH=CH—CH$_2$ | Et—F | 2-Et | SnMe$_3$ |
| 8332 | FCH$_2$—CH=CH—CH$_2$ | Et—F | 2-Et | Br |
| 8333 | FCH$_2$—CH=CH—CH$_2$ | Et—F | 2-Et | I |
| 8334 | FCH$_2$—CH=CH—CH$_2$ | Et—F | 2-Me, 6-Me | H |
| 8335 | FCH$_2$—CH=CH—CH$_2$ | Et—F | 2-Me, 6-Me | SnMe$_3$ |
| 8336 | FCH$_2$—CH=CH—CH$_2$ | Et—F | 2-Me, 6-Me | Br |
| 8337 | FCH$_2$—CH=CH—CH$_2$ | Et—F | 2-Me, 6-Me | I |
| 8338 | FCH$_2$—CH=CH—CH$_2$ | Et—F | 2-OH | H |
| 8339 | FCH$_2$—CH=CH—CH$_2$ | Et—F | 2-OH | SnMe$_3$ |
| 8340 | FCH$_2$—CH=CH—CH$_2$ | Et—F | 2-OH | Br |
| 8341 | FCH$_2$—CH=CH—CH$_2$ | Et—F | 2-OH | I |
| 8342 | FCH$_2$—CH=CH—CH$_2$ | Et—F | 2-OMe | H |
| 8343 | FCH$_2$—CH=CH—CH$_2$ | Et—F | 2-OMe | SnMe$_3$ |
| 8344 | FCH$_2$—CH=CH—CH$_2$ | Et—F | 2-OMe | Br |
| 8345 | FCH$_2$—CH=CH—CH$_2$ | Et—F | 2-OMe | I |
| 8346 | FCH$_2$—CH=CH—CH$_2$ | Et—F | 2-OMeF | H |
| 8347 | FCH$_2$—CH=CH—CH$_2$ | Et—F | 2-OMeF | SnMe$_3$ |
| 8348 | FCH$_2$—CH=CH—CH$_2$ | Et—F | 2-OMeF | Br |
| 8349 | FCH$_2$—CH=CH—CH$_2$ | Et—F | 2-OMeF | I |
| 8350 | FCH$_2$—CH=CH—CH$_2$ | Et—F | 2-OCF$_3$ | H |
| 8351 | FCH$_2$—CH=CH—CH$_2$ | Et—F | 2-OCF$_3$ | SnMe$_3$ |
| 8352 | FCH$_2$—CH=CH—CH$_2$ | Et—F | 2-OCF$_3$ | Br |
| 8353 | FCH$_2$—CH=CH—CH$_2$ | Et—F | 2-OCF$_3$ | I |
| 8354 | FCH$_2$—CH=CH—CH$_2$ | Et—F | 2-OEtF | H |
| 8355 | FCH$_2$—CH=CH—CH$_2$ | Et—F | 2-OEtF | SnMe$_3$ |
| 8356 | FCH$_2$—CH=CH—CH$_2$ | Et—F | 2-OEtF | Br |
| 8357 | FCH$_2$—CH=CH—CH$_2$ | Et—F | 2-OEtF | I |
| 8358 | FCH$_2$—CH=CH—CH$_2$ | Et—F | 2-OPrF | H |
| 8359 | FCH$_2$—CH=CH—CH$_2$ | Et—F | 2-OPrF | SnMe$_3$ |
| 8360 | FCH$_2$—CH=CH—CH$_2$ | Et—F | 2-OPrF | Br |
| 8361 | FCH$_2$—CH=CH—CH$_2$ | Et—F | 2-OPrF | I |
| 8362 | FCH$_2$—CH=CH—CH$_2$ | Et—F | 2-CF$_3$ | H |
| 8363 | FCH$_2$—CH=CH—CH$_2$ | Et—F | 2-CF$_3$ | SnMe$_3$ |
| 8364 | FCH$_2$—CH=CH—CH$_2$ | Et—F | 2-CF$_3$ | Br |
| 8365 | FCH$_2$—CH=CH—CH$_2$ | Et—F | 2-CF$_3$ | I |
| 8366 | FCH$_2$—CH=CH—CH$_2$ | Et—F | 2-Br, 6-CF$_3$ | H |
| 8367 | FCH$_2$—CH=CH—CH$_2$ | Et—F | 2-Br, 6-CF$_3$ | SnMe$_3$ |
| 8368 | FCH$_2$—CH=CH—CH$_2$ | Et—F | 2-Br, 6-CF$_3$ | Br |
| 8369 | FCH$_2$—CH=CH—CH$_2$ | Et—F | 2-Br, 6-CF$_3$ | I |
| 8370 | FCH$_2$—CH=CH—CH$_2$ | Et—F | 2-Br, 6-Br | H |
| 8371 | FCH$_2$—CH=CH—CH$_2$ | Et—F | 2-Br, 6-Br | SnMe$_3$ |
| 8372 | FCH$_2$—CH=CH—CH$_2$ | Et—F | 2-Br, 6-Br | Br |
| 8373 | FCH$_2$—CH=CH—CH$_2$ | Et—F | 2-Br, 6-Br | I |

TABLE 8

Substituent list for compounds of general structure XIII.

Structure XIII: A pyrido-pyrazinone bicyclic core with $R^1R^2N$- substituent, a methyl group, and an N-CHR$^7$-phenyl substituent bearing $R^6$.

| Compound # | $R^1 =$ | $R^2 =$ | $R^6 =$ | $R^7 =$ |
|---|---|---|---|---|
| 8374 | Bu | Et | H | H |
| 8375 | Bu | Et | 2-Cl, 4-Cl | H |
| 8376 | Bu | Et | 2-OMe, 4-OMe | H |
| 8377 | Bu | Et | 2-OH | H |
| 8378 | Bu | Et | 3-OH | H |
| 8379 | Bu | Et | 4-OH | H |
| 8380 | Bu | Et | 2-OMe | H |
| 8381 | Bu | Et | 3-OMe | H |
| 8382 | Bu | Et | 4-OMe | H |
| 8383 | Bu | Et | 2-OMeF | H |
| 8384 | Bu | Et | 3-OMeF | H |
| 8385 | Bu | Et | 4-OMeF | H |
| 8386 | Bu | Et | 2-OCF$_3$ | H |
| 8387 | Bu | Et | 3-OCF$_3$ | H |
| 8388 | Bu | Et | 4-OCF$_3$ | H |
| 8389 | Bu | Et | 2-OEtF | H |
| 8390 | Bu | Et | 3-OEtF | H |
| 8391 | Bu | Et | 4-OEtF | H |
| 8392 | Bu | Et | 2-OPrF | H |

TABLE 8-continued

Substituent list for compounds of general structure XIII.

| Compound # | R¹ = | R² = | R⁶ = | R⁷ = |
|---|---|---|---|---|
| 8393 | Bu | Et | 3-OPrF | H |
| 8394 | Bu | Et | 4-OPrF | H |
| 8395 | Bu | Et | 2-Me | H |
| 8396 | Bu | Et | 3-Me | H |
| 8397 | Bu | Et | 4-Me | H |
| 8398 | Bu | Et | 2-Br | H |
| 8399 | Bu | Et | 3-Br | H |
| 8400 | Bu | Et | 4-Br | H |
| 8401 | Bu | Et | 2-SnMe₃ | H |
| 8402 | Bu | Et | 3-SnMe₃ | H |
| 8403 | Bu | Et | 4-SnMe₃ | H |
| 8404 | Bu | Et | H | Me |
| 8405 | Bu | Et | 4-Me | Me |
| 8406 | Bu | Et | 4-Br | Me |
| 8407 | Bu | Et | 4-SnMe₃ | Me |
| 8408 | Bu | Et | 4-OH | Me |
| 8409 | Bu | Et | 4-OMe | Me |
| 8410 | Bu | Et | 4-OMeF | Me |
| 8411 | Bu | Et | 4-OCF₃ | Me |
| 8412 | Bu | Et | 4-OEtF | Me |
| 8413 | Bu | Et | 4-OPrF | Me |
| 8414 | Pr | Pr | H | H |
| 8415 | Pr | Pr | 2-Cl, 4-Cl | H |
| 8416 | Pr | Pr | 2-OMe, 4-OMe | H |
| 8417 | Pr | Pr | 2-OH | H |
| 8418 | Pr | Pr | 3-OH | H |
| 8419 | Pr | Pr | 4-OH | H |
| 8420 | Pr | Pr | 2-OMe | H |
| 8421 | Pr | Pr | 3-OMe | H |
| 8422 | Pr | Pr | 4-OMe | H |
| 8423 | Pr | Pr | 2-OMeF | H |
| 8424 | Pr | Pr | 3-OMeF | H |
| 8425 | Pr | Pr | 4-OMeF | H |
| 8426 | Pr | Pr | 2-OCF₃ | H |
| 8427 | Pr | Pr | 3-OCF₃ | H |
| 8428 | Pr | Pr | 4-OCF₃ | H |
| 8429 | Pr | Pr | 2-OEtF | H |
| 8430 | Pr | Pr | 3-OEtF | H |
| 8431 | Pr | Pr | 4-OEtF | H |
| 8432 | Pr | Pr | 2-OPrF | H |
| 8433 | Pr | Pr | 3-OPrF | H |
| 8434 | Pr | Pr | 4-OPrF | H |
| 8435 | Pr | Pr | 2-Me | H |
| 8436 | Pr | Pr | 3-Me | H |
| 8437 | Pr | Pr | 4-Me | H |
| 8438 | Pr | Pr | 2-Br | H |
| 8439 | Pr | Pr | 3-Br | H |
| 8440 | Pr | Pr | 4-Br | H |
| 8441 | Pr | Pr | 2-SnMe₃ | H |
| 8442 | Pr | Pr | 3-SnMe₃ | H |
| 8443 | Pr | Pr | 4-SnMe₃ | H |
| 8444 | Pr | Pr | H | Me |
| 8445 | Pr | Pr | 4-Me | Me |
| 8446 | Pr | Pr | 4-Br | Me |
| 8447 | Pr | Pr | 4-SnMe₃ | Me |
| 8448 | Pr | Pr | 4-OH | Me |
| 8449 | Pr | Pr | 4-OMe | Me |
| 8450 | Pr | Pr | 4-OMeF | Me |
| 8451 | Pr | Pr | 4-OCF₃ | Me |
| 8452 | Pr | Pr | 4-OEtF | Me |
| 8453 | Pr | Pr | 4-OPrF | Me |
| 8454 | Pr | Pr—F | H | H |
| 8455 | Pr | Pr—F | 2-Cl, 4-Cl | H |
| 8456 | Pr | Pr—F | 2-OMe, 4-OMe | H |
| 8457 | Pr | Pr—F | 2-OH | H |
| 8458 | Pr | Pr—F | 3-OH | H |
| 8459 | Pr | Pr—F | 4-OH | H |
| 8460 | Pr | Pr—F | 2-OMe | H |
| 8461 | Pr | Pr—F | 3-OMe | H |
| 8462 | Pr | Pr—F | 4-OMe | H |
| 8463 | Pr | Pr—F | 2-OMeF | H |
| 8464 | Pr | Pr—F | 3-OMeF | H |
| 8465 | Pr | Pr—F | 4-OMeF | H |
| 8466 | Pr | Pr—F | 2-OCF₃ | H |
| 8467 | Pr | Pr—F | 3-OCF₃ | H |
| 8468 | Pr | Pr—F | 4-OCF₃ | H |
| 8469 | Pr | Pr—F | 2-OEtF | H |
| 8470 | Pr | Pr—F | 3-OEtF | H |
| 8471 | Pr | Pr—F | 4-OEtF | H |
| 8472 | Pr | Pr—F | 2-OPrF | H |
| 8473 | Pr | Pr—F | 3-OPrF | H |
| 8474 | Pr | Pr—F | 4-OPrF | H |
| 8475 | Pr | Pr—F | 2-Me | H |
| 8476 | Pr | Pr—F | 3-Me | H |
| 8477 | Pr | Pr—F | 4-Me | H |
| 8478 | Pr | Pr—F | 2-Br | H |
| 8479 | Pr | Pr—F | 3-Br | H |
| 8480 | Pr | Pr—F | 4-Br | H |
| 8481 | Pr | Pr—F | 2-SnMe₃ | H |
| 8482 | Pr | Pr—F | 3-SnMe₃ | H |
| 8483 | Pr | Pr—F | 4-SnMe₃ | H |
| 8484 | Pr | Pr—F | H | Me |
| 8485 | Pr | Pr—F | 4-Me | Me |
| 8486 | Pr | Pr—F | 4-Br | Me |
| 8487 | Pr | Pr—F | 4-SnMe₃ | Me |
| 8488 | Pr | Pr—F | 4-OH | Me |
| 8489 | Pr | Pr—F | 4-OMe | Me |
| 8490 | Pr | Pr—F | 4-OMeF | Me |
| 8491 | Pr | Pr—F | 4-OCF₃ | Me |
| 8492 | Pr | Pr—F | 4-OEtF | Me |
| 8493 | Pr | Pr—F | 4-OPrF | Me |
| 8494 | Pr | Et—F | H | H |
| 8495 | Pr | Et—F | 2-Cl, 4-Cl | H |
| 8496 | Pr | Et—F | 2-OMe, 4-OMe | H |
| 8497 | Pr | Et—F | 2-OH | H |
| 8498 | Pr | Et—F | 3-OH | H |
| 8499 | Pr | Et—F | 4-OH | H |
| 8500 | Pr | Et—F | 2-OMe | H |
| 8501 | Pr | Et—F | 3-OMe | H |
| 8502 | Pr | Et—F | 4-OMe | H |
| 8503 | Pr | Et—F | 2-OMeF | H |
| 8504 | Pr | Et—F | 3-OMeF | H |
| 8505 | Pr | Et—F | 4-OMeF | H |
| 8506 | Pr | Et—F | 2-OCF₃ | H |
| 8507 | Pr | Et—F | 3-OCF₃ | H |
| 8508 | Pr | Et—F | 4-OCF₃ | H |
| 8509 | Pr | Et—F | 2-OEtF | H |
| 8510 | Pr | Et—F | 3-OEtF | H |
| 8511 | Pr | Et—F | 4-OEtF | H |
| 8512 | Pr | Et—F | 2-OPrF | H |

TABLE 8-continued

Substituent list for compounds of general structure XIII.

| Compound # | R¹ = | R² = | R⁶ = | R⁷ = |
|---|---|---|---|---|
| 8513 | Pr | Et—F | 3-OPrF | H |
| 8514 | Pr | Et—F | 4-OPrF | H |
| 8515 | Pr | Et—F | 2-Me | H |
| 8516 | Pr | Et—F | 3-Me | H |
| 8517 | Pr | Et—F | 4-Me | H |
| 8518 | Pr | Et—F | 2-Br | H |
| 8519 | Pr | Et—F | 3-Br | H |
| 8520 | Pr | Et—F | 4-Br | H |
| 8521 | Pr | Et—F | 2-SnMe₃ | H |
| 8522 | Pr | Et—F | 3-SnMe₃ | H |
| 8523 | Pr | Et—F | 4-SnMe₃ | H |
| 8524 | Pr | Et—F | H | Me |
| 8525 | Pr | Et—F | 4-Me | Me |
| 8526 | Pr | Et—F | 4-Br | Me |
| 8527 | Pr | Et—F | 4-SnMe₃ | Me |
| 8528 | Pr | Et—F | 4-OH | Me |
| 8529 | Pr | Et—F | 4-OMe | Me |
| 8530 | Pr | Et—F | 4-OMeF | Me |
| 8531 | Pr | Et—F | 4-OCF₃ | Me |
| 8532 | Pr | Et—F | 4-OEtF | Me |
| 8533 | Pr | Et—F | 4-OPrF | Me |
| 8534 | Pr—F | Et | H | H |
| 8535 | Pr—F | Et | 2-Cl, 4-Cl | H |
| 8536 | Pr—F | Et | 2-OMe, 4-OMe | H |
| 8537 | Pr—F | Et | 2-OH | H |
| 8538 | Pr—F | Et | 3-OH | H |
| 8539 | Pr—F | Et | 4-OH | H |
| 8540 | Pr—F | Et | 2-OMe | H |
| 8541 | Pr—F | Et | 3-OMe | H |
| 8542 | Pr—F | Et | 4-OMe | H |
| 8543 | Pr—F | Et | 2-OMeF | H |
| 8544 | Pr—F | Et | 3-OMeF | H |
| 8545 | Pr—F | Et | 4-OMeF | H |
| 8546 | Pr—F | Et | 2-OCF₃ | H |
| 8547 | Pr—F | Et | 3-OCF₃ | H |
| 8548 | Pr—F | Et | 4-OCF₃ | H |
| 8549 | Pr—F | Et | 2-OEtF | H |
| 8550 | Pr—F | Et | 3-OEtF | H |
| 8551 | Pr—F | Et | 4-OEtF | H |
| 8552 | Pr—F | Et | 2-OPrF | H |
| 8553 | Pr—F | Et | 3-OPrF | H |
| 8554 | Pr—F | Et | 4-OPrF | H |
| 8555 | Pr—F | Et | 2-Me | H |
| 8556 | Pr—F | Et | 3-Me | H |
| 8557 | Pr—F | Et | 4-Me | H |
| 8558 | Pr—F | Et | 2-Br | H |
| 8559 | Pr—F | Et | 3-Br | H |
| 8560 | Pr—F | Et | 4-Br | H |
| 8561 | Pr—F | Et | 2-SnMe₃ | H |
| 8562 | Pr—F | Et | 3-SnMe₃ | H |
| 8563 | Pr—F | Et | 4-SnMe₃ | H |
| 8564 | Pr—F | Et | H | Me |
| 8565 | Pr—F | Et | 4-Me | Me |
| 8566 | Pr—F | Et | 4-Br | Me |
| 8567 | Pr—F | Et | 4-SnMe₃ | Me |
| 8568 | Pr—F | Et | 4-OH | Me |
| 8569 | Pr—F | Et | 4-OMe | Me |
| 8570 | Pr—F | Et | 4-OMeF | Me |
| 8571 | Pr—F | Et | 4-OCF₃ | Me |
| 8572 | Pr—F | Et | 4-OEtF | Me |
| 8573 | Pr—F | Et | 4-OPrF | Me |
| 8574 | Bu | Et—F | H | H |
| 8575 | Bu | Et—F | 2-Cl, 4-Cl | H |
| 8576 | Bu | Et—F | 2-OMe, 4-OMe | H |
| 8577 | Bu | Et—F | 2-OH | H |
| 8578 | Bu | Et—F | 3-OH | H |
| 8579 | Bu | Et—F | 4-OH | H |
| 8580 | Bu | Et—F | 2-OMe | H |
| 8581 | Bu | Et—F | 3-OMe | H |
| 8582 | Bu | Et—F | 4-OMe | H |
| 8583 | Bu | Et—F | 2-OMeF | H |
| 8584 | Bu | Et—F | 3-OMeF | H |
| 8585 | Bu | Et—F | 4-OMeF | H |
| 8586 | Bu | Et—F | 2-OCF₃ | H |
| 8587 | Bu | Et—F | 3-OCF₃ | H |
| 8588 | Bu | Et—F | 4-OCF₃ | H |
| 8589 | Bu | Et—F | 2-OEtF | H |
| 8590 | Bu | Et—F | 3-OEtF | H |
| 8591 | Bu | Et—F | 4-OEtF | H |
| 8592 | Bu | Et—F | 2-OPrF | H |
| 8593 | Bu | Et—F | 3-OPrF | H |
| 8594 | Bu | Et—F | 4-OPrF | H |
| 8595 | Bu | Et—F | 2-Me | H |
| 8596 | Bu | Et—F | 3-Me | H |
| 8597 | Bu | Et—F | 4-Me | H |
| 8598 | Bu | Et—F | 2-Br | H |
| 8599 | Bu | Et—F | 3-Br | H |
| 8600 | Bu | Et—F | 4-Br | H |
| 8601 | Bu | Et—F | 2-SnMe₃ | H |
| 8602 | Bu | Et—F | 3-SnMe₃ | H |
| 8603 | Bu | Et—F | 4-SnMe₃ | H |
| 8604 | Bu | Et—F | H | Me |
| 8605 | Bu | Et—F | 4-Me | Me |
| 8606 | Bu | Et—F | 4-Br | Me |
| 8607 | Bu | Et—F | 4-SnMe₃ | Me |
| 8608 | Bu | Et—F | 4-OH | Me |
| 8609 | Bu | Et—F | 4-OMe | Me |
| 8610 | Bu | Et—F | 4-OMeF | Me |
| 8611 | Bu | Et—F | 4-OCF₃ | Me |
| 8612 | Bu | Et—F | 4-OEtF | Me |
| 8613 | Bu | Et—F | 4-OPrF | Me |
| 8614 | Bu—F | Et | H | H |
| 8615 | Bu—F | Et | 2-Cl, 4-Cl | H |
| 8616 | Bu—F | Et | 2-OMe, 4-OMe | H |
| 8617 | Bu—F | Et | 2-OH | H |
| 8618 | Bu—F | Et | 3-OH | H |
| 8619 | Bu—F | Et | 4-OH | H |
| 8620 | Bu—F | Et | 2-OMe | H |
| 8621 | Bu—F | Et | 3-OMe | H |
| 8622 | Bu—F | Et | 4-OMe | H |
| 8623 | Bu—F | Et | 2-OMeF | H |
| 8624 | Bu—F | Et | 3-OMeF | H |
| 8625 | Bu—F | Et | 4-OMeF | H |
| 8626 | Bu—F | Et | 2-OCF₃ | H |
| 8627 | Bu—F | Et | 3-OCF₃ | H |
| 8628 | Bu—F | Et | 4-OCF₃ | H |
| 8629 | Bu—F | Et | 2-OEtF | H |
| 8630 | Bu—F | Et | 3-OEtF | H |
| 8631 | Bu—F | Et | 4-OEtF | H |
| 8632 | Bu—F | Et | 2-OPrF | H |

TABLE 8-continued

Substituent list for compounds of general structure XIII.

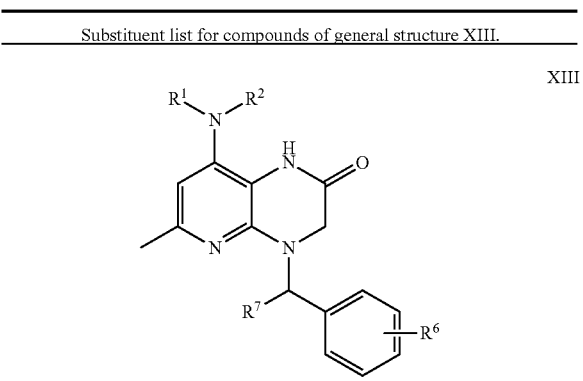

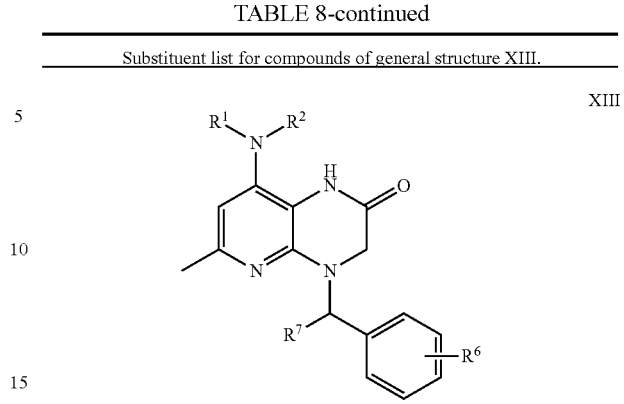

| Compound # | R$^1$ = | R$^2$ = | R$^6$ = | R$^7$ = |
|---|---|---|---|---|
| 8633 | Bu—F | Et | 3-OPrF | H |
| 8634 | Bu—F | Et | 4-OPrF | H |
| 8635 | Bu—F | Et | 2-Me | H |
| 8636 | Bu—F | Et | 3-Me | H |
| 8637 | Bu—F | Et | 4-Me | H |
| 8638 | Bu—F | Et | 2-Br | H |
| 8639 | Bu—F | Et | 3-Br | H |
| 8640 | Bu—F | Et | 4-Br | H |
| 8641 | Bu—F | Et | 2-SnMe$_3$ | H |
| 8642 | Bu—F | Et | 3-SnMe$_3$ | H |
| 8643 | Bu—F | Et | 4-SnMe$_3$ | H |
| 8644 | Bu—F | Et | H | Me |
| 8645 | Bu—F | Et | 4-Me | Me |
| 8646 | Bu—F | Et | 4-Br | Me |
| 8647 | Bu—F | Et | 4-SnMe$_3$ | Me |
| 8648 | Bu—F | Et | 4-OH | Me |
| 8649 | Bu—F | Et | 4-OMe | Me |
| 8650 | Bu—F | Et | 4-OMeF | Me |
| 8651 | Bu—F | Et | 4-OCF$_3$ | Me |
| 8652 | Bu—F | Et | 4-OEtF | Me |
| 8653 | Bu—F | Et | 4-OPrF | Me |
| 8654 | FCH$_2$—CH=CH—CH$_2$ | Me | H | H |
| 8655 | FCH$_2$—CH=CH—CH$_2$ | Me | 2-Cl, 4-Cl | H |
| 8656 | FCH$_2$—CH=CH—CH$_2$ | Me | 2-OMe, 4-OMe | H |
| 8657 | FCH$_2$—CH=CH—CH$_2$ | Me | 2-OH | H |
| 8658 | FCH$_2$—CH=CH—CH$_2$ | Me | 3-OH | H |
| 8659 | FCH$_2$—CH=CH—CH$_2$ | Me | 4-OH | H |
| 8660 | FCH$_2$—CH=CH—CH$_2$ | Me | 2-OMe | H |
| 8661 | FCH$_2$—CH=CH—CH$_2$ | Me | 3-OMe | H |
| 8662 | FCH$_2$—CH=CH—CH$_2$ | Me | 4-OMe | H |
| 8663 | FCH$_2$—CH=CH—CH$_2$ | Me | 2-OMeF | H |
| 8664 | FCH$_2$—CH=CH—CH$_2$ | Me | 3-OMeF | H |
| 8665 | FCH$_2$—CH=CH—CH$_2$ | Me | 4-OMeF | H |
| 8666 | FCH$_2$—CH=CH—CH$_2$ | Me | 2-OCF$_3$ | H |
| 8667 | FCH$_2$—CH=CH—CH$_2$ | Me | 3-OCF$_3$ | H |
| 8668 | FCH$_2$—CH=CH—CH$_2$ | Me | 4-OCF$_3$ | H |
| 8669 | FCH$_2$—CH=CH—CH$_2$ | Me | 2-OEtF | H |
| 8670 | FCH$_2$—CH=CH—CH$_2$ | Me | 3-OEtF | H |
| 8671 | FCH$_2$—CH=CH—CH$_2$ | Me | 4-OEtF | H |
| 8672 | FCH$_2$—CH=CH—CH$_2$ | Me | 2-OPrF | H |
| 8673 | FCH$_2$—CH=CH—CH$_2$ | Me | 3-OPrF | H |
| 8674 | FCH$_2$—CH=CH—CH$_2$ | Me | 4-OPrF | H |
| 8675 | FCH$_2$—CH=CH—CH$_2$ | Me | 2-Me | H |
| 8676 | FCH$_2$—CH=CH—CH$_2$ | Me | 3-Me | H |
| 8677 | FCH$_2$—CH=CH—CH$_2$ | Me | 4-Me | H |
| 8678 | FCH$_2$—CH=CH—CH$_2$ | Me | 2-Br | H |
| 8679 | FCH$_2$—CH=CH—CH$_2$ | Me | 3-Br | H |
| 8680 | FCH$_2$—CH=CH—CH$_2$ | Me | 4-Br | H |
| 8681 | FCH$_2$—CH=CH—CH$_2$ | Me | 2-SnMe$_3$ | H |
| 8682 | FCH$_2$—CH=CH—CH$_2$ | Me | 3-SnMe$_3$ | H |
| 8683 | FCH$_2$—CH=CH—CH$_2$ | Me | 4-SnMe$_3$ | H |
| 8684 | FCH$_2$—CH=CH—CH$_2$ | Me | H | Me |
| 8685 | FCH$_2$—CH=CH—CH$_2$ | Me | 4-Me | Me |
| 8686 | FCH$_2$—CH=CH—CH$_2$ | Me | 4-Br | Me |
| 8687 | FCH$_2$—CH=CH—CH$_2$ | Me | 4-SnMe$_3$ | Me |
| 8688 | FCH$_2$—CH=CH—CH$_2$ | Me | 4-OH | Me |
| 8689 | FCH$_2$—CH=CH—CH$_2$ | Me | 4-OMe | Me |
| 8690 | FCH$_2$—CH=CH—CH$_2$ | Me | 4-OMeF | Me |
| 8691 | FCH$_2$—CH=CH—CH$_2$ | Me | 4-OCF$_3$ | Me |
| 8692 | FCH$_2$—CH=CH—CH$_2$ | Me | 4-OEtF | Me |
| 8693 | FCH$_2$—CH=CH—CH$_2$ | Me | 4-OPrF | Me |
| 8694 | FCH$_2$—CH=CH—CH$_2$ | Et | H | H |
| 8695 | FCH$_2$—CH=CH—CH$_2$ | Et | 2-Cl, 4-Cl | H |
| 8696 | FCH$_2$—CH=CH—CH$_2$ | Et | 2-OMe, 4-OMe | H |
| 8697 | FCH$_2$—CH=CH—CH$_2$ | Et | 2-OH | H |
| 8698 | FCH$_2$—CH=CH—CH$_2$ | Et | 3-OH | H |
| 8699 | FCH$_2$—CH=CH—CH$_2$ | Et | 4-OH | H |
| 8700 | FCH$_2$—CH=CH—CH$_2$ | Et | 2-OMe | H |
| 8701 | FCH$_2$—CH=CH—CH$_2$ | Et | 3-OMe | H |
| 8702 | FCH$_2$—CH=CH—CH$_2$ | Et | 4-OMe | H |
| 8703 | FCH$_2$—CH=CH—CH$_2$ | Et | 2-OMeF | H |
| 8704 | FCH$_2$—CH=CH—CH$_2$ | Et | 3-OMeF | H |
| 8705 | FCH$_2$—CH=CH—CH$_2$ | Et | 4-OMeF | H |
| 8706 | FCH$_2$—CH=CH—CH$_2$ | Et | 2-OCF$_3$ | H |
| 8707 | FCH$_2$—CH=CH—CH$_2$ | Et | 3-OCF$_3$ | H |
| 8708 | FCH$_2$—CH=CH—CH$_2$ | Et | 4-OCF$_3$ | H |
| 8709 | FCH$_2$—CH=CH—CH$_2$ | Et | 2-OEtF | H |
| 8710 | FCH$_2$—CH=CH—CH$_2$ | Et | 3-OEtF | H |
| 8711 | FCH$_2$—CH=CH—CH$_2$ | Et | 4-OEtF | H |
| 8712 | FCH$_2$—CH=CH—CH$_2$ | Et | 2-OPrF | H |
| 8713 | FCH$_2$—CH=CH—CH$_2$ | Et | 3-OPrF | H |
| 8714 | FCH$_2$—CH=CH—CH$_2$ | Et | 4-OPrF | H |
| 8715 | FCH$_2$—CH=CH—CH$_2$ | Et | 2-Me | H |
| 8716 | FCH$_2$—CH=CH—CH$_2$ | Et | 3-Me | H |
| 8717 | FCH$_2$—CH=CH—CH$_2$ | Et | 4-Me | H |
| 8718 | FCH$_2$—CH=CH—CH$_2$ | Et | 2-Br | H |
| 8719 | FCH$_2$—CH=CH—CH$_2$ | Et | 3-Br | H |
| 8720 | FCH$_2$—CH=CH—CH$_2$ | Et | 4-Br | H |
| 8721 | FCH$_2$—CH=CH—CH$_2$ | Et | 2-SnMe$_3$ | H |
| 8722 | FCH$_2$—CH=CH—CH$_2$ | Et | 3-SnMe$_3$ | H |
| 8723 | FCH$_2$—CH=CH—CH$_2$ | Et | 4-SnMe$_3$ | H |
| 8724 | FCH$_2$—CH=CH—CH$_2$ | Et | H | Me |
| 8725 | FCH$_2$—CH=CH—CH$_2$ | Et | 4-Me | Me |
| 8726 | FCH$_2$—CH=CH—CH$_2$ | Et | 4-Br | Me |
| 8727 | FCH$_2$—CH=CH—CH$_2$ | Et | 4-SnMe$_3$ | Me |
| 8728 | FCH$_2$—CH=CH—CH$_2$ | Et | 4-OH | Me |
| 8729 | FCH$_2$—CH=CH—CH$_2$ | Et | 4-OMe | Me |
| 8730 | FCH$_2$—CH=CH—CH$_2$ | Et | 4-OMeF | Me |
| 8731 | FCH$_2$—CH=CH—CH$_2$ | Et | 4-OCF$_3$ | Me |
| 8732 | FCH$_2$—CH=CH—CH$_2$ | Et | 4-OEtF | Me |
| 8733 | FCH$_2$—CH=CH—CH$_2$ | Et | 4-OPrF | Me |
| 8734 | FCH$_2$—CH=CH—CH$_2$ | Et—F | H | H |
| 8735 | FCH$_2$—CH=CH—CH$_2$ | Et—F | 2-Cl, 4-Cl | H |
| 8736 | FCH$_2$—CH=CH—CH$_2$ | Et—F | 2-OMe, 4-OMe | H |
| 8737 | FCH$_2$—CH=CH—CH$_2$ | Et—F | 2-OH | H |
| 8738 | FCH$_2$—CH=CH—CH$_2$ | Et—F | 3-OH | H |
| 8739 | FCH$_2$—CH=CH—CH$_2$ | Et—F | 4-OH | H |
| 8740 | FCH$_2$—CH=CH—CH$_2$ | Et—F | 2-OMe | H |
| 8741 | FCH$_2$—CH=CH—CH$_2$ | Et—F | 3-OMe | H |
| 8742 | FCH$_2$—CH=CH—CH$_2$ | Et—F | 4-OMe | H |
| 8743 | FCH$_2$—CH=CH—CH$_2$ | Et—F | 2-OMeF | H |
| 8744 | FCH$_2$—CH=CH—CH$_2$ | Et—F | 3-OMeF | H |
| 8745 | FCH$_2$—CH=CH—CH$_2$ | Et—F | 4-OMeF | H |
| 8746 | FCH$_2$—CH=CH—CH$_2$ | Et—F | 2-OCF$_3$ | H |
| 8747 | FCH$_2$—CH=CH—CH$_2$ | Et—F | 3-OCF$_3$ | H |
| 8748 | FCH$_2$—CH=CH—CH$_2$ | Et—F | 4-OCF$_3$ | H |
| 8749 | FCH$_2$—CH=CH—CH$_2$ | Et—F | 2-OEtF | H |
| 8750 | FCH$_2$—CH=CH—CH$_2$ | Et—F | 3-OEtF | H |
| 8751 | FCH$_2$—CH=CH—CH$_2$ | Et—F | 4-OEtF | H |
| 8752 | FCH$_2$—CH=CH—CH$_2$ | Et—F | 2-OPrF | H |

TABLE 8-continued

Substituent list for compounds of general structure XIII.

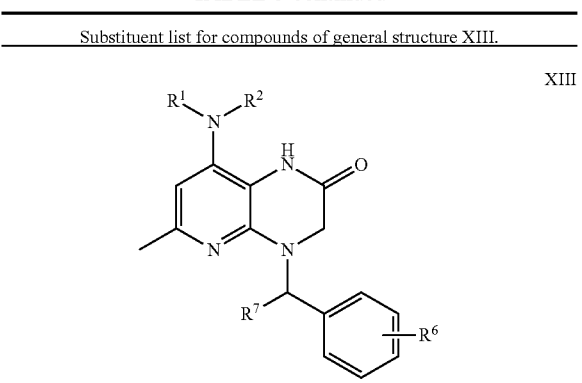

| Compound # | R$^1$ = | R$^2$ = | R$^6$ = | R$^7$ = |
|---|---|---|---|---|
| 8753 | FCH$_2$—CH=CH—CH$_2$ | Et—F | 3-OPrF | H |
| 8754 | FCH$_2$—CH=CH—CH$_2$ | Et—F | 4-OPrF | H |
| 8755 | FCH$_2$—CH=CH—CH$_2$ | Et—F | 2-Me | H |
| 8756 | FCH$_2$—CH=CH—CH$_2$ | Et—F | 3-Me | H |
| 8757 | FCH$_2$—CH=CH—CH$_2$ | Et—F | 4-Me | H |
| 8758 | FCH$_2$—CH=CH—CH$_2$ | Et—F | 2-Br | H |
| 8759 | FCH$_2$—CH=CH—CH$_2$ | Et—F | 3-Br | H |
| 8760 | FCH$_2$—CH=CH—CH$_2$ | Et—F | 4-Br | H |
| 8761 | FCH$_2$—CH=CH—CH$_2$ | Et—F | 2-SnMe$_3$ | H |
| 8762 | FCH$_2$—CH=CH—CH$_2$ | Et—F | 3-SnMe$_3$ | H |
| 8763 | FCH$_2$—CH=CH—CH$_2$ | Et—F | 4-SnMe$_3$ | H |
| 8764 | FCH$_2$—CH=CH—CH$_2$ | Et—F | H | Me |
| 8765 | FCH$_2$—CH=CH—CH$_2$ | Et—F | 4-Me | Me |
| 8766 | FCH$_2$—CH=CH—CH$_2$ | Et—F | 4-Br | Me |
| 8767 | FCH$_2$—CH=CH—CH$_2$ | Et—F | 4-SnMe$_3$ | Me |
| 8768 | FCH$_2$—CH=CH—CH$_2$ | Et—F | 4-OH | Me |
| 8769 | FCH$_2$—CH=CH—CH$_2$ | Et—F | 4-OMe | Me |
| 8770 | FCH$_2$—CH=CH—CH$_2$ | Et—F | 4-OMeF | Me |
| 8771 | FCH$_2$—CH=CH—CH$_2$ | Et—F | 4-OCF$_3$ | Me |
| 8772 | FCH$_2$—CH=CH—CH$_2$ | Et—F | 4-OEtF | Me |
| 8773 | FCH$_2$—CH=CH—CH$_2$ | Et—F | 4-OPrF | Me |

TABLE 9

Substituent list for compounds of general structure XIV.

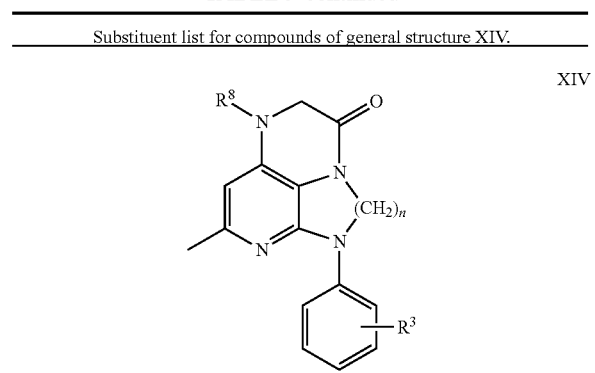

| Compound # | R$^8$ = | R$^3$ = | n = |
|---|---|---|---|
| 8774 | Bu | H | 1 |
| 8775 | Bu | 2-t-Bu | 1 |
| 8776 | Bu | 2-Br | 1 |
| 8777 | Bu | 3-Br | 1 |
| 8778 | Bu | 4-Br | 1 |
| 8779 | Bu | 2-I | 1 |
| 8780 | Bu | 3-I | 1 |
| 8781 | Bu | 4-I | 1 |
| 8782 | Bu | 2-SnMe$_3$ | 1 |
| 8783 | Bu | 3-SnMe$_3$ | 1 |
| 8784 | Bu | 4-SnMe$_3$ | 1 |
| 8785 | Bu | 2-Me | 1 |
| 8786 | Bu | 3-Me | 1 |
| 8787 | Bu | 4-Me | 1 |
| 8788 | Bu | 2-OH | 1 |
| 8789 | Bu | 3-OH | 1 |
| 8790 | Bu | 4-OH | 1 |
| 8791 | Bu | 2-OMe | 1 |
| 8792 | Bu | 3-OMe | 1 |
| 8793 | Bu | 4-OMe | 1 |
| 8794 | Bu | 2-OMeF | 1 |
| 8795 | Bu | 3-OMeF | 1 |
| 8796 | Bu | 4-OMeF | 1 |
| 8797 | Bu | 2-OCF$_3$ | 1 |
| 8798 | Bu | 3-OCF$_3$ | 1 |
| 8799 | Bu | 4-OCF$_3$ | 1 |
| 8800 | Bu | 2-OEtF | 1 |
| 8801 | Bu | 3-OEtF | 1 |
| 8802 | Bu | 4-OEtF | 1 |
| 8803 | Bu | 2-OPrF | 1 |
| 8804 | Bu | 3-OPrF | 1 |
| 8805 | Bu | 4-OPrF | 1 |
| 8806 | Bu | 2-SH | 1 |
| 8807 | Bu | 3-SH | 1 |
| 8808 | Bu | 4-SH | 1 |
| 8809 | Bu | 2-SMe | 1 |
| 8810 | Bu | 3-SMe | 1 |
| 8811 | Bu | 4-SMe | 1 |
| 8812 | Bu | 2-SMeF | 1 |
| 8813 | Bu | 3-SMeF | 1 |
| 8814 | Bu | 4-SMeF | 1 |
| 8815 | Bu | 2-SCF$_3$ | 1 |
| 8816 | Bu | 3-SCF$_3$ | 1 |
| 8817 | Bu | 4-SCF$_3$ | 1 |
| 8818 | Bu | 2-SEtF | 1 |
| 8819 | Bu | 3-SEtF | 1 |
| 8820 | Bu | 4-SEtF | 1 |
| 8821 | Bu | 2-SPrF | 1 |
| 8822 | Bu | 3-SPrF | 1 |
| 8823 | Bu | 4-SPrF | 1 |
| 8824 | Bu | 2-OMe, 4-OMe | 1 |
| 8825 | Bu | 2-Me, 5-OH | 1 |
| 8826 | Bu | 2-Me, 5-OMe | 1 |
| 8827 | Bu | 2-Me, 5-OMeF | 1 |
| 8828 | Bu | 2-Me, 5-OEtF | 1 |
| 8829 | Bu | 2-Me, 5-OPrF | 1 |
| 8830 | Bu | 2-Me, 4-OH | 1 |
| 8831 | Bu | 2-Me, 4-OMe | 1 |
| 8832 | Bu | 2-Me, 4-OMeF | 1 |
| 8833 | Bu | 2-Me, 4-OCF$_3$ | 1 |
| 8834 | Bu | 2-Me, 4-OEtF | 1 |
| 8835 | Bu | 2-Me, 4-OPrF | 1 |
| 8836 | Bu | 2-OH, 4-Me | 1 |
| 8837 | Bu | 2-OMe, 4-Me | 1 |
| 8838 | Bu | 2-OMeF, 4-Me | 1 |
| 8839 | Bu | 2-OCF$_3$, 4-Me | 1 |
| 8840 | Bu | 2-OEtF, 4-Me | 1 |
| 8841 | Bu | 2-OPrF, 4-Me | 1 |
| 8842 | Bu | 2-Cl, 4-OH | 1 |
| 8843 | Bu | 2-Cl, 4-OMe | 1 |
| 8844 | Bu | 2-Cl, 4-OMeF | 1 |
| 8845 | Bu | 2-Cl, 4-OCF$_3$ | 1 |
| 8846 | Bu | 2-Cl, 4-OEtF | 1 |
| 8847 | Bu | 2-Cl, 4-OPrF | 1 |

TABLE 9-continued

Substituent list for compounds of general structure XIV.

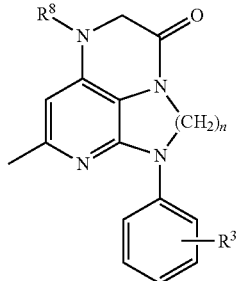

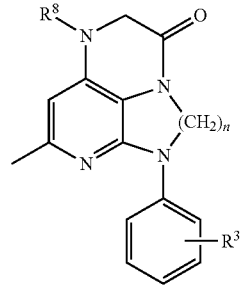

| Compound # | R⁸ = | R³ = | n = |
|---|---|---|---|
| 8848 | Bu | 2-F, 4-F | 1 |
| 8849 | Bu | 2-Cl, 4-Cl | 1 |
| 8850 | Bu | 2-Cl, 4-F | 1 |
| 8851 | Bu | 2-Cl, 4-$NO_2$ | 1 |
| 8852 | Bu | 2-Cl, 4-$NH_2$ | 1 |
| 8853 | Bu | 2-Cl, 4-NHMe | 1 |
| 8854 | Bu | 2-Cl, 4-$NMe_2$ | 1 |
| 8855 | Bu | 2-Cl, 4-$NMe_3$OTf | 1 |
| 8856 | Bu | 2-Cl, 4-$NMe_3$I | 1 |
| 8857 | Bu | 2-Cl, 5-F | 1 |
| 8858 | Bu | 2-Cl, 5-$NO_2$ | 1 |
| 8859 | Bu | 2-Cl, 5-$NH_2$ | 1 |
| 8860 | Bu | 2-Cl, 5-NHMe | 1 |
| 8861 | Bu | 2-Cl, 5-$NMe_2$ | 1 |
| 8862 | Bu | 2-Cl, 5-$NMe_3$OTf | 1 |
| 8863 | Bu | 2-Cl, 5-$NMe_3$I | 1 |
| 8864 | Bu | 2-F, 4-Cl | 1 |
| 8865 | Bu | 2-$NO_2$, 4-Cl | 1 |
| 8866 | Bu | 2-$NH_2$, 4-Cl | 1 |
| 8867 | Bu | 2-NHMe, 4-Cl | 1 |
| 8868 | Bu | 2-$NMe_2$, 4-Cl | 1 |
| 8869 | Bu | 2-$NMe_3$OTf, 4-Cl | 1 |
| 8870 | Bu | 2-$NMe_3$I, 4-Cl | 1 |
| 8871 | Bu | 2-F, 5-Cl | 1 |
| 8872 | Bu | 2-$NO_2$, 5-Cl | 1 |
| 8873 | Bu | 2-$NH_2$, 5-Cl | 1 |
| 8874 | Bu | 2-NHMe, 5-Cl | 1 |
| 8875 | Bu | 2-$NMe_2$, 5-Cl | 1 |
| 8876 | Bu | 2-$NMe_3$OTf, 5-Cl | 1 |
| 8877 | Bu | 2-$NMe_3$I, 5-Cl | 1 |
| 8878 | Bu | 2-Br, 4-F | 1 |
| 8879 | Bu | 2-Br, 4-$NO_2$ | 1 |
| 8880 | Bu | 2-Br, 4-$NH_2$ | 1 |
| 8881 | Bu | 2-Br, 4-NHMe | 1 |
| 8882 | Bu | 2-Br, 4-$NMe_2$ | 1 |
| 8883 | Bu | 2-Br, 4-$NMe_3$OTf | 1 |
| 8884 | Bu | 2-Br, 4-$NMe_3$I | 1 |
| 8885 | Bu | 2-Br, 5-F | 1 |
| 8886 | Bu | 2-Br, 5-$NO_2$ | 1 |
| 8887 | Bu | 2-Br, 5-$NH_2$ | 1 |
| 8888 | Bu | 2-Br, 5-NHMe | 1 |
| 8889 | Bu | 2-Br, 5-$NMe_2$ | 1 |
| 8890 | Bu | 2-Br, 5-$NMe_3$OTf | 1 |
| 8891 | Bu | 2-Br, 5-$NMe_3$I | 1 |
| 8892 | Bu | 2-F, 4-Br | 1 |
| 8893 | Bu | 2-$NO_2$, 4-Br | 1 |
| 8894 | Bu | 2-$NH_2$, 4-Br | 1 |
| 8895 | Bu | 2-NHMe, 4-Br | 1 |
| 8896 | Bu | 2-$NMe_2$, 4-Br | 1 |
| 8897 | Bu | 2-$NMe_3$OTf, 4-Br | 1 |
| 8898 | Bu | 2-$NMe_3$I, 4-Br | 1 |
| 8899 | Bu | 2-I, 4-F | 1 |
| 8900 | Bu | 2-I, 4-$NO_2$ | 1 |
| 8901 | Bu | 2-I, 4-$NH_2$ | 1 |
| 8902 | Bu | 2-I, 4-NHMe | 1 |
| 8903 | Bu | 2-I, 4-$NMe_2$ | 1 |
| 8904 | Bu | 2-I, 4-$NMe_3$OTf | 1 |
| 8905 | Bu | 2-I, 4-$NMe_3$I | 1 |
| 8906 | Bu | 2-F, 4-I | 1 |
| 8907 | Bu | 2-$NO_2$, 4-I | 1 |
| 8908 | Bu | 2-$NH_2$, 4-I | 1 |
| 8909 | Bu | 2-NHMe, 4-I | 1 |
| 8910 | Bu | 2-$NMe_2$, 4-I | 1 |
| 8911 | Bu | 2-$NMe_3$OTf, 4-I | 1 |
| 8912 | Bu | 2-$NMe_3$I, 4-I | 1 |
| 8913 | Bu | 2-Me, 3-F | 1 |
| 8914 | Bu | 2-Me, 3-$NO_2$ | 1 |
| 8915 | Bu | 2-Me, 3-$NH_2$ | 1 |
| 8916 | Bu | 2-Me, 3-NHMe | 1 |
| 8917 | Bu | 2-Me, 3-$NMe_2$ | 1 |
| 8918 | Bu | 2-Me, 3-$NMe_3$OTf | 1 |
| 8919 | Bu | 2-Me, 3-$NMe_3$I | 1 |
| 8920 | Bu | 2-Me, 4-F | 1 |
| 8921 | Bu | 2-Me, 4-$NO_2$ | 1 |
| 8922 | Bu | 2-Me, 4-$NH_2$ | 1 |
| 8923 | Bu | 2-Me, 4-NHMe | 1 |
| 8924 | Bu | 2-Me, 4-$NMe_2$ | 1 |
| 8925 | Bu | 2-Me, 4-$NMe_3$OTf | 1 |
| 8926 | Bu | 2-Me, 4-$NMe_3$I | 1 |
| 8927 | Bu | 2-Me, 5-F | 1 |
| 8928 | Bu | 2-Me, 5-$NO_2$ | 1 |
| 8929 | Bu | 2-Me, 5-$NH_2$ | 1 |
| 8930 | flu | 2-Me, 5-NHMe | 1 |
| 8931 | Bu | 2-Me, 5-$NMe_2$ | 1 |
| 8932 | Bu | 2-Me, 5-$NMe_3$OTf | 1 |
| 8933 | Bu | 2-Me, 5-$NMe_3$I | 1 |
| 8934 | Bu | 2-F, 4-Me | 1 |
| 8935 | Bu | 2-$NO_2$, 4-Me | 1 |
| 8936 | Bu | 2-$NH_2$, 4-Me | 1 |
| 8937 | Bu | 2-NHMe, 4-Me | 1 |
| 8938 | Bu | 2-$NMe_2$, 4-Me | 1 |
| 8939 | Bu | 2-$NMe_3$, 4-Me | 1 |
| 8940 | Bu | 2-$NMe_3$OTf, 4-Me | 1 |
| 8941 | Bu | 2-$NMe_3$I, 4-Me | 1 |
| 8942 | Bu | 2-$SnMe_3$, 4-F | 1 |
| 8943 | Bu | 2-$SnMe_3$, 5-F | 1 |
| 8944 | Bu | 2-F, 4-$SnMe_3$ | 1 |
| 8945 | Bu | 2-Br, 6-Cl, 4-F | 1 |
| 8946 | Bu | 2-Br, 6-Cl, 4-$NO_2$ | 1 |
| 8947 | Bu | 2-Br, 6-Cl, 4-$NH_2$ | 1 |
| 8948 | Bu | 2-Br, 6-Cl, 4-NHMe | 1 |
| 8949 | Bu | 2-Br, 6-Cl, 4-$NMe_2$ | 1 |
| 8950 | Bu | 2-Br, 6-Cl, 4-$NMe_3$OTf | 1 |
| 8951 | Bu | 2-Br, 6-Cl, 4-$NMe_3$I | 1 |
| 8952 | Bu | 2-Me, 6-Cl, 4-F | 1 |
| 8953 | Bu | 2-$SnMe_3$, 6-Cl, 4-F | 1 |
| 8954 | Bu | 2-Cl, 4-Me | 1 |
| 8955 | Bu | 2-Cl, 4-Br | 1 |
| 8956 | Bu | 2-Cl, 4-$SnMe_3$ | 1 |
| 8957 | Bu | 2-Br, 4-Cl | 1 |
| 8958 | Bu | 2-$SnMe_3$, 4-Cl | 1 |
| 8959 | Bu | 2-Me, 4-Cl | 1 |
| 8960 | Bu | 2-Br, 4-Br | 1 |
| 8961 | Bu | 2-Br, 4-Me | 1 |
| 8962 | Bu | 2-Br, 4-$SnMe_3$ | 1 |
| 8963 | Bu | 2-$SnMe_3$, 4-Br | 1 |
| 8964 | Bu | 2-Me, 4-Br | 1 |
| 8965 | Bu | 2-Me, 4-$SnMe_3$ | 1 |
| 8966 | Bu | 2-$SnMe_3$, 4-Me | 1 |
| 8967 | Bu | 2-Me, 4-Me | 1 |

TABLE 9-continued

Substituent list for compounds of general structure XIV.

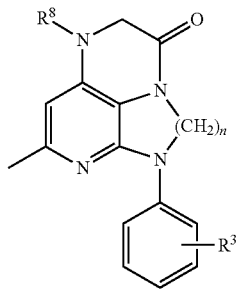

XIV

| Compound # | R⁸ = | R³ = | n = |
|---|---|---|---|
| 8968 | Bu | 2-Et, 4-Br | 1 |
| 8969 | Bu | 2-Et, 4-SnMe₃ | 1 |
| 8970 | Bu | 2-Et, 4-Me | 1 |
| 8971 | Bu | 2-Me, 4-Me, 6-Me | 1 |
| 8972 | Bu | 2-Me, 4-Br, 6-Me | 1 |
| 8973 | Bu | 2-Me, 4-SnMe3, 6-Me | 1 |
| 8974 | Bu | 2-Et, 6-Me | 1 |
| 8975 | Bu | 2-Br, 4-i-Pr | 1 |
| 8976 | Bu | 2-SnMe₃, 4-i-Pr | 1 |
| 8977 | Bu | 2-Me, 4-i-Pr | 1 |
| 8978 | Bu | 2-Br, 4-Br, 6-Br | 1 |
| 8979 | Bu | 2-Br, 4-Me, 6-Br | 1 |
| 8980 | Bu | 2-Br, 4-SnMe₃, 6-Br | 1 |
| 8981 | Bu | 2-SnMe₃, 4-Br, 6-Br | 1 |
| 8982 | Bu | 2-Br, 4-Br, 6-Me | 1 |
| 8983 | Bu | 2-Br, 4-CF₃, 6-Br | 1 |
| 8984 | Bu | 2-Br, 4-Br, 6-CF₃ | 1 |
| 8985 | Bu | 2-CF₃, 4-CF₃ | 1 |
| 8986 | Bu | 2-Cl, 4-CF₃ | 1 |
| 8987 | Bu | 2-CF₃, 4-Cl | 1 |
| 8988 | Bu | 2-Br, 4-CF₃ | 1 |
| 8989 | Bu | 2-SnMe₃, 4-CF₃ | 1 |
| 8990 | Bu | 2-Me, 4-CF₃ | 1 |
| 8991 | Bu | 2-CF₃, 4-Br | 1 |
| 8992 | Bu | 2-CF₃, 4-SnMe₃ | 1 |
| 8993 | Bu | 2-CF₃, 4-Me | 1 |
| 8994 | Bu | 2-Br, 4-OH | 1 |
| 8995 | Bu | 2-Br, 4-OMe | 1 |
| 8996 | Bu | 2-Br, 4-OMeF | 1 |
| 8997 | Bu | 2-Br, 4-OCF₃ | 1 |
| 8998 | Bu | 2-Br, 4-OEtF | 1 |
| 8999 | Bu | 2-Br, 4-OPrF | 1 |
| 9000 | Bu | 2-OH, 4-Br | 1 |
| 9001 | Bu | 2-OMe, 4-Br | 1 |
| 9002 | Bu | 2-OMeF, 4-Br | 1 |
| 9003 | Bu | 2-OCF₃, 4-Br | 1 |
| 9004 | Bu | 2-OEtF, 4-Br | 1 |
| 9005 | Bu | 2-OPrF, 4-Br | 1 |
| 9006 | Bu | 2-I, 4-OH | 1 |
| 9007 | Bu | 2-I, 4-OMe | 1 |
| 9008 | Bu | 2-I, 4-OMeF | 1 |
| 9009 | Bu | 2-I, 4-OCF₃ | 1 |
| 9010 | Bu | 2-I, 4-OEtF | 1 |
| 9011 | Bu | 2-I, 4-OPrF | 1 |
| 9012 | Bu | 2-OH, 4-I | 1 |
| 9013 | Bu | 2-OMe, 4-I | 1 |
| 9014 | Bu | 2-OMeF, 4-I | 1 |
| 9015 | Bu | 2-OCF₃, 4-I | 1 |
| 9016 | Bu | 2-OEtF, 4-I | 1 |
| 9017 | Bu | 2-OPrF, 4-I | 1 |
| 9018 | Bu | 2-SnMe₃, 4-OH | 1 |
| 9019 | Bu | 2-SnMe₃, 4-OMe | 1 |
| 9020 | Bu | 2-SnMe₃, 4-OMeF | 1 |
| 9021 | Bu | 2-SnMe₃, 4-OCF₃ | 1 |
| 9022 | Bu | 2-SnMe₃, 4-OEtF | 1 |
| 9023 | Bu | 2-SnMe₃, 4-OPrF | 1 |
| 9024 | Bu | 2-OH, 4-SnMe₃ | 1 |
| 9025 | Bu | 2-OMe, 4-SnMe₃ | 1 |
| 9026 | Bu | 2-OMeF, 4-SnMe₃ | 1 |
| 9027 | Bu | 2-OCF₃, 4-SnMe₃ | 1 |
| 9028 | Bu | 2-OEtF, 4-SnMe₃ | 1 |
| 9029 | Bu | 2-OPrF, 4-SnMe₃ | 1 |
| 9030 | Bu | H | 2 |
| 9031 | Bu | 2-t-Bu | 2 |
| 9032 | Bu | 2-Br | 2 |
| 9033 | Bu | 3-Br | 2 |
| 9034 | Bu | 4-Br | 2 |
| 9035 | Bu | 2-I | 2 |
| 9036 | Bu | 3-I | 2 |
| 9037 | Bu | 4-I | 2 |
| 9038 | Bu | 2-SnMe₃ | 2 |
| 9039 | Bu | 3-SnMe₃ | 2 |
| 9040 | Bu | 4-SnMe₃ | 2 |
| 9041 | Bu | 2-Me | 2 |
| 9042 | Bu | 3-Me | 2 |
| 9043 | Bu | 4-Me | 2 |
| 9044 | Bu | 2-OH | 2 |
| 9045 | Bu | 3-OH | 2 |
| 9046 | Bu | 4-OH | 2 |
| 9047 | Bu | 2-OMe | 2 |
| 9048 | Bu | 3-OMe | 2 |
| 9049 | Bu | 4-OMe | 2 |
| 9050 | Bu | 2-OMeF | 2 |
| 9051 | Bu | 3-OMeF | 2 |
| 9052 | Bu | 4-OMeF | 2 |
| 9053 | Bu | 2-OCF₃ | 2 |
| 9054 | Bu | 3-OCF₃ | 2 |
| 9055 | Bu | 4-OCF₃ | 2 |
| 9056 | Bu | 2-OEtF | 2 |
| 9057 | Bu | 3-OEtF | 2 |
| 9058 | Bu | 4-OEtF | 2 |
| 9059 | Bu | 2-OPrF | 2 |
| 9060 | Bu | 3-OPrF | 2 |
| 9061 | Bu | 4-OPrF | 2 |
| 9062 | Bu | 2-SH | 2 |
| 9063 | Bu | 3-SH | 2 |
| 9064 | Bu | 4-SH | 2 |
| 9065 | Bu | 2-SMe | 2 |
| 9066 | Bu | 3-SMe | 2 |
| 9067 | Bu | 4-SMe | 2 |
| 9068 | Bu | 2-SMeF | 2 |
| 9069 | Bu | 3-SMeF | 2 |
| 9070 | Bu | 4-SMeF | 2 |
| 9071 | Bu | 2-SCF₃ | 2 |
| 9072 | Bu | 3-SCF₃ | 2 |
| 9073 | Bu | 4-SCF₃ | 2 |
| 9074 | Bu | 2-SEtF | 2 |
| 9075 | Bu | 3-SEtF | 2 |
| 9076 | Bu | 4-SEtF | 2 |
| 9077 | Bu | 2-SPrF | 2 |
| 9078 | Bu | 3-SPrF | 2 |
| 9079 | Bu | 4-SPrF | 2 |
| 9080 | Bu | 2-OMe, 4-OMe | 2 |
| 9081 | Bu | 2-Me, 5-OH | 2 |
| 9082 | Bu | 2-Me, 5-OMe | 2 |
| 9083 | Bu | 2-Me, 5-OMeF | 2 |
| 9084 | Bu | 2-Me, 5-OEtF | 2 |
| 9085 | Bu | 2-Me, 5-OPrF | 2 |
| 9086 | Bu | 2-Me, 4-OH | 2 |
| 9087 | Bu | 2-Me, 4-OMeF | 2 |

TABLE 9-continued

Substituent list for compounds of general structure XIV.

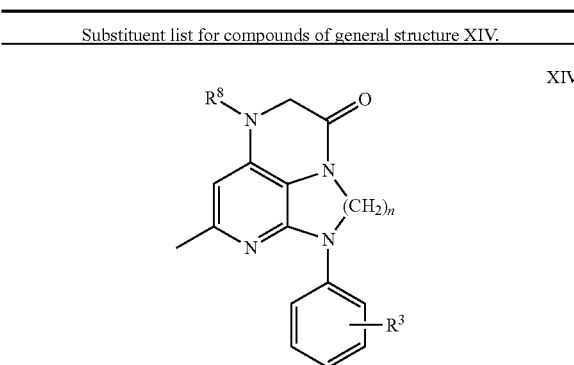

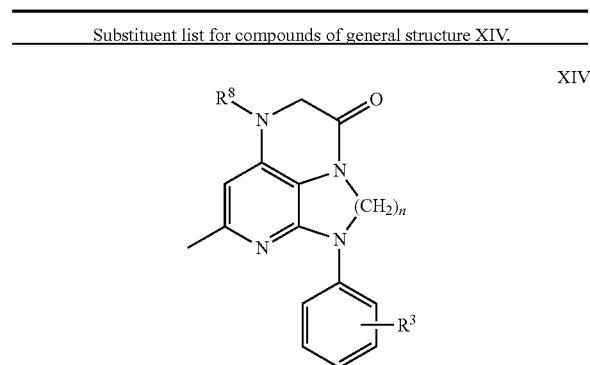

| Compound # | R⁸ = | R³ = | n = |
|---|---|---|---|
| 9088 | Bu | 2-Me, 4-OCF₃ | 2 |
| 9089 | Bu | 2-Me, 4-OEtF | 2 |
| 9090 | Bu | 2-Me, 4-OPrF | 2 |
| 9091 | Bu | 2-OH, 4-Me | 2 |
| 9092 | Bu | 2-OMe, 4-Me | 2 |
| 9093 | Bu | 2-OMeF, 4-Me | 2 |
| 9094 | Bu | 2-OCF₃, 4-Me | 2 |
| 9095 | Bu | 2-OEtF, 4-Me | 2 |
| 9096 | Bu | 2-OPrF, 4-Me | 2 |
| 9097 | Bu | 2-Cl, 4-OH | 2 |
| 9098 | Bu | 2-Cl, 4-OMeF | 2 |
| 9099 | Bu | 2-Cl, 4-OCF₃ | 2 |
| 9100 | Bu | 2-Cl, 4-OEtF | 2 |
| 9101 | Bu | 2-Cl, 4-OPrF | 2 |
| 9102 | Bu | 2-F, 4-F | 2 |
| 9103 | Bu | 2-Cl, 4-F | 2 |
| 9104 | Bu | 2-Cl, 4-NO₂ | 2 |
| 9105 | Bu | 2-Cl, 4-NH₂ | 2 |
| 9106 | Bu | 2-Cl, 4-NHMe | 2 |
| 9107 | flu | 2-Cl, 4-NMe₂ | 2 |
| 9108 | Bu | 2-Cl, 4-NMe₃OTf | 2 |
| 9109 | Bu | 2-Cl, 4-NMe₃I | 2 |
| 9110 | Bu | 2-Cl, 5-F | 2 |
| 9111 | Bu | 2-Cl, 5-NO₂ | 2 |
| 9112 | Bu | 2-Cl, 5-NH₂ | 2 |
| 9113 | Bu | 2-Cl, 5-NHMe | 2 |
| 9114 | Bu | 2-Cl, 5-NMe₂ | 2 |
| 9115 | Bu | 2-Cl, 5-NMe₃OTf | 2 |
| 9116 | Bu | 2-Cl, 5-NMe₃I | 2 |
| 9117 | Bu | 2-F, 4-Cl | 2 |
| 9118 | Bu | 2-NO₂, 4-Cl | 2 |
| 9119 | Bu | 2-NH₂, 4-Cl | 2 |
| 9120 | Bu | 2-NHMe, 4-Cl | 2 |
| 9121 | Bu | 2-NMe₂, 4-Cl | 2 |
| 9122 | Bu | 2-NMe₃OTf, 4-Cl | 2 |
| 9123 | Bu | 2-NMe₃I, 4-Cl | 2 |
| 9124 | Bu | 2-F, 5-Cl | 2 |
| 9125 | Bu | 2-NO₂, 5-Cl | 2 |
| 9126 | Bu | 2-NH₂, 5-Cl | 2 |
| 9127 | Bu | 2-NHMe, 5-Cl | 2 |
| 9128 | Bu | 2-NMe₂, 5-Cl | 2 |
| 9129 | Bu | 2-NMe₃OTf, 5-Cl | 2 |
| 9130 | Bu | 2-NMe₃I, 5-Cl | 2 |
| 9131 | Bu | 2-Br, 4-F | 2 |
| 9132 | Bu | 2-Br, 4-NO₂ | 2 |
| 9133 | Bu | 2-Br, 4-NH₂ | 2 |
| 9134 | Bu | 2-Br, 4-NHMe | 2 |
| 9135 | Bu | 2-Br, 4-NMe₂ | 2 |
| 9136 | Bu | 2-Br, 4-NMe₃OTf | 2 |
| 9137 | Bu | 2-Br, 4-NMe₃I | 2 |
| 9138 | Bu | 2-Br, 5-F | 2 |
| 9139 | Bu | 2-Br, 5-NO₂ | 2 |
| 9140 | Bu | 2-Br, 5-NH₂ | 2 |
| 9141 | Bu | 2-Br, 5-NHMe | 2 |
| 9142 | Bu | 2-Br, 5-NMe₂ | 2 |
| 9143 | Bu | 2-Br, 5-NMe₃OTf | 2 |
| 9144 | Bu | 2-Br, 5-NMe₃I | 2 |
| 9145 | Bu | 2-F, 4-Br | 2 |
| 9146 | Bu | 2-NO₂, 4-Br | 2 |
| 9147 | Bu | 2-NH₂, 4-Br | 2 |
| 9148 | Bu | 2-NHMe, 4-Br | 2 |
| 9149 | Bu | 2-NMe₂, 4-Br | 2 |
| 9150 | Bu | 2-NMe₃OTf, 4-Br | 2 |
| 9151 | Bu | 2-NMe₃I, 4-Br | 2 |
| 9152 | Bu | 2-I, 4-F | 2 |
| 9153 | Bu | 2-I, 4-NO₂ | 2 |
| 9154 | Bu | 2-I, 4-NH₂ | 2 |
| 9155 | Bu | 2-I, 4-NHMe | 2 |
| 9156 | Bu | 2-I, 4-NMe₂ | 2 |
| 9157 | Bu | 2-I, 4-NMe₃OTf | 2 |
| 9158 | Bu | 2-I, 4-NMe₃I | 2 |
| 9159 | Bu | 2-F, 4-I | 2 |
| 9160 | Bu | 2-NO₂, 4-I | 2 |
| 9161 | Bu | 2-NH₂, 4-I | 2 |
| 9162 | Bu | 2-NHMe, 4-I | 2 |
| 9163 | Bu | 2-NMe₂, 4-I | 2 |
| 9164 | Bu | 2-NMe₃OTf, 4-I | 2 |
| 9165 | Bu | 2-NMe₃I, 4-I | 2 |
| 9166 | Bu | 2-Me, 3-F | 2 |
| 9167 | Bu | 2-Me, 3-NO₂ | 2 |
| 9168 | Bu | 2-Me, 3-NH₂ | 2 |
| 9169 | Bu | 2-Me, 3-NHMe | 2 |
| 9170 | Bu | 2-Me, 3-NMe₂ | 2 |
| 9171 | Bu | 2-Me, 3-NMe₃OTf | 2 |
| 9172 | Bu | 2-Me, 3-NMe₃I | 2 |
| 9173 | Bu | 2-Me, 4-F | 2 |
| 9174 | Bu | 2-Me, 4-NO₂ | 2 |
| 9175 | Bu | 2-Me, 4-NH₂ | 2 |
| 9176 | Bu | 2-Me, 4-NHMe | 2 |
| 9177 | Bu | 2-Me, 4-NMe₂ | 2 |
| 9178 | Bu | 2-Me, 4-NMe₃OTf | 2 |
| 9179 | Bu | 2-Me, 4-NMe₃I | 2 |
| 9180 | Bu | 2-Me, 5-F | 2 |
| 9181 | Bu | 2-Me, 5-NO₂ | 2 |
| 9182 | Bu | 2-Me, 5-NH₂ | 2 |
| 9183 | Bu | 2-Me, 5-NHMe | 2 |
| 9184 | Bu | 2-Me, 5-NMe₂ | 2 |
| 9185 | Bu | 2-Me, 5-NMe₃OTf | 2 |
| 9186 | Bu | 2-Me, 5-NMe₃I | 2 |
| 9187 | Bu | 2-F, 4-Me | 2 |
| 9188 | Bu | 2-NO₂, 4-Me | 2 |
| 9189 | Bu | 2-NH₂, 4-Me | 2 |
| 9190 | Bu | 2-NHMe, 4-Me | 2 |
| 9191 | Bu | 2-NMe₂, 4-Me | 2 |
| 9192 | Bu | 2-NMe₃, 4-Me | 2 |
| 9193 | Bu | 2-NMe₃OTf, 4-Me | 2 |
| 9194 | Bu | 2-NMe₃I, 4-Me | 2 |
| 9195 | Bu | 2-SnMe₃, 4-F | 2 |
| 9196 | Bu | 2-SnMe₃, 5-F | 2 |
| 9197 | Bu | 2-F, 4-SnMe₃ | 2 |
| 9198 | Bu | 2-Br, 6-Cl, 4-F | 2 |
| 9199 | Bu | 2-Br, 6-Cl, 4-NO₂ | 2 |
| 9200 | Bu | 2-Br, 6-Cl, 4-NH₂ | 2 |
| 9201 | Bu | 2-Br, 6-Cl, 4-NHMe | 2 |
| 9202 | Bu | 2-Br, 6-Cl, 4-NMe₂ | 2 |
| 9203 | Bu | 2-Br, 6-Cl, 4-NMe₃OTf | 2 |
| 9204 | Bu | 2-Br, 6-Cl, 4-NMe₃I | 2 |
| 9205 | Bu | 2-Me, 6-Cl, 4-F | 2 |
| 9206 | Bu | 2-SnMe₃, 6-Cl, 4-F | 2 |
| 9207 | Bu | 2-Cl, 4-Me | 2 |

TABLE 9-continued

Substituent list for compounds of general structure XIV.

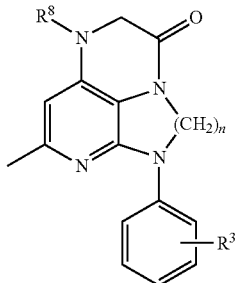

| Compound # | $R^8$ = | $R^3$ = | n = |
|---|---|---|---|
| 9208 | Bu | 2-Cl, 4-Br | 2 |
| 9209 | Bu | 2-Cl, 4-SnMe$_3$ | 2 |
| 9210 | Bu | 2-Br, 4-Cl | 2 |
| 9211 | Bu | 2-SnMe$_3$, 4-Cl | 2 |
| 9212 | Bu | 2-Me, 4-Cl | 2 |
| 9213 | Bu | 2-Br, 4-Br | 2 |
| 9214 | Bu | 2-Br, 4-Me | 2 |
| 9215 | Bu | 2-Br, 4-SnMe$_3$ | 2 |
| 9216 | Bu | 2-SnMe$_3$, 4-Br | 2 |
| 9217 | Bu | 2-Me, 4-Br | 2 |
| 9218 | Bu | 2-Me, 4-SnMe$_3$ | 2 |
| 9219 | Bu | 2-SnMe$_3$, 4-Me | 2 |
| 9220 | Bu | 2-Me, 4-Me | 2 |
| 9221 | Bu | 2-Et, 4-Br | 2 |
| 9222 | Bu | 2-Et, 4-SnMe$_3$ | 2 |
| 9223 | Bu | 2-Et, 4-Me | 2 |
| 9224 | Bu | 2-Me, 4-Br, 6-Me | 2 |
| 9225 | Bu | 2-Me, 4-SnMe$_3$, 6-Me | 2 |
| 9226 | Bu | 2-Et, 6-Me | 2 |
| 9227 | Bu | 2-SnMe$_3$, 4-i-Pr | 2 |
| 9228 | Bu | 2-Me, 4-i-Pr | 2 |
| 9229 | Bu | 2-Br, 4-Br, 6-Br | 2 |
| 9230 | Bu | 2-Br, 4-Me, 6-Br | 2 |
| 9231 | Bu | 2-Br, 4-SnMe$_3$, 6-Br | 2 |
| 9232 | Bu | 2-SnMe$_3$, 4-Br, 6-Br | 2 |
| 9233 | Bu | 2-Br, 4-Br, 6-Me | 2 |
| 9234 | Bu | 2-Br, 4-CF$_3$, 6-Br | 2 |
| 9235 | Bu | 2-Br, 4-Br, 6-CF$_3$ | 2 |
| 9236 | Bu | 2-CF$_3$, 4-CF$_3$ | 2 |
| 9237 | Bu | 2-Cl, 4-CF$_3$ | 2 |
| 9238 | Bu | 2-CF$_3$, 4-Cl | 2 |
| 9239 | Bu | 2-Br, 4-CF$_3$ | 2 |
| 9240 | Bu | 2-SnMe$_3$, 4-CF$_3$ | 2 |
| 9241 | Bu | 2-Me, 4-CF$_3$ | 2 |
| 9242 | Bu | 2-CF$_3$, 4-Br | 2 |
| 9243 | Bu | 2-CF$_3$, 4-SnMe$_3$ | 2 |
| 9244 | Bu | 2-CF$_3$, 4-Me | 2 |
| 9245 | Bu | 2-Br, 4-OH | 2 |
| 9246 | Bu | 2-Br, 4-OMe | 2 |
| 9247 | Bu | 2-Br, 4-OMeF | 2 |
| 9248 | Bu | 2-Br, 4-OCF$_3$ | 2 |
| 9249 | Bu | 2-Br, 4-OEtF | 2 |
| 9250 | Bu | 2-Br, 4-OPrF | 2 |
| 9251 | Bu | 2-OH, 4-Br | 2 |
| 9252 | Bu | 2-OMe, 4-Br | 2 |
| 9253 | Bu | 2-OMeF, 4-Br | 2 |
| 9254 | Bu | 2-OCF$_3$, 4-Br | 2 |
| 9255 | Bu | 2-OEtF, 4-Br | 2 |
| 9256 | Bu | 2-OPrF, 4-Br | 2 |
| 9257 | Bu | 2-I, 4-OH | 2 |
| 9258 | Bu | 2-I, 4-OMe | 2 |
| 9259 | Bu | 2-I, 4-OMeF | 2 |
| 9260 | Bu | 2-I, 4-OCF$_3$ | 2 |
| 9261 | Bu | 2-I, 4-OEtF | 2 |
| 9262 | Bu | 2-I, 4-OPrF | 2 |
| 9263 | Bu | 2-OH, 4-I | 2 |
| 9264 | Bu | 2-OMe, 4-I | 2 |
| 9265 | Bu | 2-OMeF, 4-I | 2 |
| 9266 | Bu | 2-OCF$_3$, 4-I | 2 |
| 9267 | Bu | 2-OEtF, 4-I | 2 |

TABLE 9-continued

Substituent list for compounds of general structure XIV.

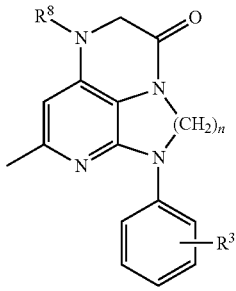

| Compound # | $R^8$ = | $R^3$ = | n = |
|---|---|---|---|
| 9268 | Bu | 2-OPrF, 4-I | 2 |
| 9269 | Bu | 2-SnMe$_3$, 4-OH | 2 |
| 9270 | Bu | 2-SnMe$_3$, 4-OMe | 2 |
| 9271 | Bu | 2-SnMe$_3$, 4-OMeF | 2 |
| 9272 | Bu | 2-SnMe$_3$, 4-OCF$_3$ | 2 |
| 9273 | Bu | 2-SnMe$_3$, 4-OEtF | 2 |
| 9274 | Bu | 2-SnMe$_3$, 4-OPrF | 2 |
| 9275 | Bu | 2-OH, 4-SnMe$_3$ | 2 |
| 9276 | Bu | 2-OMe, 4-SnMe$_3$ | 2 |
| 9277 | Bu | 2-OMeF, 4-SnMe$_3$ | 2 |
| 9278 | Bu | 2-OCF$_3$, 4-SnMe$_3$ | 2 |
| 9279 | Bu | 2-OEtF, 4-SnMe$_3$ | 2 |
| 9280 | Bu | 2-OPrF, 4-SnMe$_3$ | 2 |
| 9281 | Bu—F | H | 1 |
| 9282 | Bu—F | 2-t-Bu | 1 |
| 9283 | Bu—F | 2-Br | 1 |
| 9284 | Bu—F | 3-Br | 1 |
| 9285 | Bu—F | 4-Br | 1 |
| 9286 | Bu—F | 2-I | 1 |
| 9287 | Bu—F | 3-I | 1 |
| 9288 | Bu—F | 4-I | 1 |
| 9289 | Bu—F | 2-SnMe3 | 1 |
| 9290 | Bu—F | 3-SnMe3 | 1 |
| 9291 | Bu—F | 4-SnMe3 | 1 |
| 9292 | Bu—F | 2-Me | 1 |
| 9293 | Bu—F | 3-Me | 1 |
| 9294 | Bu—F | 4-Me | 1 |
| 9295 | Bu—F | 2-OH | 1 |
| 9296 | Bu—F | 3-OH | 1 |
| 9297 | Bu—F | 4-OH | 1 |
| 9298 | Bu—F | 2-OMe | 1 |
| 9299 | Bu—F | 3-OMe | 1 |
| 9300 | Bu—F | 4-OMe | 1 |
| 9301 | Bu—F | 2-OMeF | 1 |
| 9302 | Bu—F | 3-OMeF | 1 |
| 9303 | Bu—F | 4-OMeF | 1 |
| 9304 | Bu—F | 2-OCF$_3$ | 1 |
| 9305 | Bu—F | 3-OCF$_3$ | 1 |
| 9306 | Bu—F | 4-OCF$_3$ | 1 |
| 9307 | Bu—F | 2-OEtF | 1 |
| 9308 | Bu—F | 3-OEtF | 1 |
| 9309 | Bu—F | 4-OEtF | 1 |
| 9310 | Bu—F | 2-OPrF | 1 |
| 9311 | Bu—F | 3-OPrF | 1 |
| 9312 | Bu—F | 4-OPrF | 1 |
| 9313 | Bu—F | 2-SH | 1 |
| 9314 | Bu—F | 3-SH | 1 |
| 9315 | Bu—F | 4-SH | 1 |
| 9316 | Bu—F | 2-SMe | 1 |
| 9317 | Bu—F | 3-SMe | 1 |
| 9318 | Bu—F | 4-SMe | 1 |
| 9319 | Bu—F | 2-SMeF | 1 |
| 9320 | Bu—F | 3-SMeF | 1 |
| 9321 | Bu—F | 4-SMeF | 1 |
| 9322 | Bu—F | 2-SCF$_3$ | 1 |
| 9323 | Bu—F | 3-SCF$_3$ | 1 |
| 9324 | Bu—F | 4-SCF$_3$ | 1 |
| 9325 | Bu—F | 2-SEtF | 1 |
| 9326 | Bu—F | 3-SEtF | 1 |
| 9327 | Bu—F | 4-SEtF | 1 |

TABLE 9-continued

Substituent list for compounds of general structure XIV.

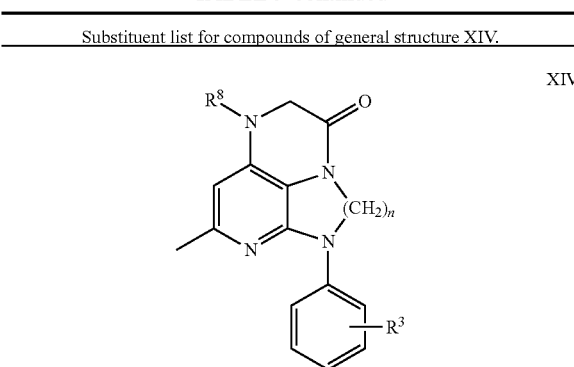

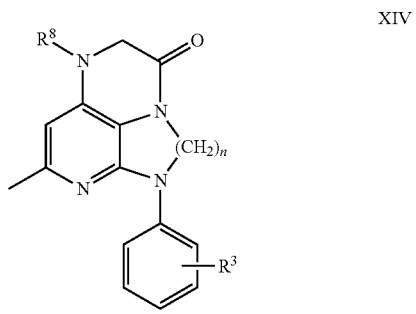

| Compound # | R⁸ = | R³ = | n = |
|---|---|---|---|
| 9328 | Bu—F | 2-SPrF | 1 |
| 9329 | Bu—F | 3-SPrF | 1 |
| 9330 | Bu—F | 4-SPrF | 1 |
| 9331 | Bu—F | 2-OMe, 4-OMe | 1 |
| 9332 | Bu—F | 2-Me, 5-OH | 1 |
| 9333 | Bu—F | 2-Me, 5-OMe | 1 |
| 9334 | Bu—F | 2-Me, 5-OMeF | 1 |
| 9335 | Bu—F | 2-Me, 5-OEtF | 1 |
| 9336 | Bu—F | 2-Me, 5-OPrF | 1 |
| 9337 | Bu—F | 2-Me, 4-OH | 1 |
| 9338 | Bu—F | 2-Me, 4-OMe | 1 |
| 9339 | Bu—F | 2-Me, 4-OMeF | 1 |
| 9340 | Bu—F | 2-Me, 4-OCF₃ | 1 |
| 9341 | Bu—F | 2-Me, 4-OEtF | 1 |
| 9342 | Bu—F | 2-Me, 4-OPrF | 1 |
| 9343 | Bu—F | 2-OH, 4-Me | 1 |
| 9344 | Bu—F | 2-OMe, 4-Me | 1 |
| 9345 | Bu—F | 2-OMeF, 4-Me | 1 |
| 9346 | Bu—F | 2-OCF₃, 4-Me | 1 |
| 9347 | Bu—F | 2-OEtF, 4-Me | 1 |
| 9348 | Bu—F | 2-OPrF, 4-Me | 1 |
| 9349 | Bu—F | 2-Cl, 4-OH | 1 |
| 9350 | Bu—F | 2-Cl, 4-OMe | 1 |
| 9351 | Bu—F | 2-Cl, 4-OMeF | 1 |
| 9352 | Bu—F | 2-Cl, 4-OCF₃ | 1 |
| 9353 | Bu—F | 2-Cl, 4-OEtF | 1 |
| 9354 | Bu—F | 2-Cl, 4-OPrF | 1 |
| 9355 | Bu—F | 2-F, 4-F | 1 |
| 9356 | Bu—F | 2-Cl, 4-Cl | 1 |
| 9357 | Bu—F | 2-Cl, 4-F | 1 |
| 9358 | Bu—F | 2-Cl, 4-NO₂ | 1 |
| 9359 | Bu—F | 2-Cl, 4-NH₂ | 1 |
| 9360 | Bu—F | 2-Cl, 4-NHMe | 1 |
| 9361 | Bu—F | 2-Cl, 4-NMe₂ | 1 |
| 9362 | Bu—F | 2-Cl, 4-NMe₃OTf | 1 |
| 9363 | Bu—F | 2-Cl, 4-NMe₃I | 1 |
| 9364 | Bu—F | 2-Cl, 5-F | 1 |
| 9365 | Bu—F | 2-Cl, 5-NO₂ | 1 |
| 9366 | Bu—F | 2-Cl, 5-NH₂ | 1 |
| 9367 | Bu—F | 2-Cl, 5-NHMe | 1 |
| 9368 | Bu—F | 2-Cl, 5-NMe₂ | 1 |
| 9369 | Bu—F | 2-Cl, 5-NMe₃OTf | 1 |
| 9370 | Bu—F | 2-Cl, 5-NMe₃I | 1 |
| 9371 | Bu—F | 2-F, 4-Cl | 1 |
| 9372 | Bu—F | 2-NO₂, 4-Cl | 1 |
| 9373 | Bu—F | 2-NH₂, 4-Cl | 1 |
| 9374 | Bu—F | 2-NHMe, 4-Cl | 1 |
| 9375 | Bu—F | 2-NMe₂, 4-Cl | 1 |
| 9376 | Bu—F | 2-NMe₃OTf, 4-Cl | 1 |
| 9377 | Bu—F | 2-NMe₃I, 4-Cl | 1 |
| 9378 | Bu—F | 2-F, 5-Cl | 1 |
| 9379 | Bu—F | 2-NO₂, 5-Cl | 1 |
| 9380 | Bu—F | 2-NH₂, 5-Cl | 1 |
| 9381 | Bu—F | 2-NHMe, 5-Cl | 1 |
| 9382 | Bu—F | 2-NMe₂, 5-Cl | 1 |
| 9383 | Bu—F | 2-NMe₃OTf, 5-Cl | 1 |
| 9384 | Bu—F | 2-NMe₃I, 5-Cl | 1 |
| 9385 | Bu—F | 2-Br, 4-F | 1 |
| 9386 | Bu—F | 2-Br, 4-NO₂ | 1 |
| 9387 | Bu—F | 2-Br, 4-NH₂ | 1 |
| 9388 | Bu—F | 2-Br, 4-NHMe | 1 |
| 9389 | Bu—F | 2-Br, 4-NMe₂ | 1 |
| 9390 | Bu—F | 2-Br, 4-NMe₃OTf | 1 |
| 9391 | Bu—F | 2-Br, 4-NMe₃I | 1 |
| 9392 | Bu—F | 2-Br, 5-F | 1 |
| 9393 | Bu—F | 2-Br, 5-NO₂ | 1 |
| 9394 | Bu—F | 2-Br, 5-NH₂ | 1 |
| 9395 | Bu—F | 2-Br, 5-NHMe | 1 |
| 9396 | Bu—F | 2-Br, 5-NMe₂ | 1 |
| 9397 | Bu—F | 2-Br, 5-NMe₃OTf | 1 |
| 9398 | Bu—F | 2-Br, 5-NMe₃I | 1 |
| 9399 | Bu—F | 2-F, 4-Br | 1 |
| 9400 | Bu—F | 2-NO₂, 4-Br | 1 |
| 9401 | Bu—F | 2-NH₂, 4-Br | 1 |
| 9402 | Bu—F | 2-NHMe, 4-Br | 1 |
| 9403 | Bu—F | 2-NMe₂, 4-Br | 1 |
| 9404 | Bu—F | 2-NMe₃OTf, 4-Br | 1 |
| 9405 | Bu—F | 2-NMe₃I, 4-Br | 1 |
| 9406 | Bu—F | 2-I, 4-F | 1 |
| 9407 | Bu—F | 2-I, 4-NO₂ | 1 |
| 9408 | Bu—F | 2-I, 4-NH₂ | 1 |
| 9409 | Bu—F | 2-I, 4-NHMe | 1 |
| 9410 | Bu—F | 2-I, 4-NMe₂ | 1 |
| 9411 | Bu—F | 2-I, 4-NMe₃OTf | 1 |
| 9412 | Bu—F | 2-I, 4-NMe₃I | 1 |
| 9413 | Bu—F | 2-F, 4-I | 1 |
| 9414 | Bu—F | 2-NO₂, 4-I | 1 |
| 9415 | Bu—F | 2-NH₂, 4-I | 1 |
| 9416 | Bu—F | 2-NHMe, 4-I | 1 |
| 9417 | Bu—F | 2-NMe₂, 4-I | 1 |
| 9418 | Bu—F | 2-NMe₃OTf, 4-I | 1 |
| 9419 | Bu—F | 2-NMe₃I, 4-I | 1 |
| 9420 | Bu—F | 2-Me, 3-F | 1 |
| 9421 | Bu—F | 2-Me, 3-NO₂ | 1 |
| 9422 | Bu—F | 2-Me, 3-NH₂ | 1 |
| 9423 | Bu—F | 2-Me, 3-NHMe | 1 |
| 9424 | Bu—F | 2-Me, 3-NMe₂ | 1 |
| 9425 | Bu—F | 2-Me, 3-NMe₃OTf | 1 |
| 9426 | Bu—F | 2-Me, 3-NMe₃I | 1 |
| 9427 | Bu—F | 2-Me, 4-F | 1 |
| 9428 | Bu—F | 2-Me, 4-NO₂ | 1 |
| 9429 | Bu—F | 2-Me, 4-NH₂ | 1 |
| 9430 | Bu—F | 2-Me, 4-NHMe | 1 |
| 9431 | Bu—F | 2-Me, 4-NMe₂ | 1 |
| 9432 | Bu—F | 2-Me, 4-NMe₃OTf | 1 |
| 9433 | Bu—F | 2-Me, 4-NMe₃I | 1 |
| 9434 | Bu—F | 2-Me, 5-F | 1 |
| 9435 | Bu—F | 2-Me, 5-NO₂ | 1 |
| 9436 | Bu—F | 2-Me, 5-NH₂ | 1 |
| 9437 | Bu—F | 2-Me, 5-NHMe | 1 |
| 9438 | Bu—F | 2-Me, 5-NMe₂ | 1 |
| 9439 | Bu—F | 2-Me, 5-NMe₃OTf | 1 |
| 9440 | Bu—F | 2-Me, 5-NMe₃I | 1 |
| 9441 | Bu—F | 2-F, 4-Me | 1 |
| 9442 | Bu—F | 2-NO₂, 4-Me | 1 |
| 9443 | Bu—F | 2-NH₂, 4-Me | 1 |
| 9444 | Bu—F | 2-NHMe, 4-Me | 1 |
| 9445 | Bu—F | 2-NMe₂, 4-Me | 1 |
| 9446 | Bu—F | 2-NMe₃, 4-Me | 1 |
| 9447 | Bu—F | 2-NMe₃OTf, 4-Me | 1 |

TABLE 9-continued

Substituent list for compounds of general structure XIV.

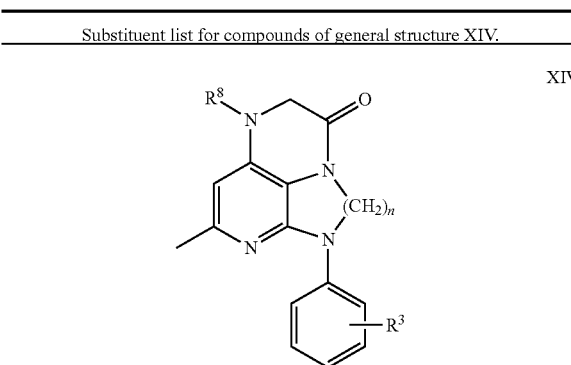

| Compound # | R⁸ = | R³ = | n = |
|---|---|---|---|
| 9448 | Bu—F | 2-NMe₃I, 4-Me | 1 |
| 9449 | Bu—F | 2-SnMe₃, 4-F | 1 |
| 9450 | Bu—F | 2-SnMe₃, 5-F | 1 |
| 9451 | Bu—F | 2-F, 4-SnMe₃ | 1 |
| 9452 | Bu—F | 2-Br, 6-Cl, 4-F | 1 |
| 9453 | Bu—F | 2-Br, 6-Cl, 4-NO₂ | 1 |
| 9454 | Bu—F | 2-Br, 6-Cl, 4-NH₂ | 1 |
| 9455 | Bu—F | 2-Br, 6-Cl, 4-NHMe | 1 |
| 9456 | Bu—F | 2-Br, 6-Cl, 4-NMe₂ | 1 |
| 9457 | Bu—F | 2-Br, 6-Cl, 4-NMe₃OTf | 1 |
| 9458 | Bu—F | 2-Br, 6-Cl, 4-NMe₃I | 1 |
| 9459 | Bu—F | 2-Me, 6-Cl, 4-F | 1 |
| 9460 | Bu—F | 2-SnMe₃, 6-Cl, 4-F | 1 |
| 9461 | Bu—F | 2-Cl, 4-Me | 1 |
| 9462 | Bu—F | 2-Cl, 4-Br | 1 |
| 9463 | Bu—F | 2-Cl, 4-SnMe₃ | 1 |
| 9464 | Bu—F | 2-Br, 4-Cl | 1 |
| 9465 | Bu—F | 2-SnMe₃, 4-Cl | 1 |
| 9466 | Bu—F | 2-Me, 4-Cl | 1 |
| 9467 | Bu—F | 2-Br, 4-Br | 1 |
| 9468 | Bu—F | 2-Br, 4-Me | 1 |
| 9469 | Bu—F | 2-Br, 4-SnMe₃ | 1 |
| 9470 | Bu—F | 2-SnMe₃, 4-Br | 1 |
| 9471 | Bu—F | 2-Me, 4-Br | 1 |
| 9472 | Bu—F | 2-Me, 4-SnMe₃ | 1 |
| 9473 | Bu—F | 2-SnMe₃, 4-Me | 1 |
| 9474 | Bu—F | 2-Me, 4-Me | 1 |
| 9475 | Bu—F | 2-Et, 4-Br | 1 |
| 9476 | Bu—F | 2-Et, 4-SnMe₃ | 1 |
| 9477 | Bu—F | 2-Et, 4-Me | 1 |
| 9478 | Bu—F | 2-Me, 4-Me, 6-Me | 1 |
| 9479 | Bu—F | 2-Me, 4-Br, 6-Me | 1 |
| 9480 | Bu—F | 2-Me, 4-SnMe₃, 6-Me | 1 |
| 9481 | Bu—F | 2-Et, 6-Me | 1 |
| 9482 | Bu—F | 2-Br, 4-i-Pr | 1 |
| 9483 | Bu—F | 2-SnMe₃, 4-i-Pr | 1 |
| 9484 | Bu—F | 2-Me, 4-i-Pr | 1 |
| 9485 | Bu—F | 2-Br, 4-Br, 6-Br | 1 |
| 9486 | Bu—F | 2-Br, 4-Me, 6-Br | 1 |
| 9487 | Bu—F | 2-Br, 4-SnMe₃, 6-Br | 1 |
| 9488 | Bu—F | 2-SnMe₃, 4-Br, 6-Br | 1 |
| 9489 | Bu—F | 2-Br, 4-Br, 6-Me | 1 |
| 9490 | Bu—F | 2-Br, 4-CF₃, 6-Br | 1 |
| 9491 | Bu—F | 2-Br, 4-Br, 6-CF₃ | 1 |
| 9492 | Bu—F | 2-CF₃, 4-CF₃ | 1 |
| 9493 | Bu—F | 2-Cl, 4-CF₃ | 1 |
| 9494 | Bu—F | 2-CF₃, 4-Cl | 1 |
| 9495 | Bu—F | 2-Br, 4-CF₃ | 1 |
| 9496 | Bu—F | 2-SnMe₃, 4-CF₃ | 1 |
| 9497 | Bu—F | 2-Me, 4-CF₃ | 1 |
| 9498 | Bu—F | 2-CF₃, 4-Br | 1 |
| 9499 | Bu—F | 2-CF₃, 4-SnMe₃ | 1 |
| 9500 | Bu—F | 2-CF₃, 4-Me | 1 |
| 9501 | Bu—F | 2-Br, 4-OH | 1 |
| 9502 | Bu—F | 2-Br, 4-OMe | 1 |
| 9503 | Bu—F | 2-Br, 4-OMeF | 1 |
| 9504 | Bu—F | 2-Br, 4-OCF₃ | 1 |
| 9505 | Bu—F | 2-Br, 4-OEtF | 1 |
| 9506 | Bu—F | 2-Br, 4-OPrF | 1 |
| 9507 | Bu—F | 2-OH, 4-Br | 1 |

TABLE 9-continued

Substituent list for compounds of general structure XIV.

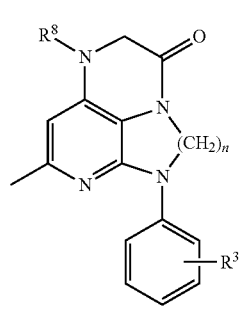

| Compound # | R⁸ = | R³ = | n = |
|---|---|---|---|
| 9508 | Bu—F | 2-OMe, 4-Br | 1 |
| 9509 | Bu—F | 2-OMeF, 4-Br | 1 |
| 9510 | Bu—F | 2-OCF₃, 4-Br | 1 |
| 9511 | Bu—F | 2-OEtF, 4-Br | 1 |
| 9512 | Bu—F | 2-OPrF, 4-Br | 1 |
| 9513 | Bu—F | 2-I, 4-OH | 1 |
| 9514 | Bu—F | 2-I, 4-OMe | 1 |
| 9515 | Bu—F | 2-I, 4-OMeF | 1 |
| 9516 | Bu—F | 2-I, 4-OCF₃ | 1 |
| 9517 | Bu—F | 2-I, 4-OEtF | 1 |
| 9518 | Bu—F | 2-I, 4-OPrF | 1 |
| 9519 | Bu—F | 2-OH, 4-I | 1 |
| 9520 | Bu—F | 2-OMe, 4-I | 1 |
| 9521 | Bu—F | 2-OMeF, 4-I | 1 |
| 9522 | Bu—F | 2-OCF₃, 4-I | 1 |
| 9523 | Bu—F | 2-OEtF, 4-I | 1 |
| 9524 | Bu—F | 2-OPrF, 4-I | 1 |
| 9525 | Bu—F | 2-SnMe₃, 4-OH | 1 |
| 9526 | Bu—F | 2-SnMe₃, 4-OMe | 1 |
| 9527 | Bu—F | 2-SnMe₃, 4-OMeF | 1 |
| 9528 | Bu—F | 2-SnMe₃, 4-OCF₃ | 1 |
| 9529 | Bu—F | 2-SnMe₃, 4-OEtF | 1 |
| 9530 | Bu—F | 2-SnMe₃, 4-OPrF | 1 |
| 9531 | Bu—F | 2-OH, 4-SnMe₃ | 1 |
| 9532 | Bu—F | 2-OMe, 4-SnMe₃ | 1 |
| 9533 | Bu—F | 2-OMeF, 4-SnMe₃ | 1 |
| 9534 | Bu—F | 2-OCF₃, 4-SnMe₃ | 1 |
| 9535 | Bu—F | 2-OEtF, 4-SnMe₃ | 1 |
| 9536 | Bu—F | 2-OPrF, 4-SnMe₃ | 1 |
| 9537 | Bu—F | H | 2 |
| 9538 | Bu—F | 2-t-Bu | 2 |
| 9539 | Bu—F | 2-Br | 2 |
| 9540 | Bu—F | 3-Br | 2 |
| 9541 | Bu—F | 4-Br | 2 |
| 9542 | Bu—F | 2-I | 2 |
| 9543 | Bu—F | 3-I | 2 |
| 9544 | Bu—F | 4-I | 2 |
| 9545 | Bu—F | 2-SnMe₃ | 2 |
| 9546 | Bu—F | 3-SnMe₃ | 2 |
| 9547 | Bu—F | 4-SnMe₃ | 2 |
| 9548 | Bu—F | 2-Me | 2 |
| 9549 | Bu—F | 3-Me | 2 |
| 9550 | Bu—F | 4-Me | 2 |
| 9551 | Bu—F | 2-OH | 2 |
| 9552 | Bu—F | 3-OH | 2 |
| 9553 | Bu—F | 4-OH | 2 |
| 9554 | Bu—F | 2-OMe | 2 |
| 9555 | Bu—F | 3-OMe | 2 |
| 9556 | Bu—F | 4-OMe | 2 |
| 9557 | Bu—F | 2-OMeF | 2 |
| 9558 | Bu—F | 3-OMeF | 2 |
| 9559 | Bu—F | 4-OMeF | 2 |
| 9560 | Bu—F | 2-OCF₃ | 2 |
| 9561 | Bu—F | 3-OCF₃ | 2 |
| 9562 | Bu—F | 4-OCF₃ | 2 |
| 9563 | Bu—F | 2-OEtF | 2 |
| 9564 | Bu—F | 3-OEtF | 2 |
| 9565 | Bu—F | 4-OEtF | 2 |
| 9566 | Bu—F | 2-OPrF | 2 |
| 9567 | Bu—F | 3-OPrF | 2 |

TABLE 9-continued

Substituent list for compounds of general structure XIV.

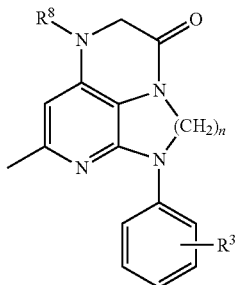

| Compound # | R⁸ = | R³ = | n = |
|---|---|---|---|
| 9568 | Bu—F | 4-OPrF | 2 |
| 9569 | Bu—F | 2-SH | 2 |
| 9570 | Bu—F | 3-SH | 2 |
| 9571 | Bu—F | 4-SH | 2 |
| 9572 | Bu—F | 2-SMe | 2 |
| 9573 | Bu—F | 3-SMe | 2 |
| 9574 | Bu—F | 4-SMe | 2 |
| 9575 | Bu—F | 2-SMeF | 2 |
| 9576 | Bu—F | 3-SMeF | 2 |
| 9577 | Bu—F | 4-SMeF | 2 |
| 9578 | Bu—F | 2-SCF$_3$ | 2 |
| 9579 | Bu—F | 3-SCF$_3$ | 2 |
| 9580 | Bu—F | 4-SCF$_3$ | 2 |
| 9581 | Bu—F | 2-SEtF | 2 |
| 9582 | Bu—F | 3-SEtF | 2 |
| 9583 | Bu—F | 4-SEtF | 2 |
| 9584 | Bu—F | 2-SPrF | 2 |
| 9585 | Bu—F | 3-SPrF | 2 |
| 9586 | Bu—F | 4-SPrF | 2 |
| 9587 | Bu—F | 2-OMe, 4-OMe | 2 |
| 9588 | Bu—F | 2-Me, 5-OH | 2 |
| 9589 | Bu—F | 2-Me, 5-OMe | 2 |
| 9590 | Bu—F | 2-Me, 5-OMeF | 2 |
| 9591 | Bu—F | 2-Me, 5-OEtF | 2 |
| 9592 | Bu—F | 2-Me, 5-OPrF | 2 |
| 9593 | Bu—F | 2-Me, 4-OH | 2 |
| 9594 | Bu—F | 2-Me, 4-OMe | 2 |
| 9595 | Bu—F | 2-Me, 4-OMeF | 2 |
| 9596 | Bu—F | 2-Me, 4-OCF$_3$ | 2 |
| 9597 | Bu—F | 2-Me, 4-OEtF | 2 |
| 9598 | Bu—F | 2-Me, 4-OPrF | 2 |
| 9599 | Bu—F | 2-OH, 4-Me | 2 |
| 9600 | Bu—F | 2-OMe, 4-Me | 2 |
| 9601 | Bu—F | 2-OMeF, 4-Me | 2 |
| 9602 | Bu—F | 2-OCF$_3$, 4-Me | 2 |
| 9603 | Bu—F | 2-OEtF, 4-Me | 2 |
| 9604 | Bu—F | 2-OPrF, 4-Me | 2 |
| 9605 | Bu—F | 2-Cl, 4-OH | 2 |
| 9606 | Bu—F | 2-Cl, 4-OMe | 2 |
| 9607 | Bu—F | 2-Cl, 4-OMeF | 2 |
| 9608 | Bu—F | 2-Cl, 4-OCF$_3$ | 2 |
| 9609 | Bu—F | 2-Cl, 4-OEtF | 2 |
| 9610 | Bu—F | 2-Cl, 4-OPrF | 2 |
| 9611 | Bu—F | 2-F, 4-F | 2 |
| 9612 | Bu—F | 2-Cl, 4-Cl | 2 |
| 9613 | Bu—F | 2-Cl, 4-F | 2 |
| 9614 | Bu—F | 2-Cl, 4-NO$_2$ | 2 |
| 9615 | Bu—F | 2-Cl, 4-NH$_2$ | 2 |
| 9616 | Bu—F | 2-Cl, 4-NHMe | 2 |
| 9617 | Bu—F | 2-Cl, 4-NMe$_2$ | 2 |
| 9618 | Bu—F | 2-Cl, 4-NMe$_3$OTf | 2 |
| 9619 | Bu—F | 2-Cl, 4-NMe$_3$I | 2 |
| 9620 | Bu—F | 2-Cl, 5-F | 2 |
| 9621 | Bu—F | 2-Cl, 5-NO$_2$ | 2 |
| 9622 | Bu—F | 2-Cl, 5-NH$_2$ | 2 |
| 9623 | Bu—F | 2-Cl, 5-NHMe | 2 |
| 9624 | Bu—F | 2-Cl, 5-NMe$_2$ | 2 |
| 9625 | Bu—F | 2-Cl, 5-NMe$_3$OTf | 2 |
| 9626 | Bu—F | 2-Cl, 5-NMe$_3$I | 2 |
| 9627 | Bu—F | 2-F, 4-Cl | 2 |
| 9628 | Bu—F | 2-NO$_2$, 4-Cl | 2 |
| 9629 | Bu—F | 2-NH$_2$, 4-Cl | 2 |
| 9630 | Bu—F | 2-NHMe, 4-Cl | 2 |
| 9631 | Bu—F | 2-NMe$_2$, 4-Cl | 2 |
| 9632 | Bu—F | 2-NMe$_3$OTf, 4-Cl | 2 |
| 9633 | Bu—F | 2-NMe$_3$I, 4-Cl | 2 |
| 9634 | Bu—F | 2-F, 5-Cl | 2 |
| 9635 | Bu—F | 2-NO$_2$, 5-Cl | 2 |
| 9636 | Bu—F | 2-NH$_2$, 5-Cl | 2 |
| 9637 | Bu—F | 2-NHMe, 5-Cl | 2 |
| 9638 | Bu—F | 2-NMe$_2$, 5-Cl | 2 |
| 9639 | Bu—F | 2-NMe$_3$OTf, 5-Cl | 2 |
| 9640 | Bu—F | 2-NMe$_3$I, 5-Cl | 2 |
| 9641 | Bu—F | 2-Br, 4-F | 2 |
| 9642 | Bu—F | 2-Br, 4-NO$_2$ | 2 |
| 9643 | Bu—F | 2-Br, 4-NH$_2$ | 2 |
| 9644 | Bu—F | 2-Br, 4-NHMe | 2 |
| 9645 | Bu—F | 2-Br, 4-NMe$_2$ | 2 |
| 9646 | Bu—F | 2-Br, 4-NMe$_3$OTf | 2 |
| 9647 | Bu—F | 2-Br, 4-NMe$_3$I | 2 |
| 9648 | Bu—F | 2-Br, 5-F | 2 |
| 9649 | Bu—F | 2-Br, 5-NO$_2$ | 2 |
| 9650 | Bu—F | 2-Br, 5-NH$_2$ | 2 |
| 9651 | Bu—F | 2-Br, 5-NHMe | 2 |
| 9652 | Bu—F | 2-Br, 5-NMe$_2$ | 2 |
| 9653 | Bu—F | 2-Br, 5-NMe$_3$OTf | 2 |
| 9654 | Bu—F | 2-Br, 5-NMe$_3$I | 2 |
| 9655 | Bu—F | 2-F, 4-Br | 2 |
| 9656 | Bu—F | 2-NO$_2$, 4-Br | 2 |
| 9657 | Bu—F | 2-NH$_2$, 4-Br | 2 |
| 9658 | Bu—F | 2-NHMe, 4-Br | 2 |
| 9659 | Bu—F | 2-NMe$_2$, 4-Br | 2 |
| 9660 | Bu—F | 2-NMe$_3$OTf, 4-Br | 2 |
| 9661 | Bu—F | 2-NMe$_3$I, 4-Br | 2 |
| 9662 | Bu—F | 2-I, 4-F | 2 |
| 9663 | Bu—F | 2-I, 4-NO$_2$ | 2 |
| 9664 | Bu—F | 2-I, 4-NH$_2$ | 2 |
| 9665 | Bu—F | 2-I, 4-NHMe | 2 |
| 9666 | Bu—F | 2-I, 4-NMe$_2$ | 2 |
| 9667 | Bu—F | 2-I, 4-NMe$_3$OTf | 2 |
| 9668 | Bu—F | 2-I, 4-NMe$_3$I | 2 |
| 9669 | Bu—F | 2-F, 4-I | 2 |
| 9670 | Bu—F | 2-NO$_2$, 4-I | 2 |
| 9671 | Bu—F | 2-NH$_2$, 4-I | 2 |
| 9672 | Bu—F | 2-NHMe, 4-I | 2 |
| 9673 | Bu—F | 2-NMe$_2$, 4-I | 2 |
| 9674 | Bu—F | 2-NMe$_3$OTf, 4-I | 2 |
| 9675 | Bu—F | 2-NMe$_3$I, 4-I | 2 |
| 9676 | Bu—F | 2-Me, 3-F | 2 |
| 9677 | Bu—F | 2-Me, 3-NO$_2$ | 2 |
| 9678 | Bu—F | 2-Me, 3-NH$_2$ | 2 |
| 9679 | Bu—F | 2-Me, 3-NHMe | 2 |
| 9680 | Bu—F | 2-Me, 3-NMe$_2$ | 2 |
| 9681 | Bu—F | 2-Me, 3-NMe$_3$OTf | 2 |
| 9682 | Bu—F | 2-Me, 3-NMe$_3$I | 2 |
| 9683 | Bu—F | 2-Me, 4-F | 2 |
| 9684 | Bu—F | 2-Me, 4-NO$_2$ | 2 |
| 9685 | Bu—F | 2-Me, 4-NH$_2$ | 2 |
| 9686 | Bu—F | 2-Me, 4-NHMe | 2 |
| 9687 | Bu—F | 2-Me, 4-NMe$_2$ | 2 |

TABLE 9-continued

Substituent list for compounds of general structure XIV.

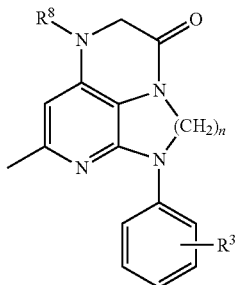

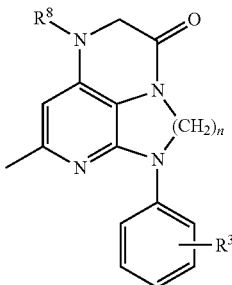

| Compound # | R[8] = | R[3] = | n = |
|---|---|---|---|
| 9688 | Bu—F | 2-Me, 4-NMe₃OTf | 2 |
| 9689 | Bu—F | 2-Me, 4-NMe₃I | 2 |
| 9690 | Bu—F | 2-Me, 5-F | 2 |
| 9691 | Bu—F | 2-Me, 5-NO₂ | 2 |
| 9692 | Bu—F | 2-Me, 5-NH₂ | 2 |
| 9693 | Bu—F | 2-Me, 5-NHMe | 2 |
| 9694 | Bu—F | 2-Me, 5-NMe₂ | 2 |
| 9695 | Bu—F | 2-Me, 5-NMe₃OTf | 2 |
| 9696 | Bu—F | 2-Me, 5-NMe₃I | 2 |
| 9697 | Bu—F | 2-F, 4-Me | 2 |
| 9698 | Bu—F | 2-NO₂, 4-Me | 2 |
| 9699 | Bu—F | 2-NH₂, 4-Me | 2 |
| 9700 | Bu—F | 2-NHMe, 4-Me | 2 |
| 9701 | Bu—F | 2-NMe₂, 4-Me | 2 |
| 9702 | Bu—F | 2-NMe₃, 4-Me | 2 |
| 9703 | Bu—F | 2-NMe₃OTf, 4-Me | 2 |
| 9704 | Bu—F | 2-NMe₃I, 4-Me | 2 |
| 9705 | Bu—F | 2-SnMe₃, 4-F | 2 |
| 9706 | Bu—F | 2-SnMe₃, 5-F | 2 |
| 9707 | Bu—F | 2-F, 4-SnMe₃ | 2 |
| 9708 | Bu—F | 2-Br, 6-Cl, 4-F | 2 |
| 9709 | Bu—F | 2-Br, 6-Cl, 4-NO₂ | 2 |
| 9710 | Bu—F | 2-Br, 6-Cl, 4-NH₂ | 2 |
| 9711 | Bu—F | 2-Br, 6-Cl, 4-NHMe | 2 |
| 9712 | Bu—F | 2-Br, 6-Cl, 4-NMe₂ | 2 |
| 9713 | Bu—F | 2-Br, 6-Cl, 4-NMe₃OTf | 2 |
| 9714 | Bu—F | 2-Br, 6-Cl, 4-NMe₃I | 2 |
| 9715 | Bu—F | 2-Me, 6-Cl, 4-F | 2 |
| 9716 | Bu—F | 2-SnMe₃, 6-Cl, 4-F | 2 |
| 9717 | Bu—F | 2-Cl, 4-Me | 2 |
| 9718 | Bu—F | 2-Cl, 4-Br | 2 |
| 9719 | Bu—F | 2-Cl, 4-SnMe₃ | 2 |
| 9720 | Bu—F | 2-Br, 4-Cl | 2 |
| 9721 | Bu—F | 2-SnMe₃, 4-Cl | 2 |
| 9722 | Bu—F | 2-Me, 4-Cl | 2 |
| 9723 | Bu—F | 2-Br, 4-Br | 2 |
| 9724 | Bu—F | 2-Br, 4-Me | 2 |
| 9725 | Bu—F | 2-Br, 4-SnMe₃ | 2 |
| 9726 | Bu—F | 2-SnMe₃, 4-Br | 2 |
| 9727 | Bu—F | 2-Me, 4-Br | 2 |
| 9728 | Bu—F | 2-Me, 4-SnMe₃ | 2 |
| 9729 | Bu—F | 2-SnMe₃, 4-Me | 2 |
| 9730 | Bu—F | 2-Me, 4-Me | 2 |
| 9731 | Bu—F | 2-Et, 4-Br | 2 |
| 9732 | Bu—F | 2-Et, 4-SnMe₃ | 2 |
| 9733 | Bu—F | 2-Et, 4-Me | 2 |
| 9734 | Bu—F | 2-Me, 4-Me, 6-Me | 2 |
| 9735 | Bu—F | 2-Me, 4-Br, 6-Me | 2 |
| 9736 | Bu—F | 2-Me, 4-SnMe₃, 6-Me | 2 |
| 9737 | Bu—F | 2-Et, 6-Me | 2 |
| 9738 | Bu—F | 2-Br, 4-i-Pr | 2 |
| 9739 | Bu—F | 2-SnMe₃, 4-i-Pr | 2 |
| 9740 | Bu—F | 2-Me, 4-i-Pr | 2 |
| 9741 | Bu—F | 2-Br, 4-Br, 6-Br | 2 |
| 9742 | Bu—F | 2-Br, 4-Me, 6-Br | 2 |
| 9743 | Bu—F | 2-Br, 4-SnMe₃, 6-Br | 2 |
| 9744 | Bu—F | 2-SnMe₃, 4-Br, 6-Br | 2 |
| 9745 | Bu—F | 2-Br, 4-Br, 6-Me | 2 |
| 9746 | Bu—F | 2-Br, 4-CF₃, 6-Br | 2 |
| 9747 | Bu—F | 2-Br, 4-Br, 6-CF₃ | 2 |
| 9748 | Bu—F | 2-CF₃, 4-CF₃ | 2 |
| 9749 | Bu—F | 2-Cl, 4-CF₃ | 2 |
| 9750 | Bu—F | 2-CF₃, 4-Cl | 2 |
| 9751 | Bu—F | 2-Br, 4-CF₃ | 2 |
| 9752 | Bu—F | 2-SnMe₃, 4-CF₃ | 2 |
| 9753 | Bu—F | 2-Me, 4-CF₃ | 2 |
| 9754 | Bu—F | 2-CF₃, 4-Br | 2 |
| 9755 | Bu—F | 2-CF₃, 4-SnMe₃ | 2 |
| 9756 | Bu—F | 2-CF₃, 4-Me | 2 |
| 9757 | Bu—F | 2-Br, 4-OH | 2 |
| 9758 | Bu—F | 2-Br, 4-OMe | 2 |
| 9759 | Bu—F | 2-Br, 4-OMeF | 2 |
| 9760 | Bu—F | 2-Br, 4-OCF₃ | 2 |
| 9761 | Bu—F | 2-Br, 4-OEtF | 2 |
| 9762 | Bu—F | 2-Br, 4-OPrF | 2 |
| 9763 | Bu—F | 2-OH, 4-Br | 2 |
| 9764 | Bu—F | 2-OMe, 4-Br | 2 |
| 9765 | Bu—F | 2-OMeF, 4-Br | 2 |
| 9766 | Bu—F | 2-OCF₃, 4-Br | 2 |
| 9767 | Bu—F | 2-OEtF, 4-Br | 2 |
| 9768 | Bu—F | 2-OPrF, 4-Br | 2 |
| 9769 | Bu—F | 2-I, 4-OH | 2 |
| 9770 | Bu—F | 2-I, 4-OMe | 2 |
| 9771 | Bu—F | 2-I, 4-OMeF | 2 |
| 9772 | Bu—F | 2-I, 4-OCF₃ | 2 |
| 9773 | Bu—F | 2-I, 4-OEtF | 2 |
| 9774 | Bu—F | 2-I, 4-OPrF | 2 |
| 9775 | Bu—F | 2-OH, 4-I | 2 |
| 9776 | Bu—F | 2-OMe, 4-I, | 2 |
| 9777 | Bu—F | 2-OMeF, 4-I | 2 |
| 9778 | Bu—F | 2-OCF₃, 4-I | 2 |
| 9779 | Bu—F | 2-OEtF, 4-I | 2 |
| 9780 | Bu—F | 2-OPrF, 4-I | 2 |
| 9781 | Bu—F | 2-SnMe₃, 4-OH | 2 |
| 9782 | Bu—F | 2-SnMe₃, 4-OMe | 2 |
| 9783 | Bu—F | 2-SnMe₃, 4-OMeF | 2 |
| 9784 | Bu—F | 2-SnMe₃, 4-OCF₃ | 2 |
| 9785 | Bu—F | 2-SnMe₃, 4-OEtF | 2 |
| 9786 | Bu—F | 2-SnMe₃, 4-OPrF | 2 |
| 9787 | Bu—F | 2-OH, 4-SnMe₃ | 2 |
| 9788 | Bu—F | 2-OMe, 4-SnMe₃ | 2 |
| 9789 | Bu—F | 2-OMeF, 4-SnMe₃ | 2 |
| 9790 | Bu—F | 2-OCF₃, 4-SnMe₃ | 2 |
| 9791 | Bu—F | 2-OEtF, 4-SnMe₃ | 2 |
| 9792 | Bu—F | 2-OPrF, 4-SnMe₃ | 2 |
| 9793 | Pr | H | 1 |
| 9794 | Pr | 2-t-Bu | 1 |
| 9795 | Pr | 2-Br | 1 |
| 9796 | Pr | 3-Br | 1 |
| 9797 | Pr | 4-Br | 1 |
| 9798 | Pr | 2-I | 1 |
| 9799 | Pr | 3-I | 1 |
| 9800 | Pr | 4-I | 1 |
| 9801 | Pr | 2-SnMe₃ | 1 |
| 9802 | Pr | 3-SnMe₃ | 1 |
| 9803 | Pr | 4-SnMe₃ | 1 |
| 9804 | Pr | 2-Me | 1 |
| 9805 | Pr | 3-Me | 1 |
| 9806 | Pr | 4-Me | 1 |
| 9807 | Pr | 2-OH | 1 |

TABLE 9-continued

Substituent list for compounds of general structure XIV.

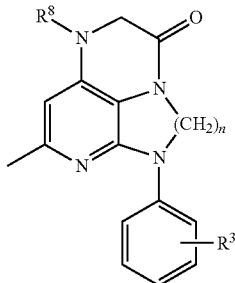

| Compound # | R⁸ = | R³ = | n = |
|---|---|---|---|
| 9808 | Pr | 3-OH | 1 |
| 9809 | Pr | 4-OH | 1 |
| 9810 | Pr | 2-OMe | 1 |
| 9811 | Pr | 3-OMe | 1 |
| 9812 | Pr | 4-OMe | 1 |
| 9813 | Pr | 2-OMeF | 1 |
| 9814 | Pr | 3-OMeF | 1 |
| 9815 | Pr | 4-OMeF | 1 |
| 9816 | Pr | 2-OCF$_3$ | 1 |
| 9817 | Pr | 3-OCF$_3$ | 1 |
| 9818 | Pr | 4-OCF$_3$ | 1 |
| 9819 | Pr | 2-OEtF | 1 |
| 9820 | Pr | 3-OEtF | 1 |
| 9821 | Pr | 4-OEtF | 1 |
| 9822 | Pr | 2-OPrF | 1 |
| 9823 | Pr | 3-OPrF | 1 |
| 9824 | Pr | 4-OPrF | 1 |
| 9825 | Pr | 2-SH | 1 |
| 9826 | Pr | 3-SH | 1 |
| 9827 | Pr | 4-SH | 1 |
| 9828 | Pr | 2-SMe | 1 |
| 9829 | Pr | 3-SMe | 1 |
| 9830 | Pr | 4-SMe | 1 |
| 9831 | Pr | 2-SMeF | 1 |
| 9832 | Pr | 3-SMeF | 1 |
| 9833 | Pr | 4-SMeF | 1 |
| 9834 | Pr | 2-SCF$_3$ | 1 |
| 9835 | Pr | 3-SCF$_3$ | 1 |
| 9836 | Pr | 4-SCF$_3$ | 1 |
| 9837 | Pr | 2-SEtF | 1 |
| 9838 | Pr | 3-SEtF | 1 |
| 9839 | Pr | 4-SEtF | 1 |
| 9840 | Pr | 2-SPrF | 1 |
| 9841 | Pr | 3-SPrF | 1 |
| 9842 | Pr | 4-SPrF | 1 |
| 9843 | Pr | 2-OMe, 4-OMe | 1 |
| 9844 | Pr | 2-Me, 5-OH | 1 |
| 9845 | Pr | 2-Me, 5-OMe | 1 |
| 9846 | Pr | 2-Me, 5-OMeF | 1 |
| 9847 | Pr | 2-Me, 5-OEtF | 1 |
| 9848 | Pr | 2-Me, 5-OPrF | 1 |
| 9849 | Pr | 2-Me, 4-OH | 1 |
| 9850 | Pr | 2-Me, 4-OMe | 1 |
| 9851 | Pr | 2-Me, 4-OMeF | 1 |
| 9852 | Pr | 2-Me, 4-OCF$_3$ | 1 |
| 9853 | Pr | 2-Me, 4-OEtF | 1 |
| 9854 | Pr | 2-Me, 4-OPrF | 1 |
| 9855 | Pr | 2-OH, 4-Me | 1 |
| 9856 | Pr | 2-OMe, 4-Me | 1 |
| 9857 | Pr | 2-OMeF, 4-Me | 1 |
| 9858 | Pr | 2-OCF$_3$, 4-Me | 1 |
| 9859 | Pr | 2-OEtF, 4-Me | 1 |
| 9860 | Pr | 2-OPrF, 4-Me | 1 |
| 9861 | Pr | 2-Cl, 4-OH | 1 |
| 9862 | Pr | 2-Cl, 4-OMe | 1 |
| 9863 | Pr | 2-Cl, 4-OMeF | 1 |
| 9864 | Pr | 2-Cl, 4-OCF$_3$ | 1 |
| 9865 | Pr | 2-Cl, 4-OEtF | 1 |
| 9866 | Pr | 2-Cl, 4-OPrF | 1 |
| 9867 | Pr | 2-F, 4-F | 1 |

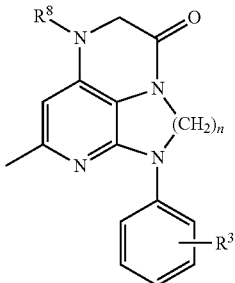

| Compound # | R⁸ = | R³ = | n = |
|---|---|---|---|
| 9868 | Pr | 2-Cl, 4-Cl | 1 |
| 9869 | Pr | 2-Cl, 4-F | 1 |
| 9870 | Pr | 2-Cl, 4-NO$_2$ | 1 |
| 9871 | Pr | 2-Cl, 4-NH$_2$ | 1 |
| 9872 | Pr | 2-Cl, 4-NHMe | 1 |
| 9873 | Pr | 2-Cl, 4-NMe$_2$ | 1 |
| 9874 | Pr | 2-Cl, 4-NMe$_3$OTf | 1 |
| 9875 | Pr | 2-Cl, 4-NMe$_3$I | 1 |
| 9876 | Pr | 2-Cl, 5-F | 1 |
| 9877 | Pr | 2-Cl, 5-NO$_2$ | 1 |
| 9878 | Pr | 2-Cl, 5-NH$_2$ | 1 |
| 9879 | Pr | 2-Cl, 5-NHMe | 1 |
| 9880 | Pr | 2-Cl, 5-NMe$_2$ | 1 |
| 9881 | Pr | 2-Cl, 5-NMe$_3$OTf | 1 |
| 9882 | Pr | 2-Cl, 5-NMe$_3$I | 1 |
| 9883 | Pr | 2-F, 4-Cl | 1 |
| 9884 | Pr | 2-NO$_2$, 4-Cl | 1 |
| 9885 | Pr | 2-NH$_2$, 4-Cl | 1 |
| 9886 | Pr | 2-NHMe, 4-Cl | 1 |
| 9887 | Pr | 2-NMe$_2$, 4-Cl | 1 |
| 9888 | Pr | 2-NMe$_3$OTf, 4-Cl | 1 |
| 9889 | Pr | 2-NMe$_3$I, 4-Cl | 1 |
| 9890 | Pr | 2-F, 5-Cl | 1 |
| 9891 | Pr | 2-NO$_2$, 5-Cl | 1 |
| 9892 | Pr | 2-NH$_2$, 5-Cl | 1 |
| 9893 | Pr | 2-NHMe, 5-Cl | 1 |
| 9894 | Pr | 2-NMe$_2$, 5-Cl | 1 |
| 9895 | Pr | 2-NMe$_3$OTf, 5-Cl | 1 |
| 9896 | Pr | 2-NMe$_3$I, 5-Cl | 1 |
| 9897 | Pr | 2-Br, 4-F | 1 |
| 9898 | Pr | 2-Br, 4-NO$_2$ | 1 |
| 9899 | Pr | 2-Br, 4-NH$_2$ | 1 |
| 9900 | Pr | 2-Br, 4-NHMe | 1 |
| 9901 | Pr | 2-Br, 4-NMe$_2$ | 1 |
| 9902 | Pr | 2-Br, 4-NMe$_3$OTf | 1 |
| 9903 | Pr | 2-Br, 4-NMe$_3$I | 1 |
| 9904 | Pr | 2-Br, 5-F | 1 |
| 9905 | Pr | 2-Br, 5-NO$_2$ | 1 |
| 9906 | Pr | 2-Br, 5-NH$_2$ | 1 |
| 9907 | Pr | 2-Br, 5-NHMe | 1 |
| 9908 | Pr | 2-Br, 5-NMe$_2$ | 1 |
| 9909 | Pr | 2-Br, 5-NMe$_3$OTf | 1 |
| 9910 | Pr | 2-Br, 5-NMe$_3$I | 1 |
| 9911 | Pr | 2-F, 4-Br | 1 |
| 9912 | Pr | 2-NO$_2$, 4-Br | 1 |
| 9913 | Pr | 2-NH$_2$, 4-Br | 1 |
| 9914 | Pr | 2-NHMe, 4-Br | 1 |
| 9915 | Pr | 2-NMe$_2$, 4-Br | 1 |
| 9916 | Pr | 2-NMe$_3$OTf, 4-Br | 1 |
| 9917 | Pr | 2-NMe$_3$I, 4-Br | 1 |
| 9918 | Pr | 2-I, 4-F | 1 |
| 9919 | Pr | 2-I, 4-NO$_2$ | 1 |
| 9920 | Pr | 2-I, 4-NH$_2$ | 1 |
| 9921 | Pr | 2-I, 4-NHMe | 1 |
| 9922 | Pr | 2-I, 4-NMe$_2$ | 1 |
| 9923 | Pr | 2-I, 4-NMe$_3$OTf | 1 |
| 9924 | Pr | 2-I, 4-NMe$_3$I | 1 |
| 9925 | Pr | 2-F, 4-I | 1 |
| 9926 | Pr | 2-NO$_2$, 4-I | 1 |
| 9927 | Pr | 2-NH$_2$, 4-I | 1 |

TABLE 9-continued

Substituent list for compounds of general structure XIV.

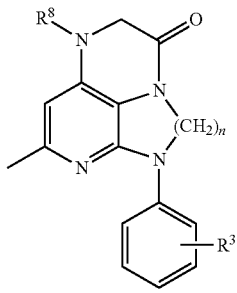

XIV

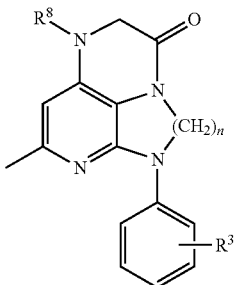

XIV

| Compound # | R⁸ = | R³ = | n = | Compound # | R⁸ = | R³ = | n = |
|---|---|---|---|---|---|---|---|
| 9928 | Pr | 2-NHMe, 4-I | 1 | 9988 | Pr | 2-Et, 4-SnMe₃ | 1 |
| 9929 | Pr | 2-NMe₂, 4-I | 1 | 9989 | Pr | 2-Et, 4-Me | 1 |
| 9930 | Pr | 2-NMe₃OTf, 4-I | 1 | 9990 | Pr | 2-Me, 4-Me, 6-Me | 1 |
| 9931 | Pr | 2-NMe₃I, 4-I | 1 | 9991 | Pr | 2-Me, 4-Br, 6-Me | 1 |
| 9932 | Pr | 2-Me, 3-F | 1 | 9992 | Pr | 2-Me, 4-SnMe₃, 6-Me | 1 |
| 9933 | Pr | 2-Me, 3-NO₂ | 1 | 9993 | Pr | 2-Et, 6-Me | 1 |
| 9934 | Pr | 2-Me, 3-NH₂ | 1 | 9994 | Pr | 2-Br, 4-i-Pr | 1 |
| 9935 | Pr | 2-Me, 3-NHMe | 1 | 9995 | Pr | 2-SnMe₃, 4-i-Pr | 1 |
| 9936 | Pr | 2-Me, 3-NMe₂ | 1 | 9996 | Pr | 2-Me, 4-i-Pr | 1 |
| 9937 | Pr | 2-Me, 3-NMe₃OTf | 1 | 9997 | Pr | 2-Br, 4-Br, 6-Br | 1 |
| 9938 | Pr | 2-Me, 3-NMe₃I | 1 | 9998 | Pr | 2-Br, 4-Me, 6-Br | 1 |
| 9939 | Pr | 2-Me, 4-F | 1 | 9999 | Pr | 2-Br, 4-SnMe₃, 6-Br | 1 |
| 9940 | Pr | 2-Me, 4-NO₂ | 1 | 10000 | Pr | 2-SnMe₃, 4-Br, 6-Br | 1 |
| 9941 | Pr | 2-Me, 4-NH₂ | 1 | 10001 | Pr | 2-Br, 4-Br, 6-Me | 1 |
| 9942 | Pr | 2-Me, 4-NHMe | 1 | 10002 | Pr | 2-Br, 4-CF₃, 6-Br | 1 |
| 9943 | Pr | 2-Me, 4-NMe₂ | 1 | 10003 | Pr | 2-Br, 4-Br, 6-CF₃ | 1 |
| 9944 | Pr | 2-Me, 4-NMe₃OTf | 1 | 10004 | Pr | 2-CF₃, 4-CF₃ | 1 |
| 9945 | Pr | 2-Me, 4-NMe₃I | 1 | 10005 | Pr | 2-Cl, 4-CF₃ | 1 |
| 9946 | Pr | 2-Me, 5-F | 1 | 10006 | Pr | 2-CF₃, 4-Cl | 1 |
| 9947 | Pr | 2-Me, 5-NO₂ | 1 | 10007 | Pr | 2-Br, 4-CF₃ | 1 |
| 9948 | Pr | 2-Me, 5-NH₂ | 1 | 10008 | Pr | 2-SnMe₃, 4-CF₃ | 1 |
| 9949 | Pr | 2-Me, 5-NHMe | 1 | 10009 | Pr | 2-Me, 4-CF₃ | 1 |
| 9950 | Pr | 2-Me, 5-NMe₂ | 1 | 10010 | Pr | 2-CF₃, 4-Br | 1 |
| 9951 | Pr | 2-Me, 5-NMe₃OTf | 1 | 10011 | Pr | 2-CF₃, 4-SnMe₃ | 1 |
| 9952 | Pr | 2-Me, 5-NMe₃I | 1 | 10012 | Pr | 2-CF₃, 4-Me | 1 |
| 9953 | Pr | 2-F, 4-Me | 1 | 10013 | Pr | 2-Br, 4-OH | 1 |
| 9954 | Pr | 2-NO₂, 4-Me | 1 | 10014 | Pr | 2-Br, 4-OMe | 1 |
| 9955 | Pr | 2-NH₂, 4-Me | 1 | 10015 | Pr | 2-Br, 4-OMeF | 1 |
| 9956 | Pr | 2-NHMe, 4-Me | 1 | 10016 | Pr | 2-Br, 4-OCF₃ | 1 |
| 9957 | Pr | 2-NMe₂, 4-Me | 1 | 10017 | Pr | 2-Br, 4-OEtF | 1 |
| 9958 | Pr | 2-NMe₃, 4-Me | 1 | 10018 | Pr | 2-Br, 4-OPrF | 1 |
| 9959 | Pr | 2-NMe₃OTf, 4-Me | 1 | 10019 | Pr | 2-OH, 4-Br | 1 |
| 9960 | Pr | 2-NMe₃I, 4-Me | 1 | 10020 | Pr | 2-OMe, 4-Br | 1 |
| 9961 | Pr | 2-SnMe₃, 4-F | 1 | 10021 | Pr | 2-OMeF, 4-Br | 1 |
| 9962 | Pr | 2-SnMe₃, 5-F | 1 | 10022 | Pr | 2-OCF₃, 4-Br | 1 |
| 9963 | Pr | 2-F, 4-SnMe₃ | 1 | 10023 | Pr | 2-OEtF, 4-Br | 1 |
| 9964 | Pr | 2-Br, 6-Cl, 4-F | 1 | 10024 | Pr | 2-OPrF, 4-Br | 1 |
| 9965 | Pr | 2-Br, 6-Cl, 4-NO₂ | 1 | 10025 | Pr | 2-I, 4-OH | 1 |
| 9966 | Pr | 2-Br, 6-Cl, 4-NH₂ | 1 | 10026 | Pr | 2-I, 4-OMe | 1 |
| 9967 | Pr | 2-Br, 6-Cl, 4-NHMe | 1 | 10027 | Pr | 2-I, 4-OMeF | 1 |
| 9968 | Pr | 2-Br, 6-Cl, 4-NMe₂ | 1 | 10028 | Pr | 2-I, 4-OCF₃ | 1 |
| 9969 | Pr | 2-Br, 6-Cl, 4-NMe₃OTf | 1 | 10029 | Pr | 2-I, 4-OEtF | 1 |
| 9970 | Pr | 2-Br, 6-Cl, 4-NMe₃I | 1 | 10030 | Pr | 2-I, 4-OPrF | 1 |
| 9971 | Pr | 2-Me, 6-Cl, 4-F | 1 | 10031 | Pr | 2-OH, 4-I | 1 |
| 9972 | Pr | 2-SnMe₃, 6-Cl, 4-F | 1 | 10032 | Pr | 2-OMe, 4-I | 1 |
| 9973 | Pr | 2-Cl, 4-Me | 1 | 10033 | Pr | 2-OMeF, 4-I | 1 |
| 9974 | Pr | 2-Cl, 4-Br | 1 | 10034 | Pr | 2-OCF₃, 4-I | 1 |
| 9975 | Pr | 2-Cl, 4-SnMe₃ | 1 | 10035 | Pr | 2-OEtF, 4-I | 1 |
| 9976 | Pr | 2-Br, 4-Cl | 1 | 10036 | Pr | 2-OPrF, 4-I | 1 |
| 9977 | Pr | 2-SnMe₃, 4-Cl | 1 | 10037 | Pr | 2-SnMe₃, 4-OH | 1 |
| 9978 | Pr | 2-Me, 4-Cl | 1 | 10038 | Pr | 2-SnMe₃, 4-OMe | 1 |
| 9979 | Pr | 2-Br, 4-Br | 1 | 10039 | Pr | 2-SnMe₃, 4-OMeF | 1 |
| 9980 | Pr | 2-Br, 4-Me | 1 | 10040 | Pr | 2-SnMe₃, 4-OCF₃ | 1 |
| 9981 | Pr | 2-Br, 4-SnMe₃ | 1 | 10041 | Pr | 2-SnMe₃, 4-OEtF | 1 |
| 9982 | Pr | 2-SnMe₃, 4-Br | 1 | 10042 | Pr | 2-SnMe₃, 4-OPrF | 1 |
| 9983 | Pr | 2-Me, 4-Br | 1 | 10043 | Pr | 2-OH, 4-SnMe₃ | 1 |
| 9984 | Pr | 2-Me, 4-SnMe₃ | 1 | 10044 | Pr | 2-OMe, 4-SnMe₃ | 1 |
| 9985 | Pr | 2-SnMe₃, 4-Me | 1 | 10045 | Pr | 2-OMeF, 4-SnMe₃ | 1 |
| 9986 | Pr | 2-Me, 4-Me | 1 | 10046 | Pr | 2-OCF₃, 4-SnMe₃ | 1 |
| 9987 | Pr | 2-Et, 4-Br | 1 | 10047 | Pr | 2-OEtF, 4-SnMe₃ | 1 |

TABLE 9-continued

Substituent list for compounds of general structure XIV.

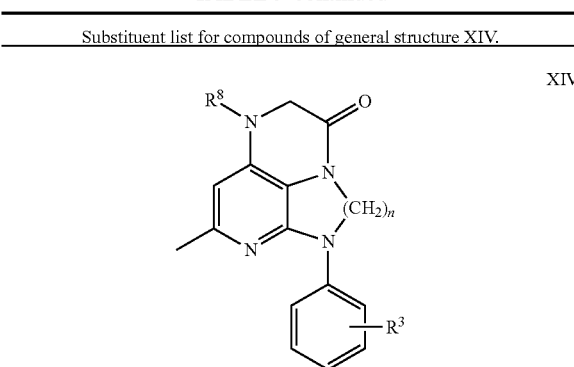

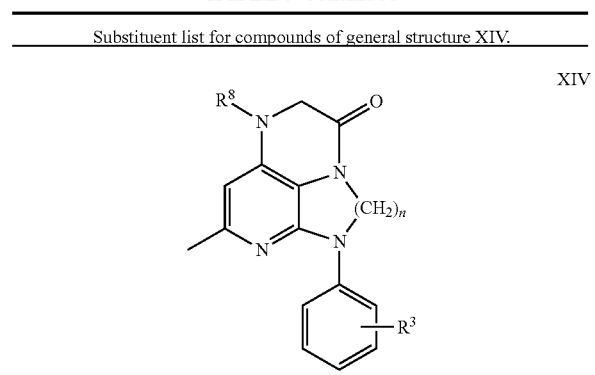

| Compound # | $R^8$ = | $R^3$ = | n = |
|---|---|---|---|
| 10048 | Pr | 2-OPrF, 4-SnMe$_3$ | 1 |
| 10049 | Pr | H | 2 |
| 10050 | Pr | 2-t-Bu | 2 |
| 10051 | Pr | 2-Br | 2 |
| 10052 | Pr | 3-Br | 2 |
| 10053 | Pr | 4-Br | 2 |
| 10054 | Pr | 2-I | 2 |
| 10055 | Pr | 3-I | 2 |
| 10056 | Pr | 4-I | 2 |
| 10057 | Pr | 2-SnMe$_3$ | 2 |
| 10058 | Pr | 3-SnMe$_3$ | 2 |
| 10059 | Pr | 4-SnMe$_3$ | 2 |
| 10060 | Pr | 2-Me | 2 |
| 10061 | Pr | 3-Me | 2 |
| 10062 | Pr | 4-Me | 2 |
| 10063 | Pr | 2-OH | 2 |
| 10064 | Pr | 3-OH | 2 |
| 10065 | Pr | 4-OH | 2 |
| 10066 | Pr | 2-OMe | 2 |
| 10067 | Pr | 3-OMe | 2 |
| 10068 | Pr | 4-OMe | 2 |
| 10069 | Pr | 2-OMeF | 2 |
| 10070 | Pr | 3-OMeF | 2 |
| 10071 | Pr | 4-OMeF | 2 |
| 10072 | Pr | 2-OCF$_3$ | 2 |
| 10073 | Pr | 3-OCF$_3$ | 2 |
| 10074 | Pr | 4-OCF$_3$ | 2 |
| 10075 | Pr | 2-OEtF | 2 |
| 10076 | Pr | 3-OEtF | 2 |
| 10077 | Pr | 4-OEtF | 2 |
| 10078 | Pr | 2-OPrF | 2 |
| 10079 | Pr | 3-OPrF | 2 |
| 10080 | Pr | 4-OPrF | 2 |
| 10081 | Pr | 2-SH | 2 |
| 10082 | Pr | 3-SH | 2 |
| 10083 | Pr | 4-SH | 2 |
| 10084 | Pr | 2-SMe | 2 |
| 10085 | Pr | 3-SMe | 2 |
| 10086 | Pr | 4-SMe | 2 |
| 10087 | Pr | 2-SMeF | 2 |
| 10088 | Pr | 3-SMeF | 2 |
| 10089 | Pr | 4-SMeF | 2 |
| 10090 | Pr | 2-SCF$_3$ | 2 |
| 10091 | Pr | 3-SCF$_3$ | 2 |
| 10092 | Pr | 4-SCF$_3$ | 2 |
| 10093 | Pr | 2-SEtF | 2 |
| 10094 | Pr | 3-SEtF | 2 |
| 10095 | Pr | 4-SEtF | 2 |
| 10096 | Pr | 2-SPrF | 2 |
| 10097 | Pr | 3-SPrF | 2 |
| 10098 | Pr | 4-SPrF | 2 |
| 10099 | Pr | 2-OMe, 4-OMe | 2 |
| 10100 | Pr | 2-Me, 5-OH | 2 |
| 10101 | Pr | 2-Me, 5-OMe | 2 |
| 10102 | Pr | 2-Me, 5-OMeF | 2 |
| 10103 | Pr | 2-Me, 5-OEtF | 2 |
| 10104 | Pr | 2-Me, 5-OPrF | 2 |
| 10105 | Pr | 2-Me, 4-OH | 2 |
| 10106 | Pr | 2-Me, 4-OMe | 2 |
| 10107 | Pr | 2-Me, 4-OMeF | 2 |
| 10108 | Pr | 2-Me, 4-OCF$_3$ | 2 |
| 10109 | Pr | 2-Me, 4-OEtF | 2 |
| 10110 | Pr | 2-Me, 4-OPrF | 2 |
| 10111 | Pr | 2-OH, 4-Me | 2 |
| 10112 | Pr | 2-OMe, 4-Me | 2 |
| 10113 | Pr | 2-OMeF, 4-Me | 2 |
| 10114 | Pr | 2-OCF$_3$, 4-Me | 2 |
| 10115 | Pr | 2-OEtF, 4-Me | 2 |
| 10116 | Pr | 2-OPrF, 4-Me | 2 |
| 10117 | Pr | 2-Cl, 4-OH | 2 |
| 10118 | Pr | 2-Cl, 4-OMe | 2 |
| 10119 | Pr | 2-Cl, 4-OMeF | 2 |
| 10120 | Pr | 2-Cl, 4-OCF$_3$ | 2 |
| 10121 | Pr | 2-Cl, 4-OEtF | 2 |
| 10122 | Pr | 2-Cl, 4-OPrF | 2 |
| 10123 | Pr | 2-F, 4-F | 2 |
| 10124 | Pr | 2-Cl, 4-Cl | 2 |
| 10125 | Pr | 2-Cl, 4-F | 2 |
| 10126 | Pr | 2-Cl, 4-NO$_2$ | 2 |
| 10127 | Pr | 2-Cl, 4-NH$_2$ | 2 |
| 10128 | Pr | 2-Cl, 4-NHMe | 2 |
| 10129 | Pr | 2-Cl, 4-NMe$_2$ | 2 |
| 10130 | Pr | 2-Cl, 4-NMe$_3$OTf | 2 |
| 10131 | Pr | 2-Cl, 4-NMe$_3$I | 2 |
| 10132 | Pr | 2-Cl, 5-F | 2 |
| 10133 | Pr | 2-Cl, 5-NO$_2$ | 2 |
| 10134 | Pr | 2-Cl, 5-NH$_2$ | 2 |
| 10135 | Pr | 2-Cl, 5-NHMe | 2 |
| 10136 | Pr | 2-Cl, 5-NMe$_2$ | 2 |
| 10137 | Pr | 2-Cl, 5-NMe$_3$OTf | 2 |
| 10138 | Pr | 2-Cl, 5-NMe$_3$I | 2 |
| 10139 | Pr | 2-F, 4-Cl | 2 |
| 10140 | Pr | 2-NO$_2$, 4-Cl | 2 |
| 10141 | Pr | 2-NH$_2$, 4-Cl | 2 |
| 10142 | Pr | 2-NHMe, 4-Cl | 2 |
| 10143 | Pr | 2-NMe$_2$, 4-Cl | 2 |
| 10144 | Pr | 2-NMe$_3$OTf, 4-Cl | 2 |
| 10145 | Pr | 2-NMe$_3$I, 4-Cl | 2 |
| 10146 | Pr | 2-F, 5-Cl | 2 |
| 10147 | Pr | 2-NO$_2$, 5-Cl | 2 |
| 10148 | Pr | 2-NH$_2$, 5-Cl | 2 |
| 10149 | Pr | 2-NHMe, 5-Cl | 2 |
| 10150 | Pr | 2-NMe$_2$, 5-Cl | 2 |
| 10151 | Pr | 2-NMe$_3$OTf, 5-Cl | 2 |
| 10152 | Pr | 2-NMe$_3$I, 5-Cl | 2 |
| 10153 | Pr | 2-Br, 4-F | 2 |
| 10154 | Pr | 2-Br, 4-NO$_2$ | 2 |
| 10155 | Pr | 2-Br, 4-NH$_2$ | 2 |
| 10156 | Pr | 2-Br, 4-NHMe | 2 |
| 10157 | Pr | 2-Br, 4-NMe$_2$ | 2 |
| 10158 | Pr | 2-Br, 4-NMe$_3$OTf | 2 |
| 10159 | Pr | 2-Br, 4-NMe$_3$I | 2 |
| 10160 | Pr | 2-Br, 5-F | 2 |
| 10161 | Pr | 2-Br, 5-NO$_2$ | 2 |
| 10162 | Pr | 2-Br, 5-NH$_2$ | 2 |
| 10163 | Pr | 2-Br, 5-NHMe | 2 |
| 10164 | Pr | 2-Br, 5-NMe$_2$ | 2 |
| 10165 | Pr | 2-Br, 5-NMe$_3$OTf | 2 |
| 10166 | Pr | 2-Br, 5-NMe$_3$I | 2 |
| 10167 | Pr | 2-F, 4-Br | 2 |

TABLE 9-continued

Substituent list for compounds of general structure XIV.

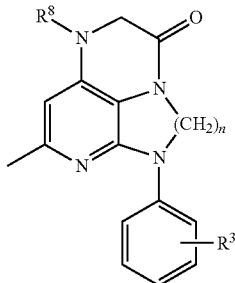

XIV

| Compound # | $R^8$ = | $R^3$ = | n = |
|---|---|---|---|
| 10168 | Pr | 2-NO$_2$, 4-Br | 2 |
| 10169 | Pr | 2-NH$_2$, 4-Br | 2 |
| 10170 | Pr | 2-NHMe, 4-Br | 2 |
| 10171 | Pr | 2-NMe$_2$, 4-Br | 2 |
| 10172 | Pr | 2-NMe$_3$OTf, 4-Br | 2 |
| 10173 | Pr | 2-NMe$_3$I, 4-Br | 2 |
| 10174 | Pr | 2-I, 4-F | 2 |
| 10175 | Pr | 2-I, 4-NO$_2$ | 2 |
| 10176 | Pr | 2-I, 4-NH$_2$ | 2 |
| 10177 | Pr | 2-I, 4-NHMe | 2 |
| 10178 | Pr | 2-I, 4-NMe$_2$ | 2 |
| 10179 | Pr | 2-I, 4-NMe$_3$OTf | 2 |
| 10180 | Pr | 2-I, 4-NMe$_3$I | 2 |
| 10181 | Pr | 2-F, 4-I | 2 |
| 10182 | Pr | 2-NO$_2$, 4-I | 2 |
| 10183 | Pr | 2-NH$_2$, 4-I | 2 |
| 10184 | Pr | 2-NHMe, 4-I | 2 |
| 10185 | Pr | 2-NMe$_2$, 4-I | 2 |
| 10186 | Pr | 2-NMe$_3$OTf, 4-I | 2 |
| 10187 | Pr | 2-NMe$_3$I, 4-I | 2 |
| 10188 | Pr | 2-Me, 3-F | 2 |
| 10189 | Pr | 2-Me, 3-NO$_2$ | 2 |
| 10190 | Pr | 2-Me, 3-NH$_2$ | 2 |
| 10191 | Pr | 2-Me, 3-NHMe | 2 |
| 10192 | Pr | 2-Me, 3-NMe$_2$ | 2 |
| 10193 | Pr | 2-Me, 3-NMe$_3$OTf | 2 |
| 10194 | Pr | 2-Me, 3-NMe$_3$I | 2 |
| 10195 | Pr | 2-Me, 4-F | 2 |
| 10196 | Pr | 2-Me, 4-NO$_2$ | 2 |
| 10197 | Pr | 2-Me, 4-NH$_2$ | 2 |
| 10198 | Pr | 2-Me, 4-NHMe | 2 |
| 10199 | Pr | 2-Me, 4-NMe$_2$ | 2 |
| 10200 | Pr | 2-Me, 4-NMe$_3$OTf | 2 |
| 10201 | Pr | 2-Me, 4-NMe$_3$I | 2 |
| 10202 | Pr | 2-Me, 5-F | 2 |
| 10203 | Pr | 2-Me, 5-NO$_2$ | 2 |
| 10204 | Pr | 2-Me, 5-NH$_2$ | 2 |
| 10205 | Pr | 2-Me, 5-NHMe | 2 |
| 10206 | Pr | 2-Me, 5-NMe$_2$ | 2 |
| 10207 | Pr | 2-Me, 5-NMe$_3$OTf | 2 |
| 10208 | Pr | 2-Me, 5-NMe$_3$I | 2 |
| 10209 | Pr | 2-F, 4-Me | 2 |
| 10210 | Pr | 2-NO$_2$, 4-Me | 2 |
| 10211 | Pr | 2-NH$_2$, 4-Me | 2 |
| 10212 | Pr | 2-NHMe, 4-Me | 2 |
| 10213 | Pr | 2-NMe$_2$, 4-Me | 2 |
| 10214 | Pr | 2-NMe$_3$, 4-Me | 2 |
| 10215 | Pr | 2-NMe$_3$OTf, 4-Me | 2 |
| 10216 | Pr | 2-NMe$_3$I, 4-Me | 2 |
| 10217 | Pr | 2-SnMe$_3$, 4-F | 2 |
| 10218 | Pr | 2-SnMe$_3$, 5-F | 2 |
| 10219 | Pr | 2-F, 4-SnMe$_3$ | 2 |
| 10220 | Pr | 2-Br, 6-Cl, 4-F | 2 |
| 10221 | Pr | 2-Br, 6-Cl, 4-NO$_2$ | 2 |
| 10222 | Pr | 2-Br, 6-Cl, 4-NH$_2$ | 2 |
| 10223 | Pr | 2-Br, 6-Cl, 4-NHMe | 2 |
| 10224 | Pr | 2-Br, 6-Cl, 4-NMe$_2$ | 2 |
| 10225 | Pr | 2-Br, 6-Cl, 4-NMe$_3$OTf | 2 |
| 10226 | Pr | 2-Br, 6-Cl, 4-NMe$_3$I | 2 |
| 10227 | Pr | 2-Me, 6-Cl, 4-F | 2 |

TABLE 9-continued

Substituent list for compounds of general structure XIV.

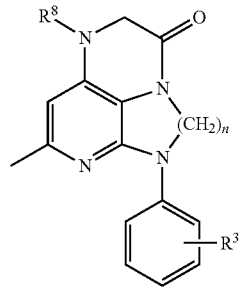

XIV

| Compound # | $R^8$ = | $R^3$ = | n = |
|---|---|---|---|
| 10228 | Pr | 2-SnMe$_3$, 6-Cl, 4-F | 2 |
| 10229 | Pr | 2-Cl, 4-Me | 2 |
| 10230 | Pr | 2-Cl, 4-Br | 2 |
| 10231 | Pr | 2-Cl, 4-SnMe$_3$ | 2 |
| 10232 | Pr | 2-Br, 4-Cl | 2 |
| 10233 | Pr | 2-SnMe$_3$, 4-Cl | 2 |
| 10234 | Pr | 2-Me, 4-Cl | 2 |
| 10235 | Pr | 2-Br, 4-Br | 2 |
| 10236 | Pr | 2-Br, 4-Me | 2 |
| 10237 | Pr | 2-Br, 4-SnMe$_3$ | 2 |
| 10238 | Pr | 2-SnMe$_3$, 4-Br | 2 |
| 10239 | Pr | 2-Me, 4-Br | 2 |
| 10240 | Pr | 2-Me, 4-SnMe$_3$ | 2 |
| 10241 | Pr | 2-SnMe$_3$, 4-Me | 2 |
| 10242 | Pr | 2-Me, 4-Me | 2 |
| 10243 | Pr | 2-Et, 4-Br | 2 |
| 10244 | Pr | 2-Et, 4-SnMe$_3$ | 2 |
| 10245 | Pr | 2-Et, 4-Me | 2 |
| 10246 | Pr | 2-Me, 4-Me, 6-Me | 2 |
| 10247 | Pr | 2-Me, 4-Br, 6-Me | 2 |
| 10248 | Pr | 2-Me, 4-SnMe$_3$, 6-Me | 2 |
| 10249 | Pr | 2-Et, 6-Me | 2 |
| 10250 | Pr | 2-Br, 4-i-Pr | 2 |
| 10251 | Pr | 2-SnMe$_3$, 4-i-Pr | 2 |
| 10252 | Pr | 2-Me, 4-i-Pr | 2 |
| 10253 | Pr | 2-Br, 4-Br, 6-Br | 2 |
| 10254 | Pr | 2-Br, 4-Me, 6-Br | 2 |
| 10255 | Pr | 2-Br, 4-SnMe$_3$, 6-Br | 2 |
| 10256 | Pr | 2-SnMe$_3$, 4-Br, 6-Br | 2 |
| 10257 | Pr | 2-Br, 4-Br, 6-Me | 2 |
| 10258 | Pr | 2-Br, 4-CF$_3$, 6-Br | 2 |
| 10259 | Pr | 2-Br, 4-Br, 6-CF$_3$ | 2 |
| 10260 | Pr | 2-CF$_3$, 4-CF$_3$ | 2 |
| 10261 | Pr | 2-Cl, 4-CF$_3$ | 2 |
| 10262 | Pr | 2-CF$_3$, 4-Cl | 2 |
| 10263 | Pr | 2-Br, 4-CF$_3$ | 2 |
| 10264 | Pr | 2-SnMe$_3$, 4-CF$_3$ | 2 |
| 10265 | Pr | 2-Me, 4-CF$_3$ | 2 |
| 10266 | Pr | 2-CF$_3$, 4-Br | 2 |
| 10267 | Pr | 2-CF$_3$, 4-SnMe$_3$ | 2 |
| 10268 | Pr | 2-CF$_3$, 4-Me | 2 |
| 10269 | Pr | 2-Br, 4-OH | 2 |
| 10270 | Pr | 2-Br, 4-OMe | 2 |
| 10271 | Pr | 2-Br, 4-OMeF | 2 |
| 10272 | Pr | 2-Br, 4-OCF$_3$ | 2 |
| 10273 | Pr | 2-Br, 4-OEtF | 2 |
| 10274 | Pr | 2-Br, 4-OPrF | 2 |
| 10275 | Pr | 2-OH, 4-Br | 2 |
| 10276 | Pr | 2-OMe, 4-Br | 2 |
| 10277 | Pr | 2-OMeF, 4-Br | 2 |
| 10278 | Pr | 2-OCF$_3$, 4-Br | 2 |
| 10279 | Pr | 2-OEtF, 4-Br | 2 |
| 10280 | Pr | 2-OPrF, 4-Br | 2 |
| 10281 | Pr | 2-I, 4-OH | 2 |
| 10282 | Pr | 2-I, 4-OMe | 2 |
| 10283 | Pr | 2-I, 4-OMeF | 2 |
| 10284 | Pr | 2-I, 4-OCF$_3$ | 2 |
| 10285 | Pr | 2-I, 4-OEtF | 2 |
| 10286 | Pr | 2-I, 4-OPrF | 2 |
| 10287 | Pr | 2-OH, 4-I | 2 |

TABLE 9-continued

Substituent list for compounds of general structure XIV.

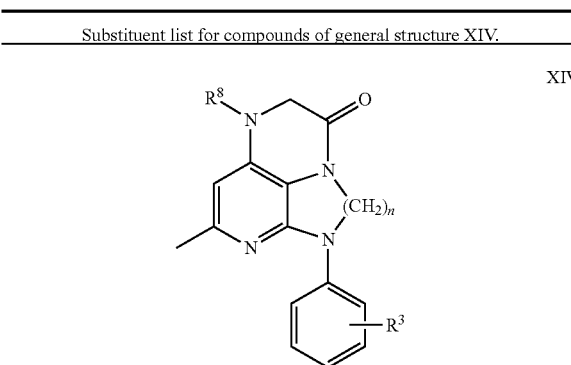

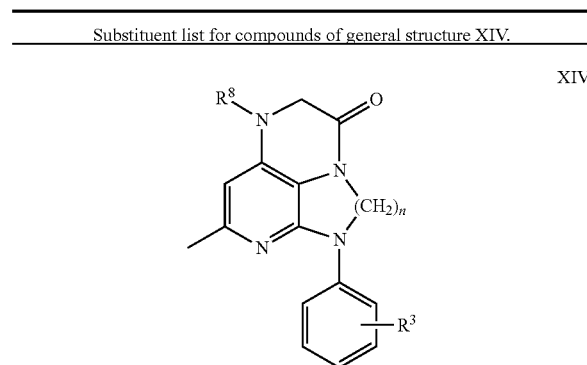

| Compound # | R⁸ = | R³ = | n = |
|---|---|---|---|
| 10288 | Pr | 2-OMe, 4-I | 2 |
| 10289 | Pr | 2-OMeF, 4-I | 2 |
| 10290 | Pr | 2-OCF₃, 4-I | 2 |
| 10291 | Pr | 2-OEtF, 4-I | 2 |
| 10292 | Pr | 2-OPrF, 4-I | 2 |
| 10293 | Pr | 2-SnMe₃, 4-OH | 2 |
| 10294 | Pr | 2-SnMe₃, 4-OMe | 2 |
| 10295 | Pr | 2-SnMe₃, 4-OMeF | 2 |
| 10296 | Pr | 2-SnMe₃, 4-OCF₃ | 2 |
| 10297 | Pr | 2-SnMe₃, 4-OEtF | 2 |
| 10298 | Pr | 2-SnMe₃, 4-OPrF | 2 |
| 10299 | Pr | 2-OH, 4-SnMe₃ | 2 |
| 10300 | Pr | 2-OMe, 4-SnMe₃ | 2 |
| 10301 | Pr | 2-OMeF, 4-SnMe₃ | 2 |
| 10302 | Pr | 2-OCF₃, 4-SnMe₃ | 2 |
| 10303 | Pr | 2-OEtF, 4-SnMe₃ | 2 |
| 10304 | Pr | 2-OPrF, 4-SnMe₃ | 2 |
| 10305 | Pr—F | H | 1 |
| 10306 | Pr—F | 2-t-Bu | 1 |
| 10307 | Pr—F | 2-Br | 1 |
| 10308 | Pr—F | 3-Br | 1 |
| 10309 | Pr—F | 4-Br | 1 |
| 10310 | Pr—F | 2-I | 1 |
| 10311 | Pr—F | 3-I | 1 |
| 10312 | Pr—F | 4-I | 1 |
| 10313 | Pr—F | 2-SnMe₃ | 1 |
| 10314 | Pr—F | 3-SnMe₃ | 1 |
| 10315 | Pr—F | 4-SnMe₃ | 1 |
| 10316 | Pr—F | 2-Me | 1 |
| 10317 | Pr—F | 3-Me | 1 |
| 10318 | Pr—F | 4-Me | 1 |
| 10319 | Pr—F | 2-OH | 1 |
| 10320 | Pr—F | 3-OH | 1 |
| 10321 | Pr—F | 4-OH | 1 |
| 10322 | Pr—F | 2-OMe | 1 |
| 10323 | Pr—F | 3-OMe | 1 |
| 10324 | Pr—F | 4-OMe | 1 |
| 10325 | Pr—F | 2-OMeF | 1 |
| 10326 | Pr—F | 3-OMeF | 1 |
| 10327 | Pr—F | 4-OMeF | 1 |
| 10328 | Pr—F | 2-OCF₃ | 1 |
| 10329 | Pr—F | 3-OCF₃ | 1 |
| 10330 | Pr—F | 4-OCF₃ | 1 |
| 10331 | Pr—F | 2-OEtF | 1 |
| 10332 | Pr—F | 3-OEtF | 1 |
| 10333 | Pr—F | 4-OEtF | 1 |
| 10334 | Pr—F | 2-OPrF | 1 |
| 10335 | Pr—F | 3-OPrF | 1 |
| 10336 | Pr—F | 4-OPrF | 1 |
| 10337 | Pr—F | 2-SH | 1 |
| 10338 | Pr—F | 3-SH | 1 |
| 10339 | Pr—F | 4-SH | 1 |
| 10340 | Pr—F | 2-SMe | 1 |
| 10341 | Pr—F | 3-SMe | 1 |
| 10342 | Pr—F | 4-SMe | 1 |
| 10343 | Pr—F | 2-SMeF | 1 |
| 10344 | Pr—F | 3-SMeF | 1 |
| 10345 | Pr—F | 4-SMeF | 1 |
| 10346 | Pr—F | 2-SCF₃ | 1 |
| 10347 | Pr—F | 3-SCF₃ | 1 |
| 10348 | Pr—F | 4-SCF₃ | 1 |
| 10349 | Pr—F | 2-SEtF | 1 |
| 10350 | Pr—F | 3-SEtF | 1 |
| 10351 | Pr—F | 4-SEtF | 1 |
| 10352 | Pr—F | 2-SPrF | 1 |
| 10353 | Pr—F | 3-SPrF | 1 |
| 10354 | Pr—F | 4-SPrF | 1 |
| 10355 | Pr—F | 2-OMe, 4-OMe | 1 |
| 10356 | Pr—F | 2-Me, 5-OH | 1 |
| 10357 | Pr—F | 2-Me, 5-OMe | 1 |
| 10358 | Pr—F | 2-Me, 5-OMeF | 1 |
| 10359 | Pr—F | 2-Me, 5-OEtF | 1 |
| 10360 | Pr—F | 2-Me, 5-OPrF | 1 |
| 10361 | Pr—F | 2-Me, 4-OH | 1 |
| 10362 | Pr—F | 2-Me, 4-OMe | 1 |
| 10363 | Pr—F | 2-Me, 4-OMeF | 1 |
| 10364 | Pr—F | 2-Me, 4-OCF₃ | 1 |
| 10365 | Pr—F | 2-Me, 4-OEtF | 1 |
| 10366 | Pr—F | 2-Me, 4-OPrF | 1 |
| 10367 | Pr—F | 2-OH, 4-Me | 1 |
| 10368 | Pr—F | 2-OMe, 4-Me | 1 |
| 10369 | Pr—F | 2-OMeF, 4-Me | 1 |
| 10370 | Pr—F | 2-OCF₃, 4-Me | 1 |
| 10371 | Pr—F | 2-OEtF, 4-Me | 1 |
| 10372 | Pr—F | 2-OPrF, 4-Me | 1 |
| 10373 | Pr—F | 2-Cl, 4-OH | 1 |
| 10374 | Pr—F | 2-Cl, 4-OMe | 1 |
| 10375 | Pr—F | 2-Cl, 4-OMeF | 1 |
| 10376 | Pr—F | 2-Cl, 4-OCF₃ | 1 |
| 10377 | Pr—F | 2-Cl, 4-OEtF | 1 |
| 10378 | Pr—F | 2-Cl, 4-OPrF | 1 |
| 10379 | Pr—F | 2-F, 4-F | 1 |
| 10380 | Pr—F | 2-Cl, 4-Cl | 1 |
| 10381 | Pr—F | 2-Cl, 4-F | 1 |
| 10382 | Pr—F | 2-Cl, 4-NO₂ | 1 |
| 10383 | Pr—F | 2-Cl, 4-NH₂ | 1 |
| 10384 | Pr—F | 2-Cl, 4-NHMe | 1 |
| 10385 | Pr—F | 2-Cl, 4-NMe₂ | 1 |
| 10386 | Pr—F | 2-Cl, 4-NMe₃OTf | 1 |
| 10387 | Pr—F | 2-Cl, 4-NMe₃I | 1 |
| 10388 | Pr—F | 2-Cl, 5-F | 1 |
| 10389 | Pr—F | 2-Cl, 5-NO₂ | 1 |
| 10390 | Pr—F | 2-Cl, 5-NH₂ | 1 |
| 10391 | Pr—F | 2-Cl, 5-NHMe | 1 |
| 10392 | Pr—F | 2-Cl, 5-NMe₂ | 1 |
| 10393 | Pr—F | 2-Cl, 5-NMe₃OTf | 1 |
| 10394 | Pr—F | 2-Cl, 5-NMe₃I | 1 |
| 10395 | Pr—F | 2-F, 4-Cl | 1 |
| 10396 | Pr—F | 2-NO₂, 4-Cl | 1 |
| 10397 | Pr—F | 2-NH₂, 4-Cl | 1 |
| 10398 | Pr—F | 2-NHMe, 4-Cl | 1 |
| 10399 | Pr—F | 2-NMe₂, 4-Cl | 1 |
| 10400 | Pr—F | 2-NMe₃OTf, 4-Cl | 1 |
| 10401 | Pr—F | 2-NMe₃I, 4-Cl | 1 |
| 10402 | Pr—F | 2-F, 5-Cl | 1 |
| 10403 | Pr—F | 2-NO₂, 5-Cl | 1 |
| 10404 | Pr—F | 2-NH₂, 5-Cl | 1 |
| 10405 | Pr—F | 2-NHMe, 5-Cl | 1 |
| 10406 | Pr—F | 2-NMe₂, 5-Cl | 1 |
| 10407 | Pr—F | 2-NMe₃OTf, 5-Cl | 1 |

TABLE 9-continued

Substituent list for compounds of general structure XIV.

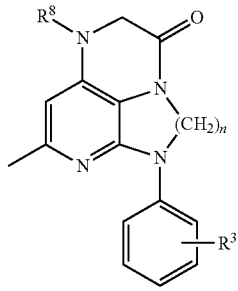

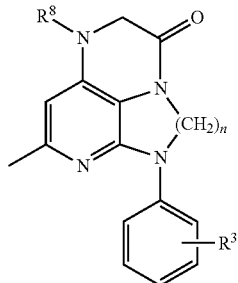

| Compound # | R⁸ = | R³ = | n = |
|---|---|---|---|
| 10408 | Pr—F | 2-NMe₃I, 5-Cl | 1 |
| 10409 | Pr—F | 2-Br, 4-F | 1 |
| 10410 | Pr—F | 2-Br, 4-NO₂ | 1 |
| 10411 | Pr—F | 2-Br, 4-NH₂ | 1 |
| 10412 | Pr—F | 2-Br, 4-NHMe | 1 |
| 10413 | Pr—F | 2-Br, 4-NMe₂ | 1 |
| 10414 | Pr—F | 2-Br, 4-NMe₃OTf | 1 |
| 10415 | Pr—F | 2-Br, 4-NMe₃I | 1 |
| 10416 | Pr—F | 2-Br, 5-F | 1 |
| 10417 | Pr—F | 2-Br, 5-NO₂ | 1 |
| 10418 | Pr—F | 2-Br, 5-NH₂ | 1 |
| 10419 | Pr—F | 2-Br, 5-NHMe | 1 |
| 10420 | Pr—F | 2-Br, 5-NMe₂ | 1 |
| 10421 | Pr—F | 2-Br, 5-NMe₃OTf | 1 |
| 10422 | Pr—F | 2-Br, 5-NMe₃I | 1 |
| 10423 | Pr—F | 2-F, 4-Br | 1 |
| 10424 | Pr—F | 2-NO₂, 4-Br | 1 |
| 10425 | Pr—F | 2-NH₂, 4-Br | 1 |
| 10426 | Pr—F | 2-NHMe, 4-Br | 1 |
| 10427 | Pr—F | 2-NMe₂, 4-Br | 1 |
| 10428 | Pr—F | 2-NMe₃OTf, 4-Br | 1 |
| 10429 | Pr—F | 2-NMe₃I, 4-Br | 1 |
| 10430 | Pr—F | 2-I, 4-F | 1 |
| 10431 | Pr—F | 2-I, 4-NO₂ | 1 |
| 10432 | Pr—F | 2-I, 4-NH₂ | 1 |
| 10433 | Pr—F | 2-I, 4-NHMe | 1 |
| 10434 | Pr—F | 2-I, 4-NMe₂ | 1 |
| 10435 | Pr—F | 2-I, 4-NMe₃OTf | 1 |
| 10436 | Pr—F | 2-I, 4-NMe₃I | 1 |
| 10437 | Pr—F | 2-F, 4-I | 1 |
| 10438 | Pr—F | 2-NO₂, 4-I | 1 |
| 10439 | Pr—F | 2-NH₂, 4-I | 1 |
| 10440 | Pr—F | 2-NHMe, 4-I | 1 |
| 10441 | Pr—F | 2-NMe₂, 4-I | 1 |
| 10442 | Pr—F | 2-NMe₃OTf, 4-I | 1 |
| 10443 | Pr—F | 2-NMe₃I, 4-I | 1 |
| 10444 | Pr—F | 2-Me, 3-F | 1 |
| 10445 | Pr—F | 2-Me, 3-NO₂ | 1 |
| 10446 | Pr—F | 2-Me, 3-NH₂ | 1 |
| 10447 | Pr—F | 2-Me, 3-NHMe | 1 |
| 10448 | Pr—F | 2-Me, 3-NMe₂ | 1 |
| 10449 | Pr—F | 2-Me, 3-NMe₃OTf | 1 |
| 10450 | Pr—F | 2-Me, 3-NMe₃I | 1 |
| 10451 | Pr—F | 2-Me, 4-F | 1 |
| 10452 | Pr—F | 2-Me, 4-NO₂ | 1 |
| 10453 | Pr—F | 2-Me, 4-NH₂ | 1 |
| 10454 | Pr—F | 2-Me, 4-NHMe | 1 |
| 10455 | Pr—F | 2-Me, 4-NMe₂ | 1 |
| 10456 | Pr—F | 2-Me, 4-NMe₃OTf | 1 |
| 10457 | Pr—F | 2-Me, 4-NMe₃I | 1 |
| 10458 | Pr—F | 2-Me, 5-F | 1 |
| 10459 | Pr—F | 2-Me, 5-NO₂ | 1 |
| 10460 | Pr—F | 2-Me, 5-NH₂ | 1 |
| 10461 | Pr—F | 2-Me, 5-NHMe | 1 |
| 10462 | Pr—F | 2-Me, 5-NMe₂ | 1 |
| 10463 | Pr—F | 2-Me, 5-NMe₃OTf | 1 |
| 10464 | Pr—F | 2-Me, 5-NMe₃I | 1 |
| 10465 | Pr—F | 2-F, 4-Me | 1 |
| 10466 | Pr—F | 2-NO₂, 4-Me | 1 |
| 10467 | Pr—F | 2-NH₂, 4-Me | 1 |
| 10468 | Pr—F | 2-NHMe, 4-Me | 1 |
| 10469 | Pr—F | 2-NMe₂, 4-Me | 1 |
| 10470 | Pr—F | 2-NMe₃, 4-Me | 1 |
| 10471 | Pr—F | 2-NMe₃OTf, 4-Me | 1 |
| 10472 | Pr—F | 2-NMe₃I, 4-Me | 1 |
| 10473 | Pr—F | 2-SnMe₃, 4-F | 1 |
| 10474 | Pr—F | 2-SnMe₃, 5-F | 1 |
| 10475 | Pr—F | 2-F, 4-SnMe₃ | 1 |
| 10476 | Pr—F | 2-Br, 6-Cl, 4-F | 1 |
| 10477 | Pr—F | 2-Br, 6-Cl, 4-NO₂ | 1 |
| 10478 | Pr—F | 2-Br, 6-Cl, 4-NH₂ | 1 |
| 10479 | Pr—F | 2-Br, 6-Cl, 4-NHMe | 1 |
| 10480 | Pr—F | 2-Br, 6-Cl, 4-NMe₂ | 1 |
| 10481 | Pr—F | 2-Br, 6-Cl, 4-NMe₃OTf | 1 |
| 10482 | Pr—F | 2-Br, 6-Cl, 4-NMe₃I | 1 |
| 10483 | Pr—F | 2-Me, 6-Cl, 4-F | 1 |
| 10484 | Pr—F | 2-SnMe₃, 6-Cl, 4-F | 1 |
| 10485 | Pr—F | 2-Cl, 4-Me | 1 |
| 10486 | Pr—F | 2-Cl, 4-Br | 1 |
| 10487 | Pr—F | 2-Cl, 4-SnMe₃ | 1 |
| 10488 | Pr—F | 2-Br, 4-Cl | 1 |
| 10489 | Pr—F | 2-SnMe₃, 4-Cl | 1 |
| 10490 | Pr—F | 2-Me, 4-Cl | 1 |
| 10491 | Pr—F | 2-Br, 4-Br | 1 |
| 10492 | Pr—F | 2-Br, 4-Me | 1 |
| 10493 | Pr—F | 2-Br, 4-SnMe₃ | 1 |
| 10494 | Pr—F | 2-SnMe₃, 4-Br | 1 |
| 10495 | Pr—F | 2-Me, 4-Br | 1 |
| 10496 | Pr—F | 2-Me, 4-SnMe₃ | 1 |
| 10497 | Pr—F | 2-SnMe₃, 4-Me | 1 |
| 10498 | Pr—F | 2-Me, 4-Me | 1 |
| 10499 | Pr—F | 2-Et, 4-Br | 1 |
| 10500 | Pr—F | 2-Et, 4-SnMe₃ | 1 |
| 10501 | Pr—F | 2-Et, 4-Me | 1 |
| 10502 | Pr—F | 2-Me, 4-Me, 6-Me | 1 |
| 10503 | Pr—F | 2-Me, 4-Br, 6-Me | 1 |
| 10504 | Pr—F | 2-Me, 4-SnMe₃, 6-Me | 1 |
| 10505 | Pr—F | 2-Et, 6-Me | 1 |
| 10506 | Pr—F | 2-Br, 4-i-Pr | 1 |
| 10507 | Pr—F | 2-SnMe₃, 4-i-Pr | 1 |
| 10508 | Pr—F | 2-Me, 4-i-Pr | 1 |
| 10509 | Pr—F | 2-Br, 4-Br, 6-Br | 1 |
| 10510 | Pr—F | 2-Br, 4-Me, 6-Br | 1 |
| 10511 | Pr—F | 2-Br, 4-SnMe₃, 6-Br | 1 |
| 10512 | Pr—F | 2-SnMe₃, 4-Br, 6-Br | 1 |
| 10513 | Pr—F | 2-Br, 4-Br, 6-Me | 1 |
| 10514 | Pr—F | 2-Br, 4-CF₃, 6-Br | 1 |
| 10515 | Pr—F | 2-Br, 4-Br, 6-CF₃ | 1 |
| 10516 | Pr—F | 2-CF₃, 4-CF₃ | 1 |
| 10517 | Pr—F | 2-Cl, 4-CF₃ | 1 |
| 10518 | Pr—F | 2-CF₃, 4-Cl | 1 |
| 10519 | Pr—F | 2-Br, 4-CF₃ | 1 |
| 10520 | Pr—F | 2-SnMe₃, 4-CF₃ | 1 |
| 10521 | Pr—F | 2-Me, 4-CF₃ | 1 |
| 10522 | Pr—F | 2-CF₃, 4-Br | 1 |
| 10523 | Pr—F | 2-CF₃, 4-SnMe₃ | 1 |
| 10524 | Pr—F | 2-CF₃, 4-Me | 1 |
| 10525 | Pr—F | 2-Br, 4-OH | 1 |
| 10526 | Pr—F | 2-Br, 4-OMe | 1 |
| 10527 | Pr—F | 2-Br, 4-OMeF | 1 |

TABLE 9-continued

Substituent list for compounds of general structure XIV.

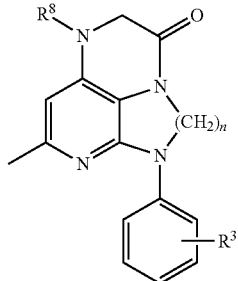

XIV

| Compound # | R⁸ = | R³ = | n = |
|---|---|---|---|
| 10528 | Pr—F | 2-Br, 4-OCF₃ | 1 |
| 10529 | Pr—F | 2-Br, 4-OEtF | 1 |
| 10530 | Pr—F | 2-Br, 4-OPrF | 1 |
| 10531 | Pr—F | 2-OH, 4-Br | 1 |
| 10532 | Pr—F | 2-OMe, 4-Br | 1 |
| 10533 | Pr—F | 2-OMeF, 4-Br | 1 |
| 10534 | Pr—F | 2-OCF₃, 4-Br | 1 |
| 10535 | Pr—F | 2-OEtF, 4-Br | 1 |
| 10536 | Pr—F | 2-OPrF, 4-Br | 1 |
| 10537 | Pr—F | 2-I, 4-OH | 1 |
| 10538 | Pr—F | 2-I, 4-OMe | 1 |
| 10539 | Pr—F | 2-I, 4-OMeF | 1 |
| 10540 | Pr—F | 2-I, 4-OCF₃ | 1 |
| 10541 | Pr—F | 2-I, 4-OEtF | 1 |
| 10542 | Pr—F | 2-I, 4-OPrF | 1 |
| 10543 | Pr—F | 2-OH, 4-I | 1 |
| 10544 | Pr—F | 2-OMe, 4-I | 1 |
| 10545 | Pr—F | 2-OMeF, 4-I | 1 |
| 10546 | Pr—F | 2-OCF₃, 4-I | 1 |
| 10547 | Pr—F | 2-OEtF, 4-I | 1 |
| 10548 | Pr—F | 2-OPrF, 4-I | 1 |
| 10549 | Pr—F | 2-SnMe₃, 4-OH | 1 |
| 10550 | Pr—F | 2-SnMe₃, 4-OMe | 1 |
| 10551 | Pr—F | 2-SnMe₃, 4-OMeF | 1 |
| 10552 | Pr—F | 2-SnMe₃, 4-OCF₃ | 1 |
| 10553 | Pr—F | 2-SnMe₃, 4-OEtF | 1 |
| 10554 | Pr—F | 2-SnMe₃, 4-OPrF | 1 |
| 10555 | Pr—F | 2-OH, 4-SnMe₃ | 1 |
| 10556 | Pr—F | 2-OMe, 4-SnMe₃ | 1 |
| 10557 | Pr—F | 2-OMeF, 4-SnMe₃ | 1 |
| 10558 | Pr—F | 2-OCF₃, 4-SnMe₃ | 1 |
| 10559 | Pr—F | 2-OEtF, 4-SnMe₃ | 1 |
| 10560 | Pr—F | 2-OPrF, 4-SnMe₃ | 1 |
| 10561 | Pr—F | H | 2 |
| 10562 | Pr—F | 2-t-Bu | 2 |
| 10563 | Pr—F | 2-Br | 2 |
| 10564 | Pr—F | 3-Br | 2 |
| 10565 | Pr—F | 4-Br | 2 |
| 10566 | Pr—F | 2-I | 2 |
| 10567 | Pr—F | 3-I | 2 |
| 10568 | Pr—F | 4-I | 2 |
| 10569 | Pr—F | 2-SnMe₃ | 2 |
| 10570 | Pr—F | 3-SnMe₃ | 2 |
| 10571 | Pr—F | 4-SnMe₃ | 2 |
| 10572 | Pr—F | 2-Me | 2 |
| 10573 | Pr—F | 3-Me | 2 |
| 10574 | Pr—F | 4-Me | 2 |
| 10575 | Pr—F | 2-OH | 2 |
| 10576 | Pr—F | 3-OH | 2 |
| 10577 | Pr—F | 4-OH | 2 |
| 10578 | Pr—F | 2-OMe | 2 |
| 10579 | Pr—F | 3-OMe | 2 |
| 10580 | Pr—F | 4-OMe | 2 |
| 10581 | Pr—F | 2-OMeF | 2 |
| 10582 | Pr—F | 3-OMeF | 2 |
| 10583 | Pr—F | 4-OMeF | 2 |
| 10584 | Pr—F | 2-OCF₃ | 2 |
| 10585 | Pr—F | 3-OCF₃ | 2 |
| 10586 | Pr—F | 4-OCF₃ | 2 |
| 10587 | Pr—F | 2-OEtF | 2 |
| 10588 | Pr—F | 3-OEtF | 2 |
| 10589 | Pr—F | 4-OEtF | 2 |
| 10590 | Pr—F | 2-OPrF | 2 |
| 10591 | Pr—F | 3-OPrF | 2 |
| 10592 | Pr—F | 4-OPrF | 2 |
| 10593 | Pr—F | 2-SH | 2 |
| 10594 | Pr—F | 3-SH | 2 |
| 10595 | Pr—F | 4-SH | 2 |
| 10596 | Pr—F | 2-SMe | 2 |
| 10597 | Pr—F | 3-SMe | 2 |
| 10598 | Pr—F | 4-SMe | 2 |
| 10599 | Pr—F | 2-SMeF | 2 |
| 10600 | Pr—F | 3-SMeF | 2 |
| 10601 | Pr—F | 4-SMeF | 2 |
| 10602 | Pr—F | 2-SCF₃ | 2 |
| 10603 | Pr—F | 3-SCF₃ | 2 |
| 10604 | Pr—F | 4-SCF₃ | 2 |
| 10605 | Pr—F | 2-SEtF | 2 |
| 10606 | Pr—F | 3-SEtF | 2 |
| 10607 | Pr—F | 4-SEtF | 2 |
| 10608 | Pr—F | 2-SPrF | 2 |
| 10609 | Pr—F | 3-SPrF | 2 |
| 10610 | Pr—F | 4-SPrF | 2 |
| 10611 | Pr—F | 2-OMe, 4-OMe | 2 |
| 10612 | Pr—F | 2-Me, 5-OH | 2 |
| 10613 | Pr—F | 2-Me, 5-OMe | 2 |
| 10614 | Pr—F | 2-Me, 5-OMeF | 2 |
| 10615 | Pr—F | 2-Me, 5-OEtF | 2 |
| 10616 | Pr—F | 2-Me, 5-OPrF | 2 |
| 10617 | Pr—F | 2-Me, 4-OH | 2 |
| 10618 | Pr—F | 2-Me, 4-OMe | 2 |
| 10619 | Pr—F | 2-Me, 4-OMeF | 2 |
| 10620 | Pr—F | 2-Me, 4-OCF₃ | 2 |
| 10621 | Pr—F | 2-Me, 4-OEtF | 2 |
| 10622 | Pr—F | 2-Me, 4-OPrF | 2 |
| 10623 | Pr—F | 2-OH, 4-Me | 2 |
| 10624 | Pr—F | 2-OMe, 4-Me | 2 |
| 10625 | Pr—F | 2-OMeF, 4-Me | 2 |
| 10626 | Pr—F | 2-OCF₃, 4-Me | 2 |
| 10627 | Pr—F | 2-OEtF, 4-Me | 2 |
| 10628 | Pr—F | 2-OPrF, 4-Me | 2 |
| 10629 | Pr—F | 2-Cl, 4-OH | 2 |
| 10630 | Pr—F | 2-Cl, 4-OMe | 2 |
| 10631 | Pr—F | 2-Cl, 4-OMeF | 2 |
| 10632 | Pr—F | 2-Cl, 4-OCF₃ | 2 |
| 10633 | Pr—F | 2-Cl, 4-OEtF | 2 |
| 10634 | Pr—F | 2-Cl, 4-OPrF | 2 |
| 10635 | Pr—F | 2-F, 4-F | 2 |
| 10636 | Pr—F | 2-Cl, 4-Cl | 2 |
| 10637 | Pr—F | 2-Cl, 4-F | 2 |
| 10638 | Pr—F | 2-Cl, 4-NO₂ | 2 |
| 10639 | Pr—F | 2-Cl, 4-NH₂ | 2 |
| 10640 | Pr—F | 2-Cl, 4-NHMe | 2 |
| 10641 | Pr—F | 2-Cl, 4-NMe₂ | 2 |
| 10642 | Pr—F | 2-Cl, 4-NMe₃OTf | 2 |
| 10643 | Pr—F | 2-Cl, 4-NMe₃I | 2 |
| 10644 | Pr—F | 2-Cl, 5-F | 2 |
| 10645 | Pr—F | 2-Cl, 5-NO₂ | 2 |
| 10646 | Pr—F | 2-Cl, 5-NH₂ | 2 |
| 10647 | Pr—F | 2-Cl, 5-NHMe | 2 |

TABLE 9-continued

Substituent list for compounds of general structure XIV.

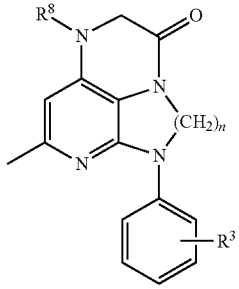

| Compound # | R⁸ = | R³ = | n = |
|---|---|---|---|
| 10648 | Pr—F | 2-Cl, 5-NMe₂ | 2 |
| 10649 | Pr—F | 2-Cl, 5-NMe₃OTf | 2 |
| 10650 | Pr—F | 2-Cl, 5-NMe₃I | 2 |
| 10651 | Pr—F | 2-F, 4-Cl | 2 |
| 10652 | Pr—F | 2-NO₂, 4-Cl | 2 |
| 10653 | Pr—F | 2-NH₂, 4-Cl | 2 |
| 10654 | Pr—F | 2-NHMe, 4-Cl | 2 |
| 10655 | Pr—F | 2-NMe₂, 4-Cl | 2 |
| 10656 | Pr—F | 2-NMe₃OTf, 4-Cl | 2 |
| 10657 | Pr—F | 2-NMe₃I, 4-Cl | 2 |
| 10658 | Pr—F | 2-F, 5-Cl | 2 |
| 10659 | Pr—F | 2-NO₂, 5-Cl | 2 |
| 10660 | Pr—F | 2-NH₂, 5-Cl | 2 |
| 10661 | Pr—F | 2-NHMe, 5-Cl | 2 |
| 10662 | Pr—F | 2-NMe₂, 5-Cl | 2 |
| 10663 | Pr—F | 2-NMe₃OTf, 5-Cl | 2 |
| 10664 | Pr—F | 2-NMe₂1, 5-Cl | 2 |
| 10665 | Pr—F | 2-Br, 4-F | 2 |
| 10666 | Pr—F | 2-Br, 4-NO₂ | 2 |
| 10667 | Pr—F | 2-Br, 4-NH₂ | 2 |
| 10668 | Pr—F | 2-Br, 4-NHMe | 2 |
| 10669 | Pr—F | 2-Br, 4-NMe₂ | 2 |
| 10670 | Pr—F | 2-Br, 4-NMe₃OTf | 2 |
| 10671 | Pr—F | 2-Br, 4-NMe₃I | 2 |
| 10672 | Pr—F | 2-Br, 5-F | 2 |
| 10673 | Pr—F | 2-Br, 5-NO₂ | 2 |
| 10674 | Pr—F | 2-Br, 5-NH₂ | 2 |
| 10675 | Pr—F | 2-Br, 5-NHMe | 2 |
| 10676 | Pr—F | 2-Br, 5-NMe₂ | 2 |
| 10677 | Pr—F | 2-Br, 5-NMe₃OTf | 2 |
| 10678 | Pr—F | 2-Br, 5-NMe₃I | 2 |
| 10679 | Pr—F | 2-F, 4-Br | 2 |
| 10680 | Pr—F | 2-NO₂, 4-Br | 2 |
| 10681 | Pr—F | 2-NH₂, 4-Br | 2 |
| 10682 | Pr—F | 2-NHMe, 4-Br | 2 |
| 10683 | Pr—F | 2-NMe₂, 4-Br | 2 |
| 10684 | Pr—F | 2-NMe₃OTf, 4-Br | 2 |
| 10685 | Pr—F | 2-NMe₃I, 4-Br | 2 |
| 10686 | Pr—F | 2-I, 4-F | 2 |
| 10687 | Pr—F | 2-I, 4-NO₂ | 2 |
| 10688 | Pr—F | 2-I, 4-NH₂ | 2 |
| 10689 | Pr—F | 2-I, 4-NHMe | 2 |
| 10690 | Pr—F | 2-I, 4-NMe₂ | 2 |
| 10691 | Pr—F | 2-I, 4-NMe₃OTf | 2 |
| 10692 | Pr—F | 2-I, 4-NMe₃I | 2 |
| 10693 | Pr—F | 2-F, 4-I | 2 |
| 10694 | Pr—F | 2-NO₂, 4-I | 2 |
| 10695 | Pr—F | 2-NH₂, 4-I | 2 |
| 10696 | Pr—F | 2-NHMe, 4-I | 2 |
| 10697 | Pr—F | 2-NMe₂, 4-I | 2 |
| 10698 | Pr—F | 2-NMe₃OTf, 4-I | 2 |
| 10699 | Pr—F | 2-NMe₃I, 4-I | 2 |
| 10700 | Pr—F | 2-Me, 3-F | 2 |
| 10701 | Pr—F | 2-Me, 3-NO₂ | 2 |
| 10702 | Pr—F | 2-Me, 3-NH₂ | 2 |
| 10703 | Pr—F | 2-Me, 3-NHMe | 2 |
| 10704 | Pr—F | 2-Me, 3-NMe₂ | 2 |
| 10705 | Pr—F | 2-Me, 3-NMe₃OTf | 2 |
| 10706 | Pr—F | 2-Me, 3-NMe₃I | 2 |
| 10707 | Pr—F | 2-Me, 4-F | 2 |

TABLE 9-continued

Substituent list for compounds of general structure XIV.

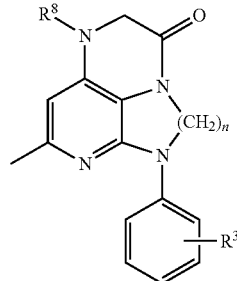

| Compound # | R⁸ = | R³ = | n = |
|---|---|---|---|
| 10708 | Pr—F | 2-Me, 4-NO₂ | 2 |
| 10709 | Pr—F | 2-Me, 4-NH₂ | 2 |
| 10710 | Pr—F | 2-Me, 4-NHMe | 2 |
| 10711 | Pr—F | 2-Me, 4-NMe₂ | 2 |
| 10712 | Pr—F | 2-Me, 4-NMe₃OTf | 2 |
| 10713 | Pr—F | 2-Me, 4-NMe₃I | 2 |
| 10714 | Pr—F | 2-Me, 5-F | 2 |
| 10715 | Pr—F | 2-Me, 5-NO₂ | 2 |
| 10716 | Pr—F | 2-Me, 5-NH₂ | 2 |
| 10717 | Pr—F | 2-Me, 5-NHMe | 2 |
| 10718 | Pr—F | 2-Me, 5-NMe₂ | 2 |
| 10719 | Pr—F | 2-Me, 5-NMe₃OTf | 2 |
| 10720 | Pr—F | 2-Me, 5-NMe₃I | 2 |
| 10721 | Pr—F | 2-F, 4-Me | 2 |
| 10722 | Pr—F | 2-NO₂, 4-Me | 2 |
| 10723 | Pr—F | 2-NH₂, 4-Me | 2 |
| 10724 | Pr—F | 2-NHMe, 4-Me | 2 |
| 10725 | Pr—F | 2-NMe₂, 4-Me | 2 |
| 10726 | Pr—F | 2-NMe₃, 4-Me | 2 |
| 10727 | Pr—F | 2-NMe₃OTf 4-Me | 2 |
| 10728 | Pr—F | 2-NMe₃I, 4-Me | 2 |
| 10729 | Pr—F | 2-SnMe₃, 4-F | 2 |
| 10730 | Pr—F | 2-SnMe₃, 5-F | 2 |
| 10731 | Pr—F | 2-F, 4-SnMe₃ | 2 |
| 10732 | Pr—F | 2-Br, 6-Cl, 4-F | 2 |
| 10733 | Pr—F | 2-Br, 6-Cl, 4-NO₂ | 2 |
| 10734 | Pr—F | 2-Br, 6-Cl, 4-NH₂ | 2 |
| 10735 | Pr—F | 2-Br, 6-Cl, 4-NHMe | 2 |
| 10736 | Pr—F | 2-Br, 6-Cl, 4-NMe₂ | 2 |
| 10737 | Pr—F | 2-Br, 6-Cl, 4-NMeOTf | 2 |
| 10738 | Pr—F | 2-Br, 6-Cl, 4-NMe₃I | 2 |
| 10739 | Pr—F | 2-Me, 6-Cl, 4-F | 2 |
| 10740 | Pr—F | 2-SnMe₃, 6-Cl, 4-F | 2 |
| 10741 | Pr—F | 2-Cl, 4-Me | 2 |
| 10742 | Pr—F | 2-Cl, 4-Br | 2 |
| 10743 | Pr—F | 2-Cl, 4-SnMe₃ | 2 |
| 10744 | Pr—F | 2-Br, 4-Cl | 2 |
| 10745 | Pr—F | 2-SnMe₃, 4-Cl | 2 |
| 10746 | Pr—F | 2-Me, 4-Cl | 2 |
| 10747 | Pr—F | 2-Br, 4-Br | 2 |
| 10748 | Pr—F | 2-Br, 4-Me | 2 |
| 10749 | Pr—F | 2-Br, 4-SnMe₃ | 2 |
| 10750 | Pr—F | 2-SnMe₃, 4-Br | 2 |
| 10751 | Pr—F | 2-Me, 4-Br | 2 |
| 10752 | Pr—F | 2-Me, 4-SnMe₃ | 2 |
| 10753 | Pr—F | 2-SnMe₃, 4-Me | 2 |
| 10754 | Pr—F | 2-Me, 4-Me | 2 |
| 10755 | Pr—F | 2-Et, 4-Br | 2 |
| 10756 | Pr—F | 2-Et, 4-SnMe₃ | 2 |
| 10757 | Pr—F | 2-Et, 4-Me | 2 |
| 10758 | Pr—F | 2-Me, 4-Me, 6-Me | 2 |
| 10759 | Pr—F | 2-Me, 4-Br, 6-Me | 2 |
| 10760 | Pr—F | 2-Me, 4-SnMe₃, 6-Me | 2 |
| 10761 | Pr—F | 2-Et, 6-Me | 2 |
| 10762 | Pr—F | 2-Br, 4-i-Pr | 2 |
| 10763 | Pr—F | 2-SnMe₃, 4-i-Pr | 2 |
| 10764 | Pr—F | 2-Me, 4-i-Pr | 2 |
| 10765 | Pr—F | 2-Br, 4-Br, 6-Br | 2 |
| 10766 | Pr—F | 2-Br, 4-Me, 6-Br | 2 |
| 10767 | Pr—F | 2-Br, 4-SnMe₃, 6-Br | 2 |

TABLE 9-continued

Substituent list for compounds of general structure XIV.

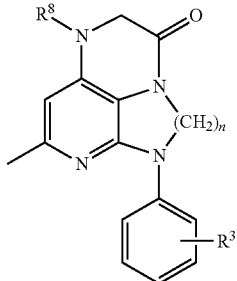

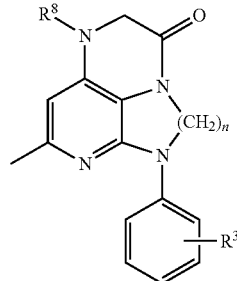

| Compound # | R8 = | R3 = | n = |
|---|---|---|---|
| 10768 | Pr—F | 2-SnMe3, 4-Br, 6-Br | 2 |
| 10769 | Pr—F | 2-Br, 4-Br, 6-Me | 2 |
| 10770 | Pr—F | 2-Br, 4-CF3, 6-Br | 2 |
| 10771 | Pr—F | 2-Br, 4-Br, 6-CF3 | 2 |
| 10772 | Pr—F | 2-CF3, 4-CF3 | 2 |
| 10773 | Pr—F | 2-Cl, 4-CF3 | 2 |
| 10774 | Pr—F | 2-CF3, 4-Cl | 2 |
| 10775 | Pr—F | 2-Br, 4-CF3 | 2 |
| 10776 | Pr—F | 2-SnMe3, 4-CF3 | 2 |
| 10777 | Pr—F | 2-Me, 4-CF3 | 2 |
| 10778 | Pr—F | 2-CF3, 4-Br | 2 |
| 10779 | Pr—F | 2-CF3, 4-SnMe3 | 2 |
| 10780 | Pr—F | 2-CF3, 4-Me | 2 |
| 10781 | Pr—F | 2-Br, 4-OH | 2 |
| 10782 | Pr—F | 2-Br, 4-OMe | 2 |
| 10783 | Pr—F | 2-Br, 4-OMeF | 2 |
| 10784 | Pr—F | 2-Br, 4-OCF3 | 2 |
| 10785 | Pr—F | 2-Br, 4-OEtF | 2 |
| 10786 | Pr—F | 2-Br, 4-OPrF | 2 |
| 10787 | Pr—F | 2-OH, 4-Br | 2 |
| 10788 | Pr—F | 2-OMe, 4-Br | 2 |
| 10789 | Pr—F | 2-OMeF, 4-Br | 2 |
| 10790 | Pr—F | 2-OCF3, 4-Br | 2 |
| 10791 | Pr—F | 2-OEtF, 4-Br | 2 |
| 10792 | Pr—F | 2-OPrF, 4-Br | 2 |
| 10793 | Pr—F | 2-I, 4-OH | 2 |
| 10794 | Pr—F | 2-I, 4-OMe | 2 |
| 10795 | Pr—F | 2-I, 4-OMeF | 2 |
| 10796 | Pr—F | 2-I, 4-OCF3 | 2 |
| 10797 | Pr—F | 2-I, 4-OEtF | 2 |
| 10798 | Pr—F | 2-I, 4-OPrF | 2 |
| 10799 | Pr—F | 2-OH, 4-I | 2 |
| 10800 | Pr—F | 2-OMe, 4-I | 2 |
| 10801 | Pr—F | 2-OMeF, 4-I | 2 |
| 10802 | Pr—F | 2-OCF3, 4-I | 2 |
| 10803 | Pr—F | 2-OEtF, 4-I | 2 |
| 10804 | Pr—F | 2-OPrF, 4-I | 2 |
| 10805 | Pr—F | 2-SnMe3, 4-OH | 2 |
| 10806 | Pr—F | 2-SnMe3, 4-OMe | 2 |
| 10807 | Pr—F | 2-SnMe3, 4-OMeF | 2 |
| 10808 | Pr—F | 2-SnMe3, 4-OCF3 | 2 |
| 10809 | Pr—F | 2-SnMe3, 4-OEtF | 2 |
| 10810 | Pr—F | 2-SnMe3, 4-OPrF | 2 |
| 10811 | Pr—F | 2-OH, 4-SnMe3 | 2 |
| 10812 | Pr—F | 2-OMe, 4-SnMe3 | 2 |
| 10813 | Pr—F | 2-OMeF, 4-SnMe3 | 2 |
| 10814 | Pr—F | 2-OCF3, 4-SnMe3 | 2 |
| 10815 | Pr—F | 2-OEtF, 4-SnMe3 | 2 |
| 10816 | Pr—F | 2-OPrF, 4-SnMe3 | 2 |
| 10817 | Et | H | 1 |
| 10818 | Et | 2-t-Bu | 1 |
| 10819 | Et | 2-Br | 1 |
| 10820 | Et | 3-Br | 1 |
| 10821 | Et | 4-Br | 1 |
| 10822 | Et | 2-I | 1 |
| 10823 | Et | 3-I | 1 |
| 10824 | Et | 4-I | 1 |
| 10825 | Et | 2-SnMe3 | 1 |
| 10826 | Et | 3-SnMe3 | 1 |
| 10827 | Et | 4-SnMe3 | 1 |
| 10828 | Et | 2-Me | 1 |
| 10829 | Et | 3-Me | 1 |
| 10830 | Et | 4-Me | 1 |
| 10831 | Et | 2-OH | 1 |
| 10832 | Et | 3-OH | 1 |
| 10833 | Et | 4-OH | 1 |
| 10834 | Et | 2-OMe | 1 |
| 10835 | Et | 3-OMe | 1 |
| 10836 | Et | 4-OMe | 1 |
| 10837 | Et | 2-OMeF | 1 |
| 10838 | Et | 3-OMeF | 1 |
| 10839 | Et | 4-OMeF | 1 |
| 10840 | Et | 2-OCF3 | 1 |
| 10841 | Et | 3-OCF3 | 1 |
| 10842 | Et | 4-OCF3 | 1 |
| 10843 | Et | 2-OEtF | 1 |
| 10844 | Et | 3-OEtF | 1 |
| 10845 | Et | 4-OEtF | 1 |
| 10846 | Et | 2-OPrF | 1 |
| 10847 | Et | 3-OPrF | 1 |
| 10848 | Et | 4-OPrF | 1 |
| 10849 | Et | 2-SH | 1 |
| 10850 | Et | 3-SH | 1 |
| 10851 | Et | 4-SH | 1 |
| 10852 | Et | 2-SMe | 1 |
| 10853 | Et | 3-SMe | 1 |
| 10854 | Et | 4-SMe | 1 |
| 10855 | Et | 2-SMeF | 1 |
| 10856 | Et | 3-SMeF | 1 |
| 10857 | Et | 4-SMeF | 1 |
| 10858 | Et | 2-SCF3 | 1 |
| 10859 | Et | 3-SCF3 | 1 |
| 10860 | Et | 4-SCF3 | 1 |
| 10861 | Et | 2-SEtF | 1 |
| 10862 | Et | 3-SEtF | 1 |
| 10863 | Et | 4-SEtF | 1 |
| 10864 | Et | 2-SPrF | 1 |
| 10865 | Et | 3-SPrF | 1 |
| 10866 | Et | 4-SPrF | 1 |
| 10867 | Et | 2-OMe, 4-OMe | 1 |
| 10868 | Et | 2-Me, 5-OH | 1 |
| 10869 | Et | 2-Me, 5-OMe | 1 |
| 10870 | Et | 2-Me, 5-OMeF | 1 |
| 10871 | Et | 2-Me, 5-OEtF | 1 |
| 10872 | Et | 2-Me, 5-OPrF | 1 |
| 10873 | Et | 2-Me, 4-OH | 1 |
| 10874 | Et | 2-Me, 4-OMe | 1 |
| 10875 | Et | 2-Me, 4-OMeF | 1 |
| 10876 | Et | 2-Me, 4-OCF3 | 1 |
| 10877 | Et | 2-Me, 4-OEtF | 1 |
| 10878 | Et | 2-Me, 4-OPrF | 1 |
| 10879 | Et | 2-OH, 4-Me | 1 |
| 10880 | Et | 2-OMe, 4-Me | 1 |
| 10881 | Et | 2-OMeF, 4-Me | 1 |
| 10882 | Et | 2-OCF3, 4-Me | 1 |
| 10883 | Et | 2-OEtF, 4-Me | 1 |
| 10884 | Et | 2-OPrF, 4-Me | 1 |
| 10885 | Et | 2-Cl, 4-OH | 1 |
| 10886 | Et | 2-Cl, 4-OMe | 1 |
| 10887 | Et | 2-Cl, 4-OMeF | 1 |

TABLE 9-continued

Substituent list for compounds of general structure XIV.

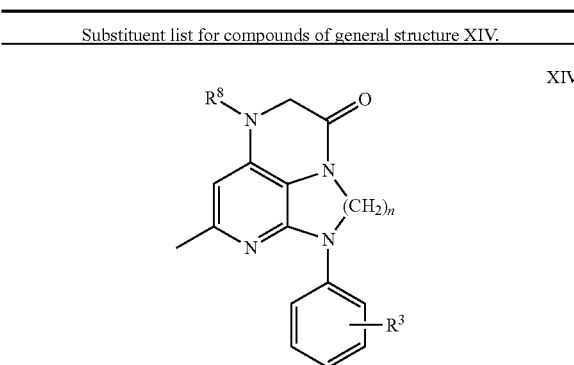

| Compound # | R⁸ = | R³ = | n = |
|---|---|---|---|
| 10888 | Et | 2-Cl, 4-OCF₃ | 1 |
| 10889 | Et | 2-Cl, 4-OEtF | 1 |
| 10890 | Et | 2-Cl, 4-OPrF | 1 |
| 10891 | Et | 2-F, 4-F | 1 |
| 10892 | Et | 2-Cl, 4-Cl | 1 |
| 10893 | Et | 2-Cl, 4-F | 1 |
| 10894 | Et | 2-Cl, 4-NO₂ | 1 |
| 10895 | Et | 2-Cl, 4-NH₂ | 1 |
| 10896 | Et | 2-Cl, 4-NHMe | 1 |
| 10897 | Et | 2-Cl, 4-NMe₂ | 1 |
| 10898 | Et | 2-Cl, 4-NMe₃OTf | 1 |
| 10899 | Et | 2-Cl, 4-NMe₃I | 1 |
| 10900 | Et | 2-Cl, 5-F | 1 |
| 10901 | Et | 2-Cl, 5-NO₂ | 1 |
| 10902 | Et | 2-Cl, 5-NH₂ | 1 |
| 10903 | Et | 2-Cl, 5-NHMe | 1 |
| 10904 | Et | 2-Cl, 5-NMe₂ | 1 |
| 10905 | Et | 2-Cl, 5-NMe₃OTf | 1 |
| 10906 | Et | 2-Cl, 5-NMe₃I | 1 |
| 10907 | Et | 2-F, 4-Cl | 1 |
| 10908 | Et | 2-NO₂, 4-Cl | 1 |
| 10909 | Et | 2-NH₂, 4-Cl | 1 |
| 10910 | Et | 2-NHMe, 4-Cl | 1 |
| 10911 | Et | 2-NMe₂, 4-Cl | 1 |
| 10912 | Et | 2-NMe₃OTf, 4-Cl | 1 |
| 10913 | Et | 2-NMe₃I, 4-Cl | 1 |
| 10914 | Et | 2-F, 5-Cl | 1 |
| 10915 | Et | 2-NO₂, 5-Cl | 1 |
| 10916 | Et | 2-NH₂, 5-Cl | 1 |
| 10917 | Et | 2-NHMe, 5-Cl | 1 |
| 10918 | Et | 2-NMe₂, 5-Cl | 1 |
| 10919 | Et | 2-NMe₃OTf, 5-Cl | 1 |
| 10920 | Et | 2-NMe₃I, 5-Cl | 1 |
| 10921 | Et | 2-Br, 4-F | 1 |
| 10922 | Et | 2-Br, 4-NO₂ | 1 |
| 10923 | Et | 2-Br, 4-NH₂ | 1 |
| 10924 | Et | 2-Br, 4-NHMe | 1 |
| 10925 | Et | 2-Br, 4-NMe₂ | 1 |
| 10926 | Et | 2-Br, 4-NMe₃OTf | 1 |
| 10927 | Et | 2-Br, 4-NMe₃I | 1 |
| 10928 | Et | 2-Br, 5-F | 1 |
| 10929 | Et | 2-Br, 5-NO₂ | 1 |
| 10930 | Et | 2-Br, 5-NH₂ | 1 |
| 10931 | Et | 2-Br, 5-NHMe | 1 |
| 10932 | Et | 2-Br, 5-NMe₂ | 1 |
| 10933 | Et | 2-Br, 5-NMe₃OTf | 1 |
| 10934 | Et | 2-Br, 5-NMe₃I | 1 |
| 10935 | Et | 2-F, 4-Br | 1 |
| 10936 | Et | 2-NO₂, 4-Br | 1 |
| 10937 | Et | 2-NH₂, 4-Br | 1 |
| 10938 | Et | 2-NHMe, 4-Br | 1 |
| 10939 | Et | 2-NMe₂, 4-Br | 1 |
| 10940 | Et | 2-NMe₃OTf, 4-Br | 1 |
| 10941 | Et | 2-NMe₃I, 4-Br | 1 |
| 10942 | Et | 2-I, 4-F | 1 |
| 10943 | Et | 2-I, 4-NO₂ | 1 |
| 10944 | Et | 2-I, 4-NH₂ | 1 |
| 10945 | Et | 2-I, 4-NHMe | 1 |
| 10946 | Et | 2-I, 4-NMe₂ | 1 |
| 10947 | Et | 2-I, 4-NMe₃OTf | 1 |
| 10948 | Et | 2-I, 4-NMe₃I | 1 |
| 10949 | Et | 2-F, 4-I | 1 |
| 10950 | Et | 2-NO₂, 4-I | 1 |
| 10951 | Et | 2-NH₂, 4-I | 1 |
| 10952 | Et | 2-NHMe, 4-I | 1 |
| 10953 | Et | 2-NMe₂, 4-I | 1 |
| 10954 | Et | 2-NMe₃OTf, 4-I | 1 |
| 10955 | Et | 2-NMe₃I, 4-I | 1 |
| 10956 | Et | 2-Me, 3-F | 1 |
| 10957 | Et | 2-Me, 3-NO₂ | 1 |
| 10958 | Et | 2-Me, 3-NH₂ | 1 |
| 10959 | Et | 2-Me, 3-NHMe | 1 |
| 10960 | Et | 2-Me, 3-NMe₂ | 1 |
| 10961 | Et | 2-Me, 3-NMe₃OTf | 1 |
| 10962 | Et | 2-Me, 3-NMe₃I | 1 |
| 10963 | Et | 2-Me, 4-F | 1 |
| 10964 | Et | 2-Me, 4-NO₂ | 1 |
| 10965 | Et | 2-Me, 4-NH₂ | 1 |
| 10966 | Et | 2-Me, 4-NHMe | 1 |
| 10967 | Et | 2-Me, 4-NMe₂ | 1 |
| 10968 | Et | 2-Me, 4-NMe₃OTf | 1 |
| 10969 | Et | 2-Me, 4-NMe₃I | 1 |
| 10970 | Et | 2-Me, 5-F | 1 |
| 10971 | Et | 2-Me, 5-NO₂ | 1 |
| 10972 | Et | 2-Me, 5-NH₂ | 1 |
| 10973 | Et | 2-Me, 5-NHMe | 1 |
| 10974 | Et | 2-Me, 5-NMe₂ | 1 |
| 10975 | Et | 2-Me, 5-NMe₃OTf | 1 |
| 10976 | Et | 2-Me, 5-NMe₃I | 1 |
| 10977 | Et | 2-F, 4-Me | 1 |
| 10978 | Et | 2-NO₂, 4-Me | 1 |
| 10979 | Et | 2-NH₂, 4-Me | 1 |
| 10980 | Et | 2-NHMe, 4-Me | 1 |
| 10981 | Et | 2-NMe₂, 4-Me | 1 |
| 10982 | Et | 2-NMe₃, 4-Me | 1 |
| 10983 | Et | 2-NMe₃OTf, 4-Me | 1 |
| 10984 | Et | 2-NMe₃I, 4-Me | 1 |
| 10985 | Et | 2-SnMe₃, 4-F | 1 |
| 10986 | Et | 2-SnMe₃, 5-F | 1 |
| 10987 | Et | 2-F, 4-SnMe₃ | 1 |
| 10988 | Et | 2-Br, 6-Cl, 4-F | 1 |
| 10989 | Et | 2-Br, 6-Cl, 4-NO₂ | 1 |
| 10990 | Et | 2-Br, 6-Cl, 4-NH₂ | 1 |
| 10991 | Et | 2-Br, 6-Cl, 4-NHMe | 1 |
| 10992 | Et | 2-Br, 6-Cl, 4-NMe₂ | 1 |
| 10993 | Et | 2-Br, 6-Cl, 4-NMe₃OTf | 1 |
| 10994 | Et | 2-Br, 6-Cl, 4-NMe₃I | 1 |
| 10995 | Et | 2-Me, 6-Cl, 4-F | 1 |
| 10996 | Et | 2-SnMe₃, 6-Cl, 4-F | 1 |
| 10997 | Et | 2-Cl, 4-Me | 1 |
| 10998 | Et | 2-Cl, 4-Br | 1 |
| 10999 | Et | 2-Cl, 4-SnMe₃ | 1 |
| 11000 | Et | 2-Br, 4-Cl | 1 |
| 11001 | Et | 2-SnMe₃, 4-Cl | 1 |
| 11002 | Et | 2-Me, 4-Cl | 1 |
| 11003 | Et | 2-Br, 4-Br | 1 |
| 11004 | Et | 2-Br, 4-Me | 1 |
| 11005 | Et | 2-Br, 4-SnMe₃ | 1 |
| 11006 | Et | 2-SnMe₃, 4-Br | 1 |
| 11007 | Et | 2-Me, 4-Br | 1 |

TABLE 9-continued

Substituent list for compounds of general structure XIV.

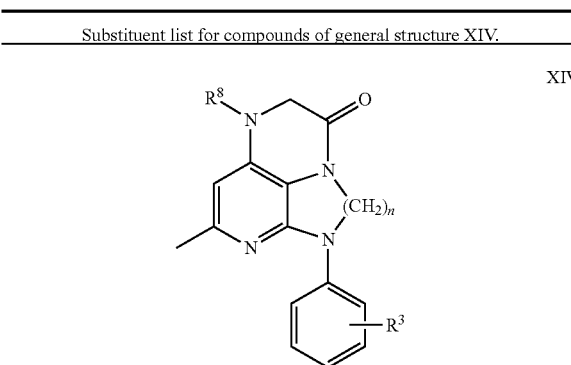

XIV

| Compound # | R⁸ = | R³ = | n = |
|---|---|---|---|
| 11008 | Et | 2-Me, 4-SnMe₃ | 1 |
| 11009 | Et | 2-SnMe₃, 4-Me | 1 |
| 11010 | Et | 2-Me, 4-Me | 1 |
| 11011 | Et | 2-Et, 4-Br | 1 |
| 11012 | Et | 2-Et, 4-SnMe₃ | 1 |
| 11013 | Et | 2-Et, 4-Me | 1 |
| 11014 | Et | 2-Me, 4-Me, 6-Me | 1 |
| 11015 | Et | 2-Me, 4-Br, 6-Me | 1 |
| 11016 | Et | 2-Me, 4-SnMe₃, 6-Me | 1 |
| 11017 | Et | 2-Et, 6-Me | 1 |
| 11018 | Et | 2-Br, 4-i-Pr | 1 |
| 11019 | Et | 2-SnMe₃, 4-i-Pr | 1 |
| 11020 | Et | 2-Me, 4-i-Pr | 1 |
| 11021 | Et | 2-Br, 4-Br, 6-Br | 1 |
| 11022 | Et | 2-Br, 4-Me, 6-Br | 1 |
| 11023 | Et | 2-Br, 4-SnMe₃, 6-Br | 1 |
| 11024 | Et | 2-SnMe₃, 4-Br, 6-Br | 1 |
| 11025 | Et | 2-Br, 4-Br, 6-Me | 1 |
| 11026 | Et | 2-Br, 4-CF₃, 6-Br | 1 |
| 11027 | Et | 2-Br, 4-Br, 6-CF₃ | 1 |
| 11028 | Et | 2-CF₃, 4-CF₃ | 1 |
| 11029 | Et | 2-Cl, 4-CF₃ | 1 |
| 11030 | Et | 2-CF₃, 4-Cl | 1 |
| 11031 | Et | 2-Br, 4-CF₃ | 1 |
| 11032 | Et | 2-SnMe₃, 4-CF₃ | 1 |
| 11033 | Et | 2-Me, 4-CF₃ | 1 |
| 11034 | Et | 2-CF₃, 4-Br | 1 |
| 11035 | Et | 2-CF₃, 4-SnMe₃ | 1 |
| 11036 | Et | 2-CF₃, 4-Me | 1 |
| 11037 | Et | 2-Br, 4-OH | 1 |
| 11038 | Et | 2-Br, 4-OMe | 1 |
| 11039 | Et | 2-Br, 4-OMeF | 1 |
| 11040 | Et | 2-Br, 4-OCF₃ | 1 |
| 11041 | Et | 2-Br, 4-OEtF | 1 |
| 11042 | Et | 2-Br, 4-OPrF | 1 |
| 11043 | Et | 2-OH, 4-Br | 1 |
| 11044 | Et | 2-OMe, 4-Br | 1 |
| 11045 | Et | 2-OMeF, 4-Br | 1 |
| 11046 | Et | 2-OCF₃, 4-Br | 1 |
| 11047 | Et | 2-OEtF, 4-Br | 1 |
| 11048 | Et | 2-OPrF, 4-Br | 1 |
| 11049 | Et | 2-I, 4-OH | 1 |
| 11050 | Et | 2-I, 4-OMe | 1 |
| 11051 | Et | 2-I, 4-OMeF | 1 |
| 11052 | Et | 2-I, 4-OCF₃ | 1 |
| 11053 | Et | 2-I, 4-OEtF | 1 |
| 11054 | Et | 2-I, 4-OPrF | 1 |
| 11055 | Et | 2-OH, 4-I | 1 |
| 11056 | Et | 2-OMe, 4-I | 1 |
| 11057 | Et | 2-OMeF, 4-I | 1 |
| 11058 | Et | 2-OCF₃, 4-I | 1 |
| 11059 | Et | 2-OEtF, 4-I | 1 |
| 11060 | Et | 2-OPrF, 4-I | 1 |
| 11061 | Et | 2-SnMe₃, 4-OH | 1 |
| 11062 | Et | 2-SnMe₃, 4-OMe | 1 |
| 11063 | Et | 2-SnMe₃, 4-OMeF | 1 |
| 11064 | Et | 2-SnMe₃, 4-OCF₃ | 1 |
| 11065 | Et | 2-SnMe₃, 4-OEtF | 1 |
| 11066 | Et | 2-SnMe₃, 4-OPrF | 1 |
| 11067 | Et | 2-OH, 4-SnMe₃ | 1 |
| 11068 | Et | 2-OMe, 4-SnMe₃ | 1 |
| 11069 | Et | 2-OMeF, 4-SnMe₃ | 1 |
| 11070 | Et | 2-OCF₃, 4-SnMe₃ | 1 |
| 11071 | Et | 2-OEtF, 4-SnMe₃ | 1 |
| 11072 | Et | 2-OPrF, 4-SnMe₃ | 1 |
| 11073 | Et | H | 2 |
| 11074 | Et | 2-t-Bu | 2 |
| 11075 | Et | 2-Br | 2 |
| 11076 | Et | 3-Br | 2 |
| 11077 | Et | 4-Br | 2 |
| 11078 | Et | 2-I | 2 |
| 11079 | Et | 3-I | 2 |
| 11080 | Et | 4-I | 2 |
| 11081 | Et | 2-SnMe₃ | 2 |
| 11082 | Et | 3-SnMe₃ | 2 |
| 11083 | Et | 4-SnMe₃ | 2 |
| 11084 | Et | 2-Me | 2 |
| 11085 | Et | 3-Me | 2 |
| 11086 | Et | 4-Me | 2 |
| 11087 | Et | 2-OH | 2 |
| 11088 | Et | 3-OH | 2 |
| 11089 | Et | 4-OH | 2 |
| 11090 | Et | 2-OMe | 2 |
| 11091 | Et | 3-OMe | 2 |
| 11092 | Et | 4-OMe | 2 |
| 11093 | Et | 2-OMeF | 2 |
| 11094 | Et | 3-OMeF | 2 |
| 11095 | Et | 4-OMeF | 2 |
| 11096 | Et | 2-OCF₃ | 2 |
| 11097 | Et | 3-OCF₃ | 2 |
| 11098 | Et | 4-OCF₃ | 2 |
| 11099 | Et | 2-OEtF | 2 |
| 11100 | Et | 3-OEtF | 2 |
| 11101 | Et | 4-OEtF | 2 |
| 11102 | Et | 2-OPrF | 2 |
| 11103 | Et | 3-OPrF | 2 |
| 11104 | Et | 4-OPrF | 2 |
| 11105 | Et | 2-SH | 2 |
| 11106 | Et | 3-SH | 2 |
| 11107 | Et | 4-SH | 2 |
| 11108 | Et | 2-SMe | 2 |
| 11109 | Et | 3-SMe | 2 |
| 11110 | Et | 4-SMe | 2 |
| 11111 | Et | 2-SMeF | 2 |
| 11112 | Et | 3-SMeF | 2 |
| 11113 | Et | 4-SMeF | 2 |
| 11114 | Et | 2-SCF₃ | 2 |
| 11115 | Et | 3-SCF₃ | 2 |
| 11116 | Et | 4-SCF₃ | 2 |
| 11117 | Et | 2-SEtF | 2 |
| 11118 | Et | 3-SEtF | 2 |
| 11119 | Et | 4-SEtF | 2 |
| 11120 | Et | 2-SPrF | 2 |
| 11121 | Et | 3-SPrF | 2 |
| 11122 | Et | 4-SPrF | 2 |
| 11123 | Et | 2-OMe, 4-OMe | 2 |
| 11124 | Et | 2-Me, 5-OH | 2 |
| 11125 | Et | 2-Me, 5-OMe | 2 |
| 11126 | Et | 2-Me, 5-OMeF | 2 |
| 11127 | Et | 2-Me, 5-OEtF | 2 |

TABLE 9-continued

Substituent list for compounds of general structure XIV.

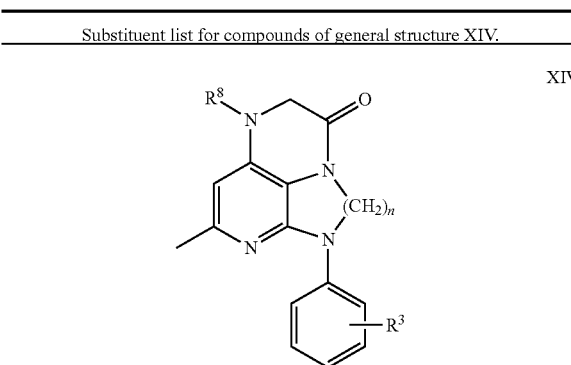

| Compound # | R$^8$ = | R$^3$ = | n = |
|---|---|---|---|
| 11128 | Et | 2-Me, 5-OPrF | 2 |
| 11129 | Et | 2-Me, 4-OH | 2 |
| 11130 | Et | 2-Me, 4-OMe | 2 |
| 11131 | Et | 2-Me, 4-OMeF | 2 |
| 11132 | Et | 2-Me, 4-OCF$_3$ | 2 |
| 11133 | Et | 2-Me, 4-OEtF | 2 |
| 11134 | Et | 2-Me, 4-OPrF | 2 |
| 11135 | Et | 2-OH, 4-Me | 2 |
| 11136 | Et | 2-OMe, 4-Me | 2 |
| 11137 | Et | 2-OMeF, 4-Me | 2 |
| 11138 | Et | 2-OCF$_3$, 4-Me | 2 |
| 11139 | Et | 2-OEtF, 4-Me | 2 |
| 11140 | Et | 2-OPrF, 4-Me | 2 |
| 11141 | Et | 2-Cl, 4-OH | 2 |
| 11142 | Et | 2-Cl, 4-OMe | 2 |
| 11143 | Et | 2-Cl, 4-OMeF | 2 |
| 11144 | Et | 2-Cl, 4-OCF$_3$ | 2 |
| 11145 | Et | 2-Cl, 4-OEtF | 2 |
| 11146 | Et | 2-Cl, 4-OPrF | 2 |
| 11147 | Et | 2-F, 4-F | 2 |
| 11148 | Et | 2-Cl, 4-Cl | 2 |
| 11149 | Et | 2-Cl, 4-F | 2 |
| 11150 | Et | 2-Cl, 4-NO$_2$ | 2 |
| 11151 | Et | 2-Cl, 4-NH$_2$ | 2 |
| 11152 | Et | 2-Cl, 4-NHMe | 2 |
| 11153 | Et | 2-Cl, 4-NMe$_2$ | 2 |
| 11154 | Et | 2-Cl, 4-NMe$_3$OTf | 2 |
| 11155 | Et | 2-Cl, 4-NMe$_3$I | 2 |
| 11156 | Et | 2-Cl, 5-F | 2 |
| 11157 | Et | 2-Cl, 5-NO$_2$ | 2 |
| 11158 | Et | 2-Cl, 5-NH$_2$ | 2 |
| 11159 | Et | 2-Cl, 5-NHMe | 2 |
| 11160 | Et | 2-Cl, 5-NMe$_2$ | 2 |
| 11161 | Et | 2-Cl, 5-NMe$_3$OTf | 2 |
| 11162 | Et | 2-Cl, 5-NMe$_3$I | 2 |
| 11163 | Et | 2-F, 4-Cl | 2 |
| 11164 | Et | 2-NO$_2$, 4-Cl | 2 |
| 11165 | Et | 2-NH$_2$, 4-Cl | 2 |
| 11166 | Et | 2-NHMe, 4-Cl | 2 |
| 11167 | Et | 2-NMe$_2$, 4-Cl | 2 |
| 11168 | Et | 2-NMe$_3$OTf, 4-Cl | 2 |
| 11169 | Et | 2-NMe$_3$I, 4-Cl | 2 |
| 11170 | Et | 2-F, 5-Cl | 2 |
| 11171 | Et | 2-NO$_2$, 5-Cl | 2 |
| 11172 | Et | 2-NH$_2$, 5-Cl | 2 |
| 11173 | Et | 2-NHMe, 5-Cl | 2 |
| 11174 | Et | 2-NMe$_2$, 5-Cl | 2 |
| 11175 | Et | 2-NMe$_3$OTf, 5-Cl | 2 |
| 11176 | Et | 2-NMe$_3$I, 5-Cl | 2 |
| 11177 | Et | 2-Br, 4-F | 2 |
| 11178 | Et | 2-Br, 4-NO$_2$ | 2 |
| 11179 | Et | 2-Br, 4-NH$_2$ | 2 |
| 11180 | Et | 2-Br, 4-NHMe | 2 |
| 11181 | Et | 2-Br, 4-NMe$_2$ | 2 |
| 11182 | Et | 2-Br, 4-NMe$_3$OTf | 2 |
| 11183 | Et | 2-Br, 4-NMe$_3$I | 2 |
| 11184 | Et | 2-Br, 5-F | 2 |
| 11185 | Et | 2-Br, 5-NO$_2$ | 2 |
| 11186 | Et | 2-Br, 5-NH$_2$ | 2 |
| 11187 | Et | 2-Br, 5-NHMe | 2 |
| 11188 | Et | 2-Br, 5-NMe$_2$ | 2 |
| 11189 | Et | 2-Br, 5-NMe$_3$OTf | 2 |
| 11190 | Et | 2-Br, 5-NMe$_3$I | 2 |
| 11191 | Et | 2-F, 4-Br | 2 |
| 11192 | Et | 2-NO$_2$, 4-Br | 2 |
| 11193 | Et | 2-NH$_2$, 4-Br | 2 |
| 11194 | Et | 2-NHMe, 4-Br | 2 |
| 11195 | Et | 2-NMe$_2$, 4-Br | 2 |
| 11196 | Et | 2-NMe$_3$OTf, 4-Br | 2 |
| 11197 | Et | 2-NMe$_3$I, 4-Br | 2 |
| 11198 | Et | 2-I, 4-F | 2 |
| 11199 | Et | 2-I, 4-NO$_2$ | 2 |
| 11200 | Et | 2-I, 4-NH$_2$ | 2 |
| 11201 | Et | 2-I, 4-NHMe | 2 |
| 11202 | Et | 2-I, 4-NMe$_2$ | 2 |
| 11203 | Et | 2-I, 4-NMe$_3$OTf | 2 |
| 11204 | Et | 2-I, 4-NMe$_3$I | 2 |
| 11205 | Et | 2-F, 4-I | 2 |
| 11206 | Et | 2-NO$_2$, 4-I | 2 |
| 11207 | Et | 2-NH$_2$, 4-I | 2 |
| 11208 | Et | 2-NHMe, 4-I | 2 |
| 11209 | Et | 2-NMe$_2$, 4-I | 2 |
| 11210 | Et | 2-NMe$_3$OTf, 4-I | 2 |
| 11211 | Et | 2-NMe$_3$I, 4-I | 2 |
| 11212 | Et | 2-Me, 3-F | 2 |
| 11213 | Et | 2-Me, 3-NO$_2$ | 2 |
| 11214 | Et | 2-Me, 3-NH$_2$ | 2 |
| 11215 | Et | 2-Me, 3-NHMe | 2 |
| 11216 | Et | 2-Me, 3-NMe$_2$ | 2 |
| 11217 | Et | 2-Me, 3-NMe$_3$OTf | 2 |
| 11218 | Et | 2-Me, 3-NMe$_3$I | 2 |
| 11219 | Et | 2-Me, 4-F | 2 |
| 11220 | Et | 2-Me, 4-NO$_2$ | 2 |
| 11221 | Et | 2-Me, 4-NH$_2$ | 2 |
| 11222 | Et | 2-Me, 4-NHMe | 2 |
| 11223 | Et | 2-Me, 4-NMe$_2$ | 2 |
| 11224 | Et | 2-Me, 4-NMe$_3$OTf | 2 |
| 11225 | Et | 2-Me, 4-NMe$_3$I | 2 |
| 11226 | Et | 2-Me, 5-F | 2 |
| 11227 | Et | 2-Me, 5-NO$_2$ | 2 |
| 11228 | Et | 2-Me, 5-NH$_2$ | 2 |
| 11229 | Et | 2-Me, 5-NHMe | 2 |
| 11230 | Et | 2-Me, 5-NMe$_2$ | 2 |
| 11231 | Et | 2-Me, 5-NMe$_3$OTf | 2 |
| 11232 | Et | 2-Me, 5-NMe$_3$I | 2 |
| 11233 | Et | 2-F, 4-Me | 2 |
| 11234 | Et | 2-NO$_2$, 4-Me | 2 |
| 11235 | Et | 2-NH$_2$, 4-Me | 2 |
| 11236 | Et | 2-NHMe, 4-Me | 2 |
| 11237 | Et | 2-NMe$_2$, 4-Me | 2 |
| 11238 | Et | 2-NMe$_3$, 4-Me | 2 |
| 11239 | Et | 2-NMe$_3$OTf, 4-Me | 2 |
| 11240 | Et | 2-NMe$_3$I, 4-Me | 2 |
| 11241 | Et | 2-SnMe$_3$, 4-F | 2 |
| 11242 | Et | 2-SnMe$_3$, 5-F | 2 |
| 11243 | Et | 2-F, 4-SnMe$_3$ | 2 |
| 11244 | Et | 2-Br, 6-Cl, 4-F | 2 |
| 11245 | Et | 2-Br, 6-Cl, 4-NO$_2$ | 2 |
| 11246 | Et | 2-Br, 6-Cl, 4-NH$_2$ | 2 |
| 11247 | Et | 2-Br, 6-Cl, 4-NHMe | 2 |

TABLE 9-continued

Substituent list for compounds of general structure XIV.

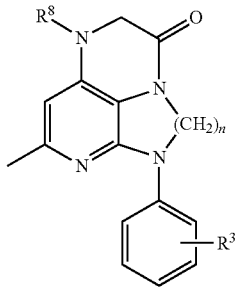

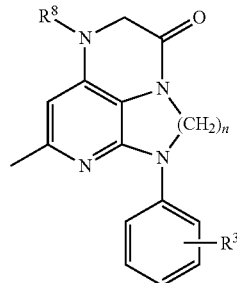

| Compound # | R[8] = | R[3] = | n = |
|---|---|---|---|
| 11248 | Et | 2-Br, 6-Cl, 4-NMe$_2$ | 2 |
| 11249 | Et | 2-Br, 6-Cl, 4NMe$_3$OTf | 2 |
| 11250 | Et | 2-Br, 6-Cl, 4-NMe$_3$I | 2 |
| 11251 | Et | 2-Me, 6-Cl, 4-F | 2 |
| 11252 | Et | 2-SnMe$_3$, 6-Cl, 4-F | 2 |
| 11253 | Et | 2-Cl, 4-Me | 2 |
| 11254 | Et | 2-Cl, 4-Br | 2 |
| 11255 | Et | 2-Cl, 4-SnMe$_3$ | 2 |
| 11256 | Et | 2-Br, 4-Cl | 2 |
| 11257 | Et | 2-SnMe$_3$, 4-Cl | 2 |
| 11258 | Et | 2-Me, 4-Cl | 2 |
| 11259 | Et | 2-Br, 4-Br | 2 |
| 11260 | Et | 2-Br, 4-Me | 2 |
| 11261 | Et | 2-Br, 4-SnMe$_3$ | 2 |
| 11262 | Et | 2-SnMe$_3$, 4-Br | 2 |
| 11263 | Et | 2-Me, 4-Br | 2 |
| 11264 | Et | 2-Me, 4-SnMe$_3$ | 2 |
| 11265 | Et | 2-SnMe$_3$, 4-Me | 2 |
| 11266 | Et | 2-Me, 4-Me | 2 |
| 11267 | Et | 2-Et, 4-Br | 2 |
| 11268 | Et | 2-Et, 4-SnMe$_3$ | 2 |
| 11269 | Et | 2-Et, 4-Me | 2 |
| 11270 | Et | 2-Me, 4-Me, 6-Me | 2 |
| 11271 | Et | 2-Me, 4-Br, 6-Me | 2 |
| 11272 | Et | 2-Me, 4-SnMe$_3$, 6-Me | 2 |
| 11273 | Et | 2-Et, 6-Me | 2 |
| 11274 | Et | 2-Br, 4-i-Pr | 2 |
| 11275 | Et | 2-SnMe$_3$, 4-i-Pr | 2 |
| 11276 | Et | 2-Me, 4-i-Pr | 2 |
| 11277 | Et | 2-Br, 4-Br, 6-Br | 2 |
| 11278 | Et | 2-Br, 4-Me, 6-Br | 2 |
| 11279 | Et | 2-Br, 4-SnMe$_3$, 6-Br | 2 |
| 11280 | Et | 2-SnMe$_3$, 4-Br, 6-Br | 2 |
| 11281 | Et | 2-Br, 4-Br, 6-Me | 2 |
| 11282 | Et | 2-Br, 4-CF$_3$, 6-Br | 2 |
| 11283 | Et | 2-Br, 4-Br, 6-CF$_3$ | 2 |
| 11284 | Et | 2-CF$_3$, 4-CF$_3$ | 2 |
| 11285 | Et | 2-Cl, 4-CF$_3$ | 2 |
| 11286 | Et | 2-CF$_3$, 4-Cl | 2 |
| 11287 | Et | 2-Br, 4-CF$_3$ | 2 |
| 11288 | Et | 2-SnMe$_3$, 4-CF$_3$ | 2 |
| 11289 | Et | 2-Me, 4-CF$_3$ | 2 |
| 11290 | Et | 2-CF$_3$, 4-Br | 2 |
| 11291 | Et | 2-CF$_3$, 4-SnMe$_3$ | 2 |
| 11292 | Et | 2-CF$_3$, 4-Me | 2 |
| 11293 | Et | 2-Br, 4-OH | 2 |
| 11294 | Et | 2-Br, 4-OMe | 2 |
| 11295 | Et | 2-Br, 4-OMeF | 2 |
| 11296 | Et | 2-Br, 4-OCF$_3$ | 2 |
| 11297 | Et | 2-Br, 4-OEtF | 2 |
| 11298 | Et | 2-Br, 4-OPrF | 2 |
| 11299 | Et | 2-OH, 4-Br | 2 |
| 11300 | Et | 2-OMe, 4-Br | 2 |
| 11301 | Et | 2-OMeF, 4-Br | 2 |
| 11302 | Et | 2-OCF$_3$, 4-Br | 2 |
| 11303 | Et | 2-OEtF, 4-Br | 2 |
| 11304 | Et | 2-OPrF, 4-Br | 2 |
| 11305 | Et | 2-I, 4-OH | 2 |
| 11306 | Et | 2-I, 4-OMe | 2 |
| 11307 | Et | 2-I, 4-OMeF | 2 |
| 11308 | Et | 2-I, 4-OCF$_3$ | 2 |
| 11309 | Et | 2-I, 4-OEtF | 2 |
| 11310 | Et | 2-I, 4-OPrF | 2 |
| 11311 | Et | 2-OH, 4-I | 2 |
| 11312 | Et | 2-OMe, 4-I | 2 |
| 11313 | Et | 2-OMeF, 4-I | 2 |
| 11314 | Et | 2-OCF$_3$, 4-I | 2 |
| 11315 | Et | 2-OEtF, 4-I | 2 |
| 11316 | Et | 2-OPrF, 4-I | 2 |
| 11317 | Et | 2-SnMe$_3$, 4-OH | 2 |
| 11318 | Et | 2-SnMe$_3$, 4-OMe | 2 |
| 11319 | Et | 2-SnMe$_3$, 4-OMeF | 2 |
| 11320 | Et | 2-SnMe$_3$, 4-OCF$_3$ | 2 |
| 11321 | Et | 2-SnMe$_3$, 4-OEtF | 2 |
| 11322 | Et | 2-SnMe$_3$, 4-OPrF | 2 |
| 11323 | Et | 2-OH, 4-SnMe$_3$ | 2 |
| 11324 | Et | 2-OMe, 4-SnMe$_3$ | 2 |
| 11325 | Et | 2-OMeF, 4-SnMe$_3$ | 2 |
| 11326 | Et | 2-OCF$_3$, 4-SnMe$_3$ | 2 |
| 11327 | Et | 2-OEtF, 4-SnMe$_3$ | 2 |
| 11328 | Et | 2-OPrF, 4-SnMe$_3$ | 2 |
| 11329 | Et—F | H | 1 |
| 11330 | Et—F | 2-t-Bu | 1 |
| 11331 | Et—F | 2-Br | 1 |
| 11332 | Et—F | 3-Br | 1 |
| 11333 | Et—F | 4-Br | 1 |
| 11334 | Et—F | 2-I | 1 |
| 11335 | Et—F | 3-I | 1 |
| 11336 | Et—F | 4-I | 1 |
| 11337 | Et—F | 2-SnMe$_3$ | 1 |
| 11338 | Et—F | 3-SnMe$_3$ | 1 |
| 11339 | Et—F | 4-SnMe$_3$ | 1 |
| 11340 | Et—F | 2-Me | 1 |
| 11341 | Et—F | 3-Me | 1 |
| 11342 | Et—F | 4-Me | 1 |
| 11343 | Et—F | 2-OH | 1 |
| 11344 | Et—F | 3-OH | 1 |
| 11345 | Et—F | 4-OH | 1 |
| 11346 | Et—F | 2-OMe | 1 |
| 11347 | Et—F | 3-OMe | 1 |
| 11348 | Et—F | 4-OMe | 1 |
| 11349 | Et—F | 2-OMeF | 1 |
| 11350 | Et—F | 3-OMeF | 1 |
| 11351 | Et—F | 4-OMeF | 1 |
| 11352 | Et—F | 2-OCF$_3$ | 1 |
| 11353 | Et—F | 3-OCF$_3$ | 1 |
| 11354 | Et—F | 4-OCF$_3$ | 1 |
| 11355 | Et—F | 2-OEtF | 1 |
| 11356 | Et—F | 3-OEtF | 1 |
| 11357 | Et—F | 4-OEtF | 1 |
| 11358 | Et—F | 2-OPrF | 1 |
| 11359 | Et—F | 3-OPrF | 1 |
| 11360 | Et—F | 4-OPrF | 1 |
| 11361 | Et—F | 2-SH | 1 |
| 11362 | Et—F | 3-SH | 1 |
| 11363 | Et—F | 4-SH | 1 |
| 11364 | Et—F | 2-SMe | 1 |
| 11365 | Et—F | 3-SMe | 1 |
| 11366 | Et—F | 4-SMe | 1 |
| 11367 | Et—F | 2-SMeF | 1 |

TABLE 9-continued

Substituent list for compounds of general structure XIV.

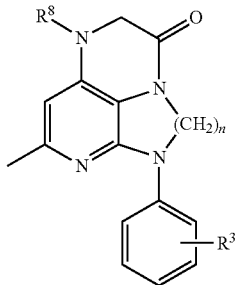

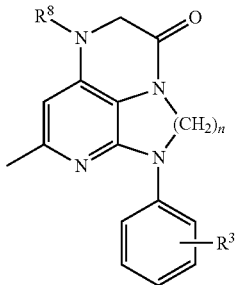

| Compound # | R⁸ = | R³ = | n = |
|---|---|---|---|
| 11368 | Et—F | 3-SMeF | 1 |
| 11369 | Et—F | 4-SMeF | 1 |
| 11370 | Et—F | 2-SCF$_3$ | 1 |
| 11371 | Et—F | 3-SCF$_3$ | 1 |
| 11372 | Et—F | 4-SCF$_3$ | 1 |
| 11373 | Et—F | 2-SEtF | 1 |
| 11374 | Et—F | 3-SEtF | 1 |
| 11375 | Et—F | 4-SEtF | 1 |
| 11376 | Et—F | 2-SPrF | 1 |
| 11377 | Et—F | 3-SPrF | 1 |
| 11378 | Et—F | 4-SPrF | 1 |
| 11379 | Et—F | 2-OMe, 4-OMe | 1 |
| 11380 | Et—F | 2-Me, 5-OH | 1 |
| 11381 | Et—F | 2-Me, 5-OMe | 1 |
| 11382 | Et—F | 2-Me, 5-OMeF | 1 |
| 11383 | Et—F | 2-Me, 5-OEtF | 1 |
| 11384 | Et—F | 2-Me, 5-OPrF | 1 |
| 11385 | Et—F | 2-Me, 4-OH | 1 |
| 11386 | Et—F | 2-Me, 4-OMe | 1 |
| 11387 | Et—F | 2-Me, 4-OMeF | 1 |
| 11388 | Et—F | 2-Me, 4-OCF$_3$ | 1 |
| 11389 | Et—F | 2-Me, 4-OEtF | 1 |
| 11390 | Et—F | 2-Me, 4-OPrF | 1 |
| 11391 | Et—F | 2-OH, 4-Me | 1 |
| 11392 | Et—F | 2-OMe, 4-Me | 1 |
| 11393 | Et—F | 2-OMeF, 4-Me | 1 |
| 11394 | Et—F | 2-OCF$_3$, 4-Me | 1 |
| 11395 | Et—F | 2-OEtF, 4-Me | 1 |
| 11396 | Et—F | 2-OPrF, 4-Me | 1 |
| 11397 | Et—F | 2-Cl, 4-OH | 1 |
| 11398 | Et—F | 2-Cl, 4-OMe | 1 |
| 11399 | Et—F | 2-Cl, 4-OMeF | 1 |
| 11400 | Et—F | 2-Cl, 4-OCF$_3$ | 1 |
| 11401 | Et—F | 2-Cl, 4-OEtF | 1 |
| 11402 | Et—F | 2-Cl, 4-OPrF | 1 |
| 11403 | Et—F | 2-F, 4-F | 1 |
| 11404 | Et—F | 2-Cl, 4-Cl | 1 |
| 11405 | Et—F | 2-Cl, 4-F | 1 |
| 11406 | Et—F | 2-Cl, 4-NO$_2$ | 1 |
| 11407 | Et—F | 2-Cl, 4-NH$_2$ | 1 |
| 11408 | Et—F | 2-Cl, 4-NHMe | 1 |
| 11409 | Et—F | 2-Cl, 4-NMe$_2$ | 1 |
| 11410 | Et—F | 2-Cl, 4-NMe$_3$OTf | 1 |
| 11411 | Et—F | 2-Cl, 4-NMe$_3$I | 1 |
| 11412 | Et—F | 2-Cl, 5-F | 1 |
| 11413 | Et—F | 2-Cl, 5-NO$_2$ | 1 |
| 11414 | Et—F | 2-Cl, 5-NH$_2$ | 1 |
| 11415 | Et—F | 2-Cl, 5-NHMe | 1 |
| 11416 | Et—F | 2-Cl, 5-NMe$_2$ | 1 |
| 11417 | Et—F | 2-Cl, 5-NMe$_3$OTf | 1 |
| 11418 | Et—F | 2-Cl, 5-NMe$_3$I | 1 |
| 11419 | Et—F | 2-F, 4-Cl | 1 |
| 11420 | Et—F | 2-NO$_2$, 4-Cl | 1 |
| 11421 | Et—F | 2-NH$_2$, 4-Cl | 1 |
| 11422 | Et—F | 2-NHMe, 4-Cl | 1 |
| 11423 | Et—F | 2-NMe$_2$, 4-Cl | 1 |
| 11424 | Et—F | 2-NMe$_3$OTf, 4-Cl | 1 |
| 11425 | Et—F | 2-NMe$_3$I, 4-Cl | 1 |
| 11426 | Et—F | 2-F, 5-Cl | 1 |
| 11427 | Et—F | 2-NO$_2$, 5-Cl | 1 |
| 11428 | Et—F | 2-NH$_2$, 5-Cl | 1 |
| 11429 | Et—F | 2-NHMe, 5-Cl | 1 |
| 11430 | Et—F | 2-NMe$_2$, 5-Cl | 1 |
| 11431 | Et—F | 2-NMe$_3$OTf, 5-Cl | 1 |
| 11432 | Et—F | 2-NMe$_3$I, 5-Cl | 1 |
| 11433 | Et—F | 2-Br, 4-F | 1 |
| 11434 | Et—F | 2-Br, 4-NO$_2$ | 1 |
| 11435 | Et—F | 2-Br, 4-NH$_2$ | 1 |
| 11436 | Et—F | 2-Br, 4-NHMe | 1 |
| 11437 | Et—F | 2-Br, 4-NMe$_2$ | 1 |
| 11438 | Et—F | 2-Br, 4-NMe$_3$OTf | 1 |
| 11439 | Et—F | 2-Br, 4-NMe$_3$I | 1 |
| 11440 | Et—F | 2-Br, 5-F | 1 |
| 11441 | Et—F | 2-Br, 5-NO$_2$ | 1 |
| 11442 | Et—F | 2-Br, 5-NH$_2$ | 1 |
| 11443 | Et—F | 2-Br, 5-NHMe | 1 |
| 11444 | Et—F | 2-Br, 5-NMe$_2$ | 1 |
| 11445 | Et—F | 2-Br, 5-NMe$_3$OTf | 1 |
| 11446 | Et—F | 2-Br, 5-NMe$_3$I | 1 |
| 11447 | Et—F | 2-F, 4-Br | 1 |
| 11448 | Et—F | 2-NO$_2$, 4-Br | 1 |
| 11449 | Et—F | 2-NH$_2$, 4-Br | 1 |
| 11450 | Et—F | 2-NHMe, 4-Br | 1 |
| 11451 | Et—F | 2-NMe$_2$, 4-Br | 1 |
| 11452 | Et—F | 2-NMe$_3$OTf, 4-Br | 1 |
| 11453 | Et—F | 2-NMe$_3$I, 4-Br | 1 |
| 11454 | Et—F | 2-I, 4-F | 1 |
| 11455 | Et—F | 2-I, 4-NO$_2$ | 1 |
| 11456 | Et—F | 2-I, 4-NH$_2$ | 1 |
| 11457 | Et—F | 2-I, 4-NHMe | 1 |
| 11458 | Et—F | 2-I, 4-NMe$_2$ | 1 |
| 11459 | Et—F | 2-I, 4-NMe$_3$OTf | 1 |
| 11460 | Et—F | 2-I, 4-NMe$_3$I | 1 |
| 11461 | Et—F | 2-F, 4-I | 1 |
| 11462 | Et—F | 2-NO$_2$, 4-I | 1 |
| 11463 | Et—F | 2-NH$_2$, 4-I | 1 |
| 11464 | Et—F | 2-NHMe, 4-I | 1 |
| 11465 | Et—F | 2-NMe$_2$, 4-I | 1 |
| 11466 | Et—F | 2-NMe$_3$OTf, 4-I | 1 |
| 11467 | Et—F | 2-NMe$_3$I, 4-I | 1 |
| 11468 | Et—F | 2-Me, 3-F | 1 |
| 11469 | Et—F | 2-Me, 3-NO$_2$ | 1 |
| 11470 | Et—F | 2-Me, 3-NH$_2$ | 1 |
| 11471 | Et—F | 2-Me, 3-NHMe | 1 |
| 11472 | Et—F | 2-Me, 3-NMe$_2$ | 1 |
| 11473 | Et—F | 2-Me, 3-NMe$_3$OTf | 1 |
| 11474 | Et—F | 2-Me, 3-NMe$_3$I | 1 |
| 11475 | Et—F | 2-Me, 4-F | 1 |
| 11476 | Et—F | 2-Me, 4-NO$_2$ | 1 |
| 11477 | Et—F | 2-Me, 4-NH$_2$ | 1 |
| 11478 | Et—F | 2-Me, 4-NHMe | 1 |
| 11479 | Et—F | 2-Me, 4-NMe$_2$ | 1 |
| 11480 | Et—F | 2-Me, 4-NMe$_3$OTf | 1 |
| 11481 | Et—F | 2-Me, 4-NMe$_3$I | 1 |
| 11482 | Et—F | 2-Me, 5-F | 1 |
| 11483 | Et—F | 2-Me, 5-NO$_2$ | 1 |
| 11484 | Et—F | 2-Me, 5-NH$_2$ | 1 |
| 11485 | Et—F | 2-Me, 5-NHMe | 1 |
| 11486 | Et—F | 2-Me, 5-NMe$_2$ | 1 |
| 11487 | Et—F | 2-Me, 5-NMe$_3$OTf | 1 |

TABLE 9-continued

Substituent list for compounds of general structure XIV.

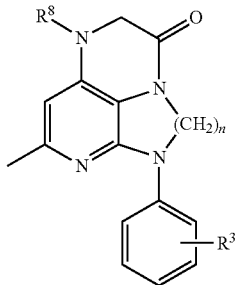

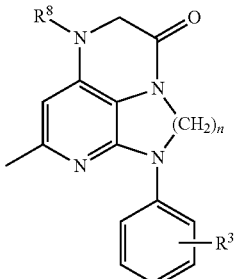

| Compound # | $R^8$ = | $R^3$ = | n = |
|---|---|---|---|
| 11488 | Et—F | 2-Me, 5-NMe$_3$I | 1 |
| 11489 | Et—F | 2-F, 4-Me | 1 |
| 11490 | Et—F | 2-NO$_2$, 4-Me | 1 |
| 11491 | Et—F | 2-NH$_2$, 4-Me | 1 |
| 11492 | Et—F | 2-NHMe, 4-Me | 1 |
| 11493 | Et—F | 2-NMe$_2$, 4-Me | 1 |
| 11494 | Et—F | 2-NMe$_3$, 4-Me | 1 |
| 11495 | Et—F | 2-NMe$_3$OTf, 4-Me | 1 |
| 11496 | Et—F | 2-NMe$_3$I, 4-Me | 1 |
| 11497 | Et—F | 2-SnMe$_3$, 4-F | 1 |
| 11498 | Et—F | 2-SnMe$_3$, 5-F | 1 |
| 11499 | Et—F | 2-F, 4-SnMe$_3$ | 1 |
| 11500 | Et—F | 2-Br, 6-Cl, 4-F | 1 |
| 11501 | Et—F | 2-Br, 6-Cl, 4-NO$_2$ | 1 |
| 11502 | Et—F | 2-Br, 6-Cl, 4-NH$_2$ | 1 |
| 11503 | Et—F | 2-Br, 6-Cl, 4-NHMe | 1 |
| 11504 | Et—F | 2-Br, 6-Cl, 4-NMe$_2$ | 1 |
| 11505 | Et—F | 2-Br, 6-Cl, 4-NMe$_3$OTf | 1 |
| 11506 | Et—F | 2-Br, 6-Cl, 4-NMe$_3$I | 1 |
| 11507 | Et—F | 2-Me, 6-Cl, 4-F | 1 |
| 11508 | Et—F | 2-SnMe$_3$, 6-Cl, 4-F | 1 |
| 11509 | Et—F | 2-Cl, 4-Me | 1 |
| 11510 | Et—F | 2-Cl, 4-Br | 1 |
| 11511 | Et—F | 2-Cl, 4-SnMe$_3$ | 1 |
| 11512 | Et—F | 2-Br, 4-Cl | 1 |
| 11513 | Et—F | 2-SnMe$_3$, 4-Cl | 1 |
| 11514 | Et—F | 2-Me, 4-Cl | 1 |
| 11515 | Et—F | 2-Br, 4-Br | 1 |
| 11516 | Et—F | 2-Br, 4-Me | 1 |
| 11517 | Et—F | 2-Br, 4-SnMe$_3$ | 1 |
| 11518 | Et—F | 2-SnMe$_3$, 4-Br | 1 |
| 11519 | Et—F | 2-Me, 4-Br | 1 |
| 11520 | Et—F | 2-Me, 4-SnMe$_3$ | 1 |
| 11521 | Et—F | 2-SnMe$_3$, 4-Me | 1 |
| 11522 | Et—F | 2-Me, 4-Me | 1 |
| 11523 | Et—F | 2-Et, 4-Br | 1 |
| 11524 | Et—F | 2-Et, 4-SnMe$_3$ | 1 |
| 11525 | Et—F | 2-Et, 4-Me | 1 |
| 11526 | Et—F | 2-Me, 4-Me, 6-Me | 1 |
| 11527 | Et—F | 2-Me, 4-Br, 6-Me | 1 |
| 11528 | Et—F | 2-Me, 4-SnMe$_3$, 6-Me | 1 |
| 11529 | Et—F | 2-Et, 6-Me | 1 |
| 11530 | Et—F | 2-Br, 4-i-Pr | 1 |
| 11531 | Et—F | 2-SnMe$_3$, 4-i-Pr | 1 |
| 11532 | Et—F | 2-Me, 4-i-Pr | 1 |
| 11533 | Et—F | 2-Br, 4-Br, 6-Br | 1 |
| 11534 | Et—F | 2-Br, 4-Me, 6-Br | 1 |
| 11535 | Et—F | 2-Br, 4-SnMe$_3$, 6-Br | 1 |
| 11536 | Et—F | 2-SnMe$_3$, 4-Br, 6-Br | 1 |
| 11537 | Et—F | 2-Br, 4-Br, 6-Me | 1 |
| 11538 | Et—F | 2-Br, 4-CF$_3$, 6-Br | 1 |
| 11539 | Et—F | 2-Br, 4-Br, 6-CF$_3$ | 1 |
| 11540 | Et—F | 2-CF$_3$, 4-CF$_3$ | 1 |
| 11541 | Et—F | 2-Cl, 4-CF$_3$ | 1 |
| 11542 | Et—F | 2-CF$_3$, 4-Cl | 1 |
| 11543 | Et—F | 2-Br, 4-CF$_3$ | 1 |
| 11544 | Et—F | 2-SnMe$_3$, 4-CF$_3$ | 1 |
| 11545 | Et—F | 2-Me, 4-CF$_3$ | 1 |
| 11546 | Et—F | 2-CF$_3$, 4-Br | 1 |
| 11547 | Et—F | 2-CF$_3$, 4-SnMe$_3$ | 1 |
| 11548 | Et—F | 2-CF$_3$, 4-Me | 1 |
| 11549 | Et—F | 2-Br, 4-OH | 1 |
| 11550 | Et—F | 2-Br, 4-OMe | 1 |
| 11551 | Et—F | 2-Br, 4-OMeF | 1 |
| 11552 | Et—F | 2-Br, 4-OCF$_3$ | 1 |
| 11553 | Et—F | 2-Br, 4-OEtF | 1 |
| 11554 | Et—F | 2-Br, 4-OPrF | 1 |
| 11555 | Et—F | 2-OH, 4-Br | 1 |
| 11556 | Et—F | 2-OMe, 4-Br | 1 |
| 11557 | Et—F | 2-OMeF, 4-Br | 1 |
| 11558 | Et—F | 2-OCF$_3$, 4-Br | 1 |
| 11559 | Et—F | 2-OEtF, 4-Br | 1 |
| 11560 | Et—F | 2-OPrF, 4-Br | 1 |
| 11561 | Et—F | 2-I, 4-OH | 1 |
| 11562 | Et—F | 2-I, 4-OMe | 1 |
| 11563 | Et—F | 2-I, 4-OMeF | 1 |
| 11564 | Et—F | 2-I, 4-OCF$_3$ | 1 |
| 11565 | Et—F | 2-I, 4-OEtF | 1 |
| 11566 | Et—F | 2-I, 4-OPrF | 1 |
| 11567 | Et—F | 2-OH, 4-I | 1 |
| 11568 | Et—F | 2-OMe, 4-I | 1 |
| 11569 | Et—F | 2-OMeF, 4-I | 1 |
| 11570 | Et—F | 2-OCF$_3$, 4-I | 1 |
| 11571 | Et—F | 2-OEtF, 4-I | 1 |
| 11572 | Et—F | 2-OPrF, 4-I | 1 |
| 11573 | Et—F | 2-SnMe$_3$, 4-OH | 1 |
| 11574 | Et—F | 2-SnMe$_3$, 4-OMe | 1 |
| 11575 | Et—F | 2-SnMe$_3$, 4-OMeF | 1 |
| 11576 | Et—F | 2-SnMe$_3$, 4-OCF$_3$ | 1 |
| 11577 | Et—F | 2-SnMe$_3$, 4-OEtF | 1 |
| 11578 | Et—F | 2-SnMe$_3$, 4-OPrF | 1 |
| 11579 | Et—F | 2-OH, 4-SnMe$_3$ | 1 |
| 11580 | Et—F | 2-OMe, 4-SnMe$_3$ | 1 |
| 11581 | Et—F | 2-OMeF, 4-SnMe$_3$ | 1 |
| 11582 | Et—F | 2-OCF$_3$, 4-SnMe$_3$ | 1 |
| 11583 | Et—F | 2-OEtF, 4-SnMe$_3$ | 1 |
| 11584 | Et—F | 2-OPrF, 4-SnMe$_3$ | 1 |
| 11585 | Et—F | H | 2 |
| 11586 | Et—F | 2-t-Bu | 2 |
| 11587 | Et—F | 2-Br | 2 |
| 11588 | Et—F | 3-Br | 2 |
| 11589 | Et—F | 4-Br | 2 |
| 11590 | Et—F | 2-I | 2 |
| 11591 | Et—F | 3-I | 2 |
| 11592 | Et—F | 4-I | 2 |
| 11593 | Et—F | 2-SnMe$_3$ | 2 |
| 11594 | Et—F | 3-SnMe$_3$ | 2 |
| 11595 | Et—F | 4-SnMe$_3$ | 2 |
| 11596 | Et—F | 2-Me | 2 |
| 11597 | Et—F | 3-Me | 2 |
| 11598 | Et—F | 4-Me | 2 |
| 11599 | Et—F | 2-OH | 2 |
| 11600 | Et—F | 3-OH | 2 |
| 11601 | Et—F | 4-OH | 2 |
| 11602 | Et—F | 2-OMe | 2 |
| 11603 | Et—F | 3-OMe | 2 |
| 11604 | Et—F | 4-OMe | 2 |
| 11605 | Et—F | 2-OMeF | 2 |
| 11606 | Et—F | 3-OMeF | 2 |
| 11607 | Et—F | 4-OMeF | 2 |

TABLE 9-continued

Substituent list for compounds of general structure XIV.

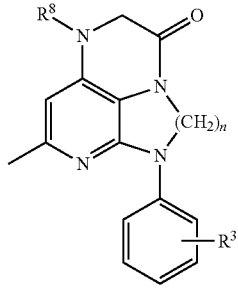

| Compound # | R⁸ = | R³ = | n = |
|---|---|---|---|
| 11608 | Et—F | 2-OCF₃ | 2 |
| 11609 | Et—F | 3-OCF₃ | 2 |
| 11610 | Et—F | 4-OCF₃ | 2 |
| 11611 | Et—F | 2-OEtF | 2 |
| 11612 | Et—F | 3-OEtF | 2 |
| 11613 | Et—F | 4-OEtF | 2 |
| 11614 | Et—F | 2-OPrF | 2 |
| 11615 | Et—F | 3-OPrF | 2 |
| 11616 | Et—F | 4-OPrF | 2 |
| 11617 | Et—F | 2-SH | 2 |
| 11618 | Et—F | 3-SH | 2 |
| 11619 | Et—F | 4-SH | 2 |
| 11620 | Et—F | 2-SMe | 2 |
| 11621 | Et—F | 3-SMe | 2 |
| 11622 | Et—F | 4-SMe | 2 |
| 11623 | Et—F | 2-SMeF | 2 |
| 11624 | Et—F | 3-SMeF | 2 |
| 11625 | Et—F | 4-SMeF | 2 |
| 11626 | Et—F | 2-SCF₃ | 2 |
| 11627 | Et—F | 3-SCF₃ | 2 |
| 11628 | Et—F | 4-SCF₃ | 2 |
| 11629 | Et—F | 2-SEtF | 2 |
| 11630 | Et—F | 3-SEtF | 2 |
| 11631 | Et—F | 4-SEtF | 2 |
| 11632 | Et—F | 2-SPrF | 2 |
| 11633 | Et—F | 3-SPrF | 2 |
| 11634 | Et—F | 4-SPrF | 2 |
| 11635 | Et—F | 2-OMe, 4-OMe | 2 |
| 11636 | Et—F | 2-Me, 5-OH | 2 |
| 11637 | Et—F | 2-Me, 5-OMe | 2 |
| 11638 | Et—F | 2-Me, 5-OMeF | 2 |
| 11639 | Et—F | 2-Me, 5-OEtF | 2 |
| 11640 | Et—F | 2-Me, 5-OPrF | 2 |
| 11641 | Et—F | 2-Me, 4-OH | 2 |
| 11642 | Et—F | 2-Me, 4-OMe | 2 |
| 11643 | Et—F | 2-Me, 4-OMeF | 2 |
| 11644 | Et—F | 2-Me, 4-OCF₃ | 2 |
| 11645 | Et—F | 2-Me, 4-OEtF | 2 |
| 11646 | Et—F | 2-Me, 4-OPrF | 2 |
| 11647 | Et—F | 2-OH, 4-Me | 2 |
| 11648 | Et—F | 2-OMe, 4-Me | 2 |
| 11649 | Et—F | 2-OMeF, 4-Me | 2 |
| 11650 | Et—F | 2-OCF₃, 4-Me | 2 |
| 11651 | Et—F | 2-OEtF, 4-Me | 2 |
| 11652 | Et—F | 2-OPrF, 4-Me | 2 |
| 11653 | Et—F | 2-Cl, 4-OH | 2 |
| 11654 | Et—F | 2-Cl, 4-OMe | 2 |
| 11655 | Et—F | 2-Cl, 4-OMeF | 2 |
| 11656 | Et—F | 2-Cl, 4-OCF₃ | 2 |
| 11657 | Et—F | 2-Cl, 4-OEtF | 2 |
| 11658 | Et—F | 2-Cl, 4-OPrF | 2 |
| 11659 | Et—F | 2-F, 4-F | 2 |
| 11660 | Et—F | 2-Cl, 4-Cl | 2 |
| 11661 | Et—F | 2-Cl, 4-F | 2 |
| 11662 | Et—F | 2-Cl, 4-NO₂ | 2 |
| 11663 | Et—F | 2-Cl, 4-NH₂ | 2 |
| 11664 | Et—F | 2-Cl, 4-NHMe | 2 |
| 11665 | Et—F | 2-Cl, 4-NMe₂ | 2 |
| 11666 | Et—F | 2-Cl, 4-NMe₃OTf | 2 |
| 11667 | Et—F | 2-Cl, 4-NMe₃I | 2 |

TABLE 9-continued

Substituent list for compounds of general structure XIV.

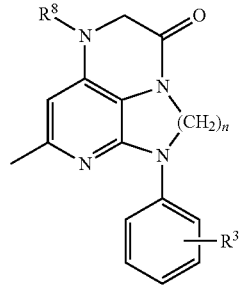

| Compound # | R⁸ = | R³ = | n = |
|---|---|---|---|
| 11668 | Et—F | 2-Cl, 5-F | 2 |
| 11669 | Et—F | 2-Cl, 5-NO₂ | 2 |
| 11670 | Et—F | 2-Cl, 5-NH₂ | 2 |
| 11671 | Et—F | 2-Cl, 5-NHMe | 2 |
| 11672 | Et—F | 2-Cl, 5-NMe₂ | 2 |
| 11673 | Et—F | 2-Cl, 5-NMe₃OTf | 2 |
| 11674 | Et—F | 2-Cl, 5-NMe₃I | 2 |
| 11675 | Et—F | 2-F, 4-Cl | 2 |
| 11676 | Et—F | 2-NO₂, 4-Cl | 2 |
| 11677 | Et—F | 2-NH₂, 4-Cl | 2 |
| 11678 | Et—F | 2-NHMe, 4-Cl | 2 |
| 11679 | Et—F | 2-NMe₂, 4-Cl | 2 |
| 11680 | Et—F | 2-NMe₃OTf, 4-Cl | 2 |
| 11681 | Et—F | 2-NMe₃I, 4-Cl | 2 |
| 11682 | Et—F | 2-F, 5-Cl | 2 |
| 11683 | Et—F | 2-NO₂, 5-Cl | 2 |
| 11684 | Et—F | 2-NH₂, 5-Cl | 2 |
| 11685 | Et—F | 2-NHMe, 5-Cl | 2 |
| 11686 | Et—F | 2-NMe₂, 5-Cl | 2 |
| 11687 | Et—F | 2-NMe₃OTf, 5-Cl | 2 |
| 11688 | Et—F | 2-NMe₃I, 5-Cl | 2 |
| 11689 | Et—F | 2-Br, 4-F | 2 |
| 11690 | Et—F | 2-Br, 4-NO₂ | 2 |
| 11691 | Et—F | 2-Br, 4-NH₂ | 2 |
| 11692 | Et—F | 2-Br, 4-NHMe | 2 |
| 11693 | Et—F | 2-Br, 4-NMe₂ | 2 |
| 11694 | Et—F | 2-Br, 4-NMe₃OTf | 2 |
| 11695 | Et—F | 2-Br, 4-NMe₃I | 2 |
| 11696 | Et—F | 2-Br, 5-F | 2 |
| 11697 | Et—F | 2-Br, 5-NO₂ | 2 |
| 11698 | Et—F | 2-Br, 5-NH₂ | 2 |
| 11699 | Et—F | 2-Br, 5-NHMe | 2 |
| 11700 | Et—F | 2-Br, 5-NMe₂ | 2 |
| 11701 | Et—F | 2-Br, 5-NMe₃OTf | 2 |
| 11702 | Et—F | 2-Br, 5-NMe₃I | 2 |
| 11703 | Et—F | 2-F, 4-Br | 2 |
| 11704 | Et—F | 2-NO₂, 4-Br | 2 |
| 11705 | Et—F | 2-NH₂, 4-Br | 2 |
| 11706 | Et—F | 2-NHMe, 4-Br | 2 |
| 11707 | Et—F | 2-NMe₂, 4-Br | 2 |
| 11708 | Et—F | 2-NMe₃OTf, 4-Br | 2 |
| 11709 | Et—F | 2-NMe₃I, 4-Br | 2 |
| 11710 | Et—F | 2-I, 4-F | 2 |
| 11711 | Et—F | 2-I, 4-NO₂ | 2 |
| 11712 | Et—F | 2-I, 4-NH₂ | 2 |
| 11713 | Et—F | 2-I, 4-NHMe | 2 |
| 11714 | Et—F | 2-I, 4-NMe₂ | 2 |
| 11715 | Et—F | 2-I, 4-NMe₃OTf | 2 |
| 11716 | Et—F | 2-I, 4-NMe₃I | 2 |
| 11717 | Et—F | 2-F, 4-I | 2 |
| 11718 | Et—F | 2-NO₂, 4-I | 2 |
| 11719 | Et—F | 2-NH₂, 4-I | 2 |
| 11720 | Et—F | 2-NHMe, 4-I | 2 |
| 11721 | Et—F | 2-NMe₂, 4-I | 2 |
| 11722 | Et—F | 2-NMe₃OTf, 4-I | 2 |
| 11723 | Et—F | 2-NMe₃I, 4-I | 2 |
| 11724 | Et—F | 2-Me, 3-F | 2 |
| 11725 | Et—F | 2-Me, 3-NO₂ | 2 |
| 11726 | Et—F | 2-Me, 3-NH₂ | 2 |
| 11727 | Et—F | 2-Me, 3-NHMe | 2 |

TABLE 9-continued

Substituent list for compounds of general structure XIV.

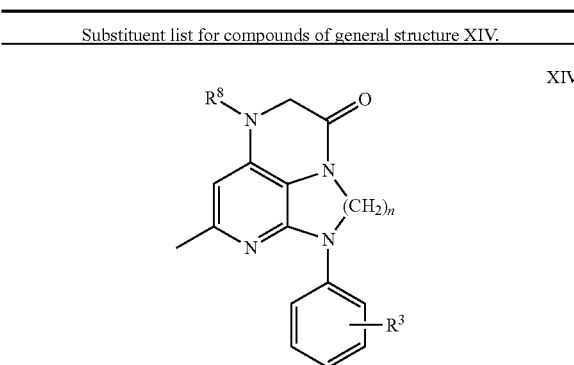

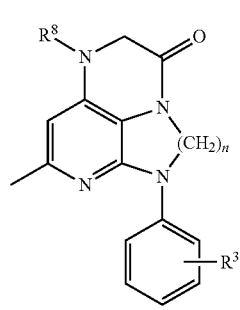

| Compound # | R$^8$ = | R$^3$ = | n = |
|---|---|---|---|
| 11728 | Et—F | 2-Me, 3-NMe$_2$ | 2 |
| 11729 | Et—F | 2-Me, 3-NMe$_3$OTf | 2 |
| 11730 | Et—F | 2-Me, 3-NMe$_3$I | 2 |
| 11731 | Et—F | 2-Me, 4-F | 2 |
| 11732 | Et—F | 2-Me, 4-NO$_2$ | 2 |
| 11733 | Et—F | 2-Me, 4-NH$_2$ | 2 |
| 11734 | Et—F | 2-Me, 4-NHMe | 2 |
| 11735 | Et—F | 2-Me, 4-NMe$_2$ | 2 |
| 11736 | Et—F | 2-Me, 4-NMe$_3$OTf | 2 |
| 11737 | Et—F | 2-Me, 4-NMe$_3$I | 2 |
| 11738 | Et—F | 2-Me, 5-F | 2 |
| 11739 | Et—F | 2-Me, 5-NO$_2$ | 2 |
| 11740 | Et—F | 2-Me, 5-NH$_2$ | 2 |
| 11741 | Et—F | 2-Me, 5-NHMe | 2 |
| 11742 | Et—F | 2-Me, 5-NMe$_2$ | 2 |
| 11743 | Et—F | 2-Me, 5-NMe$_3$OTf | 2 |
| 11744 | Et—F | 2-Me, 5-NMe$_3$I | 2 |
| 11745 | Et—F | 2-F, 4-Me | 2 |
| 11746 | Et—F | 2-NO$_2$, 4-Me | 2 |
| 11747 | Et—F | 2-NH$_2$, 4-Me | 2 |
| 11748 | Et—F | 2-NHMe, 4-Me | 2 |
| 11749 | Et—F | 2-NMe$_2$, 4-Me | 2 |
| 11750 | Et—F | 2-NMe$_3$, 4-Me | 2 |
| 11751 | Et—F | 2-NMe$_3$OTf, 4-Me | 2 |
| 11752 | Et—F | 2-NMe$_3$I, 4-Me | 2 |
| 11753 | Et—F | 2-SnMe$_3$, 4-F | 2 |
| 11754 | Et—F | 2-SnMe$_3$, 5-F | 2 |
| 11755 | Et—F | 2-F, 4-SnMe$_3$ | 2 |
| 11756 | Et—F | 2-Br, 6-Cl, 4-F | 2 |
| 11757 | Et—F | 2-Br, 6-Cl, 4-NO$_2$ | 2 |
| 11758 | Et—F | 2-Br, 6-Cl, 4-NH$_2$ | 2 |
| 11759 | Et—F | 2-Br, 6-Cl, 4-NHMe | 2 |
| 11760 | Et—F | 2-Br, 6-Cl, 4-NMe$_2$ | 2 |
| 11761 | Et—F | 2-Br, 6-Cl, 4-NMe$_3$OTf | 2 |
| 11762 | Et—F | 2-Br, 6-Cl, 4-NMe$_3$I | 2 |
| 11763 | Et—F | 2-Me, 6-Cl, 4-F | 2 |
| 11764 | Et—F | 2-SaMe$_3$, 6-Cl, 4-F | 2 |
| 11765 | Et—F | 2-Cl, 4-Me | 2 |
| 11766 | Et—F | 2-Cl, 4-Br | 2 |
| 11767 | Et—F | 2-Cl, 4-SnMe$_3$ | 2 |
| 11768 | Et—F | 2-Br, 4-Cl | 2 |
| 11769 | Et—F | 2-SnMe$_3$, 4-Cl | 2 |
| 11770 | Et—F | 2-Me, 4-Cl | 2 |
| 11771 | Et—F | 2-Br, 4-Br | 2 |
| 11772 | Et—F | 2-Br, 4-Me | 2 |
| 11773 | Et—F | 2-Br, 4-SnMe$_3$ | 2 |
| 11774 | Et—F | 2-SnMe$_3$, 4-Br | 2 |
| 11775 | Et—F | 2-Me, 4-Br | 2 |
| 11776 | Et—F | 2-Me, 4-SnMe$_3$ | 2 |
| 11777 | Et—F | 2-SnMe$_3$, 4-Me | 2 |
| 11778 | Et—F | 2-Me, 4-Me | 2 |
| 11779 | Et—F | 2-Et, 4-Br | 2 |
| 11780 | Et—F | 2-Et, 4-SnMe$_3$ | 2 |
| 11781 | Et—F | 2-Et, 4-Me | 2 |
| 11782 | Et—F | 2-Me, 4-Me, 6-Me | 2 |
| 11783 | Et—F | 2-Me, 4-Br, 6-Me | 2 |
| 11784 | Et—F | 2-Me, 4-SnMe$_3$, 6-Me | 2 |
| 11785 | Et—F | 2-Et, 6-Me | 2 |
| 11786 | Et—F | 2-Br, 4-i-Pr | 2 |
| 11787 | Et—F | 2-SnMe$_3$, 4-i-Pr | 2 |
| 11788 | Et—F | 2-Me, 4-i-Pr | 2 |
| 11789 | Et—F | 2-Br, 4-Br, 6-Br | 2 |
| 11790 | Et—F | 2-Br, 4-Me, 6-Br | 2 |
| 11791 | Et—F | 2-Br, 4-SnMe$_3$, 6-Br | 2 |
| 11792 | Et—F | 2-SnMe$_3$, 4-Br, 6-Br | 2 |
| 11793 | Et—F | 2-Br, 4-Br, 6-Me | 2 |
| 11794 | Et—F | 2-Br, 4-CF$_3$, 6-Br | 2 |
| 11795 | Et—F | 2-Br, 4-Br, 6-CF$_3$ | 2 |
| 11796 | Et—F | 2-CF$_3$, 4-CF$_3$ | 2 |
| 11797 | Et—F | 2-Cl, 4-CF$_3$ | 2 |
| 11798 | Et—F | 2-CF$_3$, 4-Cl | 2 |
| 11799 | Et—F | 2-Br, 4-CF$_3$ | 2 |
| 11800 | Et—F | 2-SnMe$_3$, 4-CF$_3$ | 2 |
| 11801 | Et—F | 2-Me, 4-CF$_3$ | 2 |
| 11802 | Et—F | 2-CF$_3$, 4-Br | 2 |
| 11803 | Et—F | 2-CF$_3$, 4-SnMe$_3$ | 2 |
| 11804 | Et—F | 2-CF$_3$, 4-Me | 2 |
| 11805 | Et—F | 2-Br, 4-OH | 2 |
| 11806 | Et—F | 2-Br, 4-OMe | 2 |
| 11807 | Et—F | 2-Br, 4-OMeF | 2 |
| 11808 | Et—F | 2-Br, 4-OCF$_3$ | 2 |
| 11809 | Et—F | 2-Br, 4-OEtF | 2 |
| 11810 | Et—F | 2-Br, 4-OPrF | 2 |
| 11811 | Et—F | 2-OH, 4-Br | 2 |
| 11812 | Et—F | 2-OMe, 4-Br | 2 |
| 11813 | Et—F | 2-OMeF, 4-Br | 2 |
| 11814 | Et—F | 2-OCF$_3$, 4-Br | 2 |
| 11815 | Et—F | 2-OEtF, 4-Br | 2 |
| 11816 | Et—F | 2-OPrF, 4-Br | 2 |
| 11817 | Et—F | 2-I, 4-OH | 2 |
| 11818 | Et—F | 2-I, 4-OMe | 2 |
| 11819 | Et—F | 2-I, 4-OMeF | 2 |
| 11820 | Et—F | 2-I, 4-OCF$_3$ | 2 |
| 11821 | Et—F | 2-I, 4-OEtF | 2 |
| 11822 | Et—F | 2-I, 4-OPrF | 2 |
| 11823 | Et—F | 2-OH, 4-I | 2 |
| 11824 | Et—F | 2-OMe, 4-I | 2 |
| 11825 | Et—F | 2-OMeF, 4-I | 2 |
| 11826 | Et—F | 2-OCF$_3$, 4-I | 2 |
| 11827 | Et—F | 2-OEtF, 4-I | 2 |
| 11828 | Et—F | 2-OPrF, 4-I | 2 |
| 11829 | Et—F | 2-SnMe$_3$, 4-OH | 2 |
| 11830 | Et—F | 2-SnMe$_3$, 4-OMe | 2 |
| 11831 | Et—F | 2-SnMe$_3$, 4-OMeF | 2 |
| 11832 | Et—F | 2-SnMe$_3$, 4-OCF$_3$ | 2 |
| 11833 | Et—F | 2-SnMe$_3$, 4-OEtF | 2 |
| 11834 | Et—F | 2-SnMe$_3$, 4-OPrF | 2 |
| 11835 | Et—F | 2-OH, 4-SnMe$_3$ | 2 |
| 11836 | Et—F | 2-OMe, 4-SnMe$_3$ | 2 |
| 11837 | Et—F | 2-OMeF, 4-SnMe$_3$ | 2 |
| 11838 | Et—F | 2-OCF$_3$, 4-SnMe$_3$ | 2 |
| 11839 | Et—F | 2-OEtF, 4-SnMe$_3$ | 2 |
| 11840 | Et—F | 2-OPrF, 4-SnMe$_3$ | 2 |
| 11841 | Me | H | 1 |
| 11842 | Me | 2-t-Bu | 1 |
| 11843 | Me | 2-Br | 1 |
| 11844 | Me | 3-Br | 1 |
| 11845 | Me | 4-Br | 1 |
| 11846 | Me | 2-I | 1 |
| 11847 | Me | 3-I | 1 |

TABLE 9-continued

Substituent list for compounds of general structure XIV.

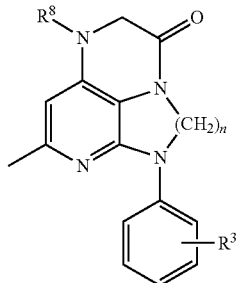

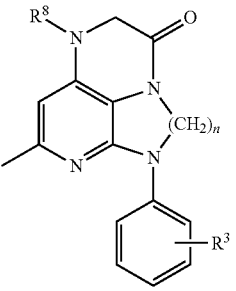

| Compound # | R⁸ = | R³ = | n = |
|---|---|---|---|
| 11848 | Me | 4-I | 1 |
| 11849 | Me | 2-SnMe₃ | 1 |
| 11850 | Me | 3-SnMe₃ | 1 |
| 11851 | Me | 4-SnMe₃ | 1 |
| 11852 | Me | 2-Me | 1 |
| 11853 | Me | 3-Me | 1 |
| 11854 | Me | 4-Me | 1 |
| 11855 | Me | 2-OH | 1 |
| 11856 | Me | 3-OH | 1 |
| 11857 | Me | 4-OH | 1 |
| 11858 | Me | 2-OMe | 1 |
| 11859 | Me | 3-OMe | 1 |
| 11860 | Me | 4-OMe | 1 |
| 11861 | Me | 2-OMeF | 1 |
| 11862 | Me | 3-OMeF | 1 |
| 11863 | Me | 4-OMeF | 1 |
| 11864 | Me | 2-OCF₃ | 1 |
| 11865 | Me | 3-OCF₃ | 1 |
| 11866 | Me | 4-OCF₃ | 1 |
| 11867 | Me | 2-OEtF | 1 |
| 11868 | Me | 3-OEtF | 1 |
| 11869 | Me | 4-OEtF | 1 |
| 11870 | Me | 2-OPrF | 1 |
| 11871 | Me | 3-OPrF | 1 |
| 11872 | Me | 4-OPrF | 1 |
| 11873 | Me | 2-SH | 1 |
| 11874 | Me | 3-SH | 1 |
| 11875 | Me | 4-SH | 1 |
| 11876 | Me | 2-SMe | 1 |
| 11877 | Me | 3-SMe | 1 |
| 11878 | Me | 4-SMe | 1 |
| 11879 | Me | 2-SMeF | 1 |
| 11880 | Me | 3-SMeF | 1 |
| 11881 | Me | 4-SMeF | 1 |
| 11882 | Me | 2-SCF₃ | 1 |
| 11883 | Me | 3-SCF₃ | 1 |
| 11884 | Me | 4-SCF₃ | 1 |
| 11885 | Me | 2-SEtF | 1 |
| 11886 | Me | 3-SEtF | 1 |
| 11887 | Me | 4-SEtF | 1 |
| 11888 | Me | 2-SPrF | 1 |
| 11889 | Me | 3-SPrF | 1 |
| 11890 | Me | 4-SPrF | 1 |
| 11891 | Me | 2-OMe, 4-OMe | 1 |
| 11892 | Me | 2-Me, 5-OH | 1 |
| 11893 | Me | 2-Me, 5-OMe | 1 |
| 11894 | Me | 2-Me, 5-OMeF | 1 |
| 11895 | Me | 2-Me, 5-OEtF | 1 |
| 11896 | Me | 2-Me, 5-OPrF | 1 |
| 11897 | Me | 2-Me, 4-OH | 1 |
| 11898 | Me | 2-Me, 4-OMe | 1 |
| 11899 | Me | 2-Me, 4-OMeF | 1 |
| 11900 | Me | 2-Me, 4-OCF₃ | 1 |
| 11901 | Me | 2-Me, 4-OEtF | 1 |
| 11902 | Me | 2-Me, 4-OPrF | 1 |
| 11903 | Me | 2-OH, 4-Me | 1 |
| 11904 | Me | 2-OMe, 4-Me | 1 |
| 11905 | Me | 2-OMeF, 4-Me | 1 |
| 11906 | Me | 2-OCF₃, 4-Me | 1 |
| 11907 | Me | 2-OEtF, 4-Me | 1 |
| 11908 | Me | 2-OPrF, 4-Me | 1 |
| 11909 | Me | 2-Cl, 4-OH | 1 |
| 11910 | Me | 2-Cl, 4-OMe | 1 |
| 11911 | Me | 2-Cl, 4-OMeF | 1 |
| 11912 | Me | 2-Cl, 4-OCF₃ | 1 |
| 11913 | Me | 2-Cl, 4-OEtF | 1 |
| 11914 | Me | 2-Cl, 4-OPrF | 1 |
| 11915 | Me | 2-F, 4-F | 1 |
| 11916 | Me | 2-Cl, 4-Cl | 1 |
| 11917 | Me | 2-Cl, 4-F | 1 |
| 11918 | Me | 2-Cl, 4-NO₂ | 1 |
| 11919 | Me | 2-Cl, 4-NH₂ | 1 |
| 11920 | Me | 2-Cl, 4-NHMe | 1 |
| 11921 | Me | 2-Cl, 4-NMe₂ | 1 |
| 11922 | Me | 2-Cl, 4-NMe₃OTf | 1 |
| 11923 | Me | 2-Cl, 4-NMe₃I | 1 |
| 11924 | Me | 2-Cl, 5-F | 1 |
| 11925 | Me | 2-Cl, 5-NO₂ | 1 |
| 11926 | Me | 2-Cl, 5-NH₂ | 1 |
| 11927 | Me | 2-Cl, 5-NHMe | 1 |
| 11928 | Me | 2-Cl, 5-NMe₂ | 1 |
| 11929 | Me | 2-Cl, 5-NMe₃OTf | 1 |
| 11930 | Me | 2-Cl, 5-NMe₃I | 1 |
| 11931 | Me | 2-F, 4-Cl | 1 |
| 11932 | Me | 2-NO₂, 4-Cl | 1 |
| 11933 | Me | 2-NH₂, 4-Cl | 1 |
| 11934 | Me | 2-NHMe, 4-Cl | 1 |
| 11935 | Me | 2-NMe₂, 4-Cl | 1 |
| 11936 | Me | 2-NMe₃OTf, 4-Cl | 1 |
| 11937 | Me | 2-NMe₃I, 4-Cl | 1 |
| 11938 | Me | 2-F, 5-Cl | 1 |
| 11939 | Me | 2-NO₂, 5-Cl | 1 |
| 11940 | Me | 2-NH₂, 5-Cl | 1 |
| 11941 | Me | 2-NHMe, 5-Cl | 1 |
| 11942 | Me | 2-NMe₂, 5-Cl | 1 |
| 11943 | Me | 2-NMe₃OTf, 5-Cl | 1 |
| 11944 | Me | 2-NMe₃I, 5-Cl | 1 |
| 11945 | Me | 2-Br, 4-F | 1 |
| 11946 | Me | 2-Br, 4-NO₂ | 1 |
| 11947 | Me | 2-Br, 4-NH₂ | 1 |
| 11948 | Me | 2-Br, 4-NHMe | 1 |
| 11949 | Me | 2-Br, 4-NMe₂ | 1 |
| 11950 | Me | 2-Br, 4-NMe₃OTf | 1 |
| 11951 | Me | 2-Br, 4-NMe₃I | 1 |
| 11952 | Me | 2-Br, 5-F | 1 |
| 11953 | Me | 2-Br, 5-NO₂ | 1 |
| 11954 | Me | 2-Br, 5-NH₂ | 1 |
| 11955 | Me | 2-Br, 5-NHMe | 1 |
| 11956 | Me | 2-Br, 5-NMe₂ | 1 |
| 11957 | Me | 2-Br, 5-NMe₃OTf | 1 |
| 11958 | Me | 2-Br, 5-NMe₃I | 1 |
| 11959 | Me | 2-F, 4-Br | 1 |
| 11960 | Me | 2-NO₂, 4-Br | 1 |
| 11961 | Me | 2-NH₂, 4-Br | 1 |
| 11962 | Me | 2-NHMe, 4-Br | 1 |
| 11963 | Me | 2-NMe₂, 4-Br | 1 |
| 11964 | Me | 2-NMe₃OTf, 4-Br | 1 |
| 11965 | Me | 2-NMe₃I, 4-Br | 1 |
| 11966 | Me | 2-I, 4-F | 1 |
| 11967 | Me | 2-I, 4-NO₂ | 1 |

TABLE 9-continued

Substituent list for compounds of general structure XIV.

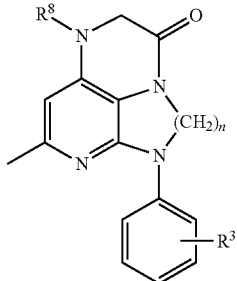

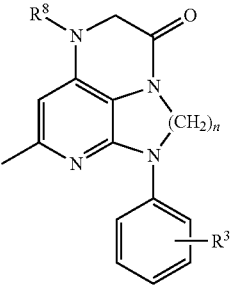

| Compound # | $R^8$ = | $R^3$ = | n = |
|---|---|---|---|
| 11968 | Me | 2-I, 4-NH$_2$ | 1 |
| 11969 | Me | 2-I, 4-NHMe | 1 |
| 11970 | Me | 2-I, 4-NMe$_2$ | 1 |
| 11971 | Me | 2-I, 4-NMe$_3$OTf | 1 |
| 11972 | Me | 2-I, 4-NMe$_3$I | 1 |
| 11973 | Me | 2-F, 4-I | 1 |
| 11974 | Me | 2-NO$_2$, 4-I | 1 |
| 11975 | Me | 2-NH$_2$, 4-I | 1 |
| 11976 | Me | 2-NHMe, 4-I | 1 |
| 11977 | Me | 2-NMe$_2$, 4-I | 1 |
| 11978 | Me | 2-NMe$_3$OTf, 4-I | 1 |
| 11979 | Me | 2-NMe$_3$I, 4-I | 1 |
| 11980 | Me | 2-Me, 3-F | 1 |
| 11981 | Me | 2-Me, 3-NO$_2$ | 1 |
| 11982 | Me | 2-Me, 3-NH$_2$ | 1 |
| 11983 | Me | 2-Me, 3-NHMe | 1 |
| 11984 | Me | 2-Me, 3-NMe$_2$ | 1 |
| 11985 | Me | 2-Me, 3-NMe$_3$OTf | 1 |
| 11986 | Me | 2-Me, 3-NMe$_3$I | 1 |
| 11987 | Me | 2-Me, 4-F | 1 |
| 11988 | Me | 2-Me, 4-NO$_2$ | 1 |
| 11989 | Me | 2-Me, 4-NH$_2$ | 1 |
| 11990 | Me | 2-Me, 4-NHMe | 1 |
| 11991 | Me | 2-Me, 4-NMe$_2$ | 1 |
| 11992 | Me | 2-Me, 4-NMe$_3$OTf | 1 |
| 11993 | Me | 2-Me, 4-NMe$_3$I | 1 |
| 11994 | Me | 2-Me, 5-F | 1 |
| 11995 | Me | 2-Me, 5-NO$_2$ | 1 |
| 11996 | Me | 2-Me, 5-NH$_2$ | 1 |
| 11997 | Me | 2-Me, 5-NHMe | 1 |
| 11998 | Me | 2-Me, 5-NMe$_2$ | 1 |
| 11999 | Me | 2-Me, 5-NMe$_3$OTf | 1 |
| 12000 | Me | 2-Me, 5-NMe$_3$I | 1 |
| 12001 | Me | 2-F, 4-Me | 1 |
| 12002 | Me | 2-NO$_2$, 4-Me | 1 |
| 12003 | Me | 2-NH$_2$, 4-Me | 1 |
| 12004 | Me | 2-NHMe, 4-Me | 1 |
| 12005 | Me | 2-NMe$_2$, 4-Me | 1 |
| 12006 | Me | 2-NMe$_3$, 4-Me | 1 |
| 12007 | Me | 2-NMe$_3$OTf, 4-Me | 1 |
| 12008 | Me | 2-NMe$_3$I, 4-Me | 1 |
| 12009 | Me | 2-SnMe$_3$, 4-F | 1 |
| 12010 | Me | 2-SnMe$_3$, 5-F | 1 |
| 12011 | Me | 2-F, 4-SnMe$_3$ | 1 |
| 12012 | Me | 2-Br, 6-Cl, 4-F | 1 |
| 12013 | Me | 2-Br, 6-Cl, 4-NO$_2$ | 1 |
| 12014 | Me | 2-Br, 6-Cl, 4-NH$_2$ | 1 |
| 12015 | Me | 2-Br, 6-Cl, 4-NHMe | 1 |
| 12016 | Me | 2-Br, 6-Cl, 4-NMe$_2$ | 1 |
| 12017 | Me | 2-Br, 6-Cl, 4-NMe$_3$OTf | 1 |
| 12018 | Me | 2-Br, 6-Cl, 4-NMe$_3$I | 1 |
| 12019 | Me | 2-Me, 6-Cl, 4-F | 1 |
| 12020 | Me | 2-SnMe$_3$, 6-Cl, 4-F1 | 1 |
| 12021 | Me | 2-Cl, 4-Me | 1 |
| 12022 | Me | 2-Cl, 4-Br | 1 |
| 12023 | Me | 2-Cl, 4-SnMe$_3$ | 1 |
| 12024 | Me | 2-Br, 4-Cl | 1 |
| 12025 | Me | 2-SnMe$_3$, 4-Cl | 1 |
| 12026 | Me | 2-Me, 4-Cl | 1 |
| 12027 | Me | 2-Br, 4-Br | 1 |
| 12028 | Me | 2-Br, 4-Me | 1 |
| 12029 | Me | 2-Br, 4-SnMe$_3$ | 1 |
| 12030 | Me | 2-SnMe$_3$, 4-Br | 1 |
| 12031 | Me | 2-Me, 4-Br | 1 |
| 12032 | Me | 2-Me, 4-SnMe$_3$ | 1 |
| 12033 | Me | 2-SnMe$_3$, 4-Me | 1 |
| 12034 | Me | 2-Me, 4-Me | 1 |
| 12035 | Me | 2-Et, 4-Br | 1 |
| 12036 | Me | 2-Et, 4-SnMe$_3$ | 1 |
| 12037 | Me | 2-Et, 4-Me | 1 |
| 12038 | Me | 2-Me, 4-Me, 6-Me | 1 |
| 12039 | Me | 2-Me, 4-Br, 6-Me | 1 |
| 12040 | Me | 2-Me, 4-SnMe$_3$, 6-Me | 1 |
| 12041 | Me | 2-Et, 6-Me | 1 |
| 12042 | Me | 2-Br, 4-i-Pr | 1 |
| 12043 | Me | 2-SnMe$_3$, 4-i-Pr | 1 |
| 12044 | Me | 2-Me, 4-i-Pr | 1 |
| 12045 | Me | 2-Br, 4-Br, 6-Br | 1 |
| 12046 | Me | 2-Br, 4-Me, 6-Br | 1 |
| 12047 | Me | 2-Br, 4-SnMe$_3$, 6-Br | 1 |
| 12048 | Me | 2-SnMe$_3$, 4-Br, 6-Br | 1 |
| 12049 | Me | 2-Br, 4-Br, 6-Me | 1 |
| 12050 | Me | 2-Br, 4-CF$_3$, 6-Br | 1 |
| 12051 | Me | 2-Br, 4-Br, 6-CF$_3$ | 1 |
| 12052 | Me | 2-CF$_3$, 4-CF$_3$ | 1 |
| 12053 | Me | 2-Cl, 4-CF$_3$ | 1 |
| 12054 | Me | 2-CF$_3$, 4-Cl | 1 |
| 12055 | Me | 2-Br, 4-CF$_3$ | 1 |
| 12056 | Me | 2-SnMe$_3$, 4-CF$_3$ | 1 |
| 12057 | Me | 2-Me, 4-CF$_3$ | 1 |
| 12058 | Me | 2-CF$_3$, 4-Br | 1 |
| 12059 | Me | 2-CF$_3$, 4-SnMe$_3$ | 1 |
| 12060 | Me | 2-CF$_3$, 4-Me | 1 |
| 12061 | Me | 2-Br, 4-OH | 1 |
| 12062 | Me | 2-Br, 4-OMe | 1 |
| 12063 | Me | 2-Br, 4-OMeF | 1 |
| 12064 | Me | 2-Br, 4-OCF$_3$ | 1 |
| 12065 | Me | 2-Br, 4-OEtF | 1 |
| 12066 | Me | 2-Br, 4-OPrF | 1 |
| 12067 | Me | 2-OH, 4-Br | 1 |
| 12068 | Me | 2-OMe, 4-Br | 1 |
| 12069 | Me | 2-OMeF, 4-Br | 1 |
| 12070 | Me | 2-OCF$_3$, 4-Br | 1 |
| 12071 | Me | 2-OEtF, 4-Br | 1 |
| 12072 | Me | 2-OPrF, 4-Br | 1 |
| 12073 | Me | 2-I, 4-OH | 1 |
| 12074 | Me | 2-I, 4-OMe | 1 |
| 12075 | Me | 2-I, 4-OMeF | 1 |
| 12076 | Me | 2-I, 4-OCF$_3$ | 1 |
| 12077 | Me | 2-I, 4-OEtF | 1 |
| 12078 | Me | 2-I, 4-OPrF | 1 |
| 12079 | Me | 2-OH, 4-I | 1 |
| 12080 | Me | 2-OMe, 4-I | 1 |
| 12081 | Me | 2-OMeF, 4-I | 1 |
| 12082 | Me | 2-OCF$_3$, 4-I | 1 |
| 12083 | Me | 2-OEtF, 4-I | 1 |
| 12084 | Me | 2-OPrF, 4-I | 1 |
| 12085 | Me | 2-SnMe$_3$, 4-OH | 1 |
| 12086 | Me | 2-SnMe$_3$, 4-OMe | 1 |
| 12087 | Me | 2-SnMe$_3$, 4-OMeF | 1 |

TABLE 9-continued

Substituent list for compounds of general structure XIV.

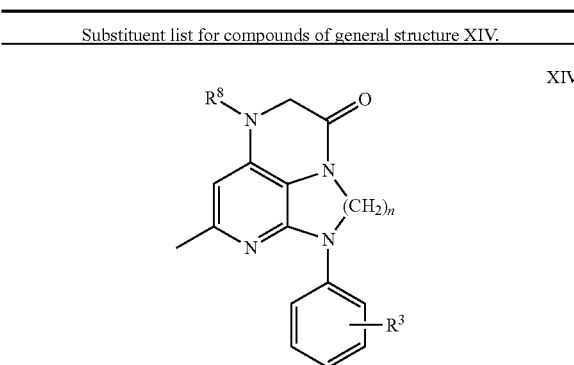

| Compound # | R⁸ = | R³ = | n = |
|---|---|---|---|
| 12088 | Me | 2-SnMe₃, 4-OCF₃ | 1 |
| 12089 | Me | 2-SnMe₃, 4-OEtF | 1 |
| 12090 | Me | 2-SnMe₃, 4-OPrF | 1 |
| 12091 | Me | 2-OH, 4-SnMe₃ | 1 |
| 12092 | Me | 2-OMe, 4-SnMe₃ | 1 |
| 12093 | Me | 2-OMeF, 4-SnMe₃ | 1 |
| 12094 | Me | 2-OCF₃, 4-SnMe₃ | 1 |
| 12095 | Me | 2-OEtF, 4-SnMe₃ | 1 |
| 12096 | Me | 2-OPrF, 4-SnMe₃ | 1 |
| 12097 | Me | H | 2 |
| 12098 | Me | 2-t-Bu | 2 |
| 12099 | Me | 2-Br | 2 |
| 12100 | Me | 3-Br | 2 |
| 12101 | Me | 4-Br | 2 |
| 12102 | Me | 2-I | 2 |
| 12103 | Me | 3-I | 2 |
| 12104 | Me | 4-I | 2 |
| 12105 | Me | 2-SnMe₃ | 2 |
| 12106 | Me | 3-SnMe₃ | 2 |
| 12107 | Me | 4-SnMe₃ | 2 |
| 12108 | Me | 2-Me | 2 |
| 12109 | Me | 3-Me | 2 |
| 12110 | Me | 4-Me | 2 |
| 12111 | Me | 2-OH | 2 |
| 12112 | Me | 3-OH | 2 |
| 12113 | Me | 4-OH | 2 |
| 12114 | Me | 2-OMe | 2 |
| 12115 | Me | 3-OMe | 2 |
| 12116 | Me | 4-OMe | 2 |
| 12117 | Me | 2-OMeF | 2 |
| 12118 | Me | 3-OMeF | 2 |
| 12119 | Me | 4-OMeF | 2 |
| 12120 | Me | 2-OCF₃ | 2 |
| 12121 | Me | 3-OCF₃ | 2 |
| 12122 | Me | 4-OCF₃ | 2 |
| 12123 | Me | 2-OEtF | 2 |
| 12124 | Me | 3-OEtF | 2 |
| 12125 | Me | 4-OEtF | 2 |
| 12126 | Me | 2-OPrF | 2 |
| 12127 | Me | 3-OPrF | 2 |
| 12128 | Me | 4-OPrF | 2 |
| 12129 | Me | 2-SH | 2 |
| 12130 | Me | 3-SH | 2 |
| 12131 | Me | 4-SH | 2 |
| 12132 | Me | 2-SMe | 2 |
| 12133 | Me | 3-SMe | 2 |
| 12134 | Me | 4-SMe | 2 |
| 12135 | Me | 2-SMeF | 2 |
| 12136 | Me | 3-SMeF | 2 |
| 12137 | Me | 4-SMeF | 2 |
| 12138 | Me | 2-SCF₃ | 2 |
| 12139 | Me | 3-SCF₃ | 2 |
| 12140 | Me | 4-SCF₃ | 2 |
| 12141 | Me | 2-SEtF | 2 |
| 12142 | Me | 3-SEtF | 2 |
| 12143 | Me | 4-SEtF | 2 |
| 12144 | Me | 2-SPrF | 2 |
| 12145 | Me | 3-SPrF | 2 |
| 12146 | Me | 4-SPrF | 2 |
| 12147 | Me | 2-OMe, 4-OMe | 2 |
| 12148 | Me | 2-Me, 5-OH | 2 |
| 12149 | Me | 2-Me, 5-OMe | 2 |
| 12150 | Me | 2-Me, 5-OMeF | 2 |
| 12151 | Me | 2-Me, 5-OEtF | 2 |
| 12152 | Me | 2-Me, 5-OPrF | 2 |
| 12153 | Me | 2-Me, 4-OH | 2 |
| 12154 | Me | 2-Me, 4-OMe | 2 |
| 12155 | Me | 2-Me, 4-OMeF | 2 |
| 12156 | Me | 2-Me, 4-OCF₃ | 2 |
| 12157 | Me | 2-Me, 4-OEtF | 2 |
| 12158 | Me | 2-Me, 4-OPrF | 2 |
| 12159 | Me | 2-OH, 4-Me | 2 |
| 12160 | Me | 2-OMe, 4-Me | 2 |
| 12161 | Me | 2-OMeF, 4-Me | 2 |
| 12162 | Me | 2-OCF₃, 4-Me | 2 |
| 12163 | Me | 2-OEtF, 4-Me | 2 |
| 12164 | Me | 2-OPrF, 4-Me | 2 |
| 12165 | Me | 2-Cl, 4-OH | 2 |
| 12166 | Me | 2-Cl, 4-OMe | 2 |
| 12167 | Me | 2-Cl, 4-OMeF | 2 |
| 12168 | Me | 2-Cl, 4-OCF₃ | 2 |
| 12169 | Me | 2-Cl, 4-OEtF | 2 |
| 12170 | Me | 2-Cl, 4-OPrF | 2 |
| 12171 | Me | 2-F, 4-F | 2 |
| 12172 | Me | 2-Cl, 4-Cl | 2 |
| 12173 | Me | 2-Cl, 4-F | 2 |
| 12174 | Me | 2-Cl, 4-NO₂ | 2 |
| 12175 | Me | 2-Cl, 4-NH₂ | 2 |
| 12176 | Me | 2-Cl, 4-NHMe | 2 |
| 12177 | Me | 2-Cl, 4-NMe₂ | 2 |
| 12178 | Me | 2-Cl, 4-NMe₃OTf | 2 |
| 12179 | Me | 2-Cl, 4-NMe₃I | 2 |
| 12180 | Me | 2-Cl, 5-F | 2 |
| 12181 | Me | 2-Cl, 5-NO₂ | 2 |
| 12182 | Me | 2-Cl, 5-NH₂ | 2 |
| 12183 | Me | 2-Cl, 5-NHMe | 2 |
| 12184 | Me | 2-Cl, 5-NMe₂ | 2 |
| 12185 | Me | 2-Cl, 5-NMe₃OTf | 2 |
| 12186 | Me | 2-Cl, 5-NMe₃I | 2 |
| 12187 | Me | 2-F, 4-Cl | 2 |
| 12188 | Me | 2-NO₂, 4-Cl | 2 |
| 12189 | Me | 2-NH₂, 4-Cl | 2 |
| 12190 | Me | 2-NHMe, 4-Cl | 2 |
| 12191 | Me | 2-NMe₂, 4-Cl | 2 |
| 12192 | Me | 2-NMe₃OTf, 4-Cl | 2 |
| 12193 | Me | 2-NMe₃I, 4-Cl | 2 |
| 12194 | Me | 2-F, 5-Cl | 2 |
| 12195 | Me | 2-NO₂, 5-Cl | 2 |
| 12196 | Me | 2-NH₂, 5-Cl | 2 |
| 12197 | Me | 2-NHMe, 5-Cl | 2 |
| 12198 | Me | 2-NMe₂, 5-Cl | 2 |
| 12199 | Me | 2-NMe₃OTf, 5-Cl | 2 |
| 12200 | Me | 2-NMe₃I, 5-Cl | 2 |
| 12201 | Me | 2-Br, 4-F | 2 |
| 12202 | Me | 2-Br, 4-NO₂ | 2 |
| 12203 | Me | 2-Br, 4-NH₂ | 2 |
| 12204 | Me | 2-Br, 4-NHMe | 2 |
| 12205 | Me | 2-Br, 4-NMe₂ | 2 |
| 12206 | Me | 2-Br, 4-NMe₃OTf | 2 |
| 12207 | Me | 2-Br, 4-NMe₃I | 2 |

TABLE 9-continued

Substituent list for compounds of general structure XIV.

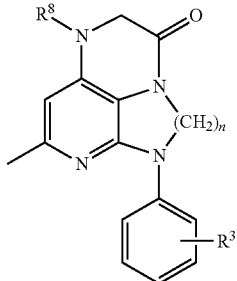

| Compound # | R⁸ = | R³ = | n = |
|---|---|---|---|
| 12208 | Me | 2-Br, 5-F | 2 |
| 12209 | Me | 2-Br, 5-NO₂ | 2 |
| 12210 | Me | 2-Br, 5-NH₂ | 2 |
| 12211 | Me | 2-Br, 5-NHMe | 2 |
| 12212 | Me | 2-Br, 5-NMe₂ | 2 |
| 12213 | Me | 2-Br, 5-NMe₃OTf | 2 |
| 12214 | Me | 2-Br, 5-NMe₃I | 2 |
| 12215 | Me | 2-F, 4-Br | 2 |
| 12216 | Me | 2-NO₂, 4-Br | 2 |
| 12217 | Me | 2-NH₂, 4-Br | 2 |
| 12218 | Me | 2-NHMe, 4-Br | 2 |
| 12219 | Me | 2-NMe₂, 4-Br | 2 |
| 12220 | Me | 2-NMe₃OTf, 4-Br | 2 |
| 12221 | Me | 2-NMe₃I, 4-Br | 2 |
| 12222 | Me | 2-I, 4-F | 2 |
| 12223 | Me | 2-I, 4-NO₂ | 2 |
| 12224 | Me | 2-I, 4-NH₂ | 2 |
| 12225 | Me | 2-I, 4-NHMe | 2 |
| 12226 | Me | 2-I, 4-NMe₂ | 2 |
| 12227 | Me | 2-I, 4-NMe₃OTf | 2 |
| 12228 | Me | 2-I, 4-NMe₃I | 2 |
| 12229 | Me | 2-F, 4-I | 2 |
| 12230 | Me | 2-NO₂, 4-I | 2 |
| 12231 | Me | 2-NH₂, 4-I | 2 |
| 12232 | Me | 2-NHMe, 4-I | 2 |
| 12233 | Me | 2-NMe₂, 4-I | 2 |
| 12234 | Me | 2-NMe₃OTf, 4-I | 2 |
| 12235 | Me | 2-NMe₃I, 4-I | 2 |
| 12236 | Me | 2-Me, 3-F | 2 |
| 12237 | Me | 2-Me, 3-NO₂ | 2 |
| 12238 | Me | 2-Me, 3-NH₂ | 2 |
| 12239 | Me | 2-Me, 3-NHMe | 2 |
| 12240 | Me | 2-Me, 3-NMe₂ | 2 |
| 12241 | Me | 2-Me, 3-NMe₃OTf | 2 |
| 12242 | Me | 2-Me, 3-NMe₃I | 2 |
| 12243 | Me | 2-Me, 4-F | 2 |
| 12244 | Me | 2-Me, 4-NO₂ | 2 |
| 12245 | Me | 2-Me, 4-NH₂ | 2 |
| 12246 | Me | 2-Me, 4-NHMe | 2 |
| 12247 | Me | 2-Me, 4-NMe₂ | 2 |
| 12248 | Me | 2-Me, 4-NMe₃OTf | 2 |
| 12249 | Me | 2-Me, 4-NMe₃I | 2 |
| 12250 | Me | 2-Me, 5-F | 2 |
| 12251 | Me | 2-Me, 5-NO₂ | 2 |
| 12252 | Me | 2-Me, 5-NH₂ | 2 |
| 12253 | Me | 2-Me, 5-NHMe | 2 |
| 12254 | Me | 2-Me, 5-NMe₂ | 2 |
| 12255 | Me | 2-Me, 5-NMe₃OTf | 2 |
| 12256 | Me | 2-Me, 5-NMe₃I | 2 |
| 12257 | Me | 2-F, 4-Me | 2 |
| 12258 | Me | 2-NO₂, 4-Me | 2 |
| 12259 | Me | 2-NH₂, 4-Me | 2 |
| 12260 | Me | 2-NHMe, 4-Me | 2 |
| 12261 | Me | 2-NMe₂, 4-Me | 2 |
| 12262 | Me | 2-NMe₃, 4-Me | 2 |
| 12263 | Me | 2-NMe₃OTf, 4-Me | 2 |
| 12264 | Me | 2-NMe₃I, 4-Me | 2 |
| 12265 | Me | 2-SnMe₃, 4-F | 2 |
| 12266 | Me | 2-SnMe₃, 5-F | 2 |
| 12267 | Me | 2-F, 4-SnMe₃ | 2 |

TABLE 9-continued

Substituent list for compounds of general structure XIV.

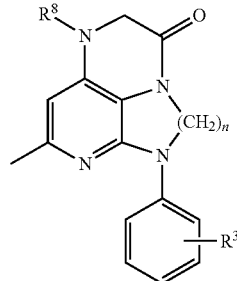

| Compound # | R⁸ = | R³ = | n = |
|---|---|---|---|
| 12268 | Me | 2-Br, 6-Cl, 4-F | 2 |
| 12269 | Me | 2-Br, 6-Cl, 4-NO₂ | 2 |
| 12270 | Me | 2-Br, 6-Cl, 4-NH₂ | 2 |
| 12271 | Me | 2-Br, 6-Cl, 4-NHMe | 2 |
| 12272 | Me | 2-Br, 6-Cl, 4-NMe₂ | 2 |
| 12273 | Me | 2-Br, 6-Cl, 4-NMe₃OTf | 2 |
| 12274 | Me | 2-Br, 6-Cl, 4-NMe₃I | 2 |
| 12275 | Me | 2-Me, 6-Cl, 4-F | 2 |
| 12276 | Me | 2-SnMe₃, 6-Cl, 4-F | 2 |
| 12277 | Me | 2-Cl, 4-Me | 2 |
| 12278 | Me | 2-Cl, 4-Br | 2 |
| 12279 | Me | 2-Cl, 4-SnMe₃ | 2 |
| 12280 | Me | 2-Br, 4-Cl | 2 |
| 12281 | Me | 2-SnMe₃, 4-Cl | 2 |
| 12282 | Me | 2-Me, 4-Cl | 2 |
| 12283 | Me | 2-Br, 4-Br | 2 |
| 12284 | Me | 2-Br, 4-Me | 2 |
| 12285 | Me | 2-Br, 4-SnMe₃ | 2 |
| 12286 | Me | 2-SnMe₃, 4-Br | 2 |
| 12287 | Me | 2-Me, 4-Br | 2 |
| 12288 | Me | 2-Me, 4-SnMe₃ | 2 |
| 12289 | Me | 2-SnMe₃, 4-Me | 2 |
| 12290 | Me | 2-Me, 4-Me | 2 |
| 12291 | Me | 2-Et, 4-Br | 2 |
| 12292 | Me | 2-Et, 4-SnMe₃ | 2 |
| 12293 | Me | 2-Et, 4-Me | 2 |
| 12294 | Me | 2-Me, 4-Me, 6-Me | 2 |
| 12295 | Me | 2-Me, 4-Br, 6-Me | 2 |
| 12296 | Me | 2-Me, 4-SnMe₃, 6-Me | 2 |
| 12297 | Me | 2-Et, 6-Me | 2 |
| 12298 | Me | 2-Br, 4-i-Pr | 2 |
| 12299 | Me | 2-SnMe₃, 4-i-Pr | 2 |
| 12300 | Me | 2-Me, 4-i-Pr | 2 |
| 12301 | Me | 2-Br, 4-Br, 6-Br | 2 |
| 12302 | Me | 2-Br, 4-Me, 6-Br | 2 |
| 12303 | Me | 2-Br, 4-SnMe₃, 6-Br | 2 |
| 12304 | Me | 2-SnMe₃, 4-Br, 6-Br | 2 |
| 12305 | Me | 2-Br, 4-Br, 6-Me | 2 |
| 12306 | Me | 2-Br, 4-CF₃, 6-Br | 2 |
| 12307 | Me | 2-Br, 4-Br, 6-CF₃ | 2 |
| 12308 | Me | 2-CF₃, 4-CF₃ | 2 |
| 12309 | Me | 2-Cl, 4-CF₃ | 2 |
| 12310 | Me | 2-CF₃, 4-Cl | 2 |
| 12311 | Me | 2-Br, 4-CF₃ | 2 |
| 12312 | Me | 2-SnMe₃, 4-CF₃ | 2 |
| 12313 | Me | 2-Me, 4-CF₃ | 2 |
| 12314 | Me | 2-CF₃, 4-Br | 2 |
| 12315 | Me | 2-CF₃, 4-SnMe₃ | 2 |
| 12316 | Me | 2-CF₃, 4-Me | 2 |
| 12317 | Me | 2-Br, 4-OH | 2 |
| 12318 | Me | 2-Br, 4-OMe | 2 |
| 12319 | Me | 2-Br, 4-OMeF | 2 |
| 12320 | Me | 2-Br, 4-OCF₃ | 2 |
| 12321 | Me | 2-Br, 4-OEtF | 2 |
| 12322 | Me | 2-Br, 4-OPrF | 2 |
| 12323 | Me | 2-OH, 4-Br | 2 |
| 12324 | Me | 2-OMe, 4-Br | 2 |
| 12325 | Me | 2-OMeF, 4-Br | 2 |
| 12326 | Me | 2-OCF₃, 4-Br | 2 |
| 12327 | Me | 2-OEtF, 4-Br | 2 |

TABLE 9-continued

Substituent list for compounds of general structure XIV.

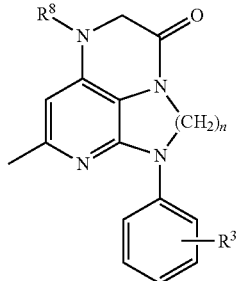

XIV

| Compound # | R⁸ = | R³ = | n = |
|---|---|---|---|
| 12328 | Me | 2-OPrF, 4-Br | 2 |
| 12329 | Me | 2-I, 4-OH | 2 |
| 12330 | Me | 2-I, 4-OMe | 2 |
| 12331 | Me | 2-I, 4-OMeF | 2 |
| 12332 | Me | 2-I, 4-OCF₃ | 2 |
| 12333 | Me | 2-I, 4-OEtF | 2 |
| 12334 | Me | 2-I, 4-OPrF | 2 |
| 12335 | Me | 2-OH, 4-I | 2 |
| 12336 | Me | 2-OMe, 4-I | 2 |
| 12337 | Me | 2-OMeF, 4-I | 2 |
| 12338 | Me | 2-OCF₃, 4-I | 2 |
| 12339 | Me | 2-OEtF, 4-I | 2 |
| 12340 | Me | 2-OPrF, 4-I | 2 |
| 12341 | Me | 2-SnMe₃, 4-OH | 2 |
| 12342 | Me | 2-SnMe₃, 4-OMe | 2 |
| 12343 | Me | 2-SnMe₃, 4-OMeF | 2 |
| 12344 | Me | 2-SnMe₃, 4-OCF₃ | 2 |
| 12345 | Me | 2-SnMe₃, 4-OEtF | 2 |
| 12346 | Me | 2-SnMe₃, 4-OPrF | 2 |
| 12347 | Me | 2-OH, 4-SnMe₃ | 2 |
| 12348 | Me | 2-OMe, 4-SnMe₃ | 2 |
| 12349 | Me | 2-OMeF, 4-SnMe₃ | 2 |
| 12350 | Me | 2-OCF₃, 4-SnMe₃ | 2 |
| 12351 | Me | 2-OEtF, 4-SnMe₃ | 2 |
| 12352 | Me | 2-OPrF, 4-SnMe₃ | 2 |
| 12353 | Me—F | H | 1 |
| 12354 | Me—F | 2-t-Bu | 1 |
| 12355 | Me—F | 2-Br | 1 |
| 12356 | Me—F | 3-Br | 1 |
| 12357 | Me—F | 4-Br | 1 |
| 12358 | Me—F | 2-I | 1 |
| 12359 | Me—F | 3-I | 1 |
| 12360 | Me—F | 4-I | 1 |
| 12361 | Me—F | 2-SnMe₃ | 1 |
| 12362 | Me—F | 3-SnMe₃ | 1 |
| 12363 | Me—F | 4-SnMe₃ | 1 |
| 12364 | Me—F | 2-Me | 1 |
| 12365 | Me—F | 3-Me | 1 |
| 12366 | Me—F | 4-Me | 1 |
| 12367 | Me—F | 2-OH | 1 |
| 12368 | Me—F | 3-OH | 1 |
| 12369 | Me—F | 4-OH | 1 |
| 12370 | Me—F | 2-OMe | 1 |
| 12371 | Me—F | 3-OMe | 1 |
| 12372 | Me—F | 4-OMe | 1 |
| 12373 | Me—F | 2-OMeF | 1 |
| 12374 | Me—F | 3-OMeF | 1 |
| 12375 | Me—F | 4-OMeF | 1 |
| 12376 | Me—F | 2-OCF₃ | 1 |
| 12377 | Me—F | 3-OCF₃ | 1 |
| 12378 | Me—F | 4-OCF₃ | 1 |
| 12379 | Me—F | 2-OEtF | 1 |
| 12380 | Me—F | 3-OEtF | 1 |
| 12381 | Me—F | 4-OEtF | 1 |
| 12382 | Me—F | 2-OPrF | 1 |
| 12383 | Me—F | 3-OPrF | 1 |
| 12384 | Me—F | 4-OPrF | 1 |
| 12385 | Me—F | 2-SH | 1 |
| 12386 | Me—F | 3-SH | 1 |
| 12387 | Me—F | 4-SH | 1 |

TABLE 9-continued

Substituent list for compounds of general structure XIV.

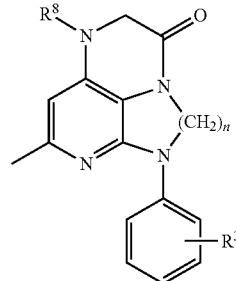

XIV

| Compound # | R⁸ = | R³ = | n = |
|---|---|---|---|
| 12388 | Me—F | 2-SMe | 1 |
| 12389 | Me—F | 3-SMe | 1 |
| 12390 | Me—F | 4-SMe | 1 |
| 12391 | Me—F | 2-SMeF | 1 |
| 12392 | Me—F | 3-SMeF | 1 |
| 12393 | Me—F | 4-SMeF | 1 |
| 12394 | Me—F | 2-SCF₃ | 1 |
| 12395 | Me—F | 3-SCF₃ | 1 |
| 12396 | Me—F | 4-SCF₃ | 1 |
| 12397 | Me—F | 2-SEtF | 1 |
| 12398 | Me—F | 3-SEtF | 1 |
| 12399 | Me—F | 4-SEtF | 1 |
| 12400 | Me—F | 2-SPrF | 1 |
| 12401 | Me—F | 3-SPrF | 1 |
| 12402 | Me—F | 4-SPrF | 1 |
| 12403 | Me—F | 2-OMe, 4-OMe | 1 |
| 12404 | Me—F | 2-Me, 5-OH | 1 |
| 12405 | Me—F | 2-Me, 5-OMe | 1 |
| 12406 | Me—F | 2-Me, 5-OMeF | 1 |
| 12407 | Me—F | 2-Me, 5-OEtF | 1 |
| 12408 | Me—F | 2-Me, 5-OPrF | 1 |
| 12409 | Me—F | 2-Me, 4-OH | 1 |
| 12410 | Me—F | 2-Me, 4-OMe | 1 |
| 12411 | Me—F | 2-Me, 4-OMeF | 1 |
| 12412 | Me—F | 2-Me, 4-OCF₃ | 1 |
| 12413 | Me—F | 2-Me, 4-OEtF | 1 |
| 12414 | Me—F | 2-Me, 4-OPrF | 1 |
| 12415 | Me—F | 2-OH, 4-Me | 1 |
| 12416 | Me—F | 2-OMe, 4-Me | 1 |
| 12417 | Me—F | 2-OMeF, 4-Me | 1 |
| 12418 | Me—F | 2-OCF₃, 4-Me | 1 |
| 12419 | Me—F | 2-OEtF, 4-Me | 1 |
| 12420 | Me—F | 2-OPrF, 4-Me | 1 |
| 12421 | Me—F | 2-Cl, 4-OH | 1 |
| 12422 | Me—F | 2-Cl, 4-OMe | 1 |
| 12423 | Me—F | 2-Cl, 4-OMeF | 1 |
| 12424 | Me—F | 2-Cl, 4-OCF₃ | 1 |
| 12425 | Me—F | 2-Cl, 4-OEtF | 1 |
| 12426 | Me—F | 2-Cl, 4-OPrF | 1 |
| 12427 | Me—F | 2-F, 4-F | 1 |
| 12428 | Me—F | 2-Cl, 4-Cl | 1 |
| 12429 | Me—F | 2-Cl, 4-F | 1 |
| 12430 | Me—F | 2-Cl, 4-NO₂ | 1 |
| 12431 | Me—F | 2-Cl, 4-NH₂ | 1 |
| 12432 | Me—F | 2-Cl, 4-NHMe | 1 |
| 12433 | Me—F | 2-Cl, 4-NMe₂ | 1 |
| 12434 | Me—F | 2-Cl, 4-NMe₃OTf | 1 |
| 12435 | Me—F | 2-Cl, 4-NMe₃I | 1 |
| 12436 | Me—F | 2-Cl, 5-F | 1 |
| 12437 | Me—F | 2-Cl, 5-NO₂ | 1 |
| 12438 | Me—F | 2-Cl, 5-NH₂ | 1 |
| 12439 | Me—F | 2-Cl, 5-NHMe | 1 |
| 12440 | Me—F | 2-Cl, 5-NMe₂ | 1 |
| 12441 | Me—F | 2-Cl, 5-NMe₃OTf | 1 |
| 12442 | Me—F | 2-Cl, 5-NMe₃I | 1 |
| 12443 | Me—F | 2-F, 4-Cl | 1 |
| 12444 | Me—F | 2-NO₂, 4-Cl | 1 |
| 12445 | Me—F | 2-NH₂, 4-Cl | 1 |
| 12446 | Me—F | 2-NHMe, 4-Cl | 1 |
| 12447 | Me—F | 2-NMe₂, 4-Cl | 1 |

TABLE 9-continued

Substituent list for compounds of general structure XIV.

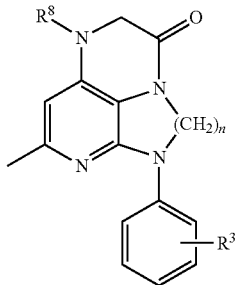

| Compound # | $R^8$ = | $R^3$ = | n = |
|---|---|---|---|
| 12448 | Me—F | 2-NMe$_3$OTf, 4-Cl | 1 |
| 12449 | Me—F | 2-NMe$_3$I, 4-Cl | 1 |
| 12450 | Me—F | 2-F, 5-Cl | 1 |
| 12451 | Me—F | 2-NO$_2$, 5-Cl | 1 |
| 12452 | Me—F | 2-NH$_2$, 5-Cl | 1 |
| 12453 | Me—F | 2-NHMe, 5-Cl | 1 |
| 12454 | Me—F | 2-NMe$_2$, 5-Cl | 1 |
| 12455 | Me—F | 2-NMe$_3$OTf, 5-Cl | 1 |
| 12456 | Me—F | 2-NMe$_3$I, 5-Cl | 1 |
| 12457 | Me—F | 2-Br, 4-F | 1 |
| 12458 | Me—F | 2-Br, 4-NO$_2$ | 1 |
| 12459 | Me—F | 2-Br, 4-NH$_2$ | 1 |
| 12460 | Me—F | 2-Br, 4-NHMe | 1 |
| 12461 | Me—F | 2-Br, 4-NMe$_2$ | 1 |
| 12462 | Me—F | 2-Br, 4-NMe$_3$OTf | 1 |
| 12463 | Me—F | 2-Br, 4-NMe$_3$I | 1 |
| 12464 | Me—F | 2-Br, 5-F | 1 |
| 12465 | Me—F | 2-Br, 5-NO$_2$ | 1 |
| 12466 | Me—F | 2-Br, 5-NH$_2$ | 1 |
| 12467 | Me—F | 2-Br, 5-NHMe | 1 |
| 12468 | Me—F | 2-Br, 5-NMe$_2$ | 1 |
| 12469 | Me—F | 2-Br, 5-NMe$_3$OTf | 1 |
| 12470 | Me—F | 2-Br, 5-NMe$_3$I | 1 |
| 12471 | Me—F | 2-F, 4-Br | 1 |
| 12472 | Me—F | 2-NO$_2$, 4-Br | 1 |
| 12473 | Me—F | 2-NH$_2$, 4-Br | 1 |
| 12474 | Me—F | 2-NHMe, 4-Br | 1 |
| 12475 | Me—F | 2-NMe$_2$, 4-Br | 1 |
| 12476 | Me—F | 2-NMe$_3$OTf, 4-Br | 1 |
| 12477 | Me—F | 2-NMe$_3$I, 4-Br | 1 |
| 12478 | Me—F | 2-I, 4-F | 1 |
| 12479 | Me—F | 2-I, 4-NO$_2$ | 1 |
| 12480 | Me—F | 2-I, 4-NH$_2$ | 1 |
| 12481 | Me—F | 2-I, 4-NHMe | 1 |
| 12482 | Me—F | 2-I, 4-NMe$_2$ | 1 |
| 12483 | Me—F | 2-I, 4-NMe$_3$OTf | 1 |
| 12484 | Me—F | 2-I, 4-NMe$_3$I | 1 |
| 12485 | Me—F | 2-F, 4-I | 1 |
| 12486 | Me—F | 2-NO$_2$, 4-I | 1 |
| 12487 | Me—F | 2-NH$_2$, 4-I | 1 |
| 12488 | Me—F | 2-NHMe, 4-I | 1 |
| 12489 | Me—F | 2-NMe$_2$, 4-I | 1 |
| 12490 | Me—F | 2-NMe$_3$OTf, 4-I | 1 |
| 12491 | Me—F | 2-NMe$_3$I, 4-I | 1 |
| 12492 | Me—F | 2-Me, 3-F | 1 |
| 12493 | Me—F | 2-Me, 3-NO$_2$ | 1 |
| 12494 | Me—F | 2-Me, 3-NH$_2$ | 1 |
| 12495 | Me—F | 2-Me, 3-NHMe | 1 |
| 12496 | Me—F | 2-Me, 3-NMe$_2$ | 1 |
| 12497 | Me—F | 2-Me, 3-NMe$_3$OTf | 1 |
| 12498 | Me—F | 2-Me, 3-NMe$_3$I | 1 |
| 12499 | Me—F | 2-Me, 4-F | 1 |
| 12500 | Me—F | 2-Me, 4-NO$_2$ | 1 |
| 12501 | Me—F | 2-Me, 4-NH$_2$ | 1 |
| 12502 | Me—F | 2-Me, 4-NHMe | 1 |
| 12503 | Me—F | 2-Me, 4-NMe$_2$ | 1 |
| 12504 | Me—F | 2-Me, 4-NMe$_3$OTf | 1 |
| 12505 | Me—F | 2-Me, 4-NMe$_3$I | 1 |
| 12506 | Me—F | 2-Me, 5-F | 1 |
| 12507 | Me—F | 2-Me, 5-NO$_2$ | 1 |

TABLE 9-continued

Substituent list for compounds of general structure XIV.

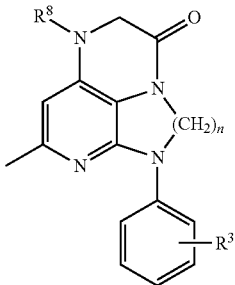

| Compound # | $R^8$ = | $R^3$ = | n = |
|---|---|---|---|
| 12508 | Me—F | 2-Me, 5-NH$_2$ | 1 |
| 12509 | Me—F | 2-Me, 5-NHMe | 1 |
| 12510 | Me—F | 2-Me, 5-NMe$_2$ | 1 |
| 12511 | Me—F | 2-Me, 5-NMe$_3$OTf | 1 |
| 12512 | Me—F | 2-Me, 5-NMe$_3$I | 1 |
| 12513 | Me—F | 2-F, 4-Me | 1 |
| 12514 | Me—F | 2-NO$_2$, 4-Me | 1 |
| 12515 | Me—F | 2-NH$_2$, 4-Me | 1 |
| 12516 | Me—F | 2-NHMe, 4-Me | 1 |
| 12517 | Me—F | 2-NMe$_2$, 4-Me | 1 |
| 12518 | Me—F | 2-NMe$_3$, 4-Me | 1 |
| 12519 | Me—F | 2-NMe$_3$OTf, 4-Me | 1 |
| 12520 | Me—F | 2-NMe$_3$I, 4-Me | 1 |
| 12521 | Me—F | 2-SnMe$_3$, 4-F | 1 |
| 12522 | Me—F | 2-SnMe$_3$, 5-F | 1 |
| 12523 | Me—F | 2-F, 4-SnMe$_3$ | 1 |
| 12524 | Me—F | 2-Br, 6-Cl, 4-F | 1 |
| 12525 | Me—F | 2-Br, 6-Cl, 4-NO$_2$ | 1 |
| 12526 | Me—F | 2-Br, 6-Cl, 4-NH$_2$ | 1 |
| 12527 | Me—F | 2-Br, 6-Cl, 4-NHMe | 1 |
| 12528 | Me—F | 2-Br, 6-Cl, 4-NMe$_2$ | 1 |
| 12529 | Me—F | 2-Br, 6-Cl, 4-NMe$_3$OTf | 1 |
| 12530 | Me—F | 2-Br, 6-Cl, 4-NMe$_3$I | 1 |
| 12531 | Me—F | 2-Me, 6-Cl, 4-F | 1 |
| 12532 | Me—F | 2-SnMe$_3$, 6-Cl, 4-F | 1 |
| 12533 | Me—F | 2-Cl, 4-Me | 1 |
| 12534 | Me—F | 2-Cl, 4-Br | 1 |
| 12535 | Me—F | 2-Cl, 4-SnMe$_3$ | 1 |
| 12536 | Me—F | 2-Br, 4-Cl | 1 |
| 12537 | Me—F | 2-SnMe$_3$, 4-Cl | 1 |
| 12538 | Me—F | 2-Me, 4-Cl | 1 |
| 12539 | Me—F | 2-Br, 4-Br | 1 |
| 12540 | Me—F | 2-Br, 4-Me | 1 |
| 12541 | Me—F | 2-Br, 4-SnMe$_3$ | 1 |
| 12542 | Me—F | 2-SnMe$_3$, 4-Br | 1 |
| 12543 | Me—F | 2-Me, 4-Br | 1 |
| 12544 | Me—F | 2-Me, 4-SnMe$_3$ | 1 |
| 12545 | Me—F | 2-SnMe$_3$, 4-Me | 1 |
| 12546 | Me—F | 2-Me, 4-Me | 1 |
| 12547 | Me—F | 2-Et, 4-Br | 1 |
| 12548 | Me—F | 2-Et, 4-SnMe$_3$ | 1 |
| 12549 | Me—F | 2-Et, 4-Me | 1 |
| 12550 | Me—F | 2-Me, 4-Me, 6-Me | 1 |
| 12551 | Me—F | 2-Me, 4-Br, 6-Me | 1 |
| 12552 | Me—F | 2-Me, 4-SnMe$_3$, 6-Me | 1 |
| 12553 | Me—F | 2-Et, 6-Me | 1 |
| 12554 | Me—F | 2-Br, 4-i-Pr | 1 |
| 12555 | Me—F | 2-SnMe$_3$, 4-i-Pr | 1 |
| 12556 | Me—F | 2-Me, 4-i-Pr | 1 |
| 12557 | Me—F | 2-Br, 4-Br, 6-Br | 1 |
| 12558 | Me—F | 2-Br, 4-Me, 6-Br | 1 |
| 12559 | Me—F | 2-Br, 4-SnMe$_3$, 6-Br | 1 |
| 12560 | Me—F | 2-SnMe$_3$, 4-Br, 6-Br | 1 |
| 12561 | Me—F | 2-Br, 4-Br, 6-Me | 1 |
| 12562 | Me—F | 2-Br, 4-CF$_3$, 6-Br | 1 |
| 12563 | Me—F | 2-Br, 4-Br, 6-CF$_3$ | 1 |
| 12564 | Me—F | 2-CF$_3$, 4-CF$_3$ | 1 |
| 12565 | Me—F | 2-Cl, 4-CF$_3$ | 1 |
| 12566 | Me—F | 2-CF$_3$, 4-Cl | 1 |
| 12567 | Me—F | 2-Br, 4-CF$_3$ | 1 |

TABLE 9-continued

Substituent list for compounds of general structure XIV.

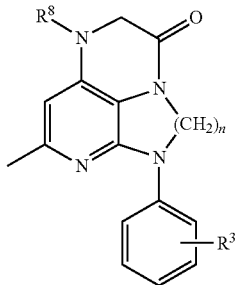

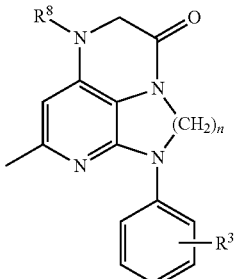

| Compound # | R$^8$ = | R$^3$ = | n = |
|---|---|---|---|
| 12568 | Me—F | 2-SnMe$_3$, 4-CF$_3$ | 1 |
| 12569 | Me—F | 2-Me, 4-CF$_3$ | 1 |
| 12570 | Me—F | 2-CF$_3$, 4-Br | 1 |
| 12571 | Me—F | 2-CF$_3$, 4-SnMe$_3$ | 1 |
| 12572 | Me—F | 2-CF$_3$, 4-Me | 1 |
| 12573 | Me—F | 2-Br, 4-OH | 1 |
| 12574 | Me—F | 2-Br, 4-OMe | 1 |
| 12575 | Me—F | 2-Br, 4-OMeF | 1 |
| 12576 | Me—F | 2-Br, 4-OCF$_3$ | 1 |
| 12577 | Me—F | 2-Br, 4-OEtF | 1 |
| 12578 | Me—F | 2-Br, 4-OPrF | 1 |
| 12579 | Me—F | 2-OH, 4-Br | 1 |
| 12580 | Me—F | 2-OMe, 4-Br | 1 |
| 12581 | Me—F | 2-OMeF, 4-Br | 1 |
| 12582 | Me—F | 2-OCF$_3$, 4-Br | 1 |
| 12583 | Me—F | 2-OEtF, 4-Br | 1 |
| 12584 | Me—F | 2-OPrF, 4-Br | 1 |
| 12585 | Me—F | 2-I, 4-OH | 1 |
| 12586 | Me—F | 2-I, 4-OMe | 1 |
| 12587 | Me—F | 2-I, 4-OMeF | 1 |
| 12588 | Me—F | 2-I, 4-OCF$_3$ | 1 |
| 12589 | Me—F | 2-I, 4-OEtF | 1 |
| 12590 | Me—F | 2-I, 4-OPrF | 1 |
| 12591 | Me—F | 2-OH, 4-I | 1 |
| 12592 | Me—F | 2-OMe, 4-I | 1 |
| 12593 | Me—F | 2-OMeF, 4-I | 1 |
| 12594 | Me—F | 2-OCF$_3$, 4-I | 1 |
| 12595 | Me—F | 2-OEtF, 4-I | 1 |
| 12596 | Me—F | 2-OPrF, 4-I | 1 |
| 12597 | Me—F | 2-SnMe$_3$, 4-OH | 1 |
| 12598 | Me—F | 2-SnMe$_3$, 4-OMe | 1 |
| 12599 | Me—F | 2-SnMe$_3$, 4-OMeF | 1 |
| 12600 | Me—F | 2-SnMe$_3$, 4-OCF$_3$ | 1 |
| 12601 | Me—F | 2-SnMe$_3$, 4-OEtF | 1 |
| 12602 | Me—F | 2-SnMe$_3$, 4-OPrF | 1 |
| 12603 | Me—F | 2-OH, 4-SnMe$_3$ | 1 |
| 12604 | Me—F | 2-OMe, 4-SnMe$_3$ | 1 |
| 12605 | Me—F | 2-OMeF, 4-SnMe$_3$ | 1 |
| 12606 | Me—F | 2-OCF$_3$, 4-SnMe$_3$ | 1 |
| 12607 | Me—F | 2-OEtF, 4-SnMe$_3$ | 1 |
| 12608 | Me—F | 2-OPrF, 4-SnMe$_3$ | 1 |
| 12609 | Me—F | H | 2 |
| 12610 | Me—F | 2-t-Bu | 2 |
| 12611 | Me—F | 2-Br | 2 |
| 12612 | Me—F | 3-Br | 2 |
| 12613 | Me—F | 4-Br | 2 |
| 12614 | Me—F | 2-I | 2 |
| 12615 | Me—F | 3-I | 2 |
| 12616 | Me—F | 4-I | 2 |
| 12617 | Me—F | 2-SnMe$_3$ | 2 |
| 12618 | Me—F | 3-SnMe$_3$ | 2 |
| 12619 | Me—F | 4-SnMe$_3$ | 2 |
| 12620 | Me—F | 2-Me | 2 |
| 12621 | Me—F | 3-Me | 2 |
| 12622 | Me—F | 4-Me | 2 |
| 12623 | Me—F | 2-OH | 2 |
| 12624 | Me—F | 3-OH | 2 |
| 12625 | Me—F | 4-OH | 2 |
| 12626 | Me—F | 2-OMe | 2 |
| 12627 | Me—F | 3-OMe | 2 |
| 12628 | Me—F | 4-OMe | 2 |
| 12629 | Me—F | 2-OMeF | 2 |
| 12630 | Me—F | 3-OMeF | 2 |
| 12631 | Me—F | 4-OMeF | 2 |
| 12632 | Me—F | 2-OCF$_3$ | 2 |
| 12633 | Me—F | 3-OCF$_3$ | 2 |
| 12634 | Me—F | 4-OCF$_3$ | 2 |
| 12635 | Me—F | 2-OEtF | 2 |
| 12636 | Me—F | 3-OEtF | 2 |
| 12637 | Me—F | 4-OEtF | 2 |
| 12638 | Me—F | 2-OPrF | 2 |
| 12639 | Me—F | 3-OPrF | 2 |
| 12640 | Me—F | 4-OPrF | 2 |
| 12641 | Me—F | 2-SH | 2 |
| 12642 | Me—F | 3-SH | 2 |
| 12643 | Me—F | 4-SH | 2 |
| 12644 | Me—F | 2-SMe | 2 |
| 12645 | Me—F | 3-SMe | 2 |
| 12646 | Me—F | 4-SMe | 2 |
| 12647 | Me—F | 2-SMeF | 2 |
| 12648 | Me—F | 3-SMeF | 2 |
| 12649 | Me—F | 4-SMeF | 2 |
| 12650 | Me—F | 2-SCF$_3$ | 2 |
| 12651 | Me—F | 3-SCF$_3$ | 2 |
| 12652 | Me—F | 4-SCF$_3$ | 2 |
| 12653 | Me—F | 2-SEtF | 2 |
| 12654 | Me—F | 3-SEtF | 2 |
| 12655 | Me—F | 4-SEtF | 2 |
| 12656 | Me—F | 2-SPrF | 2 |
| 12657 | Me—F | 3-SPrF | 2 |
| 12658 | Me—F | 4-SPrF | 2 |
| 12659 | Me—F | 2-OMe, 4-OMe | 2 |
| 12660 | Me—F | 2-Me, 5-OH | 2 |
| 12661 | Me—F | 2-Me, 5-OMe | 2 |
| 12662 | Me—F | 2-Me, 5-OMeF | 2 |
| 12663 | Me—F | 2-Me, 5-OEtF | 2 |
| 12664 | Me—F | 2-Me, 5-OPrF | 2 |
| 12665 | Me—F | 2-Me, 4-OH | 2 |
| 12666 | Me—F | 2-Me, 4-OMe | 2 |
| 12667 | Me—F | 2-Me, 4-OMeF | 2 |
| 12668 | Me—F | 2-Me, 4-OCF$_3$ | 2 |
| 12669 | Me—F | 2-Me, 4-OEtF | 2 |
| 12670 | Me—F | 2-Me, 4-OPrF | 2 |
| 12671 | Me—F | 2-OH, 4-Me | 2 |
| 12672 | Me—F | 2-OMe, 4-Me | 2 |
| 12673 | Me—F | 2-OMeF, 4-Me | 2 |
| 12674 | Me—F | 2-OCF$_3$, 4-Me | 2 |
| 12675 | Me—F | 2-OEtF, 4-Me | 2 |
| 12676 | Me—F | 2-OPrF, 4-Me | 2 |
| 12677 | Me—F | 2-Cl, 4-OH | 2 |
| 12678 | Me—F | 2-Cl, 4-OMe | 2 |
| 12679 | Me—F | 2-Cl, 4-OMeF | 2 |
| 12680 | Me—F | 2-Cl, 4-OCF$_3$ | 2 |
| 12681 | Me—F | 2-Cl, 4-OEtF | 2 |
| 12682 | Me—F | 2-Cl, 4-OPrF | 2 |
| 12683 | Me—F | 2-F, 4-F | 2 |
| 12684 | Me—F | 2-Cl, 4-Cl | 2 |
| 12685 | Me—F | 2-Cl, 4-F | 2 |
| 12686 | Me—F | 2-Cl, 4-NO$_2$ | 2 |
| 12687 | Me—F | 2-Cl, 4-NH$_2$ | 2 |

TABLE 9-continued

Substituent list for compounds of general structure XIV.

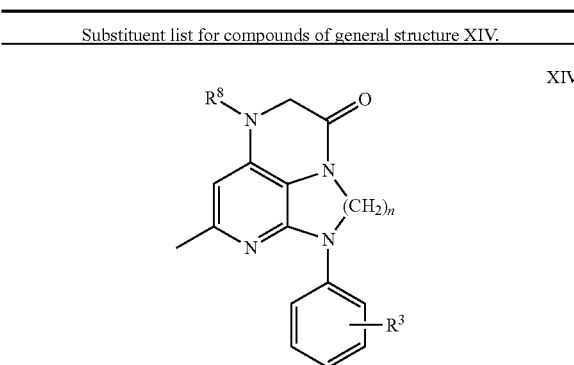

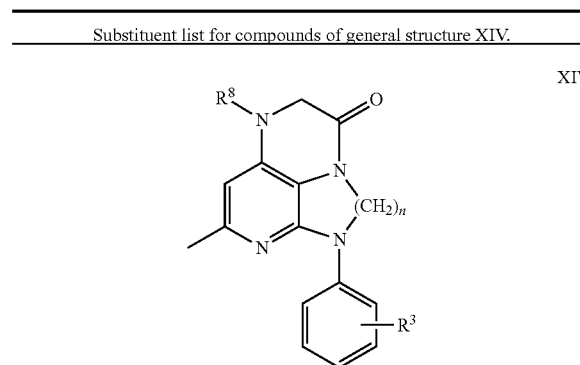

| Compound # | R[8] = | R[3] = | n = |
|---|---|---|---|
| 12688 | Me—F | 2-Cl, 4-NHMe | 2 |
| 12689 | Me—F | 2-Cl, 4-NMe$_2$ | 2 |
| 12690 | Me—F | 2-Cl, 4-NMe$_3$OTf | 2 |
| 12691 | Me—F | 2-Cl, 4-NMe$_3$I | 2 |
| 12692 | Me—F | 2-Cl, 5-F | 2 |
| 12693 | Me—F | 2-Cl, 5-NO$_2$ | 2 |
| 12694 | Me—F | 2-Cl, 5-NH$_2$ | 2 |
| 12695 | Me—F | 2-Cl, 5-NHMe | 2 |
| 12696 | Me—F | 2-Cl, 5-NMe$_2$ | 2 |
| 12697 | Me—F | 2-Cl, 5-NMe$_3$OTf | 2 |
| 12698 | Me—F | 2-Cl, 5-NMe$_3$I | 2 |
| 12699 | Me—F | 2-F, 4-Cl | 2 |
| 12700 | Me—F | 2-NO$_2$, 4-Cl | 2 |
| 12701 | Me—F | 2-NH$_2$, 4-Cl | 2 |
| 12702 | Me—F | 2-NHMe, 4-Cl | 2 |
| 12703 | Me—F | 2-NMe$_2$, 4-Cl | 2 |
| 12704 | Me—F | 2-NMe$_3$OTf, 4-Cl | 2 |
| 12705 | Me—F | 2-NMe$_3$I, 4-Cl | 2 |
| 12706 | Me—F | 2-F, 5-Cl | 2 |
| 12707 | Me—F | 2-NO$_2$, 5-Cl | 2 |
| 12708 | Me—F | 2-NH$_2$, 5-Cl | 2 |
| 12709 | Me—F | 2-NHMe, 5-Cl | 2 |
| 12710 | Me—F | 2-NMe$_2$, 5-Cl | 2 |
| 12711 | Me—F | 2-NMe$_3$OTf, 5-Cl | 2 |
| 12712 | Me—F | 2-NMe$_3$I, 5-Cl | 2 |
| 12713 | Me—F | 2-Br, 4-F | 2 |
| 12714 | Me—F | 2-Br, 4-NO$_2$ | 2 |
| 12715 | Me—F | 2-Br, 4-NH$_2$ | 2 |
| 12716 | Me—F | 2-Br, 4-NHMe | 2 |
| 12717 | Me—F | 2-Br, 4-NMe$_2$ | 2 |
| 12718 | Me—F | 2-Br, 4-NMe$_3$OTf | 2 |
| 12719 | Me—F | 2-Br, 4-NMe$_3$I | 2 |
| 12720 | Me—F | 2-Br, 5-F | 2 |
| 12721 | Me—F | 2-Br, 5-NO$_2$ | 2 |
| 12722 | Me—F | 2-Br, 5-NH$_2$ | 2 |
| 12723 | Me—F | 2-Br, 5-NHMe | 2 |
| 12724 | Me—F | 2-Br, 5-NMe$_2$ | 2 |
| 12725 | Me—F | 2-Br, 5-NMe$_3$OTf | 2 |
| 12726 | Me—F | 2-Br, 5-NMe$_3$I | 2 |
| 12727 | Me—F | 2-F, 4-Br | 2 |
| 12728 | Me—F | 2-NO$_2$, 4-Br | 2 |
| 12729 | Me—F | 2-NH$_2$, 4-Br | 2 |
| 12730 | Me—F | 2-NHMe, 4-Br | 2 |
| 12731 | Me—F | 2-NMe$_2$, 4-Br | 2 |
| 12732 | Me—F | 2-NMe$_3$OTf, 4-Br | 2 |
| 12733 | Me—F | 2-NMe$_3$I, 4-Br | 2 |
| 12734 | Me—F | 2-I, 4-F | 2 |
| 12735 | Me—F | 2-I, 4-NO$_2$ | 2 |
| 12736 | Me—F | 2-I, 4-NH$_2$ | 2 |
| 12737 | Me—F | 2-I, 4-NHMe | 2 |
| 12738 | Me—F | 2-I, 4-NMe$_2$ | 2 |
| 12739 | Me—F | 2-I, 4-NMe$_3$OTf | 2 |
| 12740 | Me—F | 2-I, 4-NMe$_3$I | 2 |
| 12741 | Me—F | 2-F, 4-I | 2 |
| 12742 | Me—F | 2-NO$_2$, 4-I | 2 |
| 12743 | Me—F | 2-NH$_2$, 4-I | 2 |
| 12744 | Me—F | 2-NHMe, 4-I | 2 |
| 12745 | Me—F | 2-NMe$_2$, 4-I | 2 |
| 12746 | Me—F | 2-NMe$_3$OTf, 4-I | 2 |
| 12747 | Me—F | 2-NMe$_3$I, 4-I | 2 |
| 12748 | Me—F | 2-Me, 3-F | 2 |
| 12749 | Me—F | 2-Me, 3-NO$_2$ | 2 |
| 12750 | Me—F | 2-Me, 3-NH$_2$ | 2 |
| 12751 | Me—F | 2-Me, 3-NHMe | 2 |
| 12752 | Me—F | 2-Me, 3-NMe$_2$ | 2 |
| 12753 | Me—F | 2-Me, 3-NMe$_3$OTf | 2 |
| 12754 | Me—F | 2-Me, 3-NMe$_3$I | 2 |
| 12755 | Me—F | 2-Me, 4-F | 2 |
| 12756 | Me—F | 2-Me, 4-NO$_2$ | 2 |
| 12757 | Me—F | 2-Me, 4-NH$_2$ | 2 |
| 12758 | Me—F | 2-Me, 4-NHMe | 2 |
| 12759 | Me—F | 2-Me, 4-NMe$_2$ | 2 |
| 12760 | Me—F | 2-Me, 4-NMe$_3$OTf | 2 |
| 12761 | Me—F | 2-Me, 4-NMe$_3$I | 2 |
| 12762 | Me—F | 2-Me, 5-F | 2 |
| 12763 | Me—F | 2-Me, 5-NO$_2$ | 2 |
| 12764 | Me—F | 2-Me, 5-NH$_2$ | 2 |
| 12765 | Me—F | 2-Me, 5-NHMe | 2 |
| 12766 | Me—F | 2-Me, 5-NMe$_2$ | 2 |
| 12767 | Me—F | 2-Me, 5-NMe$_3$OTf | 2 |
| 12768 | Me—F | 2-Me, 5-NMe$_3$I | 2 |
| 12769 | Me—F | 2-F, 4-Me | 2 |
| 12770 | Me—F | 2-NO$_2$, 4-Me | 2 |
| 12771 | Me—F | 2-NH$_2$, 4-Me | 2 |
| 12772 | Me—F | 2-NHMe, 4-Me | 2 |
| 12773 | Me—F | 2-NMe$_2$, 4-Me | 2 |
| 12774 | Me—F | 2-NMe$_3$, 4-Me | 2 |
| 12775 | Me—F | 2-NMe$_3$OTf, 4-Me | 2 |
| 12776 | Me—F | 2-NMe$_3$I, 4-Me | 2 |
| 12777 | Me—F | 2-SnMe$_3$, 4-F | 2 |
| 12778 | Me—F | 2-SnMe$_3$, 5-F | 2 |
| 12779 | Me—F | 2-F, 4-SnMe$_3$ | 2 |
| 12780 | Me—F | 2-Br, 6-Cl, 4-F | 2 |
| 12781 | Me—F | 2-Br, 6-Cl, 4-NO$_2$ | 2 |
| 12782 | Me—F | 2-Br, 6-Cl, 4-NH$_2$ | 2 |
| 12783 | Me—F | 2-Br, 6-Cl, 4-NHMe | 2 |
| 12784 | Me—F | 2-Br, 6-Cl, 4-NMe$_2$ | 2 |
| 12785 | Me—F | 2-Br, 6-Cl, 4-NMe$_3$OTf | 2 |
| 12786 | Me—F | 2-Br, 6-Cl, 4-NMe$_3$I | 2 |
| 12787 | Me—F | 2-Me, 6-Cl, 4-F | 2 |
| 12788 | Me—F | 2-SnMe$_3$, 6-Cl, 4-F | 2 |
| 12789 | Me—F | 2-Cl, 4-Me | 2 |
| 12790 | Me—F | 2-Cl, 4-Br | 2 |
| 12791 | Me—F | 2-Cl, 4-SnMe$_3$ | 2 |
| 12792 | Me—F | 2-Br, 4-Cl | 2 |
| 12793 | Me—F | 2-SnMe$_3$, 4-Cl | 2 |
| 12794 | Me—F | 2-Me, 4-Cl | 2 |
| 12795 | Me—F | 2-Br, 4-Br | 2 |
| 12796 | Me—F | 2-Br, 4-Me | 2 |
| 12797 | Me—F | 2-Br, 4-SnMe$_3$ | 2 |
| 12798 | Me—F | 2-SnMe$_3$, 4-Br | 2 |
| 12799 | Me—F | 2-Me, 4-Br | 2 |
| 12800 | Me—F | 2-Me, 4-SnMe$_3$ | 2 |
| 12801 | Me—F | 2-SnMe$_3$, 4-Me | 2 |
| 12802 | Me—F | 2-Me, 4-Me | 2 |
| 12803 | Me—F | 2-Et, 4-Br | 2 |
| 12804 | Me—F | 2-Et, 4-SnMe$_3$ | 2 |
| 12805 | Me—F | 2-Et, 4-Me | 2 |
| 12806 | Me—F | 2-Me, 4-Me, 6-Me | 2 |
| 12807 | Me—F | 2-Me, 4-Br, 6-Me | 2 |

TABLE 9-continued

Substituent list for compounds of general structure XIV.

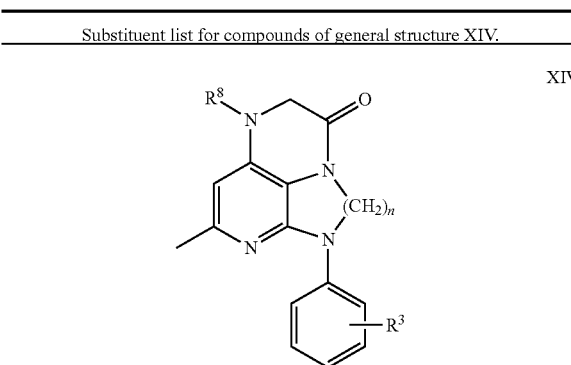

| Compound # | R⁸ = | R³ = | n = |
|---|---|---|---|
| 12808 | Me—F | 2-Me, 4-SnMe₃, 6-Me | 2 |
| 12809 | Me—F | 2-Et, 6-Me | 2 |
| 12810 | Me—F | 2-Br, 4-i-Pr | 2 |
| 12811 | Me—F | 2-SnMe₃, 4-i-Pr | 2 |
| 12812 | Me—F | 2-Me, 4-i-Pr | 2 |
| 12813 | Me—F | 2-Br, 4-Br, 6-Br | 2 |
| 12814 | Me—F | 2-Br, 4-Me, 6-Br | 2 |
| 12815 | Me—F | 2-Br, 4-SnMe₃, 6-Br | 2 |
| 12816 | Me—F | 2-SnMe₃, 4-Br, 6-Br | 2 |
| 12817 | Me—F | 2-Br, 4-Br, 6-Me | 2 |
| 12818 | Me—F | 2-Br, 4-CF₃, 6-Br | 2 |
| 12819 | Me—F | 2-Br, 4-Br, 6-CF₃ | 2 |
| 12820 | Me—F | 2-CF₃, 4-CF₃ | 2 |
| 12821 | Me—F | 2-Cl, 4-CF₃ | 2 |
| 12822 | Me—F | 2-CF₃, 4-Cl | 2 |
| 12823 | Me—F | 2-Br, 4-CF₃ | 2 |
| 12824 | Me—F | 2-SnMe₃, 4-CF₃ | 2 |
| 12825 | Me—F | 2-Me, 4-CF₃ | 2 |
| 12826 | Me—F | 2-CF₃, 4-Br | 2 |
| 12827 | Me—F | 2-CF₃, 4-SnMe₃ | 2 |
| 12828 | Me—F | 2-CF₃, 4-Me | 2 |
| 12829 | Me—F | 2-Br, 4-OH | 2 |
| 12830 | Me—F | 2-Br, 4-OMe | 2 |
| 12831 | Me—F | 2-Br, 4-OMeF | 2 |
| 12832 | Me—F | 2-Br, 4-OCF₃ | 2 |
| 12833 | Me—F | 2-Br, 4-OEtF | 2 |
| 12834 | Me—F | 2-Br, 4-OPrF | 2 |
| 12835 | Me—F | 2-OH, 4-Br | 2 |
| 12836 | Me—F | 2-OMe, 4-Br | 2 |
| 12837 | Me—F | 2-OMeF, 4-Br | 2 |
| 12838 | Me—F | 2-OCF₃, 4-Br | 2 |
| 12839 | Me—F | 2-OEtF, 4-Br | 2 |
| 12840 | Me—F | 2-OPrF, 4-Br | 2 |
| 12841 | Me—F | 2-I, 4-OH | 2 |
| 12842 | Me—F | 2-I, 4-OMe | 2 |
| 12843 | Me—F | 2-I, 4-OMeF | 2 |
| 12844 | Me—F | 2-I, 4-OCF₃ | 2 |
| 12845 | Me—F | 2-I, 4-OEtF | 2 |
| 12846 | Me—F | 2-I, 4-OPrF | 2 |
| 12847 | Me—F | 2-OH, 4-I | 2 |
| 12848 | Me—F | 2-OMe, 4-I | 2 |
| 12849 | Me—F | 2-OMeF, 4-I | 2 |
| 12850 | Me—F | 2-OCF₃, 4-I | 2 |
| 12851 | Me—F | 2-OEtF, 4-I | 2 |
| 12852 | Me—F | 2-OPrF, 4-I | 2 |
| 12853 | Me—F | 2-SnMe₃, 4-OH | 2 |
| 12854 | Me—F | 2-SnMe₃, 4-OMe | 2 |
| 12855 | Me—F | 2-SnMe₃, 4-OMeF | 2 |
| 12856 | Me—F | 2-SnMe₃, 4-OCF₃ | 2 |
| 12857 | Me—F | 2-SnMe₃, 4-OEtF | 2 |
| 12858 | Me—F | 2-SnMe₃, 4-OPrF | 2 |
| 12859 | Me—F | 2-OH, 4-SnMe₃ | 2 |
| 12860 | Me—F | 2-OMe, 4-SnMe₃ | 2 |
| 12861 | Me—F | 2-OMeF, 4-SnMe₃ | 2 |
| 12862 | Me—F | 2-OCF₃, 4-SnMe₃ | 2 |
| 12863 | Me—F | 2-OEtF, 4-SnMe₃ | 2 |
| 12864 | Me—F | 2-OPrF, 4-SnMe₃ | 2 |
| 12865 | FCH₂—CH=CH—CH₂ | H | 1 |
| 12866 | FCH₂—CH=CH—CH₂ | 2-t-Bu | 1 |
| 12867 | FCH₂—CH=CH—CH₂ | 2-Br | 1 |

TABLE 9-continued

Substituent list for compounds of general structure XIV.

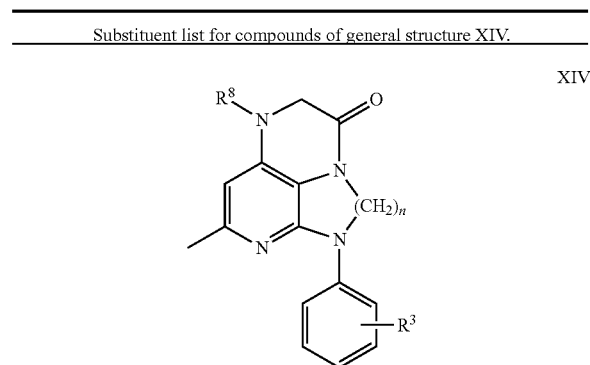

| Compound # | R⁸ = | R³ = | n = |
|---|---|---|---|
| 12868 | FCH₂—CH=CH—CH₂ | 3-Br | 1 |
| 12869 | FCH₂—CH=CH—CH₂ | 4-Br | 1 |
| 12870 | FCH₂—CH=CH—CH₂ | 2-I | 1 |
| 12871 | FCH₂—CH=CH—CH₂ | 3-I | 1 |
| 12872 | FCH₂—CH=CH—CH₂ | 4-I | 1 |
| 12873 | FCH₂—CH=CH—CH₂ | 2-SnMe₃ | 1 |
| 12874 | FCH₂—CH=CH—CH₂ | 3-SnMe₃ | 1 |
| 12875 | FCH₂—CH=CH—CH₂ | 4-SnMe₃ | 1 |
| 12876 | FCH₂—CH=CH—CH₂ | 2-Me | 1 |
| 12877 | FCH₂—CH=CH—CH₂ | 3-Me | 1 |
| 12878 | FCH₂—CH=CH—CH₂ | 4-Me | 1 |
| 12879 | FCH₂—CH=CH—CH₂ | 2-OH | 1 |
| 12880 | FCH₂—CH=CH—CH₂ | 3-OH | 1 |
| 12881 | FCH₂—CH=CH—CH₂ | 4-OH | 1 |
| 12882 | FCH₂—CH=CH—CH₂ | 2-OMe | 1 |
| 12883 | FCH₂—CH=CH—CH₂ | 3-OMe | 1 |
| 12884 | FCH₂—CH=CH—CH₂ | 4-OMe | 1 |
| 12885 | FCH₂—CH=CH—CH₂ | 2-OMeF | 1 |
| 12886 | FCH₂—CH=CH—CH₂ | 3-OMeF | 1 |
| 12887 | FCH₂—CH=CH—CH₂ | 4-OMeF | 1 |
| 12888 | FCH₂—CH=CH—CH₂ | 2-OCF₃ | 1 |
| 12889 | FCH₂—CH=CH—CH₂ | 3-OCF₃ | 1 |
| 12890 | FCH₂—CH=CH—CH₂ | 4-OCF₃ | 1 |
| 12891 | FCH₂—CH=CH—CH₂ | 2-OEtF | 1 |
| 12892 | FCH₂—CH=CH—CH₂ | 3-OEtF | 1 |
| 12893 | FCH₂—CH=CH—CH₂ | 4-OEtF | 1 |
| 12894 | FCH₂—CH=CH—CH₂ | 2-OPrF | 1 |
| 12895 | FCH₂—CH=CH—CH₂ | 3-OPrF | 1 |
| 12896 | FCH₂—CH=CH—CH₂ | 4-OPrF | 1 |
| 12897 | FCH₂—CH=CH—CH₂ | 2-SH | 1 |
| 12898 | FCH₂—CH=CH—CH₂ | 3-SH | 1 |
| 12899 | FCH₂—CH=CH—CH₂ | 4-SH | 1 |
| 12900 | FCH₂—CH=CH—CH₂ | 2-SMe | 1 |
| 12901 | FCH₂—CH=CH—CH₂ | 3-SMe | 1 |
| 12902 | FCH₂—CH=CH—CH₂ | 4-SMe | 1 |
| 12903 | FCH₂—CH=CH—CH₂ | 2-SMeF | 1 |
| 12904 | FCH₂—CH=CH—CH₂ | 3-SMeF | 1 |
| 12905 | FCH₂—CH=CH—CH₂ | 4-SMeF | 1 |
| 12906 | FCH₂—CH=CH—CH₂ | 2-SCF₃ | 1 |
| 12907 | FCH₂—CH=CH—CH₂ | 3-SCF₃ | 1 |
| 12908 | FCH₂—CH=CH—CH₂ | 4-SCF₃ | 1 |
| 12909 | FCH₂—CH=CH—CH₂ | 2-SEtF | 1 |
| 12910 | FCH₂—CH=CH—CH₂ | 3-SEtF | 1 |
| 12911 | FCH₂—CH=CH—CH₂ | 4-SEtF | 1 |
| 12912 | FCH₂—CH=CH—CH₂ | 2-SPrF | 1 |
| 12913 | FCH₂—CH=CH—CH₂ | 3-SPrF | 1 |
| 12914 | FCH₂—CH=CH—CH₂ | 4-SPrF | 1 |
| 12915 | FCH₂—CH=CH—CH₂ | 2-OMe, 4-OMe | 1 |
| 12916 | FCH₂—CH=CH—CH₂ | 2-Me, 5-OH | 1 |
| 12917 | FCH₂—CH=CH—CH₂ | 2-Me, 5-OMe | 1 |
| 12918 | FCH₂—CH=CH—CH₂ | 2-Me, 5-OMeF | 1 |
| 12919 | FCH₂—CH=CH—CH₂ | 2-Me, 5-OEtF | 1 |
| 12920 | FCH₂—CH=CH—CH₂ | 2-Me, 5-OPrF | 1 |
| 12921 | FCH₂—CH=CH—CH₂ | 2-Me, 4-OH | 1 |
| 12922 | FCH₂—CH=CH—CH₂ | 2-Me, 4-OMe | 1 |
| 12923 | FCH₂—CH=CH—CH₂ | 2-Me, 4-OMeF | 1 |
| 12924 | FCH₂—CH=CH—CH₂ | 2-Me, 4-OCF₃ | 1 |
| 12925 | FCH₂—CH=CH—CH₂ | 2-Me, 4-OEtF | 1 |
| 12926 | FCH₂—CH=CH—CH₂ | 2-Me, 4-OPrF | 1 |
| 12927 | FCH₂—CH=CH—CH₂ | 2-OH, 4-Me | 1 |

TABLE 9-continued

Substituent list for compounds of general structure XIV.

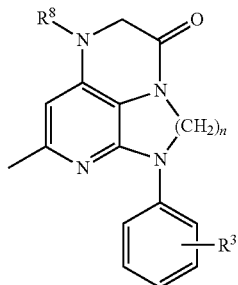

XIV

| Compound # | $R^8 =$ | $R^3 =$ | n = |
|---|---|---|---|
| 12928 | $FCH_2-CH=CH-CH_2$ | 2-OMe, 4-Me | 1 |
| 12929 | $FCH_2-CH=CH-CH_2$ | 2-OMeF, 4-Me | 1 |
| 12930 | $FCH_2-CH=CH-CH_2$ | 2-OCF$_3$, 4-Me | 1 |
| 12931 | $FCH_2-CH=CH-CH_2$ | 2-OEtF, 4-Me | 1 |
| 12932 | $FCH_2-CH=CH-CH_2$ | 2-OPrF, 4-Me | 1 |
| 12933 | $FCH_2-CH=CH-CH_2$ | 2-Cl, 4-OH | 1 |
| 12934 | $FCH_2-CH=CH-CH_2$ | 2-Cl, 4-OMe | 1 |
| 12935 | $FCH_2-CH=CH-CH_2$ | 2-Cl, 4-OMeF | 1 |
| 12936 | $FCH_2-CH=CH-CH_2$ | 2-Cl, 4-OCF$_3$ | 1 |
| 12937 | $FCH_2-CH=CH-CH_2$ | 2-Cl, 4-OEtF | 1 |
| 12938 | $FCH_2-CH=CH-CH_2$ | 2-Cl, 4-OPrF | 1 |
| 12939 | $FCH_2-CH=CH-CH_2$ | 2-F, 4-F | 1 |
| 12940 | $FCH_2-CH=CH-CH_2$ | 2-Cl, 4-Cl | 1 |
| 12941 | $FCH_2-CH=CH-CH_2$ | 2-Cl, 4-F | 1 |
| 12942 | $FCH_2-CH=CH-CH_2$ | 2-Cl, 4-NO$_2$ | 1 |
| 12943 | $FCH_2-CH=CH-CH_2$ | 2-Cl, 4-NH$_2$ | 1 |
| 12944 | $FCH_2-CH=CH-CH_2$ | 2-Cl, 4-NHMe | 1 |
| 12945 | $FCH_2-CH=CH-CH_2$ | 2-Cl, 4-NMe$_2$ | 1 |
| 12946 | $FCH_2-CH=CH-CH_2$ | 2-Cl, 4-NMe$_3$OTf | 1 |
| 12947 | $FCH_2-CH=CH-CH_2$ | 2-Cl, 4-NMe$_3$I | 1 |
| 12948 | $FCH_2-CH=CH-CH_2$ | 2-Cl, 5-F | 1 |
| 12949 | $FCH_2-CH=CH-CH_2$ | 2-Cl, 5-NO$_2$ | 1 |
| 12950 | $FCH_2-CH=CH-CH_2$ | 2-Cl, 5-NH$_2$ | 1 |
| 12951 | $FCH_2-CH=CH-CH_2$ | 2-Cl, 5-NHMe | 1 |
| 12952 | $FCH_2-CH=CH-CH_2$ | 2-Cl, 5-NMe$_2$ | 1 |
| 12953 | $FCH_2-CH=CH-CH_2$ | 2-Cl, 5-NMe$_3$OTf | 1 |
| 12954 | $FCH_2-CH=CH-CH_2$ | 2-Cl, 5-NMe$_3$I | 1 |
| 12955 | $FCH_2-CH=CH-CH_2$ | 2-F, 4-Cl | 1 |
| 12956 | $FCH_2-CH=CH-CH_2$ | 2-NO$_2$, 4-Cl | 1 |
| 12957 | $FCH_2-CH=CH-CH_2$ | 2-NH$_2$, 4-Cl | 1 |
| 12958 | $FCH_2-CH=CH-CH_2$ | 2-NHMe, 4-Cl | 1 |
| 12959 | $FCH_2-CH=CH-CH_2$ | 2-NMe$_2$, 4-Cl | 1 |
| 12960 | $FCH_2-CH=CH-CH_2$ | 2-NMe$_3$OTf, 4-Cl | 1 |
| 12961 | $FCH_2-CH=CH-CH_2$ | 2-NMe$_3$I, 4-Cl | 1 |
| 12962 | $FCH_2-CH=CH-CH_2$ | 2-F, 5-Cl | 1 |
| 12963 | $FCH_2-CH=CH-CH_2$ | 2-NO$_2$, 5-Cl | 1 |
| 12964 | $FCH_2-CH=CH-CH_2$ | 2-NH$_2$, 5-Cl | 1 |
| 12965 | $FCH_2-CH=CH-CH_2$ | 2-NHMe, 5-Cl | 1 |
| 12966 | $FCH_2-CH=CH-CH_2$ | 2-NMe$_2$, 5-Cl | 1 |
| 12967 | $FCH_2-CH=CH-CH_2$ | 2-NMe$_3$OTf, 5-Cl | 1 |
| 12968 | $FCH_2-CH=CH-CH_2$ | 2-NMe$_3$I, 5-Cl | 1 |
| 12969 | $FCH_2-CH=CH-CH_2$ | 2-Br, 4-F | 1 |
| 12970 | $FCH_2-CH=CH-CH_2$ | 2-Br, 4-NO$_2$ | 1 |
| 12971 | $FCH_2-CH=CH-CH_2$ | 2-Br, 4-NH$_2$ | 1 |
| 12972 | $FCH_2-CH=CH-CH_2$ | 2-Br, 4-NHMe | 1 |
| 12973 | $FCH_2-CH=CH-CH_2$ | 2-Br, 4-NMe$_2$ | 1 |
| 12974 | $FCH_2-CH=CH-CH_2$ | 2-Br, 4-NMe$_3$OTf | 1 |
| 12975 | $FCH_2-CH=CH-CH_2$ | 2-Br, 4-NMe$_3$I | 1 |
| 12976 | $FCH_2-CH=CH-CH_2$ | 2-Br, 5-F | 1 |
| 12977 | $FCH_2-CH=CH-CH_2$ | 2-Br, 5-NO$_2$ | 1 |
| 12978 | $FCH_2-CH=CH-CH_2$ | 2-Br, 5-NH$_2$ | 1 |
| 12979 | $FCH_2-CH=CH-CH_2$ | 2-Br, 5-NHMe | 1 |
| 12980 | $FCH_2-CH=CH-CH_2$ | 2-Br, 5-NMe$_2$ | 1 |
| 12981 | $FCH_2-CH=CH-CH_2$ | 2-Br, 5-NMe$_3$OTf | 1 |
| 12982 | $FCH_2-CH=CH-CH_2$ | 2-Br, 5-NMe$_3$I | 1 |
| 12983 | $FCH_2-CH=CH-CH_2$ | 2-F, 4-Br | 1 |
| 12984 | $FCH_2-CH=CH-CH_2$ | 2-NO$_2$, 4-Br | 1 |
| 12985 | $FCH_2-CH=CH-CH_2$ | 2-NH$_2$, 4-Br | 1 |
| 12986 | $FCH_2-CH=CH-CH_2$ | 2-NHMe, 4-Br | 1 |
| 12987 | $FCH_2-CH=CH-CH_2$ | 2-NMe$_2$, 4-Br | 1 |

TABLE 9-continued

Substituent list for compounds of general structure XIV.

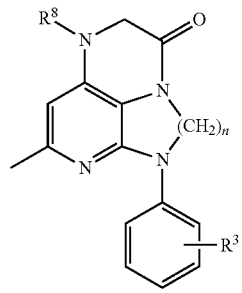

XIV

| Compound # | $R^8 =$ | $R^3 =$ | n = |
|---|---|---|---|
| 12988 | $FCH_2-CH=CH-CH_2$ | 2-NMe$_3$OTf, 4-Br | 1 |
| 12989 | $FCH_2-CH=CH-CH_2$ | 2-NMe$_3$I, 4-Br | 1 |
| 12990 | $FCH_2-CH=CH-CH_2$ | 2-I, 4-F | 1 |
| 12991 | $FCH_2-CH=CH-CH_2$ | 2-I, 4-NO$_2$ | 1 |
| 12992 | $FCH_2-CH=CH-CH_2$ | 2-I, 4-NH$_2$ | 1 |
| 12993 | $FCH_2-CH=CH-CH_2$ | 2-I, 4-NHMe | 1 |
| 12994 | $FCH_2-CH=CH-CH_2$ | 2-I, 4-NMe$_2$ | 1 |
| 12995 | $FCH_2-CH=CH-CH_2$ | 2-I, 4-NMe$_3$OTf | 1 |
| 12996 | $FCH_2-CH=CH-CH_2$ | 2-I, 4-NMe$_3$I | 1 |
| 12997 | $FCH_2-CH=CH-CH_2$ | 2-F, 4-I | 1 |
| 12998 | $FCH_2-CH=CH-CH_2$ | 2-NO$_2$, 4-I | 1 |
| 12999 | $FCH_2-CH=CH-CH_2$ | 2-NH$_2$, 4-I | 1 |
| 13000 | $FCH_2-CH=CH-CH_2$ | 2-NHMe, 4-I | 1 |
| 13001 | $FCH_2-CH=CH-CH_2$ | 2-NMe$_2$, 4-I | 1 |
| 13002 | $FCH_2-CH=CH-CH_2$ | 2-NMe$_3$OTf, 4-I | 1 |
| 13003 | $FCH_2-CH=CH-CH_2$ | 2-NMe$_3$I, 4-I | 1 |
| 13004 | $FCH_2-CH=CH-CH_2$ | 2-Me, 3-F | 1 |
| 13005 | $FCH_2-CH=CH-CH_2$ | 2-Me, 3-NO$_2$ | 1 |
| 13006 | $FCH_2-CH=CH-CH_2$ | 2-Me, 3-NH$_2$ | 1 |
| 13007 | $FCH_2-CH=CH-CH_2$ | 2-Me, 3-NHMe | 1 |
| 13008 | $FCH_2-CH=CH-CH_2$ | 2-Me, 3-NMe$_2$ | 1 |
| 13009 | $FCH_2-CH=CH-CH_2$ | 2-Me, 3-NMe$_3$OTf | 1 |
| 13010 | $FCH_2-CH=CH-CH_2$ | 2-Me, 3-NMe$_3$I | 1 |
| 13011 | $FCH_2-CH=CH-CH_2$ | 2-Me, 4-F | 1 |
| 13012 | $FCH_2-CH=CH-CH_2$ | 2-Me, 4-NO$_2$ | 1 |
| 13013 | $FCH_2-CH=CH-CH_2$ | 2-Me, 4-NH$_2$ | 1 |
| 13014 | $FCH_2-CH=CH-CH_2$ | 2-Me, 4-NHMe | 1 |
| 13015 | $FCH_2-CH=CH-CH_2$ | 2-Me, 4-NMe2 | 1 |
| 13016 | $FCH_2-CH=CH-CH_2$ | 2-Me, 4-NMe$_3$OTf | 1 |
| 13017 | $FCH_2-CH=CH-CH_2$ | 2-Me, 4-NMe$_3$I | 1 |
| 13018 | $FCH_2-CH=CH-CH_2$ | 2-Me, 5-F | 1 |
| 13019 | $FCH_2-CH=CH-CH_2$ | 2-Me, 5-NO$_2$ | 1 |
| 13020 | $FCH_2-CH=CH-CH_2$ | 2-Me, 5-NH$_2$ | 1 |
| 13021 | $FCH_2-CH=CH-CH_2$ | 2-Me, 5-NHMe | 1 |
| 13022 | $FCH_2-CH=CH-CH_2$ | 2-Me, 5-NMe$_2$ | 1 |
| 13023 | $FCH_2-CH=CH-CH_2$ | 2-Me, 5-NMe$_3$OTf | 1 |
| 13024 | $FCH_2-CH=CH-CH_2$ | 2-Me, 5-NMe$_3$I | 1 |
| 13025 | $FCH_2-CH=CH-CH_2$ | 2-F, 4-Me | 1 |
| 13026 | $FCH_2-CH=CH-CH_2$ | 2-NO$_2$, 4-Me | 1 |
| 13027 | $FCH_2-CH=CH-CH_2$ | 2-NH$_2$, 4-Me | 1 |
| 13028 | $FCH_2-CH=CH-CH_2$ | 2-NHMe, 4-Me | 1 |
| 13029 | $FCH_2-CH=CH-CH_2$ | 2-NMe$_2$, 4-Me | 1 |
| 13030 | $FCH_2-CH=CH-CH_2$ | 2-NMe$_3$, 4-Me | 1 |
| 13031 | $FCH_2-CH=CH-CH_2$ | 2-NMe$_3$OTf, 4-Me | 1 |
| 13032 | $FCH_2-CH=CH-CH_2$ | 2-NMe$_3$I, 4-Me | 1 |
| 13033 | $FCH_2-CH=CH-CH_2$ | 2-SnMe$_3$, 4-F | 1 |
| 13034 | $FCH_2-CH=CH-CH_2$ | 2-SnMe$_3$, 5-F | 1 |
| 13035 | $FCH_2-CH=CH-CH_2$ | 2-F, 4-SnMe$_3$ | 1 |
| 13036 | $FCH_2-CH=CH-CH_2$ | 2-Br, 6-Cl, 4-F | 1 |
| 13037 | $FCH_2-CH=CH-CH_2$ | 2-Br, 6-Cl, 4-NO$_2$ | 1 |
| 13038 | $FCH_2-CH=CH-CH_2$ | 2-Br, 6-Cl, 4-NH$_2$ | 1 |
| 13039 | $FCH_2-CH=CH-CH_2$ | 2-Br, 6-Cl, 4-NHMe | 1 |
| 13040 | $FCH_2-CH=CH-CH_2$ | 2-Br, 6-Cl, 4-NMe$_2$ | 1 |
| 13041 | $FCH_2-CH=CH-CH_2$ | 2-Br, 6-Cl, 4-NMe$_3$OTf | 1 |
| 13042 | $FCH_2-CH=CH-CH_2$ | 2-Br, 6-Cl, 4-NMe$_3$I | 1 |
| 13043 | $FCH_2-CH=CH-CH_2$ | 2-Me, 6-Cl, 4-F | 1 |
| 13044 | $FCH_2-CH=CH-CH_2$ | 2-SnMe$_3$, 6-Cl, 4-F | 1 |
| 13045 | $FCH_2-CH=CH-CH_2$ | 2-Cl, 4-Me | 1 |
| 13046 | $FCH_2-CH=CH-CH_2$ | 2-Cl, 4-Br | 1 |
| 13047 | $FCH_2-CH=CH-CH_2$ | 2-Cl, 4-SnMe$_3$ | 1 |

TABLE 9-continued

Substituent list for compounds of general structure XIV.

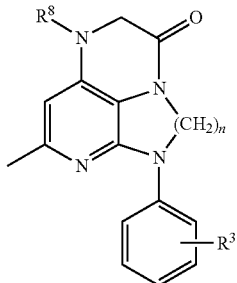

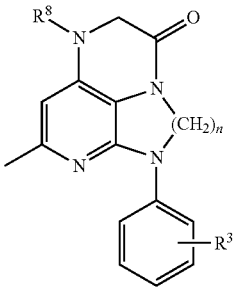

| Compound # | $R^8 =$ | $R^3 =$ | n = |
|---|---|---|---|
| 13048 | $FCH_2—CH=CH—CH_2$ | 2-Br, 4-Cl | 1 |
| 13049 | $FCH_2—CH=CH—CH_2$ | 2-$SnMe_3$, 4-Cl | 1 |
| 13050 | $FCH_2—CH=CH—CH_2$ | 2-Me, 4-Cl | 1 |
| 13051 | $FCH_2—CH=CH—CH_2$ | 2-Br, 4-Br | 1 |
| 13052 | $FCH_2—CH=CH—CH_2$ | 2-Br, 4-Me | 1 |
| 13053 | $FCH_2—CH=CH—CH_2$ | 2-Br, 4-$SnMe_3$ | 1 |
| 13054 | $FCH_2—CH=CH—CH_2$ | 2-$SnMe_3$, 4-Br | 1 |
| 13055 | $FCH_2—CH=CH—CH_2$ | 2-Me, 4-Br | 1 |
| 13056 | $FCH_2—CH=CH—CH_2$ | 2-Me, 4-$SnMe_3$ | 1 |
| 13057 | $FCH_2—CH=CH—CH_2$ | 2-$SnMe_3$, 4-Me | 1 |
| 13058 | $FCH_2—CH=CH—CH_2$ | 2-Me, 4-Me | 1 |
| 13059 | $FCH_2—CH=CH—CH_2$ | 2-Et, 4-Br | 1 |
| 13060 | $FCH_2—CH=CH—CH_2$ | 2-Et, 4-$SnMe_3$ | 1 |
| 13061 | $FCH_2—CH=CH—CH_2$ | 2-Et, 4-Me | 1 |
| 13062 | $FCH_2—CH=CH—CH_2$ | 2-Me, 4-Me, 6-Me | 1 |
| 13063 | $FCH_2—CH=CH—CH_2$ | 2-Me, 4-Br, 6-Me | 1 |
| 13064 | $FCH_2—CH=CH—CH_2$ | 2-Me, 4-$SnMe_3$, 6-Me | 1 |
| 13065 | $FCH_2—CH=CH—CH_2$ | 2-Et, 6-Me | 1 |
| 13066 | $FCH_2—CH=CH—CH_2$ | 2-Br, 4-i-Pr | 1 |
| 13067 | $FCH_2—CH=CH—CH_2$ | 2-$SnMe_3$, 4-i-Pr | 1 |
| 13068 | $FCH_2—CH=CH—CH_2$ | 2-Me, 4-i-Pr | 1 |
| 13069 | $FCH_2—CH=CH—CH_2$ | 2-Br, 4-Br, 6-Br | 1 |
| 13070 | $FCH_2—CH=CH—CH_2$ | 2-Br, 4-Me, 6-Br | 1 |
| 13071 | $FCH_2—CH=CH—CH_2$ | 2-Br, 4-$SnMe_3$, 6-Br | 1 |
| 13072 | $FCH_2—CH=CH—CH_2$ | 2-$SnMe_3$, 4-Br, 6-Br | 1 |
| 13073 | $FCH_2—CH=CH—CH_2$ | 2-Br, 4-Br, 6-Me | 1 |
| 13074 | $FCH_2—CH=CH—CH_2$ | 2-Br, 4-CF3, 6-Br | 1 |
| 13075 | $FCH_2—CH=CH—CH_2$ | 2-Br, 4-Br, 6-$CF_3$ | 1 |
| 13076 | $FCH_2—CH=CH—CH_2$ | 2-$CF_3$, 4-$CF_3$ | 1 |
| 13077 | $FCH_2—CH=CH—CH_2$ | 2-Cl, 4-$CF_3$ | 1 |
| 13078 | $FCH_2—CH=CH—CH_2$ | 2-$CF_3$, 4-Cl | 1 |
| 13079 | $FCH_2—CH=CH—CH_2$ | 2-Br, 4-$CF_3$ | 1 |
| 13080 | $FCH_2—CH=CH—CH_2$ | 2-$SnMe_3$, 4-$CF_3$ | 1 |
| 13081 | $FCH_2—CH=CH—CH_2$ | 2-Me, 4-$CF_3$ | 1 |
| 13082 | $FCH_2—CH=CH—CH_2$ | 2-$CF_3$, 4-Br | 1 |
| 13083 | $FCH_2—CH=CH—CH_2$ | 2-$CF_3$, 4-$SnMe_3$ | 1 |
| 13084 | $FCH_2—CH=CH—CH_2$ | 2-$CF_3$, 4-Me | 1 |
| 13085 | $FCH_2—CH=CH—CH_2$ | 2-Br, 4-OH | 1 |
| 13086 | $FCH_2—CH=CH—CH_2$ | 2-Br, 4-OMe | 1 |
| 13087 | $FCH_2—CH=CH—CH_2$ | 2-Br, 4-OMeF | 1 |
| 13088 | $FCH_2—CH=CH—CH_2$ | 2-Br, 4-$OCF_3$ | 1 |
| 13089 | $FCH_2—CH=CH—CH_2$ | 2-Br, 4-OEtF | 1 |
| 13090 | $FCH_2—CH=CH—CH_2$ | 2-Br, 4-OPrF | 1 |
| 13091 | $FCH_2—CH=CH—CH_2$ | 2-OH, 4-Br | 1 |
| 13092 | $FCH_2—CH=CH—CH_2$ | 2-OMe, 4-Br | 1 |
| 13093 | $FCH_2—CH=CH—CH_2$ | 2-OMeF, 4-Br | 1 |
| 13094 | $FCH_2—CH=CH—CH_2$ | 2-$OCF_3$, 4-Br | 1 |
| 13095 | $FCH_2—CH=CH—CH_2$ | 2-OEtF, 4-Br | 1 |
| 13096 | $FCH_2—CH=CH—CH_2$ | 2-OPrF, 4-Br | 1 |
| 13097 | $FCH_2—CH=CH—CH_2$ | 2-I, 4-OH | 1 |
| 13098 | $FCH_2—CH=CH—CH_2$ | 2-I, 4-OMe | 1 |
| 13099 | $FCH_2—CH=CH—CH_2$ | 2-I, 4-OMeF | 1 |
| 13100 | $FCH_2—CH=CH—CH_2$ | 2-I, 4-$OCF_3$ | 1 |
| 13101 | $FCH_2—CH=CH—CH_2$ | 2-I, 4-OEtF | 1 |
| 13102 | $FCH_2—CH=CH—CH_2$ | 2-I, 4-OPrF | 1 |
| 13103 | $FCH_2—CH=CH—CH_2$ | 2-OH, 4-I | 1 |
| 13104 | $FCH_2—CH=CH—CH_2$ | 2-OMe, 4-I | 1 |
| 13105 | $FCH_2—CH=CH—CH_2$ | 2-OMeF, 4-I | 1 |
| 13106 | $FCH_2—CH=CH—CH_2$ | 2-$OCF_3$, 4-I | 1 |
| 13107 | $FCH_2—CH=CH—CH_2$ | 2-OEtF, 4-I | 1 |
| 13108 | $FCH_2—CH=CH—CH_2$ | 2-OPrF, 4-I | 1 |
| 13109 | $FCH_2—CH=CH—CH_2$ | 2-$SnMe_3$, 4-OH | 1 |
| 13110 | $FCH_2—CH=CH—CH_2$ | 2-$SnMe_3$, 4-OMe | 1 |
| 13111 | $FCH_2—CH=CH—CH_2$ | 2-$SnMe_3$, 4-OMeF | 1 |
| 13112 | $FCH_2—CH=CH—CH_2$ | 2-$SnMe_3$, 4-$OCF_3$ | 1 |
| 13113 | $FCH_2—CH=CH—CH_2$ | 2-$SnMe_3$, 4-OEtF | 1 |
| 13114 | $FCH_2—CH=CH—CH_2$ | 2-$SnMe_3$, 4-OPrF | 1 |
| 13115 | $FCH_2—CH=CH—CH_2$ | 2-OH, 4-$SnMe_3$ | 1 |
| 13116 | $FCH_2—CH=CH—CH_2$ | 2-OMe, 4-$SnMe_3$ | 1 |
| 13117 | $FCH_2—CH=CH—CH_2$ | 2-OMeF, 4-$SnMe_3$ | 1 |
| 13118 | $FCH_2—CH=CH—CH_2$ | 2-$OCF_3$, 4-$SnMe_3$ | 1 |
| 13119 | $FCH_2—CH=CH—CH_2$ | 2-OEtF, 4-$SnMe_3$ | 1 |
| 13120 | $FCH_2—CH=CH—CH_2$ | 2-OPrF, 4-$SnMe_3$ | 1 |
| 13121 | $FCH_2—CH=CH—CH_2$ | H | 2 |
| 13122 | $FCH_2—CH=CH—CH_2$ | 2-t-Bu | 2 |
| 13123 | $FCH_2—CH=CH—CH_2$ | 2-Br | 2 |
| 13124 | $FCH_2—CH=CH—CH_2$ | 3-Br | 2 |
| 13125 | $FCH_2—CH=CH—CH_2$ | 4-Br | 2 |
| 13126 | $FCH_2—CH=CH—CH_2$ | 2-I | 2 |
| 13127 | $FCH_2—CH=CH—CH_2$ | 3-I | 2 |
| 13128 | $FCH_2—CH=CH—CH_2$ | 4-I | 2 |
| 13129 | $FCH_2—CH=CH—CH_2$ | 2-$SnMe_3$ | 2 |
| 13130 | $FCH_2—CH=CH—CH_2$ | 3-$SnMe_3$ | 2 |
| 13131 | $FCH_2—CH=CH—CH_2$ | 4-$SnMe_3$ | 2 |
| 13132 | $FCH_2—CH=CH—CH_2$ | 2-Me | 2 |
| 13133 | $FCH_2—CH=CH—CH_2$ | 3-Me | 2 |
| 13134 | $FCH_2—CH=CH—CH_2$ | 4-Me | 2 |
| 13135 | $FCH_2—CH=CH—CH_2$ | 2-OH | 2 |
| 13136 | $FCH_2—CH=CH—CH_2$ | 3-OH | 2 |
| 13137 | $FCH_2—CH=CH—CH_2$ | 4-OH | 2 |
| 13138 | $FCH_2—CH=CH—CH_2$ | 2-OMe | 2 |
| 13139 | $FCH_2—CH=CH—CH_2$ | 3-OMe | 2 |
| 13140 | $FCH_2—CH=CH—CH_2$ | 4-OMe | 2 |
| 13141 | $FCH_2—CH=CH—CH_2$ | 2-OMeF | 2 |
| 13142 | $FCH_2—CH=CH—CH_2$ | 3-OMeF | 2 |
| 13143 | $FCH_2—CH=CH—CH_2$ | 4-OMeF | 2 |
| 13144 | $FCH_2—CH=CH—CH_2$ | 2-$OCF_3$ | 2 |
| 13145 | $FCH_2—CH=CH—CH_2$ | 3-$OCF_3$ | 2 |
| 13146 | $FCH_2—CH=CH—CH_2$ | 4-$OCF_3$ | 2 |
| 13147 | $FCH_2—CH=CH—CH_2$ | 2-OEtF | 2 |
| 13148 | $FCH_2—CH=CH—CH_2$ | 3-OEtF | 2 |
| 13149 | $FCH_2—CH=CH—CH_2$ | 4-OEtF | 2 |
| 13150 | $FCH_2—CH=CH—CH_2$ | 2-OPrF | 2 |
| 13151 | $FCH_2—CH=CH—CH_2$ | 3-OPrF | 2 |
| 13152 | $FCH_2—CH=CH—CH_2$ | 4-OPrF | 2 |
| 13153 | $FCH_2—CH=CH—CH_2$ | 2-SH | 2 |
| 13154 | $FCH_2—CH=CH—CH_2$ | 3-SH | 2 |
| 13155 | $FCH_2—CH=CH—CH_2$ | 4-SH | 2 |
| 13156 | $FCH_2—CH=CH—CH_2$ | 2-SMe | 2 |
| 13157 | $FCH_2—CH=CH—CH_2$ | 3-SMe | 2 |
| 13158 | $FCH_2—CH=CH—CH_2$ | 4-SMe | 2 |
| 13159 | $FCH_2—CH=CH—CH_2$ | 2-SMeF | 2 |
| 13160 | $FCH_2—CH=CH—CH_2$ | 3-SMeF | 2 |
| 13161 | $FCH_2—CH=CH—CH_2$ | 4-SMeF | 2 |
| 13162 | $FCH_2—CH=CH—CH_2$ | 2-$SCF_3$ | 2 |
| 13163 | $FCH_2—CH=CH—CH_2$ | 3-$SCF_3$ | 2 |
| 13164 | $FCH_2—CH=CH—CH_2$ | 4-$SCF_3$ | 2 |
| 13165 | $FCH_2—CH=CH—CH_2$ | 2-SEtF | 2 |
| 13166 | $FCH_2—CH=CH—CH_2$ | 3-SEtF | 2 |
| 13167 | $FCH_2—CH=CH—CH_2$ | 4-SEtF | 2 |

TABLE 9-continued

Substituent list for compounds of general structure XIV.

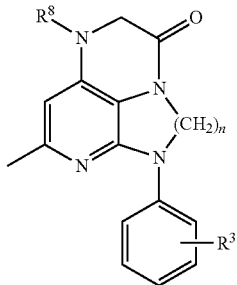

XIV

| Compound # | R⁸ = | R³ = | n = |
|---|---|---|---|
| 13168 | FCH₂—CH=CH—CH₂ | 2-SPrF | 2 |
| 13169 | FCH₂—CH=CH—CH₂ | 3-SPrF | 2 |
| 13170 | FCH₂—CH=CH—CH₂ | 4-SPrF | 2 |
| 13171 | FCH₂—CH=CH—CH₂ | 2-OMe, 4-OMe | 2 |
| 13172 | FCH₂—CH=CH—CH₂ | 2-Me, 5-OH | 2 |
| 13173 | FCH₂—CH=CH—CH₂ | 2-Me, 5-OMe | 2 |
| 13174 | FCH₂—CH=CH—CH₂ | 2-Me, 5-OMeF | 2 |
| 13175 | FCH₂—CH=CH—CH₂ | 2-Me, 5-OEtF | 2 |
| 13176 | FCH₂—CH=CH—CH₂ | 2-Me, 5-OPrF | 2 |
| 13177 | FCH₂—CH=CH—CH₂ | 2-Me, 4-OH | 2 |
| 13178 | FCH₂—CH=CH—CH₂ | 2-Me, 4-OMe | 2 |
| 13179 | FCH₂—CH=CH—CH₂ | 2-Me, 4-OMeF | 2 |
| 13180 | FCH₂—CH=CH—CH₂ | 2-Me, 4-OCF₃ | 2 |
| 13181 | FCH₂—CH=CH—CH₂ | 2-Me, 4-OEtF | 2 |
| 13182 | FCH₂—CH=CH—CH₂ | 2-Me, 4-OPrF | 2 |
| 13183 | FCH₂—CH=CH—CH₂ | 2-OH, 4-Me | 2 |
| 13184 | FCH₂—CH=CH—CH₂ | 2-OMe, 4-Me | 2 |
| 13185 | FCH₂—CH=CH—CH₂ | 2-OMeF, 4-Me | 2 |
| 13186 | FCH₂—CH=CH—CH₂ | 2-OCF₃, 4-Me | 2 |
| 13187 | FCH₂—CH=CH—CH₂ | 2-OEtF, 4-Me | 2 |
| 13188 | FCH₂—CH=CH—CH₂ | 2-OPrF, 4-Me | 2 |
| 13189 | FCH₂—CH=CH—CH₂ | 2-Cl, 4-OH | 2 |
| 13190 | FCH₂—CH=CH—CH₂ | 2-Cl, 4-OMe | 2 |
| 13191 | FCH₂—CH=CH—CH₂ | 2-Cl, 4-OMeF | 2 |
| 13192 | FCH₂—CH=CH—CH₂ | 2-Cl, 4-OCF₃ | 2 |
| 13193 | FCH₂—CH=CH—CH₂ | 2-Cl, 4-OEtF | 2 |
| 13194 | FCH₂—CH=CH—CH₂ | 2-Cl, 4-OPrF | 2 |
| 13195 | FCH₂—CH=CH—CH₂ | 2-F, 4-F | 2 |
| 13196 | FCH₂—CH=CH—CH₂ | 2-Cl, 4-Cl | 2 |
| 13197 | FCH₂—CH=CH—CH₂ | 2-Cl, 4-F | 2 |
| 13198 | FCH₂—CH=CH—CH₂ | 2-Cl, 4-NO₂ | 2 |
| 13199 | FCH₂—CH=CH—CH₂ | 2-Cl, 4-NH₂ | 2 |
| 13200 | FCH₂—CH=CH—CH₂ | 2-Cl, 4-NHMe | 2 |
| 13201 | FCH₂—CH=CH—CH₂ | 2-Cl, 4-NMe₂ | 2 |
| 13202 | FCH₂—CH=CH—CH₂ | 2-Cl, 4-NMe₃OTf | 2 |
| 13203 | FCH₂—CH=CH—CH₂ | 2-Cl, 4-NMe₃I | 2 |
| 13204 | FCH₂—CH=CH—CH₂ | 2-Cl, 5-F | 2 |
| 13205 | FCH₂—CH=CH—CH₂ | 2-Cl, 5-NO₂ | 2 |
| 13206 | FCH₂—CH=CH—CH₂ | 2-Cl, 5-NH₂ | 2 |
| 13207 | FCH₂—CH=CH—CH₂ | 2-Cl, 5-NHMe | 2 |
| 13208 | FCH₂—CH=CH—CH₂ | 2-Cl, 5-NMe₂ | 2 |
| 13209 | FCH₂—CH=CH—CH₂ | 2-Cl, 5-NMe₃OTf | 2 |
| 13210 | FCH₂—CH=CH—CH₂ | 2-Cl, 5-NMe₃I | 2 |
| 13211 | FCH₂—CH=CH—CH₂ | 2-F, 4-Cl | 2 |
| 13212 | FCH₂—CH=CH—CH₂ | 2-NO₂, 4-Cl | 2 |
| 13213 | FCH₂—CH=CH—CH₂ | 2-NH₂, 4-Cl | 2 |
| 13214 | FCH₂—CH=CH—CH₂ | 2-NHMe, 4-Cl | 2 |
| 13215 | FCH₂—CH=CH—CH₂ | 2-NMe₂, 4-Cl | 2 |
| 13216 | FCH₂—CH=CH—CH₂ | 2-NMe₃OTf, 4-Cl | 2 |
| 13217 | FCH₂—CH=CH—CH₂ | 2-NMe₃I, 4-Cl | 2 |
| 13218 | FCH₂—CH=CH—CH₂ | 2-F, 5-Cl | 2 |
| 13219 | FCH₂—CH=CH—CH₂ | 2-NO₂, 5-Cl | 2 |
| 13220 | FCH₂—CH=CH—CH₂ | 2-NH₂, 5-Cl | 2 |
| 13221 | FCH₂—CH=CH—CH₂ | 2-NHMe, 5-Cl | 2 |
| 13222 | FCH₂—CH=CH—CH₂ | 2-NMe₂, 5-Cl | 2 |
| 13223 | FCH₂—CH=CH—CH₂ | 2-NMe₃OTf, 5-Cl | 2 |
| 13224 | FCH₂—CH=CH—CH₂ | 2-NMe₃I, 5-Cl | 2 |
| 13225 | FCH₂—CH=CH—CH₂ | 2-Br, 4-F | 2 |
| 13226 | FCH₂—CH=CH—CH₂ | 2-Br, 4-NO₂ | 2 |
| 13227 | FCH₂—CH=CH—CH₂ | 2-Br, 4-NH₂ | 2 |

TABLE 9-continued

Substituent list for compounds of general structure XIV.

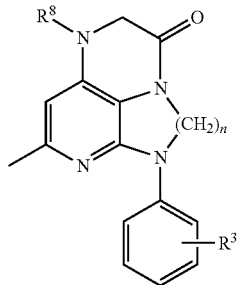

XIV

| Compound # | R⁸ = | R³ = | n = |
|---|---|---|---|
| 13228 | FCH₂—CH=CH—CH₂ | 2-Br, 4-NHMe | 2 |
| 13229 | FCH₂—CH=CH—CH₂ | 2-Br, 4-NMe₂ | 2 |
| 13230 | FCH₂—CH=CH—CH₂ | 2-Br, 4-NMe₃OTf | 2 |
| 13231 | FCH₂—CH=CH—CH₂ | 2-Br, 4-NMe₃I | 2 |
| 13232 | FCH₂—CH=CH—CH₂ | 2-Br, 5-F | 2 |
| 13233 | FCH₂—CH=CH—CH₂ | 2-Br, 5-NO₂ | 2 |
| 13234 | FCH₂—CH=CH—CH₂ | 2-Br, 5-NH₂ | 2 |
| 13235 | FCH₂—CH=CH—CH₂ | 2-Br, 5-NHMe | 2 |
| 13236 | FCH₂—CH=CH—CH₂ | 2-Br, 5-NMe₂ | 2 |
| 13237 | FCH₂—CH=CH—CH₂ | 2-Br, 5-NMe₃OTf | 2 |
| 13238 | FCH₂—CH=CH—CH₂ | 2-Br, 5-NMe₃I | 2 |
| 13239 | FCH₂—CH=CH—CH₂ | 2-F, 4-Br | 2 |
| 13240 | FCH₂—CH=CH—CH₂ | 2-NO₂, 4-Br | 2 |
| 13241 | FCH₂—CH=CH—CH₂ | 2-NH₂, 4-Br | 2 |
| 13242 | FCH₂—CH=CH—CH₂ | 2-NHMe, 4-Br | 2 |
| 13243 | FCH₂—CH=CH—CH₂ | 2-NMe₂, 4-Br | 2 |
| 13244 | FCH₂—CH=CH—CH₂ | 2-NMe₃OTf, 4-Br | 2 |
| 13245 | FCH₂—CH=CH—CH₂ | 2-NMe₃I, 4-Br | 2 |
| 13246 | FCH₂—CH=CH—CH₂ | 2-I, 4-F | 2 |
| 13247 | FCH₂—CH=CH—CH₂ | 2-I, 4-NO₂ | 2 |
| 13248 | FCH₂—CH=CH—CH₂ | 2-I, 4-NH₂ | 2 |
| 13249 | FCH₂—CH=CH—CH₂ | 2-I, 4-NHMe | 2 |
| 13250 | FCH₂—CH=CH—CH₂ | 2-I, 4-NMe₂ | 2 |
| 13251 | FCH₂—CH=CH—CH₂ | 2-I, 4-NMe₃OTf | 2 |
| 13252 | FCH₂—CH=CH—CH₂ | 2-I, 4-NMe₃I | 2 |
| 13253 | FCH₂—CH=CH—CH₂ | 2-F, 4-I | 2 |
| 13254 | FCH₂—CH=CH—CH₂ | 2-NO₂, 4-I | 2 |
| 13255 | FCH₂—CH=CH—CH₂ | 2-NH₂, 4-I | 2 |
| 13256 | FCH₂—CH=CH—CH₂ | 2-NHMe, 4-I | 2 |
| 13257 | FCH₂—CH=CH—CH₂ | 2-NMe₂, 4-I | 2 |
| 13258 | FCH₂—CH=CH—CH₂ | 2-NMe₃OTf, 4-I | 2 |
| 13259 | FCH₂—CH=CH—CH₂ | 2-NMe₃I, 4-I | 2 |
| 13260 | FCH₂—CH=CH—CH₂ | 2-Me, 3-F | 2 |
| 13261 | FCH₂—CH=CH—CH₂ | 2-Me, 3-NO₂ | 2 |
| 13262 | FCH₂—CH=CH—CH₂ | 2-Me, 3-NH₂ | 2 |
| 13263 | FCH₂—CH=CH—CH₂ | 2-Me, 3-NHMe | 2 |
| 13264 | FCH₂—CH=CH—CH₂ | 2-Me, 3-NMe₂ | 2 |
| 13265 | FCH₂—CH=CH—CH₂ | 2-Me, 3-NMe₃OTf | 2 |
| 13266 | FCH₂—CH=CH—CH₂ | 2-Me, 3-NMe₃I | 2 |
| 13267 | FCH₂—CH=CH—CH₂ | 2-Me, 4-F | 2 |
| 13268 | FCH₂—CH=CH—CH₂ | 2-Me, 4-NO₂ | 2 |
| 13269 | FCH₂—CH=CH—CH₂ | 2-Me, 4-NH₂ | 2 |
| 13270 | FCH₂—CH=CH—CH₂ | 2-Me, 4-NHMe | 2 |
| 13271 | FCH₂—CH=CH—CH₂ | 2-Me, 4-NMe₂ | 2 |
| 13272 | FCH₂—CH=CH—CH₂ | 2-Me, 4-NMe₃OTf | 2 |
| 13273 | FCH₂—CH=CH—CH₂ | 2-Me, 4-NMe₃I | 2 |
| 13274 | FCH₂—CH=CH—CH₂ | 2-Me, 5-F | 2 |
| 13275 | FCH₂—CH=CH—CH₂ | 2-Me, 5-NO₂ | 2 |
| 13276 | FCH₂—CH=CH—CH₂ | 2-Me, 5-NH₂ | 2 |
| 13277 | FCH₂—CH=CH—CH₂ | 2-Me, 5-NHMe | 2 |
| 13278 | FCH₂—CH=CH—CH₂ | 2-Me, 5-NMe₂ | 2 |
| 13279 | FCH₂—CH=CH—CH₂ | 2-Me, 5-NMe₃OTf | 2 |
| 13280 | FCH₂—CH=CH—CH₂ | 2-Me, 5-NMe₃I | 2 |
| 13281 | FCH₂—CH=CH—CH₂ | 2-F, 4-Me | 2 |
| 13282 | FCH₂—CH=CH—CH₂ | 2-NO₂, 4-Me | 2 |
| 13283 | FCH₂—CH=CH—CH₂ | 2-NH₂, 4-Me | 2 |
| 13284 | FCH₂—CH=CH—CH₂ | 2-NHMe, 4-Me | 2 |
| 13285 | FCH₂—CH=CH—CH₂ | 2-NMe₂, 4-Me | 2 |
| 13286 | FCH₂—CH=CH—CH₂ | 2-NMe₃, 4-Me | 2 |
| 13287 | FCH₂—CH=CH—CH₂ | 2-NMe₃OTf, 4-Me | 2 |

TABLE 9-continued

Substituent list for compounds of general structure XIV.

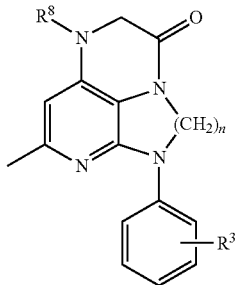

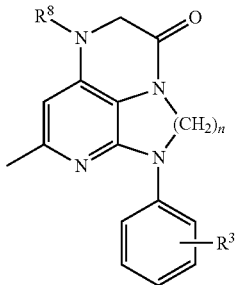

| Compound # | $R^8$ = | $R^3$ = | n = |
|---|---|---|---|
| 13288 | FCH$_2$—CH=CH—CH$_2$ | 2-NMe$_3$I, 4-Me | 2 |
| 13289 | FCH$_2$—CH=CH—CH$_2$ | 2-SnMe$_3$, 4-F | 2 |
| 13290 | FCH$_2$—CH=CH—CH$_2$ | 2-SnMe$_3$, 5-F | 2 |
| 13291 | FCH$_2$—CH=CH—CH$_2$ | 2-F, 4-SnMe$_3$ | 2 |
| 13292 | FCH$_2$—CH=CH—CH$_2$ | 2-Br, 6-Cl, 4-F | 2 |
| 13293 | FCH$_2$—CH=CH—CH$_2$ | 2-Br, 6-Cl, 4-NO$_2$ | 2 |
| 13294 | FCH$_2$—CH=CH—CH$_2$ | 2-Br, 6-Cl, 4-NH$_2$ | 2 |
| 13295 | FCH$_2$—CH=CH—CH$_2$ | 2-Br, 6-Cl, 4-NHMe | 2 |
| 13296 | FCH$_2$—CH=CH—CH$_2$ | 2-Br, 6-Cl, 4-NMe$_2$ | 2 |
| 13297 | FCH$_2$—CH=CH—CH$_2$ | 2-Br, 6-Cl, 4-NMe$_3$OTf | 2 |
| 13298 | FCH$_2$—CH=CH—CH$_2$ | 2-Br, 6-Cl, 4-NMe$_3$I | 2 |
| 13299 | FCH$_2$—CH=CH—CH$_2$ | 2-Me, 6-Cl, 4-F | 2 |
| 13300 | FCH$_2$—CH=CH—CH$_2$ | 2-SnMe$_3$, 6-Cl, 4-F | 2 |
| 13301 | FCH$_2$—CH=CH—CH$_2$ | 2-Cl, 4-Me | 2 |
| 13302 | FCH$_2$—CH=CH—CH$_2$ | 2-Cl, 4-Br | 2 |
| 13303 | FCH$_2$—CH=CH—CH$_2$ | 2-Cl, 4-SnMe$_3$ | 2 |
| 13304 | FCH$_2$—CH=CH—CH$_2$ | 2-Br, 4-Cl | 2 |
| 13305 | FCH$_2$—CH=CH—CH$_2$ | 2-SnMe$_3$, 4-Cl | 2 |
| 13306 | FCH$_2$—CH=CH—CH$_2$ | 2-Me, 4-Cl | 2 |
| 13307 | FCH$_2$—CH=CH—CH$_2$ | 2-Br, 4-Br | 2 |
| 13308 | FCH$_2$—CH=CH—CH$_2$ | 2-Br, 4-Me | 2 |
| 13309 | FCH$_2$—CH=CH—CH$_2$ | 2-Br, 4-SnMe$_3$ | 2 |
| 13310 | FCH$_2$—CH=CH—CH$_2$ | 2-SnMe$_3$, 4-Br | 2 |
| 13311 | FCH$_2$—CH=CH—CH$_2$ | 2-Me, 4-SnMe$_3$ | 2 |
| 13312 | FCH$_2$—CH=CH—CH$_2$ | 2-Me, 4-SnMe$_3$ | 2 |
| 13313 | FCH$_2$—CH=CH—CH$_2$ | 2-SnMe$_3$, 4-Me | 2 |
| 13314 | FCH$_2$—CH=CH—CH$_2$ | 2-Me, 4-Me | 2 |
| 13315 | FCH$_2$—CH=CH—CH$_2$ | 2-Et, 4-Br | 2 |
| 13316 | FCH$_2$—CH=CH—CH$_2$ | 2-Et, 4-SnMe$_3$ | 2 |
| 13317 | FCH$_2$—CH=CH—CH$_2$ | 2-Et, 4-Me | 2 |
| 13318 | FCH$_2$—CH=CH—CH$_2$ | 2-Me, 4-Me, 6-Me | 2 |
| 13319 | FCH$_2$—CH=CH—CH$_2$ | 2-Me, 4-Br, 6-Me | 2 |
| 13320 | FCH$_2$—CH=CH—CH$_2$ | 2-Me, 4-SnMe$_3$, 6-Me | 2 |
| 13321 | FCH$_2$—CH=CH—CH$_2$ | 2-Et, 6-Me | 2 |
| 13322 | FCH$_2$—CH=CH—CH$_2$ | 2-Br, 4-i-Pr | 2 |
| 13323 | FCH$_2$—CH=CH—CH$_2$ | 2-SnMe$_3$, 4-i-Pr | 2 |
| 13324 | FCH$_2$—CH=CH—CH$_2$ | 2-Me, 4-i-Pr | 2 |
| 13325 | FCH$_2$—CH=CH—CH$_2$ | 2-Br, 4-Br, 6-Br | 2 |
| 13326 | FCH$_2$—CH=CH—CH$_2$ | 2-Br, 4-Me, 6-Br | 2 |
| 13327 | FCH$_2$—CH=CH—CH$_2$ | 2-Br, 4-SnMe$_3$, 6-Br | 2 |
| 13328 | FCH$_2$—CH=CH—CH$_2$ | 2-SnMe$_3$, 4-Br, 6-Br | 2 |
| 13329 | FCH$_2$—CH=CH—CH$_2$ | 2-Br, 4-Br, 6-Me | 2 |
| 13330 | FCH$_2$—CH=CH—CH$_2$ | 2-Br, 4-CF$_3$, 6-Br | 2 |
| 13331 | FCH$_2$—CH=CH—CH$_2$ | 2-Br, 4-Br, 6-CF$_3$ | 2 |
| 13332 | FCH$_2$—CH=CH—CH$_2$ | 2-CF$_3$, 4-CF$_3$ | 2 |
| 13333 | FCH$_2$—CH=CH—CH$_2$ | 2-Cl, 4-CF$_3$ | 2 |
| 13334 | FCH$_2$—CH=CH—CH$_2$ | 2-CF$_3$, 4-Cl | 2 |
| 13335 | FCH$_2$—CH=CH—CH$_2$ | 2-Br, 4-CF$_3$ | 2 |
| 13336 | FCH$_2$—CH=CH—CH$_2$ | 2-SnMe$_3$, 4-CF$_3$ | 2 |
| 13337 | FCH$_2$—CH=CH—CH$_2$ | 2-Me, 4-CF$_3$ | 2 |
| 13338 | FCH$_2$—CH=CH—CH$_2$ | 2-CF$_3$, 4-Br | 2 |
| 13339 | FCH$_2$—CH=CH—CH$_2$ | 2-CF$_3$, 4-SnMe$_3$ | 2 |
| 13340 | FCH$_2$—CH=CH—CH$_2$ | 2-CF$_3$, 4-Me | 2 |
| 13341 | FCH$_2$—CH=CH—CH$_2$ | 2-Br, 4-OH | 2 |
| 13342 | FCH$_2$—CH=CH—CH$_2$ | 2-Br, 4-OMe | 2 |
| 13343 | FCH$_2$—CH=CH—CH$_2$ | 2-Br, 4-OMeF | 2 |
| 13344 | FCH$_2$—CH=CH—CH$_2$ | 2-Br, 4-OCF$_3$ | 2 |
| 13345 | FCH$_2$—CH=CH—CH$_2$ | 2-Br, 4-OEtF | 2 |
| 13346 | FCH$_2$—CH=CH—CH$_2$ | 2-Br, 4-OPrF | 2 |
| 13347 | FCH$_2$—CH=CH—CH$_2$ | 2-OH, 4-Br | 2 |
| 13348 | FCH$_2$—CH=CH—CH$_2$ | 2-OMe, 4-Br | 2 |
| 13349 | FCH$_2$—CH=CH—CH$_2$ | 2-OMeF, 4-Br | 2 |
| 13350 | FCH$_2$—CH=CH—CH$_2$ | 2-OCF$_3$, 4-Br | 2 |
| 13351 | FCH$_2$—CH=CH—CH$_2$ | 2-OEtF, 4-Br | 2 |
| 13352 | FCH$_2$—CH=CH—CH$_2$ | 2-OPrF, 4-Br | 2 |
| 13353 | FCH$_2$—CH=CH—CH$_2$ | 2-I, 4-OH | 2 |
| 13354 | FCH$_2$—CH=CH—CH$_2$ | 2-I, 4-OMe | 2 |
| 13355 | FCH$_2$—CH=CH—CH$_2$ | 2-I, 4-OMeF | 2 |
| 13356 | FCH$_2$—CH=CH—CH$_2$ | 2-I, 4-OCF$_3$ | 2 |
| 13357 | FCH$_2$—CH=CH—CH$_2$ | 2-I, 4-OEtF | 2 |
| 13358 | FCH$_2$—CH=CH—CH$_2$ | 2-I, 4-OPrF | 2 |
| 13359 | FCH$_2$—CH=CH—CH$_2$ | 2-OH, 4-I | 2 |
| 13360 | FCH$_2$—CH=CH—CH$_2$ | 2-OMe, 4-I | 2 |
| 13361 | FCH$_2$—CH=CH—CH$_2$ | 2-OMeF, 4-I | 2 |
| 13362 | FCH$_2$—CH=CH—CH$_2$ | 2-OCF$_3$, 4-I | 2 |
| 13363 | FCH$_2$—CH=CH—CH$_2$ | 2-OEtF, 4-I | 2 |
| 13364 | FCH$_2$—CH=CH—CH$_2$ | 2-OPrF, 4-I | 2 |
| 13365 | FCH$_2$—CH=CH—CH$_2$ | 2-SnMe$_3$, 4-OH | 2 |
| 13366 | FCH$_2$—CH=CH—CH$_2$ | 2-SnMe$_3$, 4-OMe | 2 |
| 13367 | FCH$_2$—CH=CH—CH$_2$ | 2-SnMe$_3$, 4-OMeF | 2 |
| 13368 | FCH$_2$—CH=CH—CH$_2$ | 2-SnMe$_3$, 4-OCF$_3$ | 2 |
| 13369 | FCH$_2$—CH=CH—CH$_2$ | 2-SnMe$_3$, 4-OEtF | 2 |
| 13370 | FCH$_2$—CH=CH—CH$_2$ | 2-SnMe$_3$, 4-OPrF | 2 |
| 13371 | FCH$_2$—CH=CH—CH$_2$ | 2-OH, 4-SnMe$_3$ | 2 |
| 13372 | FCH$_2$—CH=CH—CH$_2$ | 2-OMe, 4-SnMe$_3$ | 2 |
| 13373 | FCH$_2$—CH=CH—CH$_2$ | 2-OMeF, 4-SnMe$_3$ | 2 |
| 13374 | FCH$_2$—CH=CH—CH$_2$ | 2-OCF$_3$, 4-SnMe$_3$ | 2 |
| 13375 | FCH$_2$—CH=CH—CH$_2$ | 2-OEtF, 4-SnMe$_3$ | 2 |
| 13376 | FCH$_2$—CH=CH—CH$_2$ | 2-OPrF, 4-SnMe$_3$ | 2 |
| 13377 | Bn | H | 1 |
| 13378 | Bn | 2-t-Bu | 1 |
| 13379 | Bn | 2-Br | 1 |
| 13380 | Bn | 3-Br | 1 |
| 13381 | Bn | 4-Br | 1 |
| 13382 | Bn | 2-I | 1 |
| 13383 | Bn | 3-I | 1 |
| 13384 | Bn | 4-I | 1 |
| 13385 | Bn | 2-SnMe$_3$ | 1 |
| 13386 | Bn | 3-SnMe$_3$ | 1 |
| 13387 | Bn | 4-SnMe$_3$ | 1 |
| 13388 | Bn | 2-Me | 1 |
| 13389 | Bn | 3-Me | 1 |
| 13390 | Bn | 4-Me | 1 |
| 13391 | Bn | 2-OH | 1 |
| 13392 | Bn | 3-OH | 1 |
| 13393 | Bn | 4-OH | 1 |
| 13394 | Bn | 2-OMe | 1 |
| 13395 | Bn | 3-OMe | 1 |
| 13396 | Bn | 4-OMe | 1 |
| 3397 | Bn | 2-OMeF | 1 |
| 13398 | Bn | 3-OMeF | 1 |
| 13399 | Bn | 4-OMeF | 1 |
| 13400 | Bn | 2-OCF$_3$ | 1 |
| 13401 | Bn | 3-OCF$_3$ | 1 |
| 13402 | Bn | 4-OCF$_3$ | 1 |
| 13403 | Bn | 2-OEtF | 1 |
| 13404 | Bn | 3-OEtF | 1 |
| 13405 | Bn | 4-OEtF | 1 |
| 13406 | Bn | 2-OPrF | 1 |
| 13407 | Bn | 3-OPrF | 1 |

TABLE 9-continued

Substituent list for compounds of general structure XIV.

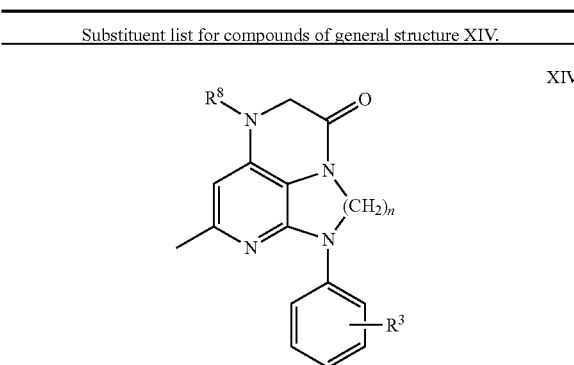

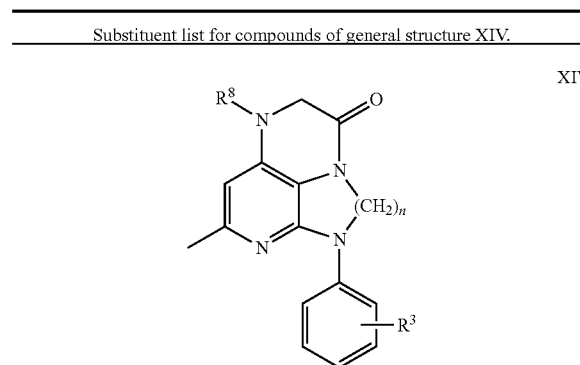

| Compound # | $R^8$ = | $R^3$ = | n = |
|---|---|---|---|
| 13408 | Bn | 4-OPrF | 1 |
| 13409 | Bn | 2-SH | 1 |
| 13410 | Bn | 3-SH | 1 |
| 13411 | Bn | 4-SH | 1 |
| 13412 | Bn | 2-SMe | 1 |
| 13413 | Bn | 3-SMe | 1 |
| 13414 | Bn | 4-SMe | 1 |
| 13415 | Bn | 2-SMeF | 1 |
| 13416 | Bn | 3-SMeF | 1 |
| 13417 | Bn | 4-SMeF | 1 |
| 13418 | Bn | 2-SCF$_3$ | 1 |
| 13419 | Bn | 3-SCF$_3$ | 1 |
| 13420 | Bn | 4-SCF$_3$ | 1 |
| 13421 | Bn | 2-SEtF | 1 |
| 13422 | Bn | 3-SEtF | 1 |
| 13423 | Bn | 4-SEtF | 1 |
| 13424 | Bn | 2-SPrF | 1 |
| 13425 | Bn | 3-SPrF | 1 |
| 13426 | Bn | 4-SPrF | 1 |
| 13427 | Bn | 2-OMe, 4-OMe | 1 |
| 13428 | Bn | 2-Me, 5-OH | 1 |
| 13429 | Bn | 2-Me, 5-OMe | 1 |
| 13430 | Bn | 2-Me, 5-OMeF | 1 |
| 13431 | Bn | 2-Me, 5-OEtF | 1 |
| 13432 | Bn | 2-Me, 5-OPrF | 1 |
| 13433 | Bn | 2-Me, 4-OH | 1 |
| 13434 | Bn | 2-Me, 4-OMe | 1 |
| 13435 | Bn | 2-Me, 4-OMeF | 1 |
| 13436 | Bn | 2-Me, 4-OCF$_3$ | 1 |
| 13437 | Bn | 2-Me, 4-OEtF | 1 |
| 13438 | Bn | 2-Me, 4-OPrF | 1 |
| 13439 | Bn | 2-OH, 4-Me | 1 |
| 13440 | Bn | 2-OMe, 4-Me | 1 |
| 13441 | Bn | 2-OMeF, 4-Me | 1 |
| 13442 | Bn | 2-OCF$_3$, 4-Me | 1 |
| 13443 | Bn | 2-OEtF, 4-Me | 1 |
| 13444 | Bn | 2-OPrF, 4-Me | 1 |
| 13445 | Bn | 2-Cl, 4-OH | 1 |
| 13446 | Bn | 2-Cl, 4-OMe | 1 |
| 13447 | Bn | 2-Cl, 4-OMeF | 1 |
| 13448 | Bn | 2-Cl, 4-OCF$_3$ | 1 |
| 13449 | Bn | 2-Cl, 4-OEtF | 1 |
| 13450 | Bn | 2-Cl, 4-OPrF | 1 |
| 13451 | Bn | 2-F, 4-F | 1 |
| 13452 | Bn | 2-Cl, 4-Cl | 1 |
| 13453 | Bn | 2-Cl, 4-F | 1 |
| 13454 | Bn | 2-Cl, 4-NO$_2$ | 1 |
| 13455 | Bn | 2-Cl, 4-NH$_2$ | 1 |
| 13456 | Bn | 2-Cl, 4-NHMe | 1 |
| 13457 | Bn | 2-Cl, 4-NMe$_2$ | 1 |
| 13458 | Bn | 2-Cl, 4-NMe$_3$OTf | 1 |
| 13459 | Bn | 2-Cl, 4-NMe$_3$I | 1 |
| 13460 | Bn | 2-Cl, 5-F | 1 |
| 13461 | Bn | 2-Cl, 5-NO$_2$ | 1 |
| 13462 | Bn | 2-Cl, 5-NH$_2$ | 1 |
| 13463 | Bn | 2-Cl, 5-NHMe | 1 |
| 13464 | Bn | 2-Cl, 5-NMe$_2$ | 1 |
| 13465 | Bn | 2-Cl, 5-NMe$_3$OTf | 1 |
| 13466 | Bn | 2-Cl, 5-NMe$_3$I | 1 |
| 13467 | Bn | 2-F, 4-Cl | 1 |
| 13468 | Bn | 2-NO$_2$, 4-Cl | 1 |
| 13469 | Bn | 2-NH$_2$, 4-Cl | 1 |
| 13470 | Bn | 2-NHMe, 4-Cl | 1 |
| 13471 | Bn | 2-NMe$_2$, 4-Cl | 1 |
| 13472 | Bn | 2-NMe$_3$OTf, 4-Cl | 1 |
| 13473 | Bn | 2-NMe$_3$I, 4-Cl | 1 |
| 13474 | Bn | 2-F, 5-Cl | 1 |
| 13475 | Bn | 2-NO$_2$, 5-Cl | 1 |
| 13476 | Bn | 2-NH$_2$, 5-Cl | 1 |
| 13477 | Bn | 2-NHMe, 5-Cl | 1 |
| 13478 | Bn | 2-NMe$_2$, 5-Cl | 1 |
| 13479 | Bn | 2-NMe$_3$OTf, 5-Cl | 1 |
| 13480 | Bn | 2-NMe$_3$I, 5-Cl | 1 |
| 13481 | Bn | 2-Br, 4-F | 1 |
| 13482 | Bn | 2-Br, 4-NO$_2$ | 1 |
| 13483 | Bn | 2-Br, 4-NH$_2$ | 1 |
| 13484 | Bn | 2-Br, 4-NHMe | 1 |
| 13485 | Bn | 2-Br, 4-NMe$_2$ | 1 |
| 13486 | Bn | 2-Br, 4-NMe$_3$OTf | 1 |
| 13487 | Bn | 2-Br, 4-NMe$_3$I | 1 |
| 13488 | Bn | 2-Br, 5-F | 1 |
| 13489 | Bn | 2-Br, 5-NO$_2$ | 1 |
| 13490 | Bn | 2-Br, 5-NH$_2$ | 1 |
| 13491 | Bn | 2-Br, 5-NHMe | 1 |
| 13492 | Bn | 2-Br, 5-NMe$_2$ | 1 |
| 13493 | Bn | 2-Br, 5-NMe$_3$OTf | 1 |
| 13494 | Bn | 2-Br, 5-NMe$_3$I | 1 |
| 13495 | Bn | 2-F, 4-Br | 1 |
| 13496 | Bn | 2-NO$_2$, 4-Br | 1 |
| 13497 | Bn | 2-NH$_2$, 4-Br | 1 |
| 13498 | Bn | 2-NHMe, 4-Br | 1 |
| 13499 | Bn | 2-NMe$_2$, 4-Br | 1 |
| 13500 | Bn | 2-NMe$_3$OTf, 4-Br | 1 |
| 13501 | Bn | 2-NMe$_3$I, 4-Br | 1 |
| 13502 | Bn | 2-I, 4-F | 1 |
| 13503 | Bn | 2-I, 4-NO$_2$ | 1 |
| 13504 | Bn | 2-I, 4-NH$_2$ | 1 |
| 13505 | Bn | 2-I, 4-NHMe | 1 |
| 13506 | Bn | 2-I, 4-NMe$_2$ | 1 |
| 13507 | Bn | 2-I, 4-NMe$_3$OTf | 1 |
| 13508 | Bn | 2-I, 4-NMe$_3$I | 1 |
| 13509 | Bn | 2-F, 4-I | 1 |
| 13510 | Bn | 2-NO$_2$, 4-I | 1 |
| 13511 | Bn | 2-NH$_2$, 4-I | 1 |
| 13512 | Bn | 2-NHMe, 4-I | 1 |
| 13513 | Bn | 2-NMe$_2$, 4-I | 1 |
| 13514 | Bn | 2-NMe$_3$OTf, 4-I | 1 |
| 13515 | Bn | 2-NMe$_3$I, 4-I | 1 |
| 13516 | Bn | 2-Me, 3-F | 1 |
| 13517 | Bn | 2-Me, 3-NO$_2$ | 1 |
| 13518 | Bn | 2-Me, 3-NH$_2$ | 1 |
| 13519 | Bn | 2-Me, 3-NHMe | 1 |
| 13520 | Bn | 2-Me, 3-NMe$_2$ | 1 |
| 13521 | Bn | 2-Me, 3-NMe$_3$OTf | 1 |
| 13522 | Bn | 2-Me, 3-NMe$_2$I | 1 |
| 13523 | Bn | 2-Me, 4-F | 1 |
| 13524 | Bn | 2-Me, 4-NO$_2$ | 1 |
| 13525 | Bn | 2-Me, 4-NH$_2$ | 1 |
| 13526 | Bn | 2-Me, 4-NHMe | 1 |
| 13527 | Bn | 2-Me, 4-NMe$_2$ | 1 |

TABLE 9-continued

Substituent list for compounds of general structure XIV.

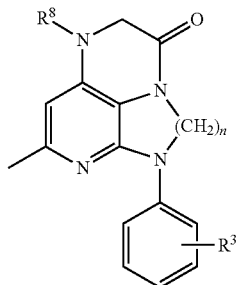

XIV

| Compound # | R⁸ = | R³ = | n = |
|---|---|---|---|
| 13528 | Bn | 2-Me, 4-NMe₃OTf | 1 |
| 13529 | Bn | 2-Me, 4-NMe₃I | 1 |
| 13530 | Bn | 2-Me, 5-F | 1 |
| 13531 | Bn | 2-Me, 5-NO₂ | 1 |
| 13532 | Bn | 2-Me, 5-NH₂ | 1 |
| 13533 | Bn | 2-Me, 5-NHMe | 1 |
| 13534 | Bn | 2-Me, 5-NMe₂ | 1 |
| 13535 | Bn | 2-Me, 5-NMe₃OTf | 1 |
| 13536 | Bn | 2-Me, 5-NMe₃I | 1 |
| 13537 | Bn | 2-F, 4-Me | 1 |
| 13538 | Bn | 2-NO₂, 4-Me | 1 |
| 13539 | Bn | 2-NH₂, 4-Me | 1 |
| 13540 | Bn | 2-NHMe, 4-Me | 1 |
| 13541 | Bn | 2-NMe₂, 4-Me | 1 |
| 13542 | Bn | 2-NMe₃, 4-Me | 1 |
| 13543 | Bn | 2-NMe₃OTf, 4-Me | 1 |
| 13544 | Bn | 2-NMe₃I, 4-Me | 1 |
| 13545 | Bn | 2-SnMe₃, 4-F | 1 |
| 13546 | Bn | 2-SnMe₃, 5-F | 1 |
| 13547 | Bn | 2-F, 4-SnMe₃ | 1 |
| 13548 | Bn | 2-Br, 6-Cl, 4-F | 1 |
| 13549 | Bn | 2-Br, 6-Cl, 4-NO₂ | 1 |
| 13550 | Bn | 2-Br, 6-Cl, 4-NH₂ | 1 |
| 13551 | Bn | 2-Br, 6-Cl, 4-NHMe | 1 |
| 13552 | Bn | 2-Br, 6-Cl, 4-NMe₂ | 1 |
| 13553 | Bn | 2-Br, 6-Cl, 4-NMe₃OTf | 1 |
| 13554 | Bn | 2-Br, 6-Cl, 4-NMe₃I | 1 |
| 13555 | Bn | 2-Me, 6-Cl, 4-F | 1 |
| 13556 | Bn | 2-SnMe₃, 6-Cl, 4-F | 1 |
| 13557 | Bn | 2-Cl, 4-Me | 1 |
| 13558 | Bn | 2-Cl, 4-Br | 1 |
| 13559 | Bn | 2-Cl, 4-SnMe₃ | 1 |
| 13560 | Bn | 2-Br, 4-Cl | 1 |
| 13561 | Bn | 2-SnMe₃, 4-Cl | 1 |
| 13562 | Bn | 2-Me, 4-Cl | 1 |
| 13563 | Bn | 2-Br, 4-Br | 1 |
| 13564 | Bn | 2-Br, 4-Me | 1 |
| 13565 | Bn | 2-Br, 4-SnMe₃ | 1 |
| 13566 | Bn | 2-SnMe₃, 4-Br | 1 |
| 13567 | En | 2-Me, 4-Br | 1 |
| 13568 | Bn | 2-Me, 4-SnMe₃ | 1 |
| 13569 | Bn | 2-SnMe₃, 4-Me | 1 |
| 13570 | Bn | 2-Me, 4-Me | 1 |
| 13571 | Bn | 2-Et, 4-Br | 1 |
| 13572 | Bn | 2-Et, 4-SnMe₃ | 1 |
| 13573 | Bn | 2-Et, 4-Me | 1 |
| 13574 | Bn | 2-Me, 4-Me, 6-Me | 1 |
| 13575 | Bn | 2-Me, 4-Br, 6-Me | 1 |
| 13576 | Bn | 2-Me, 4-SnMe₃, 6-Me | 1 |
| 13577 | Bn | 2-Et, 6-Me | 1 |
| 13578 | Bn | 2-Br, 4-i-Pr | 1 |
| 13579 | Bn | 2-SnMe₃, 4-i-Pr | 1 |
| 13580 | Bn | 2-Me, 4-i-Pr | 1 |
| 13581 | Bn | 2-Br, 4-Br, 6-Br | 1 |
| 13582 | Bn | 2-Br, 4-Me, 6-Br | 1 |
| 13583 | Bn | 2-Br, 4-SnMe₃, 6-Br | 1 |
| 13584 | Bn | 2-SnMe3, 4-Br, 6-Br | 1 |
| 13585 | Bn | 2-Br, 4-Br, 6-Me | 1 |
| 13586 | Bn | 2-Br, 4-CF₃, 6-Br | 1 |
| 13587 | Bn | 2-Br, 4-Br, 6-CF₃ | 1 |

TABLE 9-continued

Substituent list for compounds of general structure XIV.

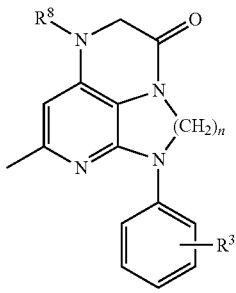

XIV

| Compound # | R⁸ = | R³ = | n = |
|---|---|---|---|
| 13588 | Bn | 2-CF₃, 4-CF₃ | 1 |
| 13589 | Bn | 2-Cl, 4-CF₃ | 1 |
| 13590 | Bn | 2-CF₃, 4-Cl | 1 |
| 13591 | Bn | 2-Br, 4-CF₃ | 1 |
| 13592 | Bn | 2-SnMe₃, 4-CF₃ | 1 |
| 13593 | Bn | 2-Me, 4-CF₃ | 1 |
| 13594 | Bn | 2-CF₃, 4-Br | 1 |
| 13595 | Bn | 2-CF₃, 4-SnMe₃ | 1 |
| 13596 | Bn | 2-CF₃, 4-Me | 1 |
| 13597 | Bn | 2-Br, 4-OH | 1 |
| 13598 | Bn | 2-Br, 4-OMe | 1 |
| 13599 | Bn | 2-Br, 4-OMeF | 1 |
| 13600 | Bn | 2-Br, 4-OCF₃ | 1 |
| 13601 | Bn | 2-Br, 4-OEtF | 1 |
| 13602 | Bn | 2-Br, 4-OPrF | 1 |
| 13603 | Bn | 2-OH, 4-Br | 1 |
| 13604 | Bn | 2-OMe, 4-Br | 1 |
| 13605 | Bn | 2-OMeF, 4-Br | 1 |
| 13606 | Bn | 2-OCF₃, 4-Br | 1 |
| 13607 | Bn | 2-OEtF, 4-Br | 1 |
| 13608 | Bn | 2-OPrF, 4-Br | 1 |
| 13609 | Bn | 2-I, 4-OH | 1 |
| 13610 | Bn | 2-I, 4-OMe | 1 |
| 13611 | Bn | 2-I, 4-OMeF | 1 |
| 13612 | Bn | 2-I, 4-OCF₃ | 1 |
| 13613 | Bn | 2-I, 4-OEtF | 1 |
| 13614 | Bn | 2-I, 4-OPrF | 1 |
| 13615 | Bn | 2-OH, 4-I | 1 |
| 13616 | Bn | 2-OMe, 4-I | 1 |
| 13617 | Bn | 2-OMeF, 4-I | 1 |
| 13618 | Bn | 2-OCF₃, 4-I | 1 |
| 13619 | Bn | 2-OEtF, 4-I | 1 |
| 13620 | Bn | 2-OPrF, 4-I | 1 |
| 13621 | Bn | 2-SnMe₃, 4-OH | 1 |
| 13622 | Bn | 2-SnMe₃, 4-OMe | 1 |
| 13623 | Bn | 2-SnMe₃, 4-OMeF | 1 |
| 13624 | Bn | 2-SnMe₃, 4-OCF₃ | 1 |
| 13625 | Bn | 2-SnMe₃, 4-OEtF | 1 |
| 13626 | Bn | 2-SnMe₃, 4-OPrF | 1 |
| 13627 | Bn | 2-OH, 4-SnMe₃ | 1 |
| 13628 | Bn | 2-OMe, 4-SnMe₃ | 1 |
| 13629 | Bn | 2-OMeF, 4-SnMe₃ | 1 |
| 13630 | Bn | 2-OCF₃, 4-SnMe₃ | 1 |
| 13631 | Bn | 2-OEtF, 4-SnMe₃ | 1 |
| 13632 | Bn | 2-OPrF, 4-SnMe₃ | 1 |
| 13633 | Bn | H | 2 |
| 13634 | Bn | 2-t-Bu | 2 |
| 13635 | Bn | 2-Br | 2 |
| 13636 | Bn | 3-Br | 2 |
| 13637 | Bn | 4-Br | 2 |
| 13638 | Bn | 2-I | 2 |
| 13639 | Bn | 3-I | 2 |
| 13640 | Bn | 4-I | 2 |
| 13641 | Bn | 2-SnMe₃ | 2 |
| 13642 | Bn | 3-SnMe₃ | 2 |
| 13643 | Bn | 4-SnMe₃ | 2 |
| 13644 | Bn | 2-Me | 2 |
| 13645 | Bn | 3-Me | 2 |
| 13646 | Bn | 4-Me | 2 |
| 13647 | Bn | 2-OH | 2 |

TABLE 9-continued

Substituent list for compounds of general structure XIV.

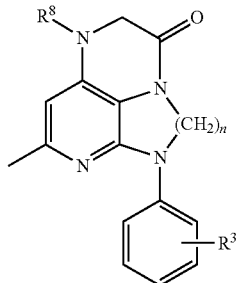

XIV

| Compound # | R⁸ = | R³ = | n = |
|---|---|---|---|
| 13648 | Bn | 3-OH | 2 |
| 13649 | Bn | 4-OH | 2 |
| 13650 | Bn | 2-OMe | 2 |
| 13651 | Bn | 3-OMe | 2 |
| 13652 | Bn | 4-OMe | 2 |
| 13653 | Bn | 2-OMeF | 2 |
| 13654 | Bn | 3-OMeF | 2 |
| 13655 | Bn | 4-OMeF | 2 |
| 13656 | Bn | 2-OCF₃ | 2 |
| 13657 | Bn | 3-OCF₃ | 2 |
| 13658 | Bn | 4-OCF₃ | 2 |
| 13659 | Bn | 2-OEtF | 2 |
| 13660 | Bn | 3-OEtF | 2 |
| 13661 | Bn | 4-OEtF | 2 |
| 13662 | Bn | 2-OPrF | 2 |
| 13663 | Bn | 3-OPrF | 2 |
| 13664 | Bn | 4-OPrF | 2 |
| 13665 | Bn | 2-SH | 2 |
| 13666 | Bn | 3-SH | 2 |
| 13667 | Bn | 4-SH | 2 |
| 13668 | Bn | 2-SMe | 2 |
| 13669 | Bn | 3-SMe | 2 |
| 13670 | Bn | 4-SMe | 2 |
| 13671 | Bn | 2-SMeF | 2 |
| 13672 | Bn | 3-SMeF | 2 |
| 13673 | Bn | 4-SMeF | 2 |
| 13674 | Bn | 2-SCF₃ | 2 |
| 13675 | Bn | 3-SCF₃ | 2 |
| 13676 | Bn | 4-SCF₃ | 2 |
| 13677 | Bn | 2-SEtF | 2 |
| 13678 | Bn | 3-SEtF | 2 |
| 13679 | Bn | 4-SEtF | 2 |
| 13680 | Bn | 2-SPrF | 2 |
| 13681 | Bn | 3-SPrF | 2 |
| 13682 | Bn | 4-SPrF | 2 |
| 13683 | Bn | 2-OMe, 4-OMe | 2 |
| 13684 | Bn | 2-Me, 5-OH | 2 |
| 13685 | Bn | 2-Me, 5-OMe | 2 |
| 13686 | Bn | 2-Me, 5-OMeF | 2 |
| 13687 | Bn | 2-Me, 5-OEtF | 2 |
| 13688 | Bn | 2-Me, 5-OPrF | 2 |
| 13689 | Bn | 2-Me, 4-OH | 2 |
| 13690 | Bn | 2-Me, 4-OMe | 2 |
| 13691 | Bn | 2-Me, 4-OMeF | 2 |
| 13692 | Bn | 2-Me, 4-OCF₃ | 2 |
| 13693 | Bn | 2-Me, 4-OEtF | 2 |
| 13694 | Bn | 2-Me, 4-OPrF | 2 |
| 13695 | Bn | 2-OH, 4-Me | 2 |
| 13696 | Bn | 2-OMe, 4-Me | 2 |
| 13697 | Bn | 2-OMeF, 4-Me | 2 |
| 13698 | Bn | 2-OCF₃, 4-Me | 2 |
| 13699 | Bn | 2-OEtF, 4-Me | 2 |
| 13700 | Bn | 2-OPrF, 4-Me | 2 |
| 13701 | Bn | 2-Cl, 4-OH | 2 |
| 13702 | Bn | 2-Cl, 4-OMe | 2 |
| 13703 | Bn | 2-Cl, 4-OMeF | 2 |
| 13704 | Bn | 2-Cl, 4-OCF₃ | 2 |
| 13705 | Bn | 2-Cl, 4-OEtF | 2 |
| 13706 | Bn | 2-Cl, 4-OPrF | 2 |
| 13707 | Bn | 2-F, 4-F | 2 |
| 13708 | Bn | 2-Cl, 4-Cl | 2 |
| 13709 | Bn | 2-Cl, 4-F | 2 |
| 13710 | Bn | 2-Cl, 4-NO₂ | 2 |
| 13711 | Bn | 2-Cl, 4-NH₂ | 2 |
| 13712 | Bn | 2-Cl, 4-NHMe | 2 |
| 13713 | Bn | 2-Cl, 4-NMe₂ | 2 |
| 13714 | Bn | 2-Cl, 4-NMe₃OTf | 2 |
| 13715 | Bn | 2-Cl, 4-NMe₃I | 2 |
| 13716 | Bn | 2-Cl, 5-F | 2 |
| 13717 | Bn | 2-Cl, 5-NO₂ | 2 |
| 13718 | Bn | 2-Cl, 5-NH₂ | 2 |
| 13719 | Bn | 2-Cl, 5-NHMe | 2 |
| 13720 | Bn | 2-Cl, 5-NMe₂ | 2 |
| 13721 | Bn | 2-Cl, 5-NMe₃OTf | 2 |
| 13722 | Bn | 2-Cl, 5-NMe₃I | 2 |
| 13723 | Bn | 2-F, 4-Cl | 2 |
| 13724 | Bn | 2-NO₂, 4-Cl | 2 |
| 13725 | Bn | 2-NH₂, 4-Cl | 2 |
| 13726 | Bn | 2-NHMe, 4-Cl | 2 |
| 13727 | Bn | 2-NMe₂, 4-Cl | 2 |
| 13728 | Bn | 2-NMe₃OTf, 4-Cl | 2 |
| 13729 | Bn | 2-NMe₃I, 4-Cl | 2 |
| 13730 | Bn | 2-F, 5-Cl | 2 |
| 13731 | Bn | 2-NO₂, 5-Cl | 2 |
| 13732 | Bn | 2-NH₂, 5-Cl | 2 |
| 13733 | Bn | 2-NHMe, 5-Cl | 2 |
| 13734 | Bn | 2-NMe₂, 5-Cl | 2 |
| 13735 | Bn | 2-NMe₃OTf, 5-Cl₂ | 2 |
| 13736 | Bn | 2-NMe₃I, 5-Cl | 2 |
| 13737 | Bn | 2-Br, 4-F | 2 |
| 13738 | Bn | 2-Br, 4-NO₂ | 2 |
| 13739 | Bn | 2-Br, 4-NH₂ | 2 |
| 13740 | Bn | 2-Br, 4-NHMe | 2 |
| 13741 | Bn | 2-Br, 4-NMe₂ | 2 |
| 13742 | Bn | 2-Br, 4-NMe₃OTf | 2 |
| 13743 | Bn | 2-Br, 4-NMe₃I | 2 |
| 13744 | Bn | 2-Br, 5-F | 2 |
| 13745 | Bn | 2-Br, 5-NO₂ | 2 |
| 13746 | Bn | 2-Br, 5-NH₂ | 2 |
| 13747 | Bn | 2-Br, 5-NHMe | 2 |
| 13748 | Bn | 2-Br, 5-NMe₂ | 2 |
| 13749 | Bn | 2-Br, 5-NMe₃OTf | 2 |
| 13750 | Bn | 2-Br, 5-NMe₃I | 2 |
| 13751 | Bn | 2-F, 4-Br | 2 |
| 13752 | Bn | 2-NO₂, 4-Br | 2 |
| 13753 | Bn | 2-NH₂, 4-Br | 2 |
| 13754 | Bn | 2-NHMe, 4-Br | 2 |
| 13755 | Bn | 2-NMe₂, 4-Br | 2 |
| 13756 | Bn | 2-NMe₃OTf, 4-Br | 2 |
| 13757 | Bn | 2-NMe₃I, 4-Br | 2 |
| 13758 | Bn | 2-I, 4-F | 2 |
| 13759 | Bn | 2-I, 4-NO₂ | 2 |
| 13760 | Bn | 2-I, 4-NH₂ | 2 |
| 13761 | Bn | 2-I, 4-NHMe | 2 |
| 13762 | Bn | 2-I, 4-NMe₂ | 2 |
| 13763 | Bn | 2-I, 4-NMe₃OTf | 2 |
| 13764 | Bn | 2-I, 4-NMe₃I | 2 |
| 13765 | Bn | 2-F, 4-I | 2 |
| 13766 | Bn | 2-NO₂, 4-I | 2 |
| 13767 | Bn | 2-NH₂, 4-I | 2 |

TABLE 9-continued

Substituent list for compounds of general structure XIV.

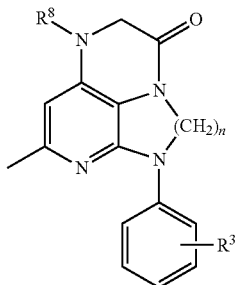

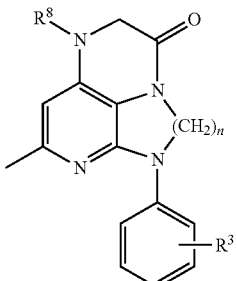

| Compound # | $R^8$ = | $R^3$ = | n = |
|---|---|---|---|
| 13768 | Bn | 2-NHMe, 4-I | 2 |
| 13769 | Bn | 2-NMe$_2$, 4-I | 2 |
| 13770 | Bn | 2-NMe$_3$OTf, 4-I | 2 |
| 13771 | Bn | 2-NMe$_3$I, 4-I | 2 |
| 13772 | Bn | 2-Me, 3-F | 2 |
| 13773 | Bn | 2-Me, 3-NO$_2$ | 2 |
| 13774 | Bn | 2-Me, 3-NH$_2$ | 2 |
| 13775 | Bn | 2-Me, 3-NHMe | 2 |
| 13776 | Bn | 2-Me, 3-NMe$_2$ | 2 |
| 13777 | Bn | 2-Me, 3-NMe$_3$OTf | 2 |
| 13778 | Bn | 2-Me, 3-NMe$_3$I | 2 |
| 13779 | Bn | 2-Me, 4-F | 2 |
| 13780 | Bn | 2-Me, 4-NO$_2$ | 2 |
| 13781 | Bn | 2-Me, 4-NH$_2$ | 2 |
| 13782 | Bn | 2-Me, 4-NHMe | 2 |
| 13783 | Bn | 2-Me, 4-NMe$_2$ | 2 |
| 13784 | Bn | 2-Me, 4-NMe$_3$OTf | 2 |
| 13785 | Bn | 2-Me, 4-NMe$_3$I | 2 |
| 13786 | Bn | 2-Me, 5-F | 2 |
| 13787 | Bn | 2-Me, 5-NO$_2$ | 2 |
| 13788 | Bn | 2-Me, 5-NH$_2$ | 2 |
| 13789 | Bn | 2-Me, 5-NHMe | 2 |
| 13790 | Bn | 2-Me, 5-NMe$_2$ | 2 |
| 13791 | Bn | 2-Me, 5-NMe$_3$OTf | 2 |
| 13792 | Bn | 2-Me, 5-NMe$_3$I | 2 |
| 13793 | Bn | 2-F, 4-Me | 2 |
| 13794 | Bn | 2-NO$_2$, 4-Me | 2 |
| 13795 | Bn | 2-NH$_2$, 4-Me | 2 |
| 13796 | Bn | 2-NHMe, 4-Me | 2 |
| 13797 | Bn | 2-NMe$_2$, 4-Me | 2 |
| 13798 | Bn | 2-NMe$_3$, 4-Me | 2 |
| 13799 | Bn | 2-NMe$_3$OTf, 4-Me | 2 |
| 13800 | Bn | 2-NMe$_3$I, 4-Me | 2 |
| 13801 | Bn | 2-SnMe$_3$, 4-F | 2 |
| 13802 | Bn | 2-SnMe$_3$, 5-F | 2 |
| 13803 | Bn | 2-F, 4-SnMe$_3$ | 2 |
| 13804 | Bn | 2-Br, 4-Cl, 4-F | 2 |
| 13805 | Bn | 2-Br, 6-Cl, 4-NO$_2$ | 2 |
| 13806 | Bn | 2-Br, 6-Cl, 4-NH$_2$ | 2 |
| 13807 | Bn | 2-Br, 6-Cl, 4-NHMe | 2 |
| 13808 | Bn | 2-Br, 6-Cl, 4-NMe$_2$ | 2 |
| 13809 | Bn | 2-Br, 6-Cl, 4-NMe$_3$OTf | 2 |
| 13810 | Bn | 2-Br, 6-Cl, 4-NMe$_3$I | 2 |
| 13811 | Bn | 2-Me, 6-Cl, 4-F | 2 |
| 13812 | Bn | 2-SnMe$_3$, 6-Cl, 4-F | 2 |
| 13813 | Bn | 2-Cl, 4-Me | 2 |
| 13814 | Bn | 2-Cl, 4-Br | 2 |
| 13815 | Bn | 2-Cl, 4-SnMe$_3$ | 2 |
| 13816 | Bn | 2-Br, 4-Cl | 2 |
| 13817 | Bn | 2-SnMe$_3$, 4-Cl | 2 |
| 13818 | Bn | 2-Me, 4-Cl | 2 |
| 13819 | Bn | 2-Br, 4-Br | 2 |
| 13820 | Bn | 2-Br, 4-Me | 2 |
| 13821 | Bn | 2-Br, 4-SnMe$_3$ | 2 |
| 13822 | Bn | 2-SnMe$_3$, 4-Br | 2 |
| 13823 | Bn | 2-Me, 4-Br | 2 |
| 13824 | Bn | 2-Me, 4-SnMe$_3$ | 2 |
| 13825 | Bn | 2-SnMe$_3$, 4-Me | 2 |
| 13826 | Bn | 2-Me, 4-Me | 2 |
| 13827 | Bn | 2-Et, 4-Br | 2 |
| 13828 | Bn | 2-Et, 4-SnMe$_3$ | 2 |
| 13829 | Bn | 2-Et, 4-Me | 2 |
| 13830 | Bn | 2-Me, 4-Me, 6-Me | 2 |
| 13831 | Bn | 2-Me, 4-Br, 6-Me | 2 |
| 13832 | Bn | 2-Me, 4-SnMe$_3$, 6-Me | 2 |
| 13833 | Bn | 2-Et, 6-Me | 2 |
| 13834 | Bn | 2-Br, 4-i-Pr | 2 |
| 13835 | Bn | 2-SnMe$_3$, 4-i-Pr | 2 |
| 13836 | Bn | 2-Me, 4-i-Pr | 2 |
| 13837 | Bn | 2-Br, 4-Br, 6-Br | 2 |
| 13838 | Bn | 2-Br, 4-Me, 6-Br | 2 |
| 13839 | Bn | 2-Br, 4-SnMe$_3$, 6-Br | 2 |
| 13840 | Bn | 2-SnMe$_3$, 4-Br, 6-Br | 2 |
| 13841 | Bn | 2-Br, 4-Br, 6-Me | 2 |
| 13842 | Bn | 2-Br, 4-CF$_3$, 6-Br | 2 |
| 13843 | Bn | 2-Br, 4-Br, 6-CF$_3$ | 2 |
| 13844 | Bn | 2-CF$_3$, 4-CF$_3$ | 2 |
| 13845 | Bn | 2-Cl, 4-CF$_3$ | 2 |
| 13846 | Bn | 2-CF$_3$, 4-Cl | 2 |
| 13847 | Bn | 2-Br, 4-CF$_3$ | 2 |
| 13848 | Bn | 2-SnMe$_3$, 4-CF$_3$ | 2 |
| 13849 | Bn | 2-Me, 4-CF$_3$ | 2 |
| 13850 | Bn | 2-CF$_3$, 4-Br | 2 |
| 13851 | Bn | 2-CF$_3$, 4-SnMe$_3$ | 2 |
| 13852 | Bn | 2-CF$_3$, 4-Me | 2 |
| 13853 | Bn | 2-Br, 4-OH | 2 |
| 13854 | Bn | 2-Br, 4-OMe | 2 |
| 13855 | Bn | 2-Br, 4-OMeF | 2 |
| 13856 | Bn | 2-Br, 4-OCF$_3$ | 2 |
| 13857 | Bn | 2-Br, 4-OEtF | 2 |
| 13858 | Bn | 2-Br, 4-OPrF | 2 |
| 13859 | Bn | 2-OH, 4-Br | 2 |
| 13860 | Bn | 2-OMe, 4-Br | 2 |
| 13861 | Bn | 2-OMeF, 4-Br | 2 |
| 13862 | Bn | 2-OCF$_3$, 4-Br | 2 |
| 13863 | Bn | 2-OEtF, 4-Br | 2 |
| 13864 | Bn | 2-OPrF, 4-Br | 2 |
| 13865 | Bn | 2-I, 4-OH | 2 |
| 13866 | Bn | 2-I, 4-OMe | 2 |
| 13867 | Bn | 2-I, 4-OMeF | 2 |
| 13868 | Bn | 2-I, 4-OCF$_3$ | 2 |
| 13869 | Bn | 2-I, 4-OEtF | 2 |
| 13870 | Bn | 2-I, 4-OPrF | 2 |
| 13871 | Bn | 2-OH, 4-I | 2 |
| 13872 | Bn | 2-OMe, 4-I | 2 |
| 13873 | Bn | 2-OMeF, 4-I | 2 |
| 13874 | Bn | 2-OCF$_3$, 4-I | 2 |
| 13875 | Bn | 2-OEtF, 4-I | 2 |
| 13876 | Bn | 2-OPrF, 4-I | 2 |
| 13877 | Bn | 2-SnMe$_3$, 4-OH | 2 |
| 13878 | Bn | 2-SnMe$_3$, 4-OMe | 2 |
| 13879 | Bn | 2-SnMe$_3$, 4-OMeF | 2 |
| 13880 | Bn | 2-SnMe$_3$, 4-OCF$_3$ | 2 |
| 13881 | Bn | 2-SnMe$_3$, 4-OEtF | 2 |
| 13882 | Bn | 2-SnMe$_3$, 4-OPrF | 2 |
| 13883 | Bn | 2-OH, 4-SnMe$_3$ | 2 |
| 13884 | Bn | 2-OMe, 4-SnMe$_3$ | 2 |
| 13885 | Bn | 2-OMeF, 4-SnMe$_3$ | 2 |
| 13886 | Bn | 2-OCF$_3$, 4-SnMe$_3$ | 2 |
| 13887 | Bn | 2-OEtF, 4-SnMe$_3$ | 2 |

TABLE 9-continued

Substituent list for compounds of general structure XIV.

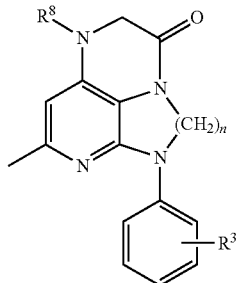

XIV

| Compound # | R$^8$ = | R$^3$ = | n = |
|---|---|---|---|
| 13888 | Bn | 2-OPrF, 4-SnMe$_3$ | 2 |
| 13889 | H | H | 1 |
| 13890 | H | 2-t-Bu | 1 |
| 13891 | H | 2-Br | 1 |
| 13892 | H | 3-Br | 1 |
| 13893 | H | 4-Br | 1 |
| 13894 | H | 2-I | 1 |
| 13895 | H | 3-I | 1 |
| 13896 | H | 4-I | 1 |
| 13897 | H | 2-SnMe$_3$ | 1 |
| 13898 | H | 3-SnMe$_3$ | 1 |
| 13899 | H | 4-SnMe$_3$ | 1 |
| 13900 | H | 2-Me | 1 |
| 13901 | H | 3-Me | 1 |
| 13902 | H | 4-Me | 1 |
| 13903 | H | 2-OH | 1 |
| 13904 | H | 3-OH | 1 |
| 13905 | H | 4-OH | 1 |
| 13906 | H | 2-OMe | 1 |
| 13907 | H | 3-OMe | 1 |
| 13908 | H | 4-OMe | 1 |
| 13909 | H | 2-OMeF | 1 |
| 13910 | H | 3-OMeF | 1 |
| 13911 | H | 4-OMeF | 1 |
| 13912 | H | 2-OCF$_3$ | 1 |
| 13913 | H | 3-OCF$_3$ | 1 |
| 13914 | H | 4-OCF$_3$ | 1 |
| 13915 | H | 2-OEtF | 1 |
| 13916 | H | 3-OEtF | 1 |
| 13917 | H | 4-OEtF | 1 |
| 13918 | H | 2-OPrF | 1 |
| 13919 | H | 3-OPrF | 1 |
| 13920 | H | 4-OPrF | 1 |
| 13921 | H | 2-SH | 1 |
| 13922 | H | 3-SH | 1 |
| 13923 | H | 4-SH | 1 |
| 13924 | H | 2-SMe | 1 |
| 13925 | H | 3-SMe | 1 |
| 13926 | H | 4-SMe | 1 |
| 13927 | H | 2-SMeF | 1 |
| 13928 | H | 3-SMeF | 1 |
| 13929 | H | 4-SMeF | 1 |
| 13930 | H | 2-SCF$_3$ | 1 |
| 13931 | H | 3-SCF$_3$ | 1 |
| 13932 | H | 4-SCF$_3$ | 1 |
| 13933 | H | 2-SEtF | 1 |
| 13934 | H | 3-SEtF | 1 |
| 13935 | H | 4-SEtF | 1 |
| 13936 | H | 2-SPrF | 1 |
| 13937 | H | 3-SPrF | 1 |
| 13938 | H | 4-SPrF | 1 |
| 13939 | H | 2-OMe, 4-OMe | 1 |
| 13940 | H | 2-Me, 5-OH | 1 |
| 13941 | H | 2-Me, 5-OMe | 1 |
| 13942 | H | 2-Me, 5-OMeF | 1 |
| 13943 | H | 2-Me, 5-OEtF | 1 |
| 13944 | H | 2-Me, 5-OPrF | 1 |
| 13945 | H | 2-Me, 4-OH | 1 |
| 13946 | H | 2-Me, 4-OMe | 1 |
| 13947 | H | 2-Me, 4-OMeF | 1 |

TABLE 9-continued

Substituent list for compounds of general structure XIV.

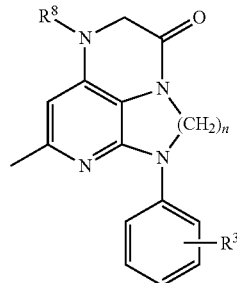

XIV

| Compound # | R$^8$ = | R$^3$ = | n = |
|---|---|---|---|
| 13948 | H | 2-Me, 4-OCF$_3$ | 1 |
| 13949 | H | 2-Me, 4-OEtF | 1 |
| 13950 | H | 2-Me, 4-OPrF | 1 |
| 13951 | H | 2-OH, 4-Me | 1 |
| 13952 | H | 2-OMe, 4-Me | 1 |
| 13953 | H | 2-OMeF, 4-Me | 1 |
| 13954 | H | 2-OCF$_3$, 4-Me | 1 |
| 13955 | H | 2-OEtF, 4-Me | 1 |
| 13956 | H | 2-OPrF, 4-Me | 1 |
| 13957 | H | 2-Cl, 4-OH | 1 |
| 13958 | H | 2-Cl, 4-OMe | 1 |
| 13959 | H | 2-Cl, 4-OMeF | 1 |
| 13960 | H | 2-Cl, 4-OCF$_3$ | 1 |
| 13961 | H | 2-Cl, 4-OEtF | 1 |
| 13962 | H | 2-Cl, 4-OPrF | 1 |
| 13963 | H | 2-F, 4-F | 1 |
| 13964 | H | 2-Cl, 4-Cl | 1 |
| 13965 | H | 2-Cl, 4-F | 1 |
| 13966 | H | 2-Cl, 4-NO$_2$ | 1 |
| 13967 | H | 2-Cl, 4-NH$_2$ | 1 |
| 13968 | H | 2-Cl, 4-NHMe | 1 |
| 13969 | H | 2-Cl, 4-NMe$_2$ | 1 |
| 13970 | H | 2-Cl, 4-NMe$_3$OTf | 1 |
| 13971 | H | 2-Cl, 4-NMe$_3$I | 1 |
| 13972 | H | 2-Cl, 5-F | 1 |
| 13973 | H | 2-Cl, 5-NO$_2$ | 1 |
| 13974 | H | 2-Cl, 5-NH$_2$ | 1 |
| 13975 | H | 2-Cl, 5-NHMe | 1 |
| 13976 | H | 2-Cl, 5-NMe$_2$ | 1 |
| 13977 | H | 2-Cl, 5-NMe$_3$OTf | 1 |
| 13978 | H | 2-Cl, 5-NMe$_3$I | 1 |
| 13979 | H | 2-F, 4-Cl | 1 |
| 13980 | H | 2-NO$_2$, 4-Cl | 1 |
| 13981 | H | 2-NH$_2$, 4-Cl | 1 |
| 13982 | H | 2-NHMe, 4-Cl | 1 |
| 13983 | H | 2-NMe$_2$, 4-Cl | 1 |
| 13984 | H | 2-NMe$_3$OTf, 4-Cl | 1 |
| 13985 | H | 2-NMe$_3$I, 4-Cl | 1 |
| 13986 | H | 2-F, 5-Cl | 1 |
| 13987 | H | 2-NO$_2$, 5-Cl | 1 |
| 13988 | H | 2-NH$_2$, 5-Cl | 1 |
| 13989 | H | 2-NHMe, 5-Cl | 1 |
| 13990 | H | 2-NMe$_2$, 5-Cl | 1 |
| 13991 | H | 2-NMe$_3$OTf, 5-Cl | 1 |
| 13992 | H | 2-NMe$_3$I, 5-Cl | 1 |
| 13993 | H | 2-Br, 4-F | 1 |
| 13994 | H | 2-Br, 4-NO$_2$ | 1 |
| 13995 | H | 2-Br, 4-NH$_2$ | 1 |
| 13996 | H | 2-Br, 4-NHMe | 1 |
| 13997 | H | 2-Br, 4-NMe$_2$ | 1 |
| 13998 | H | 2-Br, 4-NMe$_3$OTf | 1 |
| 13999 | H | 2-Br, 4-NMe$_3$I | 1 |
| 14000 | H | 2-Br, 5-F | 1 |
| 14001 | H | 2-Br, 5-NO$_2$ | 1 |
| 14002 | H | 2-Br, 5-NH$_2$ | 1 |
| 14003 | H | 2-Br, 5-NHMe | 1 |
| 14004 | H | 2-Br, 5-NMe$_2$ | 1 |
| 14005 | H | 2-Br, 5-NMe$_3$OTf | 1 |
| 14006 | H | 2-Br, 5-NMe$_3$I | 1 |
| 14007 | H | 2-F, 4-Br | 1 |

TABLE 9-continued

Substituent list for compounds of general structure XIV.

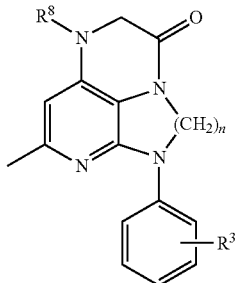

| Compound # | R⁸ = | R³ = | n = |
|---|---|---|---|
| 14008 | H | 2-NO₂, 4-Br | 1 |
| 14009 | H | 2-NH₂, 4-Br | 1 |
| 14010 | H | 2-NHMe, 4-Br | 1 |
| 14011 | H | 2-NMe₂, 4-Br | 1 |
| 14012 | H | 2-NMe₃OTf, 4-Br | 1 |
| 14013 | H | 2-NMe₃I, 4-Br | 1 |
| 14014 | H | 2-I, 4-F | 1 |
| 14015 | H | 2-I, 4-NO₂ | 1 |
| 14016 | H | 2-I, 4-NH₂ | 1 |
| 14017 | H | 2-I, 4-NHMe | 1 |
| 14018 | H | 2-I, 4-NMe₂ | 1 |
| 14019 | H | 2-I, 4-NMe₃OTf | 1 |
| 14020 | H | 2-I, 4-NMe₃I | 1 |
| 14021 | H | 2-F, 4-I | 1 |
| 14022 | H | 2-NO₂, 4-I | 1 |
| 14023 | H | 2-NH₂, 4-I | 1 |
| 14024 | H | 2-NHMe, 4-I | 1 |
| 14025 | H | 2-NMe₂, 4-I | 1 |
| 14026 | H | 2-NMe₃OTf, 4-I | 1 |
| 14027 | H | 2-NMe₃I, 4-I | 1 |
| 14028 | H | 2-Me, 3-F | 1 |
| 14029 | H | 2-Me, 3-NO₂ | 1 |
| 14030 | H | 2-Me, 3-NH₂ | 1 |
| 14031 | H | 2-Me, 3-NHMe | 1 |
| 14032 | H | 2-Me, 3-NMe₂ | 1 |
| 14033 | H | 2-Me, 3-NMe₃OTf | 1 |
| 14034 | H | 2-Me, 3-NMe₃I | 1 |
| 14035 | H | 2-Me, 4-F | 1 |
| 14036 | H | 2-Me, 4-NO₂ | 1 |
| 14037 | H | 2-Me, 4-NH₂ | 1 |
| 14038 | H | 2-Me, 4-NHMe | 1 |
| 14039 | H | 2-Me, 4-NMe₂ | 1 |
| 14040 | H | 2-Me, 4-NMe₃OTf | 1 |
| 14041 | H | 2-Me, 4-NMe₃I | 1 |
| 14042 | H | 2-Me, 5-F | 1 |
| 14043 | H | 2-Me, 5-NO₂ | 1 |
| 14044 | H | 2-Me, 5-NH₂ | 1 |
| 14045 | H | 2-Me, 5-NHMe | 1 |
| 14046 | H | 2-Me, 5-NMe₂ | 1 |
| 14047 | H | 2-Me, 5-NMe₃OTf | 1 |
| 14048 | H | 2-Me, 5-NMe₃I | 1 |
| 14049 | H | 2-F, 4-Me | 1 |
| 14050 | H | 2-NO₂, 4-Me | 1 |
| 14051 | H | 2-NH₂, 4-Me | 1 |
| 14052 | H | 2-NHMe, 4-Me | 1 |
| 14053 | H | 2-NMe₂, 4-Me | 1 |
| 14054 | H | 2-NMe₃, 4-Me | 1 |
| 14055 | H | 2-NMe₃OTf, 4-Me | 1 |
| 14056 | H | 2-NMe₃I, 4-Me | 1 |
| 14057 | H | 2-SnMe₃, 4-F | 1 |
| 14058 | H | 2-SnMe₃, 5-F | 1 |
| 14059 | H | 2-F, 4-SnMe₃ | 1 |
| 14060 | H | 2-Br, 6-Cl, 4-F | 1 |
| 14061 | H | 2-Br, 6-Cl, 4-NO₂ | 1 |
| 14062 | H | 2-Br, 6-Cl, 4-NH₂ | 1 |
| 14063 | H | 2-Br, 6-Cl, 4-NHMe | 1 |
| 14064 | H | 2-Br, 6-Cl, 4-NMe₂ | 1 |
| 14065 | H | 2-Br, 6-Cl, 4-NMe₃OTf | 1 |
| 14066 | H | 2-Br, 6-Cl, 4-NMe₃I | 1 |
| 14067 | H | 2-Me, 6-Cl, 4-F | 1 |

TABLE 9-continued

Substituent list for compounds of general structure XIV.

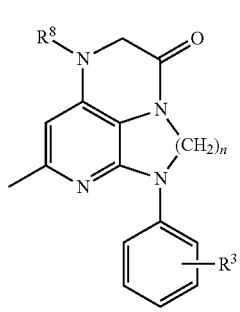

| Compound # | R⁸ = | R³ = | n = |
|---|---|---|---|
| 14068 | H | 2-SnMe₃, 6-Cl, 4-F | 1 |
| 14069 | H | 2-Cl, 4-Me | 1 |
| 14070 | H | 2-Cl, 4-Br | 1 |
| 14071 | H | 2-Cl, 4-SnMe₃ | 1 |
| 14072 | H | 2-Br, 4-Cl | 1 |
| 14073 | H | 2-SnMe₃, 4-Cl | 1 |
| 14074 | H | 2-Me, 4-Cl | 1 |
| 14075 | H | 2-Br, 4-Br | 1 |
| 14076 | H | 2-Br, 4-Me | 1 |
| 14077 | H | 2-Br, 4-SnMe₃ | 1 |
| 14078 | H | 2-SnMe₃, 4-Br | 1 |
| 14079 | H | 2-Me, 4-Br | 1 |
| 14080 | H | 2-Me, 4-SnMe₃ | 1 |
| 14081 | H | 2-SnMe₃, 4-Me | 1 |
| 14082 | H | 2-Me, 4-Me | 1 |
| 14083 | H | 2-Et, 4-Br | 1 |
| 14084 | H | 2-Et, 4-SnMe₃ | 1 |
| 14085 | H | 2-Et, 4-Me | 1 |
| 14086 | H | 2-Me, 4-Me, 6-Me | 1 |
| 14087 | H | 2-Me, 4-Br, 6-Me | 1 |
| 14088 | H | 2-Me, 4-SnMe₃, 6-Me | 1 |
| 14089 | H | 2-Et, 6-Me | 1 |
| 14090 | H | 2-Br, 4-i-Pr | 1 |
| 14091 | H | 2-SnMe₃, 4-i-Pr | 1 |
| 14092 | H | 2-Me, 4-i-Pr | 1 |
| 14093 | H | 2-Br, 4-Br, 6-Br | 1 |
| 14094 | H | 2-Br, 4-Me, 6-Br | 1 |
| 14095 | H | 2-Br, 4-SnMe₃, 6-Br | 1 |
| 14096 | H | 2-SnMe₃, 4-Br, 6-Br | 1 |
| 14097 | H | 2-Br, 4-Br, 6-Me | 1 |
| 14098 | H | 2-Br, 4-CF₃, 6-Br | 1 |
| 14099 | H | 2-Br, 4-Br, 6-CF₃ | 1 |
| 14100 | H | 2-CF₃, 4-CF₃ | 1 |
| 14101 | H | 2-Cl, 4-CF₃ | 1 |
| 14102 | H | 2-CF₃, 4-Cl | 1 |
| 14103 | H | 2-Br, 4-CF₃ | 1 |
| 14104 | H | 2-SnMe₃, 4-CF₃ | 1 |
| 14105 | H | 2-Me, 4-CF₃ | 1 |
| 14106 | H | 2-CF₃, 4-Br | 1 |
| 14107 | H | 2-CF₃, 4-SnMe₃ | 1 |
| 14108 | H | 2-CF₃, 4-Me | 1 |
| 14109 | H | 2-Br, 4-OH | 1 |
| 14110 | H | 2-Br, 4-OMe | 1 |
| 14111 | H | 2-Br, 4-OMeF | 1 |
| 14112 | H | 2-Br, 4-OCF₃ | 1 |
| 14113 | H | 2-Br, 4-OEtF | 1 |
| 14114 | H | 2-Br, 4-OPrF | 1 |
| 14115 | H | 2-OH, 4-Br | 1 |
| 14116 | H | 2-OMe, 4-Br | 1 |
| 14117 | H | 2-OMeF, 4-Br | 1 |
| 14118 | H | 2-OCF₃, 4-Br | 1 |
| 14119 | H | 2-OEtF, 4-Br | 1 |
| 14120 | H | 2-OPrF, 4-Br | 1 |
| 14121 | H | 2-I, 4-OH | 1 |
| 14122 | H | 2-I, 4-OMe | 1 |
| 14123 | H | 2-I, 4-OMeF | 1 |
| 14124 | H | 2-I, 4-OCF₃ | 1 |
| 14125 | H | 2-I, 4-OEtF | 1 |
| 14126 | H | 2-I, 4-OPrF | 1 |
| 14127 | H | 2-OH, 4-I | 1 |

TABLE 9-continued

Substituent list for compounds of general structure XIV.

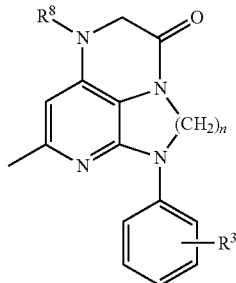

| Compound # | R⁸ = | R³ = | n = |
|---|---|---|---|
| 14128 | H | 2-OMe, 4-I | 1 |
| 14129 | H | 2-OMeF, 4-I | 1 |
| 14130 | H | 2-OCF₃, 4-I | 1 |
| 14131 | H | 2-OEtF, 4-I | 1 |
| 14132 | H | 2-OPrF, 4-I | 1 |
| 14133 | H | 2-SnMe₃, 4-OH | 1 |
| 14134 | H | 2-SnMe₃, 4-OMe | 1 |
| 14135 | H | 2-SnMe₃, 4-OMeF | 1 |
| 14136 | H | 2-SnMe₃, 4-OCF₃ | 1 |
| 14137 | H | 2-SnMe₃, 4-OEtF | 1 |
| 14138 | H | 2-SnMe₃, 4-OPrF | 1 |
| 14139 | H | 2-OH, 4-SnMe₃ | 1 |
| 14140 | H | 2-OMe, 4-SnMe₃ | 1 |
| 14141 | H | 2-OMeF, 4-SnMe₃ | 1 |
| 14142 | H | 2-OCF₃, 4-SnMe₃ | 1 |
| 14143 | H | 2-OEtF, 4-SnMe₃ | 1 |
| 14144 | H | 2-OPrF, 4-SnMe₃ | 1 |
| 14145 | H | H | 2 |
| 14146 | H | 2-t-Bu | 2 |
| 14147 | H | 2-Br | 2 |
| 14148 | H | 3-Br | 2 |
| 14149 | H | 4-Br | 2 |
| 14150 | H | 2-I | 2 |
| 14151 | H | 3-I | 2 |
| 14152 | H | 4-I | 2 |
| 14153 | H | 2-SnMe₃ | 2 |
| 14154 | H | 3-SnMe₃ | 2 |
| 14155 | H | 4-SnMe₃ | 2 |
| 14156 | H | 2-Me | 2 |
| 14157 | H | 3-Me | 2 |
| 14158 | H | 4-Me | 2 |
| 14159 | H | 2-OH | 2 |
| 14160 | H | 3-OH | 2 |
| 14161 | H | 4-OH | 2 |
| 14162 | H | 2-OMe | 2 |
| 14163 | H | 3-OMe | 2 |
| 14164 | H | 4-OMe | 2 |
| 14165 | H | 2-OMeF | 2 |
| 14166 | H | 3-OMeF | 2 |
| 14167 | H | 4-OMeF | 2 |
| 14168 | H | 2-OCF₃ | 2 |
| 14169 | H | 3-OCF₃ | 2 |
| 14170 | H | 4-OCF₃ | 2 |
| 14171 | H | 2-OEtF | 2 |
| 14172 | H | 3-OEtF | 2 |
| 14173 | H | 4-OEtF | 2 |
| 14174 | H | 2-OPrF | 2 |
| 14175 | H | 3-OPrF | 2 |
| 14176 | H | 4-OPrF | 2 |
| 14177 | H | 2-SH | 2 |
| 14178 | H | 3-SH | 2 |
| 14179 | H | 4-SH | 2 |
| 14180 | H | 2-SMe | 2 |
| 14181 | H | 3-SMe | 2 |
| 14182 | H | 4-SMe | 2 |
| 14183 | H | 2-SMeF | 2 |
| 14184 | H | 3-SMeF | 2 |
| 14185 | H | 4-SMeF | 2 |
| 14186 | H | 2-SCF₃ | 2 |
| 14187 | H | 3-SCF₃ | 2 |

TABLE 9-continued

Substituent list for compounds of general structure XIV.

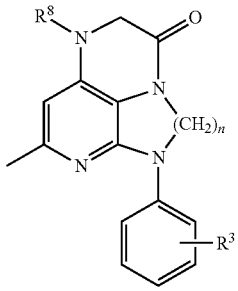

| Compound # | R⁸ = | R³ = | n = |
|---|---|---|---|
| 14188 | H | 4-SCF₃ | 2 |
| 14189 | H | 2-SEtF | 2 |
| 14190 | H | 3-SEtF | 2 |
| 14191 | H | 4-SEtF | 2 |
| 14192 | H | 2-SPrF | 2 |
| 14193 | H | 3-SPrF | 2 |
| 14194 | H | 4-SPrF | 2 |
| 14195 | H | 2-OMe, 4-OMe | 2 |
| 14196 | H | 2-Me, 5-OH | 2 |
| 14197 | H | 2-Me, 5-OMe | 2 |
| 14198 | H | 2-Me, 5-OMeF | 2 |
| 14199 | H | 2-Me, 5-OEtF | 2 |
| 14200 | H | 2-Me, 5-OPrF | 2 |
| 14201 | H | 2-Me, 4-OH | 2 |
| 14202 | H | 2-Me, 4-OMe | 2 |
| 14203 | H | 2-Me, 4-OMeF | 2 |
| 14204 | H | 2-Me, 4-OCF₃ | 2 |
| 14205 | H | 2-Me, 4-OEtF | 2 |
| 14206 | H | 2-Me, 4-OPrF | 2 |
| 14207 | H | 2-OH, 4-Me | 2 |
| 14208 | H | 2-OMe, 4-Me | 2 |
| 14209 | H | 2-OMeF, 4-Me | 2 |
| 14210 | H | 2-OCF₃, 4-Me | 2 |
| 14211 | H | 2-OEtF, 4-Me | 2 |
| 14212 | H | 2-OPrF, 4-Me | 2 |
| 14213 | H | 2-Cl, 4-OH | 2 |
| 14214 | H | 2-Cl, 4-OMe | 2 |
| 14215 | H | 2-Cl, 4-OMeF | 2 |
| 14216 | H | 2-Cl, 4-OCF₃ | 2 |
| 14217 | H | 2-Cl, 4-OEtF | 2 |
| 14218 | H | 2-Cl, 4-OPrF | 2 |
| 14219 | H | 2-F, 4-F | 2 |
| 14220 | H | 2-Cl, 4-Cl | 2 |
| 14221 | H | 2-Cl, 4-F | 2 |
| 14222 | H | 2-Cl, 4-NO₂ | 2 |
| 14223 | H | 2-Cl, 4-NH₂ | 2 |
| 14224 | H | 2-Cl, 4-NHMe | 2 |
| 14225 | H | 2-Cl, 4-NMe₂ | 2 |
| 14226 | H | 2-Cl, 4-NMe₃OTf | 2 |
| 14227 | H | 2-Cl, 4-NMe₃I | 2 |
| 14228 | H | 2-Cl, 5-F | 2 |
| 14229 | H | 2-Cl, 5-NO₂ | 2 |
| 14230 | H | 2-Cl, 5-NH₂ | 2 |
| 14231 | H | 2-Cl, 5-NHMe | 2 |
| 14232 | H | 2-Cl, 5-NMe₂ | 2 |
| 14233 | H | 2-Cl, 5-NMe₃OTf | 2 |
| 14234 | H | 2-Cl, 5-NMe₃I | 2 |
| 14235 | H | 2-F, 4-Cl | 2 |
| 14236 | H | 2-NO₂, 4-Cl | 2 |
| 14237 | H | 2-NH₂, 4-Cl | 2 |
| 14238 | H | 2-NHMe, 4-Cl | 2 |
| 14239 | H | 2-NMe₂, 4-Cl | 2 |
| 14240 | H | 2-NMe₃OTf, 4-Cl | 2 |
| 14241 | H | 2-NMe₃I, 4-Cl | 2 |
| 14242 | H | 2-F, 5-Cl | 2 |
| 14243 | H | 2-NO₂, 5-Cl | 2 |
| 14244 | H | 2-NH₂, 5-Cl | 2 |
| 14245 | H | 2-NHMe, 5-Cl | 2 |
| 14246 | H | 2-NMe₂, 5-Cl | 2 |
| 14247 | H | 2-NMe₃OTf, 5-Cl | 2 |

TABLE 9-continued

Substituent list for compounds of general structure XIV.

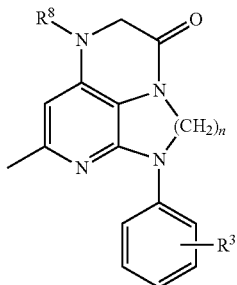

XIV

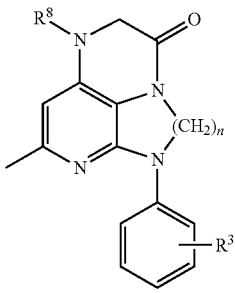

XIV

| Compound # | R⁸ = | R³ = | n = | Compound # | R⁸ = | R³ = | n = |
|---|---|---|---|---|---|---|---|
| 14248 | H | 2-NMe₃I, 5-Cl | 2 | 14308 | H | 2-NHMe, 4-Me | 2 |
| 14249 | H | 2-Br, 4-F | 2 | 14309 | H | 2-NMe₂, 4-Me | 2 |
| 14250 | H | 2-Br, 4-NO₂ | 2 | 14310 | H | 2-NMe₃, 4-Me | 2 |
| 14251 | H | 2-Br, 4-NH₂ | 2 | 14311 | H | 2-NMe₃OTf, 4-Me | 2 |
| 14252 | H | 2-Br, 4-NHMe | 2 | 14312 | H | 2-NMe₃I, 4-Me | 2 |
| 14253 | H | 2-Br, 4-NMe₂ | 2 | 14313 | H | 2-SnMe₃, 4-F | 2 |
| 14254 | H | 2-Br, 4-NMe₃OTf | 2 | 14314 | H | 2-SnMe₃, 5-F | 2 |
| 14255 | H | 2-Br, 4-NMe₃I | 2 | 14315 | H | 2-F, 4-SnMe₃ | 2 |
| 14256 | H | 2-Br, 5-F | 2 | 14316 | H | 2-Br, 6-Cl, 4-F | 2 |
| 14257 | H | 2-Br, 5-NO₂ | 2 | 14317 | H | 2-Br, 6-Cl, 4-NO₂ | 2 |
| 14258 | H | 2-Br, 5-NH₂ | 2 | 14318 | H | 2-Br, 6-Cl, 4-NH₂ | 2 |
| 14259 | H | 2-Br, 5-NHMe | 2 | 14319 | H | 2-Br, 6-Cl, 4-NHMe | 2 |
| 14260 | H | 2-Br, 5-NMe₂ | 2 | 14320 | H | 2-Br, 6-Cl, 4-NMe₂ | 2 |
| 14261 | H | 2-Br, 5-NMe₃OTf | 2 | 14321 | H | 2-Br, 6-Cl, 4-NMe₃OTf | 2 |
| 14262 | H | 2-Br, 5-NMe₃I | 2 | 14322 | H | 2-Br, 6-Cl, 4-NMe₃I | 2 |
| 14263 | H | 2-F, 4-Br | 2 | 14323 | H | 2-Me, 6-Cl, 4-F | 2 |
| 14264 | H | 2-NO₂, 4-Br | 2 | 14324 | H | 2-SnMe₃, 6-Cl, 4-F | 2 |
| 14265 | H | 2-NH₂, 4-Br | 2 | 14325 | H | 2-Cl, 4-Me | 2 |
| 14266 | H | 2-NHMe, 4-Br | 2 | 14326 | H | 2-Cl, 4-Br | 2 |
| 14267 | H | 2-NMe₂, 4-Br | 2 | 14327 | H | 2-Cl, 4-SnMe₃ | 2 |
| 14268 | H | 2-NMe₃OTf, 4-Br | 2 | 14328 | H | 2-Br, 4-Cl | 2 |
| 14269 | H | 2-NMe₃I, 4-Br | 2 | 14329 | H | 2-SnMe₃, 4-Cl | 2 |
| 14270 | H | 2-I, 4-F | 2 | 14330 | H | 2-Me, 4-Cl | 2 |
| 14271 | H | 2-I, 4-NO₂ | 2 | 14331 | H | 2-Br, 4-Br | 2 |
| 14272 | H | 2-I, 4-NH₂ | 2 | 14332 | H | 2-Br, 4-Me | 2 |
| 14273 | H | 2-I, 4-NHMe | 2 | 14333 | H | 2-Br, 4-SnMe₃ | 2 |
| 14274 | H | 2-I, 4-NMe₂ | 2 | 14334 | H | 2-SnMe₃, 4-Br | 2 |
| 14275 | H | 2-I, 4-NMe₃OTf | 2 | 14335 | H | 2-Me, 4-Br | 2 |
| 14276 | H | 2-I, 4-NMe₃I | 2 | 14336 | H | 2-Me, 4-SnMe₃ | 2 |
| 14277 | H | 2-F, 4-I | 2 | 14337 | H | 2-SnMe₃, 4-Me | 2 |
| 14278 | H | 2-NO₂, 4-I | 2 | 14338 | H | 2-Me, 4-Me | 2 |
| 14279 | H | 2-NH₂, 4-I | 2 | 14339 | H | 2-Et, 4-Br | 2 |
| 14280 | H | 2-NHMe, 4-I | 2 | 14340 | H | 2-Et, 4-SnMe₃ | 2 |
| 14281 | H | 2-NMe₂, 4-I | 2 | 14341 | H | 2-Et, 4-Me | 2 |
| 14282 | H | 2-NMe₃OTf, 4-I | 2 | 14342 | H | 2-Me, 4-Me, 6-Me | 2 |
| 14283 | H | 2-NMe₃I, 4-I | 2 | 14343 | H | 2-Me, 4-Br, 6-Me | 2 |
| 14284 | H | 2-Me, 3-F | 2 | 14344 | H | 2-Me, 4-SnMe₃, 6-Me | 2 |
| 14285 | H | 2-Me, 3-NO₂ | 2 | 14345 | H | 2-Et, 6-Me | 2 |
| 14286 | H | 2-Me, 3-NH₂ | 2 | 14346 | H | 2-Br, 4-i-Pr | 2 |
| 14287 | H | 2-Me, 3-NHMe | 2 | 14347 | H | 2-SnMe₃, 4-i-Pr | 2 |
| 14288 | H | 2-Me, 3-NMe₂ | 2 | 14348 | H | 2-Me, 4-i-Pr | 2 |
| 14289 | H | 2-Me, 3-NMe₃OTf | 2 | 14349 | H | 2-Br, 4-Br, 6-Br | 2 |
| 14290 | H | 2-Me, 3-NMe₃I | 2 | 14350 | H | 2-Br, 4-Me, 6-Br | 2 |
| 14291 | H | 2-Me, 4-F | 2 | 14351 | H | 2-Br, 4-SnMe₃, 6-Br | 2 |
| 14292 | H | 2-Me, 4-NO₂ | 2 | 14352 | H | 2-SnMe₃, 4-Br, 6-Br | 2 |
| 14293 | H | 2-Me, 4-NH₂ | 2 | 14353 | H | 2-Br, 4-Br, 6-Me | 2 |
| 14294 | H | 2-Me, 4-NHMe | 2 | 14354 | H | 2-Br, 4-CF₃, 6-Br | 2 |
| 14295 | H | 2-Me, 4-NMe₂ | 2 | 14355 | H | 2-Br, 4-Br, 6-CF₃ | 2 |
| 14296 | H | 2-Me, 4-NMe₃OTf | 2 | 14356 | H | 2-CF₃, 4-CF₃ | 2 |
| 14297 | H | 2-Me, 4-NMe₃I | 2 | 14357 | H | 2-Cl, 4-CF₃ | 2 |
| 14298 | H | 2-Me, 5-F | 2 | 14358 | H | 2-CF₃, 4-Cl | 2 |
| 14299 | H | 2-Me, 5-NO₂ | 2 | 14359 | H | 2-Br, 4-CF₃ | 2 |
| 14300 | H | 2-Me, 5-NH₂ | 2 | 14360 | H | 2-SnMe₃, 4-CF₃ | 2 |
| 14301 | H | 2-Me, 5-NHMe | 2 | 14361 | H | 2-Me, 4-CF₃ | 2 |
| 14302 | H | 2-Me, 5-NMe₂ | 2 | 14362 | H | 2-CF₃, 4-Br | 2 |
| 14303 | H | 2-Me, 5-NMe₃OTf | 2 | 14363 | H | 2-CF₃, SnMe₃ | 2 |
| 14304 | H | 2-Me, 5-NMe₃I | 2 | 14364 | H | 2-CF₃, 4-Me | 2 |
| 14305 | H | 2-F, 4-Me | 2 | 14365 | H | 2-Br, 4-OH | 2 |
| 14306 | H | 2-NO₂, 4-Me | 2 | 14366 | H | 2-Br, 4-OMe | 2 |
| 14307 | H | 2-NH₂, 4-Me | 2 | 14367 | H | 2-Br, 4-OMeF | 2 |

TABLE 9-continued

Substituent list for compounds of general structure XIV.

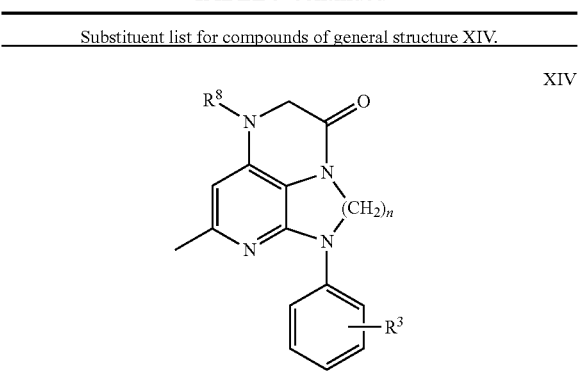

XIV

| Compound # | R⁸ = | R³ = | n = |
|---|---|---|---|
| 14368 | H | 2-Br, 4-OCF₃ | 2 |
| 14369 | H | 2-Br, 4-OEtF | 2 |
| 14370 | H | 2-Br, 4-OPrF | 2 |
| 14371 | H | 2-OH, 4-Br | 2 |
| 14372 | H | 2-OMe, 4-Br | 2 |
| 14373 | H | 2-OMeF, 4-Br | 2 |
| 14374 | H | 2-OCF₃, 4-Br | 2 |
| 14375 | H | 2-OEtF, 4-Br | 2 |
| 14376 | H | 2-OPrF, 4-Br | 2 |
| 14377 | H | 2-I, 4-OH | 2 |
| 14378 | H | 2-I, 4-OMe | 2 |
| 14379 | H | 2-I, 4-OMeF | 2 |
| 14380 | H | 2-I, 4-OCF₃ | 2 |
| 14381 | H | 2-I, 4-OEtF | 2 |
| 14382 | H | 2-I, 4-OPrF | 2 |
| 14383 | H | 2-OH, 4-I | 2 |
| 14384 | H | 2-OMe, 4-I | 2 |
| 14385 | H | 2-OMeF, 4-I | 2 |
| 14386 | H | 2-OCF₃, 4-I | 2 |
| 14387 | H | 2-OEtF, 4-I | 2 |
| 14388 | H | 2-OPrF, 4-I | 2 |
| 14389 | H | 2-SnMe₃, 4-OH | 2 |
| 14390 | H | 2-SnMe₃, 4-OMe | 2 |
| 14391 | H | 2-SnMe₃, 4-OMeF | 2 |
| 14392 | H | 2-SnMe₃, 4-OCF₃ | 2 |
| 14393 | H | 2-SnMe₃, 4-OEtF | 2 |
| 14394 | H | 2-SnMe₃, 4-OPrF | 2 |
| 14395 | H | 2-OH, 4-SnMe₃ | 2 |
| 14396 | H | 2-OMe, 4-SnMe₃ | 2 |
| 14397 | H | 2-OMeF, 4-SnMe₃ | 2 |
| 14398 | H | 2-OCF₃, 4-SnMe₃ | 2 |
| 14399 | H | 2-OEtF, 4-SnMe₃ | 2 |
| 14400 | H | 2-OPrF, 4-SnMe₃ | 2 |

TABLE 10

Substituent list for compounds of general structure XV.

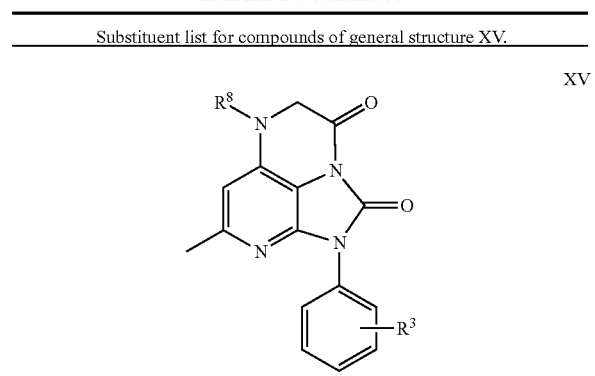

XV

| Compound # | R¹ = | R³ = |
|---|---|---|
| 14401 | Bu | H |
| 14402 | Bu | 2-t-Bu |
| 14403 | Bu | 2-Br |
| 14404 | Bu | 3-Br |
| 14405 | Bu | 4-Br |
| 14406 | Bu | 2-I |
| 14407 | Bu | 3-I |
| 14408 | Bu | 4-I |
| 14409 | Bu | 2-SnMe₃ |
| 14410 | Bu | 3-SnMe₃ |
| 14411 | Bu | 4-SnMe₃ |
| 14412 | Bu | 2-Me |
| 14413 | Bu | 3-Me |
| 14414 | Bu | 4-Me |
| 14415 | Bu | 2-OH |
| 14416 | Bu | 3-OH |
| 14417 | Bu | 4-OH |
| 14418 | Bu | 2-OMe |
| 14419 | Bu | 3-OMe |
| 14420 | Bu | 4-OMe |
| 14421 | Bu | 2-OMeF |
| 14422 | Bu | 3-OMeF |
| 14423 | Bu | 4-OMeF |
| 14424 | Bu | 2-OCF₃ |
| 14425 | Bu | 3-OCF₃ |
| 14426 | Bu | 4-OCF₃ |
| 14427 | Bu | 2-OEtF |
| 14428 | Bu | 3-OEtF |
| 14429 | Bu | 4-OEtF |
| 14430 | Bu | 2-OPrF |
| 14431 | Bu | 3-OPrF |
| 14432 | Bu | 4-OPrF |
| 14433 | Bu | 2-SH |
| 14434 | Bu | 3-SH |
| 14435 | Bu | 4-SH |
| 14436 | Bu | 2-SMe |
| 14437 | Bu | 3-SMe |
| 14438 | Bu | 4-SMe |
| 14439 | Bu | 2-SMeF |
| 14440 | Bu | 3-SMeF |
| 14441 | Bu | 4-SMeF |
| 14442 | Bu | 2-SCF₃ |
| 14443 | Bu | 3-SCF₃ |
| 14444 | Bu | 4-SCF₃ |
| 14445 | Bu | 2-SEtF |
| 14446 | Bu | 3-SEtF |
| 14447 | Bu | 4-SEtF |
| 14448 | Bu | 2-SPrF |
| 14449 | Bu | 3-SPrF |
| 14450 | Bu | 4-SPrF |
| 14451 | Bu | 2-OMe, 4-OMe |
| 14452 | Bu | 2-Me, 5-OH |
| 14453 | Bu | 2-Me, 5-OMe |
| 14454 | Bu | 2-Me, 5-OMeF |
| 14455 | Bu | 2-Me, 5-OEtF |
| 14456 | Bu | 2-Me, 5-OPrF |
| 14457 | Bu | 2-Me, 4-OH |
| 14458 | Bu | 2-Me, 4-OMe |
| 14459 | Bu | 2-Me, 4-OMeF |
| 14460 | Bu | 2-Me, 4-OCF₃ |
| 14461 | Bu | 2-Me, 4-OEtF |
| 14462 | Bu | 2-Me, 4-OPrF |

TABLE 10-continued

Substituent list for compounds of general structure XV.

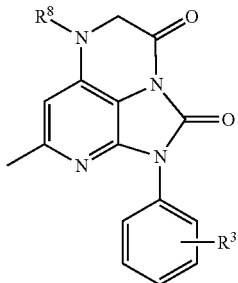

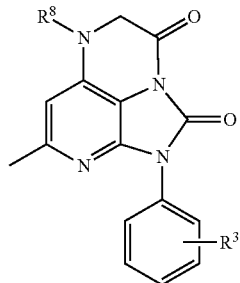

| Compound # | R¹ = | R³ = |
|---|---|---|
| 14463 | Bu | 2-OH, 4-Me |
| 14464 | Bu | 2-OMe, 4-Me |
| 14465 | Bu | 2-OMeF, 4-Me |
| 14466 | Bu | 2-OCF$_3$, 4-Me |
| 14467 | Bu | 2-OEtF, 4-Me |
| 14468 | Bu | 2-OPrF, 4-Me |
| 14469 | Bu | 2-Cl, 4-OH |
| 14470 | Bu | 2-Cl, 4-OMe |
| 14471 | Bu | 2-Cl, 4-OMeF |
| 14472 | Bu | 2-Cl, 4-OCF$_3$ |
| 14473 | Bu | 2-Cl, 4-OEtF |
| 14474 | Bu | 2-Cl, 4-OPrF |
| 14475 | Bu | 2-F, 4-F |
| 14476 | Bu | 2-Cl, 4-Cl |
| 14477 | Bu | 2-Cl, 4-F |
| 14478 | Bu | 2-Cl, 4-NO$_2$ |
| 14479 | Bu | 2-Cl, 4-NH$_2$ |
| 14480 | Bu | 2-Cl, 4-NHMe |
| 14481 | Bu | 2-Cl, 4-NMe$_2$ |
| 14482 | Bu | 2-Cl, 4-NMe$_3$OTf |
| 14483 | Bu | 2-Cl, 4-NMe$_3$I |
| 14484 | Bu | 2-Cl, 5-F |
| 14485 | Bu | 2-Cl, 5-NO$_2$ |
| 14486 | Bu | 2-Cl, 5-NH$_2$ |
| 14487 | Bu | 2-Cl, 5-NHMe |
| 14488 | Bu | 2-Cl, 5-NMe$_2$ |
| 14489 | Bu | 2-Cl, 5-NMe$_3$OTf |
| 14490 | Bu | 2-Cl, 5-NMe$_3$I |
| 14491 | Bu | 2-F, 4-Cl |
| 14492 | Bu | 2-NO$_2$, 4-Cl |
| 14493 | Bu | 2-NH$_2$, 4-Cl |
| 14494 | Bu | 2-NHMe, 4-Cl |
| 14495 | Bu | 2-NMe$_2$, 4-Cl |
| 14496 | Bu | 2-NMe$_3$OTf, 4-Cl |
| 14497 | Bu | 2-NMe$_3$I, 4-Cl |
| 14498 | Bu | 2-F, 5-Cl |
| 14499 | Bu | 2-NO$_2$, 5-Cl |
| 14500 | Bu | 2-NH$_2$, 5-Cl |
| 14501 | Bu | 2-NHMe, 5-Cl |
| 14502 | Bu | 2-NMe$_2$, 5-Cl |
| 14503 | Bu | 2-NMe$_3$OTf, 5-Cl |
| 14504 | Bu | 2-NMe$_3$I, 5-Cl |
| 14505 | Bu | 2-Br, 4-F |
| 14506 | Bu | 2-Br, 4-NO$_2$ |
| 14507 | Bu | 2-Br, 4-NH$_2$ |
| 14508 | Bu | 2-Br, 4-NHMe |
| 14509 | Bu | 2-Br, 4-NMe$_2$ |
| 14510 | Bu | 2-Br, 4-NMe$_3$OTf |
| 14511 | Bu | 2-Br, 4-NMe$_3$I |
| 14512 | Bu | 2-Br, 5-F |
| 14513 | Bu | 2-Br, 5-NO$_2$ |
| 14514 | Bu | 2-Br, 5-NH$_2$ |
| 14515 | Bu | 2-Br, 5-NHMe |
| 14516 | Bu | 2-Br, 5-NMe$_2$ |
| 14517 | Bu | 2-Br, 5-NMe$_3$OTf |
| 14518 | Bu | 2-Br, 5-NMe$_3$I |
| 14519 | Bu | 2-F, 4-Br |
| 14520 | Bu | 2-NO$_2$, 4-Br |
| 14521 | Bu | 2-NH$_2$, 4-Br |
| 14522 | Bu | 2-NHMe, 4-Br |
| 14523 | Bu | 2-NMe$_2$, 4-Br |
| 14524 | Bu | 2-NMe$_3$OTf, 4-Br |
| 14525 | Bu | 2-NMe$_3$I, 4-Br |
| 14526 | Bu | 2-I, 4-F |
| 14527 | Bu | 2-I, 4-NO$_2$ |
| 14528 | Bu | 2-I, 4-NH$_2$ |
| 14529 | Bu | 2-I, 4-NHMe |
| 14530 | Bu | 2-I, 4-NMe$_2$ |
| 14531 | Bu | 2-I, 4-NMe$_3$OTf |
| 14532 | Bu | 2-I, 4-NMe$_3$I |
| 14533 | Bu | 2-F, 4-I |
| 14534 | Bu | 2-NO$_2$, 4-I |
| 14535 | Bu | 2-NH$_2$, 4-I |
| 14536 | Bu | 2-NHMe, 4-I |
| 14537 | Bu | 2-NMe$_2$, 4-I |
| 14538 | Bu | 2-NMe$_3$OTf, 4-I |
| 14539 | Bu | 2-NMe$_3$I, 4-I |
| 14540 | Bu | 2-Me, 3-F |
| 14541 | Bu | 2-Me, 3-NO$_2$ |
| 14542 | Bu | 2-Me, 3-NH$_2$ |
| 14543 | Bu | 2-Me, 3-NHMe |
| 14544 | Bu | 2-Me, 3-NMe$_2$ |
| 14545 | Bu | 2-Me, 3-NMe$_3$OTf |
| 14546 | Bu | 2-Me, 3-NMe$_3$I |
| 14547 | Bu | 2-Me, 4-F |
| 14548 | Bu | 2-Me, 4-NO$_2$ |
| 14549 | Bu | 2-Me, 4-NH$_2$ |
| 14550 | Bu | 2-Me, 4-NHMe |
| 14551 | Bu | 2-Me, 4-NMe$_2$ |
| 14552 | Bu | 2-Me, 4-NMe$_3$OTf |
| 14553 | Bu | 2-Me, 4-NMe$_3$I |
| 14554 | Bu | 2-Me, 5-F |
| 14555 | Bu | 2-Me, 5-NO$_2$ |
| 14556 | Bu | 2-Me, 5-NH$_2$ |
| 14557 | Bu | 2-Me, 5-NHMe |
| 14558 | Bu | 2-Me, 5-NMe$_2$ |
| 14559 | Bu | 2-Me, 5-NMe$_3$OTf |
| 14560 | Bu | 2-Me, 5-NMe$_3$I |
| 14561 | Bu | 2-F, 4-Me |
| 14562 | Bu | 2-NO$_2$, 4-Me |
| 14563 | Bu | 2-NH$_2$, 4-Me |
| 14564 | Bu | 2-NHMe, 4-Me |
| 14565 | Bu | 2-NMe$_2$, 4-Me |
| 14566 | Bu | 2-NMe$_3$, 4-Me |
| 14567 | Bu | 2-NMe$_3$OTf, 4-Me |
| 14568 | Bu | 2-NMe$_3$I, 4-Me |
| 14569 | Bu | 2-SnMe$_3$, 4-F |
| 14570 | Bu | 2-SnMe$_3$, 5-F |
| 14571 | Bu | 2-F, 4-SnMe$_3$ |
| 14572 | Bu | 2-Br, 6-Cl, 4-F |
| 14573 | Bu | 2-Br, 6-Cl, 4-NO$_2$ |
| 14574 | Bu | 2-Br, 6-Cl, 4-NH$_2$ |
| 14575 | Bu | 2-Br, 6-Cl, 4-NHMe |
| 14576 | Bu | 2-Br, 6-Cl, 4-NMe$_2$ |
| 14577 | Bu | 2-Br, 6-Cl, 4-NMe$_3$OTf |
| 14578 | Bu | 2-Br, 6-Cl, 4-NMe$_3$I |
| 14579 | Bu | 2-Me, 6-Cl, 4-F |
| 14580 | Bu | 2-SnMe$_3$, 6-Cl, 4-F |
| 14581 | Bu | 2-Cl, 4-Me |
| 14582 | Bu | 2-Cl, 4-Br |

TABLE 10-continued

Substituent list for compounds of general structure XV.

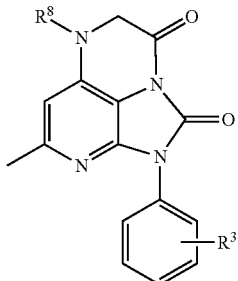

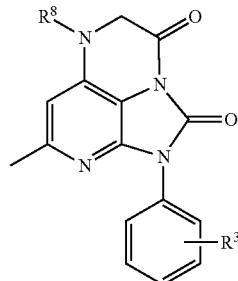

| Compound # | R¹ = | R³ = |
|---|---|---|
| 14583 | Bu | 2-Cl, 4-SnMe₃ |
| 14584 | Bu | 2-Br, 4-Cl |
| 14585 | Bu | 2-SnMe₃, 4-Cl |
| 14586 | Bu | 2-Me, 4-Cl |
| 14587 | Bu | 2-Br, 4-Br |
| 14588 | Bu | 2-Br, 4-Me |
| 14589 | Bu | 2-Br, 4-SnMe₃ |
| 14590 | Bu | 2-SnMe₃, 4-Br |
| 14591 | Bu | 2-Me, 4-Br |
| 14592 | Bu | 2-Me, 4-SnMe₃ |
| 14593 | Bu | 2-SnMe₃, 4-Me |
| 14594 | Bu | 2-Me, 4-Me |
| 14595 | Bu | 2-Et, 4-Br |
| 14596 | Bu | 2-Et, 4-SnMe₃ |
| 14597 | Bu | 2-Et, 4-Me |
| 14598 | Bu | 2-Me, 4-Me, 6-Me |
| 14599 | Bu | 2-Me, 4-Br, 6-Me |
| 14600 | Bu | 2-Me, 4-SnMe₃, 6-Me |
| 14601 | Bu | 2-Et, 6-Me |
| 14602 | Bu | 2-Br, 4-i-Pr |
| 14603 | Bu | 2-SnMe₃, 4-i-Pr |
| 14604 | Bu | 2-Me, 4-i-Pr |
| 14605 | Bu | 2-Br, 4-Br, 6-Br |
| 14606 | Bu | 2-Br, 4-Me, 6-Br |
| 14607 | Bu | 2-Br, 4-SnMe₃, 6-Br |
| 14608 | Bu | 2-SnMe₃, 4-Br, 6-Br |
| 14609 | Bu | 2-Br, 4-Br, 6-Me |
| 14610 | Bu | 2-Br, 4-CF₃, 6-Br |
| 14611 | Bu | 2-Br, 4-Br, 6-CF₃ |
| 14612 | Bu | 2-CF₃, 4-CF₃ |
| 14613 | Bu | 2-Cl, 4-CF₃ |
| 14614 | Bu | 2-CF₃, 4-Cl |
| 14615 | Bu | 2-Br, 4-CF₃ |
| 14616 | Bu | 2-SnMe₃, 4-CF₃ |
| 14617 | Bu | 2-Me, 4-CF₃ |
| 14618 | Bu | 2-CF₃, 4-Br |
| 14619 | Bu | 2-CF₃, 4-SnMe₃ |
| 14620 | Bu | 2-CF₃, 4-Me |
| 14621 | Bu | 2-Br, 4-OH |
| 14622 | Bu | 2-Br, 4-OMe |
| 14623 | Bu | 2-Br, 4-OMeF |
| 14624 | Bu | 2-Br, 4-OCF₃ |
| 14625 | Bu | 2-Br, 4-OEtF |
| 14626 | Bu | 2-Br, 4-OPrF |
| 14627 | Bu | 2-OH, 4-Br |
| 14628 | Bu | 2-OMe, 4-Br |
| 14629 | Bu | 2-OMeF, 4-Br |
| 14630 | Bu | 2-OCF₃, 4-Br |
| 14631 | Bu | 2-OEtF, 4-Br |
| 14632 | Bu | 2-OPrF, 4-Br |
| 14633 | Bu | 2-I, 4-OH |
| 14634 | Bu | 2-I, 4-OMe |
| 14635 | Bu | 2-I, 4-OMeF |
| 14636 | Bu | 2-I, 4-OCF₃ |
| 14637 | Bu | 2-I, 4-OEtF |
| 14638 | Bu | 2-I, 4-OPrF |
| 14639 | Bu | 2-OH, 4-I |
| 14640 | Bu | 2-OMe, 4-I |
| 14641 | Bu | 2-OMeF, 4-I |
| 14642 | Bu | 2-OCF₃, 4-I |
| 14643 | Bu | 2-OEtF, 4-I |
| 14644 | Bu | 2-OPrF, 4-I |
| 14645 | Bu | 2-SnMe₃, 4-OH |
| 14646 | Bu | 2-SnMe₃, 4-OMe |
| 14647 | Bu | 2-SnMe₃, 4-OMeF |
| 14648 | Bu | 2-SnMe₃, 4-OCF₃ |
| 14649 | Bu | 2-SnMe₃, 4-OEtF |
| 14650 | Bu | 2-SnMe₃, 4-OPrF |
| 14651 | Bu | 2-OH, 4-SnMe₃ |
| 14652 | Bu | 2-OMe, 4-SnMe₃ |
| 14653 | Bu | 2-OMeF, 4-SnMe₃ |
| 14654 | Bu | 2-OCF₃, 4-SnMe₃ |
| 14655 | Bu | 2-OEtF, 4-SnMe₃ |
| 14656 | Bu | 2-OPrF, 4-SnMe₃ |
| 14657 | Bu—F | H |
| 14658 | Bu—F | 2-t-Bu |
| 14659 | Bu—F | 2-Br |
| 14660 | Bu—F | 3-Br |
| 14661 | Bu—F | 4-Br |
| 14662 | Bu—F | 2-I |
| 14663 | Bu—F | 3-I |
| 14664 | Bu—F | 4-I |
| 14665 | Bu—F | 2-SnMe₃ |
| 14666 | Bu—F | 3-SnMe₃ |
| 14667 | Bu—F | 4-SnMe₃ |
| 14668 | Bu—F | 2-Me |
| 14669 | Bu—F | 3-Me |
| 14670 | Bu—F | 4-Me |
| 14671 | Bu—F | 2-OH |
| 14672 | Bu—F | 3-OH |
| 14673 | Bu—F | 4-OH |
| 14674 | Bu—F | 2-OMe |
| 14675 | Bu—F | 3-OMe |
| 14676 | Bu—F | 4-OMe |
| 14677 | Bu—F | 2-OMeF |
| 14678 | Bu—F | 3-OMeF |
| 14679 | Bu—F | 4-OMeF |
| 14680 | Bu—F | 2-OCF₃ |
| 14681 | Bu—F | 3-OCF₃ |
| 14682 | Bu—F | 4-OCF₃ |
| 14683 | Bu—F | 2-OEtF |
| 14684 | Bu—F | 3-OEtF |
| 14685 | Bu—F | 4-OEtF |
| 14686 | Bu—F | 2-OPrF |
| 14687 | Bu—F | 3-OPrF |
| 14688 | Bu—F | 4-OPrF |
| 14689 | Bu—F | 2-SH |
| 14690 | Bu—F | 3-SH |
| 14691 | Bu—F | 4-SH |
| 14692 | Bu—F | 2-SMe |
| 14693 | Bu—F | 3-SMe |
| 14694 | Bu—F | 4-SMe |
| 14695 | Bu—F | 2-SMeF |
| 14696 | Bu—F | 3-SMeF |
| 14697 | Bu—F | 4-SMeF |
| 14698 | Bu—F | 2-SCF₃ |
| 14699 | Bu—F | 3-SCF₃ |
| 14700 | Bu—F | 4-SCF₃ |
| 14701 | Bu—F | 2-SEtF |
| 14702 | Bu—F | 3-SEtF |

TABLE 10-continued

Substituent list for compounds of general structure XV.

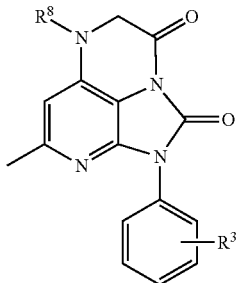

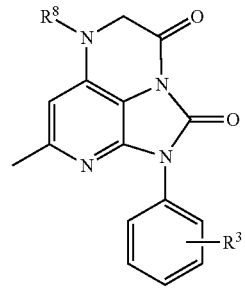

| Compound # | $R^1$ = | $R^3$ = |
|---|---|---|
| 14703 | Bu—F | 4-SEtF |
| 14704 | Bu—F | 2-SPrF |
| 14705 | Bu—F | 3-SPrF |
| 14706 | Bu—F | 4-SPrF |
| 14707 | Bu—F | 2-OMe, 4-OMe |
| 14708 | Bu—F | 2-Me, 5-OH |
| 14709 | Bu—F | 2-Me, 5-OMe |
| 14710 | Bu—F | 2-Me, 5-OMeF |
| 14711 | Bu—F | 2-Me, 5-OEtF |
| 14712 | Bu—F | 2-Me, 5-OPrF |
| 14713 | Bu—F | 2-Me, 4-OH |
| 14714 | Bu—F | 2-Me, 4-OMe |
| 14715 | Bu—F | 2-Me, 4-OMeF |
| 14716 | Bu—F | 2-Me, 4-OCF$_3$ |
| 14717 | Bu—F | 2-Me, 4-OEtF |
| 14718 | Bu—F | 2-Me, 4-OPrF |
| 14719 | Bu—F | 2-OH, 4-Me |
| 14720 | Bu—F | 2-OMe, 4-Me |
| 14721 | Bu—F | 2-OMeF, 4-Me |
| 14722 | Bu—F | 2-OCF$_3$, 4-Me |
| 14723 | Bu—F | 2-OEtF, 4-Me |
| 14724 | Bu—F | 2-OPrF, 4-Me |
| 14725 | Bu—F | 2-Cl, 4-OH |
| 14726 | Bu—F | 2-Cl, 4-OMe |
| 14727 | Bu—F | 2-Cl, 4-OMeF |
| 14728 | Bu—F | 2-Cl, 4-OCF$_3$ |
| 14729 | Bu—F | 2-Cl, 4-OEtF |
| 14730 | Bu—F | 2-Cl, 4-OPrF |
| 14731 | Bu—F | 2-F, 4-F |
| 14732 | Bu—F | 2-Cl, 4-Cl |
| 14733 | Bu—F | 2-Cl, 4-F |
| 14734 | Bu—F | 2-Cl, 4-NO$_2$ |
| 14735 | Bu—F | 2-Cl, 4-NH$_2$ |
| 14736 | Bu—F | 2-Cl, 4-NHMe |
| 14737 | Bu—F | 2-Cl, 4-NMe$_2$ |
| 14738 | Bu—F | 2-Cl, 4-NMe$_3$OTf |
| 14739 | Bu—F | 2-Cl, 4-NMe$_3$I |
| 14740 | Bu—F | 2-Cl, 5-F |
| 14741 | Bu—F | 2-Cl, 5-NO$_2$ |
| 14742 | Bu—F | 2-Cl, 5-NH$_2$ |
| 14743 | Bu—F | 2-Cl, 5-NHMe |
| 14744 | Bu—F | 2-Cl, 5-NMe$_2$ |
| 14745 | Bu—F | 2-Cl, 5-NMe$_3$OTf |
| 14746 | Bu—F | 2-Cl, 5-NMe$_3$I |
| 14747 | Bu—F | 2-F, 4-Cl |
| 14748 | Bu—F | 2-NO$_2$, 4-Cl |
| 14749 | Bu—F | 2-NH$_2$, 4-Cl |
| 14750 | Bu—F | 2-NHMe, 4-Cl |
| 14751 | Bu—F | 2-NMe$_2$, 4-Cl |
| 14752 | Bu—F | 2-NMe$_3$OTf, 4-Cl |
| 14753 | Bu—F | 2-NMe$_3$I, 4-Cl |
| 14754 | Bu—F | 2-F, 5-Cl |
| 14755 | Bu—F | 2-NO$_2$, 5-Cl |
| 14756 | Bu—F | 2-NH$_2$, 5-Cl |
| 14757 | Bu—F | 2-NHMe, 5-Cl |
| 14758 | Bu—F | 2-NMe$_2$, 5-Cl |
| 14759 | Bu—F | 2-NMe$_3$OTf, 5-Cl |
| 14760 | Bu—F | 2-NMe$_3$I, 5-Cl |
| 14761 | Bu—F | 2-Br, 4-F |
| 14762 | Bu—F | 2-Br, 4-NO$_2$ |
| 14763 | Bu—F | 2-Br, 4-NH$_2$ |
| 14764 | Bu—F | 2-Br, 4-NHMe |
| 14765 | Bu—F | 2-Br, 4-NMe$_2$ |
| 14766 | Bu—F | 2-Br, 4-NMe$_3$OTf |
| 14767 | Bu—F | 2-Br, 4-NMe$_3$I |
| 14768 | Bu—F | 2-Br, 5-F |
| 14769 | Bu—F | 2-Br, 5-NO$_2$ |
| 14770 | Bu—F | 2-Br, 5-NH$_2$ |
| 14771 | Bu—F | 2-Br, 5-NHMe |
| 14772 | Bu—F | 2-Br, 5-NMe$_2$ |
| 14773 | Bu—F | 2-Br, 5-NMe$_3$OTf |
| 14774 | Bu—F | 2-Br, 5-NMe$_3$I |
| 14775 | Bu—F | 2-F, 4-Br |
| 14776 | Bu—F | 2-NO$_2$, 4-Br |
| 14777 | Bu—F | 2-NH$_2$, 4-Br |
| 14778 | Bu—F | 2-NHMe, 4-Br |
| 14779 | Bu—F | 2-NMe$_2$, 4-Br |
| 14780 | Bu—F | 2-NMe$_3$OTf, 4-Br |
| 14781 | Bu—F | 2-NMe$_3$I, 4-Br |
| 14782 | Bu—F | 2-I, 4-F |
| 14783 | Bu—F | 2-I, 4-NO$_2$ |
| 14784 | Bu—F | 2-I, 4-NH$_2$ |
| 14785 | Bu—F | 2-I, 4-NHMe |
| 14786 | Bu—F | 2-I, 4-NMe$_2$ |
| 14787 | Bu—F | 2-I, 4-NMe$_3$OTf |
| 14788 | Bu—F | 2-I, 4-NMe$_3$I |
| 14789 | Bu—F | 2-F, 4-I |
| 14790 | Bu—F | 2-NO$_2$, 4-I |
| 14791 | Bu—F | 2-NH$_2$, 4-I |
| 14792 | Bu—F | 2-NHMe, 4-I |
| 14793 | Bu—F | 2-NMe$_2$, 4-I |
| 14794 | Bu—F | 2-NMe$_3$OTf, 4-I |
| 14795 | Bu—F | 2-NMe$_3$I, 4-I |
| 14796 | Bu—F | 2-Me, 3-F |
| 14797 | Bu—F | 2-Me, 3-NO$_2$ |
| 14798 | Bu—F | 2-Me, 3-NH$_2$ |
| 14799 | Bu—F | 2-Me, 3-NHMe |
| 14800 | Bu—F | 2-Me, 3-NMe$_2$ |
| 14801 | Bu—F | 2-Me, 3-NMe$_3$OTf |
| 14802 | Bu—F | 2-Me, 3-NMe$_3$I |
| 14803 | Bu—F | 2-Me, 4-F |
| 14804 | Bu—F | 2-Me, 4-NO$_2$ |
| 14805 | Bu—F | 2-Me, 4-NH$_2$ |
| 14806 | Bu—F | 2-Me, 4-NHMe |
| 14807 | Bu—F | 2-Me, 4-NMe$_2$ |
| 14808 | Bu—F | 2-Me, 4-NMe$_3$OTf |
| 14809 | Bu—F | 2-Me, 4-NMe$_3$I |
| 14810 | Bu—F | 2-Me, 5-F |
| 14811 | Bu—F | 2-Me, 5-NO$_2$ |
| 14812 | Bu—F | 2-Me, 5-NH$_2$ |
| 14813 | Bu—F | 2-Me, 5-NHMe |
| 14814 | Bu—F | 2-Me, 5-NMe$_2$ |
| 14815 | Bu—F | 2-Me, 5-NMe$_3$OTf |
| 14816 | Bu—F | 2-Me, 5-NMe$_3$I |
| 14817 | Bu—F | 2-F, 4-Me |
| 14818 | Bu—F | 2-NO$_2$, 4-Me |
| 14819 | Bu—F | 2-NH$_2$, 4-Me |
| 14820 | Bu—F | 2-NHMe, 4-Me |
| 14821 | Bu—F | 2-NMe$_2$, 4-Me |
| 14822 | Bu—F | 2-NMe$_3$, 4-Me |

TABLE 10-continued

Substituent list for compounds of general structure XV.

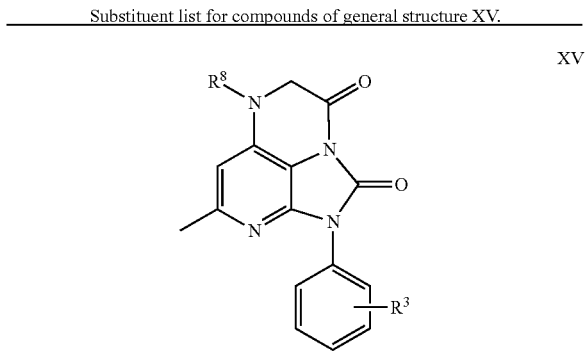

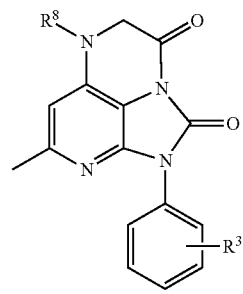

| Compound # | R¹ = | R³ = |
|---|---|---|
| 14823 | Bu—F | 2-NMe₃OTf, 4-Me |
| 14824 | Bu—F | 2-NMe₃I, 4-Me |
| 14825 | Bu—F | 2-SnMe₃, 4-F |
| 14826 | Bu—F | 2-SnMe₃, 5-F |
| 14827 | Bu—F | 2-F, 4-SnMe₃ |
| 14828 | Bu—F | 2-Br, 6-Cl, 4-F |
| 14829 | Bu—F | 2-Br, 6-Cl, 4-NO₂ |
| 14830 | Bu—F | 2-Br, 6-Cl, 4-NH₂ |
| 14831 | Bu—F | 2-Br, 6-Cl, 4-NHMe |
| 14832 | Bu—F | 2-Br, 6-Cl, 4-NMe₂ |
| 14833 | Bu—F | 2-Br, 6-Cl, 4-NMe₃OTf |
| 14834 | Bu—F | 2-Br, 6-Cl, 4-NMe₃I |
| 14835 | Bu—F | 2-Me, 6-Cl, 4-F |
| 14836 | Bu—F | 2-SnMe₃, 6-Cl, 4-F |
| 14837 | Bu—F | 2-Cl, 4-Me |
| 14838 | Bu—F | 2-Cl, 4-Br |
| 14839 | Bu—F | 2-Cl, 4-SnMe₃ |
| 14840 | Bu—F | 2-Br, 4-Cl |
| 14841 | Bu—F | 2-SnMe₃, 4-Cl |
| 14842 | Bu—F | 2-Me, 4-Cl |
| 14843 | Bu—F | 2-Br, 4-Br |
| 14844 | Bu—F | 2-Br, 4-Me |
| 14845 | Bu—F | 2-Br, 4-SnMe₃ |
| 14846 | Bu—F | 2-SnMe₃, 4-Br |
| 14847 | Bu—F | 2-Me, 4-Br |
| 14848 | Bu—F | 2-Me, 4-SnMe₃ |
| 14849 | Bu—F | 2-SnMe₃, 4-Me |
| 14850 | Bu—F | 2-Me, 4-Me |
| 14851 | Bu—F | 2-Et, 4-Br |
| 14852 | Bu—F | 2-Et, 4-SnMe₃ |
| 14853 | Bu—F | 2-Et, 4-Me |
| 14854 | Bu—F | 2-Me, 4-Me, 6-Me |
| 14855 | Bu—F | 2-Me, 4-Br, 6-Me |
| 14856 | Bu—F | 2-Me, 4-SnMe₃, 6-Me |
| 14857 | Bu—F | 2-Et, 6-Me |
| 14858 | Bu—F | 2-Br, 4-i-Pr |
| 14859 | Bu—F | 2-SnMe₃, 4-i-Pr |
| 14860 | Bu—F | 2-Me, 4-i-Pr |
| 14861 | Bu—F | 2-Br, 4-Br, 6-Br |
| 14862 | Bu—F | 2-Br, 4-Me, 6-Br |
| 14863 | Bu—F | 2-Br, 4-SnMe₃, 6-Br |
| 14864 | Bu—F | 2-SnMe₃, 4-Br, 6-Br |
| 14865 | Bu—F | 2-Br, 4-Br, 6-Me |
| 14866 | Bu—F | 2-Br, 4-CF₃, 6-Br |
| 14867 | Bu—F | 2-Br, 4-Br, 6-CF₃ |
| 14868 | Bu—F | 2-CF₃, 4-CF₃ |
| 14869 | Bu—F | 2-Cl, 4-CF₃ |
| 14870 | Bu—F | 2-CF₃, 4-Cl |
| 14871 | Bu—F | 2-Br, 4-CF₃ |
| 14872 | Bu—F | 2-SnMe₃, 4-CF₃ |
| 14873 | Bu—F | 2-Me, 4-CF₃ |
| 14874 | Bu—F | 2-CF₃, 4-Br |
| 14875 | Bu—F | 2-CF₃, 4-SnMe₃ |
| 14876 | Bu—F | 2-CF₃, 4-Me |
| 14877 | Bu—F | 2-Br, 4-OH |
| 14878 | Bu—F | 2-Br, 4-OMe |
| 14879 | Bu—F | 2-Br, 4-OMeF |
| 14880 | Bu—F | 2-Br, 4-OCF₃ |
| 14881 | Bu—F | 2-Br, 4-OEtF |
| 14882 | Bu—F | 2-Br, 4-OPrF |
| 14883 | Bu—F | 2-OH, 4-Br |
| 14884 | Bu—F | 2-OMe, 4-Br |
| 14885 | Bu—F | 2-OMeF, 4-Br |
| 14886 | Bu—F | 2-OCF₃, 4-Br |
| 14887 | Bu—F | 2-OEtF, 4-Br |
| 14888 | Bu—F | 2-OPrF, 4-Br |
| 14889 | Bu—F | 2-I, 4-OH |
| 14890 | Bu—F | 2-I, 4-OMe |
| 14891 | Bu—F | 2-I, 4-OMeF |
| 14892 | Bu—F | 2-I, 4-OCF₃ |
| 14893 | Bu—F | 2-I, 4-OEtF |
| 14894 | Bu—F | 2-I, 4-OPrF |
| 14895 | Bu—F | 2-OH, 4-I |
| 14896 | Bu—F | 2-OMe, 4-I |
| 14897 | Bu—F | 2-OMeF, 4-I |
| 14898 | Bu—F | 2-OCF₃, 4-I |
| 14899 | Bu—F | 2-OEtF, 4-I |
| 14900 | Bu—F | 2-OPrF, 4-I |
| 14901 | Bu—F | 2-SnMe₃, 4-OH |
| 14902 | Bu—F | 2-SnMe₃, 4-OMe |
| 14903 | Bu—F | 2-SnMe₃, 4-OMeF |
| 14904 | Bu—F | 2-SnMe₃, 4-OCF₃ |
| 14905 | Bu—F | 2-SnMe₃, 4-OEtF |
| 14906 | Bu—F | 2-SnMe₃, 4-OPrF |
| 14907 | Bu—F | 2-OH, 4-SnMe₃ |
| 14908 | Bu—F | 2-OMe, 4-SnMe₃ |
| 14909 | Bu—F | 2-OMeF, 4-SnMe₃ |
| 14910 | Bu—F | 2-OCF₃, 4-SnMe₃ |
| 14911 | Bu—F | 2-OEtF, 4-SnMe₃ |
| 14912 | Bu—F | 2-OPrF, 4-SnMe₃ |
| 14913 | Pr | H |
| 14914 | Pr | 2-t-Bu |
| 14915 | Pr | 2-Br |
| 14916 | Pr | 3-Br |
| 14917 | Pr | 4-Br |
| 14918 | Pr | 2-I |
| 14919 | Pr | 3-I |
| 14920 | Pr | 4-I |
| 14921 | Pr | 2-SnMe₃ |
| 14922 | Pr | 3-SnMe₃ |
| 14923 | Pr | 4-SnMe₃ |
| 14924 | Pr | 2-Me |
| 14925 | Pr | 3-Me |
| 14926 | Pr | 4-Me |
| 14927 | Pr | 2-OH |
| 14928 | Pr | 3-OH |
| 14929 | Pr | 4-OH |
| 14930 | Pr | 2-OMe |
| 14931 | Pr | 3-OMe |
| 14932 | Pr | 4-OMe |
| 14933 | Pr | 2-OMeF |
| 14934 | Pr | 3-OMeF |
| 14935 | Pr | 4-OMeF |
| 14936 | Pr | 2-OCF₃ |
| 14937 | Pr | 3-OCF₃ |
| 14938 | Pr | 4-OCF₃ |
| 14939 | Pr | 2-OEtF |
| 14940 | Pr | 3-OEtF |
| 14941 | Pr | 4-OEtF |
| 14942 | Pr | 2-OPrF |

TABLE 10-continued

Substituent list for compounds of general structure XV.

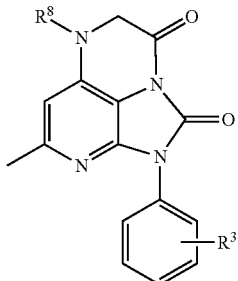

XV

| Compound # | R¹ = | R³ = |
|---|---|---|
| 14943 | Pr | 3-OPrF |
| 14944 | Pr | 4-OPrF |
| 14945 | Pr | 2-SH |
| 14946 | Pr | 3-SH |
| 14947 | Pr | 4-SH |
| 14948 | Pr | 2-SMe |
| 14949 | Pr | 3-SMe |
| 14950 | Pr | 4-SMe |
| 14951 | Pr | 2-SMeF |
| 14952 | Pr | 3-SMeF |
| 14953 | Pr | 4-SMeF |
| 14954 | Pr | 2-SCF₃ |
| 14955 | Pr | 3-SCF₃ |
| 14956 | Pr | 4-SCF₃ |
| 14957 | Pr | 2-SEtF |
| 14958 | Pr | 3-SEtF |
| 14959 | Pr | 4-SEtF |
| 14960 | Pr | 2-SPrF |
| 14961 | Pr | 3-SPrF |
| 14962 | Pr | 4-SPrF |
| 14963 | Pr | 2-OMe, 4-OMe |
| 14964 | Pr | 2-Me, 5-OH |
| 14965 | Pr | 2-Me, 5-OMe |
| 14966 | Pr | 2-Me, 5-OMeF |
| 14967 | Pr | 2-Me, 5-OEtF |
| 14968 | Pr | 2-Me, 5-OPrF |
| 14969 | Pr | 2-Me, 4-OH |
| 14970 | Pr | 2-Me, 4-OMe |
| 14971 | Pr | 2-Me, 4-OMeF |
| 14972 | Pr | 2-Me, 4-OCF₃ |
| 14973 | Pr | 2-Me, 4-OEtF |
| 14974 | Pr | 2-Me, 4-OPrF |
| 14975 | Pr | 2-OH, 4-Me |
| 14976 | Pr | 2-OMe, 4-Me |
| 14977 | Pr | 2-OMeF, 4-Me |
| 14978 | Pr | 2-OCF₃, 4-Me |
| 14979 | Pr | 2-OEtF, 4-Me |
| 14980 | Pr | 2-OPrF, 4-Me |
| 14981 | Pr | 2-Cl, 4-OH |
| 14982 | Pr | 2-Cl, 4-OMe |
| 14983 | Pr | 2-Cl, 4-OMeF |
| 14984 | Pr | 2-Cl, 4-OCF₃ |
| 14985 | Pr | 2-Cl, 4-OEtF |
| 14986 | Pr | 2-Cl, 4-OPrF |
| 14987 | Pr | 2-F, 4-F |
| 14988 | Pr | 2-Cl, 4-Cl |
| 14989 | Pr | 2-Cl, 4-F |
| 14990 | Pr | 2-Cl, 4-NO₂ |
| 14991 | Pr | 2-Cl, 4-NH₂ |
| 14992 | Pr | 2-Cl, 4-NHMe |
| 14993 | Pr | 2-Cl, 4-NMe₂ |
| 14994 | Pr | 2-Cl, 4-NMe₃OTf |
| 14995 | Pr | 2-Cl, 4-NMe₃I |
| 14996 | Pr | 2-Cl, 5-F |
| 14997 | Pr | 2-Cl, 5-NO₂ |
| 14998 | Pr | 2-Cl, 5-NH₂ |
| 14999 | Pr | 2-Cl, 5-NHMe |
| 15000 | Pr | 2-Cl, 5-NMe₂ |
| 15001 | Pr | 2-Cl, 5-NMe₃OTf |
| 15002 | Pr | 2-Cl, 5-NMe₃I |

TABLE 10-continued

Substituent list for compounds of general structure XV.

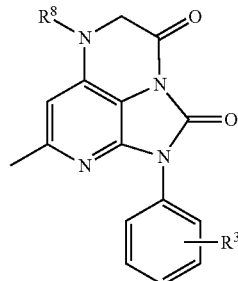

XV

| Compound # | R¹ = | R³ = |
|---|---|---|
| 15003 | Pr | 2-F, 4-Cl |
| 15004 | Pr | 2-NO₂, 4-Cl |
| 15005 | Pr | 2-NH₂, 4-Cl |
| 15006 | Pr | 2-NHMe, 4-Cl |
| 15007 | Pr | 2-NMe₂, 4-Cl |
| 15008 | Pr | 2-NMe₃OTf, 4-Cl |
| 15009 | Pr | 2-NMe₃I, 4-Cl |
| 15010 | Pr | 2-F, 5-Cl |
| 15011 | Pr | 2-NO₂, 5-Cl |
| 15012 | Pr | 2-NH₂, 5-Cl |
| 15013 | Pr | 2-NHMe, 5-Cl |
| 15014 | Pr | 2-NMe₂, 5-Cl |
| 15015 | Pr | 2-NMe₃OTf, 5-Cl |
| 15016 | Pr | 2-NMe₃I, 5-Cl |
| 15017 | Pr | 2-Br, 4-F |
| 15018 | Pr | 2-Br, 4-NO₂ |
| 15019 | Pr | 2-Br, 4-NH₂ |
| 15020 | Pr | 2-Br, 4-NHMe |
| 15021 | Pr | 2-Br, 4-NMe₂ |
| 15022 | Pr | 2-Br, 4-NMe₃OTf |
| 15023 | Pr | 2-Br, 4-NMe₃I |
| 15024 | Pr | 2-Br, 5-F |
| 15025 | Pr | 2-Br, 5-NO₂ |
| 15026 | Pr | 2-Br, 5-NH₂ |
| 15027 | Pr | 2-Br, 5-NHMe |
| 15028 | Pr | 2-Br, 5-NMe₂ |
| 15029 | Pr | 2-Br, 5-NMe₃OTf |
| 15030 | Pr | 2-Br, 5-NMe₃I |
| 15031 | Pr | 2-F, 4-Br |
| 15032 | Pr | 2-NO₂, 4-Br |
| 15033 | Pr | 2-NH₂, 4-Br |
| 15034 | Pr | 2-NHMe, 4-Br |
| 15035 | Pr | 2-NMe₂, 4-Br |
| 15036 | Pr | 2-NMe₃OTf, 4-Br |
| 15037 | Pr | 2-NMe₃I, 4-Br |
| 15038 | Pr | 2-I, 4-F |
| 15039 | Pr | 2-I, 4-NO₂ |
| 15040 | Pr | 2-I, 4-NH₂ |
| 15041 | Pr | 2-I, 4-NHMe |
| 15042 | Pr | 2-I, 4-NMe, |
| 15043 | Pr | 2-I, 4-NMe₃OTf |
| 15044 | Pr | 2-I, 4-NMe₃I |
| 15045 | Pr | 2-F, 4-I |
| 15046 | Pr | 2-NO₂, 4-I |
| 15047 | Pr | 2-NH₂, 4-I |
| 15048 | Pr | 2-NHMe, 4-I |
| 15049 | Pr | 2-NMe₂, 4-I |
| 15050 | Pr | 2-NMe₃OTf, 4-I |
| 15051 | Pr | 2-NMe₃I, 4-I |
| 15052 | Pr | 2-Me, 3-F |
| 15053 | Pr | 2-Me, 3-NO₂ |
| 15054 | Pr | 2-Me, 3-NH₂ |
| 15055 | Pr | 2-Me, 3-NHMe |
| 15056 | Pr | 2-Me, 3-NMe₂ |
| 15057 | Pr | 2-Me, 3-NMe₃OTf |
| 15058 | Pr | 2-Me, 3-NMe₃I |
| 15059 | Pr | 2-Me, 4-F |
| 15060 | Pr | 2-Me, 4-NO₂ |
| 15061 | Pr | 2-Me, 4-NH₂ |
| 15062 | Pr | 2-Me, 4-NHMe |

TABLE 10-continued

Substituent list for compounds of general structure XV.

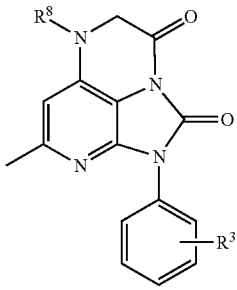

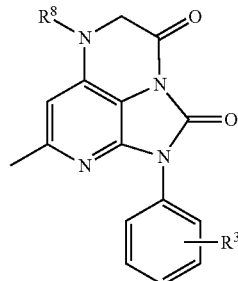

| Compound # | R¹ = | R³ = |
|---|---|---|
| 15063 | Pr | 2-Me, 4-NMe$_2$ |
| 15064 | Pr | 2-Me, 4-NMe$_3$OTf |
| 15065 | Pr | 2-Me, 4-NMe$_3$I |
| 15066 | Pr | 2-Me, 5-F |
| 15067 | Pr | 2-Me, 5-NO$_2$ |
| 15068 | Pr | 2-Me, 5-NH$_2$ |
| 15069 | Pr | 2-Me, 5-NHMe |
| 15070 | Pr | 2-Me, 5-NMe$_2$ |
| 15071 | Pr | 2-Me, 5-NMe$_3$OTf |
| 15072 | Pr | 2-Me, 5-NMe$_3$I |
| 15073 | Pr | 2-F, 4-Me |
| 15074 | Pr | 2-NO$_2$, 4-Me |
| 15075 | Pr | 2-NH$_2$, 4-Me |
| 15076 | Pr | 2-NHMe, 4-Me |
| 15077 | Pr | 2-NMe$_2$, 4-Me |
| 15078 | Pr | 2-NMe$_3$, 4-Me |
| 15079 | Pr | 2-NMe$_3$OTf, 4-Me |
| 15080 | Pr | 2-NMe$_3$I, 4-Me |
| 15081 | Pr | 2-SnMe$_3$, 4-F |
| 15082 | Pr | 2-SnMe$_3$, 5-F |
| 15083 | Pr | 2-F, 4-SnMe$_3$ |
| 15084 | Pr | 2-Br, 6-Cl, 4-F |
| 15085 | Pr | 2-Br, 6-Cl, 4-NO$_2$ |
| 15086 | Pr | 2-Br, 6-Cl, 4-NH$_2$ |
| 15087 | Pr | 2-Br, 6-Cl, 4-NHMe |
| 15088 | Pr | 2-Br, 6-Cl, 4-NMe$_2$ |
| 15089 | Pr | 2-Br, 6-Cl, 4-NMe$_3$OTf |
| 15090 | Pr | 2-Br, 6-Cl, 4-NMe$_3$I |
| 15091 | Pr | 2-Me, 6-Cl, 4-F |
| 15092 | Pr | 2-SnMe$_3$, 6-Cl, 4-F |
| 15093 | Pr | 2-Cl, 4-Me |
| 15094 | Pr | 2-Cl, 4-Br |
| 15095 | Pr | 2-Cl, 4-SnMe$_3$ |
| 15096 | Pr | 2-Br, 4-Cl |
| 15097 | Pr | 2-SnMe$_3$, 4-Cl |
| 15098 | Pr | 2-Me, 4-Cl |
| 15099 | Pr | 2-Br, 4-Br |
| 15100 | Pr | 2-Br, 4-Me |
| 15101 | Pr | 2-Br, 4-SnMe$_3$ |
| 15102 | Pr | 2-SnMe$_3$, 4-Br |
| 15103 | Pr | 2-Me, 4-Br |
| 15104 | Pr | 2-Me, 4-SnMe$_3$ |
| 15105 | Pr | 2-SnMe$_3$, 4-Me |
| 15106 | Pr | 2-Me, 4-Me |
| 15107 | Pr | 2-Et, 4-Br |
| 15108 | Pr | 2-Et, 4-SnMe$_3$ |
| 15109 | Pr | 2-Et, 4-Me |
| 15110 | Pr | 2-Me, 4-Me, 6-Me |
| 15111 | Pr | 2-Me, 4-Br, 6-Me |
| 15112 | Pr | 2-Me, 4-SnMe$_3$, 6-Me |
| 15113 | Pr | 2-Et, 6-Me |
| 15114 | Pr | 2-Br, 4-i-Pr |
| 15115 | Pr | 2-SnMe$_3$, 4-i-Pr |
| 15116 | Pr | 2-Me, 4-i-Pr |
| 15117 | Pr | 2-Br, 4-Br, 6-Br |
| 15118 | Pr | 2-Br, 4-Me, 6-Br |
| 15119 | Pr | 2-Br, 4-SnMe$_3$, 6-Br |
| 15120 | Pr | 2-SnMe$_3$, 4-Br, 6-Br |
| 15121 | Pr | 2-Br, 4-Br, 6-Me |
| 15122 | Pr | 2-Br, 4-CF$_3$, 6-Br |
| 15123 | Pr | 2-Br, 4-Br, 6-CF$_3$ |
| 15124 | Pr | 2-CF$_3$, 4-CF$_3$ |
| 15125 | Pr | 2-Cl, 4-CF$_3$ |
| 15126 | Pr | 2-CF$_3$, 4-Cl |
| 15127 | Pr | 2-Br, 4-CF$_3$ |
| 15128 | Pr | 2-SnMe$_3$, 4-CF$_3$ |
| 15129 | Pr | 2-Me, 4-CF$_3$ |
| 15130 | Pr | 2-CF$_3$, 4-Br |
| 15131 | Pr | 2-CF$_3$, 4-SnMe$_3$ |
| 15132 | Pr | 2-CF$_3$, 4-Me |
| 15133 | Pr | 2-Br, 4-OH |
| 15134 | Pr | 2-Br, 4-OMe |
| 15135 | Pr | 2-Br, 4-OMeF |
| 15136 | Pr | 2-Br, 4-OCF$_3$ |
| 15137 | Pr | 2-Br, 4-OEtF |
| 15138 | Pr | 2-Br, 4-OPrF |
| 15139 | Pr | 2-OH, 4-Br |
| 15140 | Pr | 2-OMe, 4-Br |
| 15141 | Pr | 2-OMeF, 4-Br |
| 15142 | Pr | 2-OCF$_3$, 4-Br |
| 15143 | Pr | 2-OEtF, 4-Br |
| 15144 | Pr | 2-OPrF, 4-Br |
| 15145 | Pr | 2-I, 4-OH |
| 15146 | Pr | 2-I, 4-OMe |
| 15147 | Pr | 2-I, 4-OMeF |
| 15148 | Pr | 2-I, 4-OCF$_3$ |
| 15149 | Pr | 2-I, 4-OEtF |
| 15150 | Pr | 2-I, 4-OPrF |
| 15151 | Pr | 2-OH, 4-I |
| 15152 | Pr | 2-OMe, 4-I |
| 15153 | Pr | 2-OMeF, 4-I |
| 15154 | Pr | 2-OCF$_3$, 4-I |
| 15155 | Pr | 2-OEtF, 4-I |
| 15156 | Pr | 2-OPrF, 4-I |
| 15157 | Pr | 2-SnMe$_3$, 4-OH |
| 15158 | Pr | 2-SnMe$_3$, 4-OMe |
| 15159 | Pr | 2-SnMe$_3$, 4-OMeF |
| 15160 | Pr | 2-SnMe$_3$, 4-OCF$_3$ |
| 15161 | Pr | 2-SnMe$_3$, 4-OEtF |
| 15162 | Pr | 2-SnMe$_3$, 4-OPrF |
| 15163 | Pr | 2-OH, 4-SnMe$_3$ |
| 15164 | Pr | 2-OMe, 4-SnMe$_3$ |
| 15165 | Pr | 2-OMeF, 4-SnMe$_3$ |
| 15166 | Pr | 2-OCF$_3$, 4-SnMe$_3$ |
| 15167 | Pr | 2-OEtF, 4-SnMe$_3$ |
| 15168 | Pr | 2-OPrF, 4-SnMe$_3$ |
| 15169 | Pr—F | H |
| 15170 | Pr—F | 2-t-Bu |
| 15171 | Pr—F | 2-Br |
| 15172 | Pr—F | 3-Br |
| 15173 | Pr—F | 4-Br |
| 15174 | Pr—F | 2-I |
| 15175 | Pr—F | 3-I |
| 15176 | Pr—F | 4-I |
| 15177 | Pr—F | 2-SnMe$_3$ |
| 15178 | Pr—F | 3-SnMe$_3$ |
| 15179 | Pr—F | 4-SnMe$_3$ |
| 15180 | Pr—F | 2-Me |
| 15181 | Pr—F | 3-Me |
| 15182 | Pr—F | 4-Me |

TABLE 10-continued

Substituent list for compounds of general structure XV.

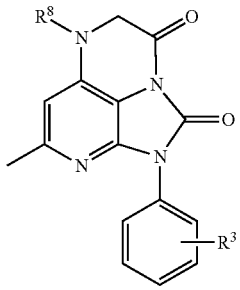

XV

| Compound # | R¹ = | R³ = |
|---|---|---|
| 15183 | Pr—F | 2-OH |
| 15184 | Pr—F | 3-OH |
| 15185 | Pr—F | 4-OH |
| 15186 | Pr—F | 2-OMe |
| 15187 | Pr—F | 3-OMe |
| 15188 | Pr—F | 4-OMe |
| 15189 | Pr—F | 2-OMeF |
| 15190 | Pr—F | 3-OMeF |
| 15191 | Pr—F | 4-OMeF |
| 15192 | Pr—F | 2-OCF₃ |
| 15193 | Pr—F | 3-OCF₃ |
| 15194 | Pr—F | 4-OCF₃ |
| 15195 | Pr—F | 2-OEtF |
| 15196 | Pr—F | 3-OEtF |
| 15197 | Pr—F | 4-OEtF |
| 15198 | Pr—F | 2-OPrF |
| 15199 | Pr—F | 3-OPrF |
| 15200 | Pr—F | 4-OPrF |
| 15201 | Pr—F | 2-SH |
| 15202 | Pr—F | 3-SH |
| 15203 | Pr—F | 4-SH |
| 15204 | Pr—F | 2-SMe |
| 15205 | Pr—F | 3-SMe |
| 15206 | Pr—F | 4-SMe |
| 15207 | Pr—F | 2-SMeF |
| 15208 | Pr—F | 3-SMeF |
| 15209 | Pr—F | 4-SMeF |
| 15210 | Pr—F | 2-SCF₃ |
| 15211 | Pr—F | 3-SCF₃ |
| 15212 | Pr—F | 4-SCF₃ |
| 15213 | Pr—F | 2-SEtF |
| 15214 | Pr—F | 3-SEtF |
| 15215 | Pr—F | 4-SEtF |
| 15216 | Pr—F | 2-SPrF |
| 15217 | Pr—F | 3-SPrF |
| 15218 | Pr—F | 4-SPrF |
| 15219 | Pr—F | 2-OMe, 4-OMe |
| 15220 | Pr—F | 2-Me, 5-OH |
| 15221 | Pr—F | 2-Me, 5-OMe |
| 15222 | Pr—F | 2-Me, 5-OMeF |
| 15223 | Pr—F | 2-Me, 5-OEtF |
| 15224 | Pr—F | 2-Me, 5-OPrF |
| 15225 | Pr—F | 2-Me, 4-OH |
| 15226 | Pr—F | 2-Me, 4-OMe |
| 15227 | Pr—F | 2-Me, 4-OMeF |
| 15228 | Pr—F | 2-Me, 4-OCF₃ |
| 15229 | Pr—F | 2-Me, 4-OEtF |
| 15230 | Pr—F | 2-Me, 4-OPrF |
| 15231 | Pr—F | 2-OH, 4-Me |
| 15232 | Pr—F | 2-OMe, 4-Me |
| 15233 | Pr—F | 2-OMeF, 4-Me |
| 15234 | Pr—F | 2-OCF₃, 4-Me |
| 15235 | Pr—F | 2-OEtF, 4-Me |
| 15236 | Pr—F | 2-OPrF, 4-Me |
| 15237 | Pr—F | 2-Cl, 4-OH |
| 15238 | Pr—F | 2-Cl, 4-OMe |
| 15239 | Pr—F | 2-Cl, 4-OMeF |
| 15240 | Pr—F | 2-Cl, 4-OCF₃ |
| 15241 | Pr—F | 2-Cl, 4-OEtF |
| 15242 | Pr—F | 2-Cl, 4-OPrF |

TABLE 10-continued

Substituent list for compounds of general structure XV.

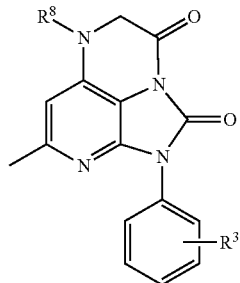

XV

| Compound # | R¹ = | R³ = |
|---|---|---|
| 15243 | Pr—F | 2-F, 4-F |
| 15244 | Pr—F | 2-Cl, 4-Cl |
| 15245 | Pr—F | 2-Cl, 4-F |
| 15246 | Pr—F | 2-Cl, 4-NO₂ |
| 15247 | Pr—F | 2-Cl, 4-NH₂ |
| 15248 | Pr—F | 2-Cl, 4-NHMe |
| 15249 | Pr—F | 2-Cl, 4-NMe₂ |
| 15250 | Pr—F | 2-Cl, 4-NMe₃OTf |
| 15251 | Pr—F | 2-Cl, 4-NMe₃I |
| 15252 | Pr—F | 2-Cl, 5-F |
| 15253 | Pr—F | 2-Cl, 5-NO₂ |
| 15254 | Pr—F | 2-Cl, 5-NH₂ |
| 15255 | Pr—F | 2-Cl, 5-NHMe |
| 15256 | Pr—F | 2-Cl, 5-NMe₂ |
| 15257 | Pr—F | 2-Cl, 5-NMe₃OTf |
| 15258 | Pr—F | 2-Cl, 5-NMe₃I |
| 15259 | Pr—F | 2-F, 4-Cl |
| 15260 | Pr—F | 2-NO₂, 4-Cl |
| 15261 | Pr—F | 2-NH₂, 4-Cl |
| 15262 | Pr—F | 2-NHMe, 4-Cl |
| 15263 | Pr—F | 2-NMe₂, 4-Cl |
| 15264 | Pr—F | 2-NMe₃OTf, 4-Cl |
| 15265 | Pr—F | 2-NMe₃I, 4-Cl |
| 15266 | Pr—F | 2-F, 5-Cl |
| 15267 | Pr—F | 2-NO₂, 5-Cl |
| 15268 | Pr—F | 2-NH₂, 5-Cl |
| 15269 | Pr—F | 2-NHMe, 5-Cl |
| 15270 | Pr—F | 2-NMe₂, 5-Cl |
| 15271 | Pr—F | 2-NMe₃OTf, 5-Cl |
| 15272 | Pr—F | 2-NMe₃I, 5-Cl |
| 15273 | Pr—F | 2-Br, 4-F |
| 15274 | Pr—F | 2-Br, 4-NO₂ |
| 15275 | Pr—F | 2-Br, 4-NH₂ |
| 15276 | Pr—F | 2-Br, 4-NHMe |
| 15277 | Pr—F | 2-Br, 4-NMe₂ |
| 15278 | Pr—F | 2-Br, 4-NMe₃OTf |
| 15279 | Pr—F | 2-Br, 4-NMe₃I |
| 15280 | Pr—F | 2-Br, 5-F |
| 15281 | Pr—F | 2-Br, 5-NO₂ |
| 15282 | Pr—F | 2-Br, 5-NH₂ |
| 15283 | Pr—F | 2-Br, 5-NHMe |
| 15284 | Pr—F | 2-Br, 5-NMe₂ |
| 15285 | Pr—F | 2-Br, 5-NMe₃OTf |
| 15286 | Pr—F | 2-Br, 5-NMe₃I |
| 15287 | Pr—F | 2-F, 4-Br |
| 15288 | Pr—F | 2-NO₂, 4-Br |
| 15289 | Pr—F | 2-NH₂, 4-Br |
| 15290 | Pr—F | 2-NHMe, 4-Br |
| 15291 | Pr—F | 2-NMe₂, 4-Br |
| 15292 | Pr—F | 2-NMe₃OTf, 4-Br |
| 15293 | Pr—F | 2-NMe₃I, 4-Br |
| 15294 | Pr—F | 2-I, 4-F |
| 15295 | Pr—F | 2-I, 4-NO₂ |
| 15296 | Pr—F | 2-I, 4-NH₂ |
| 15297 | Pr—F | 2-I, 4-NHMe |
| 15298 | Pr—F | 2-I, 4-NMe₂ |
| 15299 | Pr—F | 2-I, 4-NMe₃OTf |
| 15300 | Pr—F | 2-I, 4-NMe₃I |
| 15301 | Pr—F | 2-F, 4-I |
| 15302 | Pr—F | 2-NO₂, 4-I |

TABLE 10-continued

Substituent list for compounds of general structure XV.

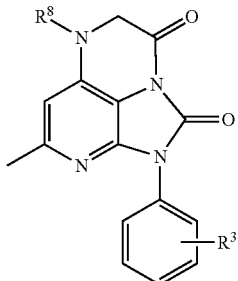

| Compound # | R$^1$ = | R$^3$ = |
|---|---|---|
| 15303 | Pr—F | 2-NH$_2$, 4-I |
| 15304 | Pr—F | 2-NHMe, 4-I |
| 15305 | Pr—F | 2-NMe$_2$, 4-I |
| 15306 | Pr—F | 2-NMe$_3$OTf, 4-I |
| 15307 | Pr—F | 2-NMe$_3$I, 4-I |
| 15308 | Pr—F | 2-Me, 3-F |
| 15309 | Pr—F | 2-Me, 3-NO$_2$ |
| 15310 | Pr—F | 2-Me, 3-NH$_2$ |
| 15311 | Pr—F | 2-Me, 3-NHMe |
| 15312 | Pr—F | 2-Me, 3-NMe$_2$ |
| 15313 | Pr—F | 2-Me, 3-NMe$_3$OTf |
| 15314 | Pr—F | 2-Me, 3-NMe$_3$I |
| 15315 | Pr—F | 2-Me, 4-F |
| 15316 | Pr—F | 2-Me, 4-NO$_2$ |
| 15317 | Pr—F | 2-Me, 4-NH$_2$ |
| 15318 | Pr—F | 2-Me, 4-NHMe |
| 15319 | Pr—F | 2-Me, 4-NMe$_2$ |
| 15320 | Pr—F | 2-Me, 4-NMe$_3$OTf |
| 15321 | Pr—F | 2-Me, 4-NMe$_3$I |
| 15322 | Pr—F | 2-Me, 5-F |
| 15323 | Pr—F | 2-Me, 5-NO$_2$ |
| 15324 | Pr—F | 2-Me, 5-NH$_2$ |
| 15325 | Pr—F | 2-Me, 5-NHMe |
| 15326 | Pr—F | 2-Me, 5-NMe$_2$ |
| 15327 | Pr—F | 2-Me, 5-NMe$_3$OTf |
| 15328 | Pr—F | 2-Me, 5-NMe$_3$I |
| 15329 | Pr—F | 2-F, 4-Me |
| 15330 | Pr—F | 2-NO$_2$, 4-Me |
| 15331 | Pr—F | 2-NH$_2$, 4-Me |
| 15332 | Pr—F | 2-NHMe, 4-Me |
| 15333 | Pr—F | 2-NMe$_2$, 4-Me |
| 15334 | Pr—F | 2-NMe$_3$, 4-Me |
| 15335 | Pr—F | 2-NMe$_3$OTf, 4-Me |
| 15336 | Pr—F | 2-NMe$_3$I, 4-Me |
| 15337 | Pr—F | 2-SnMe$_3$, 4-F |
| 15338 | Pr—F | 2-SnMe$_3$, 5-F |
| 15339 | Pr—F | 2-F, 4-SnMe$_3$ |
| 15340 | Pr—F | 2-Br, 6-Cl, 4-F |
| 15341 | Pr—F | 2-Br, 6-Cl, 4-NO$_2$ |
| 15342 | Pr—F | 2-Br, 6-Cl, 4-NH$_2$ |
| 15343 | Pr—F | 2-Br, 6-Cl, 4-NHMe |
| 15344 | Pr—F | 2-Br, 6-Cl, 4-NMe$_2$ |
| 15345 | Pr—F | 2-Br, 6-Cl, 4-NMe$_3$OTf |
| 15346 | Pr—F | 2-Br, 6-Cl, 4-NMe$_3$I |
| 15347 | Pr—F | 2-Me, 6-Cl, 4-F |
| 15348 | Pr—F | 2-SnMe$_3$, 6-Cl, 4-F |
| 15349 | Pr—F | 2-Cl, 4-Me |
| 15350 | Pr—F | 2-Cl, 4-Br |
| 15351 | Pr—F | 2-Cl, 4-SnMe$_3$ |
| 15352 | Pr—F | 2-Br, 4-Cl |
| 15353 | Pr—F | 2-SnMe$_3$, 4-Cl |
| 15354 | Pr—F | 2-Me, 4-Cl |
| 15355 | Pr—F | 2-Br, 4-Br |
| 15356 | Pr—F | 2-Br, 4-Me |
| 15357 | Pr—F | 2-Br, 4-SnMe$_3$ |
| 15358 | Pr—F | 2-SnMe$_3$, 4-Br |
| 15359 | Pr—F | 2-Me, 4-Br |
| 15360 | Pr—F | 2-Me, 4-SnMe$_3$ |
| 15361 | Pr—F | 2-SnMe$_3$, 4-Me |
| 15362 | Pr—F | 2-Me, 4-Me |

TABLE 10-continued

Substituent list for compounds of general structure XV.

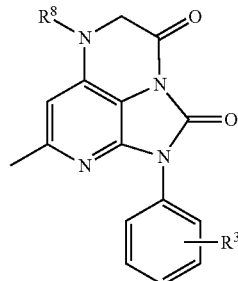

| Compound # | R$^1$ = | R$^3$ = |
|---|---|---|
| 15363 | Pr—F | 2-Et, 4-Br |
| 15364 | Pr—F | 2-Et, 4-SnMe$_3$ |
| 15365 | Pr—F | 2-Et, 4-Me |
| 15366 | Pr—F | 2-Me, 4-Me, 6-Me |
| 15367 | Pr—F | 2-Me, 4-Br, 6-Me |
| 15368 | Pr—F | 2-Me, 4-SnMe$_3$, 6-Me |
| 15369 | Pr—F | 2-Et, 6-Me |
| 15370 | Pr—F | 2-Br, 4-i-Pr |
| 15371 | Pr—F | 2-SnMe$_3$, 4-i-Pr |
| 15372 | Pr—F | 2-Me, 4-i-Pr |
| 15373 | Pr—F | 2-Br, 4-Br, 6-Br |
| 15374 | Pr—F | 2-Br, 4-Me, 6-Br |
| 15375 | Pr—F | 2-Br, 4-SnMe$_3$, 6-Br |
| 15376 | Pr—F | 2-SnMe$_3$, 4-Br, 6-Br |
| 15377 | Pr—F | 2-Br, 4-Br, 6-Me |
| 15378 | Pr—F | 2-Br, 4-CF$_3$, 6-Br |
| 15379 | Pr—F | 2-Br, 4-Br, 6-CF$_3$ |
| 15380 | Pr—F | 2-CF$_3$, 4-CF$_3$ |
| 15381 | Pr—F | 2-Cl, 4-CF$_3$ |
| 15382 | Pr—F | 2-CF$_3$, 4-Cl |
| 15383 | Pr—F | 2-Br, 4-CF$_3$ |
| 15384 | Pr—F | 2-SnMe$_3$, 4-CF$_3$ |
| 15385 | Pr—F | 2-Me, 4-CF$_3$ |
| 15386 | Pr—F | 2-CF$_3$, 4-Br |
| 15387 | Pr—F | 2-CF$_3$, 4-SnMe$_3$ |
| 15388 | Pr—F | 2-CF$_3$, 4-Me |
| 15389 | Pr—F | 2-Br, 4-OH |
| 15390 | Pr—F | 2-Br, 4-OMe |
| 15391 | Pr—F | 2-Br, 4-OMeF |
| 15392 | Pr—F | 2-Br, 4-OCF$_3$ |
| 15393 | Pr—F | 2-Br, 4-OEtF |
| 15394 | Pr—F | 2-Br, 4-OPrF |
| 15395 | Pr—F | 2-OH, 4-Br |
| 15396 | Pr—F | 2-OMe, 4-Br |
| 15397 | Pr—F | 2-OMeF, 4-Br |
| 15398 | Pr—F | 2-OCF$_3$, 4-Br |
| 15399 | Pr—F | 2-OEtF, 4-Br |
| 15400 | Pr—F | 2-OPrF, 4-Br |
| 15401 | Pr—F | 2-I, 4-OH |
| 15402 | Pr—F | 2-I, 4-OMe |
| 15403 | Pr—F | 2-I, 4-OMeF |
| 15404 | Pr—F | 2-I, 4-OCF$_3$ |
| 15405 | Pr—F | 2-I, 4-OEtF |
| 15406 | Pr—F | 2-I, 4-OPrF |
| 15407 | Pr—F | 2-OH, 4-I |
| 15408 | Pr—F | 2-OMe, 4-I |
| 15409 | Pr—F | 2-OMeF, 4-I |
| 15410 | Pr—F | 2-OCF$_3$, 4-I |
| 15411 | Pr—F | 2-OEtF, 4-I |
| 15412 | Pr—F | 2-OPrF, 4-I |
| 15413 | Pr—F | 2-SnMe$_3$, 4-OH |
| 15414 | Pr—F | 2-SnMe$_3$, 4-OMe |
| 15415 | Pr—F | 2-SnMe$_3$, 4-OMeF |
| 15416 | Pr—F | 2-SnMe$_3$, 4-OCF$_3$ |
| 15417 | Pr—F | 2-SnMe$_3$, 4-OEtF |
| 15418 | Pr—F | 2-SnMe$_3$, 4-OPrF |
| 15419 | Pr—F | 2-OH, 4-SnMe$_3$ |
| 15420 | Pr—F | 2-OMe, 4-SnMe$_3$ |
| 15421 | Pr—F | 2-OMeF, 4-SnMe$_3$ |
| 15422 | Pr—F | 2-OCF$_3$, 4-SnMe$_3$ |

TABLE 10-continued

Substituent list for compounds of general structure XV.

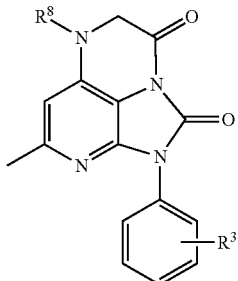

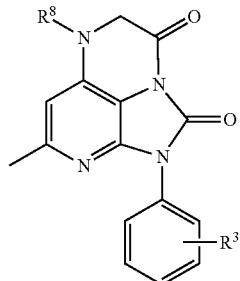

| Compound # | R¹ = | R³ = |
|---|---|---|
| 15423 | Pr—F | 2-OEtF, 4-SnMe₃ |
| 15424 | Pr—F | 2-OPrF, 4-SnMe₃ |
| 15425 | Et | H |
| 15426 | Et | 2-t-Bu |
| 15427 | Et | 2-Br |
| 15428 | Et | 3-Br |
| 15429 | Et | 4-Br |
| 15430 | Et | 2-I |
| 15431 | Et | 3-I |
| 15432 | Et | 4-I |
| 15433 | Et | 2-SnMe₃ |
| 15434 | Et | 3-SnMe₃ |
| 15435 | Et | 4-SnMe₃ |
| 15436 | Et | 2-Me |
| 15437 | Et | 3-Me |
| 15438 | Et | 4-Me |
| 15439 | Et | 2-OH |
| 15440 | Et | 3-OH |
| 15441 | Et | 4-OH |
| 15442 | Et | 2-OMe |
| 15443 | Et | 3-OMe |
| 15444 | Et | 4-OMe |
| 15445 | Et | 2-OMeF |
| 15446 | Et | 3-OMeF |
| 15447 | Et | 4-OMeF |
| 15448 | Et | 2-OCF₃ |
| 15449 | Et | 3-OCF₃ |
| 15450 | Et | 4-OCF₃ |
| 15451 | Et | 2-OEtF |
| 15452 | Et | 3-OEtF |
| 15453 | Et | 4-OEtF |
| 15454 | Et | 2-OPrF |
| 15455 | Et | 3-OPrF |
| 15456 | Et | 4-OPrF |
| 15457 | Et | 2-SH |
| 15458 | Et | 3-SH |
| 15459 | Et | 4-SH |
| 15460 | Et | 2-SMe |
| 15461 | Et | 3-SMe |
| 15462 | Et | 4-SMe |
| 15463 | Et | 2-SMeF |
| 15464 | Et | 3-SMeF |
| 15465 | Et | 4-SMeF |
| 15466 | Et | 2-SCF₃ |
| 15467 | Et | 3-SCF₃ |
| 15468 | Et | 4-SCF₃ |
| 15469 | Et | 2-SEtF |
| 15470 | Et | 3-SEtF |
| 15471 | Et | 4-SEtF |
| 15472 | Et | 2-SPrF |
| 15473 | Et | 3-SPrF |
| 15474 | Et | 4-SPrF |
| 15475 | Et | 2-OMe, 4-OMe |
| 15476 | Et | 2-Me, 5-OH |
| 15477 | Et | 2-Me, 5-OMe |
| 15478 | Et | 2-Me, 5-OMeF |
| 15479 | Et | 2-Me, 5-OEtF |
| 15480 | Et | 2-Me, 5-OPrF |
| 15481 | Et | 2-Me, 4-OH |
| 15482 | Et | 2-Me, 4-OMe |
| 15483 | Et | 2-Me, 4-OMeF |
| 15484 | Et | 2-Me, 4-OCF₃ |
| 15485 | Et | 2-Me, 4-OEtF |
| 15486 | Et | 2-Me, 4-OPrF |
| 15487 | Et | 2-OH, 4-Me |
| 15488 | Et | 2-OMe, 4-Me |
| 15489 | Et | 2-OMeF, 4-Me |
| 15490 | Et | 2-OCF₃, 4-Me |
| 15491 | Et | 2-OEtF, 4-Me |
| 15492 | Et | 2-OPrF, 4-Me |
| 15493 | Et | 2-Cl, 4-OH |
| 15494 | Et | 2-Cl, 4-OMe |
| 15495 | Et | 2-Cl, 4-OMeF |
| 15496 | Et | 2-Cl, 4-OCF₃ |
| 15497 | Et | 2-Cl, 4-OEtF |
| 15498 | Et | 2-Cl, 4-OPrF |
| 15499 | Et | 2-F, 4-F |
| 15500 | Et | 2-Cl, 4-Cl |
| 15501 | Et | 2-Cl, 4-F |
| 15502 | Et | 2-Cl, 4-NO₂ |
| 15503 | Et | 2-Cl, 4-NH₂ |
| 15504 | Et | 2-Cl, 4-NHMe |
| 15505 | Et | 2-Cl, 4-NMe₂ |
| 15506 | Et | 2-Cl, 4-NMe₃OTf |
| 15507 | Et | 2-Cl, 4-NMe₃I |
| 15508 | Et | 2-Cl, 5-F |
| 15509 | Et | 2-Cl, 5-NO₂ |
| 15510 | Et | 2-Cl, 5-NH₂ |
| 15511 | Et | 2-Cl, 5-NHMe |
| 15512 | Et | 2-Cl, 5-NMe₂ |
| 15513 | Et | 2-Cl, 5-NMe₃OTf |
| 15514 | Et | 2-Cl, 5-NMe₃I |
| 15515 | Et | 2-F, 4-Cl |
| 15516 | Et | 2-NO₂, 4-Cl |
| 15517 | Et | 2-NH₂, 4-Cl |
| 15518 | Et | 2-NHMe, 4-Cl |
| 15519 | Et | 2-NMe₂, 4-Cl |
| 15520 | Et | 2-NMe₃OTf, 4-Cl |
| 15521 | Et | 2-NMe₃I, 4-Cl |
| 15522 | Et | 2-F, 5-Cl |
| 15523 | Et | 2-NO₂, 5-Cl |
| 15524 | Et | 2-NH₂, 5-Cl |
| 15525 | Et | 2-NHMe, 5-Cl |
| 15526 | Et | 2-NMe₂, 5-Cl |
| 15527 | Et | 2-NMe₃OTf, 5-Cl |
| 15528 | Et | 2-NMe₃I, 5-Cl |
| 15529 | Et | 2-Br, 4-F |
| 15530 | Et | 2-Br, 4-NO₂ |
| 15531 | Et | 2-Br, 4-NH₂ |
| 15532 | Et | 2-Br, 4-NHMe |
| 15533 | Et | 2-Br, 4-NMe₂ |
| 15534 | Et | 2-Br, 4-NMe₃OTf |
| 15535 | Et | 2-Br, 4-NMe₃I |
| 15536 | Et | 2-Br, 5-F |
| 15537 | Et | 2-Br, 5-NO₂ |
| 15538 | Et | 2-Br, 5-NH₂ |
| 15539 | Et | 2-Br, 5-NHMe |
| 15540 | Et | 2-Br, 5-NMe₂ |
| 15541 | Et | 2-Br, 5-NMe₃OTf |
| 15542 | Et | 2-Br, 5-NMe₃I |

TABLE 10-continued

Substituent list for compounds of general structure XV.

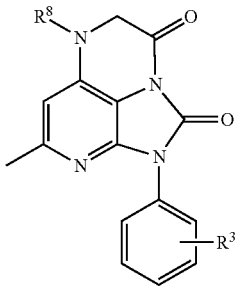

XV

| Compound # | R¹ = | R³ = |
|---|---|---|
| 15543 | Et | 2-F, 4-Br |
| 15544 | Et | 2-NO₂, 4-Br |
| 15545 | Et | 2-NH₂, 4-Br |
| 15546 | Et | 2-NHMe, 4-Br |
| 15547 | Et | 2-NMe₂, 4-Br |
| 15548 | Et | 2-NMe₃OTf, 4-Br |
| 15549 | Et | 2-NMe₃I, 4-Br |
| 15550 | Et | 2-I, 4-F |
| 15551 | Et | 2-I, 4-NO₂ |
| 15552 | Et | 2-I, 4-NH₂ |
| 15553 | Et | 2-I, 4-NHMe |
| 15554 | Et | 2-I, 4-NMe₂ |
| 15555 | Et | 2-I, 4-NMe₃OTf |
| 15556 | Et | 2-I, 4-NMe₃I |
| 15557 | Et | 2-F, 4-I |
| 15558 | Et | 2-NO₂, 4-I |
| 15559 | Et | 2-NH₂, 4-I |
| 15560 | Et | 2-NHMe, 4-I |
| 15561 | Et | 2-NMe₂, 4-I |
| 15562 | Et | 2-NMe₃OTf, 4-I |
| 15563 | Et | 2-NMe₃I, 4-I |
| 15564 | Et | 2-Me, 3-F |
| 15565 | Et | 2-Me, 3-NO₂ |
| 15566 | Et | 2-Me, 3-NH₂ |
| 15567 | Et | 2-Me, 3-NHMe |
| 15568 | Et | 2-Me, 3-NMe₂ |
| 15569 | Et | 2-Me, 3-NMe₃OTf |
| 15570 | Et | 2-Me, 3-NMe₃I |
| 15571 | Et | 2-Me, 4-F |
| 15572 | Et | 2-Me, 4-NO₂ |
| 15573 | Et | 2-Me, 4-NH₂ |
| 15574 | Et | 2-Me, 4-NHMe |
| 15575 | Et | 2-Me, 4-NMe₂ |
| 15576 | Et | 2-Me, 4-NMe₃OTf |
| 15577 | Et | 2-Me, 4-NMe₃I |
| 15578 | Et | 2-Me, 5-F |
| 15579 | Et | 2-Me, 5-NO₂ |
| 15580 | Et | 2-Me, 5-NH₂ |
| 15581 | Et | 2-Me, 5-NHMe |
| 15582 | Et | 2-Me, 5-NMe₂ |
| 15583 | Et | 2-Me, 5-NMe₃OTf |
| 15584 | Et | 2-Me, 5-NMe₃I |
| 15585 | Et | 2-F, 4-Me |
| 15586 | Et | 2-NO₂, 4-Me |
| 15587 | Et | 2-NH₂, 4-Me |
| 15588 | Et | 2-NHMe, 4-Me |
| 15589 | Et | 2-NMe₂, 4-Me |
| 15590 | Et | 2-NMe₃, 4-Me |
| 15591 | Et | 2-NMe₃OTf, 4-Me |
| 15592 | Et | 2-NMe₃I, 4-Me |
| 15593 | Et | 2-SnMe₃, 4-F |
| 15594 | Et | 2-SnMe₃, 5-F |
| 15595 | Et | 2-F, 4-SnMe₃ |
| 15596 | Et | 2-Br, 6-Cl, 4-F |
| 15597 | Et | 2-Br, 6-Cl, 4-NO₂ |
| 15598 | Et | 2-Br, 6-Cl, 4-NH₂ |
| 15599 | Et | 2-Br, 6-Cl, 4-NHMe |
| 15600 | Et | 2-Br, 6-Cl, 4-NMe₂ |
| 15601 | Et | 2-Br, 6-Cl, 4-NMe₃OTf |
| 15602 | Et | 2-Br, 6-Cl, 4-NMe₃I |

TABLE 10-continued

Substituent list for compounds of general structure XV.

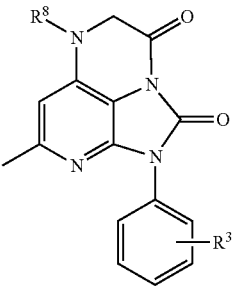

XV

| Compound # | R¹ = | R³ = |
|---|---|---|
| 15603 | Et | 2-Me, 6-Cl, 4-F |
| 15604 | Et | 2-SnMe₃, 6-Cl, 4-F |
| 15605 | Et | 2-Cl, 4-Me |
| 15606 | Et | 2-Cl, 4-Br |
| 15607 | Et | 2-Cl, 4-SnMe₃ |
| 15608 | Et | 2-Br, 4-Cl |
| 15609 | Et | 2-SnMe₃, 4-Cl |
| 15610 | Et | 2-Me, 4-Cl |
| 15611 | Et | 2-Br, 4-Br |
| 15612 | Et | 2-Br, 4-Me |
| 15613 | Et | 2-Br, 4-SnMe₃ |
| 15614 | Et | 2-SnMe₃, 4-Br |
| 15615 | Et | 2-Me, 4-Br |
| 15616 | Et | 2-Me, 4-SnMe₃ |
| 15617 | Et | 2-SnMe₃, 4-Me |
| 15618 | Et | 2-Me, 4-Me |
| 15619 | Et | 2-Et, 4-Br |
| 15620 | Et | 2-Et, 4-SnMe₃ |
| 15621 | Et | 2-Et, 4-Me |
| 15622 | Et | 2-Me, 4-Me, 6-Me |
| 15623 | Et | 2-Me, 4-Br, 6-Me |
| 15624 | Et | 2-Me, 4-SnMe₃, 6-Me |
| 15625 | Et | 2-Et, 6-Me |
| 15626 | Et | 2-Br, 4-i-Pr |
| 15627 | Et | 2-SnMe₃, 4-i-Pr |
| 15628 | Et | 2-Me, 4-i-Pr |
| 15629 | Et | 2-Br, 4-Br, 6-Br |
| 15630 | Et | 2-Br, 4-Me, 6-Br |
| 15631 | Et | 2-Br, 4-SnMe₃, 6-Br |
| 15632 | Et | 2-SnMe₃, 4-Br, 6-Br |
| 15633 | Et | 2-Br, 4-Br, 6-Me |
| 15634 | Et | 2-Br, 4-CF₃, 6-Br |
| 15635 | Et | 2-Br, 4-Br, 6-CF₃ |
| 15636 | Et | 2-CF₃, 4-CF₃ |
| 15637 | Et | 2-Cl, 4-CF₃ |
| 15638 | Et | 2-CF₃, 4-Cl |
| 15639 | Et | 2-Br, 4-CF₃ |
| 15640 | Et | 2-SnMe₃, 4-CF₃ |
| 15641 | Et | 2-Me, 4-CF₃ |
| 15642 | Et | 2-CF₃, 4-Br |
| 15643 | Et | 2-CF₃, 4-SnMe₃ |
| 15644 | Et | 2-CF₃, 4-Me |
| 15645 | Et | 2-Br, 4-OH |
| 15646 | Et | 2-Br, 4-OMe |
| 15647 | Et | 2-Br, 4-OMeF |
| 15648 | Et | 2-Br, 4-OCF₃ |
| 15649 | Et | 2-Br, 4-OEtF |
| 15650 | Et | 2-Br, 4-OPrF |
| 15651 | Et | 2-OH, 4-Br |
| 15652 | Et | 2-OMe, 4-Br |
| 15653 | Et | 2-OMeF, 4-Br |
| 15654 | Et | 2-OCF₃, 4-Br |
| 15655 | Et | 2-OEtF, 4-Br |
| 15656 | Et | 2-OPrF, 4-Br |
| 15657 | Et | 2-I, 4-OH |
| 15658 | Et | 2-I, 4-OMe |
| 15659 | Et | 2-I, 4-OMeF |
| 15660 | Et | 2-I, 4-OCF₃ |
| 15661 | Et | 2-I, 4-OEtF |
| 15662 | Et | 2-I, 4-OPrF |

TABLE 10-continued

Substituent list for compounds of general structure XV.

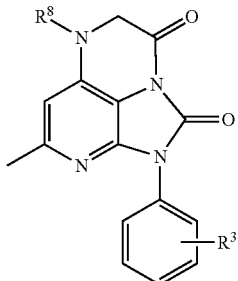

XV

| Compound # | R¹ = | R³ = |
|---|---|---|
| 15663 | Et | 2-OH, 4-I |
| 15664 | Et | 2-OMe, 4-I |
| 15665 | Et | 2-OMeF, 4-I |
| 15666 | Et | 2-OCF₃, 4-I |
| 15667 | Et | 2-OEtF, 4-I |
| 15668 | Et | 2-OPrF, 4-I |
| 15669 | Et | 2-SnMe₃, 4-OH |
| 15670 | Et | 2-SnMe₃, 4-OMe |
| 15671 | Et | 2-SnMe₃, 4-OMeF |
| 15672 | Et | 2-SnMe₃, 4-OCF₃ |
| 15673 | Et | 2-SnMe₃, 4-OEtF |
| 15674 | Et | 2-SnMe₃, 4-OPrF |
| 15675 | Et | 2-OH, 4-SnMe₃ |
| 15676 | Et | 2-OMe, 4-SnMe₃ |
| 15677 | Et | 2-OMeF, 4-SnMe₃ |
| 15678 | Et | 2-OCF₃, 4-SnMe₃ |
| 15679 | Et | 2-OEtF, 4-SnMe₃ |
| 15680 | Et | 2-OPrF, 4-SnMe₃ |
| 15681 | Et—F | H |
| 15682 | Et—F | 2-t-Bu |
| 15683 | Et—F | 2-Br |
| 15684 | Et—F | 3-Br |
| 15685 | Et—F | 4-Br |
| 15686 | Et—F | 2-I |
| 15687 | Et—F | 3-I |
| 15688 | Et—F | 4-I |
| 15689 | Et—F | 2-SnMe₃ |
| 15690 | Et—F | 3-SnMe₃ |
| 15691 | Et—F | 4-SnMe₃ |
| 15692 | Et—F | 2-Me |
| 15693 | Et—F | 3-Me |
| 15694 | Et—F | 4-Me |
| 15695 | Et—F | 2-OH |
| 15696 | Et—F | 3-OH |
| 15697 | Et—F | 4-OH |
| 15698 | Et—F | 2-OMe |
| 15699 | Et—F | 3-OMe |
| 15700 | Et—F | 4-OMe |
| 15701 | Et—F | 2-OMeF |
| 15702 | Et—F | 3-OMeF |
| 15703 | Et—F | 4-OMeF |
| 15704 | Et—F | 2-OCF₃ |
| 15705 | Et—F | 3-OCF₃ |
| 15706 | Et—F | 4-OCF₃ |
| 15707 | Et—F | 2-OEtF |
| 15708 | Et—F | 3-OEtF |
| 15709 | Et—F | 4-OEtF |
| 15710 | Et—F | 2-OPrF |
| 15711 | Et—F | 3-OPrF |
| 15712 | Et—F | 4-OPrF |
| 15713 | Et—F | 2-SH |
| 15714 | Et—F | 3-SH |
| 15715 | Et—F | 4-SH |
| 15716 | Et—F | 2-SMe |
| 15717 | Et—F | 3-SMe |
| 15718 | Et—F | 4-SMe |
| 15719 | Et—F | 2-SMeF |
| 15720 | Et—F | 3-SMeF |
| 15721 | Et—F | 4-SMeF |
| 15722 | Et—F | 2-SCF₃ |

TABLE 10-continued

Substituent list for compounds of general structure XV.

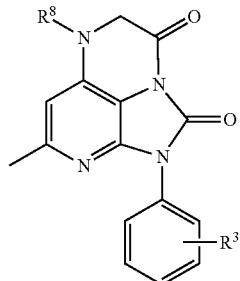

XV

| Compound # | R¹ = | R³ = |
|---|---|---|
| 15723 | Et—F | 3-SCF₃ |
| 15724 | Et—F | 4-SCF₃ |
| 15725 | Et—F | 2-SEtF |
| 15726 | Et—F | 3-SEtF |
| 15727 | Et—F | 4-SEtF |
| 15728 | Et—F | 2-SPrF |
| 15729 | Et—F | 3-SPrF |
| 15730 | Et—F | 4-SPrF |
| 15731 | Et—F | 2-OMe, 4-OMe |
| 15732 | Et—F | 2-Me, 5-OH |
| 15733 | Et—F | 2-Me, 5-OMe |
| 15734 | Et—F | 2-Me, 5-OMeF |
| 15735 | Et—F | 2-Me, 5-OEtF |
| 15736 | Et—F | 2-Me, 5-OPrF |
| 15737 | Et—F | 2-Me, 4-OH |
| 15738 | Et—F | 2-Me, 4-OMe |
| 15739 | Et—F | 2-Me, 4-OMeF |
| 15740 | Et—F | 2-Me, 4-OCF₃ |
| 15741 | Et—F | 2-Me, 4-OEtF |
| 15742 | Et—F | 2-Me, 4-OPrF |
| 15743 | Et—F | 2-OH, 4-Me |
| 15744 | Et—F | 2-OMe, 4-Me |
| 15745 | Et—F | 2-OMeF, 4-Me |
| 15746 | Et—F | 2-OCF₃, 4-Me |
| 15747 | Et—F | 2-OEtF, 4-Me |
| 15748 | Et—F | 2-OPrF, 4-Me |
| 15749 | Et—F | 2-Cl, 4-OH |
| 15750 | Et—F | 2-Cl, 4-OMe |
| 15751 | Et—F | 2-Cl, 4-OMeF |
| 15752 | Et—F | 2-Cl, 4-OCF₃ |
| 15753 | Et—F | 2-Cl, 4-OEtF |
| 15754 | Et—F | 2-Cl, 4-OPrF |
| 15755 | Et—F | 2-F, 4-F |
| 15756 | Et—F | 2-Cl, 4-Cl |
| 15757 | Et—F | 2-Cl, 4-F |
| 15758 | Et—F | 2-Cl, 4-NO₂ |
| 15759 | Et—F | 2-Cl, 4-NH₂ |
| 15760 | Et—F | 2-Cl, 4-NHMe |
| 15761 | Et—F | 2-Cl, 4-NMe₂ |
| 15762 | Et—F | 2-Cl, 4-NMe₃OTf |
| 15763 | Et—F | 2-Cl, 4-NMe₃I |
| 15764 | Et—F | 2-Cl, 5-F |
| 15765 | Et—F | 2-Cl, 5-NO₂ |
| 15766 | Et—F | 2-Cl, 5-NH₂ |
| 15767 | Et—F | 2-Cl, 5-NHMe |
| 15768 | Et—F | 2-Cl, 5-NMe₂ |
| 15769 | Et—F | 2-Cl, 5-NMe₃OTf |
| 15770 | Et—F | 2-Cl, 5-NMe₃I |
| 15771 | Et—F | 2-F, 4-Cl |
| 15772 | Et—F | 2-NO₂, 4-Cl |
| 15773 | Et—F | 2-NH₂, 4-Cl |
| 15774 | Et—F | 2-NHMe, 4-Cl |
| 15775 | Et—F | 2-NMe₂, 4-Cl |
| 15776 | Et—F | 2-NMe₃OTf, 4-Cl |
| 15777 | Et—F | 2-NMe₃I, 4-Cl |
| 15778 | Et—F | 2-F, 5-Cl |
| 15779 | Et—F | 2-NO₂, 5-Cl |
| 15780 | Et—F | 2-NH₂, 5-Cl |
| 15781 | Et—F | 2-NHMe, 5-Cl |
| 15782 | Et—F | 2-NMe₂, 5-Cl |

TABLE 10-continued

Substituent list for compounds of general structure XV.

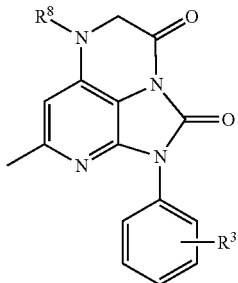

| Compound # | R¹ = | R³ = |
|---|---|---|
| 15783 | Et—F | 2-NMe₃OTf, 5-Cl |
| 15784 | Et—F | 2-NMe₃I, 5-Cl |
| 15785 | Et—F | 2-Br, 4-F |
| 15786 | Et—F | 2-Br, 4-NO₂ |
| 15787 | Et—F | 2-Br, 4-NH₂ |
| 15788 | Et—F | 2-Br, 4-NHMe |
| 15789 | Et—F | 2-Br, 4-NMe₂ |
| 15790 | Et—F | 2-Br, 4-NMe₃OTf |
| 15791 | Et—F | 2-Br, 4-NMe₃I |
| 15792 | Et—F | 2-Br, 5-F |
| 15793 | Et—F | 2-Br, 5-NO₂ |
| 15794 | Et—F | 2-Br, 5-NH₂ |
| 15795 | Et—F | 2-Br, 5-NHMe |
| 15796 | Et—F | 2-Br, 5-NMe₂ |
| 15797 | Et—F | 2-Br, 5-NMe₃OTf |
| 15798 | Et—F | 2-Br, 5-NMe₃I |
| 15799 | Et—F | 2-F, 4-Br |
| 15800 | Et—F | 2-NO₂, 4-Br |
| 15801 | Et—F | 2-NH₂, 4-Br |
| 15802 | Et—F | 2-NHMe, 4-Br |
| 15803 | Et—F | 2-NMe₂, 4-Br |
| 15804 | Et—F | 2-NMe₃OTf, 4-Br |
| 15805 | Et—F | 2-NMe₃I, 4-Br |
| 15806 | Et—F | 2-I, 4-F |
| 15807 | Et—F | 2-I, 4-NO₂ |
| 15808 | Et—F | 2-I, 4-NH₂ |
| 15809 | Et—F | 2-I, 4-NHMe |
| 15810 | Et—F | 2-I, 4-NMe₂ |
| 15811 | Et—F | 2-I, 4-NMe₃OTf |
| 15812 | Et—F | 2-I, 4-NMe₃I |
| 15813 | Et—F | 2-F, 4-I |
| 15814 | Et—F | 2-NO₂, 4-I |
| 15815 | Et—F | 2-NH₂, 4-I |
| 15816 | Et—F | 2-NHMe, 4-I |
| 15817 | Et—F | 2-NMe₂, 4-I |
| 15818 | Et—F | 2-NMe₃OTf, 4-I |
| 15819 | Et—F | 2-NMe₃I, 4-I |
| 15820 | Et—F | 2-Me, 3-F |
| 15821 | Et—F | 2-Me, 3-NO₂ |
| 15822 | Et—F | 2-Me, 3-NH₂ |
| 15823 | Et—F | 2-Me, 3-NHMe |
| 15824 | Et—F | 2-Me, 3-NMe₂ |
| 15825 | Et—F | 2-Me, 3-NMe₃OTf |
| 15826 | Et—F | 2-Me, 3-NMe₃I |
| 15827 | Et—F | 2-Me, 4-F |
| 15828 | Et—F | 2-Me, 4-NO₂ |
| 15829 | Et—F | 2-Me, 4-NH₂ |
| 15830 | Et—F | 2-Me, 4-NHMe |
| 15831 | Et—F | 2-Me, 4-NMe₂ |
| 15832 | Et—F | 2-Me, 4-NMe₃OTf |
| 15833 | Et—F | 2-Me, 4-NMe₃I |
| 15834 | Et—F | 2-Me, 5-F |
| 15835 | Et—F | 2-Me, 5-NO₂ |
| 15836 | Et—F | 2-Me, 5-NH₂ |
| 15837 | Et—F | 2-Me, 5-NHMe |
| 15838 | Et—F | 2-Me, 5-NMe₂ |
| 15839 | Et—F | 2-Me, 5-NMe₃OTf |
| 15840 | Et—F | 2-Me, 5-NMe₃I |
| 15841 | Et—F | 2-F, 4-Me |
| 15842 | Et—F | 2-NO₂, 4-Me |

TABLE 10-continued

Substituent list for compounds of general structure XV.

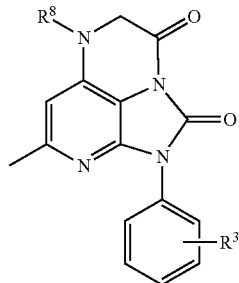

| Compound # | R¹ = | R³ = |
|---|---|---|
| 15843 | Et—F | 2-NH₂, 4-Me |
| 15844 | Et—F | 2-NHMe, 4-Me |
| 15845 | Et—F | 2-NMe₂, 4-Me |
| 15846 | Et—F | 2-NMe₃, 4-Me |
| 15847 | Et—F | 2-NMe₃OTf, 4-Me |
| 15848 | Et—F | 2-NMe₃I, 4-Me |
| 15849 | Et—F | 2-SnMe₃, 4-F |
| 15850 | Et—F | 2-SnMe₃, 5-F |
| 15851 | Et—F | 2-F, 4-SnMe₃ |
| 15852 | Et—F | 2-Br, 6-Cl, 4-F |
| 15853 | Et—F | 2-Br, 6-Cl, 4-NO₂ |
| 15854 | Et—F | 2-Br, 6-Cl, 4-NH₂ |
| 15855 | Et—F | 2-Br, 6-Cl, 4-NHMe |
| 15856 | Et—F | 2-Br, 6-Cl, 4-NMe₂ |
| 15857 | Et—F | 2-Br, 6-Cl, 4-NMe₃OTf |
| 15858 | Et—F | 2-Br, 6-Cl, 4-NMe₃I |
| 15859 | Et—F | 2-Me, 6-Cl, 4-F |
| 15860 | Et—F | 2-SnMe₃, 6-Cl, 4-F |
| 15861 | Et—F | 2-Cl, 4-Me |
| 15862 | Et—F | 2-Cl, 4-Br |
| 15863 | Et—F | 2-Cl, 4-SnMe₃ |
| 15864 | Et—F | 2-Br, 4-Cl |
| 15865 | Et—F | 2-SnMe₃, 4-Cl |
| 15866 | Et—F | 2-Me, 4-Cl |
| 15867 | Et—F | 2-Br, 4-Br |
| 15868 | Et—F | 2-Br, 4-Me |
| 15869 | Et—F | 2-Br, 4-SnMe₃ |
| 15870 | Et—F | 2-SnMe₃, 4-Br |
| 15871 | Et—F | 2-Me, 4-Br |
| 15872 | Et—F | 2-Me, 4-SnMe₃ |
| 15873 | Et—F | 2-SnMe₃, 4-Me |
| 15874 | Et—F | 2-Me, 4-Me |
| 15875 | Et—F | 2-Et, 4-Br |
| 15876 | Et—F | 2-Et, 4-SnMe₃ |
| 15877 | Et—F | 2-Et, 4-Me |
| 15878 | Et—F | 2-Me, 4-Me, 6-Me |
| 15879 | Et—F | 2-Me, 4-Br, 6-Me |
| 15880 | Et—F | 2-Me, 4-SnMe₃, 6-Me |
| 15881 | Et—F | 2-Et, 6-Me |
| 15882 | Et—F | 2-Br, 4-i-Pr |
| 15883 | Et—F | 2-SnMe₃, 4-i-Pr |
| 15884 | Et—F | 2-Me, 4-i-Pr |
| 15885 | Et—F | 2-Br, 4-Br, 6-Br |
| 15886 | Et—F | 2-Br, 4-Me, 6-Br |
| 15887 | Et—F | 2-Br, 4-SnMe₃, 6-Br |
| 15888 | Et—F | 2-SnMe₃, 4-Br, 6-Br |
| 15889 | Et—F | 2-Br, 4-Br, 6-Me |
| 15890 | Et—F | 2-Br, 4-CF₃, 6-Br |
| 15891 | Et—F | 2-Br, 4-Br, 6-CF₃ |
| 15892 | Et—F | 2-CF₃, 4-CF₃ |
| 15893 | Et—F | 2-Cl, 4-CF₃ |
| 15894 | Et—F | 2-CF₃, 4-Cl |
| 15895 | Et—F | 2-Br, 4-CF₃ |
| 15896 | Et—F | 2-SnMe₃, 4-CF₃ |
| 15897 | Et—F | 2-Me, 4-CF₃ |
| 15898 | Et—F | 2-CF₃, 4-Br |
| 15899 | Et—F | 2-CF₃, 4-SnMe₃ |
| 15900 | Et—F | 2-CF₃, 4-Me |
| 15901 | Et—F | 2-Br, 4-OH |
| 15902 | Et—F | 2-Br, 4-OMe |

TABLE 10-continued

Substituent list for compounds of general structure XV.

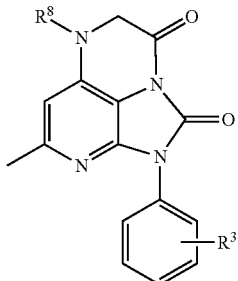

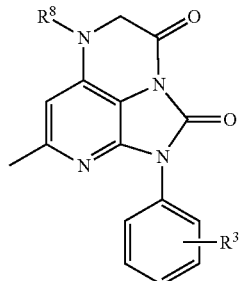

| Compound # | R¹ = | R³ = |
|---|---|---|
| 15903 | Et—F | 2-Br, 4-OMeF |
| 15904 | Et—F | 2-Br, 4-OCF₃ |
| 15905 | Et—F | 2-Br, 4-OEtF |
| 15906 | Et—F | 2-Br, 4-OPrF |
| 15907 | Et—F | 2-OH, 4-Br |
| 15908 | Et—F | 2-OMe, 4-Br |
| 15909 | Et—F | 2-OMeF, 4-Br |
| 15910 | Et—F | 2-OCF₃, 4-Br |
| 15911 | Et—F | 2-OEtF, 4-Br |
| 15912 | Et—F | 2-OPrF, 4-Br |
| 15913 | Et—F | 2-I, 4-OH |
| 15914 | Et—F | 2-I, 4-OMe |
| 15915 | Et—F | 2-I, 4-OMeF |
| 15916 | Et—F | 2-I, 4-OCF₃ |
| 15917 | Et—F | 2-I, 4-OEtF |
| 15918 | Et—F | 2-I, 4-OPrF |
| 15919 | Et—F | 2-OH, 4-I |
| 15920 | Et—F | 2-OMe, 4-I |
| 15921 | Et—F | 2-OMeF, 4-I |
| 15922 | Et—F | 2-OCF₃, 4-I |
| 15923 | Et—F | 2-OEtF, 4-I |
| 15924 | Et—F | 2-OPrF, 4-I |
| 15925 | Et—F | 2-SnMe₃, 4-OH |
| 15926 | Et—F | 2-SnMe₃, 4-OMe |
| 15927 | Et—F | 2-SnMe₃, 4-OMeF |
| 15928 | Et—F | 2-SnMe₃, 4-OCF₃ |
| 15929 | Et—F | 2-SnMe₃, 4-OEtF |
| 15930 | Et—F | 2-SnMe₃, 4-OPrF |
| 15931 | Et—F | 2-OH, 4-SnMe₃ |
| 15932 | Et—F | 2-OMe, 4-SnMe₃ |
| 15933 | Et—F | 2-OMeF, 4-SnMe₃ |
| 15934 | Et—F | 2-OCF₃, 4-SnMe₃ |
| 15935 | Et—F | 2-OEtF, 4-SnMe₃ |
| 15936 | Et—F | 2-OPrF, 4-SnMe₃ |
| 15937 | Me | H |
| 15938 | Me | 2-t-Bu |
| 15939 | Me | 2-Br |
| 15940 | Me | 3-Br |
| 15941 | Me | 4-Br |
| 15942 | Me | 2-I |
| 15943 | Me | 3-I |
| 15944 | Me | 4-I |
| 15945 | Me | 2-SnMe₃ |
| 15946 | Me | 3-SnMe₃ |
| 15947 | Me | 4-SnMe₃ |
| 15948 | Me | 2-Me |
| 15949 | Me | 3-Me |
| 15950 | Me | 4-Me |
| 15951 | Me | 2-OH |
| 15952 | Me | 3-OH |
| 15953 | Me | 4-OH |
| 15954 | Me | 2-OMe |
| 15955 | Me | 3-OMe |
| 15956 | Me | 4-OMe |
| 15957 | Me | 2-OMeF |
| 15958 | Me | 3-OMeF |
| 15959 | Me | 4-OMeF |
| 15960 | Me | 2-OCF₃ |
| 15961 | Me | 3-OCF₃ |
| 15962 | Me | 4-OCF₃ |
| 15963 | Me | 2-OEtF |
| 15964 | Me | 3-OEtF |
| 15965 | Me | 4-OEtF |
| 15966 | Me | 2-OPrF |
| 15967 | Me | 3-OPrF |
| 15968 | Me | 4-OPrF |
| 15969 | Me | 2-SH |
| 15970 | Me | 3-SH |
| 15971 | Me | 4-SH |
| 15972 | Me | 2-SMe |
| 15973 | Me | 3-SMe |
| 15974 | Me | 4-SMe |
| 15975 | Me | 2-SMeF |
| 15976 | Me | 3-SMeF |
| 15977 | Me | 4-SMeF |
| 15978 | Me | 2-SCF₃ |
| 15979 | Me | 3-SCF₃ |
| 15980 | Me | 4-SCF₃ |
| 15981 | Me | 2-SEtF |
| 15982 | Me | 3-SEtF |
| 15983 | Me | 4-SEtF |
| 15984 | Me | 2-SPrF |
| 15985 | Me | 3-SPrF |
| 15986 | Me | 4-SPrF |
| 15987 | Me | 2-OMe, 4-OMe |
| 15988 | Me | 2-Me, 5-OH |
| 15989 | Me | 2-Me, 5-OMe |
| 15990 | Me | 2-Me, 5-OMeF |
| 15991 | Me | 2-Me, 5-OEtF |
| 15992 | Me | 2-Me, 5-OPrF |
| 15993 | Me | 2-Me, 4-OH |
| 15994 | Me | 2-Me, 4-OMe |
| 15995 | Me | 2-Me, 4-OMeF |
| 15996 | Me | 2-Me, 4-OCF₃ |
| 15997 | Me | 2-Me, 4-OEtF |
| 15998 | Me | 2-Me, 4-OPrF |
| 15999 | Me | 2-OH, 4-Me |
| 16000 | Me | 2-OMe, 4-Me |
| 16001 | Me | 2-OMeF, 4-Me |
| 16002 | Me | 2-OCF₃, 4-Me |
| 16003 | Me | 2-OEtF, 4-Me |
| 16004 | Me | 2-OPrF, 4-Me |
| 16005 | Me | 2-Cl, 4-OH |
| 16006 | Me | 2-Cl, 4-OMe |
| 16007 | Me | 2-Cl, 4-OMeF |
| 16008 | Me | 2-Cl, 4-OCF₃ |
| 16009 | Me | 2-Cl, 4-OEtF |
| 16010 | Me | 2-Cl, 4-OPrF |
| 16011 | Me | 2-F, 4-F |
| 16012 | Me | 2-Cl, 4-Cl |
| 16013 | Me | 2-Cl, 4-F |
| 16014 | Me | 2-Cl, 4-NO₂ |
| 16015 | Me | 2-Cl, 4-NH₂ |
| 16016 | Me | 2-Cl, 4-NHMe |
| 16017 | Me | 2-Cl, 4-NMe₂ |
| 16018 | Me | 2-Cl, 4-NMe₃OTf |
| 16019 | Me | 2-Cl, 4-NMe₃I |
| 16020 | Me | 2-Cl, 5-F |
| 16021 | Me | 2-Cl, 5-NO₂ |
| 16022 | Me | 2-Cl, 5-NH₂ |

TABLE 10-continued

Substituent list for compounds of general structure XV.

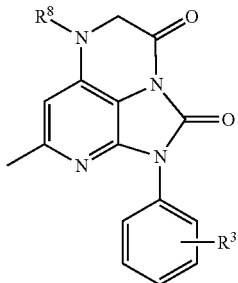

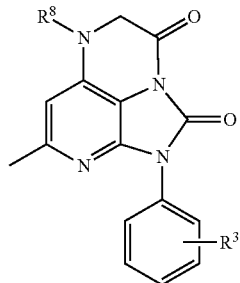

| Compound # | R$^1$ = | R$^3$ = |
|---|---|---|
| 16023 | Me | 2-Cl, 5-NHMe |
| 16024 | Me | 2-Cl, 5-NMe$_2$ |
| 16025 | Me | 2-Cl, 5-NMe$_3$OTf |
| 16026 | Me | 2-Cl, 5-NMe$_3$I |
| 16027 | Me | 2-F, 4-Cl |
| 16028 | Me | 2-NO$_2$, 4-Cl |
| 16029 | Me | 2-NH$_2$, 4-Cl |
| 16030 | Me | 2-NHMe, 4-Cl |
| 16031 | Me | 2-NMe$_2$, 4-Cl |
| 16032 | Me | 2-NMe$_3$OTf, 4-Cl |
| 16033 | Me | 2-NMe$_3$I, 4-Cl |
| 16034 | Me | 2-F, 5-Cl |
| 16035 | Me | 2-NO$_2$, 5-Cl |
| 16036 | Me | 2-NH$_2$, 5-Cl |
| 16037 | Me | 2-NHMe, 5-Cl |
| 16038 | Me | 2-NMe$_2$, 5-Cl |
| 16039 | Me | 2-NMe$_3$OTf, 5-Cl |
| 16040 | Me | 2-NMe$_3$I, 5-Cl |
| 16041 | Me | 2-Br, 4-F |
| 16042 | Me | 2-Br, 4-NO$_2$ |
| 16043 | Me | 2-Br, 4-NH$_2$ |
| 16044 | Me | 2-Br, 4-NHMe |
| 16045 | Me | 2-Br, 4-NMe$_2$ |
| 16046 | Me | 2-Br, 4-NMe$_3$OTf |
| 16047 | Me | 2-Br, 4-NMe$_3$I |
| 16048 | Me | 2-Br, 5-F |
| 16049 | Me | 2-Br, 5-NO$_2$ |
| 16050 | Me | 2-Br, 5-NH$_2$ |
| 16051 | Me | 2-Br, 5-NHMe |
| 16052 | Me | 2-Br, 5-NMe$_2$ |
| 16053 | Me | 2-Br, 5-NMe$_3$OTf |
| 16054 | Me | 2-Br, 5-NMe$_3$I |
| 16055 | Me | 2-F, 4-Br |
| 16056 | Me | 2-NO$_2$, 4-Br |
| 16057 | Me | 2-NH$_2$, 4-Br |
| 16058 | Me | 2-NHMe, 4-Br |
| 16059 | Me | 2-NMe$_2$, 4-Br |
| 16060 | Me | 2-NMe$_3$OTf, 4-Br |
| 16061 | Me | 2-NMe$_3$I, 4-Br |
| 16062 | Me | 2-I, 4-F |
| 16063 | Me | 2-I, 4-NO$_2$ |
| 16064 | Me | 2-I, 4-NH$_2$ |
| 16065 | Me | 2-I, 4-NHMe |
| 16066 | Me | 2-I, 4-NMe$_2$ |
| 16067 | Me | 2-I, 4-NMe$_3$OTf |
| 16068 | Me | 2-I, 4-NMe$_3$I |
| 16069 | Me | 2-F, 4-I |
| 16070 | Me | 2-NO$_2$, 4-I |
| 16071 | Me | 2-NH$_2$, 4-I |
| 16072 | Me | 2-NHMe, 4-I |
| 16073 | Me | 2-NMe$_2$, 4-I |
| 16074 | Me | 2-NMe$_3$OTf, 4-I |
| 16075 | Me | 2-NMe$_3$I, 4-I |
| 16076 | Me | 2-Me, 3-F |
| 16077 | Me | 2-Me, 3-NO$_2$ |
| 16078 | Me | 2-Me, 3-NH$_2$ |
| 16079 | Me | 2-Me, 3-NHMe |
| 16080 | Me | 2-Me, 3-NMe$_2$ |
| 16081 | Me | 2-Me, 3-NMe$_3$OTf |
| 16082 | Me | 2-Me, 3-NMe$_3$I |
| 16083 | Me | 2-Me, 4-F |
| 16084 | Me | 2-Me, 4-NO$_2$ |
| 16085 | Me | 2-Me, 4-NH$_2$ |
| 16086 | Me | 2-Me, 4-NHMe |
| 16087 | Me | 2-Me, 4-NMe$_2$ |
| 16088 | Me | 2-Me, 4-NMe$_3$OTf |
| 16089 | Me | 2-Me, 4-NMe$_3$I |
| 16090 | Me | 2-Me, 5-F |
| 16091 | Me | 2-Me, 5-NO$_2$ |
| 16092 | Me | 2-Me, 5-NH$_2$ |
| 16093 | Me | 2-Me, 5-NHMe |
| 16094 | Me | 2-Me, 5-NMe$_2$ |
| 16095 | Me | 2-Me, 5-NMe$_3$OTf |
| 16096 | Me | 2-Me, 5-NMe$_3$I |
| 16097 | Me | 2-F, 4-Me |
| 16098 | Me | 2-NO$_2$, 4-Me |
| 16099 | Me | 2-NH$_2$, 4-Me |
| 16100 | Me | 2-NHMe, 4-Me |
| 16101 | Me | 2-NMe$_2$, 4-Me |
| 16102 | Me | 2-NMe$_3$, 4-Me |
| 16103 | Me | 2-NMe$_3$OTf, 4-Me |
| 16104 | Me | 2-NMe$_3$I, 4-Me |
| 16105 | Me | 2-SnMe$_3$, 4-F |
| 16106 | Me | 2-SnMe$_3$, 5-F |
| 16107 | Me | 2-F, 4-SnMe$_3$ |
| 16108 | Me | 2-Br, 6-Cl, 4-F |
| 16109 | Me | 2-Br, 6-Cl, 4-NO$_2$ |
| 16110 | Me | 2-Br, 6-Cl, 4-NH$_2$ |
| 16111 | Me | 2-Br, 6-Cl, 4-NHMe |
| 16112 | Me | 2-Br, 6-Cl, 4-NMe$_2$ |
| 16113 | Me | 2-Br, 6-Cl, 4-NMe$_3$OTf |
| 16114 | Me | 2-Br, 6-Cl, 4-NMe$_3$I |
| 16115 | Me | 2-Me, 6-Cl, 4-F |
| 16116 | Me | 2-SnMe$_3$, 6-Cl, 4-F |
| 16117 | Me | 2-Cl, 4-Me |
| 16118 | Me | 2-Cl, 4-Br |
| 16119 | Me | 2-Cl, 4-SnMe$_3$ |
| 16120 | Me | 2-Br, 4-Cl |
| 16121 | Me | 2-SnMe$_3$, 4-Cl |
| 16122 | Me | 2-Me, 4-Cl |
| 16123 | Me | 2-Br, 4-Br |
| 16124 | Me | 2-Br, 4-Me |
| 16125 | Me | 2-Br, 4-SnMe$_3$ |
| 16126 | Me | 2-SnMe$_3$, 4-Br |
| 16127 | Me | 2-Me, 4-Br |
| 16128 | Me | 2-Me, 4-SnMe$_3$ |
| 16129 | Me | 2-SnMe$_3$, 4-Me |
| 16130 | Me | 2-Me, 4-Me |
| 16131 | Me | 2-Et, 4-Br |
| 16132 | Me | 2-Et, 4-SnMe$_3$ |
| 16133 | Me | 2-Et, 4-Me |
| 16134 | Me | 2-Me, 4-Me, 6-Me |
| 16135 | Me | 2-Me, 4-Br, 6-Me |
| 16136 | Me | 2-Me, 4-SnMe$_3$, 6-Me |
| 16137 | Me | 2-Et, 6-Me |
| 16138 | Me | 2-Br, 4-i-Pr |
| 16139 | Me | 2-SnMe$_3$, 4-i-Pr |
| 16140 | Me | 2-Me, 4-i-Pr |
| 16141 | Me | 2-Br, 4-Br, 6-Br |
| 16142 | Me | 2-Br, 4-Me, 6-Br |

TABLE 10-continued

Substituent list for compounds of general structure XV.

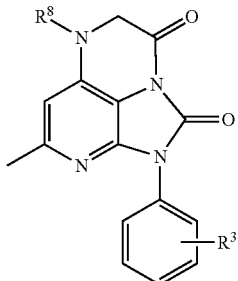

XV

| Compound # | R¹ = | R³ = |
|---|---|---|
| 16143 | Me | 2-Br, 4-SnMe₃, 6-Br |
| 16144 | Me | 2-SnMe₃, 4-Br, 6-Br |
| 16145 | Me | 2-Br, 4-Br, 6-Me |
| 16146 | Me | 2-Br, 4-CF₃, 6-Br |
| 16147 | Me | 2-Br, 4-Br, 6-CF₃ |
| 16148 | Me | 2-CF₃, 4-CF₃ |
| 16149 | Me | 2-Cl, 4-CF₃ |
| 16150 | Me | 2-CF₃, 4-Cl |
| 16151 | Me | 2-Br, 4-CF₃ |
| 16152 | Me | 2-SnMe₃, 4-CF₃ |
| 16153 | Me | 2-Me, 4-CF₃ |
| 16154 | Me | 2-CF₃, 4-Br |
| 16155 | Me | 2-CF₃, 4-SnMe₃ |
| 16156 | Me | 2-CF₃, 4-Me |
| 16157 | Me | 2-Br, 4-OH |
| 16158 | Me | 2-Br, 4-OMe |
| 16159 | Me | 2-Br, 4-OMeF |
| 16160 | Me | 2-Br, 4-OCF₃ |
| 16161 | Me | 2-Br, 4-OEtF |
| 16162 | Me | 2-Br, 4-OPrF |
| 16163 | Me | 2-OH, 4-Br |
| 16164 | Me | 2-OMe, 4-Br |
| 16165 | Me | 2-OMeF, 4-Br |
| 16166 | Me | 2-OCF₃, 4-Br |
| 16167 | Me | 2-OEtF, 4-Br |
| 16168 | Me | 2-OPrF, 4-Br |
| 16169 | Me | 2-I, 4-OH |
| 16170 | Me | 2-I, 4-OMe |
| 16171 | Me | 2-I, 4-OMeF |
| 16172 | Me | 2-I, 4-OCF₃ |
| 16173 | Me | 2-I, 4-OEtF |
| 16174 | Me | 2-I, 4-OPrF |
| 16175 | Me | 2-OH, 4-I |
| 16176 | Me | 2-OMe, 4-I |
| 16177 | Me | 2-OMeF, 4-I |
| 16178 | Me | 2-OCF₃, 4-I |
| 16179 | Me | 2-OEtF, 4-I |
| 16180 | Me | 2-OPrF, 4-I |
| 16181 | Me | 2-SnMe₃, 4-OH |
| 16182 | Me | 2-SnMe₃, 4-OMe |
| 16183 | Me | 2-SnMe₃, 4-OMeF |
| 16184 | Me | 2-SnMe₃, 4-OCF₃ |
| 16185 | Me | 2-SnMe₃, 4-OEtF |
| 16186 | Me | 2-SnMe₃, 4-OPrF |
| 16187 | Me | 2-OH, 4-SnMe₃ |
| 16188 | Me | 2-OMe, 4-SnMe₃ |
| 16189 | Me | 2-OMeF, 4-SnMe₃ |
| 16190 | Me | 2-OCF₃, 4-SnMe₃ |
| 16191 | Me | 2-OEtF, 4-SnMe₃ |
| 16192 | Me | 2-OPrF, 4-SnMe₃ |
| 16193 | Me—F | H |
| 16194 | Me—F | 2-t-Bu |
| 16195 | Me—F | 2-Br |
| 16196 | Me—F | 3-Br |
| 16197 | Me—F | 4-Br |
| 16198 | Me—F | 2-I |
| 16199 | Me—F | 3-I |
| 16200 | Me—F | 4-I |
| 16201 | Me—F | 2-SnMe₃ |
| 16202 | Me—F | 3-SnMe₃ |

TABLE 10-continued

Substituent list for compounds of general structure XV.

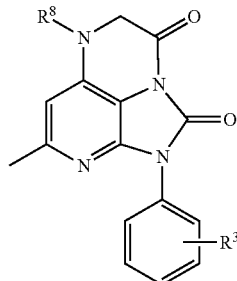

XV

| Compound # | R¹ = | R³ = |
|---|---|---|
| 16203 | Me—F | 4-SnMe₃ |
| 16204 | Me—F | 2-Me |
| 16205 | Me—F | 3-Me |
| 16206 | Me—F | 4-Me |
| 16207 | Me—F | 2-OH |
| 16208 | Me—F | 3-OH |
| 16209 | Me—F | 4-OH |
| 16210 | Me—F | 2-OMe |
| 16211 | Me—F | 3-OMe |
| 16212 | Me—F | 4-OMe |
| 16213 | Me—F | 2-OMeF |
| 16214 | Me—F | 3-OMeF |
| 16215 | Me—F | 4-OMeF |
| 16216 | Me—F | 2-OCF₃ |
| 16217 | Me—F | 3-OCF₃ |
| 16218 | Me—F | 4-OCF₃ |
| 16219 | Me—F | 2-OEtF |
| 16220 | Me—F | 3-OEtF |
| 16221 | Me—F | 4-OEtF |
| 16222 | Me—F | 2-OPrF |
| 16223 | Me—F | 3-OPrF |
| 16224 | Me—F | 4-OPrF |
| 16225 | Me—F | 2-SH |
| 16226 | Me—F | 3-SH |
| 16227 | Me—F | 4-SH |
| 16228 | Me—F | 2-SMe |
| 16229 | Me—F | 3-SMe |
| 16230 | Me—F | 4-SMe |
| 16231 | Me—F | 2-SMeF |
| 16232 | Me—F | 3-SMeF |
| 16233 | Me—F | 4-SMeF |
| 16234 | Me—F | 2-SCF₃ |
| 16235 | Me—F | 3-SCF₃ |
| 16236 | Me—F | 4-SCF₃ |
| 16237 | Me—F | 2-SEtF |
| 16238 | Me—F | 3-SEtF |
| 16239 | Me—F | 4-SEtF |
| 16240 | Me—F | 2-SPrF |
| 16241 | Me—F | 3-SPrF |
| 16242 | Me—F | 4-SPrF |
| 16243 | Me—F | 2-OMe, 4-OMe |
| 16244 | Me—F | 2-Me, 5-OH |
| 16245 | Me—F | 2-Me, 5-OMe |
| 16246 | Me—F | 2-Me, 5-OMeF |
| 16247 | Me—F | 2-Me, 5-OEtF |
| 16248 | Me—F | 2-Me, 5-OPrF |
| 16249 | Me—F | 2-Me, 4-OH |
| 16250 | Me—F | 2-Me, 4-OMe |
| 16251 | Me—F | 2-Me, 4-OMeF |
| 16252 | Me—F | 2-Me, 4-OCF₃ |
| 16253 | Me—F | 2-Me, 4-OEtF |
| 16254 | Me—F | 2-Me, 4-OPrF |
| 16255 | Me—F | 2-OH, 4-Me |
| 16256 | Me—F | 2-OMe, 4-Me |
| 16257 | Me—F | 2-OMeF, 4-Me |
| 16258 | Me—F | 2-OCF₃, 4-Me |
| 16259 | Me—F | 2-OEtF, 4-Me |
| 16260 | Me—F | 2-OPrF, 4-Me |
| 16261 | Me—F | 2-Cl, 4-OH |
| 16262 | Me—F | 2-Cl, 4-OMe |

TABLE 10-continued

Substituent list for compounds of general structure XV.

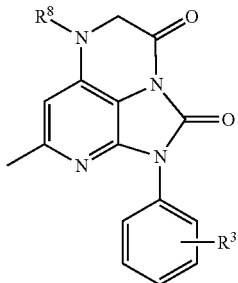

| Compound # | R¹ = | R³ = |
|---|---|---|
| 16263 | Me—F | 2-Cl, 4-OMeF |
| 16264 | Me—F | 2-Cl, 4-OCF₃ |
| 16265 | Me—F | 2-Cl, 4-OEtF |
| 16266 | Me—F | 2-Cl, 4-OPrF |
| 16267 | Me—F | 2-F, 4-F |
| 16268 | Me—F | 2-Cl, 4-Cl |
| 16269 | Me—F | 2-Cl, 4-F |
| 16270 | Me—F | 2-Cl, 4-NO₂ |
| 16271 | Me—F | 2-Cl, 4-NH₂ |
| 16272 | Me—F | 2-Cl, 4-NHMe |
| 16273 | Me—F | 2-Cl, 4-NMe₂ |
| 16274 | Me—F | 2-Cl, 4-NMe₃OTf |
| 16275 | Me—F | 2-Cl, 4-NMe₃I |
| 16276 | Me—F | 2-Cl, 5-F |
| 16277 | Me—F | 2-Cl, 5-NO₂ |
| 16278 | Me—F | 2-Cl, 5-NH₂ |
| 16279 | Me—F | 2-Cl, 5-NHMe |
| 16280 | Me—F | 2-Cl, 5-NMe₂ |
| 16281 | Me—F | 2-Cl, 5-NMe₃OTf |
| 16282 | Me—F | 2-Cl, 5-NMe₃I |
| 16283 | Me—F | 2-F, 4-Cl |
| 16284 | Me—F | 2-NO₂, 4-Cl |
| 16285 | Me—F | 2-NH₂, 4-Cl |
| 16286 | Me—F | 2-NHMe, 4-Cl |
| 16287 | Me—F | 2-NMe₂, 4-Cl |
| 16288 | Me—F | 2-NMe₃OTf, 4-Cl |
| 16289 | Me—F | 2-NMe₃I, 4-Cl |
| 16290 | Me—F | 2-F, 5-Cl |
| 16291 | Me—F | 2-NO₂, 5-Cl |
| 16292 | Me—F | 2-NH₂, 5-Cl |
| 16293 | Me—F | 2-NHMe, 5-Cl |
| 16294 | Me—F | 2-NMe₂, 5-Cl |
| 16295 | Me—F | 2-NMe₃OTf, 5-Cl |
| 16296 | Me—F | 2-NMe₃I, 5-Cl |
| 16297 | Me—F | 2-Br, 4-F |
| 16298 | Me—F | 2-Br, 4-NO₂ |
| 16299 | Me—F | 2-Br, 4-NH₂ |
| 16300 | Me—F | 2-Br, 4-NHMe |
| 16301 | Me—F | 2-Br, 4-NMe₂ |
| 16302 | Me—F | 2-Br, 4-NMe₃OTf |
| 16303 | Me—F | 2-Br, 4-NMe₃I |
| 16304 | Me—F | 2-Br, 5-F |
| 16305 | Me—F | 2-Br, 5-NO₂ |
| 16306 | Me—F | 2-Br, 5-NH₂ |
| 16307 | Me—F | 2-Br, 5-NHMe |
| 16308 | Me—F | 2-Br, 5-NMe₂ |
| 16309 | Me—F | 2-Br, 5-NMe₃OTf |
| 16310 | Me—F | 2-Br, 5-NMe₃I |
| 16311 | Me—F | 2-F, 4-Br |
| 16312 | Me—F | 2-NO₂, 4-Br |
| 16313 | Me—F | 2-NH₂, 4-Br |
| 16314 | Me—F | 2-NHMe, 4-Br |
| 16315 | Me—F | 2-NMe₂, 4-Br |
| 16316 | Me—F | 2-NMe₃OTf, 4-Br |
| 16317 | Me—F | 2-NMe₃I, 4-Br |
| 16318 | Me—F | 2-I, 4-F |
| 16319 | Me—F | 2-I, 4-NO₂ |
| 16320 | Me—F | 2-I, 4-NH₂ |
| 16321 | Me—F | 2-I, 4-NHMe |
| 16322 | Me—F | 2-I, 4-NMe₂ |

TABLE 10-continued

Substituent list for compounds of general structure XV.

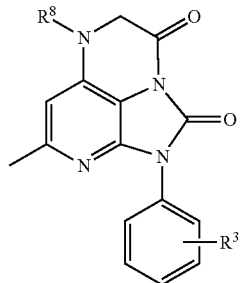

| Compound # | R¹ = | R³ = |
|---|---|---|
| 16323 | Me—F | 2-I, 4-NMe₃OTf |
| 16324 | Me—F | 2-I, 4-NMe₃I |
| 16325 | Me—F | 2-F, 4-I |
| 16326 | Me—F | 2-NO₂, 4-I |
| 16327 | Me—F | 2-NH₂, 4-I |
| 16328 | Me—F | 2-NHMe, 4-I |
| 16329 | Me—F | 2-NMe₂, 4-I |
| 16330 | Me—F | 2-NMe₃OTf, 4-I |
| 16331 | Me—F | 2-NMe₃I, 4-I |
| 16332 | Me—F | 2-Me, 3-F |
| 16333 | Me—F | 2-Me, 3-NO₂ |
| 16334 | Me—F | 2-Me, 3-NH₂ |
| 16335 | Me—F | 2-Me, 3-NHMe |
| 16336 | Me—F | 2-Me, 3-NMe₂ |
| 16337 | Me—F | 2-Me, 3-NMe₃OTf |
| 16338 | Me—F | 2-Me, 3-NMe₃I |
| 16339 | Me—F | 2-Me, 4-F |
| 16340 | Me—F | 2-Me, 4-NO₂ |
| 16341 | Me—F | 2-Me, 4-NH₂ |
| 16342 | Me—F | 2-Me, 4-NHMe |
| 16343 | Me—F | 2-Me, 4-NMe₂ |
| 16344 | Me—F | 2-Me, 4-NMe₃OTf |
| 16345 | Me—F | 2-Me, 4-NMe₃I |
| 16346 | Me—F | 2-Me, 5-F |
| 16347 | Me—F | 2-Me, 5-NO₂ |
| 16348 | Me—F | 2-Me, 5-NH₂ |
| 16349 | Me—F | 2-Me, 5-NHMe |
| 16350 | Me—F | 2-Me, 5-NMe₂ |
| 16351 | Me—F | 2-Me, 5-NMe₃OTf |
| 16352 | Me—F | 2-Me, 5-NMe₃I |
| 16353 | Me—F | 2-F, 4-Me |
| 16354 | Me—F | 2-NO₂, 4-Me |
| 16355 | Me—F | 2-NH₂, 4-Me |
| 16356 | Me—F | 2-NHMe, 4-Me |
| 16357 | Me—F | 2-NMe₂, 4-Me |
| 16358 | Me—F | 2-NMe₃, 4-Me |
| 16359 | Me—F | 2-NMe₃OTf, 4-Me |
| 16360 | Me—F | 2-NMe₃I, 4-Me |
| 16361 | Me—F | 2-SnMe₃, 4-F |
| 16362 | Me—F | 2-SnMe₃, 5-F |
| 16363 | Me—F | 2-F, 4-SnMe₃ |
| 16364 | Me—F | 2-Br, 6-Cl, 4-F |
| 16365 | Me—F | 2-Br, 6-Cl, 4-NO₂ |
| 16366 | Me—F | 2-Br, 6-Cl, 4-NH₂ |
| 16367 | Me—F | 2-Br, 6-Cl, 4-NHMe |
| 16368 | Me—F | 2-Br, 6-Cl, 4-NMe₂ |
| 16369 | Me—F | 2-Br, 6-Cl, 4-NMe₃OTf |
| 16370 | Me—F | 2-Br, 6-Cl, 4-NMe₃I |
| 16371 | Me—F | 2-Me, 6-Cl, 4-F |
| 16372 | Me—F | 2-SnMe₃, 6-Cl, 4-F |
| 16373 | Me—F | 2-Cl, 4-Me |
| 16374 | Me—F | 2-Cl, 4-Br |
| 16375 | Me—F | 2-Cl, 4-SnMe₃ |
| 16376 | Me—F | 2-Br, 4-Cl |
| 16377 | Me—F | 2-SnMe₃, 4-Cl |
| 16378 | Me—F | 2-Me, 4-Cl |
| 16379 | Me—F | 2-Br, 4-Br |
| 16380 | Me—F | 2-Br, 4-Me |
| 16381 | Me—F | 2-Br, 4-SnMe₃ |
| 16382 | Me—F | 2-SnMe₃, 4-Br |

TABLE 10-continued

Substituent list for compounds of general structure XV.

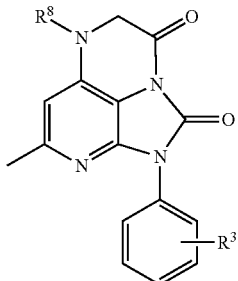

| Compound # | R¹ = | R³ = |
|---|---|---|
| 16383 | Me—F | 2-Me, 4-Br |
| 16384 | Me—F | 2-Me, 4-SnMe₃ |
| 16385 | Me—F | 2-SnMe₃, 4-Me |
| 16386 | Me—F | 2-Me, 4-Me |
| 16387 | Me—F | 2-Et, 4-Br |
| 16388 | Me—F | 2-Et, 4-SnMe₃ |
| 16389 | Me—F | 2-Et, 4-Me |
| 16390 | Me—F | 2-Me, 4-Me, 6-Me |
| 16391 | Me—F | 2-Me, 4-Br, 6-Me |
| 16392 | Me—F | 2-Me, 4-SnMe₃, 6-Me |
| 16393 | Me—F | 2-Et, 6-Me |
| 16394 | Me—F | 2-Br, 4-i-Pr |
| 16395 | Me—F | 2-SnMe₃, 4-i-Pr |
| 16396 | Me—F | 2-Me, 4-i-Pr |
| 16397 | Me—F | 2-Br, 4-Br, 6-Br |
| 16398 | Me—F | 2-Br, 4-Me, 6-Br |
| 16399 | Me—F | 2-Br, 4-SnMe₃, 6-Br |
| 16400 | Me—F | 2-SnMe₃, 4-Br, 6-Br |
| 16401 | Me—F | 2-Br, 4-Br, 6-Me |
| 16402 | Me—F | 2-Br, 4-CF₃, 6-Br |
| 16403 | Me—F | 2-Br, 4-Br, 6-CF₃ |
| 16404 | Me—F | 2-CF₃, 4-CF₃ |
| 16405 | Me—F | 2-Cl, 4-CF₃ |
| 16406 | Me—F | 2-CF₃, 4-Cl |
| 16407 | Me—F | 2-Br, 4-CF₃ |
| 16408 | Me—F | 2-SnMe₃, 4-CF₃ |
| 16409 | Me—F | 2-Me, 4-CF₃ |
| 16410 | Me—F | 2-CF₃, 4-Br |
| 16411 | Me—F | 2-CF₃, 4-SnMe₃ |
| 16412 | Me—F | 2-CF₃, 4-Me |
| 16413 | Me—F | 2-Br, 4-OH |
| 16414 | Me—F | 2-Br, 4-OMe |
| 16415 | Me—F | 2-Br, 4-OMeF |
| 16416 | Me—F | 2-Br, 4-OCF₃ |
| 16417 | Me—F | 2-Br, 4-OEtF |
| 16418 | Me—F | 2-Br, 4-OPrF |
| 16419 | Me—F | 2-OH, 4-Br |
| 16420 | Me—F | 2-OMe, 4-Br |
| 16421 | Me—F | 2-OMeF, 4-Br |
| 16422 | Me—F | 2-OCF₃, 4-Br |
| 16423 | Me—F | 2-OEtF, 4-Br |
| 16424 | Me—F | 2-OPrF, 4-Br |
| 16425 | Me—F | 2-I, 4-OH |
| 16426 | Me—F | 2-I, 4-OMe |
| 16427 | Me—F | 2-I, 4-OMeF |
| 16428 | Me—F | 2-I, 4-OCF₃ |
| 16429 | Me—F | 2-I, 4-OEtF |
| 16430 | Me—F | 2-I, 4-OPrF |
| 16431 | Me—F | 2-OH, 4-I |
| 16432 | Me—F | 2-OMe, 4-I |
| 16433 | Me—F | 2-OMeF, 4-I |
| 16434 | Me—F | 2-OCF₃, 4-I |
| 16435 | Me—F | 2-OEtF, 4-I |
| 16436 | Me—F | 2-OPrF, 4-I |
| 16437 | Me—F | 2-SnMe₃, 4-OH |
| 16438 | Me—F | 2-SnMe₃, 4-OMe |
| 16439 | Me—F | 2-SnMe₃, 4-OMeF |
| 16440 | Me—F | 2-SnMe₃, 4-OCF₃ |
| 16441 | Me—F | 2-SnMe₃, 4-OEtF |
| 16442 | Me—F | 2-SnMe₃, 4-OPrF |

TABLE 10-continued

Substituent list for compounds of general structure XV.

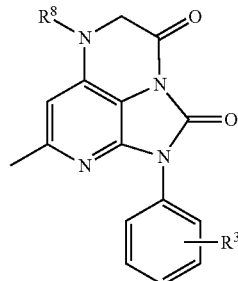

| Compound # | R¹ = | R³ = |
|---|---|---|
| 16443 | Me—F | 2-OH, 4-SnMe₃ |
| 16444 | Me—F | 2-OMe, 4-SnMe₃ |
| 16445 | Me—F | 2-OMeF, 4-SnMe₃ |
| 16446 | Me—F | 2-OCF₃, 4-SnMe₃ |
| 16447 | Me—F | 2-OEtF, 4-SnMe₃ |
| 16448 | Me—F | 2-OPrF, 4-SnMe₃ |
| 16449 | FCH₂—CH=CH—CH₂ | H |
| 16450 | FCH₂—CH=CH—CH₂ | 2-t-Bu |
| 16451 | FCH₂—CH=CH—CH₂ | 2-Br |
| 16452 | FCH₂—CH=CH—CH₂ | 3-Br |
| 16453 | FCH₂—CH=CH—CH₂ | 4-Br |
| 16454 | FCH₂—CH=CH—CH₂ | 2-I |
| 16455 | FCH₂—CH=CH—CH₂ | 3-I |
| 16456 | FCH₂—CH=CH—CH₂ | 4-I |
| 16457 | FCH₂—CH=CH—CH₂ | 2-SnMe₃ |
| 16458 | FCH₂—CH=CH—CH₂ | 3-SnMe₃ |
| 16459 | FCH₂—CH=CH—CH₂ | 4-SnMe₃ |
| 16460 | FCH₂—CH=CH—CH₂ | 2-Me |
| 16461 | FCH₂—CH=CH—CH₂ | 3-Me |
| 16462 | FCH₂—CH=CH—CH₂ | 4-Me |
| 16463 | FCH₂—CH=CH—CH₂ | 2-OH |
| 16464 | FCH₂—CH=CH—CH₂ | 3-OH |
| 16465 | FCH₂—CH=CH—CH₂ | 4-OH |
| 16466 | FCH₂—CH=CH—CH₂ | 2-OMe |
| 16467 | FCH₂—CH=CH—CH₂ | 3-OMe |
| 16468 | FCH₂—CH=CH—CH₂ | 4-OMe |
| 16469 | FCH₂—CH=CH—CH₂ | 2-OMeF |
| 16470 | FCH₂—CH=CH—CH₂ | 3-OMeF |
| 16471 | FCH₂—CH=CH—CH₂ | 4-OMeF |
| 16472 | FCH₂—CH=CH—CH₂ | 2-OCF₃ |
| 16473 | FCH₂—CH=CH—CH₂ | 3-OCF₃ |
| 16474 | FCH₂—CH=CH—CH₂ | 4-OCF₃ |
| 16475 | FCH₂—CH=CH—CH₂ | 2-OEtF |
| 16476 | FCH₂—CH=CH—CH₂ | 3-OEtF |
| 16477 | FCH₂—CH=CH—CH₂ | 4-OEtF |
| 16478 | FCH₂—CH=CH—CH₂ | 2-OPrF |
| 16479 | FCH₂—CH=CH—CH₂ | 3-OPrF |
| 16480 | FCH₂—CH=CH—CH₂ | 4-OPrF |
| 16481 | FCH₂—CH=CH—CH₂ | 2-SH |
| 16482 | FCH₂—CH=CH—CH₂ | 3-SH |
| 16483 | FCH₂—CH=CH—CH₂ | 4-SH |
| 16484 | FCH₂—CH=CH—CH₂ | 2-SMe |
| 16485 | FCH₂—CH=CH—CH₂ | 3-SMe |
| 16486 | FCH₂—CH=CH—CH₂ | 4-SMe |
| 16487 | FCH₂—CH=CH—CH₂ | 2-SMeF |
| 16488 | FCH₂—CH=CH—CH₂ | 3-SMeF |
| 16489 | FCH₂—CH=CH—CH₂ | 4-SMeF |
| 16490 | FCH₂—CH=CH—CH₂ | 2-SCF₃ |
| 16491 | FCH₂—CH=CH—CH₂ | 3-SCF₃ |
| 16492 | FCH₂—CH=CH—CH₂ | 4-SCF₃ |
| 16493 | FCH₂—CH=CH—CH₂ | 2-SEtF |
| 16494 | FCH₂—CH=CH—CH₂ | 3-SEtF |
| 16495 | FCH₂—CH=CH—CH₂ | 4-SEtF |
| 16496 | FCH₂—CH=CH—CH₂ | 2-SPrF |
| 16497 | FCH₂—CH=CH—CH₂ | 3-SPrF |
| 16498 | FCH₂—CH=CH—CH₂ | 4-SPrF |
| 16499 | FCH₂—CH=CH—CH₂ | 2-OMe, 4-OMe |
| 16500 | FCH₂—CH=CH—CH₂ | 2-Me, 5-OH |
| 16501 | FCH₂—CH=CH—CH₂ | 2-Me, 5-OMe |
| 16502 | FCH₂—CH=CH—CH₂ | 2-Me, 5-OMeF |

TABLE 10-continued

Substituent list for compounds of general structure XV.

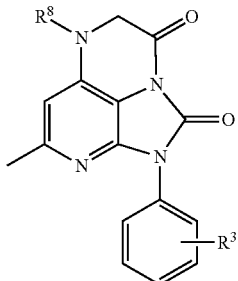

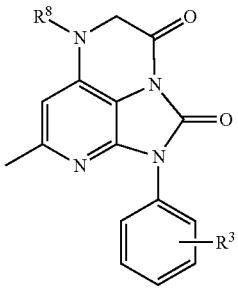

| Compound # | R¹ = | R³ = |
|---|---|---|
| 16503 | FCH$_2$—CH=CH—CH$_2$ | 2-Me, 5-OEtF |
| 16504 | FCH$_2$—CH=CH—CH$_2$ | 2-Me, 5-OPrF |
| 16505 | FCH$_2$—CH=CH—CH$_2$ | 2-Me, 4-OH |
| 16506 | FCH$_2$—CH=CH—CH$_2$ | 2-Me, 4-OMe |
| 16507 | FCH$_2$—CH=CH—CH$_2$ | 2-Me, 4-OMeF |
| 16508 | FCH$_2$—CH=CH—CH$_2$ | 2-Me, 4-OCF$_3$ |
| 16509 | FCH$_2$—CH=CH—CH$_2$ | 2-Me, 4-OEtF |
| 16510 | FCH$_2$—CH=CH—CH$_2$ | 2-Me, 4-OPrF |
| 16511 | FCH$_2$—CH=CH—CH$_2$ | 2-OH, 4-Me |
| 16512 | FCH$_2$—CH=CH—CH$_2$ | 2-OMe, 4-Me |
| 16513 | FCH$_2$—CH=CH—CH$_2$ | 2-OMeF, 4-Me |
| 16514 | FCH$_2$—CH=CH—CH$_2$ | 2-OCF$_3$, 4-Me |
| 16515 | FCH$_2$—CH=CH—CH$_2$ | 2-OEtF, 4-Me |
| 16516 | FCH$_2$—CH=CH—CH$_2$ | 2-OPrF, 4-Me |
| 16517 | FCH$_2$—CH=CH—CH$_2$ | 2-Cl, 4-OH |
| 16518 | FCH$_2$—CH=CH—CH$_2$ | 2-Cl, 4-OMe |
| 16519 | FCH$_2$—CH=CH—CH$_2$ | 2-Cl, 4-OMeF |
| 16520 | FCH$_2$—CH=CH—CH$_2$ | 2-Cl, 4-OCF$_3$ |
| 16521 | FCH$_2$—CH=CH—CH$_2$ | 2-Cl, 4-OEtF |
| 16522 | FCH$_2$—CH=CH—CH$_2$ | 2-Cl, 4-OPrF |
| 16523 | FCH$_2$—CH=CH—CH$_2$ | 2-F, 4-F |
| 16524 | FCH$_2$—CH=CH—CH$_2$ | 2-Cl, 4-Cl |
| 16525 | FCH$_2$—CH=CH—CH$_2$ | 2-Cl, 4-F |
| 16526 | FCH$_2$—CH=CH—CH$_2$ | 2-Cl, 4-NO$_2$ |
| 16527 | FCH$_2$—CH=CH—CH$_2$ | 2-Cl, 4-NH$_2$ |
| 16528 | FCH$_2$—CH=CH—CH$_2$ | 2-Cl, 4-NHMe |
| 16529 | FCH$_2$—CH=CH—CH$_2$ | 2-Cl, 4-NMe$_2$ |
| 16530 | FCH$_2$—CH=CH—CH$_2$ | 2-Cl, 4-NMe$_3$OTf |
| 16531 | FCH$_2$—CH=CH—CH$_2$ | 2-Cl, 4-NMe$_3$I |
| 16532 | FCH$_2$—CH=CH—CH$_2$ | 2-Cl, 5-F |
| 16533 | FCH$_2$—CH=CH—CH$_2$ | 2-Cl, 5-NO$_2$ |
| 16534 | FCH$_2$—CH=CH—CH$_2$ | 2-Cl, 5-NH$_2$ |
| 16535 | FCH$_2$—CH=CH—CH$_2$ | 2-Cl, 5-NHMe |
| 16536 | FCH$_2$—CH=CH—CH$_2$ | 2-Cl, 5-NMe$_2$ |
| 16537 | FCH$_2$—CH=CH—CH$_2$ | 2-Cl, 5-NMe$_3$OTf |
| 16538 | FCH$_2$—CH=CH—CH$_2$ | 2-Cl, 5-NMe$_3$I |
| 16539 | FCH$_2$—CH=CH—CH$_2$ | 2-F, 4-Cl |
| 16540 | FCH$_2$—CH=CH—CH$_2$ | 2-NO$_2$, 4-Cl |
| 16541 | FCH$_2$—CH=CH—CH$_2$ | 2-NH$_2$, 4-Cl |
| 16542 | FCH$_2$—CH=CH—CH$_2$ | 2-NHMe, 4-Cl |
| 16543 | FCH$_2$—CH=CH—CH$_2$ | 2-NMe$_2$, 4-Cl |
| 16544 | FCH$_2$—CH=CH—CH$_2$ | 2-NMe$_3$OTf, 4-Cl |
| 16545 | FCH$_2$—CH=CH—CH$_2$ | 2-NMe$_3$I, 4-Cl |
| 16546 | FCH$_2$—CH=CH—CH$_2$ | 2-F, 5-Cl |
| 16547 | FCH$_2$—CH=CH—CH$_2$ | 2-NO$_2$, 5-Cl |
| 16548 | FCH$_2$—CH=CH—CH$_2$ | 2-NH$_2$, 5-Cl |
| 16549 | FCH$_2$—CH=CH—CH$_2$ | 2-NHMe, 5-Cl |
| 16550 | FCH$_2$—CH=CH—CH$_2$ | 2-NMe$_2$, 5-Cl |
| 16551 | FCH$_2$—CH=CH—CH$_2$ | 2-NMe$_3$OTf, 5-Cl |
| 16552 | FCH$_2$—CH=CH—CH$_2$ | 2-NMe$_3$I, 5-Cl |
| 16553 | FCH$_2$—CH=CH—CH$_2$ | 2-Br, 4-F |
| 16554 | FCH$_2$—CH=CH—CH$_2$ | 2-Br, 4-NO$_2$ |
| 16555 | FCH$_2$—CH=CH—CH$_2$ | 2-Br, 4-NH$_2$ |
| 16556 | FCH$_2$—CH=CH—CH$_2$ | 2-Br, 4-NHMe |
| 16557 | FCH$_2$—CH=CH—CH$_2$ | 2-Br, 4-NMe$_2$ |
| 16558 | FCH$_2$—CH=CH—CH$_2$ | 2-Br, 4-NMe$_3$OTf |
| 16559 | FCH$_2$—CH=CH—CH$_2$ | 2-Br, 4-NMe$_3$I |
| 16560 | FCH$_2$—CH=CH—CH$_2$ | 2-Br, 5-F |
| 16561 | FCH$_2$—CH=CH—CH$_2$ | 2-Br, 5-NO$_2$ |
| 16562 | FCH$_2$—CH=CH—CH$_2$ | 2-Br, 5-NH$_2$ |
| 16563 | FCH$_2$—CH=CH—CH$_2$ | 2-Br, 5-NHMe |
| 16564 | FCH$_2$—CH=CH—CH$_2$ | 2-Br, 5-NMe$_2$ |
| 16565 | FCH$_2$—CH=CH—CH$_2$ | 2-Br, 5-NMe$_3$OTf |
| 16566 | FCH$_2$—CH=CH—CH$_2$ | 2-Br, 5-NMe$_3$I |
| 16567 | FCH$_2$—CH=CH—CH$_2$ | 2-F, 4-Br |
| 16568 | FCH$_2$—CH=CH—CH$_2$ | 2-NO$_2$, 4-Br |
| 16569 | FCH$_2$—CH=CH—CH$_2$ | 2-NH$_2$, 4-Br |
| 16570 | FCH$_2$—CH=CH—CH$_2$ | 2-NHMe, 4-Br |
| 16571 | FCH$_2$—CH=CH—CH$_2$ | 2-NMe$_2$, 4-Br |
| 16572 | FCH$_2$—CH=CH—CH$_2$ | 2-NMe$_3$OTf, 4-Br |
| 16573 | FCH$_2$—CH=CH—CH$_2$ | 2-NMe$_3$I, 4-Br |
| 16574 | FCH$_2$—CH=CH—CH$_2$ | 2-I, 4-F |
| 16575 | FCH$_2$—CH=CH—CH$_2$ | 2-I, 4-NO$_2$ |
| 16576 | FCH$_2$—CH=CH—CH$_2$ | 2-I, 4-NH$_2$ |
| 16577 | FCH$_2$—CH=CH—CH$_2$ | 2-I, 4-NHMe |
| 16578 | FCH$_2$—CH=CH—CH$_2$ | 2-I, 4-NMe$_2$ |
| 16579 | FCH$_2$—CH=CH—CH$_2$ | 2-I, 4-NMe$_3$OTf |
| 16580 | FCH$_2$—CH=CH—CH$_2$ | 2-I, 4-NMe$_3$I |
| 16581 | FCH$_2$—CH=CH—CH$_2$ | 2-F, 4-I |
| 16582 | FCH$_2$—CH=CH—CH$_2$ | 2-NO$_2$, 4-I |
| 16583 | FCH$_2$—CH=CH—CH$_2$ | 2-NH$_2$, 4-I |
| 16584 | FCH$_2$—CH=CH—CH$_2$ | 2-NHMe, 4-I |
| 16585 | FCH$_2$—CH=CH—CH$_2$ | 2-NMe$_2$, 4-I |
| 16586 | FCH$_2$—CH=CH—CH$_2$ | 2-NMe$_3$OTf, 4-I |
| 16587 | FCH$_2$—CH=CH—CH$_2$ | 2-NMe$_3$I, 4-I |
| 16588 | FCH$_2$—CH=CH—CH$_2$ | 2-Me, 3-F |
| 16589 | FCH$_2$—CH=CH—CH$_2$ | 2-Me, 3-NO$_2$ |
| 16590 | FCH$_2$—CH=CH—CH$_2$ | 2-Me, 3-NH$_2$ |
| 16591 | FCH$_2$—CH=CH—CH$_2$ | 2-Me, 3-NHMe |
| 16592 | FCH$_2$—CH=CH—CH$_2$ | 2-Me, 3-NMe$_2$ |
| 16593 | FCH$_2$—CH=CH—CH$_2$ | 2-Me, 3-NMe$_3$OTf |
| 16594 | FCH$_2$—CH=CH—CH$_2$ | 2-Me, 3-NMe$_3$I |
| 16595 | FCH$_2$—CH=CH—CH$_2$ | 2-Me, 4-F |
| 16596 | FCH$_2$—CH=CH—CH$_2$ | 2-Me, 4-NO$_2$ |
| 16597 | FCH$_2$—CH=CH—CH$_2$ | 2-Me, 4-NH$_2$ |
| 16598 | FCH$_2$—CH=CH—CH$_2$ | 2-Me, 4-NHMe |
| 16599 | FCH$_2$—CH=CH—CH$_2$ | 2-Me, 4-NMe$_2$ |
| 16600 | FCH$_2$—CH=CH—CH$_2$ | 2-Me, 4-NMe$_3$OTf |
| 16601 | FCH$_2$—CH=CH—CH$_2$ | 2-Me, 4-NMe$_3$I |
| 16602 | FCH$_2$—CH=CH—CH$_2$ | 2-Me, 5-F |
| 16603 | FCH$_2$—CH=CH—CH$_2$ | 2-Me, 5-NO$_2$ |
| 16604 | FCH$_2$—CH=CH—CH$_2$ | 2-Me, 5-NH$_2$ |
| 16605 | FCH$_2$—CH=CH—CH$_2$ | 2-Me, 5-NHMe |
| 16606 | FCH$_2$—CH=CH—CH$_2$ | 2-Me, 5-NMe$_2$ |
| 16607 | FCH$_2$—CH=CH—CH$_2$ | 2-Me, 5-NMe$_3$OTf |
| 16608 | FCH$_2$—CH=CH—CH$_2$ | 2-Me, 5-NMe$_3$I |
| 16609 | FCH$_2$—CH=CH—CH$_2$ | 2-F, 4-Me |
| 16610 | FCH$_2$—CH=CH—CH$_2$ | 2-NO$_2$, 4-Me |
| 16611 | FCH$_2$—CH=CH—CH$_2$ | 2-NH$_2$, 4-Me |
| 16612 | FCH$_2$—CH=CH—CH$_2$ | 2-NHMe, 4-Me |
| 16613 | FCH$_2$—CH=CH—CH$_2$ | 2-NMe$_2$, 4-Me |
| 16614 | FCH$_2$—CH=CH—CH$_2$ | 2-NMe$_3$, 4-Me |
| 16615 | FCH$_2$—CH=CH—CH$_2$ | 2-NMe$_3$OTf, 4-Me |
| 16616 | FCH$_2$—CH=CH—CH$_2$ | 2-NMe$_3$I, 4-Me |
| 16617 | FCH$_2$—CH=CH—CH$_2$ | 2-SnMe$_3$, 4-F |
| 16618 | FCH$_2$—CH=CH—CH$_2$ | 2-SnMe$_3$, 5-F |
| 16619 | FCH$_2$—CH=CH—CH$_2$ | 2-F, 4-SnMe$_3$ |
| 16620 | FCH$_2$—CH=CH—CH$_2$ | 2-Br, 6-Cl, 4-F |
| 16621 | FCH$_2$—CH=CH—CH$_2$ | 2-Br, 6-Cl, 4-NO$_2$ |
| 16622 | FCH$_2$—CH=CH—CH$_2$ | 2-Br, 6-Cl, 4-NH$_2$ |

TABLE 10-continued

Substituent list for compounds of general structure XV.

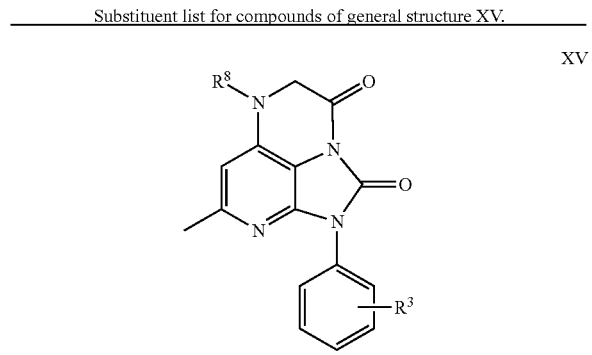

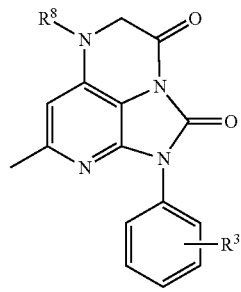

| Compound # | R¹ = | R³ = |
|---|---|---|
| 16623 | FCH₂—CH=CH—CH₂ | 2-Br, 6-Cl, 4-NHMe |
| 16624 | FCH₂—CH=CH—CH₂ | 2-Br, 6-Cl, 4-NMe₂ |
| 16625 | FCH₂—CH=CH—CH₂ | 2-Br, 6-Cl, 4-NMe₃OTf |
| 16626 | FCH₂—CH=CH—CH₂ | 2-Br, 6-Cl, 4-NMe₃I |
| 16627 | FCH₂—CH=CH—CH₂ | 2-Me, 6-Cl, 4-F |
| 16628 | FCH₂—CH=CH—CH₂ | 2-SnMe₃, 6-Cl, 4-F |
| 16629 | FCH₂—CH=CH—CH₂ | 2-Cl, 4-Me |
| 16630 | FCH₂—CH=CH—CH₂ | 2-Cl, 4-Br |
| 16631 | FCH₂—CH=CH—CH₂ | 2-Cl, 4-SnMe₃ |
| 16632 | FCH₂—CH=CH—CH₂ | 2-Br, 4-Cl |
| 16633 | FCH₂—CH=CH—CH₂ | 2-SnMe₃, 4-Cl |
| 16634 | FCH₂—CH=CH—CH₂ | 2-Me, 4-Cl |
| 16635 | FCH₂—CH=CH—CH₂ | 2-Br, 4-Br |
| 16636 | FCH₂—CH=CH—CH₂ | 2-Br, 4-Me |
| 16637 | FCH₂—CH=CH—CH₂ | 2-Br, 4-SnMe₃ |
| 16638 | FCH₂—CH=CH—CH₂ | 2-SnMe₃, 4-Br |
| 16639 | FCH₂—CH=CH—CH₂ | 2-Me, 4-Br |
| 16640 | FCH₂—CH=CH—CH₂ | 2-Me, 4-SnMe₃ |
| 16641 | FCH₂—CH=CH—CH₂ | 2-SnMe₃, 4-Me |
| 16642 | FCH₂—CH=CH—CH₂ | 2-Me, 4-Me |
| 16643 | FCH₂—CH=CH—CH₂ | 2-Et, 4-Br |
| 16644 | FCH₂—CH=CH—CH₂ | 2-Et, 4-SnMe₃ |
| 16645 | FCH₂—CH=CH—CH₂ | 2-Et, 4-Me |
| 16646 | FCH₂—CH=CH—CH₂ | 2-Me, 4-Me, 6-Me |
| 16647 | FCH₂—CH=CH—CH₂ | 2-Me, 4-Br, 6-Me |
| 16648 | FCH₂—CH=CH—CH₂ | 2-Me, 4-SnMe₃, 6-Me |
| 16649 | FCH₂—CH=CH—CH₂ | 2-Et, 6-Me |
| 16650 | FCH₂—CH=CH—CH₂ | 2-Br, 4-i-Pr |
| 16651 | FCH₂—CH=CH—CH₂ | 2-SnMe₃, 4-i-Pr |
| 16652 | FCH₂—CH=CH—CH₂ | 2-Me, 4-i-Pr |
| 16653 | FCH₂—CH=CH—CH₂ | 2-Br, 4-Br, 6-Br |
| 16654 | FCH₂—CH=CH—CH₂ | 2-Br, 4-Me, 6-Br |
| 16655 | FCH₂—CH=CH—CH₂ | 2-Br, 4-SnMe₃, 6-Br |
| 16656 | FCH₂—CH=CH—CH₂ | 2-SnMe₃, 4-Br, 6-Br |
| 16657 | FCH₂—CH=CH—CH₂ | 2-Br, 4-Br, 6-Me |
| 16658 | FCH₂—CH=CH—CH₂ | 2-Br, 4-CF₃, 6-Br |
| 16659 | FCH₂—CH=CH—CH₂ | 2-Br, 4-Br, 6-CF₃ |
| 16660 | FCH₂—CH=CH—CH₂ | 2-CF₃, 4-CF₃ |
| 16661 | FCH₂—CH=CH—CH₂ | 2-Cl, 4-CF₃ |
| 16662 | FCH₂—CH=CH—CH₂ | 2-CF₃, 4-Cl |
| 16663 | FCH₂—CH=CH—CH₂ | 2-Br, 4-CF₃ |
| 16664 | FCH₂—CH=CH—CH₂ | 2-SnMe₃, 4-CF₃ |
| 16665 | FCH₂—CH=CH—CH₂ | 2-Me, 4-CF₃ |
| 16666 | FCH₂—CH=CH—CH₂ | 2-CF₃, 4-Br |
| 16667 | FCH₂—CH=CH—CH₂ | 2-CF₃, 4-SnMe₃ |
| 16668 | FCH₂—CH=CH—CH₂ | 2-CF₃, 4-Me |
| 16669 | FCH₂—CH=CH—CH₂ | 2-Br, 4-OH |
| 16670 | FCH₂—CH=CH—CH₂ | 2-Br, 4-OMe |
| 16671 | FCH₂—CH=CH—CH₂ | 2-Br, 4-OMeF |
| 16672 | FCH₂—CH=CH—CH₂ | 2-Br, 4-OCF₃ |
| 16673 | FCH₂—CH=CH—CH₂ | 2-Br, 4-OEtF |
| 16674 | FCH₂—CH=CH—CH₂ | 2-Br, 4-OPrF |
| 16675 | FCH₂—CH=CH—CH₂ | 2-OH, 4-Br |
| 16676 | FCH₂—CH=CH—CH₂ | 2-OMe, 4-Br |
| 16677 | FCH₂—CH=CH—CH₂ | 2-OMeF, 4-Br |
| 16678 | FCH₂—CH=CH—CH₂ | 2-OCF₃, 4-Br |
| 16679 | FCH₂—CH=CH—CH₂ | 2-OEtF, 4-Br |
| 16680 | FCH₂—CH=CH—CH₂ | 2-OPrF, 4-Br |
| 16681 | FCH₂—CH=CH—CH₂ | 2-I, 4-OH |
| 16682 | FCH₂—CH=CH—CH₂ | 2-I, 4-OMe |
| 16683 | FCH₂—CH=CH—CH₂ | 2-I, 4-OMeF |
| 16684 | FCH₂—CH=CH—CH₂ | 2-I, 4-OCF₃ |
| 16685 | FCH₂—CH=CH—CH₂ | 2-I, 4-OEtF |
| 16686 | FCH₂—CH=CH—CH₂ | 2-I, 4-OPrF |
| 16687 | FCH₂—CH=CH—CH₂ | 2-OH, 4-I |
| 16688 | FCH₂—CH=CH—CH₂ | 2-OMe, 4-I |
| 16689 | FCH₂—CH=CH—CH₂ | 2-OMeF, 4-I |
| 16690 | FCH₂—CH=CH—CH₂ | 2-OCF₃, 4-I |
| 16691 | FCH₂—CH=CH—CH₂ | 2-OEtF, 4-I |
| 16692 | FCH₂—CH=CH—CH₂ | 2-OPrF, 4-I |
| 16693 | FCH₂—CH=CH—CH₂ | 2-SnMe₃, 4-OH |
| 16694 | FCH₂—CH=CH—CH₂ | 2-SnMe₃, 4-OMe |
| 16695 | FCH₂—CH=CH—CH₂ | 2-SnMe₃, 4-OMeF |
| 16696 | FCH₂—CH=CH—CH₂ | 2-SnMe₃, 4-OCF₃ |
| 16697 | FCH₂—CH=CH—CH₂ | 2-SnMe₃, 4-OEtF |
| 16698 | FCH₂—CH=CH—CH₂ | 2-SnMe₃, 4-OPrF |
| 16699 | FCH₂—CH=CH—CH₂ | 2-OH, 4-SnMe₃ |
| 16700 | FCH₂—CH=CH—CH₂ | 2-OMe, 4-SnMe₃ |
| 16701 | FCH₂—CH=CH—CH₂ | 2-OMeF, 4-SnMe₃ |
| 16702 | FCH₂—CH=CH—CH₂ | 2-OCF₃, 4-SnMe₃ |
| 16703 | FCH₂—CH=CH—CH₂ | 2-OEtF, 4-SnMe₃ |
| 16704 | FCH₂—CH=CH—CH₂ | 2-OPrF, 4-SnMe₃ |
| 16705 | Bn | H |
| 16706 | Bn | 2-t-Bu |
| 16707 | Bn | 2-Br |
| 16708 | Bn | 3-Br |
| 16709 | Bn | 4-Br |
| 16710 | Bn | 2-I |
| 16711 | Bn | 3-I |
| 16712 | Bn | 4-I |
| 16713 | Bn | 2-SnMe₃ |
| 16714 | Bn | 3-SnMe₃ |
| 16715 | Bn | 4-SnMe₃ |
| 16716 | Bn | 2-Me |
| 16717 | Bn | 3-Me |
| 16718 | Bn | 4-Me |
| 16719 | Bn | 2-OH |
| 16720 | Bn | 3-OH |
| 16721 | Bn | 4-OH |
| 16722 | Bn | 2-OMe |
| 16723 | Bn | 3-OMe |
| 16724 | Bn | 4-OMe |
| 16725 | Bn | 2-OMeF |
| 16726 | Bn | 3-OMeF |
| 16727 | Bn | 4-OMeF |
| 16728 | Bn | 2-OCF₃ |
| 16729 | Bn | 3-OCF₃ |
| 16730 | Bn | 4-OCF₃ |
| 16731 | Bn | 2-OEtF |
| 16732 | Bn | 3-OEtF |
| 16733 | Bn | 4-OEtF |
| 16734 | Bn | 2-OPrF |
| 16735 | Bn | 3-OPrF |
| 16736 | Bn | 4-OPrF |
| 16737 | Bn | 2-SH |
| 16738 | Bn | 3-SH |
| 16739 | Bn | 4-SH |
| 16740 | Bn | 2-SMe |
| 16741 | Bn | 3-SMe |
| 16742 | Bn | 4-SMe |

TABLE 10-continued

Substituent list for compounds of general structure XV.

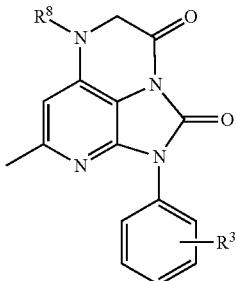

XV

| Compound # | R$^1$ = | R$^3$ = |
|---|---|---|
| 16743 | Bn | 2-SMeF |
| 16744 | Bn | 3-SMeF |
| 16745 | Bn | 4-SMeF |
| 16746 | Bn | 2-SCF$_3$ |
| 16747 | Bn | 3-SCF$_3$ |
| 16748 | Bn | 4-SCF$_3$ |
| 16749 | Bn | 2-SEtF |
| 16750 | Bn | 3-SEtF |
| 16751 | Bn | 4-SEtF |
| 16752 | Bn | 2-SPrF |
| 16753 | Bn | 3-SPrF |
| 16754 | Bn | 4-SPrF |
| 16755 | Bn | 2-OMe, 4-OMe |
| 16756 | Bn | 2-Me, 5-OH |
| 16757 | Bn | 2-Me, 5-OMe |
| 16758 | Bn | 2-Me, 5-OMeF |
| 16759 | Bn | 2-Me, 5-OEtF |
| 16760 | Bn | 2-Me, 5-OPrF |
| 16761 | Bn | 2-Me, 4-OH |
| 16762 | Bn | 2-Me, 4-OMe |
| 16763 | Bn | 2-Me, 4-OMeF |
| 16764 | Bn | 2-Me, 4-OCF$_3$ |
| 16765 | Bn | 2-Me, 4-OEtF |
| 16766 | Bn | 2-Me, 4-OPrF |
| 16767 | Bn | 2-OH, 4-Me |
| 16768 | Bn | 2-OMe, 4-Me |
| 16769 | Bn | 2-OMeF, 4-Me |
| 16770 | Bn | 2-OCF$_3$, 4-Me |
| 16771 | Bn | 2-OEtF, 4-Me |
| 16772 | Bn | 2-OPrF, 4-Me |
| 16773 | Bn | 2-Cl, 4-OH |
| 16774 | Bn | 2-Cl, 4-OMe |
| 16775 | Bn | 2-Cl, 4-OMeF |
| 16776 | Bn | 2-Cl, 4-OCF$_3$ |
| 16777 | Bn | 2-Cl, 4-OEtF |
| 16778 | Bn | 2-Cl, 4-OPrF |
| 16779 | Bn | 2-F, 4-F |
| 16780 | Bn | 2-Cl, 4-Cl |
| 16781 | Bn | 2-Cl, 4-F |
| 16782 | Bn | 2-Cl, 4-NO$_2$ |
| 16783 | Bn | 2-Cl, 4-NH$_2$ |
| 16784 | Bn | 2-Cl, 4-NHMe |
| 16785 | Bn | 2-Cl, 4-NMe$_2$ |
| 16786 | Bn | 2-Cl, 4-NMe$_3$OTf |
| 16787 | Bn | 2-Cl, 4-NMe$_3$I |
| 16788 | Bn | 2-Cl, 5-F |
| 16789 | Bn | 2-Cl, 5-NO$_2$ |
| 16790 | Bn | 2-Cl, 5-NH$_2$ |
| 16791 | Bn | 2-Cl, 5-NHMe |
| 16792 | Bn | 2-Cl, 5-NMe$_2$ |
| 16793 | Bn | 2-Cl, 5-NMe$_3$OTf |
| 16794 | Bn | 2-Cl, 5-NMe$_3$I |
| 16795 | Bn | 2-F, 4-Cl |
| 16796 | Bn | 2-NO$_2$, 4-Cl |
| 16797 | Bn | 2-NH$_2$, 4-Cl |
| 16798 | Bn | 2-NHMe, 4-Cl |
| 16799 | Bn | 2-NMe$_2$, 4-Cl |
| 16800 | Bn | 2-NMe$_3$OTf, 4-Cl |
| 16801 | Bn | 2-NMe$_3$I, 4-Cl |
| 16802 | Bn | 2-F, 5-Cl |

TABLE 10-continued

Substituent list for compounds of general structure XV.

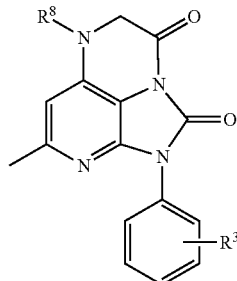

XV

| Compound # | R$^1$ = | R$^3$ = |
|---|---|---|
| 16803 | Bn | 2-NO$_2$, 5-Cl |
| 16804 | Bn | 2-NH$_2$, 5-Cl |
| 16805 | Bn | 2-NHMe, 5-Cl |
| 16806 | Bn | 2-NMe$_2$, 5-Cl |
| 16807 | Bn | 2-NMe$_3$OTf, 5-Cl |
| 16808 | Bn | 2-NMe$_3$I, 5-Cl |
| 16809 | Bn | 2-Br, 4-F |
| 16810 | Bn | 2-Br, 4-NO$_2$ |
| 16811 | Bn | 2-Br, 4-NH$_2$ |
| 16812 | Bn | 2-Br, 4-NHMe |
| 16813 | Bn | 2-Br, 4-NMe$_2$ |
| 16814 | Bn | 2-Br, 4-NMe$_3$OTf |
| 16815 | Bn | 2-Br, 4-NMe$_3$I |
| 16816 | Bn | 2-Br, 5-F |
| 16817 | Bn | 2-Br, 5-NO$_2$ |
| 16818 | Bn | 2-Br, 5-NH$_2$ |
| 16819 | Bn | 2-Br, 5-NHMe |
| 16820 | Bn | 2-Br, 5-NMe$_2$ |
| 16821 | Bn | 2-Br, 5-NMe$_3$OTf |
| 16822 | Bn | 2-Br, 5-NMe$_3$I |
| 16823 | Bn | 2-F, 4-Br |
| 16824 | Bn | 2-NO$_2$, 4-Br |
| 16825 | Bn | 2-NH$_2$, 4-Br |
| 16826 | Bn | 2-NHMe, 4-Br |
| 16827 | Bn | 2-NMe$_2$, 4-Br |
| 16828 | Bn | 2-NMe$_3$OTf, 4-Br |
| 16829 | Bn | 2-NMe$_3$I, 4-Br |
| 16830 | Bn | 2-I, 4-F |
| 16831 | Bn | 2-I, 4-NO$_2$ |
| 16832 | Bn | 2-I, 4-NH$_2$ |
| 16833 | Bn | 2-I, 4-NHMe |
| 16834 | Bn | 2-I, 4-NMe$_2$ |
| 16835 | Bn | 2-I, 4-NMe$_3$OTf |
| 16836 | Bn | 2-I, 4-NMe$_3$I |
| 16837 | Bn | 2-F, 4-I |
| 16838 | Bn | 2-NO$_2$, 4-I |
| 16839 | Bn | 2-NH$_2$, 4-I |
| 16840 | Bn | 2-NHMe, 4-I |
| 16841 | Bn | 2-NMe$_2$, 4-I |
| 16842 | Bn | 2-NMe$_3$OTf, 4-I |
| 16843 | Bn | 2-NMe$_3$I, 4-I |
| 16844 | Bn | 2-Me, 3-F |
| 16845 | Bn | 2-Me, 3-NO$_2$ |
| 16846 | Bn | 2-Me, 3-NH$_2$ |
| 16847 | Bn | 2-Me, 3-NHMe |
| 16848 | Bn | 2-Me, 3-NMe$_2$ |
| 16849 | Bn | 2-Me, 3-NMe$_3$OTf |
| 16850 | Bn | 2-Me, 3-NMe$_3$I |
| 16851 | Bn | 2-Me, 4-F |
| 16852 | Bn | 2-Me, 4-NO$_2$ |
| 16853 | Bn | 2-Me, 4-NH$_2$ |
| 16854 | Bn | 2-Me, 4-NHMe |
| 16855 | Bn | 2-Me, 4-NMe$_2$ |
| 16856 | Bn | 2-Me, 4-NMe$_3$OTf |
| 16857 | Bn | 2-Me, 4-NMe$_3$I |
| 16858 | Bn | 2-Me, 5-F |
| 16859 | Bn | 2-Me, 5-NO$_2$ |
| 16860 | Bn | 2-Me, 5-NH$_2$ |
| 16861 | Bn | 2-Me, 5-NHMe |
| 16862 | Bn | 2-Me, 5-NMe$_2$ |

TABLE 10-continued

Substituent list for compounds of general structure XV.

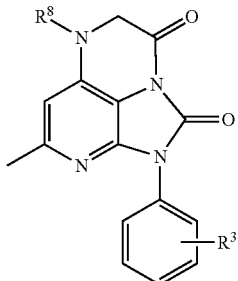

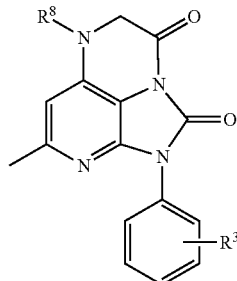

| Compound # | R¹ = | R³ = |
|---|---|---|
| 16863 | Bn | 2-Me, 5-NMe₃OTf |
| 16864 | Bn | 2-Me, 5-NMe₃I |
| 16865 | Bn | 2-F, 4-Me |
| 16866 | Bn | 2-NO₂, 4-Me |
| 16867 | Bn | 2-NH₂, 4-Me |
| 16868 | Bn | 2-NHMe, 4-Me |
| 16869 | Bn | 2-NMe₂, 4-Me |
| 16870 | Bn | 2-NMe₃, 4-Me |
| 16871 | Bn | 2-NMe₃OTf, 4-Me |
| 16872 | Bn | 2-NMe₃I, 4-Me |
| 16873 | Bn | 2-SnMe₃, 4-F |
| 16874 | Bn | 2-SnMe₃, 5-F |
| 16875 | Bn | 2-F, 4-SnMe₃ |
| 16876 | Bn | 2-Br, 6-Cl, 4-F |
| 16877 | Bn | 2-Br, 6-Cl, 4-NO₂ |
| 16878 | Bn | 2-Br, 6-Cl, 4-NH₂ |
| 16879 | Bn | 2-Br, 6-Cl, 4-NHMe |
| 16880 | Bn | 2-Br, 6-Cl, 4-NMe₂ |
| 16881 | Bn | 2-Br, 6-Cl, 4-NMe₃OTf |
| 16882 | Bn | 2-Br, 6-Cl, 4-NMe₃I |
| 16883 | Bn | 2-Me, 6-Cl, 4-F |
| 16884 | Bn | 2-SnMe₃, 6-Cl, 4-F |
| 16885 | Bn | 2-Cl, 4-Me |
| 16886 | Bn | 2-Cl, 4-Br |
| 16887 | Bn | 2-Cl, 4-SnMe₃ |
| 16888 | Bn | 2-Br, 4-Cl |
| 16889 | Bn | 2-SnMe₃, 4-Cl |
| 16890 | Bn | 2-Me, 4-Cl |
| 16891 | Bn | 2-Br, 4-Br |
| 16892 | Bn | 2-Br, 4-Me |
| 16893 | Bn | 2-Br, 4-SnMe₃ |
| 16894 | Bn | 2-SnMe₃, 4-Br |
| 16895 | Bn | 2-Me, 4-Br |
| 16896 | Bn | 2-Me, 4-SnMe₃ |
| 16897 | Bn | 2-SnMe₃, 4-Me |
| 16898 | Bn | 2-Me, 4-Me |
| 16899 | Bn | 2-Et, 4-Br |
| 16900 | Bn | 2-Et, 4-SnMe₃ |
| 16901 | Bn | 2-Et, 4-Me |
| 16902 | Bn | 2-Me, 4-Me, 6-Me |
| 16903 | Bn | 2-Me, 4-Br, 6-Me |
| 16904 | Bn | 2-Me, 4-SnMe₃, 6-Me |
| 16905 | Bn | 2-Et, 6-Me |
| 16906 | Bn | 2-Br, 4-i-Pr |
| 16907 | Bn | 2-SnMe₃, 4-i-Pr |
| 16908 | Bn | 2-Me, 4-i-Pr |
| 16909 | Bn | 2-Br, 4-Br, 6-Br |
| 16910 | Bn | 2-Br, 4-Me, 6-Br |
| 16911 | Bn | 2-Br, 4-SnMe₃, 6-Br |
| 16912 | Bn | 2-SnMe₃, 4-Br, 6-Br |
| 16913 | Bn | 2-Br, 4-Br, 6-Me |
| 16914 | Bn | 2-Br, 4-CF₃, 6-Br |
| 16915 | Bn | 2-Br, 4-Br, 6-CF₃ |
| 16916 | Bn | 2-CF₃, 4-CF₃ |
| 16917 | Bn | 2-Cl, 4-CF₃ |
| 16918 | Bn | 2-CF₃, 4-Cl |
| 16919 | Bn | 2-Br, 4-CF₃ |
| 16920 | Bn | 2-SnMe₃, 4-CF₃ |
| 16921 | Bn | 2-Me, 4-CF₃ |
| 16922 | Bn | 2-CF₃, 4-Br |
| 16923 | Bn | 2-CF₃, 4-SnMe₃ |
| 16924 | Bn | 2-CF₃, 4-Me |
| 16925 | Bn | 2-Br, 4-OH |
| 16926 | Bn | 2-Br, 4-OMe |
| 16927 | Bn | 2-Br, 4-OMeF |
| 16928 | Bn | 2-Br, 4-OCF₃ |
| 16929 | Bn | 2-Br, 4-OEtF |
| 16930 | Bn | 2-Br, 4-OPrF |
| 16931 | Bn | 2-OH, 4-Br |
| 16932 | Bn | 2-OMe, 4-Br |
| 16933 | Bn | 2-OMeF, 4-Br |
| 16934 | Bn | 2-OCF₃, 4-Br |
| 16935 | Bn | 2-OEtF, 4-Br |
| 16936 | Bn | 2-OPrF, 4-Br |
| 16937 | Bn | 2-I, 4-OH |
| 16938 | Bn | 2-I, 4-OMe |
| 16939 | Bn | 2-I, 4-OMeF |
| 16940 | Bn | 2-I, 4-OCF₃ |
| 16941 | Bn | 2-I, 4-OEtF |
| 16942 | Bn | 2-I, 4-OPrF |
| 16943 | Bn | 2-OH, 4-I |
| 16944 | Bn | 2-OMe, 4-I |
| 16945 | Bn | 2-OMeF, 4-I |
| 16946 | Bn | 2-OCF₃, 4-I |
| 16947 | Bn | 2-OEtF, 4-I |
| 16948 | Bn | 2-OPrF, 4-I |
| 16949 | Bn | 2-SnMe₃, 4-OH |
| 16950 | Bn | 2-SnMe₃, 4-OMe |
| 16951 | Bn | 2-SnMe₃, 4-OMeF |
| 16952 | Bn | 2-SnMe₃, 4-OCF₃ |
| 16953 | Bn | 2-SnMe₃, 4-OEtF |
| 16954 | Bn | 2-SnMe₃, 4-OPrF |
| 16955 | Bn | 2-OH, 4-SnMe₃ |
| 16956 | Bn | 2-OMe, 4-SnMe₃ |
| 16957 | Bn | 2-OMeF, 4-SnMe₃ |
| 16958 | Bn | 2-OCF₃, 4-SnMe₃ |
| 16959 | Bn | 2-OEtF, 4-SnMe₃ |
| 16960 | Bn | 2-OPrF, 4-SnMe₃ |
| 16961 | H | H |
| 16962 | H | 2-t-Bu |
| 16963 | H | 2-Br |
| 16964 | H | 3-Br |
| 16965 | H | 4-Br |
| 16966 | H | 2-I |
| 16967 | H | 3-I |
| 16968 | H | 4-I |
| 16969 | H | 2-SnMe₃ |
| 16970 | H | 3-SnMe₃ |
| 16971 | H | 4-SnMe₃ |
| 16972 | H | 2-Me |
| 16973 | H | 3-Me |
| 16974 | H | 4-Me |
| 16975 | H | 2-OH |
| 16976 | H | 3-OH |
| 16977 | H | 4-OH |
| 16978 | H | 2-OMe |
| 16979 | H | 3-OMe |
| 16980 | H | 4-OMe |
| 16981 | H | 2-OMeF |
| 16982 | H | 3-OMeF |

TABLE 10-continued

Substituent list for compounds of general structure XV.

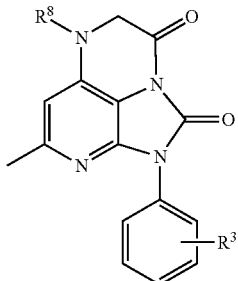

XV

| Compound # | R¹ = | R³ = |
|---|---|---|
| 16983 | H | 4-OMeF |
| 16984 | H | 2-OCF₃ |
| 16985 | H | 3-OCF₃ |
| 16986 | H | 4-OCF₃ |
| 16987 | H | 2-OEtF |
| 16988 | H | 3-OEtF |
| 16989 | H | 4-OEtF |
| 16990 | H | 2-OPrF |
| 16991 | H | 3-OPrF |
| 16992 | H | 4-OPrF |
| 16993 | H | 2-SH |
| 16994 | H | 3-SH |
| 16995 | H | 4-SH |
| 16996 | H | 2-SMe |
| 16997 | H | 3-SMe |
| 16998 | H | 4-SMe |
| 16999 | H | 2-SMeF |
| 17000 | H | 3-SMeF |
| 17001 | H | 4-SMeF |
| 17002 | H | 2-SCF₃ |
| 17003 | H | 3-SCF₃ |
| 17004 | H | 4-SCF₃ |
| 17005 | H | 2-SEtF |
| 17006 | H | 3-SEtF |
| 17007 | H | 4-SEtF |
| 17008 | H | 2-SPrF |
| 17009 | H | 3-SPrF |
| 17010 | H | 4-SPrF |
| 17011 | H | 2-OMe, 4-OMe |
| 17012 | H | 2-Me, 5-OH |
| 17013 | H | 2-Me, 5-OMe |
| 17014 | H | 2-Me, 5-OMeF |
| 17015 | H | 2-Me, 5-OEtF |
| 17016 | H | 2-Me, 5-OPrF |
| 17017 | H | 2-Me, 4-OH |
| 17018 | H | 2-Me, 4-OMe |
| 17019 | H | 2-Me, 4-OMeF |
| 17020 | H | 2-Me, 4-OCF₃ |
| 17021 | H | 2-Me, 4-OEtF |
| 17022 | H | 2-Me, 4-OPrF |
| 17023 | H | 2-OH, 4-Me |
| 17024 | H | 2-OMe, 4-Me |
| 17025 | H | 2-OMeF, 4-Me |
| 17026 | H | 2-OCF₃, 4-Me |
| 17027 | H | 2-OEtF, 4-Me |
| 17028 | H | 2-OPrF, 4-Me |
| 17029 | H | 2-Cl, 4-OH |
| 17030 | H | 2-Cl, 4-OMe |
| 17031 | H | 2-Cl, 4-OMeF |
| 17032 | H | 2-Cl, 4-OCF₃ |
| 17033 | H | 2-Cl, 4-OEtF |
| 17034 | H | 2-Cl, 4-OPrF |
| 17035 | H | 2-F, 4-F |
| 17036 | H | 2-Cl, 4-Cl |
| 17037 | H | 2-Cl, 4-F |
| 17038 | H | 2-Cl, 4-NO₂ |
| 17039 | H | 2-Cl, 4-NH₂ |
| 17040 | H | 2-Cl, 4-NHMe |
| 17041 | H | 2-Cl, 4-NMe₂ |
| 17042 | H | 2-Cl, 4-NMe₃OTf |

TABLE 10-continued

Substituent list for compounds of general structure XV.

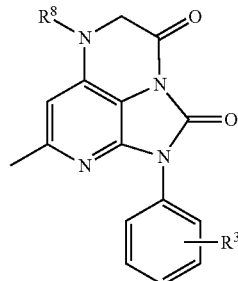

XV

| Compound # | R¹ = | R³ = |
|---|---|---|
| 17043 | H | 2-Cl, 4-NMe₃I |
| 17044 | H | 2-Cl, 5-F |
| 17045 | H | 2-Cl, 5-NO₂ |
| 17046 | H | 2-Cl, 5-NH₂ |
| 17047 | H | 2-Cl, 5-NHMe |
| 17048 | H | 2-Cl, 5-NMe₂ |
| 17049 | H | 2-Cl, 5-NMe₃OTf |
| 17050 | H | 2-Cl, 5-NMe₃I |
| 17051 | H | 2-F, 4-Cl |
| 17052 | H | 2-NO₂, 4-Cl |
| 17053 | H | 2-NH₂, 4-Cl |
| 17054 | H | 2-NHMe, 4-Cl |
| 17055 | H | 2-NMe₂, 4-Cl |
| 17056 | H | 2-NMe₃OTf, 4-Cl |
| 17057 | H | 2-NMe₃I, 4-Cl |
| 17058 | H | 2-F, 5-Cl |
| 17059 | H | 2-NO₂, 5-Cl |
| 17060 | H | 2-NH₂, 5-Cl |
| 17061 | H | 2-NHMe, 5-Cl |
| 17062 | H | 2-NMe₂, 5-Cl |
| 17063 | H | 2-NMe₃OTf, 5-Cl |
| 17064 | H | 2-NMe₃I, 5-Cl |
| 17065 | H | 2-Br, 4-F |
| 17066 | H | 2-Br, 4-NO₂ |
| 17067 | H | 2-Br, 4-NH₂ |
| 17068 | H | 2-Br, 4-NHMe |
| 17069 | H | 2-Br, 4-NMe₂ |
| 17070 | H | 2-Br, 4-NMe₃OTf |
| 17071 | H | 2-Br, 4-NMe₃I |
| 17072 | H | 2-Br, 5-F |
| 17073 | H | 2-Br, 5-NO₂ |
| 17074 | H | 2-Br, 5-NH₂ |
| 17075 | H | 2-Br, 5-NHMe |
| 17076 | H | 2-Br, 5-NMe₂ |
| 17077 | H | 2-Br, 5-NMe₃OTf |
| 17078 | H | 2-Br, 5-NMe₃I |
| 17079 | H | 2-F, 4-Br |
| 17080 | H | 2-NO₂, 4-Br |
| 17081 | H | 2-NH₂, 4-Br |
| 17082 | H | 2-NHMe, 4-Br |
| 17083 | H | 2-NMe₂, 4-Br |
| 17084 | H | 2-NMe₃OTf, 4-Br |
| 17085 | H | 2-NMe₃I, 4-Br |
| 17086 | H | 2-I, 4-F |
| 17087 | H | 2-I, 4-NO₂ |
| 17088 | H | 2-I, 4-NH₂ |
| 17089 | H | 2-I, 4-NHMe |
| 17090 | H | 2-I, 4-NMe₂ |
| 17091 | H | 2-I, 4-NMe₃OTf |
| 17092 | H | 2-I, 4-NMe₃I |
| 17093 | H | 2-F, 4-I |
| 17094 | H | 2-NO₂, 4-I |
| 17095 | H | 2-NH₂, 4-I |
| 17096 | H | 2-NHMe, 4-I |
| 17097 | H | 2-NMe₂, 4-I |
| 17098 | H | 2-NMe₃OTf, 4-I |
| 17099 | H | 2-NMe₃I, 4-I |
| 17100 | H | 2-Me, 3-F |
| 17101 | H | 2-Me, 3-NO₂ |
| 17102 | H | 2-Me, 3-NH₂ |

TABLE 10-continued

Substituent list for compounds of general structure XV.

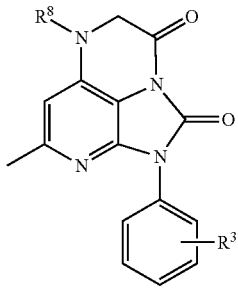

XV

| Compound # | R¹ = | R³ = |
|---|---|---|
| 17103 | H | 2-Me, 3-NHMe |
| 17104 | H | 2-Me, 3-NMe₂ |
| 17105 | H | 2-Me, 3-NMe₃OTf |
| 17106 | H | 2-Me, 3-NMe₃I |
| 17107 | H | 2-Me, 4-F |
| 17108 | H | 2-Me, 4-NO₂ |
| 17109 | H | 2-Me, 4-NH₂ |
| 17110 | H | 2-Me, 4-NHMe |
| 17111 | H | 2-Me, 4-NMe₂ |
| 17112 | H | 2-Me, 4-NMe₃OTf |
| 17113 | H | 2-Me, 4-NMe₃I |
| 17114 | H | 2-Me, 5-F |
| 17115 | H | 2-Me, 5-NO₂ |
| 17116 | H | 2-Me, 5-NH₂ |
| 17117 | H | 2-Me, 5-NHMe |
| 17118 | H | 2-Me, 5-NMe₂ |
| 17119 | H | 2-Me, 5-NMe₃OTf |
| 17120 | H | 2-Me, 5-NMe₃I |
| 17121 | H | 2-F, 4-Me |
| 17122 | H | 2-NO₂, 4-Me |
| 17123 | H | 2-NH₂, 4-Me |
| 17124 | H | 2-NHMe, 4-Me |
| 17125 | H | 2-NMe₂, 4-Me |
| 17126 | H | 2-NMe₃, 4-Me |
| 17127 | H | 2-NMe₃OTf, 4-Me |
| 17128 | H | 2-NMe₃I, 4-Me |
| 17129 | H | 2-SnMe₃, 4-F |
| 17130 | H | 2-SnMe₃, 5-F |
| 17131 | H | 2-F, 4-SnMe₃ |
| 17132 | H | 2-Br, 6-Cl, 4-F |
| 17133 | H | 2-Br, 6-Cl, 4-NO₂ |
| 17134 | H | 2-Br, 6-Cl, 4-NH₂ |
| 17135 | H | 2-Br, 6-Cl, 4-NHMe |
| 17136 | H | 2-Br, 6-Cl, 4-NMe₂ |
| 17137 | H | 2-Br, 6-Cl, 4-NMe₃OTf |
| 17138 | H | 2-Br, 6-Cl, 4-NMe₃I |
| 17139 | H | 2-Me, 6-Cl, 4-F |
| 17140 | H | 2-SnMe₃, 6-Cl, 4-F |
| 17141 | H | 2-Cl, 4-Me |
| 17142 | H | 2-Cl, 4-Br |
| 17143 | H | 2-Cl, 4-SnMe₃ |
| 17144 | H | 2-Br, 4-Cl |
| 17145 | H | 2-SnMe₃, 4-Cl |
| 17146 | H | 2-Me, 4-Cl |
| 17147 | H | 2-Br, 4-Br |
| 17148 | H | 2-Br, 4-Me |
| 17149 | H | 2-Br, 4-SnMe₃ |
| 17150 | H | 2-SnMe₃, 4-Br |
| 17151 | H | 2-Me, 4-Br |
| 17152 | H | 2-Me, 4-SnMe₃ |
| 17153 | H | 2-SnMe₃, 4-Me |
| 17154 | H | 2-Me, 4-Me |
| 17155 | H | 2-Et, 4-Br |
| 17156 | H | 2-Et, 4-SnMe₃ |
| 17157 | H | 2-Et, 4-Me |
| 17158 | H | 2-Me, 4-Me, 6-Me |
| 17159 | H | 2-Me, 4-Br, 6-Me |
| 17160 | H | 2-Me, 4-SnMe₃, 6-Me |
| 17161 | H | 2-Et, 6-Me |
| 17162 | H | 2-Br, 4-i-Pr |

TABLE 10-continued

Substituent list for compounds of general structure XV.

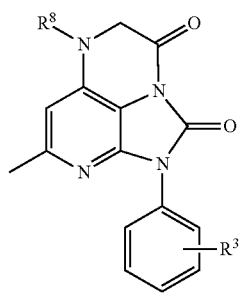

XV

| Compound # | R¹ = | R³ = |
|---|---|---|
| 17163 | H | 2-SnMe₃, 4-i-Pr |
| 17164 | H | 2-Me, 4-i-Pr |
| 17165 | H | 2-Br, 4-Br, 6-Br |
| 17166 | H | 2-Br, 4-Me, 6-Br |
| 17167 | H | 2-Br, 4-SnMe₃, 6-Br |
| 17168 | H | 2-SnMe₃, 4-Br, 6-Br |
| 17169 | H | 2-Br, 4-Br, 6-Me |
| 17170 | H | 2-Br, 4-CF₃, 6-Br |
| 17171 | H | 2-Br, 4-Br, 6-CF₃ |
| 17172 | H | 2-CF₃, 4-CF₃ |
| 17173 | H | 2-Cl, 4-CF₃ |
| 17174 | H | 2-CF₃, 4-Cl |
| 17175 | H | 2-Br, 4-CF₃ |
| 17176 | H | 2-SnMe₃, 4-CF₃ |
| 17177 | H | 2-Me, 4-CF₃ |
| 17178 | H | 2-CF₃, 4-Br |
| 17179 | H | 2-CF₃, 4-SnMe₃ |
| 17180 | H | 2-CF₃, 4-Me |
| 17181 | H | 2-Br, 4-OH |
| 17182 | H | 2-Br, 4-OMe |
| 17183 | H | 2-Br, 4-OMeF |
| 17184 | H | 2-Br, 4-OCF₃ |
| 17185 | H | 2-Br, 4-OEtF |
| 17186 | H | 2-Br, 4-OPrF |
| 17187 | H | 2-OH, 4-Br |
| 17188 | H | 2-OMe, 4-Br |
| 17189 | H | 2-OMeF, 4-Br |
| 17190 | H | 2-OCF₃, 4-Br |
| 17191 | H | 2-OEtF, 4-Br |
| 17192 | H | 2-OPrF, 4-Br |
| 17193 | H | 2-I, 4-OH |
| 17194 | H | 2-I, 4-OMe |
| 17195 | H | 2-I, 4-OMeF |
| 17196 | H | 2-I, 4-OCF₃ |
| 17197 | H | 2-I, 4-OEtF |
| 17198 | H | 2-I, 4-OPrF |
| 17199 | H | 2-OH, 4-I |
| 17200 | H | 2-OMe, 4-I |
| 17201 | H | 2-OMeF, 4-I |
| 17202 | H | 2-OCF₃, 4-I |
| 17203 | H | 2-OEtF, 4-I |
| 17204 | H | 2-OPrF, 4-I |
| 17205 | H | 2-SnMe₃, 4-OH |
| 17206 | H | 2-SnMe₃, 4-OMe |
| 17207 | H | 2-SnMe₃, 4-OMeF |
| 17208 | H | 2-SnMe₃, 4-OCF₃ |
| 17209 | H | 2-SnMe₃, 4-OEtF |
| 17210 | H | 2-SnMe₃, 4-OPrF |
| 17211 | H | 2-OH, 4-SnMe₃ |
| 17212 | H | 2-OMe, 4-SnMe₃ |
| 17213 | H | 2-OMeF, 4-SnMe₃ |
| 17214 | H | 2-OCF₃, 4-SnMe₃ |
| 17215 | H | 2-OEtF, 4-SnMe₃ |
| 17216 | H | 2-OPrF, 4-SnMe₃ |

We claim:
1. A compound selected from the group consisting of:

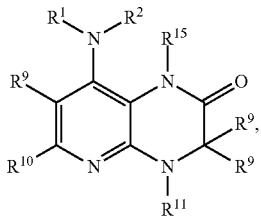
formula (1a)

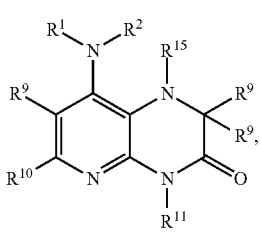
formula (1b)

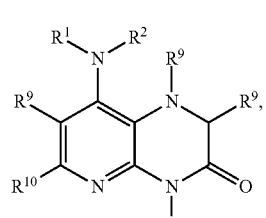
formula (2)

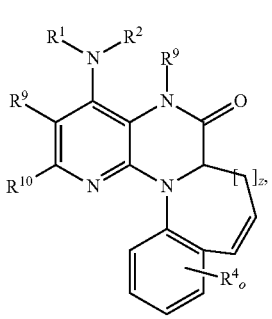
formula (3)

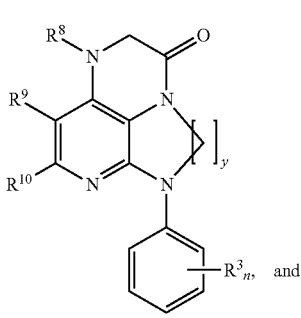
formula (4)

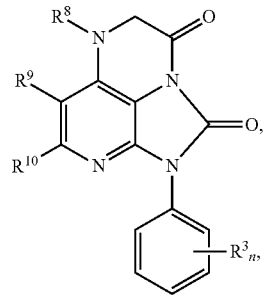
formula (5)

and a pharmaceutically acceptable salt of any of the foregoing comprising a label selected from the group consisting of: $^{2}H$, $^{3}H$, $^{11}C$, $^{13}C$, $^{14}C$, $^{32}Cl$, $^{13}N$, $^{18}F$, $^{75}Br$, $^{76}Br$, $^{123}I$, $^{124}I$, $^{125}I$, and $^{131}I$ wherein:

$R^1$ is selected from the group consisting of: —H, alkyl, alkenyl, haloalkyl, haloalkenyl,

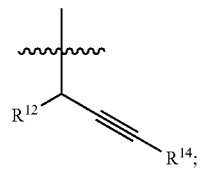

$R^2$ is selected from the group consisting of: —H, alkyl, and haloalkyl;

each $R^3$ is independently selected from the group consisting of: —H, —X, alkyl, haloalkyl, —OH, —O-alkyl, —O-haloalkyl, —NO$_2$, —NH, —NH-alkyl, —N(alkyl)$_2$, —N(alkyl)$_3$OTf, —N(alkyl)$_3$X, —Sn(alkyl)$_3$, —SH, —S-alkyl, and —S-haloalkyl, wherein n is 1, 2, or 3 and wherein if n is 2 or 3, each $R^3$ is chosen independently of any other $R^3$;

each $R^4$, $R^5$, and $R^6$ are each independently selected from the group consisting of: —H, —X, alkyl, haloalkyl, —OH, —O-alkyl, —O-haloalkyl, and —Sn(alkyl)$_3$, wherein o, p, and q are each independently 1, 2, or 3 and wherein if any of o, p, or q are 2 or 3, each of $R^4$, $R^5$, and $R^6$ are chosen independently of each other and any other $R^4$, $R^5$, and $R^6$;

$R^7$ is selected from the group consisting of: —H and alkyl;

$R^8$ is selected from the group consisting of: —H, alkyl, alkenyl, benzyl, haloalkyl, haloalkenyl, and

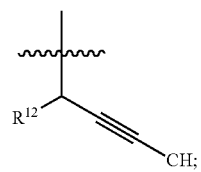

each $R^9$ are independently selected from the group consisting of: —H, halogen, alkyl, haloalkyl, and heteroalkyl;

$R^{10}$ is selected from the group consisting of: —H, halogen, alkyl, haloalkyl, and heteroalkyl;

$R^{11}$ is selected from the group consisting of:

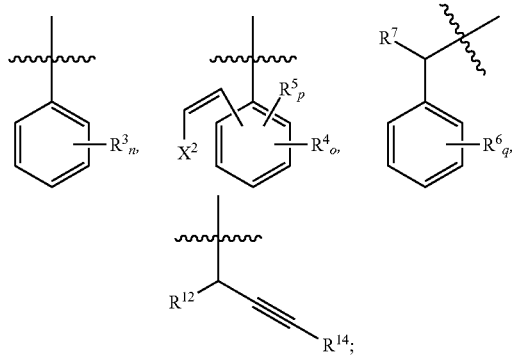

$R^{12}$ is selected from the group consisting of: —H, —OH, —O-alkyl, alkyl, X, haloalkyl, and heteroalkyl;

$R^{14}$ is selected from the group consisting of: —H, halogen, alkyl, haloalkyl, and heteroalkyl;

$R^{15}$ is selected from the group consisting of: —H, halogen, alkyl, haloalkyl, and heteroalkyl;

X is a halogen;

$X^2$ is selected from the group consisting of: —H, alkyl, —X, and —Sn(alkyl)$_3$;

y is selected from the group consisting of: 1 or 2; and z is selected from the group consisting of: 1, 2, or 3;

with the proviso that for formula (I), when $R^{11}$ is

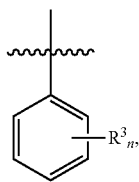

$R^1$ is butyl and $R^2$ is ethyl, $R^3$ is not: 2-Br-4-i-Pr; 2,4-Cl; 2,4,6-CH$_3$; 2-Cl-4-OCH$_3$; or 2-CH$_3$-4-OCH$_3$.

2. The compound of formula (1), according to claim 1, wherein $R^9$ is H, $R^{10}$ is methyl, and $R^{11}$ is

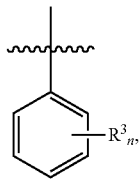

and a pharmaceutically acceptable salt of any of the foregoing.

3. The compound of formula (1), according to claim 1, wherein $R^5$ and $R^9$ are H, $R^{10}$ is methyl, p is 1, and $R^{11}$ is

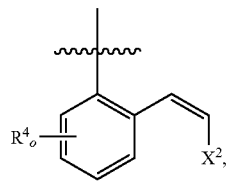

and a pharmaceutically acceptable salt of any of the foregoing.

4. The compound of formula (1), according to claim 1, wherein $R^4$ and $R^9$ are H, $R^{10}$ is methyl, o is 1, and $R^{11}$ is

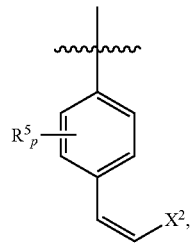

and a pharmaceutically acceptable salt of any of the foregoing.

5. The compound of formula (1), according to claim 1, wherein $R^9$ is H, $R^{10}$ is methyl, and $R^{11}$ is

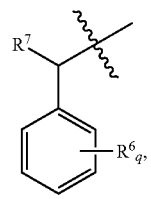

and a pharmaceutically acceptable salt of any of the foregoing.

6. The compound of formula (2), according to claim 1, wherein $R^9$ is H, $R^{10}$ is methyl, and $R^{11}$ is

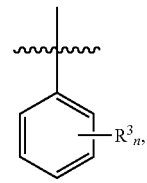

and a pharmaceutically acceptable salt of any of the foregoing.

7. The compound of formula (2), according to claim 1, wherein $R^5$ and $R^9$ are H, $R^{10}$ is methyl, p is 1, and $R^{11}$ is

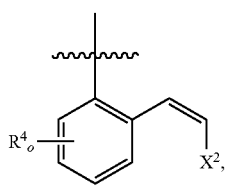

and a pharmaceutically acceptable salt of any of the foregoing.

8. The compound of formula (2), according to claim 1, wherein $R^4$ and $R^9$ are H, $R^{10}$ is methyl, o is 1, and $R^{11}$ is

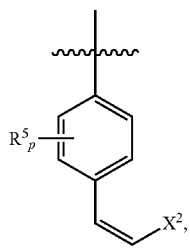

and a pharmaceutically acceptable salt of any of the foregoing.

9. The compound of formula (3), according to claim 1, wherein $R^9$ is H and $R^{10}$ is methyl, and a pharmaceutically acceptable salt of any of the foregoing.

10. The compound of formula (4), according to claim 1, wherein $R^9$ is H and $R^{10}$ is methyl, and a pharmaceutically acceptable salt of any of the foregoing.

11. The compound of formula (5), according to claim 1, wherein $R^9$ is H and $R^{10}$ is methyl, and a stereoisomer thereof, and a pharmaceutically acceptable salt of any of the foregoing.

12. A pharmaceutical composition comprising a compound of any one of claims 1-11 or a pharmaceutically acceptable salt thereof, and a pharmaceutically acceptable carrier.

* * * * *